(12) United States Patent
Lee et al.

(10) Patent No.: US 11,827,640 B2
(45) Date of Patent: Nov. 28, 2023

(54) SUBSTITUTED PYRAZOLO[1,5-A]PYRIMIDINES AS CFTR MODULATORS

(71) Applicant: ILDONG PHARMACEUTICAL CO., LTD., Seoul (KR)

(72) Inventors: Myongjae Lee, Hwaseong-si (KR); Changmok Oh, Hwaseong-si (KR); Dami Lim, Hwaseong-si (KR); Kyeong-A Kim, Hwaseong-si (KR); Seolhee Lee, Hwaseong-si (KR); Ilji Jeong, Hwaseong-si (KR); Jaeeun Ryu, Hwaseong-si (KR); Jooyun Lee, Hwaseong-si (KR); Yearin Jun, Hwaseong-si (KR); Jinsun Kwon, Hwaseong-si (KR); Te-ik Sohn, Hwaseong-si (KR); Gunhee Kim, Hwaseong-si (KR); Jungho Kim, Hwaseong-si (KR); Jongmin Yoon, Hwaseong-si (KR); Jin Hee Lee, Hwaseong-si (KR); Hongchul Yoon, Hwaseong-si (KR); Jung Woo Lee, Hwaseong-si (KR); Joontae Park, Gyeonggi-do (KR); Kyung Mi An, Gyeonggi-do (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 17/508,198

(22) Filed: Oct. 22, 2021

(65) Prior Publication Data
US 2023/0080486 A1 Mar. 16, 2023

Related U.S. Application Data

(60) Provisional application No. 63/104,979, filed on Oct. 23, 2020.

(51) Int. Cl.
*A61K 31/519* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ A61K 31/519; C07D 487/04
USPC ........................................ 514/259.3; 544/281
See application file for complete search history.

(56) References Cited

U.S. PATENT DOCUMENTS

| | | | |
|---|---|---|---|
| 4,178,449 A | 12/1979 | Dusza et al. | |
| 4,281,000 A | 7/1981 | Dusza et al. | |
| 5,688,949 A | 11/1997 | Inoue et al. | |
| 8,883,789 B2 * | 11/2014 | Heimann | C07D 513/04 544/371 |
| 2007/0129383 A1 | 6/2007 | Kuramochi et al. | |
| 2007/0270408 A1 | 11/2007 | Andersen et al. | |
| 2008/0051409 A1 | 2/2008 | Gmeiner et al. | |
| 2010/0130737 A1 | 5/2010 | Itoh et al. | |
| 2013/0143915 A1 | 6/2013 | Ellard et al. | |
| 2020/0095206 A1 | 3/2020 | Markowitz et al. | |
| 2020/0140402 A1 | 5/2020 | Verkman et al. | |

FOREIGN PATENT DOCUMENTS

| | | |
|---|---|---|
| CN | 103923105 A | 7/2014 |
| JP | 2004170323 A | 6/2004 |
| JP | 2018076234 A | 5/2018 |
| WO | WO 2003/101993 A1 | 12/2003 |
| WO | WO 2004/087153 A2 | 10/2004 |
| WO | WO 2004/089471 A2 | 10/2004 |
| WO | WO 2005/070931 A1 | 8/2005 |
| WO | WO 2006/088246 A1 | 8/2006 |
| WO | WO 2007/046548 A1 | 4/2007 |
| WO | WO 2008/004698 A2 | 1/2008 |
| WO | WO 2008/045664 A2 | 4/2008 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Glenn J. Foulds; Fenwick & West LLP

(57) ABSTRACT

The present disclosure provides CFTR modulator and phosphodiesterase 4 (PDE4) inhibitor compounds of the formula (Ia):

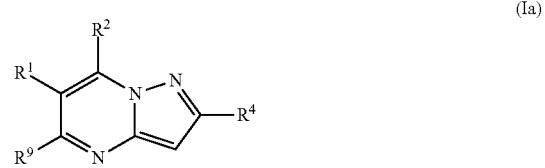

and compositions including said compounds. The compounds can provide functionality for modulating CFTR, methods for treating an eye disease or disorder, and methods for treating CFTR-related indications. The present disclosure also provides methods of using said compounds and compositions for inhibiting PDE4 in a biological system or biological sample, for treating an inflammatory disease or disorder, and for treating other PDE4-related indications. Also provided are methods of preparing said compounds and compositions, and synthetic precursors of said compounds.

24 Claims, 1 Drawing Sheet

(56) References Cited

FOREIGN PATENT DOCUMENTS

| WO | WO 2008/056176 A1 | 5/2008 |
| --- | --- | --- |
| WO | WO 2010/074284 A1 | 7/2010 |
| WO | WO 2010/086040 A1 | 8/2010 |
| WO | WO 2011/050245 A1 | 4/2011 |
| WO | WO 2013/087805 A1 | 6/2013 |
| WO | WO 2014/144455 A1 | 9/2014 |
| WO | WO 2017/112947 A1 | 6/2017 |
| WO | WO 2017/173965 A1 | 10/2017 |
| WO | WO 2018/145080 A1 | 8/2018 |
| WO | WO 2018/226150 A1 | 12/2018 |

OTHER PUBLICATIONS

Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
PCT International Search Report and Written Opinion, PCT Application No. PCT/IB2021/000710, dated Feb. 23, 2022, 13 pages.
Zhou, S. et al. "Structure-Based Discovery of new Maternal Embryonic Leucine Zipper Kinase Inhibitors." Organic & Biomolecular Chemistry, vol. 16, No. 9, Jan. 2018, pp. 1489-1495.
Chen, X. et al. "Nanomolar Potency Aminophenyltriazine CFTR Activator Reverses Corneal Epithelial Injury in a Mouse Model of Dry Eye." Journal of Ocular Pharmacology and Therapeutics, vol. 36, No. 3, Apr. 7, 2020, pp. 147-153.
Flores, A. M. et al. "Small-Molecule CFTR Activators Increase Teat Secretion and Prevent Experimental Dry Eye Disease." The FASEB Journal, vol. 30, No. 5, May 2016, pp. 1789-1797.
Lee, H. K. et al. "Isorhamnetin Ameliorates Dry Eye Disease via CFTR Activation in Mice." International Journal of Molecular Sciences, vol. 22, No. 8, Apr. 2021, pp. 1-14.
PCT International Search Report and Written Opinion, PCT Application No. PCT/IB2022/000612, dated Mar. 29, 2023, 12 pages.
Purushothaman, B. et al. "Design, Synthesis, and Biological Evaluation of Novel Catecholopyrimidine based PDE4 Inhibitor for the Treatment of Atopic Dermatitis." European Journal of Medicinal Chemistry, vol. 145, Feb. 10, 2018, pp. 673-690.

* cited by examiner

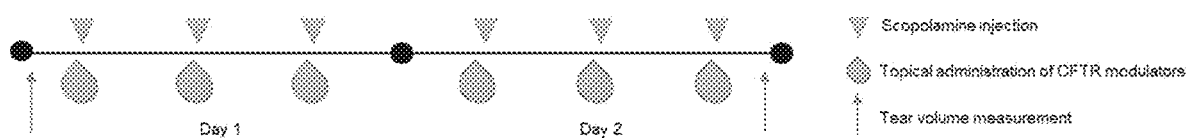

SUBSTITUTED PYRAZOLO[1,5-A]PYRIMIDINES AS CFTR MODULATORS

1. CROSS REFERENCE TO RELATED APPLICATIONS

This application claims the benefit of U.S. Provisional Application No. 63/104,979, filed Oct. 23, 2020, which is hereby incorporated in its entirety by reference.

2. BACKGROUND OF THE INVENTION

Cystic fibrosis transmembrane conductance regulator (CFTR) is a membrane protein encoded by the CFTR gene and codes for an ABC transporter-class ion channel protein that conducts chloride ions across cell membranes. Certain mutations of the CFTR gene can negatively affect chloride ion channel function, leading to dysregulation of epithelial fluid transport in many organs, such as the lung and the pancreas, resulting in cystic fibrosis. Furthermore, wild-type CFTR proteins can be modulated by a direct activation mechanism, but its inappropriate activation can lead to secretory diarrheas such as cholera.

Activators of wild-type CFTR are of interest for use in clinical indications for prosecretory therapy of constipation and dry eye disorders and for disorders of the liver, pancreas, and airways. CFTR inhibitors are of interest for treating certain secretory diarrheas and polycystic kidney disease.

Phosphodiesterase 4 (PDE4) is a key enzyme responsible for the hydrolysis of cyclic adenosine monophosphate (cAMP), an intracellular messenger that controls a variety of proinflammatory and anti-inflammatory mediators. Increased intracellular cAMP levels can result from the inhibition of PDE4, and have significant anti-inflammatory effects by blocking the recruitment of immune cells and the release of proinflammatory mediators. Hematopoietic cells such as dendritic cells, T cells, macrophages, and monocytes are controlled by PDE4.

3. SUMMARY OF THE INVENTION

The present disclosure provides CFTR modulator compounds and compositions including said compounds. The present disclosure also provides methods of using said compounds and compositions for modulating CFTR, methods for treating an eye disease or disorder and methods for treating CFTR-related indications. The present disclosure also provides PDE4 inhibiting compounds and compositions including said compounds. In some embodiments, the PDE4 inhibitor compounds of this disclosure are anti-inflammatory compounds capable of activation of target CFTR. The present disclosure also provides methods of using said compounds and compositions for inhibiting PDE4, for treating an inflammatory disease or disorder and for treating PDE4-related indications. Also provided are methods of preparing said compounds and compositions, and synthetic precursors of said compounds.

In a first aspect, the present disclosure provides a compound of formula (Ia):

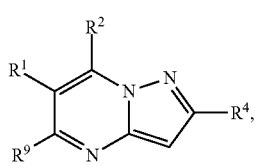

(Ia)

or a pharmaceutically acceptable salt, a solvate, a hydrate, a prodrug, or a stereoisomer thereof, wherein:

$R^1$ is selected from H, halogen, optionally substituted aryl, optionally substituted $(C_1-C_{10})$alkyl, and optionally substituted $(C_1-C_{10})$alkoxy;

$R^2$ is selected from H, optionally substituted $(C_1-C_{10})$ alkyl, optionally substituted cycloalkyl, optionally substituted aryl, optionally substituted heteroaryl, and optionally substituted heterocycle, and the optional substituents on aryl, heteroaryl, and heterocycle are independently selected from: H, OH, $NH_2$, $NO_2$, $OCF_3$, $CF_3$, halogen, optionally substituted amino, optionally substituted $(C_1-C_5)$alkyl, and optionally substituted $(C_1-C_5)$alkoxy;

$R^4$ is selected from

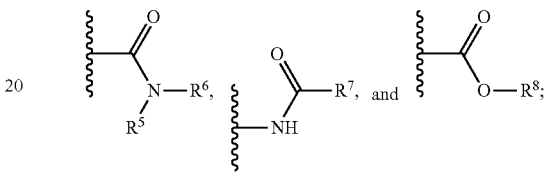

$R^5$ and $R^6$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted $(C_1-C_{10})$alkyl, optionally substituted $(C_1-C_{10})$alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$ alkyl; and $R^9$ is selected from H and halogen.

In a second aspect, the present disclosure provides a pharmaceutical composition comprising a compound (e.g., a compound of formula (Ia)-(Ie), as described herein) or a pharmaceutically acceptable salt, a solvate, a hydrate, a prodrug, or a stereoisomer thereof and a pharmaceutically acceptable excipient. In some embodiments, the pharmaceutical composition is an ophthalmic composition.

In a third aspect, the present disclosure provides a method of modulating a cystic fibrosis transmembrane conductance regulator (CFTR), including contacting a sample or biological system including a target CFTR with an effective amount of a CFTR modulating compound (e.g., of formula (Ia)-(Ie), as described herein), or a pharmaceutically acceptable salt, a solvate, a hydrate, a prodrug, or a stereoisomer thereof, to modulate CFTR.

In fourth aspect, the present disclosure provides a method of activating a cystic fibrosis transmembrane conductance regulator (CFTR) administering to a subject a therapeutically effective amount of a CFTR modulating compound (e.g., of formula (Ia)-(Ie), as described herein), or an ophthalmic composition as described herein (e.g., a composition including a compound of formula (Ia)-(Ie), as described herein).

In fifth aspect, the present disclosure provides a method of inhibiting PDE4, including contacting a sample or biological system including a target PDE4 with an effective amount of a PDE4 inhibiting compound (e.g., a compound of formula (Ia)-(Ie), as described herein), or a pharmaceutically acceptable salt, a solvate, a hydrate, a prodrug, or a stereoisomer thereof, to inhibit PDE4.

In a sixth aspect, the present disclosure provides a method of treating dry eye disease or CFTR-related indications, including administering to an eye of a subject a therapeutically effective amount of a compounds and/or an ophthalmic composition as described herein (e.g., a composition including a compound of formula (Ia)-(Ie), as described herein). In some embodiments, the method of treating dry eye disease further includes identifying a subject suffering from dry eye disease, or identifying an underlying disease or condition associated with the dry eye disease. In some embodiments, the subject may be a human subject having dry eye diseases or symptoms, or CFTR-related indications.

In a seventh aspect, the present disclosure provides a method of treating an inflammatory disease or PDE4-related indications, including administering to a subject a therapeutically effective amount of a PDE4 inhibiting compound (e.g., a compound of formula (Ia)-(Ie), as described herein), or a pharmaceutically acceptable salt, a solvate, a hydrate, a prodrug, or a stereoisomer thereof, or a pharmaceutical composition including the same. In some embodiments, the subject may be a human subject having an inflammatory disease or a PDE4-related indication.

4. BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 shows the study schedule of the mouse tear volume reduction in vivo study.

5. DETAILED DESCRIPTION OF THE INVENTION

5.1. CFTR Modulator and/or PDE4 Inhibitor Compounds

As summarized above, the present disclosure provides compounds and compositions for use in modulating CFTR. Also provided are compounds and compositions for use inhibiting PDE4. In some embodiments, the compounds of this disclosure have CFTR modulating and/or PDE4 inhibiting activity. In some embodiments, the PDE4 inhibitor compounds of this disclosure are anti-inflammatory compounds capable of activation of target CFTR.

The compounds can include a fused bicyclic core structure of pyrazolo[1,5-a]pyrimidin

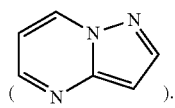

In the compounds of the present disclosure, compounds containing the pyrazolo[1,5-a]pyrimidine core can be substituted at the 2 position of the core structure with optionally substituted aryl, optionally substituted heteroaryl, and optionally substituted heterocycle substituents, at the 5 position of the core structure with halogen, at the 6 position of the core structure with halogen, optionally substituted aryl, optionally substituted ($C_1$-$C_{10}$)alkyl, and optionally substituted ($C_1$-$C_{10}$)alkoxy substituents, and at the 7 position of the core structure with optionally substituted aryl, optionally substituted heteroaryl, and optionally substituted heterocycle. In various embodiments as described herein, the optionally substituted substituents at the one or more positions of the core structure may optionally be further substituted. Compounds having such substituted pyrazolo[1,5-a]pyrimidine core structure as described herein can have desirable CFTR modulating and PDE4 inhibiting activities and find use in a variety of applications.

Accordingly, in a first aspect, the present disclosure provides a compound of formula (Ia):

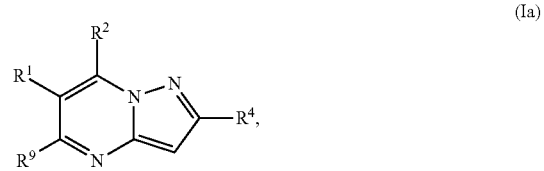

or a pharmaceutically acceptable salt, a solvate, a hydrate, a prodrug, or a stereoisomer thereof, wherein:

$R^1$ is selected from H, halogen, optionally substituted aryl, optionally substituted ($C_1$-$C_{10}$)alkyl, and optionally substituted ($C_1$-$C_{10}$)alkoxy;

$R^2$ is selected from optionally substituted H, optionally substituted ($C_1$-$C_{10}$) alkyl, optionally substituted cycloalkyl, optionally substituted aryl, optionally substituted heteroaryl, and optionally substituted heterocycle, and the optional substituents on aryl, heteroaryl, and heterocycle are independently selected from: H, OH, $NH_2$, $NO_2$, $OCF_3$, $CF_3$, halogen, optionally substituted amino, optionally substituted ($C_1$-$C_5$)alkyl, and optionally substituted ($C_1$-$C_5$)alkoxy;

$R^4$ is selected from

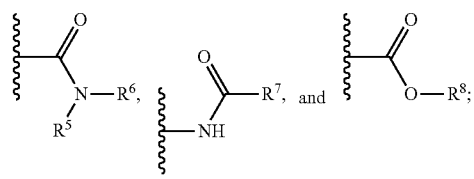

$R^5$ and $R^6$ are independently selected from H, optionally substituted ($C_1$-$C_{10}$)alkyl, optionally substituted ($C_1$-$C_{10}$) alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle; or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted ($C_1$-$C_{10}$)alkyl, optionally substituted ($C_1$-$C_{10}$)alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$ alkyl; and $R^9$ is selected from H and halogen.

In some embodiments of formula (Ia), $R^2$ is a substituted aryl. In certain cases, $R^2$ is a mono-substituted aryl. In certain cases, $R^2$ is a di-substituted aryl. In certain cases, $R^2$ is a tri-substituted aryl. In certain cases, the substituents in the di-substituted aryl or the tri-substituted aryl are adjacent one another. In certain cases, the di-substituted aryl is a 2,3-di-substituted aryl. In certain cases, the di-substituted aryl is a 3,4-di-substituted aryl. In certain cases, the di-substituted aryl is a 4,5-di-substituted aryl. In certain cases, the di-substituted aryl is a 5,6-di-substituted aryl. In certain cases, the di-substituted aryl is a 2,4-di-substituted aryl. In certain cases, the di-substituted aryl is a 2,5-di-substituted aryl. In certain cases, the di-substituted aryl is a 2,6-di-substituted aryl. In certain cases, the di-substituted aryl is a 3,5-di-substituted aryl. In certain cases, the di-substituted aryl is a 3,6-di-substituted aryl. In certain cases, the di-substituted aryl is a 4,6-di-substituted aryl. In certain cases, the tri-substituted aryl is a 2,3,4-tri-substituted aryl. In certain cases, the tri-substituted aryl is a 3,4,5-tri-substituted aryl. In certain cases, the tri-substituted aryl is a 4,5,6-tri-substituted aryl. In certain cases, the tri-substituted aryl is a 2,3,5-tri-substituted aryl. In certain cases, the tri-substituted aryl is a 2,3,6-tri-substituted aryl. In certain cases, the tri-substituted aryl is a 2,4,5-tri-substituted aryl. In certain cases, the tri-substituted aryl is a 2,4,6-tri-substituted aryl. In certain cases, the tri-substituted aryl is a 2,5,6-tri-substituted aryl. In certain cases, the tri-substituted aryl is a 3,4,6-tri-substituted aryl. In certain cases, the tri-substituted aryl is a 3,5,6-tri-substituted aryl.

In some embodiments of formula (Ia), $R^2$ is an optionally substituted heteroaryl. In another embodiment, $R^2$ is selected from optionally substituted furanyl (e.g., 2-furanyl) and optionally substituted thiophene (e.g., 2-thiopheneyl). In another embodiment, $R^2$ is an optionally substituted benzo fused heterocycle.

In some embodiments of formula (Ia), $R^2$ is a heterocycle selected from:

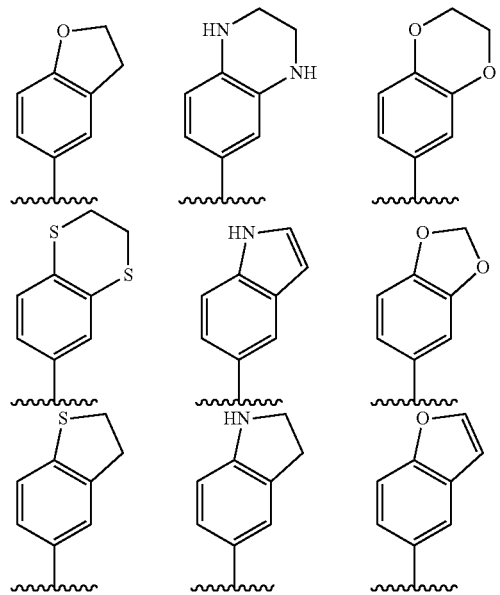

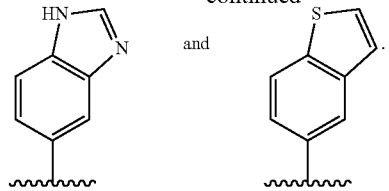

In some embodiments of formula (Ia), $R^2$ is an optionally substituted phenyl or an optionally substituted heteroaryl. In certain cases, $R^2$ is a substituted phenyl with 1 to 3 substituents or a substituted heteroaryl with 1 to 3 substituents. In certain cases, $R^2$ is a 3-substituted phenyl. In certain cases, $R^2$ is a 4-substituted phenyl. In certain cases. $R^2$ is a di-substituted phenyl. In certain cases, the substituents on the di-substituted phenyl are adjacent one another. In certain cases, the di-substituted phenyl is a 2,3-di-substituted phenyl. In certain cases, the di-substituted phenyl is a 3,4-disubstituted phenyl. In certain cases, the di-substituted phenyl is a 4,5-di-substituted phenyl. In certain cases, the di-substituted phenyl is a 5,6-di-substituted phenyl. In certain cases, the di-substituted phenyl is a 2,4-di-substituted phenyl. In certain cases, the di-substituted phenyl is a 2,5-di-substituted phenyl. In certain cases, the di-substituted phenyl is a 2,6-di-substituted phenyl. In certain cases, the di-substituted phenyl is a 3,5-di-substituted phenyl. In certain cases, the di-substituted phenyl is a 3,6-di-substituted phenyl. In certain cases, the di-substituted phenyl is a 4,6-di-substituted phenyl. In certain cases, $R^2$ is a tri-substituted phenyl. In certain cases, the tri-substituted phenyl is a 2,3,4-tri-substituted phenyl. In certain cases, the tri-substituted phenyl is a 3,4,5-tri-substituted phenyl. In certain cases, the tri-substituted phenyl is a 4,5,6-tri-substituted phenyl. In certain cases, the tri-substituted phenyl is a 2,3,5-tri-substituted phenyl. In certain cases, the tri-substituted phenyl is a 2,3,6-tri-substituted phenyl. In certain cases, the tri-substituted phenyl is a 2,4,5-tri-substituted phenyl. In certain cases, the tri-substituted phenyl is a 2,4,6-tri-substituted phenyl. In certain cases, the tri-substituted phenyl is a 2,5,6-tri-substituted phenyl. In certain cases, the tri-substituted phenyl is a 3,4,6-tri-substituted phenyl. In certain cases, the tri-substituted phenyl is a 3,5,6-tri-substituted phenyl.

In some embodiments of formula (Ia), where $R^2$ is an optionally substituted phenyl or an optionally substituted heteroaryl, the compound is of formula (Ib):

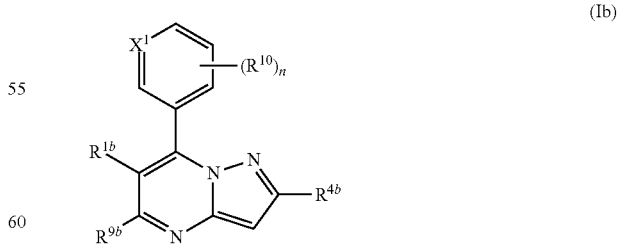

wherein:

$X^1$ is $CR^{10'}$ or N;

$R^{1b}$ is selected from H, halogen, optionally substituted aryl, optionally substituted $(C_1-C_{10})$alkyl, and optionally substituted $(C_1-C_{10})$alkoxy;

$R^{4b}$ is selected from

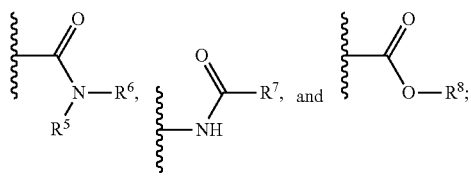

$R^5$ and $R^6$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle; or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted $(C_1-C_{10})$alkyl, optionally substituted $(C_1-C_{10})$alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$alkyl;

$R^{9b}$ is selected from H and halogen;

each $R^{10}$ and $R^{10'}$ is independently selected from H, OH, $NH_2$, $NO_2$, halogen, optionally substituted $(C_1-C_6)$alkyl, optionally substituted $(C_1-C_6)$alkoxy, and substituted amino; and n is 0 to 4.

In some embodiments of the compound of formula (Ib), each $R^{10}$ and $R^{10'}$ is independently selected from H, OH, $CH_3$, $CF_3$, $OCF_3$, $OCH_3$, $NO_2$, F, Cl, and dimethylamine.

In some embodiments of formula (Ia) or (Ib), $R^2$ is selected from:

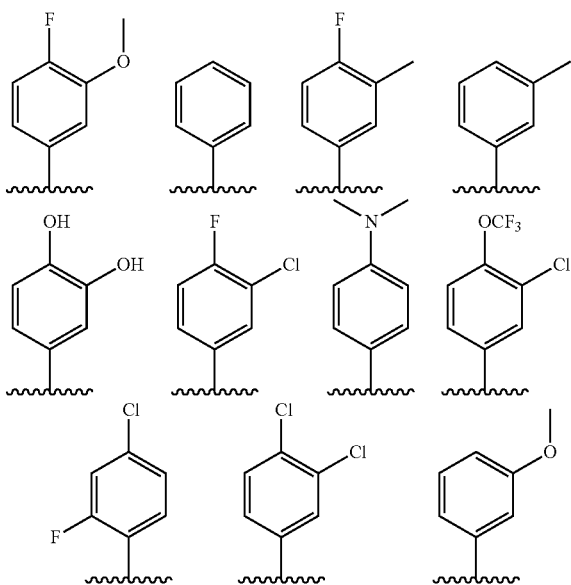

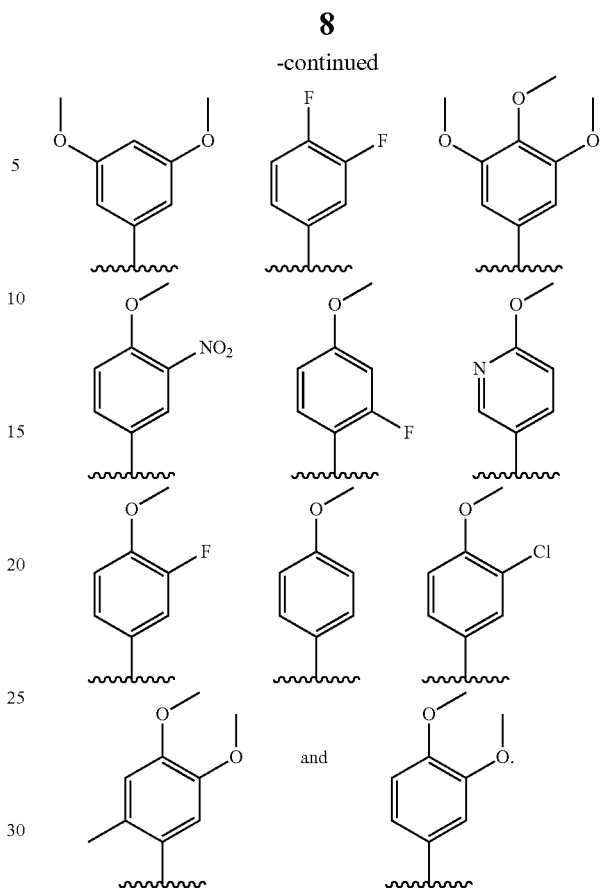

In some embodiments of formula (Ia), $R^2$ is:

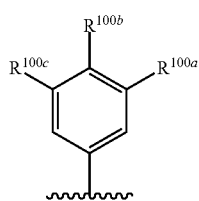

wherein:

each $R^{100a}$-$R^{100c}$ is independently selected from H, OH, $NH_2$, $NO_2$, halogen, optionally substituted $(C_1-C_6)$alkyl, optionally substituted $(C_1-C_6)$alkoxy, and substituted amino; and at least one of $R^{100a}$, $R^{100b}$, $R^{100c}$ is not H. In certain embodiments, $R^{100a}$-$R^{100c}$ are independently selected from H, $NO_2$, halogen, optionally substituted $(C_1-C_3)$alkyl, and optionally substituted $(C_1-C_3)$alkoxy. In certain embodiments, each of $R^{100a}$-$R^{100c}$ is a different group. In certain embodiments, each of $R^{100a}$-$R^{100c}$ is different and independently selected from halogen, $NO_2$, methoxy and methyl. In certain embodiments, each of $R^{100a}$-$R^{100c}$ is the same, and is not H. In certain cases, each of $R^{100a}$-$R^{100c}$ is $(C_1-C_3)$alkoxy. In certain cases, each of $R^{100a}$-$R^{100c}$ is methoxy. In certain cases, two of $R^{100a}$-$R^{100c}$ are $(C_1-C_3)$alkoxy, and the other one of $R^{100a}$-$R^{100c}$ is H. In certain cases, two of $R^{100a}$-$R^{100c}$ are methoxy, and the other one of $R^{100a}$-$R^{100c}$ is H. In certain cases, each of $R^{100a}$ and $R^{100b}$ $(C_1-C_3)$alkyl, and $R^{100c}$ is H. In certain cases, each of $R^{100a}$ and $R^{100b}$ are methoxy, and $R^{100c}$ is H.

In some embodiments of formula (Ib), the compound is of formula (Ic):

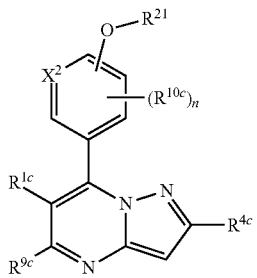

(Ic)

wherein:

$X^2$ is $CR^{10c'}$ or N;

$R^{21}$ is selected from H, and optionally substituted ($C_1$-$C_{10}$)alkyl; optionally substituted acyl; optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

$R^{1c}$ is selected from H, halogen, optionally substituted aryl, optionally substituted ($C_1$-$C_{10}$)alkyl, and optionally substituted ($C_1$-$C_{10}$)alkoxy;

$R^{4c}$ is selected from

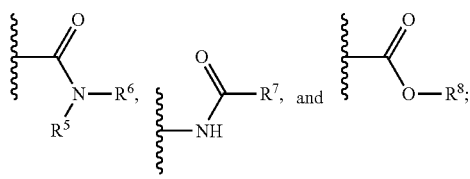

$R^5$ and $R^6$ are independently selected from H, optionally substituted ($C_1$-$C_{10}$)alkyl, optionally substituted ($C_1$-$C_{10}$)alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle; or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted ($C_1$-$C_{10}$)alkyl, optionally substituted ($C_1$-$C_{10}$)alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted ($C_1$-$C_{10}$)alkyl;

$R^{9c}$ is selected from H and halogen;

each $R^{10c}$ and $R^{11c'}$ is independently selected from H, OH, $NH_2$, $NO_2$, halogen, optionally substituted ($C_1$-$C_6$)alkyl, optionally substituted ($C_1$-$C_6$)alkoxy, and substituted amino; and n is 0 to 3.

In some embodiments of formula (Ic), $R^{21}$ is H, or optionally substituted ($C_1$-$C_6$)alkyl. In some embodiments of formula (Ic), $R^{21}$ is ($C_1$-$C_6$)alkyl. In some embodiments of formula (Ic), $R^{21}$ is methyl.

In some embodiments of formula (Ic), —O—$R^{21}$ is connected to the phenyl ring at the para-position. In some embodiments of formula (Ic), —O—$R^{21}$ is connected to the phenyl ring at the meta-position.

In certain embodiments of formula (Ic), the compound is of formula (Id):

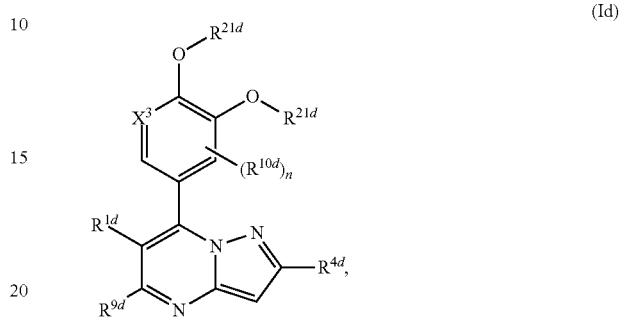

(Id)

wherein:

$X^3$ is $CR^{10d'}$ or N;

each $R^{21d}$ is independently selected from H, and optionally substituted ($C_1$-$C_{10}$)alkyl; optionally substituted acyl; optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

$R^{1d}$ is selected from H, halogen, optionally substituted aryl, optionally substituted ($C_1$-$C_{10}$)alkyl, and optionally substituted ($C_1$-$C_{10}$)alkoxy;

$R^{4d}$ is selected from

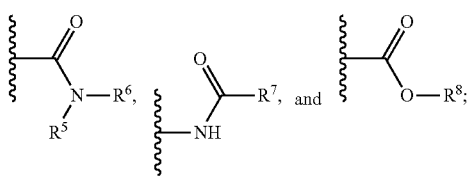

$R^5$ and $R^6$ are independently selected from H, optionally substituted ($C_1$-$C_{10}$)alkyl, optionally substituted ($C_1$-$C_{10}$)alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted ($C_1$-$C_{10}$)alkyl, optionally substituted ($C_1$-$C_{10}$)alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$alkyl;

$R^{9d}$ is selected from H and halogen;

each $R^{10d}$ and $R^{10d'}$ is independently selected from H, OH, $NH_2$, $NO_2$, halogen, optionally substituted $(C_1-C_6)$alkyl, optionally substituted $(C_1-C_6)$alkoxy, and substituted amino; and n is 0 to 2.

In some embodiments of formula (Id), each $R^{21d}$ is independently H, or optionally substituted $(C_1-C_6)$alkyl. In some embodiments of formula (Id), each $R^{21d}$ is independently $(C_1-C_6)$alkyl. In some embodiments of formula (Id), each $R^{21d}$ is methyl.

In certain embodiments of formula (Id), $X^3$ is $CR^{10d'}$. In certain embodiments of formula (Id), $X^3$ is CH. In certain embodiments of formula (Id), $X^3$ is $CR^{10d'}$, where $R^{10d'}$ is—optionally substituted $(C_1-C_6)$alkoxy. In certain embodiments of formula (Id), $X^3$ is $CR^{10d'}$, where $R^{10d'}$ is —$OCH_3$. In certain embodiments of formula (Id), $R^{10d'}$ is —$OCH_3$ and n is 0.

In certain embodiments of formula (Id), $X^3$ is N.

In certain embodiments of formula (Id), $X^3$ is $CR^{10d'}$. In certain embodiments of formula (Id), $X^3$ is $CR^{10d'}$, n is 0. In certain embodiments of formula (Id), $X^3$ is $CR^{10d'}$, and n is 1. In certain embodiments of formula (Id), when n is 1 or 2, each $R^{10d}$ is independently selected from halogen, and optionally substituted $(C_1-C_6)$alkyl.

In certain embodiments of formula (Id), each $R^{21d}$ is optionally substituted $(C_1-C_6)$alkyl, $X^3$ is $CR^{10d'}$, n is 0 or 1, and $R^{10d}$ and $R^{10d'}$ are independently optionally substituted $(C_1-C_6)$alkyl or halogen.

In certain embodiments of formula (Id), each $R^{21d}$ is methyl, $X^3$ is $CR^{10d'}$, where $R^{10d'}$ is —$OCH_3$, and n is 0.

In certain embodiments of formula (Id), each $R^{21d}$ is optionally substituted $(C_1-C_6)$alkyl, $X^3$ is CH, n is 1, and $R^{10d}$ is optionally substituted $(C_1-C_6)$alkyl or halogen. In certain embodiments of formula (Id), each $R^{21d}$ is methyl, $X^3$ is CH, and n is 1 where the $R^{10d}$ is methyl located at the ortho position.

In some embodiments of formula (Id), each $R^{21d}$ is methyl, and n is 0.

In some embodiments of formula (Ia)-(Id), any of $R^4$-$R^{4d}$ is

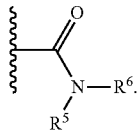

In some embodiments of formula (Ia)-(Id), $R^5$ and $R^6$ together with the nitrogen atom to which they are attached are cyclically linked to provide an optionally substituted monocyclic or bicyclic $(C_4-C_{10})$heterocycle.

In some embodiments of formula (Ia)-(Id), any of $R^4$-$R^{4d}$ is

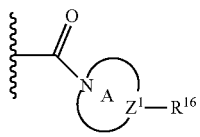

wherein:

ring A is an optionally substituted monocyclic or bicyclic $(C_4-C_{10})$heterocycle;

$Z^1$ is $CR^{14}$ or N, where $R^{14}$ is selected from H, OH, $NH_2$, CN, $CF_3$, $OCF_3$, $CH_2NH_2$, halogen, optionally substituted $(C_1-C_5)$alkyl, optionally substituted $(C_1-C_5)$alkoxy, optionally substituted cycloalkyl, optionally substituted heterocycloalkyl, optionally substituted carbocycle, and optionally substituted heterocycle; and $R^{16}$ is selected from H, halogen, —$OR^{22a}$, —$C(O)R^{22b}$, —$CO_2R^{22c}$, and —$C(O)NR^{50}R^{60}$, —$NR^{50}R^{60}$, optionally substituted aryl, optionally substituted heteroaryl, optionally substituted carbocycle, optionally substituted heterocycle, optionally substituted $(C_1-C_5)$alkyl, and optionally substituted $(C_1-C_5)$alkoxy;

$R^{22a}$, $R^{22b}$, and $R^{22c}$ are independently selected from H, optionally substituted $(C_1-C_{10})$ alkyl, optionally substituted cycloalkyl, optionally substituted aryl, optionally substituted heteroaryl, and optionally substituted heterocycle; and $R^{50}$ and $R^{60}$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^{50}$ and $R^{60}$ together with the nitrogen atom to which they are attached are cyclically linked to form an optionally substituted heterocycle, or an optionally substituted heteroaryl.

In some embodiments of formula (Ia)-(Id) when any of $R^4$-$R^{4d}$ is

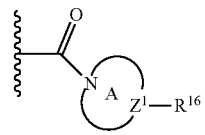

and the A ring is piperidine, then $R^{16}$ comprises at least one cyclic group selected from optionally substituted aryl, optionally substituted heteroaryl, optionally substituted carbocycle, optionally substituted heterocycle. In some cases, the A ring is piperidine and $R^{16}$ comprises an optionally substituted aryl. In some cases, the optionally substituted aryl is optionally substituted phenyl. In some cases, the A ring is piperidine and $R^{16}$ comprises an optionally substituted heteroaryl. In some cases, the A ring is piperidine and $R^{16}$ comprises an optionally substituted carbocycle. In some cases, the A ring is piperidine and $R^{16}$ comprises an optionally substituted heterocycle.

In some embodiments of formula (Ia)-(Id) when any of $R^4$-$R^{4d}$ is

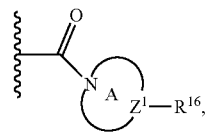

the A ring is an optionally substituted piperazine, pyrrolidine, or azetidine. In certain cases, the A ring is:

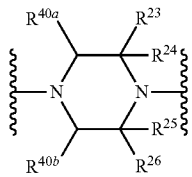

wherein:

$R^{23}$-$R^{26}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$) alkoxy, optionally substituted cycloalkyl, optionally substituted aryl, optionally substituted heteroaryl, and optionally substituted heterocycle; or one or both of $R^{23}$-$R^{24}$ and $R^{25}$-$R^{26}$ together with the carbon atom to which they are attached are cyclically linked to form an optionally substituted carbocycle or an optionally substituted heterocycle; and $R^{40a}$ and $R^{41b}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$)alkoxy, optionally substituted cycloalkyl, optionally substituted aryl, optionally substituted heteroaryl, and optionally substituted heterocycle.

In some embodiments, $R^{23}$ is selected from optionally substituted ($C_1$-$C_6$)alkyl and optionally substituted cycloalkyl; and $R^{24}$-$R^{26}$, $R^{40a}$ and $R^{40b}$ are each H. In certain cases, $R^{23}$ is selected from methyl, ethyl, propyl, isopropyl, butyl, and t-butyl. In certain cases, $R^{23}$ is methyl. In certain cases, $R^{23}$ is ethyl. In certain cases, $R^{23}$ is propyl. In certain cases, $R^{23}$ is isopropyl. In some embodiments, $R^{23}$ is ($C_1$-$C_6$) cycloalkyl. In certain cases, $R^{23}$ is cyclopropyl. In certain cases, $R^{23}$ is cyclobutyl. In certain cases, $R^{23}$ is cyclopentyl. In certain cases, $R^{23}$ is cyclohexyl.

In certain embodiments of the A ring, two of $R^{23}$, $R^{25}$, and $R^{40b}$ are independently selected from optionally substituted ($C_1$-$C_6$)alkyl and optionally substituted cycloalkyl; and the other one of $R^{23}$, $R^{25}$ and $R^{40b}$ is H, and $R^{24}$, $R^{26}$ and $R^{40a}$ are each H. In certain cases of the A ring, two of $R^{23}$, $R^{25}$, and $R^{40b}$ are optionally substituted ($C_1$-$C_6$)alkyl. In certain cases of the A ring, two of $R^{23}$, $R^{25}$, and $R^{40b}$ are each independently selected from methyl, ethyl, propyl, isopropyl, butyl, and t-butyl. In certain cases of the A ring, two of $R^{23}$, $R^{25}$, and $R^{40b}$ are methyl. In certain cases of the A ring, two of $R^{23}$, $R^{25}$, and $R^{40b}$ are ethyl. In certain cases, two of $R^{23}$, $R^{25}$, and $R^{40b}$ are propyl. In certain cases of the A ring, two of $R^{23}$, $R^{25}$, and $R^{40b}$ are isopropyl. In some embodiments of the A ring, two of $R^{23}$, $R^{25}$, and $R^{40b}$ are ($C_1$-$C_6$) cycloalkyl. In certain cases of the A ring, two of $R^{23}$, $R^{25}$, and $R^{40b}$ are cyclopropyl. In certain cases, two of $R^{23}$, $R^{25}$, and $R^{40b}$ are cyclobutyl. In certain cases of the A ring, two of $R^{23}$, $R^{25}$, and $R^{40b}$ are cyclopentyl. In certain cases of the A ring, two of $R^{23}$, $R^{25}$, and $R^{40b}$ are cyclohexyl.

In certain embodiments of the A ring, $R^{23}$ and $R^{25}$ are each independently selected from optionally substituted ($C_1$-$C_6$) alkyl, and optionally substituted cycloalkyl; and $R^{24}$, $R^{26}$ and $R^{40a}$-$R^{40b}$ are each H. In certain cases of the A ring, both $R^{23}$ and $R^{25}$ are optionally substituted ($C_1$-$C_6$)alkyl. In certain cases of the A ring, $R^{23}$ and $R^{25}$ are each independently selected from methyl, ethyl, propyl, isopropyl, butyl, and t-butyl. In certain cases of the A ring, both $R^{23}$ and $R^{25}$ are methyl. In certain cases of the A ring, both $R^{23}$ and $R^{25}$ are ethyl. In certain cases of the A ring, both $R^{23}$ and $R^{25}$ are propyl. In certain cases of the A ring, both $R^{23}$ and $R^{25}$ are isopropyl. In some embodiments of the A ring, both $R^{23}$ and $R^{25}$ are ($C_1$-$C_6$)cycloalkyl. In certain cases of the A ring, both $R^{23}$ and $R^{25}$ are cyclopropyl. In certain cases, both $R^{23}$ and $R^{25}$ are cyclobutyl. In certain cases of the A ring, both $R^{23}$ and $R^{25}$ are cyclopentyl. In certain cases of the A ring, both $R^{23}$ and $R^{25}$ are cyclohexyl.

In certain embodiments of the A ring, $R^{23}$ and $R^{40b}$ are each independently selected from optionally substituted ($C_1$-$C_6$)alkyl and optionally substituted cycloalkyl; and $R^{24}$-$R^{26}$ and $R^{40a}$ are each H. In certain cases, both $R^{23}$ and $R^{40b}$ are optionally substituted ($C_1$-$C_6$)alkyl. In certain cases, $R^{23}$ and $R^{40b}$ are each independently selected from methyl, ethyl, propyl, isopropyl, butyl, and t-butyl. In certain cases, both $R^{23}$ and $R^{40b}$ are methyl. In certain cases, both $R^{23}$ and $R^{40b}$ are ethyl. In certain cases, both $R^{23}$ and $R^{40b}$ are propyl. In certain cases, both $R^{23}$ and $R^{40b}$ are isopropyl. In some embodiments, both $R^{23}$ and $R^{40b}$ are ($C_1$-$C_6$)cycloalkyl. In certain cases, both $R^{23}$ and $R^{40b}$ are cyclopropyl. In certain cases, both $R^{23}$ and $R^{40b}$ are cyclobutyl. In certain cases, both $R^{23}$ and $R^{40b}$ are cyclopentyl. In certain cases, both $R^{23}$ and $R^{40b}$ are cyclohexyl.

In certain embodiments of the A ring. $R^{23}$ and $R^{24}$ are each independently selected from optionally substituted ($C_1$-$C_6$) alkyl and optionally substituted cycloalkyl; and $R^{25}$-$R^{26}$, $R^{40a}$ and $R^{40b}$ are each H. In certain cases, both $R^{23}$ and $R^{24}$ are optionally substituted ($C_1$-$C_6$)alkyl. In certain cases, $R^{23}$ and $R^{24}$ are each independently selected from methyl, ethyl, propyl, isopropyl, butyl, and t-butyl. In certain cases, both $R^{23}$ and $R^{24}$ are methyl. In certain cases, both $R^{23}$ and $R^{24}$ are ethyl. In certain cases, both $R^{23}$ and $R^{24}$ are propyl. In certain cases, both $R^{23}$ and $R^{25}$ are isopropyl. In some embodiments, both $R^{23}$ and $R^{24}$ are ($C_1$-$C_6$)cycloalkyl. In certain cases, both $R^{23}$ and $R^{24}$ are cyclopropyl. In certain cases, both $R^{23}$ and $R^{24}$ are cyclobutyl. In certain cases, both $R^{23}$ and $R^{24}$ are cyclopentyl. In certain cases, both $R^{23}$ and $R^{24}$ are cyclohexyl.

In certain embodiments of the A ring, $R^{23}$ and $R^{24}$ together with the carbon atom to which they are attached are cyclically linked to form a carbocycle; and $R^{25}$-$R^{26}$, $R^{40a}$ and $R^{40b}$ are each H. In some embodiments, $R^{23}$ and $R^{24}$ together with the carbon atom to which they are attached are cyclically linked to form a ($C_1$-$C_6$)cycloalkyl. In certain cases, $R^{23}$ and $R^{24}$ together with the carbon atom to which they are attached are cyclically linked to form a cyclopropyl. In certain cases, $R^{23}$ and $R^{24}$ together with the carbon atom to which they are attached are cyclically linked to form a cyclobutyl. In certain cases, $R^{23}$ and $R^{24}$ together with the carbon atom to which they are attached are cyclically linked to form a cyclopentyl. In certain cases, $R^{23}$ and $R^{24}$ together with the carbon atom to which they are attached are cyclically linked to form a cyclohexyl.

In some embodiments of formula (Ia)-(Id) when any of $R^4$-$R^{4d}$ is:

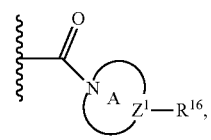

the A ring is selected from:

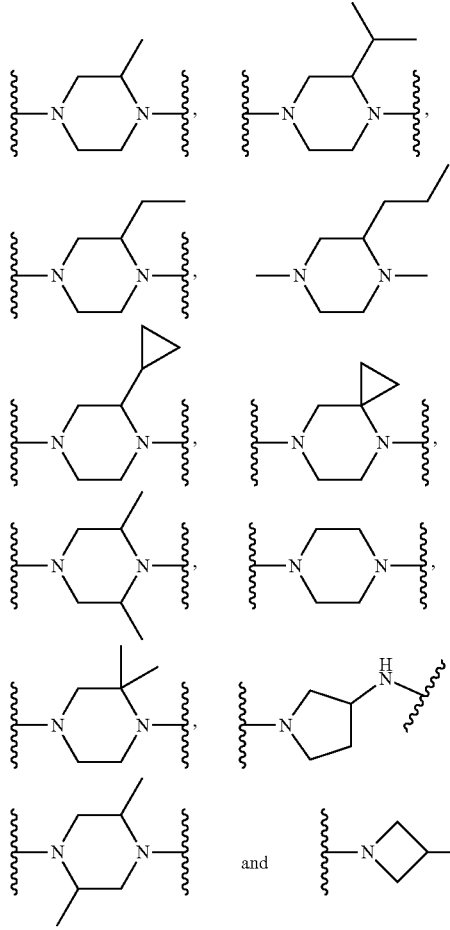

In some embodiments, $R^{16}$ is selected from H, halogen, $-OR^{22a}$, $-C(O)R^{22b}$, $-CO_2R^{22c}$, and $-C(O)NR^{50}R^{60}$, $-NR^{50}R^{60}$, optionally substituted aryl, optionally substituted heteroaryl, optionally substituted carbocycle, optionally substituted heterocycle, optionally substituted $(C_1-C_5)$ alkyl, and optionally substituted $(C_1-C_5)$alkoxy, where $R^{22a}$, $R^{22b}$, $R^{22c}$, $R^{50}$, and $R^{60}$ are as defined above.

In some embodiments of formula (Ia)-(Id) when any of $R^4$-$R^{4d}$ is:

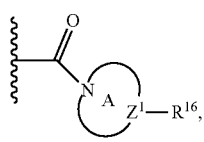

the A ring is selected from:

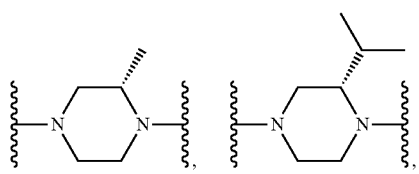

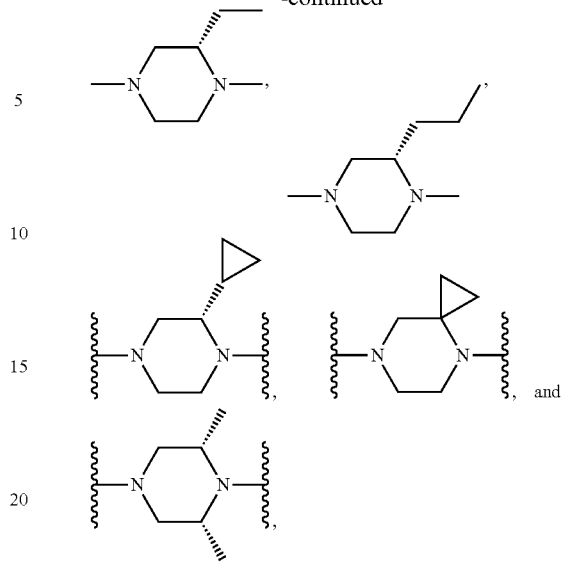

where $R^{16}$ is as defined above.

In some embodiments of formula (Ia)-(Id) any of $R^4$-$R^{4d}$ is

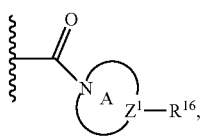

wherein $R^{16}$ is:
$-(R^{110})_nR^{210}$ wherein:
each $R^{110}$ is independently selected from optionally substituted $(C_1-C_6)$alkyl,

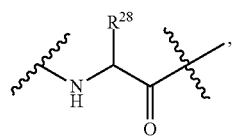

$-C(O)(R^{110a})n^1$, $-C(O)O(R^{110b})n^2$, $-S(O)(R^{110c})n^3$, $-SO_2(R^{110d})n^4$, and $-C(O)NR^{27}(R^{110e})n^5$; where $R^{110a}$-$R^{110e}$ are each independently optionally substituted $(C_1-C_6)$ alkyl

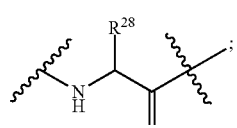

$R^{27}$-$R^{28}$ are each independently selected from H and optionally substituted $(C_1-C_6)$alkyl; and n-$n^5$ are each independently 0 to 3; and $R^{210}$ is selected from optionally substituted aryl, optionally substituted heteroaryl, optionally substituted carbocycle and optionally substituted heterocycle.

In some embodiments, $R^{110}$ is selected from —C(O)—, —C(O)O—, —C(O)NH—, —S(O)—, and —SO$_2$—; and $R^{210}$ is selected from optionally substituted aryl and optionally substituted heteroaryl. In certain embodiments, $R^{110}$ is —C(O)— and $R^{210}$ is optionally substituted aryl. In certain embodiments, $R^{110}$ is —C(O)O— and $R^{210}$ is optionally substituted aryl. In certain embodiments, $R^{110}$ is —C(O)NH— and $R^{210}$ is optionally substituted aryl. In certain embodiments, $R^{110}$ is —S(O)— and $R^{210}$ is optionally substituted aryl. In certain embodiments, $R^{110}$ is —SO$_2$— and $R^{210}$ is optionally substituted aryl. In certain embodiments, $R^{110}$ is —C(O)— and $R^{210}$ is optionally substituted heteroaryl. In certain embodiments, $R^{110}$ is —C(O)O— and $R^{210}$ is optionally substituted heteroaryl. In certain embodiments, $R^{110}$ is —C(O)NH— and $R^{210}$ is optionally substituted heteroaryl. In certain embodiments, $R^{110}$ is —S(O)— and $R^{210}$ is optionally substituted heteroaryl. In certain cases, $R^{110}$ is —SO$_2$— and $R^{210}$ is optionally substituted heteroaryl.

In some embodiments, $R^{210}$ is selected from:

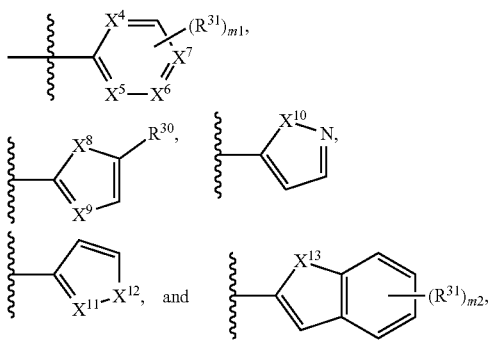

wherein:

$X^4$-$X^7$, $X^9$, and $X^{11}$ are each independently selected from CH, CR$^{31}$, S, O, and N;

$X^8$, $X^{10}$, $X^{12}$ and $X^{13}$ are each independently selected from S, O, and NR$^{29}$;

$R^{29}$ is selected from H and optionally substituted (C$_1$-C$_6$) alkyl;

$R^{30}$-$R^{32}$ are each independently selected from H, halogen, OH, NO$_2$, OCF$_3$, CF$_3$, optionally substituted amino, optionally substituted (C$_1$-C$_6$)alkyl, optionally substituted (C$_1$-C$_6$) alkoxy, optionally substituted cycloalkyl, optionally substituted aryl, optionally substituted heteroaryl, and optionally substituted heterocycle; and $m^1$-$m^2$ are each independently 0 to 5.

In some embodiments, $R^{210}$ is

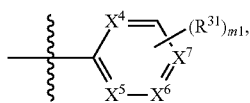

where $X^4$-$X^7$ are each independently selected from CH, CR$^{31}$, S, O, and N. In some embodiments, $R^{210}$ is

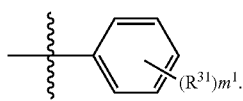

In some embodiments, $R^{210}$ is

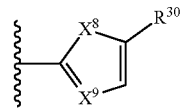

where $X^9$ is selected from CH, CR$^{31}$, S, O, and N; and $X^8$ is selected from S, O, and NR$^{29}$. In some cases, $R^{29}$ is methyl. In some embodiments of $R^{210}$ is $X^9$ is CH, CR$^{31}$, S, O, and N; and $X^8$ is selected from S, O, and NR$^{29}$. In some cases, $X^9$ is CH, and $X^8$ is S. In some cases, $R^{30}$ is H. In some cases, $R^{30}$ is methyl. In some embodiments, $X^9$ is CH, $X^8$ is S, and $R^{30}$ is H. In some cases, $X^9$ is CH, $X^8$ is NR$^{29}$, and $R^{30}$ is H. In some cases, $X^9$ is CH, and $X^8$ is NH. In some cases, $X^9$ is CH, $X^8$ is O and $R^{30}$ is (C$_1$-C$_6$)alkyl. In some cases, $X^9$ is CH, $X^8$ is O and $R^{30}$ is methyl.

In some embodiments, $R^{210}$ is

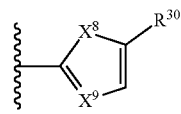

where $X^9$ is N, and $X^8$ is selected from S, O, and NR$^{29}$. In some cases, $X^8$ is NR$^{29}$. In some cases, $R^{29}$ is H. In some cases, $R^{29}$ is methyl. In some cases, $X^8$ is O. In some cases, $X^8$ is S.

In some embodiments, $R^{210}$ is

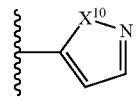

where $X^{10}$ is selected from S, O, and NR$^{29}$. In some cases, $X^{10}$ is O. In some cases, $X^{10}$ is S. In some cases, $X^{10}$ is NR$^{29}$ where $R^{29}$ is (C$_1$-C$_6$)alkyl. In some cases, $R^{29}$ is H. In some cases, $R^{29}$ is methyl.

In some embodiments, $R^{210}$ is

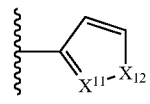

where $X^{11}$ is selected from CH, CR$^{31}$, S, O, and N, and $X^{12}$ is selected from S, O, and NR$^{29}$. In some cases, $X^{11}$ is N. In some cases, $X^{12}$ is O or S. In some cases, $X^{11}$ is N, and $X^{12}$ is O. In some cases, $X^1$ is N, and $X^{12}$ is S.

In some embodiments, $R^{210}$ is

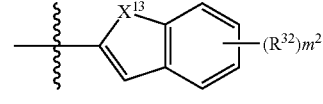

where $X^{13}$ is selected from S, O, and NR$^{29}$. In some cases, $X^{13}$ is NR$^{29}$. In some cases, $R^{29}$ is H. In some cases, $R^{29}$ is methyl. In some cases, $X^{13}$ is S. In some cases, $X^{13}$ is O.

In some embodiments of formula (Ia)-(Id), any of $R^4$-$R^{4d}$ is selected from:
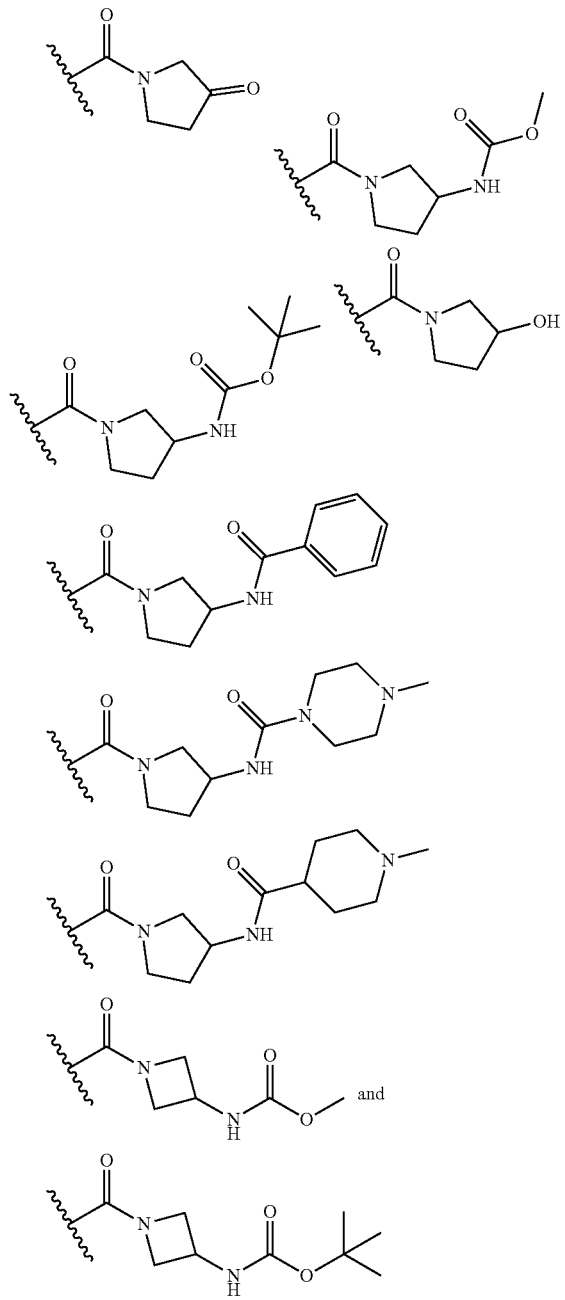
In some embodiments of formula (Ia)-(Id), any of $R^4$-$R^{4d}$ is selected from:
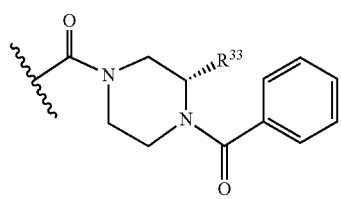
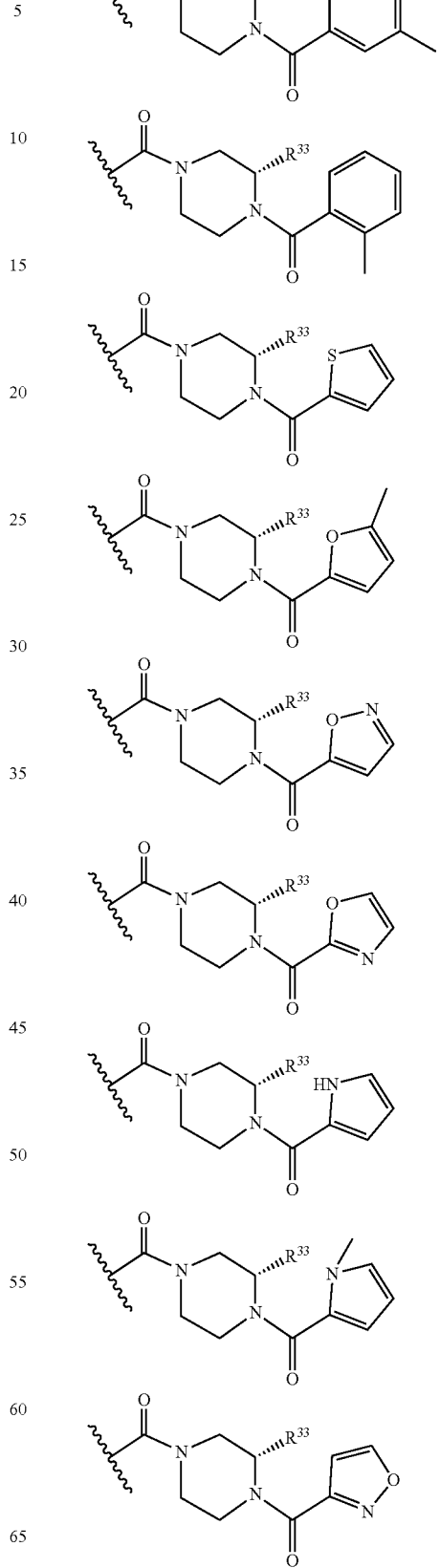

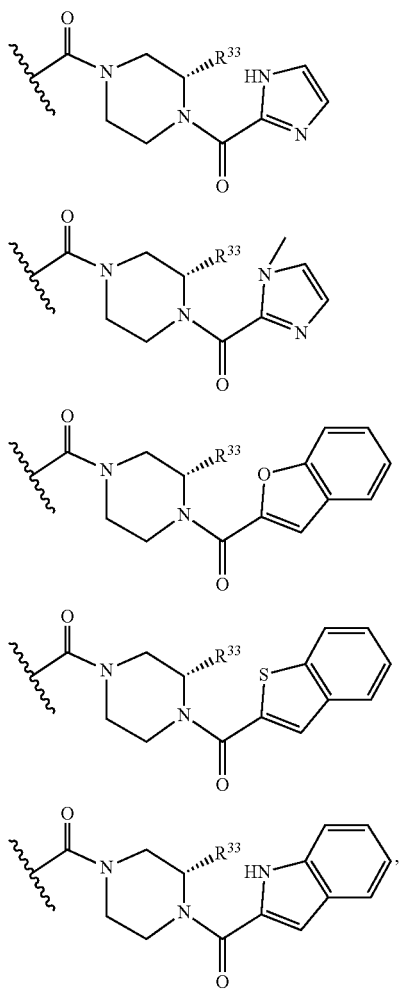

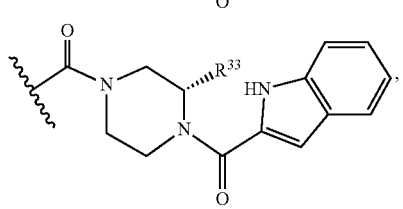

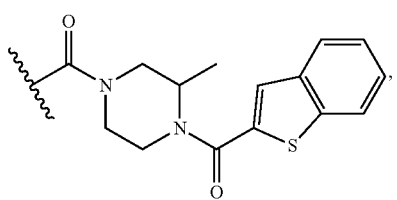

wherein:

each $R^{33}$ is independently selected from optionally substituted $(C_1-C_6)$alkyl and optionally substituted cycloalkyl. In certain cases, each $R^{33}$ is independently selected from methyl, ethyl, propyl, isopropyl, butyl, and t-butyl. In certain cases, each $R^{33}$ is methyl. In certain cases, each $R^{33}$ is ethyl. In certain cases, each $R^{33}$ is propyl. In certain cases, each $R^{33}$ is isopropyl. In some embodiments, each $R^{33}$ is independently selected from $(C_1-C_6)$cycloalkyl. In certain cases, each $R^{33}$ is cyclopropyl. In certain cases, each $R^{33}$ is cyclobutyl. In certain cases, each $R^{33}$ is cyclopentyl. In certain cases, each $R^{33}$ is cyclohexyl.

In some embodiments of formula (Ia)-(Id), any of $R^4$-$R^{4d}$ is selected from:

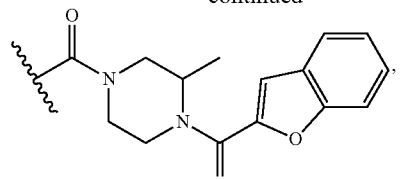

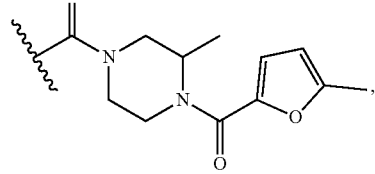

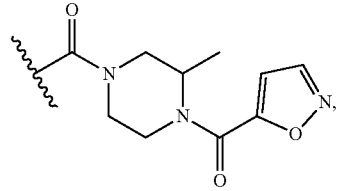

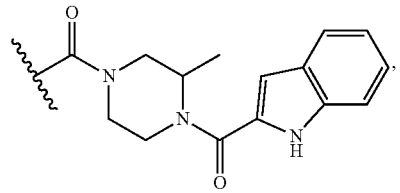

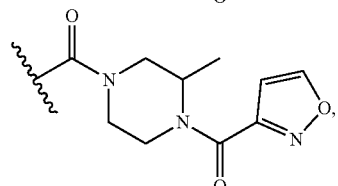

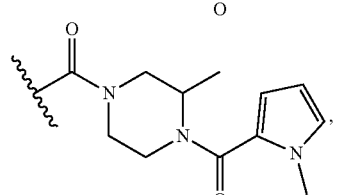

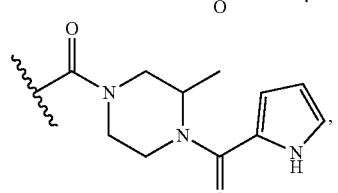

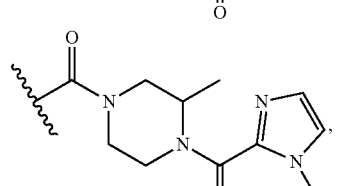

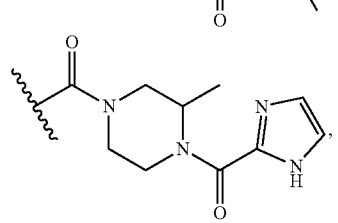

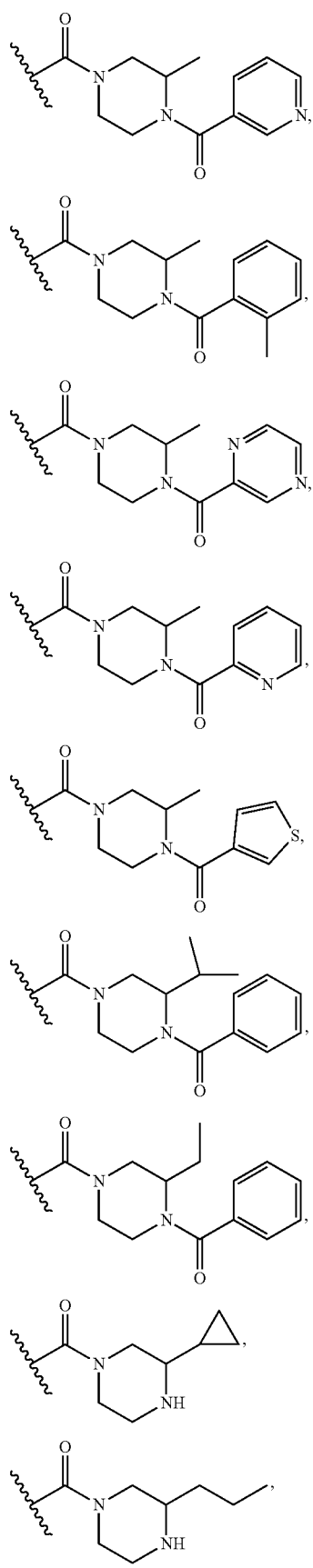
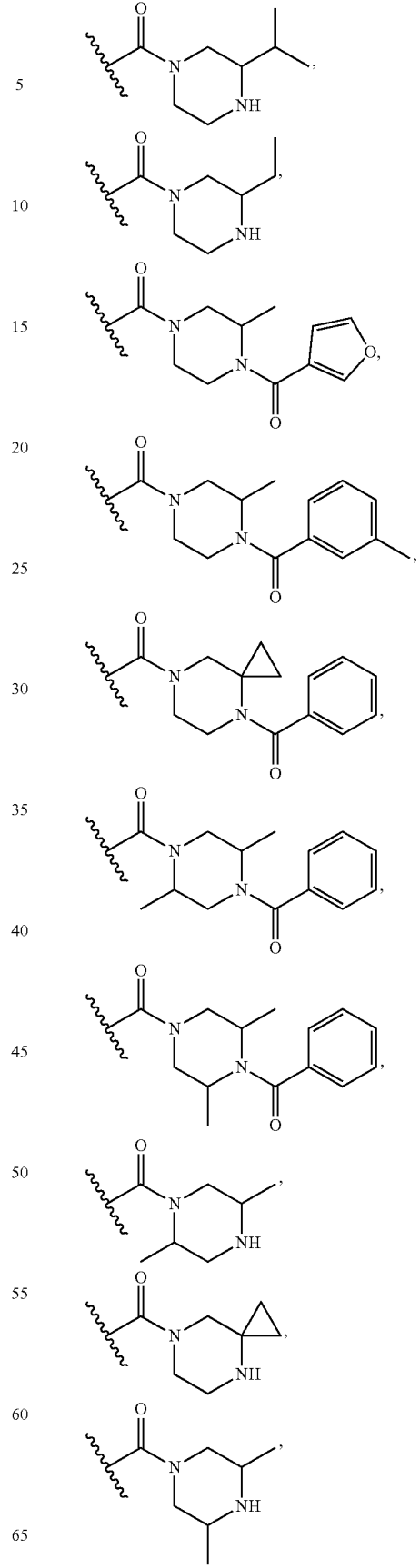

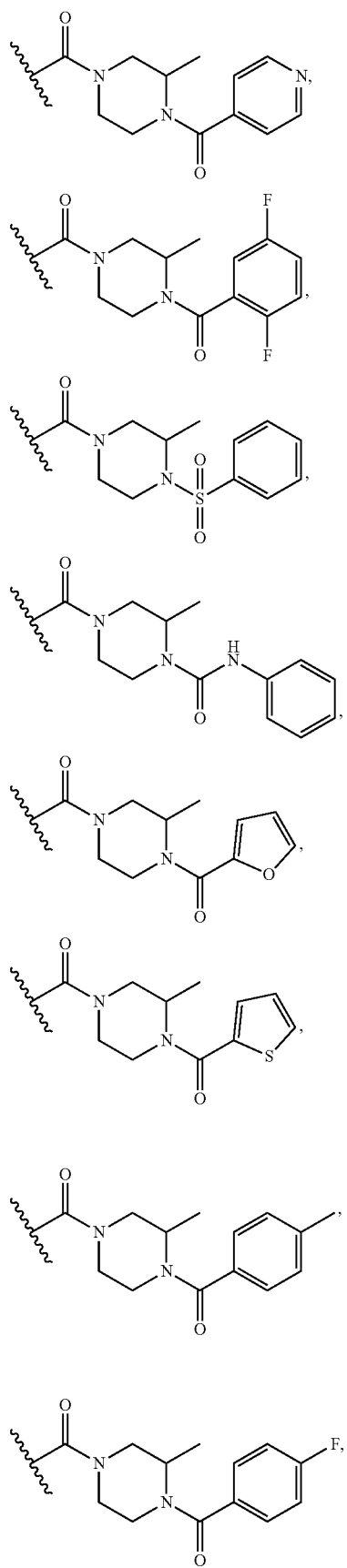
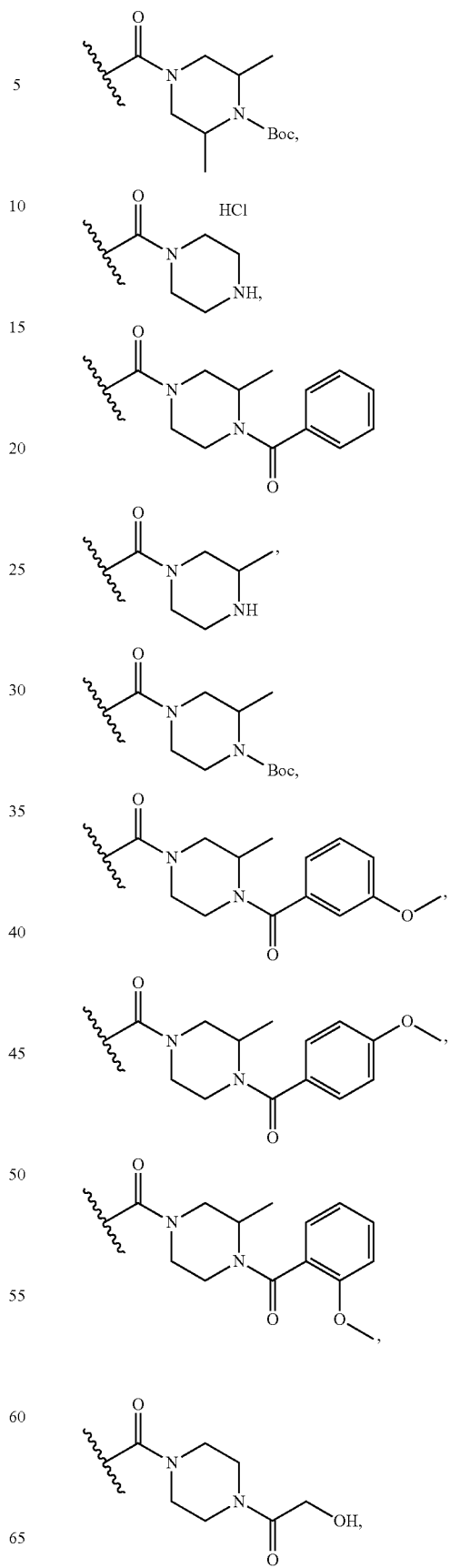

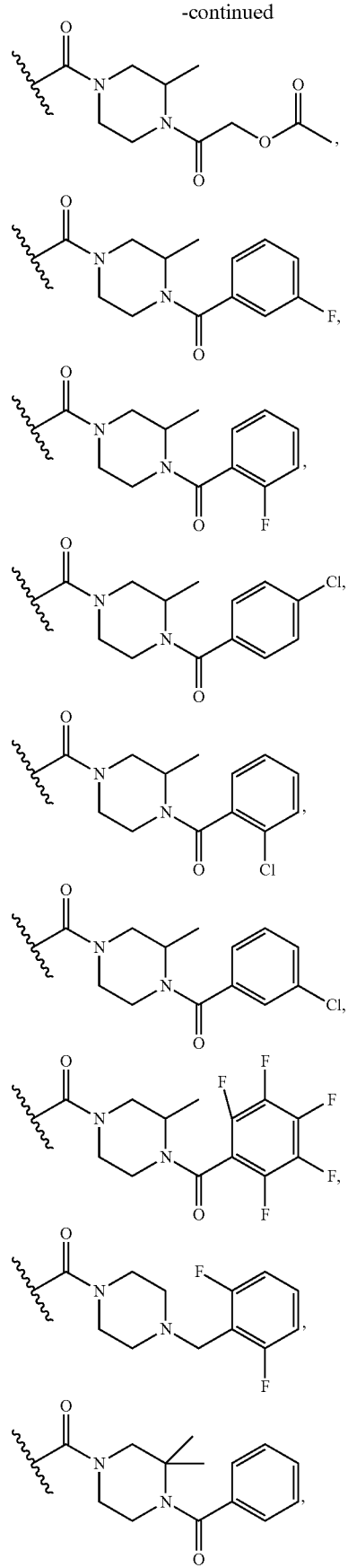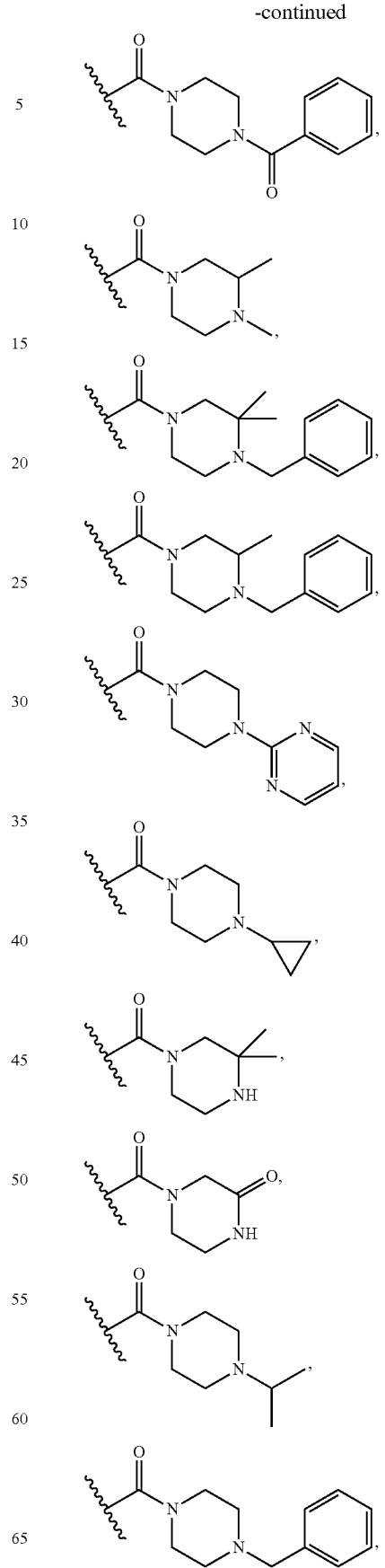

-continued

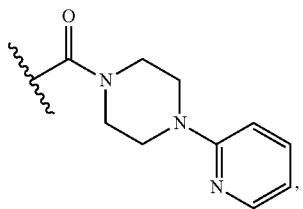

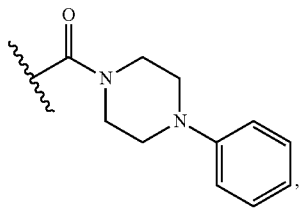

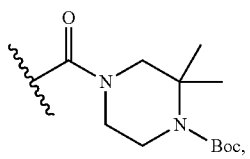

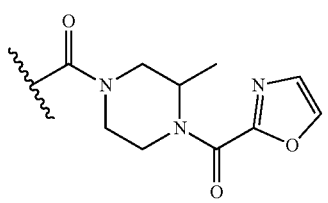

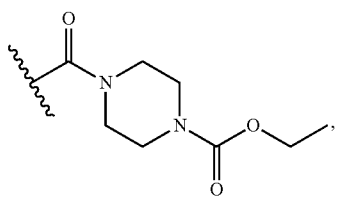

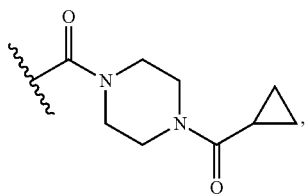

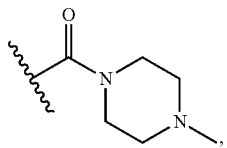

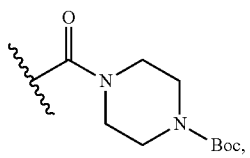

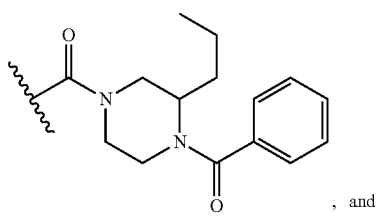
, and

-continued

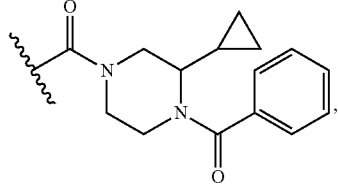

In some embodiments of formula (Ia)-(Id), any of $R^4$-$R^{4d}$ is

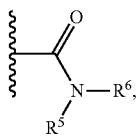

$R^5$ is H or Me, and $R^6$ is selected from:

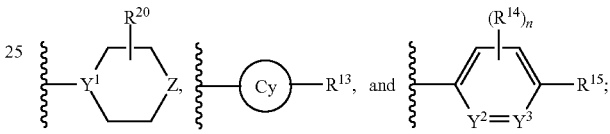

wherein:
$Y^1$, $Y^2$, and $Y^3$ are independently selected from $CR^{14}$ and N;
Z is selected from O, S, $CHR^{11}$, and $NR^{12}$;
n is 0 to 4;
$R^{11}$ is selected from H, $NH_2$, CN, $CH_2NH_2$, $NO_2$, halogen, $OR^{2a}$, $C(O)R^{2b}$, $CO_2R^{2c}$, $C(O)NR^5R^6$, optionally substituted amino, optionally substituted ($C_1$-$C_5$)alkyl, and optionally substituted ($C_1$-$C_5$)alkoxy, and optionally substituted heterocycle;
$R^{12}$ is selected from H, $NH_2$, halogen, $C(O)R^{2d}$, $CO_2R^{2e}$, $C(O)NR^5R^6$, and optionally substituted ($C_1$-$C_5$)alkyl;

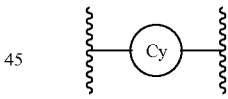

is selected from optionally substituted ($C_1$-$C_6$)alkyl-cycloalkyl, optionally substituted heterocycloalkyl, optionally substituted monocyclic or bicyclic ($C_4$-$C_{10}$)carbocycle, and optionally substituted monocyclic or bicyclic ($C_4$-$C_{10}$)heterocycle;
$R^{13}$ is selected from H, $NH_2$, CN, $CH_2NH_2$, $NO_2$, halogen, $OR^{2f}$, $C(O)R^{2g}$, $CO_2R^{2h}$, $C(O)NR^5R^6$, $NR^5R^6$, optionally substituted ($C_1$-$C_5$)alkyl, and optionally substituted ($C_1$-$C_5$)alkoxy, and optionally substituted heterocycle;
$R^{14}$ is selected from H, OH, $NH_2$, CN, $CF_3$, $OCF_3$, $CH_2NH_2$, halogen, optionally substituted ($C_1$-$C_5$)alkyl, optionally substituted ($C_1$-$C_5$)alkoxy, optionally substituted cycloalkyl, optionally substituted heterocycloalkyl, optionally substituted carbocycle, and optionally substituted heterocycle;
$R^{15}$ is selected from H, halogen, $NHC(O)R^{2i}$, $OR^{2j}$, $C(O)R^{2k}$, $OC(O)R^{2l}$, $CO_2R^{2m}$, $C(O)NR^5R^6$, $NR^5R^6$, optionally substituted ($C_1$-$C_5$)alkyl, optionally substituted ($C_1$-$C_5$) alkoxy, optionally substituted cycloalkyl, and optionally substituted heterocycle;

$R^{20}$ is selected from H, halogen, optionally substituted $(C_1-C_5)$alkyl, optionally substituted $(C_1-C_5)$alkoxy, optionally substituted carbocycle, and optionally substituted heterocycle; and $R^{2a}$-$R^{2m}$ are independently selected from H, optionally substituted $(C_1-C_{10})$ alkyl, optionally substituted cycloalkyl, optionally substituted aryl, optionally substituted heteroaryl, and optionally substituted heterocycle, and the optional substituents on alkyl, cycloalkyl, aryl, heteroaryl, and heterocycle are independently selected from: H, OH, $NH_2$, $NO_2$, $OCF_3$, $CF_3$, -halogen, heterocycle, heteroaryl, optionally substituted amino, optionally substituted $(C_1-C_5)$alkyl, and optionally substituted $(C_1-C_5)$alkoxy.

In some embodiments, $R^6$ is selected from:

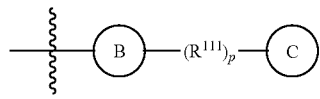

wherein:
ring B and ring C are each independently selected from optionally substituted aryl, optionally substituted heteroaryl, optionally substituted carbocycle and optionally substituted heterocycle;
each $R^{111}$ is independently selected from optionally substituted $(C_1-C_6)$alkyl,

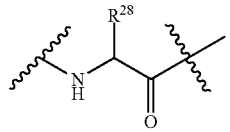

—C(O)($R^{111a}$)p$^1$, —C(O)O($R^{111b}$)p$^2$, —S(O)($R^{111c}$)p$^3$, —SO$_2$($R^{111d}$)p$^4$, and —C(O)NR$^{27}$($R^{111e}$)p$^5$; where $R^{111a}$-$R^{111e}$ are each independently optionally substituted $(C_1-C_6)$ alkyl,

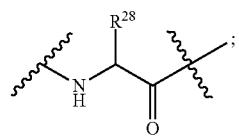

$R^{27}$-$R^{28}$ are each independently selected from H and optionally substituted $(C_1-C_6)$alkyl; and
p-p$^5$ are each independently 0 to 3.

In some embodiments of $R^6$, $R^{111}$ is selected from —C(O)—, —C(O)O—, —C(O)NH—, —S(O)—, and —SO$_2$—; and the B ring and the C ring are independently selected from optionally substituted aryl, optionally substituted carbocycle, optionally substituted heteroaryl and optionally substituted heterocycle. In certain embodiments, $R^{111}$ is —C(O)— and one or both of the B ring and the C ring is optionally substituted aryl. $R^{111}$ is —C(O)O— and one or both of the B ring and the C ring is optionally substituted aryl. $R^{111}$ is —C(O)NH— and one or both of the B ring and the C ring is optionally substituted aryl. $R^{111}$ is —S(O)— and one or both of the B ring and the C ring is optionally substituted aryl. In certain embodiments, $R^{111}$ is —SO$_2$— and one or both of the B ring and the C ring is optionally substituted aryl. In certain embodiments, $R^{111}$ is —C(O)— and one or both of the B ring and the C ring is optionally substituted carbocycle. $R^{111}$ is —C(O)O— and one or both of the B ring and the C ring is optionally substituted carbocycle. $R^{111}$ is —C(O)NH— and one or both of the B ring and the C ring is optionally substituted carbocycle. $R^{111}$ is —S(O)— and one or both of the B ring and the C ring is optionally substituted carbocycle. In certain embodiments, $R^{111}$ is —SO$_2$— and one or both of the B ring and the C ring is optionally substituted carbocycle. In certain embodiments, $R^{111}$ is —C(O)— and one or both of the B ring and the C ring is optionally substituted heteroaryl. $R^{111}$ is —C(O)O— and one or both of the B ring and the C ring is optionally substituted heteroaryl. $R^{111}$ is —C(O)NH— and one or both of the B ring and the C ring is optionally substituted heteroaryl. $R^{111}$ is —S(O)— and one or both of the B ring and the C ring is optionally substituted heteroaryl. In certain cases, $R^{111}$ is —SO$_2$— and one or both of the B ring and the C ring is optionally substituted heteroaryl. In certain embodiments, $R^{111}$ is —C(O)— and one or both of the B ring and the C ring is optionally substituted heterocycle. $R^{111}$ is —C(O)O— and one or both of the B ring and the C ring is optionally substituted heterocycle. $R^{111}$ is —C(O)NH— and one or both of the B ring and the C ring is optionally substituted heterocycle. $R^{111}$ is —S(O)— and one or both of the B ring and the C ring is optionally substituted heterocycle. In certain cases, $R^{111}$ is —SO$_2$— and one or both of the B ring and the C ring is optionally substituted heterocycle.

In certain embodiments, one or both of the B ring and the C ring are optionally substituted piperazine. In certain cases, the B ring is optionally substituted piperazine and the C ring is selected from optionally substituted aryl, optionally substituted heteroaryl, optionally substituted carbocycle and optionally substituted heterocycle. In certain cases, the C ring is optionally substituted piperazine and the B ring is selected from optionally substituted aryl, optionally substituted heteroaryl, optionally substituted carbocycle and optionally substituted heterocycle. In certain cases, both the B and the C rings are piperazine.

In some embodiments, $R^6$ is

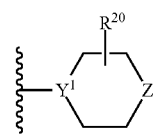

and is selected from:

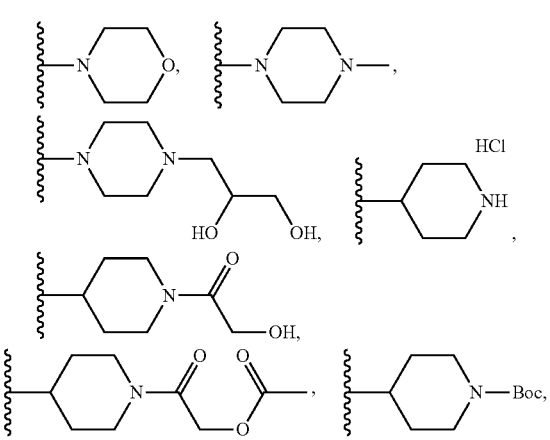

-continued

-continued

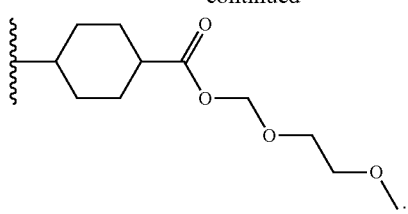

In some embodiments, $R^6$ is

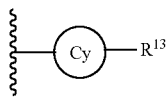

and is selected from:

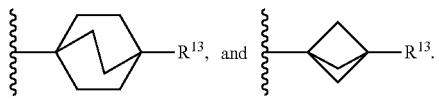

In certain embodiments, $R^{13}$ is —C(O)OR$^{41a}$, —NHC(O)R$^{41b}$, —C(O)NHR$^{41c}$, C(O)R$^{41d}$, C(O)NH$_2$, heterocycle, wherein $R^{41a}$-$R^{41d}$ are independently selected from H, optionally substituted (C$_1$-C$_6$)alkyl, optionally substituted heterocycle (e.g., morpholine, piperidine, morpholine-3-one), and optionally substituted (C$_1$-C$_6$)alkyl-heterocycle.

In some embodiments, $R^{13}$ is selected from:

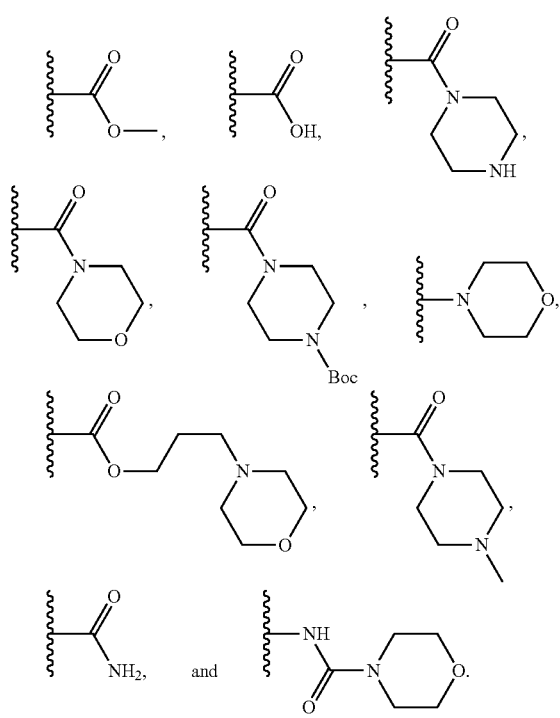

In some embodiments, $R^6$ is

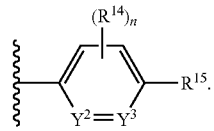

In another embodiment, $Y^2$ and $Y^3$ are each CR$^{14}$. In another embodiment, each $R^{14}$ is independently selected from H, OH, NH$_2$, CN, CF$_3$, OCF$_3$, CH$_2$NH$_2$, halogen, —C(O)R$^{42f}$, —OC(O)R$^{42g}$, optionally substituted (C$_1$-C$_5$)alkyl, and optionally substituted (C$_1$-C$_5$)alkoxy, wherein $R^{42f}$ to $R^{42g}$ are independently selected from —OH, optionally substituted amino, optionally substituted (C$_1$-C$_6$)alkyl, optionally substituted cycloalkyl, optionally substituted (C$_1$-C$_{10}$)alkoxy, optionally substituted heterocycle (e.g., piperazine, pyrrolidine, azetidine, piperidine, or morpholine), optionally substituted —O—(C$_1$-C$_6$)alkyl-heterocycle, and amino acid. In another embodiment, $R^{15}$ is selected from H, halogen, —OC(O)R$^{42a}$, —C(O)R$^{42b}$, —C(O)NHR$^{42c}$, R$^{42d}$ or —OR$^{42e}$, wherein $R^{42a}$ to $R^{42e}$ are independently selected from —OH, optionally substituted amino, optionally substituted (C$_1$-C$_6$)alkyl, optionally substituted cycloalkyl, optionally substituted (C$_1$-C$_{10}$)alkoxy, optionally substituted heterocycle (e.g., piperazine, pyrrolidine, azetidine, piperidine, or morpholine), optionally substituted —O—(C$_1$-C$_6$)alkyl-heterocycle, and amino acid. In some embodiments of $R^6$, where n is 1 or greater, one $R^{14}$ group is —C(O)R$^{42f}$, wherein $R^{42f}$ is selected from optionally substituted heterocycle (e.g., piperazine, pyrrolidine, azetidine, piperidine, ormorpholine), and optionally substituted (C$_1$-C$_{10}$)alkoxy (e.g., —OCH$_3$). In some embodiments of $R^6$, $R^{15}$ is —C(O)R$^{42b}$, wherein $R^{42b}$ is selected from optionally substituted heterocycle (e.g., piperazine, pyrrolidine, azetidine, piperidine, or morpholine), and optionally substituted (C$_1$-C$_{10}$)alkoxy (e.g., —OCH$_3$).

In some embodiments, $R^6$ is selected from:

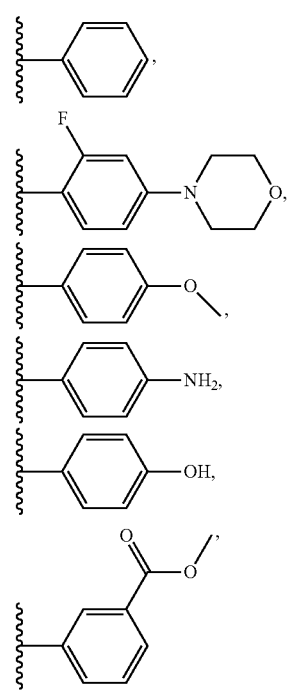

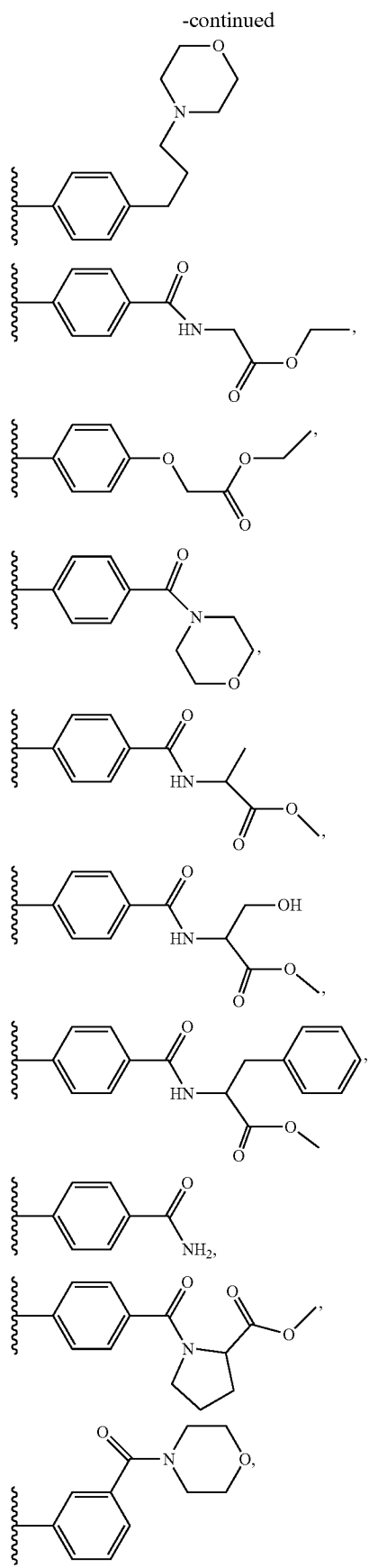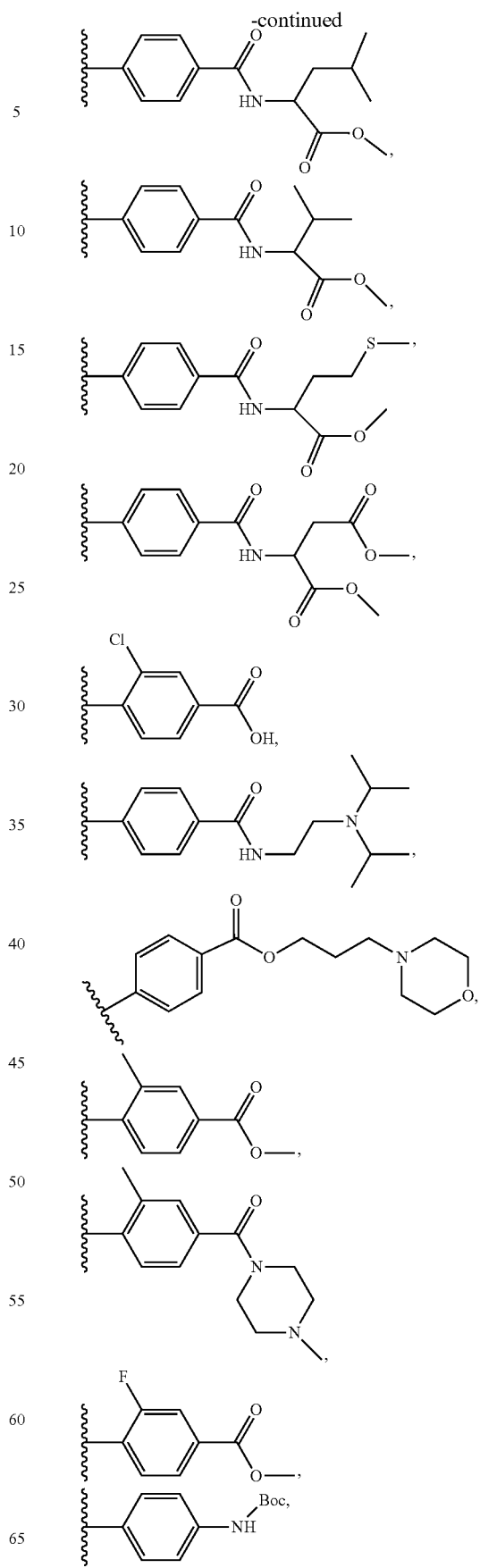

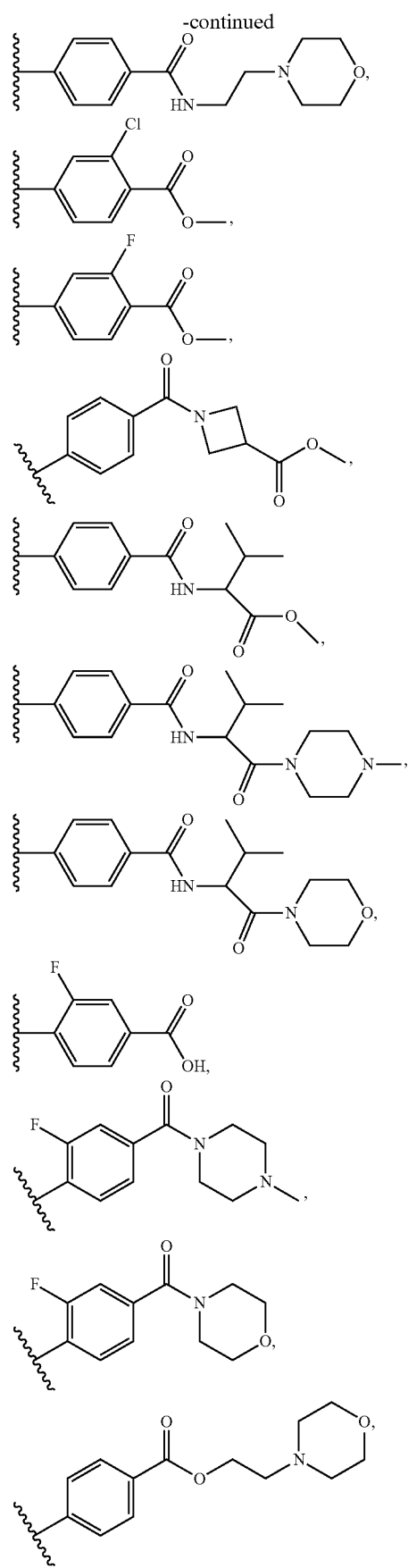
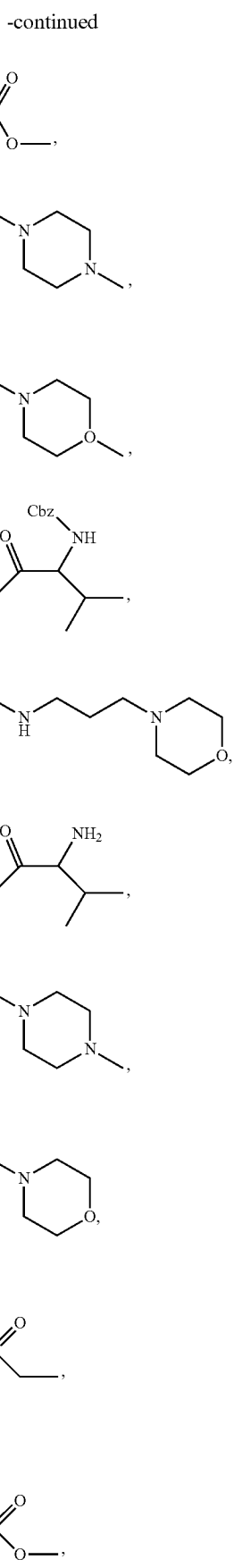

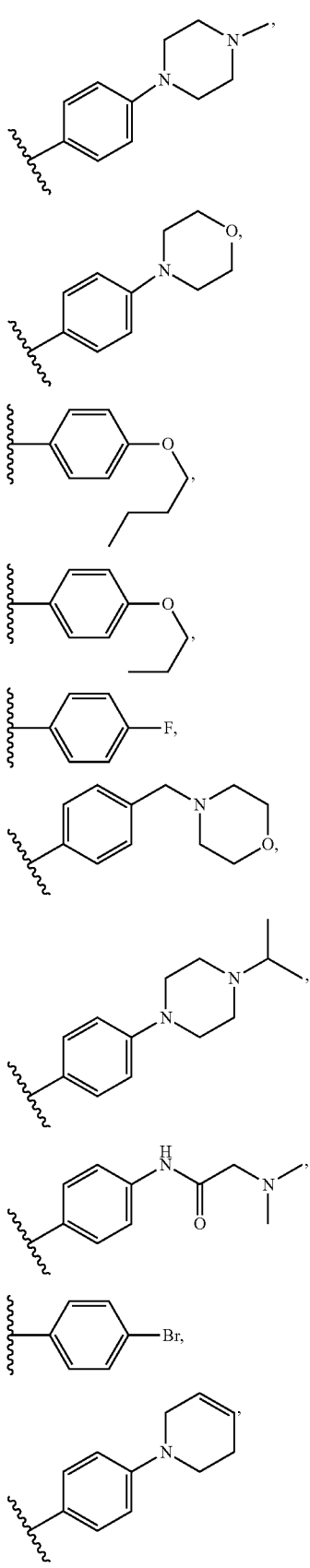

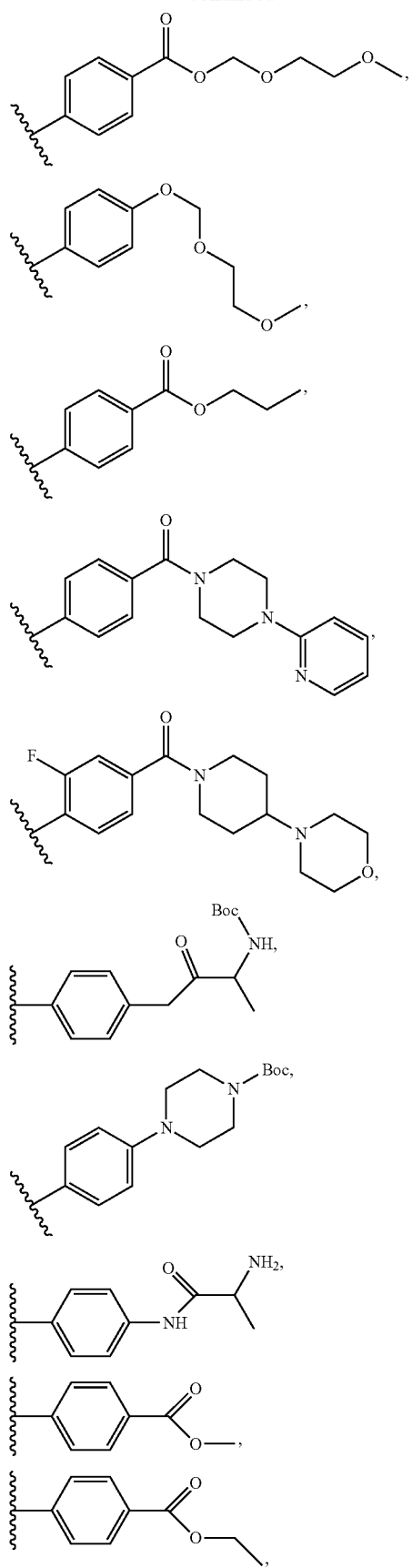
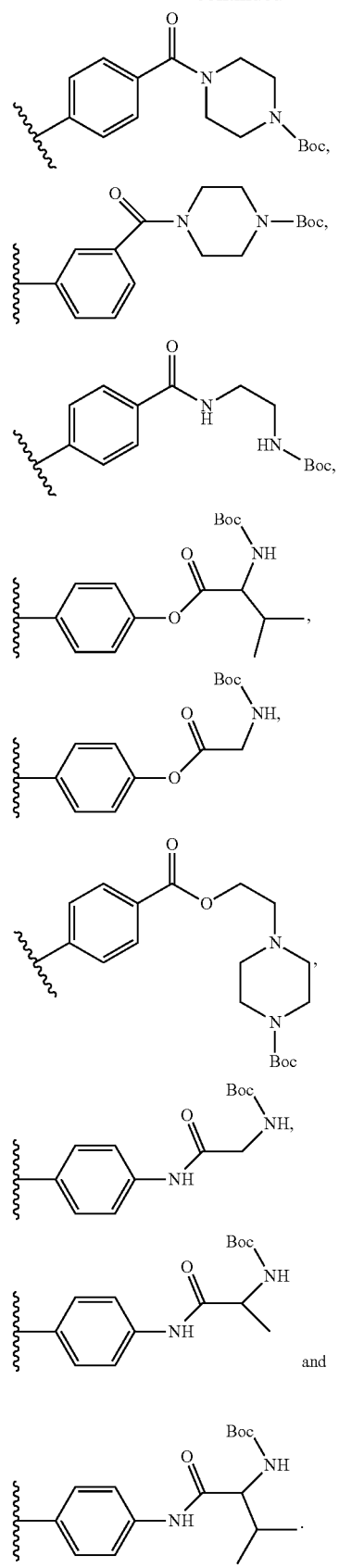

In some embodiments, $R^6$ is

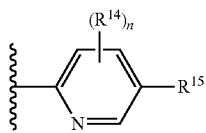

and n is 0 to 3. In another embodiment, $R^6$ is selected from:

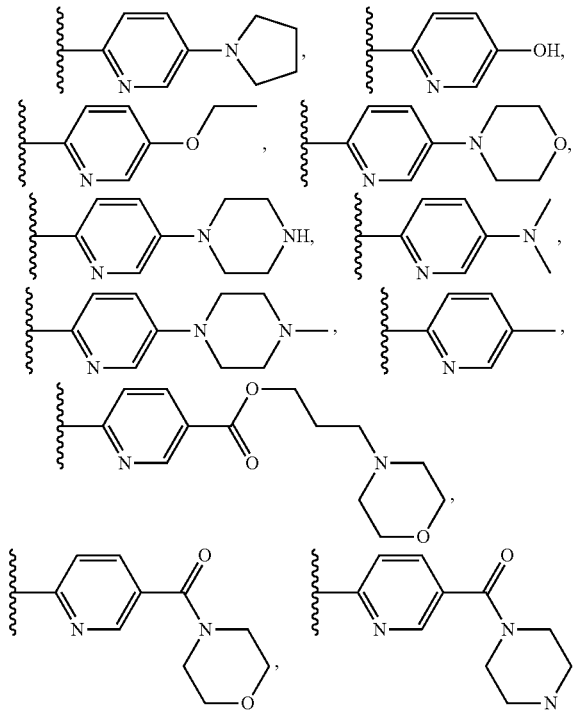

In some embodiments, $R^6$ is

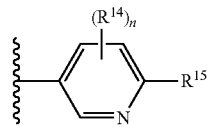

and n is 0 to 3. In some embodiments, $R^{15}$ is H, $C(O)OR^{51}$ or $C(O)R^{51}$, where $R^{51}$ is H or optionally substituted ($C_1$-$C_6$)alkyl, or optionally substituted heterocycle (e.g., morpholine or piperazine). In another embodiment, $R^6$ is selected from:

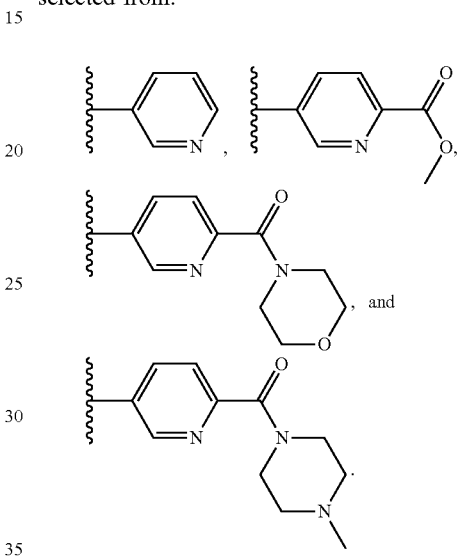

In some embodiments, $R^5$ is H or Me, and $R^6$ is selected from:

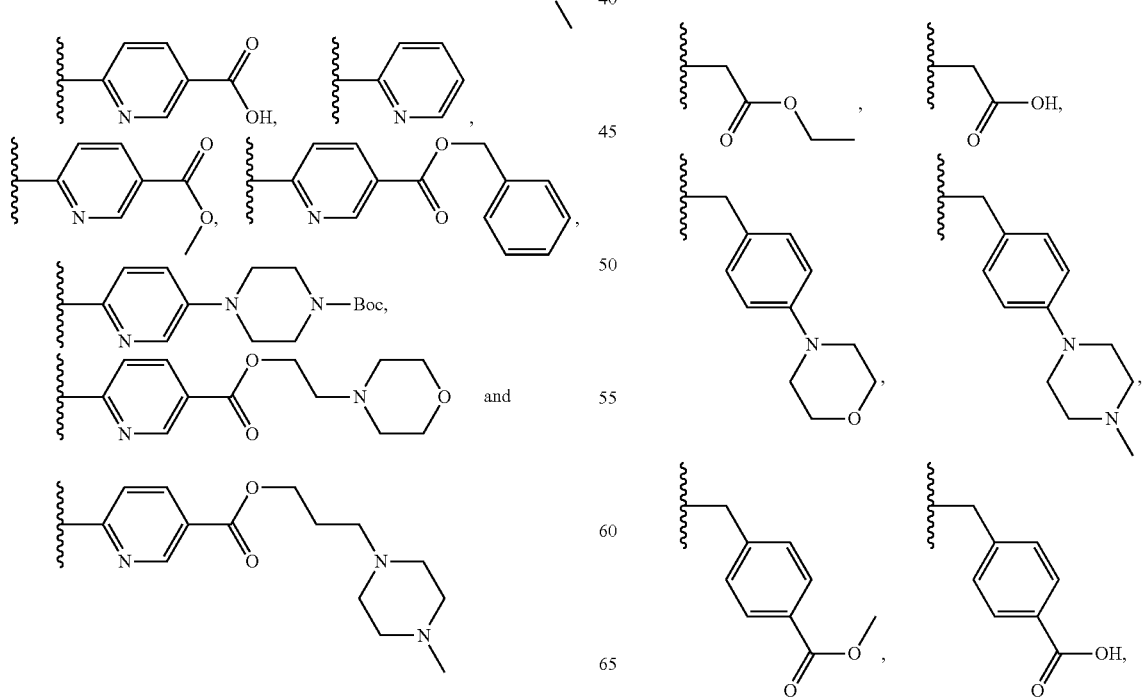

-continued

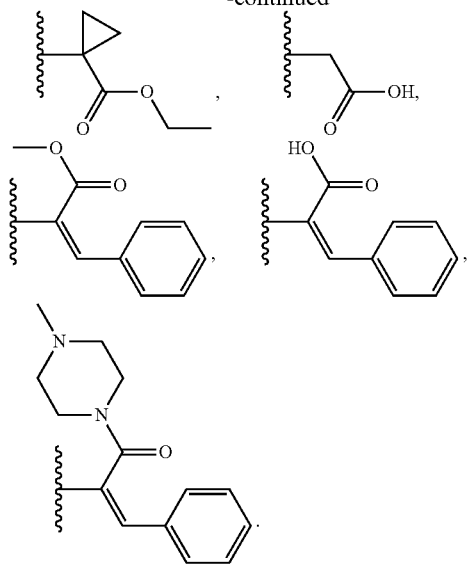

In some embodiments, $R^4$ is

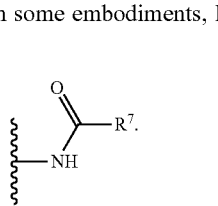

In some embodiments, $R^7$ is selected from optionally substituted N-anilino, optionally substituted phenyl and optionally substituted bicyclic carbocycle.

In some embodiments, $R^7$ is selected from:

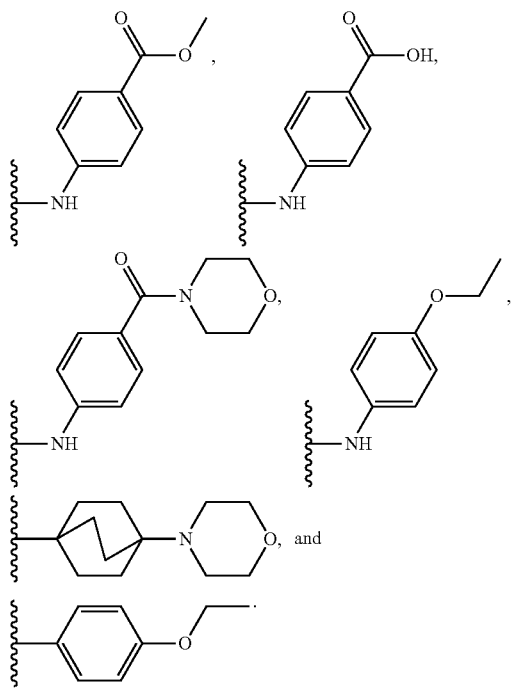

In some embodiments, the compound is of formula (Ie):

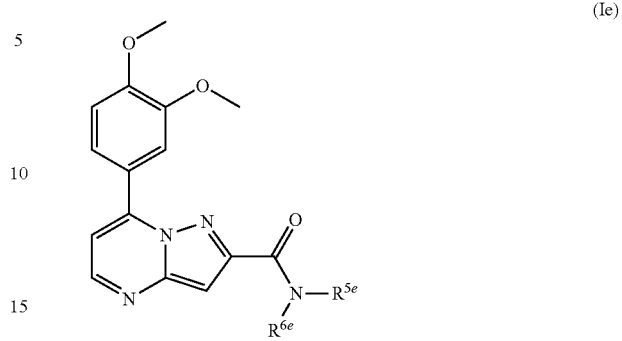

(Ie)

wherein:
$R^{5e}$ and $R^{6e}$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;
or $R^{5e}$ and $R^{6e}$ together with the nitrogen atom to which they are attached are cyclically linked to form an optionally substituted monocyclic or bicyclic heterocycle.

In some embodiments of formula (Ie), $R^{5e}$ is H or Me, and $R^{6e}$ is selected from:

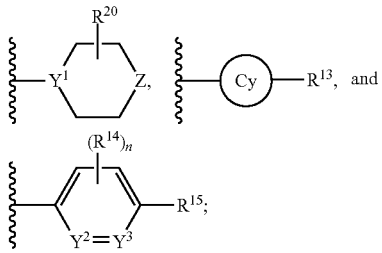

wherein:
$Y^1$, $Y^2$, and $Y^3$ are independently selected from $CR^{14}$ and N;
Z is selected from O, S, $CHR^{11}$, and $NR^{12}$;
n is 0 to 4;
$R^{11}$ is selected from H, $NH_2$, CN, $CH_2NH_2$, $NO_2$, halogen, $OR^2a$, $C(O)R^{2b}$, $CO_2R^{2c}$, $C(O)NR^5R^6$, optionally substituted amino, optionally substituted $(C_1-C_5)$alkyl, and optionally substituted $(C_1-C_5)$alkoxy, and optionally substituted heterocycle;
$R^{12}$ is selected from H, $NH_2$, halogen, $C(O)R^{2d}$, $CO_2R^{2e}$, $C(O)NR^5R^6$, and optionally substituted $(C_1-C_5)$alkyl;

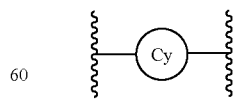

is selected from optionally substituted $(C_1-C_6)$alkyl-cycloalkyl, optionally substituted heterocycloalkyl, optionally substituted monocyclic or bicyclic $(C_4-C_{10})$carbocycle, and optionally substituted monocyclic or bicyclic $(C_4-C_{10})$heterocycle;

$R^{13}$ is selected from H, $NH_2$, CN, $CH_2NH_2$, $NO_2$, halogen, $OR^{2f}$, $C(O)R^{2g}$, $CO_2R^{2h}$, $C(O)NR^5R^6$, $NR^5R^6$, optionally substituted $(C_1$-$C_5)$alkyl, and optionally substituted $(C_1$-$C_5)$alkoxy, and optionally substituted heterocycle;

$R^{14}$ is selected from H, OH, $NH_2$, CN, $CF_3$, $OCF_3$, $CH_2NH_2$, halogen, optionally substituted $(C_1$-$C_5)$alkyl, optionally substituted $(C_1$-$C_5)$alkoxy, optionally substituted cycloalkyl, optionally substituted heterocycloalkyl, optionally substituted carbocycle, and optionally substituted heterocycle;

$R^{15}$ is selected from H, halogen, $NHC(O)R^{2i}$, $OR^{2j}$, $C(O)R^{2k}$, $OC(O)R^{2l}$, $CO_2R^{2m}$, $C(O)NR^5R^6$, $NR^5R^6$ optionally substituted $(C_1$-$C_5)$alkyl, optionally substituted $(C_1$-$C_5)$alkoxy, optionally substituted cycloalkyl, and optionally substituted heterocycle; and $R^{20}$ is selected from H, halogen, optionally substituted $(C_1$-$C_5)$alkyl, optionally substituted $(C_1$-$C_5)$alkoxy, optionally substituted carbocycle, and optionally substituted heterocycle; and $R^{2a}$-$R^{2m}$ are independently selected from H, optionally substituted $(C_1$-$C_{10})$ alkyl, optionally substituted cycloalkyl, optionally substituted aryl, optionally substituted heteroaryl, and optionally substituted heterocycle, and the optional substituents on alkyl, cycloalkyl, aryl, heteroaryl, and heterocycle are independently selected from: H, OH, $NH_2$, $NO_2$, $OCF_3$, $CF_3$, halogen, heterocycle, heteroaryl, optionally substituted amino, optionally substituted $(C_1$-$C_5)$alkyl, and optionally substituted $(C_1$-$C_5)$alkoxy.

In some embodiments, $R^{6e}$ is selected from:

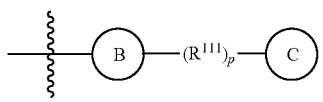

wherein:
ring B and ring C are each independently selected from optionally substituted aryl, optionally substituted heteroaryl, optionally substituted carbocycle and optionally substituted heterocycle;

each $R^{111}$ is independently selected from optionally substituted $(C_1$-$C_6)$alkyl,

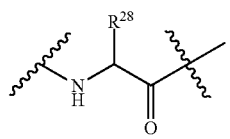

—C(O)$(R^{111a})p^1$, —C(O)O$(R^{111b})p^2$, —S(O)$(R^{111c})p^3$, —SO$_2(R^{111d})p^4$, and —C(O)NR$^{27}(R^{111e})p^5$; where $R^{111a}$-$R^{111e}$ are each independently optionally substituted $(C_1$-$C_6)$ alkyl,

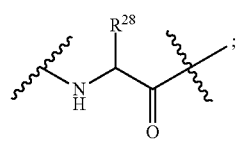

$R^{27}$-$R^{28}$ are each independently selected from H and optionally substituted $(C_1$-$C_6)$alkyl; and
p-p$^5$ are each independently 0 to 3.

In some embodiments of $R^{6e}$, $R^{111}$ is selected from —C(O)—, —C(O)O—, —C(O)NH—, —S(O)— and —SO$_2$—; and the B ring and the C ring are independently selected from optionally substituted aryl, optionally substituted carbocycle, optionally substituted heteroaryl and optionally substituted heterocycle. In certain embodiments, $R^{111}$ is —C(O)— and one or both of the B ring and the C ring is optionally substituted aryl. In certain embodiments, $R^{111}$ is —C(O)O— and one or both of the B ring and the C ring is optionally substituted aryl. In certain embodiments, $R^{111}$ is —C(O)NH— and one or both of the B ring and the C ring is optionally substituted aryl. In certain embodiments, $R^{111}$ is —S(O)— and one or both of the B ring and the C ring is optionally substituted aryl. In certain embodiments, $R^{111}$ is —SO$_2$— and one or both of the B ring and the C ring is optionally substituted aryl. In certain embodiments, $R^{111}$ is —C(O)— and one or both of the B ring and the C ring is optionally substituted carbocycle. In certain embodiments, $R^{111}$ is —C(O)O— and one or both of the B ring and the C ring is optionally substituted carbocycle. $R^{111}$ is —C(O)NH— and one or both of the B ring and the C ring is optionally substituted carbocycle. In certain embodiments, $R^{111}$ is —S(O)— and one or both of the B ring and the C ring is optionally substituted carbocycle. In certain embodiments, $R^{111}$ is —SO$_2$— and one or both of the B ring and the C ring is optionally substituted carbocycle. In certain embodiments, $R^{111}$ is —C(O)— and one or both of the B ring and the C ring is optionally substituted heteroaryl. In certain embodiments, $R^{111}$ is —C(O)O— and one or both of the B ring and the C ring is optionally substituted heteroaryl. In certain embodiments, $R^{111}$ is —C(O)NH— and one or both of the B ring and the C ring is optionally substituted heteroaryl. In certain embodiments, $R^{111}$ is —S(O)— and one or both of the B ring and the C ring is optionally substituted heteroaryl. In certain cases, $R^{111}$ is —SO$_2$— and one or both of the B ring and the C ring is optionally substituted heteroaryl. In certain embodiments, $R^{111}$ is —C(O)— and one or both of the B ring and the C ring is optionally substituted heterocycle. In certain embodiments, $R^{111}$ is —C(O)O— and one or both of the B ring and the C ring is optionally substituted heterocycle. In certain embodiments, $R^{111}$ is —C(O)NH— and one or both of the B ring and the C ring is optionally substituted heterocycle. In certain embodiments, $R^{111}$ is —S(O)— and one or both of the B ring and the C ring is optionally substituted heterocycle. In certain cases, $R^{111}$ is —SO$_2$— and one or both of the B ring and the C ring is optionally substituted heterocycle.

In certain embodiments, one or both of the B ring and the C ring are optionally substituted piperazine. In certain cases, the B ring is optionally substituted piperazine and the C ring is selected from optionally substituted aryl, optionally substituted heteroaryl, optionally substituted carbocycle and optionally substituted heterocycle. In certain cases, the C ring is optionally substituted piperazine and the B ring is selected from optionally substituted aryl, optionally substituted heteroaryl, optionally substituted carbocycle and optionally substituted heterocycle. In certain cases, both the B and the C rings are piperazine.

In some embodiments, $R^{6e}$ is

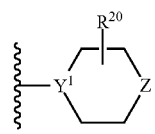

and is selected from:
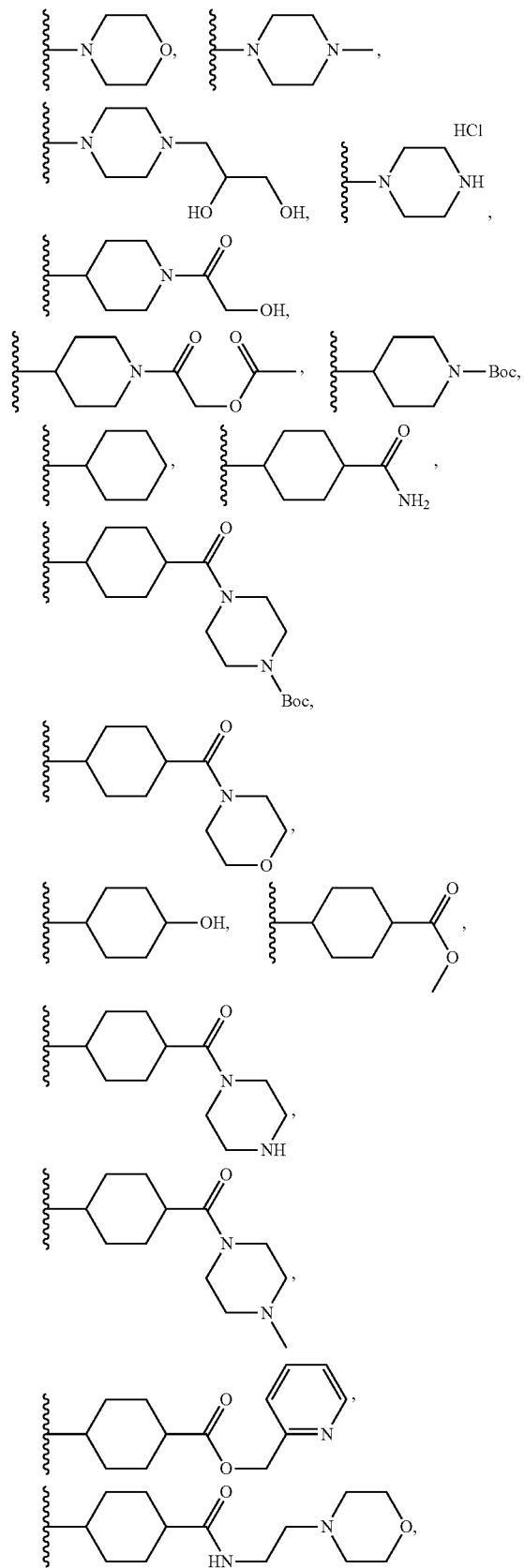
-continued
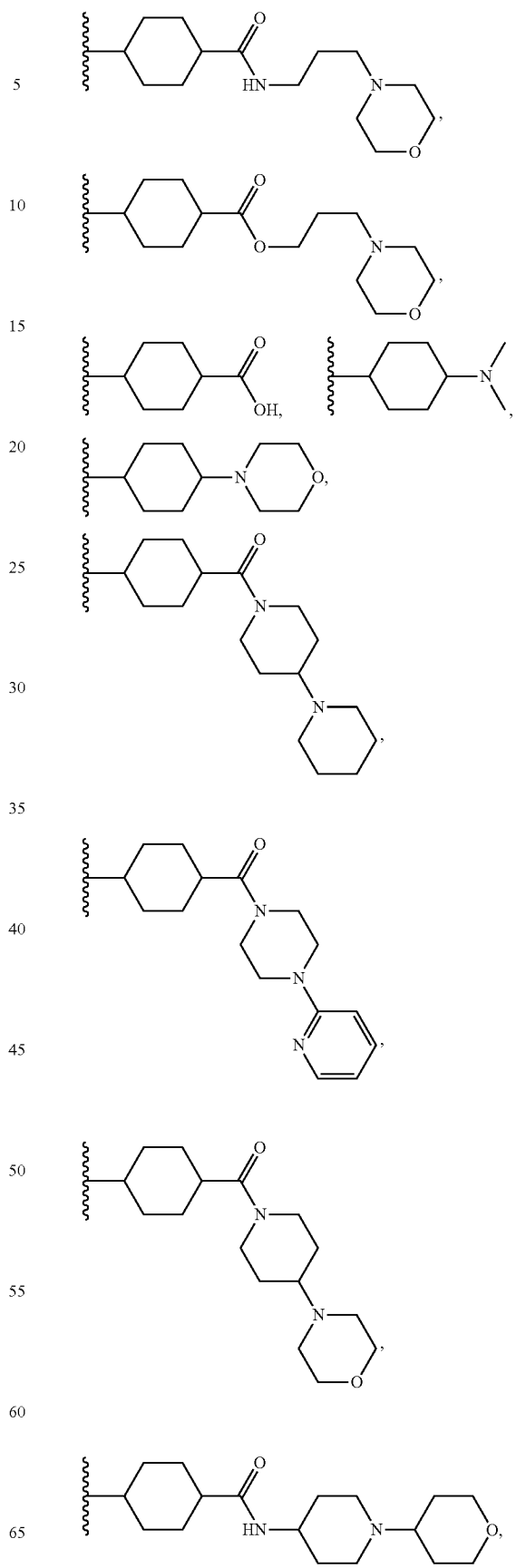

-continued

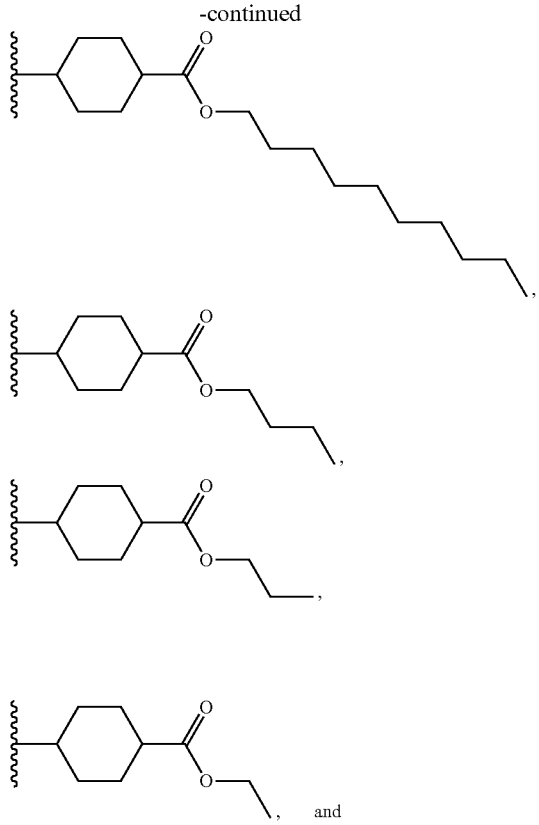

In some embodiments, $R^{13}$ is selected from:

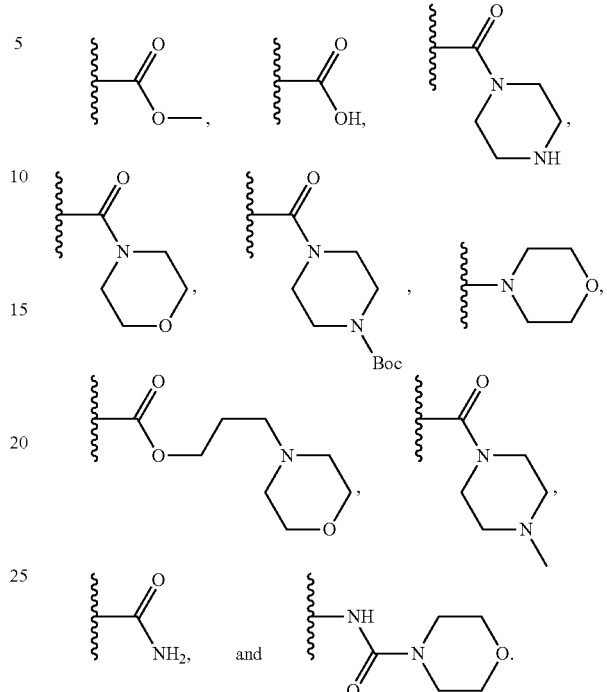

In some embodiments, $R^{6e}$ is

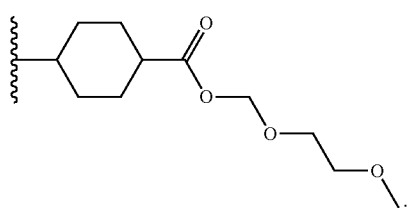

and is selected from:

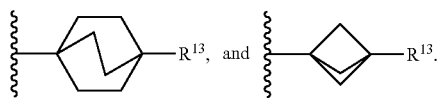

In another embodiment, $R^{13}$ is —C(O)OR$^{41a}$, —NHC(O)R$^{41b}$, —C(O)NHR$^{41c}$, or C(O)R$^{41d}$, wherein R$^{41a}$, R$^{41b}$, R$^{41c}$, and R$^{41d}$ are independently selected from H, optionally substituted ($C_1$-$C_6$)alkyl, optionally substituted heterocycle (e.g., morpholine, piperidine, morpholine-3-one), and optionally substituted ($C_1$-$C_6$)alkyl-heterocycle.

In some embodiments, $R^{6e}$ is

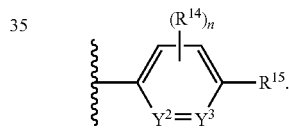

In another embodiment, $Y^2$ and $Y^3$ are each CR$^{14}$. In another embodiment, each R$^{14}$ is independently selected from H, OH, NH$_2$, CN, CF$_3$, OCF$_3$, CH$_2$NH$_2$, halogen, —C(O)R$^{42f}$, —OC(O)R$^{42g}$, optionally substituted ($C_1$-$C_5$)alkyl, and optionally substituted ($C_1$-$C_5$)alkoxy, wherein R$^{42f}$ to R$^{42g}$ are independently selected from —OH, optionally substituted amino, optionally substituted ($C_1$-$C_6$)alkyl, optionally substituted cycloalkyl, optionally substituted ($C_1$-$C_{10}$) alkoxy, optionally substituted heterocycle (e.g., piperidine, or morpholine), optionally substituted —O—($C_1$-$C_6$)alkyl-heterocycle, and amino acid. In another embodiment, R$^{15}$ is selected from H, halogen, —OC(O)R$^{42a}$, —C(O)R$^{42b}$, —C(O)NHR$^{42c}$, R$^{42d}$ or —OR$^{42e}$, wherein R$^{42a}$ to R$^{42e}$ are independently selected from —OH, optionally substituted amino, optionally substituted ($C_1$-$C_6$)alkyl, optionally substituted cycloalkyl, optionally substituted ($C_1$-$C_{10}$)alkoxy, optionally substituted heterocycle (e.g., piperidine, or morpholine), optionally substituted —O—($C_1$-$C_6$)alkyl-heterocycle, and amino acid. In some embodiments of R$^{6e}$, where n is 1 or greater, one R$^{14}$ group is —C(O)R$^{42f}$, wherein R$^{42f}$ is selected from optionally substituted heterocycle (e.g., piperidine, or morpholine), and optionally substituted ($C_1$-$C_{10}$)alkoxy (e.g., —OCH$_3$). In some embodiments of R$^{6e}$, R$^{15}$ is —C(O)R$^{42b}$, wherein R$^{42b}$ is selected from optionally substituted heterocycle (e.g., piperidine, or morpholine), and optionally substituted ($C_1$-$C_{10}$)alkoxy (e.g., —OCH$_3$).

In some embodiments $R^{6c}$ is selected from:
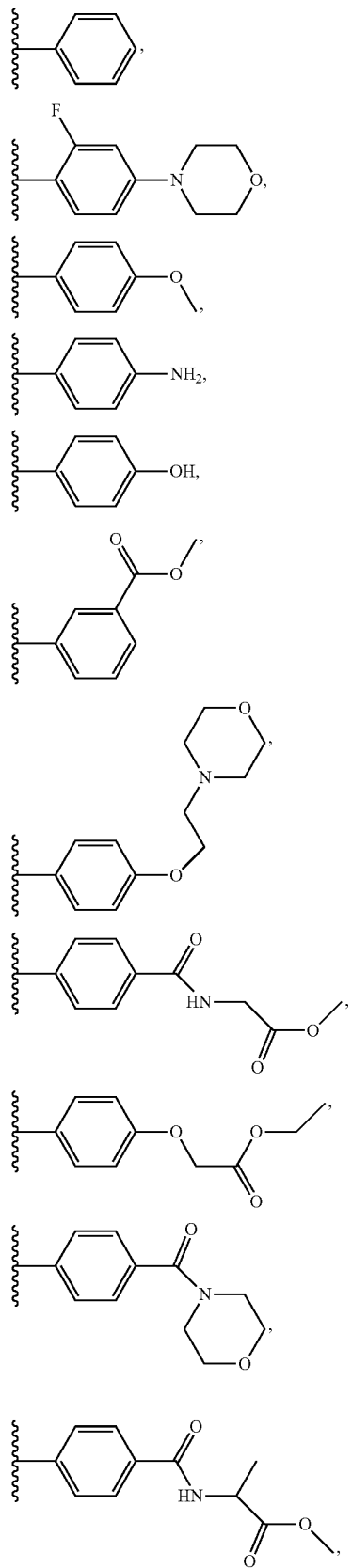
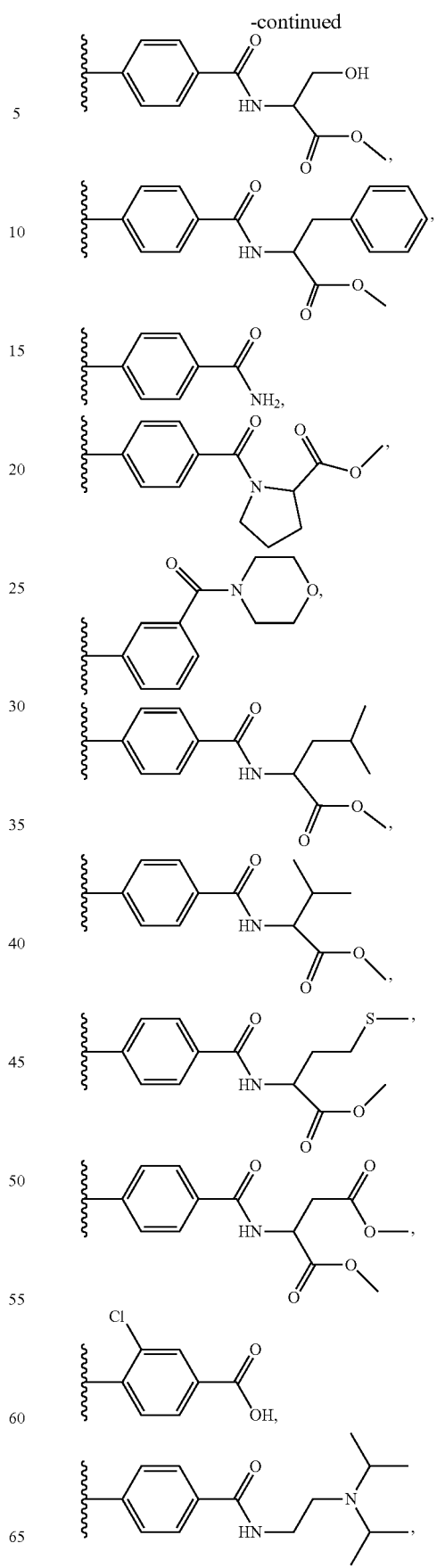

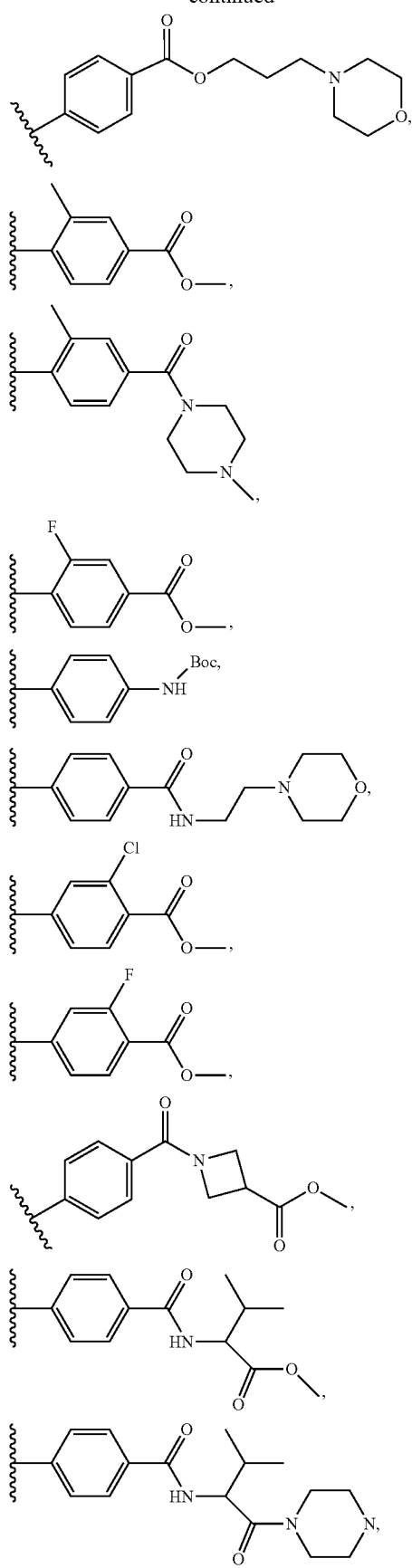
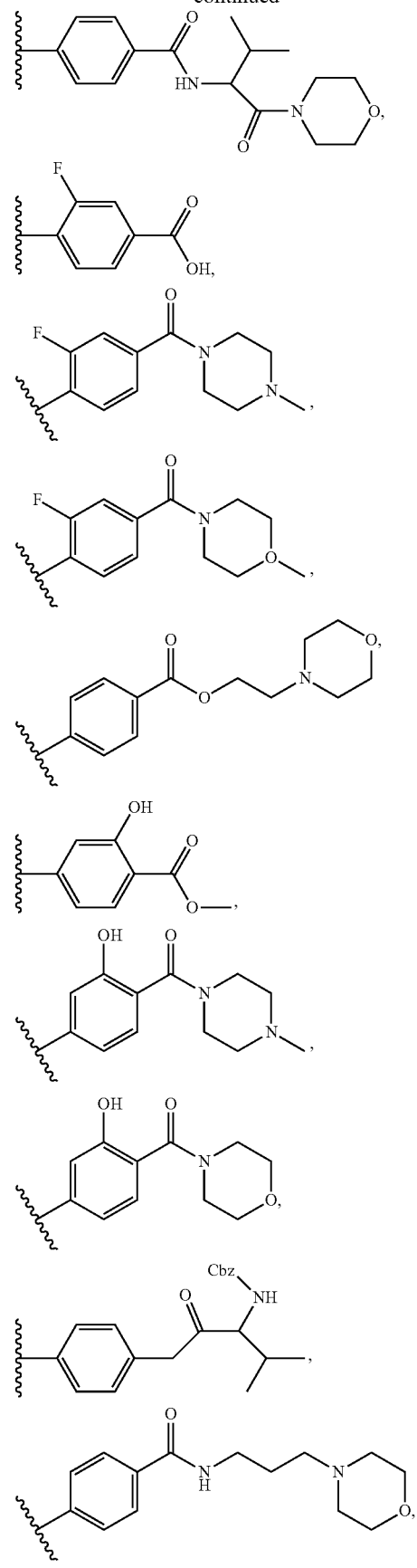

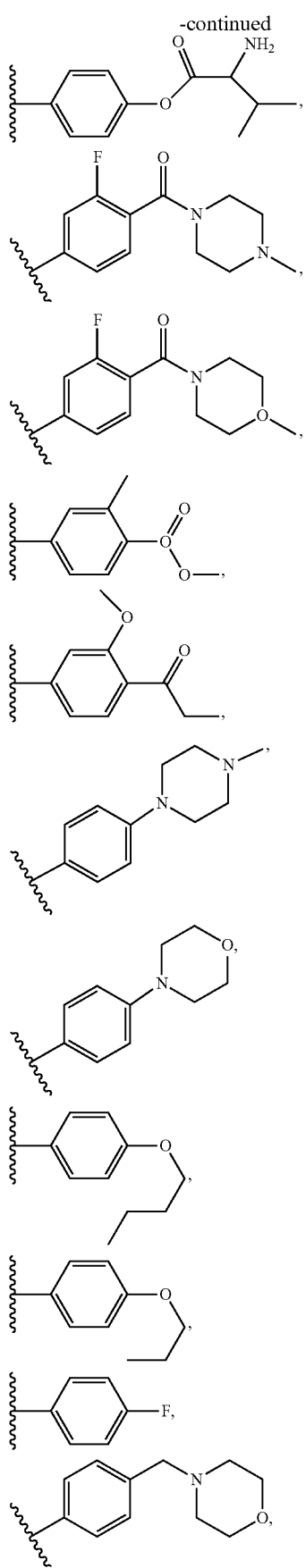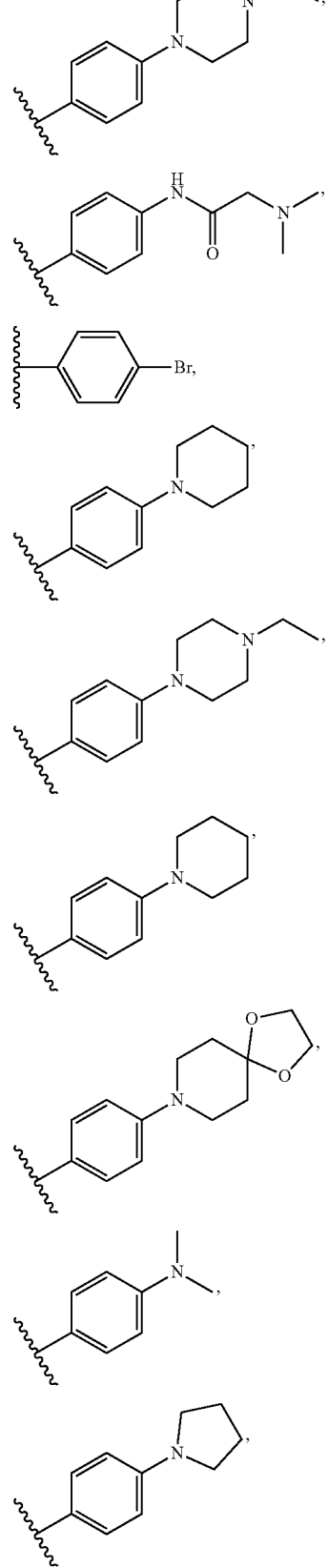

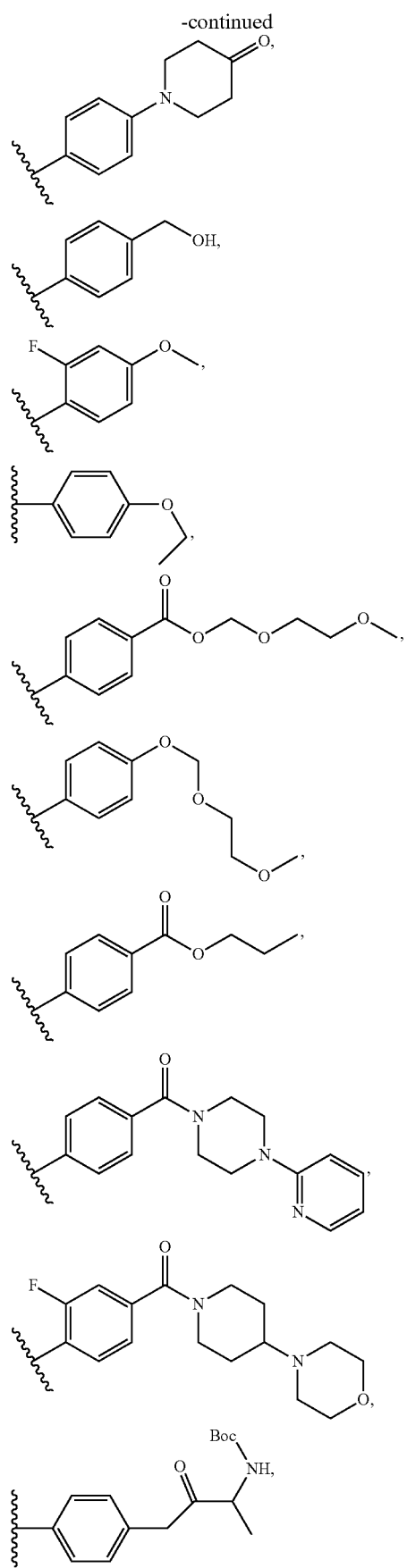
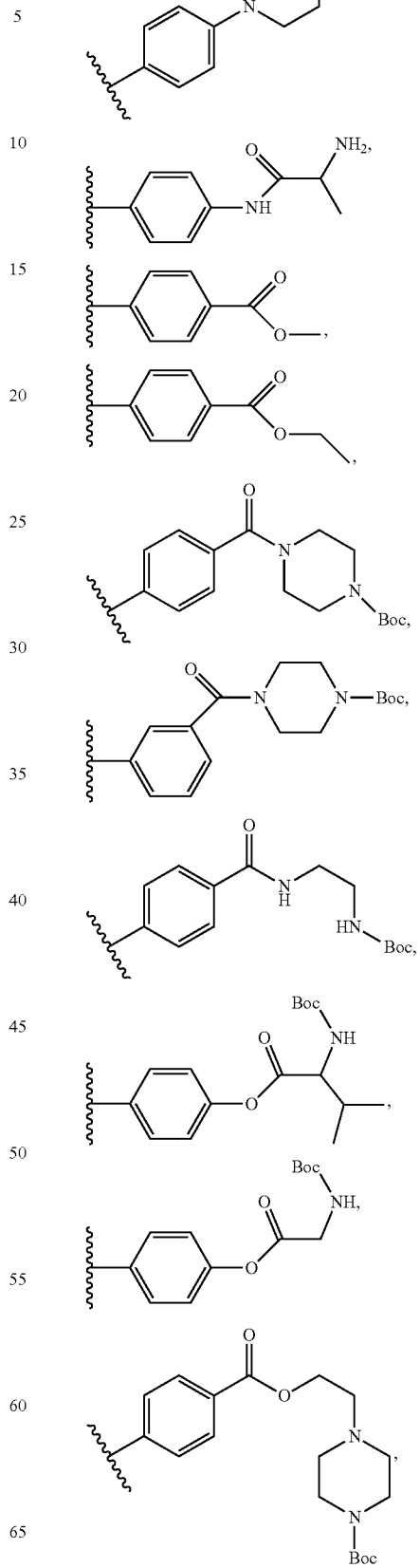

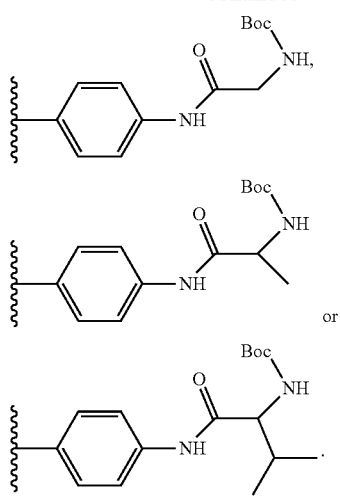
In some embodiments, $R^{6e}$ is
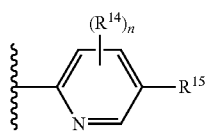
and n is 0 to 3. In another embodiment, $R^{6e}$ is selected from:
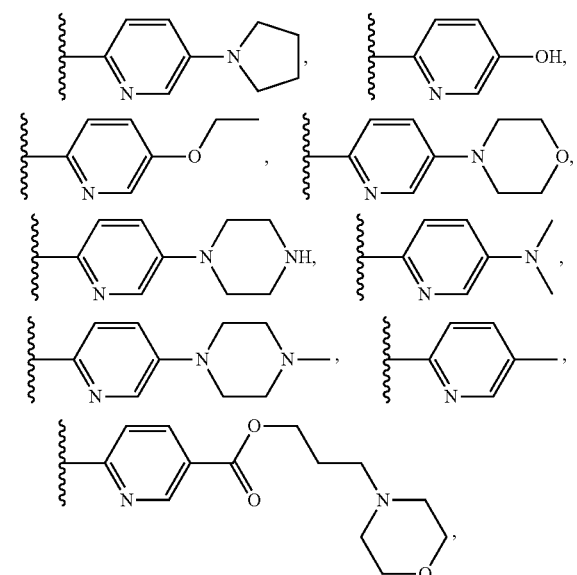
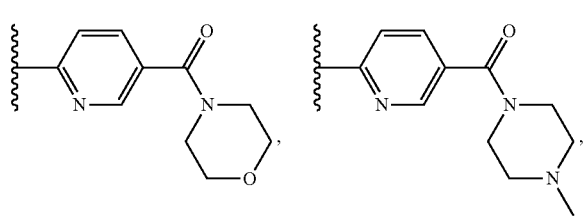
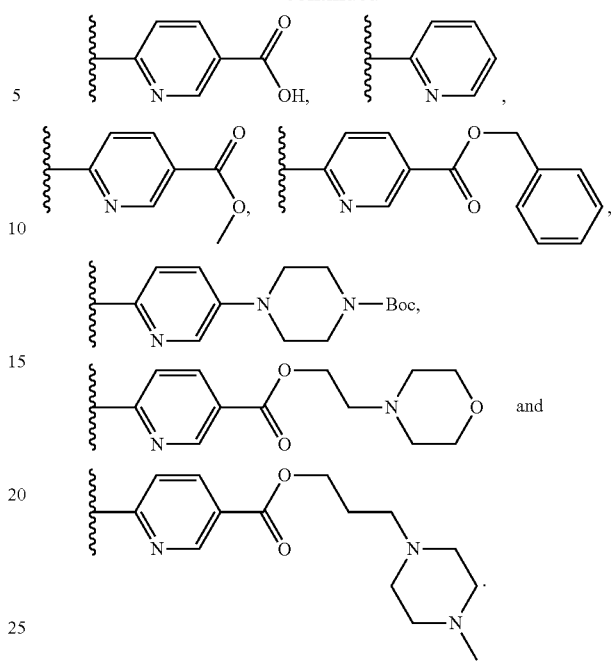
In some embodiments, $R^{6e}$ is
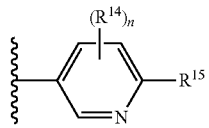
and n is 0 to 3. In some embodiments, $R^{15}$ is H, —C(O)OR$^{51}$ or —C(O)R$^{51}$, where $R^{51}$ is H, optionally substituted ($C_1$-$C_6$)alkyl, or optionally substituted heterocycle (e.g., morpholine or piperazine). In another embodiment, $R^{6e}$ is selected from:
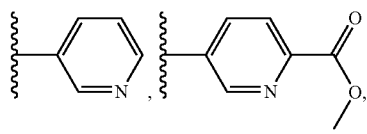
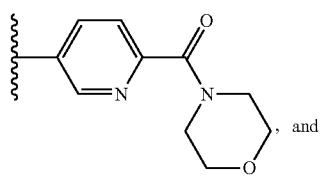
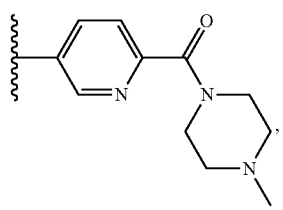

In some embodiments, $R^{5e}$ is H or Me and $R^{6e}$ is selected from:

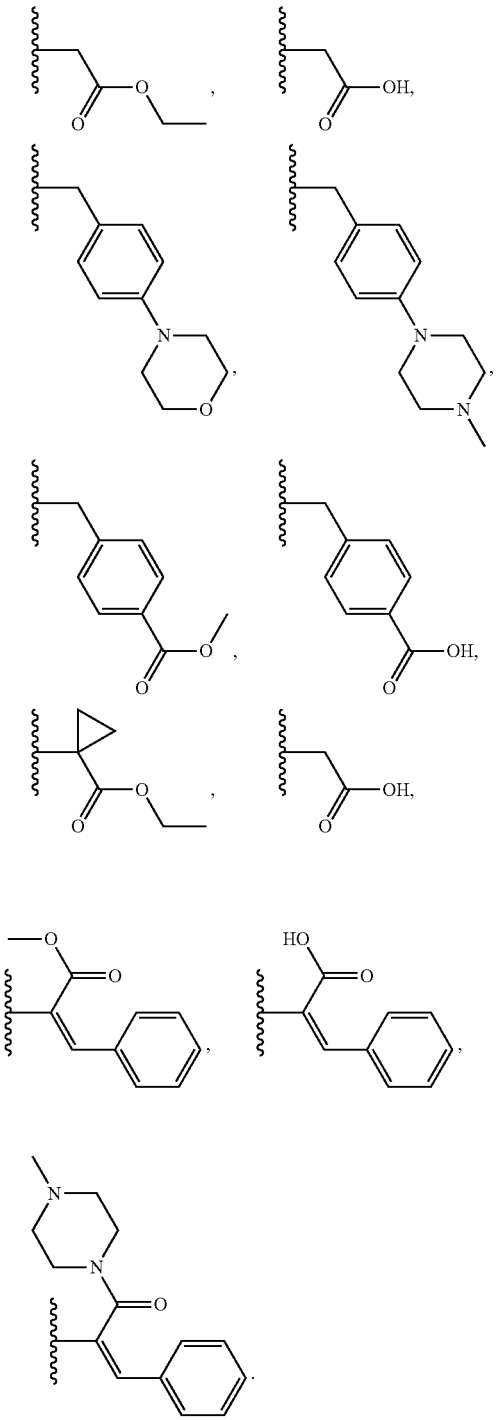

In some embodiments of formula (Ie), $R^{5e}$ and $R^{6e}$ together with the nitrogen atom to which they are attached are cyclically linked to form an optionally substituted monocyclic or bicyclic $(C_4-C_{10})$heterocycle.

In some embodiments of formula (Ie) $R^{5e}$ and $R^{6e}$ together with the nitrogen atom to which they are attached are cyclically linked to form:

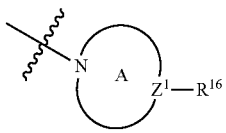

wherein:

ring A is an optionally substituted monocyclic or bicyclic $(C_4-C_{10})$heterocycle;

$Z^1$ is $CR^{14}$ or N, where $R^{14}$ is selected from H, OH, $NH_2$, CN, $CF_3$, $OCF_3$, $CH_2NH_2$, halogen, optionally substituted $(C_1-C_5)$alkyl, optionally substituted $(C_1-C_5)$alkoxy, optionally substituted cycloalkyl, optionally substituted heterocycloalkyl, optionally substituted carbocycle, and optionally substituted heterocycle; and $R^{16}$ is selected from H, halogen, $-OR^{22a}$, $-C(O)R^{22b}$, $-CO_2R^{22c}$, and $-C(O)NR^{50}R^{60}$, $-NR^{50}R^{60}$, optionally substituted aryl, optionally substituted heteroaryl, optionally substituted carbocycle, optionally substituted heterocycle, optionally substituted $(C_1-C_5)$alkyl, and optionally substituted $(C_1-C_5)$alkoxy;

$R^{22a}$, $R^{22b}$, and $R^{22c}$ are independently selected from H, optionally substituted $(C_1-C_{10})$ alkyl, optionally substituted cycloalkyl, optionally substituted aryl, optionally substituted heteroaryl, and optionally substituted heterocycle; and $R^{50}$ and $R^{60}$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^{50}$ and $R^{60}$ together with the nitrogen atom to which they are attached are cyclically linked to form an optionally substituted heterocycle, or an optionally substituted heteroaryl.

In some embodiments of formula (Ie) when $R^{5e}$ and $R^{6e}$ together form:

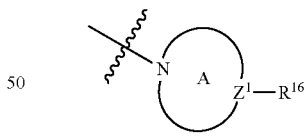

and the A ring is piperidine, then $R^{16}$ comprises at least one cyclic group selected from optionally substituted aryl, optionally substituted heteroaryl, optionally substituted carbocycle, optionally substituted heterocycle. In some cases, the A ring is piperidine and $R^{16}$ comprises an optionally substituted aryl. In some cases, the optionally substituted aryl is optionally substituted phenyl. In some cases, the A ring is piperidine and $R^{16}$ comprises an optionally substituted heteroaryl. In some cases, the A ring is piperidine and $R^{16}$ comprises an optionally substituted carbocycle. In some cases, the A ring is piperidine and $R^{16}$ comprises an optionally substituted heterocycle.

In some embodiments of formula (Ie) when $R^{5e}$ and $R^{6e}$ together form:

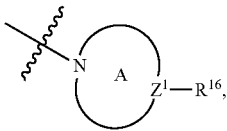

the A ring is an optionally substituted piperazine, pyrrolidine, or azetidine. In certain cases, the A ring is:

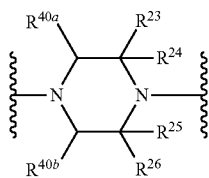

wherein:

$R^{23}$-$R^{26}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$) alkoxy, optionally substituted cycloalkyl, optionally substituted aryl, optionally substituted heteroaryl, and optionally substituted heterocycle; or one or both of $R^{23}$-$R^{24}$ and $R^{25}$-$R^{26}$ together with the carbon atom to which they are attached are cyclically linked to form an optionally substituted carbocycle or an optionally substituted heterocycle; and $R^{40a}$ and $R^{40b}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$)alkoxy, optionally substituted cycloalkyl, optionally substituted aryl, optionally substituted heteroaryl, and optionally substituted heterocycle.

In some embodiments of the A ring, $R^{23}$ is selected from optionally substituted ($C_1$-$C_6$)alkyl, optionally substituted cycloalkyl; and $R^{24}$-$R^{26}$, $R^{40a}$ and $R^{40b}$ are each H. In certain cases, $R^{23}$ is selected from methyl, ethyl, propyl, isopropyl, butyl, and t-butyl. In certain cases, $R^{23}$ is methyl. In certain cases, $R^{23}$ is ethyl. In certain cases, $R^{23}$ is propyl. In certain cases, $R^{23}$ is isopropyl. In some embodiments, $R^{23}$ is ($C_1$-$C_6$)cycloalkyl. In certain cases, $R^{23}$ is cyclopropyl. In certain cases, $R^{23}$ is cyclobutyl. In certain cases, $R^{23}$ is cyclopentyl. In certain cases, $R^{23}$ is cyclohexyl.

In certain embodiments of the A ring, two of $R^{23}$, $R^{25}$, and $R^{40b}$ are independently selected from optionally substituted ($C_1$-$C_6$)alkyl and optionally substituted cycloalkyl; and the other one of $R^{23}$, $R^{25}$ and $R^{40b}$ is H, and $R^{24}$, $R^{26}$ and $R^{40a}$ are each H. In certain cases of the A ring, two of $R^{23}$, $R^{25}$, and $R^{40b}$ are optionally substituted ($C_1$-$C_6$)alkyl. In certain cases of the A ring, two of $R^{23}$, $R^{25}$, and $R^{40b}$ are each independently selected from methyl, ethyl, propyl, isopropyl, butyl, and t-butyl. In certain cases of the A ring, two of $R^{23}$, $R^{25}$, and $R^{40b}$ are methyl. In certain cases of the A ring, two of $R^{23}$, $R^{25}$, and $R^{40b}$ are ethyl. In certain cases, two of $R^{23}$, $R^{25}$, and $R^{40b}$ are propyl. In certain cases of the A ring, two of $R^{23}$, $R^{25}$, and $R^{40b}$ are isopropyl. In some embodiments of the A ring, two of $R^{23}$, $R^{25}$, and $R^{40b}$ are ($C_1$-$C_6$)cycloalkyl. In certain cases of the A ring, two of $R^{23}$, $R^{25}$, and $R^{40b}$ are cyclopropyl. In certain cases, two of $R^{23}$, $R^{25}$, and $R^{40b}$ are cyclobutyl. In certain cases of the A ring, two of $R^{23}$, $R^{25}$, and $R^{40b}$ are cyclopentyl. In certain cases of the A ring, two of $R^{23}$, $R^{25}$, and $R^{40b}$ are cyclohexyl.

In certain embodiments of the A ring, $R^{23}$ and $R^{25}$ are each independently selected from optionally substituted ($C_1$-$C_6$) alkyl, and optionally substituted cycloalkyl; and $R^{24}$, $R^{26}$ and $R^{40a}$-$R^{40b}$ are each H. In certain cases of the A ring, both $R^{23}$ and $R^{25}$ are optionally substituted ($C_1$-$C_6$)alkyl. In certain cases of the A ring, $R^{23}$ and $R^{25}$ are each independently selected from methyl, ethyl, propyl, isopropyl, butyl, and t-butyl. In certain cases of the A ring, both $R^{23}$ and $R^{25}$ are methyl. In certain cases of the A ring, both $R^{23}$ and $R^{25}$ are ethyl. In certain cases of the A ring, both $R^{23}$ and $R^{25}$ are propyl. In certain cases of the A ring, both $R^{23}$ and $R^{25}$ are isopropyl. In some embodiments of the A ring, both $R^{23}$ and $R^{25}$ are ($C_1$-$C_6$)cycloalkyl. In certain cases of the A ring, both $R^{23}$ and $R^{25}$ are cyclopropyl. In certain cases, both $R^{23}$ and $R^{25}$ are cyclobutyl. In certain cases of the A ring, both $R^{23}$ and $R^{25}$ are cyclopentyl. In certain cases of the A ring, both $R^{23}$ and $R^{25}$ are cyclohexyl.

In certain embodiments of the A ring, $R^{23}$ and $R^{40b}$ are each independently selected from optionally substituted ($C_1$-$C_6$)alkyl and optionally substituted cycloalkyl; and $R^{24}$-$R^{26}$ and $R^{40a}$ are each H. In certain cases, both $R^{23}$ and $R^{40b}$ are optionally substituted ($C_1$-$C_6$)alkyl. In certain cases, $R^{23}$ and $R^{40b}$ are each independently selected from methyl, ethyl, propyl, isopropyl, butyl, and t-butyl. In certain cases, both $R^{23}$ and $R^{40b}$ are methyl. In certain cases, both $R^{23}$ and $R^{40b}$ are ethyl. In certain cases, both $R^{23}$ and $R^{40b}$ are propyl. In certain cases, both $R^{23}$ and $R^{40b}$ are isopropyl. In some embodiments, both $R^{23}$ and $R^{40b}$ are ($C_1$-$C_6$)cycloalkyl. In certain cases, both $R^{23}$ and $R^{40b}$ are cyclopropyl. In certain cases, both $R^{23}$ and $R^{40b}$ are cyclobutyl. In certain cases, both $R^{23}$ and $R^{40b}$ are cyclopentyl. In certain cases, both $R^{23}$ and $R^{40b}$ are cyclohexyl.

In certain embodiments of the A ring, $R^{23}$ and $R^{24}$ are each independently selected from optionally substituted ($C_1$-$C_6$) alkyl and optionally substituted cycloalkyl; and $R^{25}$-$R^{26}$, $R^{40a}$ and $R^{40b}$ are each H. In certain cases, both $R^{23}$ and $R^{24}$ are optionally substituted ($C_1$-$C_6$)alkyl. In certain cases, $R^{23}$ and $R^{24}$ are each independently selected from methyl, ethyl, propyl, isopropyl, butyl, and t-butyl. In certain cases, both $R^{23}$ and $R^{24}$ are methyl. In certain cases, both $R^{23}$ and $R^{24}$ are ethyl. In certain cases, both $R^{23}$ and $R^{24}$ are propyl. In certain cases, both $R^{23}$ and $R^{25}$ are isopropyl. In some embodiments, both $R^{23}$ and $R^{24}$ are ($C_1$-$C_6$)cycloalkyl. In certain cases, both $R^{23}$ and $R^{24}$ are cyclopropyl. In certain cases, both $R^{23}$ and $R^{24}$ are cyclobutyl. In certain cases, both $R^{23}$ and $R^{24}$ are cyclopentyl. In certain cases, both $R^{23}$ and $R^{24}$ are cyclohexyl.

In certain embodiments of the A ring, $R^{23}$ and $R^{24}$ together with the carbon atom to which they are attached are cyclically linked to form a carbocycle; and $R^{25}$-$R^{26}$, $R^{40a}$ and $R^{40b}$ are each H. In some embodiments, $R^{23}$ and $R^{24}$ together with the carbon atom to which they are attached are cyclically linked to form a ($C_1$-$C_6$)cycloalkyl. In certain cases, $R^{23}$ and $R^{24}$ together with the carbon atom to which they are attached are cyclically linked to form a cyclopropyl. In certain cases, $R^{23}$ and $R^{24}$ together with the carbon atom to which they are attached are cyclically linked to form a cyclobutyl. In certain cases, $R^{23}$ and $R^{24}$ together with the carbon atom to which they are attached are cyclically linked to form a cyclopentyl. In certain cases, $R^{23}$ and $R^{24}$ together with the carbon atom to which they are attached are cyclically linked to form a cyclohexyl.

In some embodiments of formula (Ie) when $R^{5e}$ and $R^{6e}$ together form:

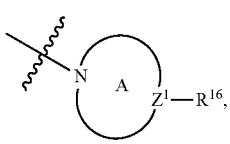

the A ring is selected from:

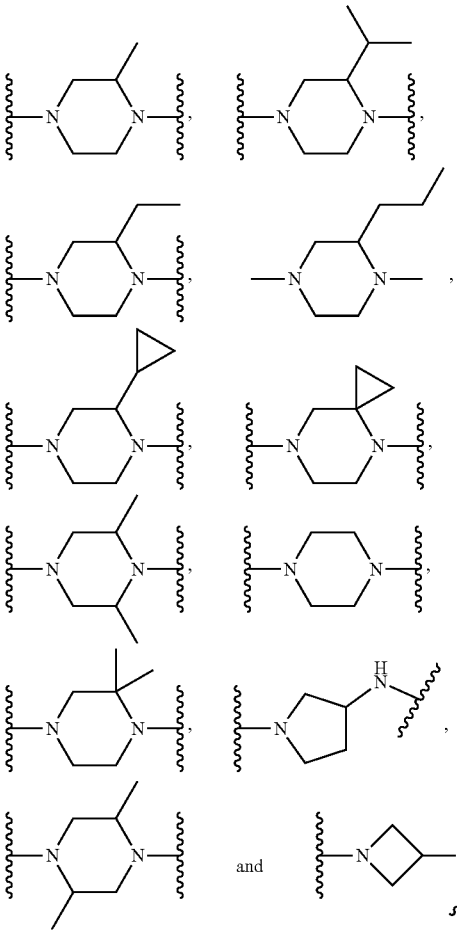

and

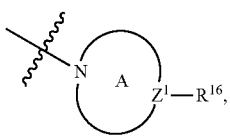

In some embodiments, $R^{16}$ is selected from H, halogen, —$OR^{22a}$, —$C(O)R^{22b}$, —$CO_2R^{22c}$, and —$C(O)NR^{50}R^{60}$, —$NR^{50}R^{60}$, optionally substituted aryl, optionally substituted heteroaryl, optionally substituted carbocycle, optionally substituted heterocycle, optionally substituted $(C_1$-$C_5)$ alkyl, and optionally substituted $(C_1$-$C_5)$alkoxy, where $R^{22a}$, $R^{22b}$, $R^{22c}$, $R^{50}$, and $R^{60}$ are as defined above.

In some embodiments of formula (Ie) when $R^{5e}$ and $R^{6e}$ together form:

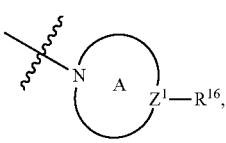

the A ring is selected from:

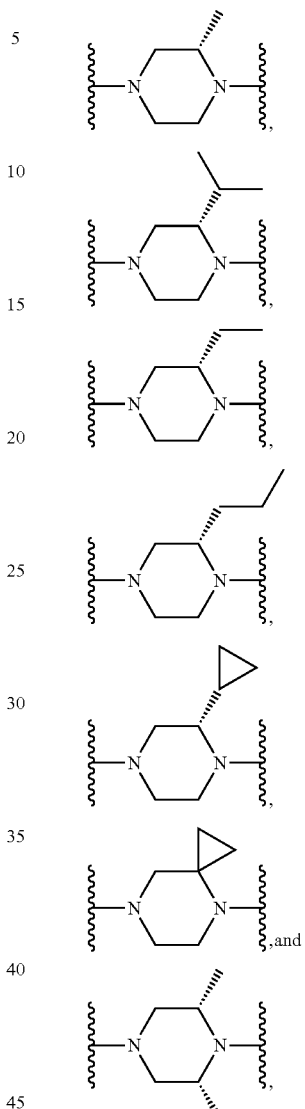

where $R^{16}$ is as defined above.

In some embodiments of formula (Ie), $R^{5e}$ and $R^{6e}$ together form:

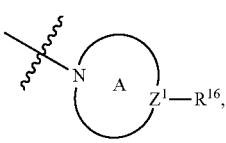

wherein $R^{16}$ is:

—$(R^{110})_nR^{210}$ wherein:
each $R^{110}$ is independently selected from optionally substituted $(C_1$-$C_6)$alkyl,

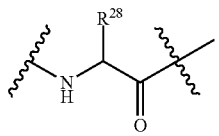

—C(O)($R^{110a}$)$n^1$, —C(O)O($R^{110b}$)$n^2$, —S(O)($R^{110c}$)$n^3$, —SO$_2$($R^{110d}$)$n^4$, and —C(O)NR$^{27}$($R^{110e}$)$n^5$; where $R^{110a}$-$R^{110e}$ are each independently optionally substituted (C$_1$-C$_6$) alkyl,

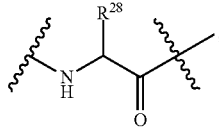

$R^{27}$-$R^{211}$ are each independently selected from H and optionally substituted (C$_1$-C$_6$)alkyl; and n-$n^5$ are each independently 0 to 3; and $R^{210}$ is selected from optionally substituted aryl, optionally substituted heteroaryl, optionally substituted carbocycle and optionally substituted heterocycle.

In some embodiments, $R^{110}$ is selected from —C(O)—, —C(O)O—, —C(O)NH—, —S(O)—, and —SO$_2$—; and $R^{210}$ is selected from optionally substituted aryl and optionally substituted heteroaryl. In certain embodiments, $R^{110}$ is —C(O)— and $R^{210}$ is optionally substituted aryl. In certain embodiments, $R^{110}$ is —C(O)O— and $R^{210}$ is optionally substituted aryl. In certain embodiments, $R^{110}$ is —C(O)NH— and $R^{210}$ is optionally substituted aryl. In certain embodiments, $R^{110}$ is —S(O)— and $R^{210}$ is optionally substituted aryl. In certain embodiments, $R^{110}$ is —SO$_2$— and $R^{210}$ is optionally substituted aryl. In certain embodiments, $R^{110}$ is —C(O)— and $R^{210}$ is optionally substituted aryl. In certain embodiments, $R^{110}$ is —C(O)O— and $R^{210}$ is optionally substituted heteroaryl. In certain embodiments, $R^{110}$ is —C(O)NH— and $R^{210}$ is optionally substituted heteroaryl. In certain embodiments, $R^{110}$ is —S(O)— and $R^{210}$ is optionally substituted heteroaryl. In certain cases, $R^{110}$ is —SO$_2$— and $R^{210}$ is optionally substituted heteroaryl.

In some embodiments, $R^{210}$ is selected from:

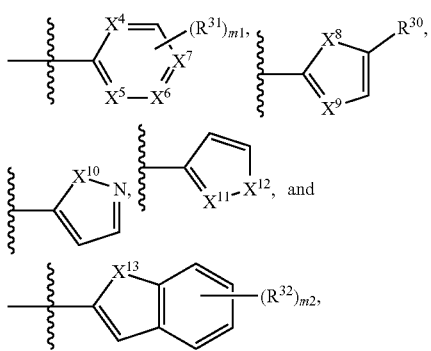

wherein:
wherein:
$X^4$-$X^7$, $X^9$, and $X^{11}$ are each independently selected from CH, CR$^{31}$, S, O, and N;
$X^8$, $X^{10}$, $X^{12}$ and $X^{13}$ are each independently selected from S, O, and NR$^{29}$;

$R^{29}$ is selected from H and optionally substituted (C$_1$-C$_6$) alkyl;

$R^{30}$-$R^{32}$ are each independently selected from H, halogen, OH, NO$_2$, OCF$_3$, CF$_3$, optionally substituted amino, optionally substituted (C$_1$-C$_6$)alkyl, optionally substituted (C$_1$-C$_6$) alkoxy, optionally substituted cycloalkyl, optionally substituted aryl, optionally substituted heteroaryl, and optionally substituted heterocycle; and $m^1$-$m^2$ are each independently 0 to 5.

In some embodiments, $R^{210}$ is

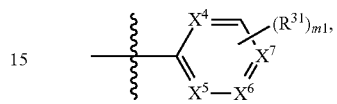

where $X^4$-$X^7$ are each independently selected from CH, CR$^{31}$, S, O, and N. In some embodiments, $R^{210}$ is

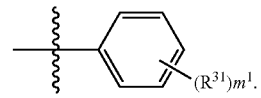

In some embodiments, $R^{210}$ is

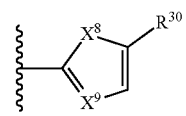

where $X^9$ is selected from CH, CR$^{31}$, S, O, and N; and $X^8$ is selected from S, O, and NR$^{29}$. In some cases, $R^{29}$ is methyl. In some embodiments of $R^{210}$ is $X^9$ is CH, CR$^{31}$, S, O, and N; and $X^8$ is selected from S, O, and NR$^{29}$. In some cases, $X^9$ is CH, and $X^8$ is S. In some cases, $R^{30}$ is H. In some cases, $R^{30}$ is methyl. In some embodiments, $X^9$ is CH, $X^8$ is S, and $R^{30}$ is H. In some cases, $X^9$ is CH, $X^8$ is NR$^{29}$, and $R^{30}$ is H. In some cases, $X^9$ is CH, and $X^8$ is NH. In some cases, $X^9$ is CH, $X^8$ is O and $R^{30}$ is (C$_1$-C$_6$)alkyl. In some cases, $X^9$ is CH, $X^8$ is O and $R^{30}$ is methyl.

In some embodiments, $R^{210}$ is

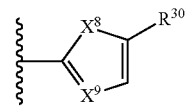

where $X^9$ is N, and $X^8$ is selected from S, O, and NR$^{29}$. In some cases, $X^8$ is NR$^9$. In some cases, $R^{29}$ is H. In some cases, $R^{29}$ is methyl. In some cases, $X^8$ is O. In some cases, $X^8$ is S.

In some embodiments, $R^{210}$ is

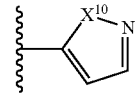

where $X^{10}$ is selected from S, O, and $NR^{29}$. In some cases, $X^{10}$ is O. In some cases, $X^{10}$ is S. In some cases, $X^{10}$ is $NR^{29}$ where $R^{29}$ is $(C_1-C_6)$alkyl. In some cases, $R^{29}$ is H. In some cases, $R^{29}$ is methyl.

In some embodiments, $R^{210}$ is

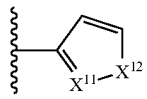

where $X^{11}$ is selected from CH, $CR^{31}$, S, O, and N, and $X^{12}$ is selected from S, O, and $NR^{29}$. In some cases, $X^{11}$ is N. In some cases, $X^{12}$ is O or S. In some cases, $X^{11}$ is N, and $X^{12}$ is O. In some cases, $X^{11}$ is N, and $X^{12}$ is S.

In some embodiments, $R^{210}$ is

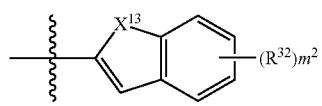

where $X^{13}$ is selected from S, O, and $NR^{29}$. In some cases, $X^{13}$ is $NR^{29}$. In some cases, $R^{29}$ is H. In some cases, $R^{29}$ is methyl. In some cases, $X^{13}$ is S. In some cases, $X^{13}$ is O.

In some embodiments of formula (Ie),

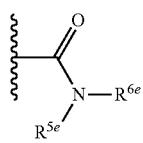

is selected from:

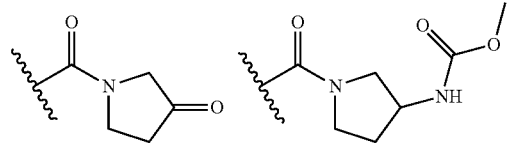

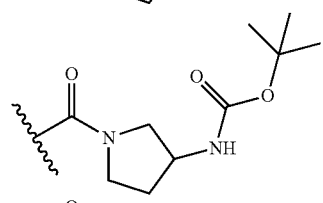

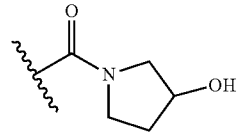

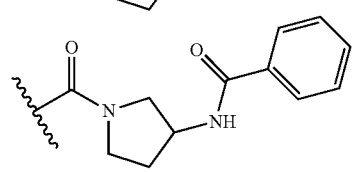

-continued

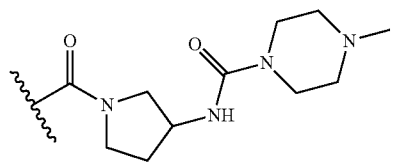

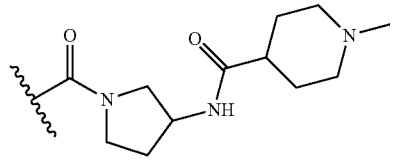

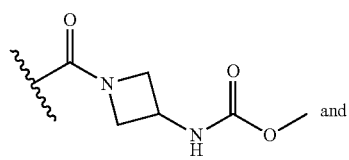 and

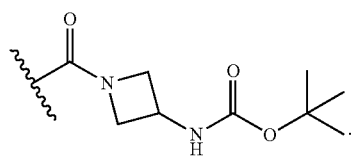

In some embodiments of formula (Ie),

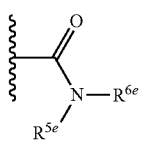

is selected from:

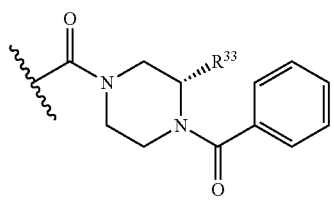

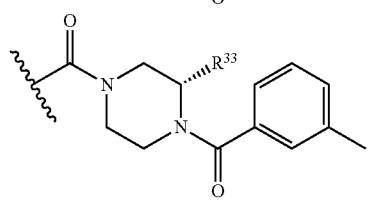

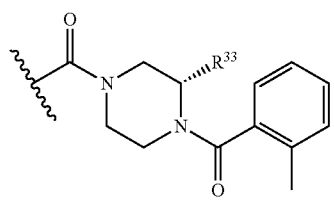

-continued

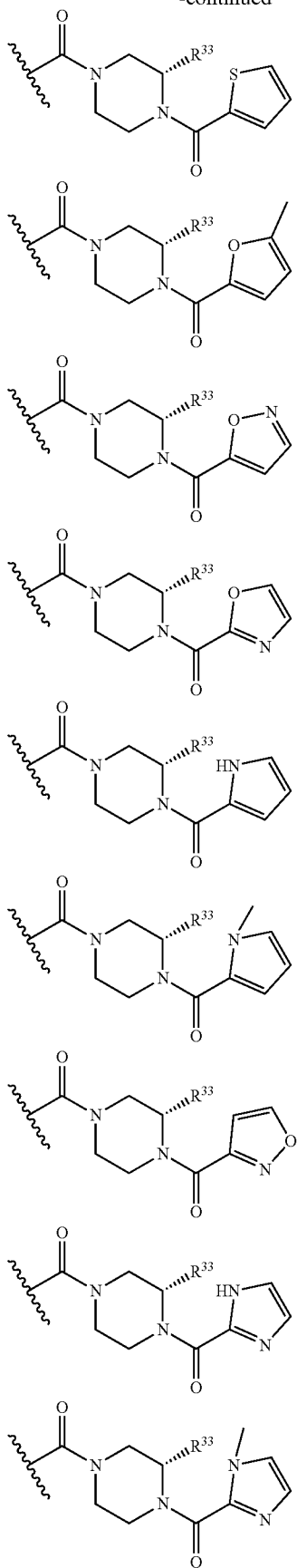

-continued

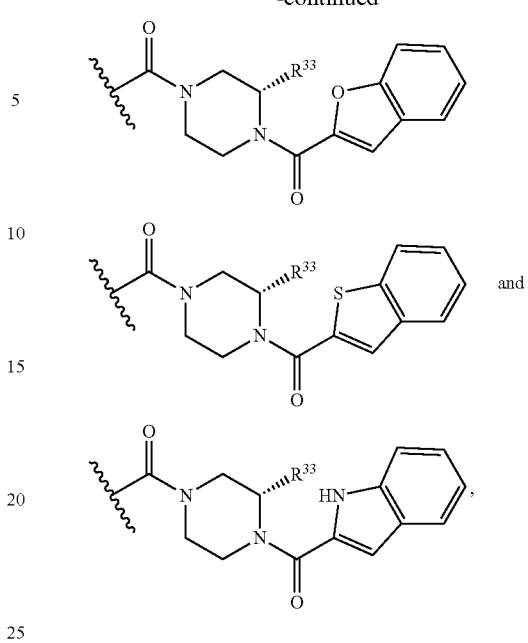

and wherein:

each $R^{33}$ is independently selected from optionally substituted $(C_1\text{-}C_6)$alkyl and optionally substituted cycloalkyl. In certain cases, each $R^{33}$ is independently selected from methyl, ethyl, propyl, isopropyl, butyl, and t-butyl. In certain cases, each $R^{33}$ is methyl. In certain cases, each $R^{33}$ is ethyl. In certain cases, each $R^{33}$ is propyl. In certain cases, each $R^{33}$ is isopropyl. In some embodiments, each $R^{33}$ is independently selected from $(C_1\text{-}C_6)$cycloalkyl. In certain cases, each $R^{33}$ is cyclopropyl. In certain cases, each $R^{33}$ is cyclobutyl. In certain cases, each $R^{33}$ is cyclopentyl. In certain cases, each $R^{33}$ is cyclohexyl.

In some embodiments of formula (Ie),

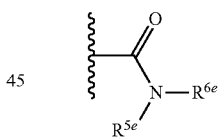

is selected from:

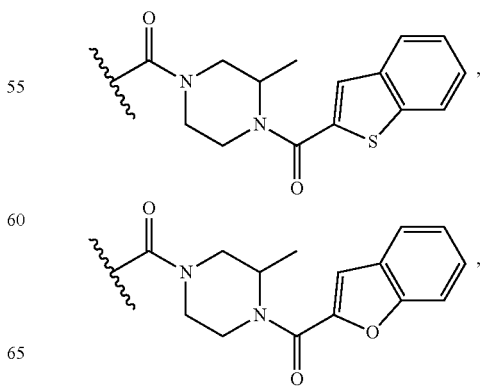

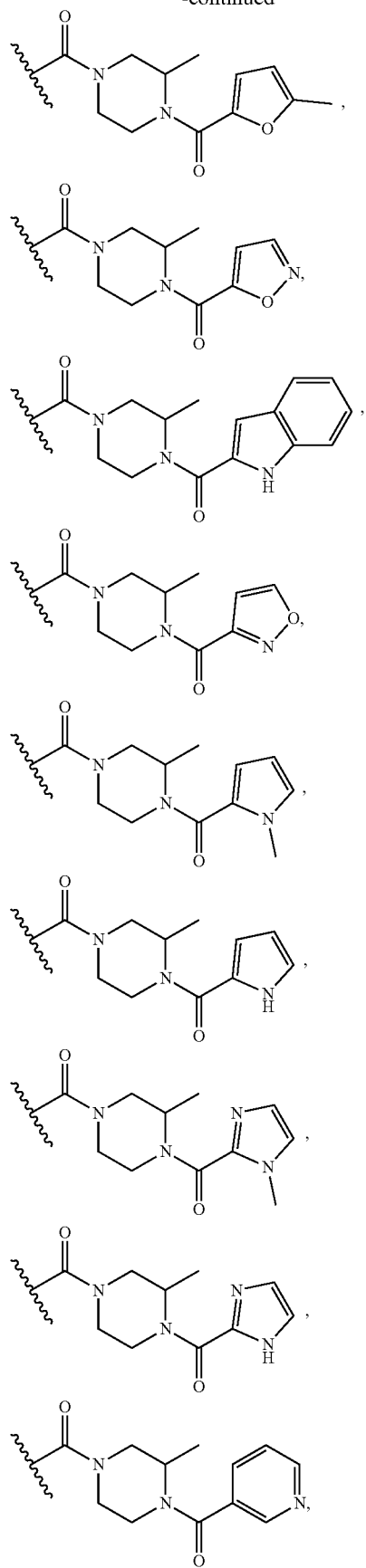
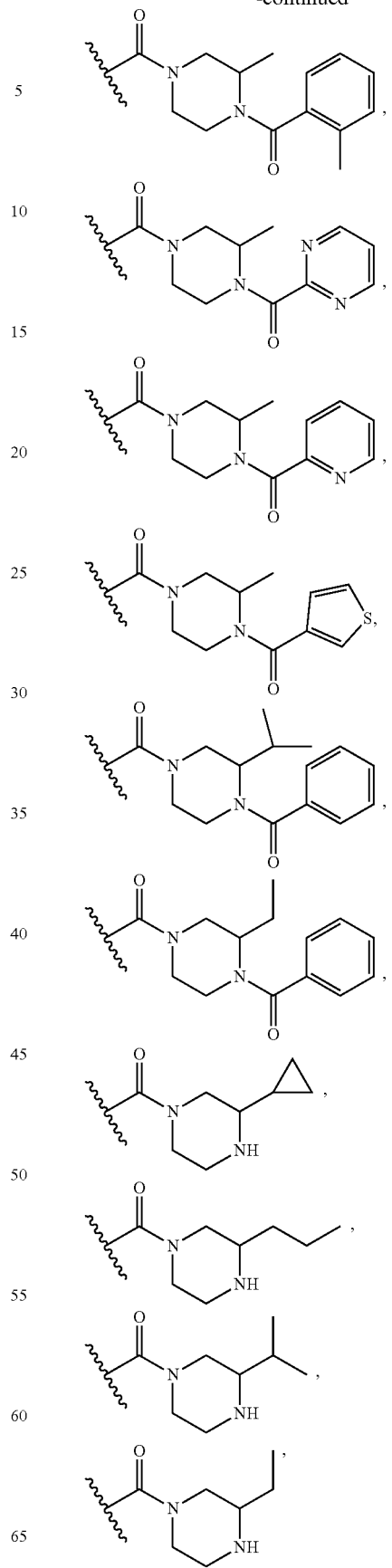

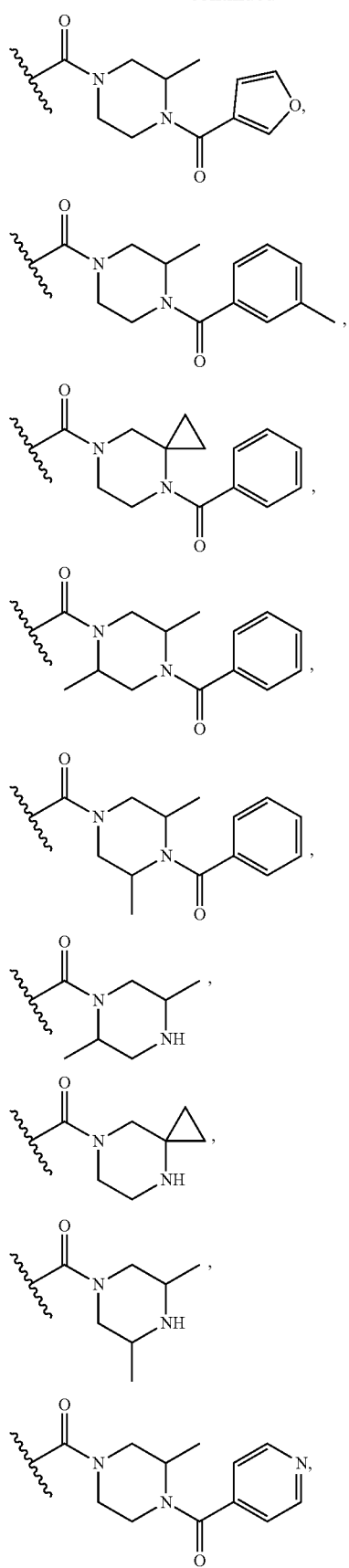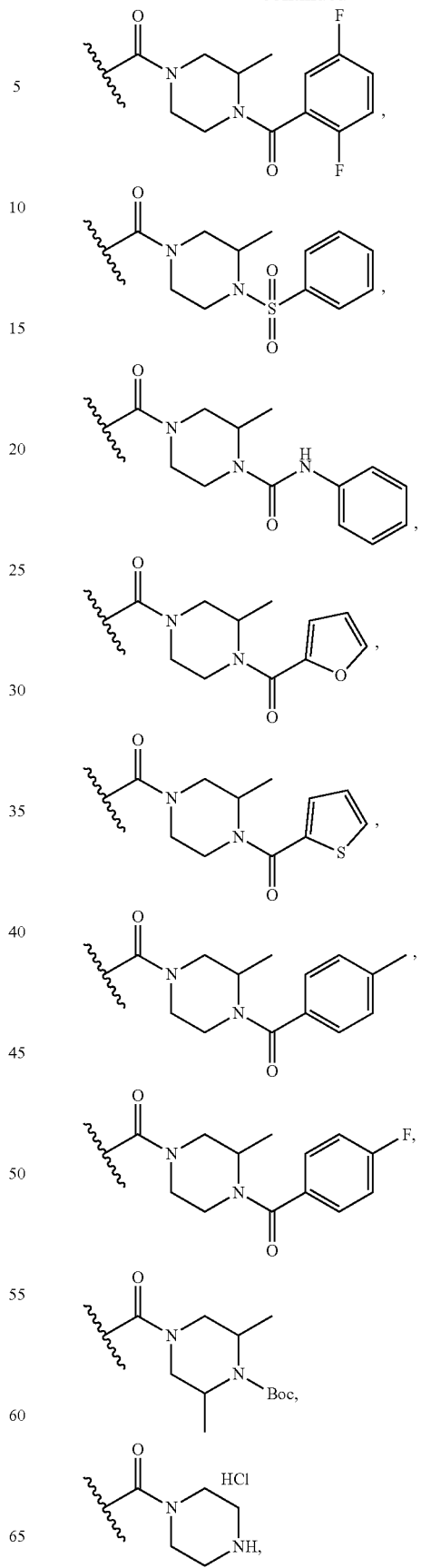

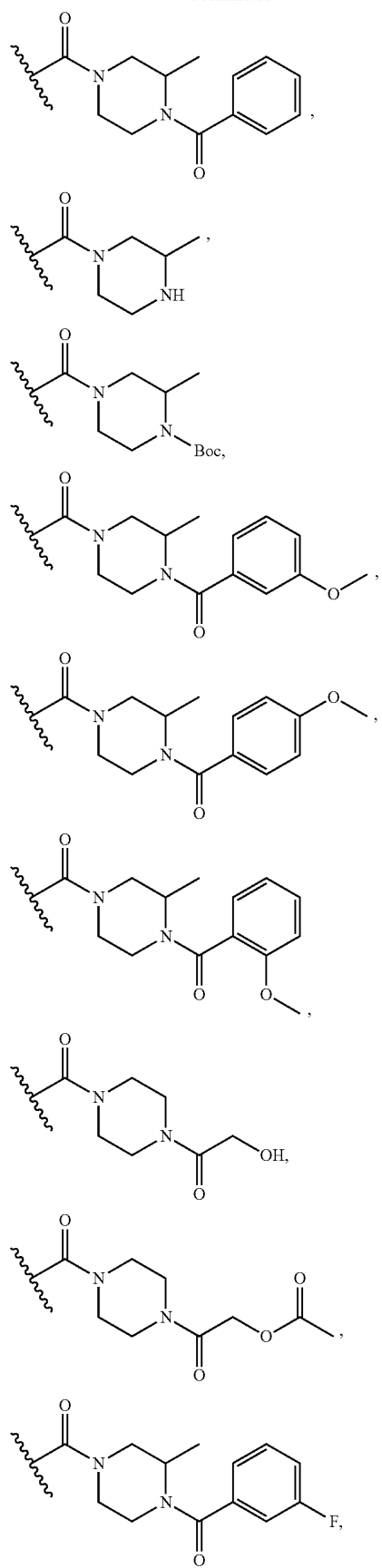
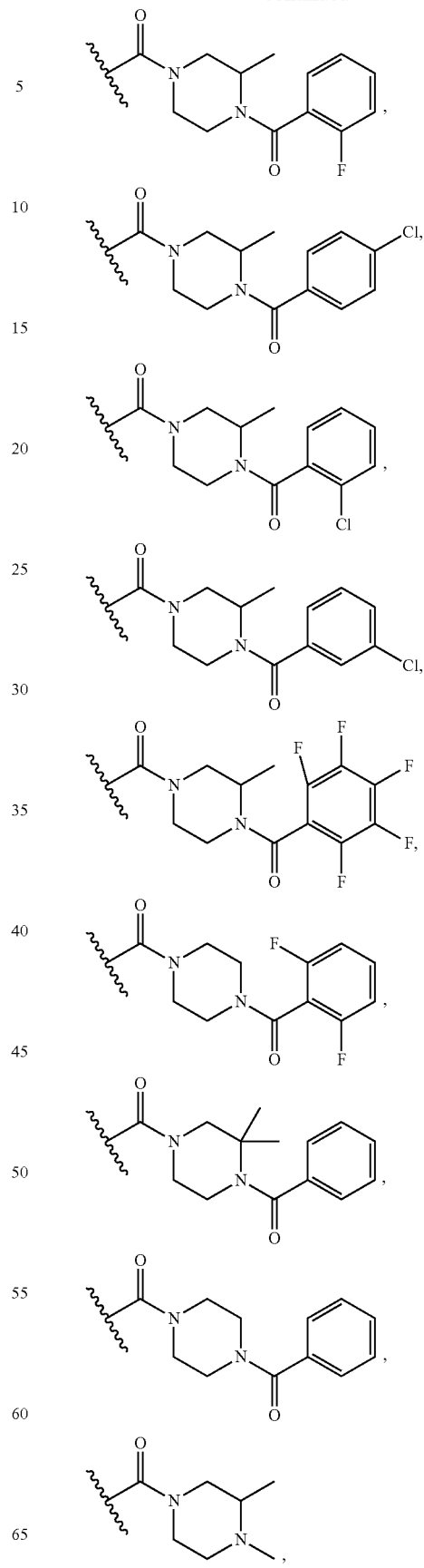

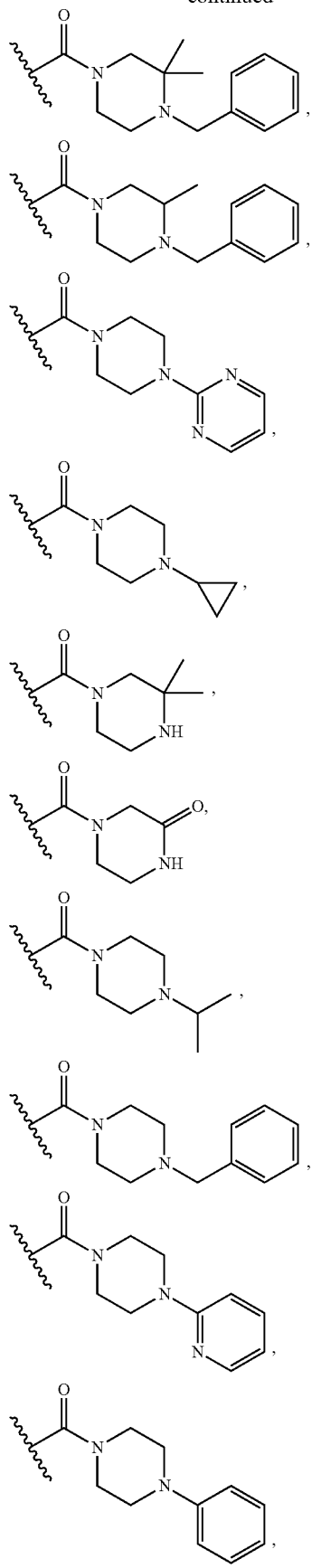
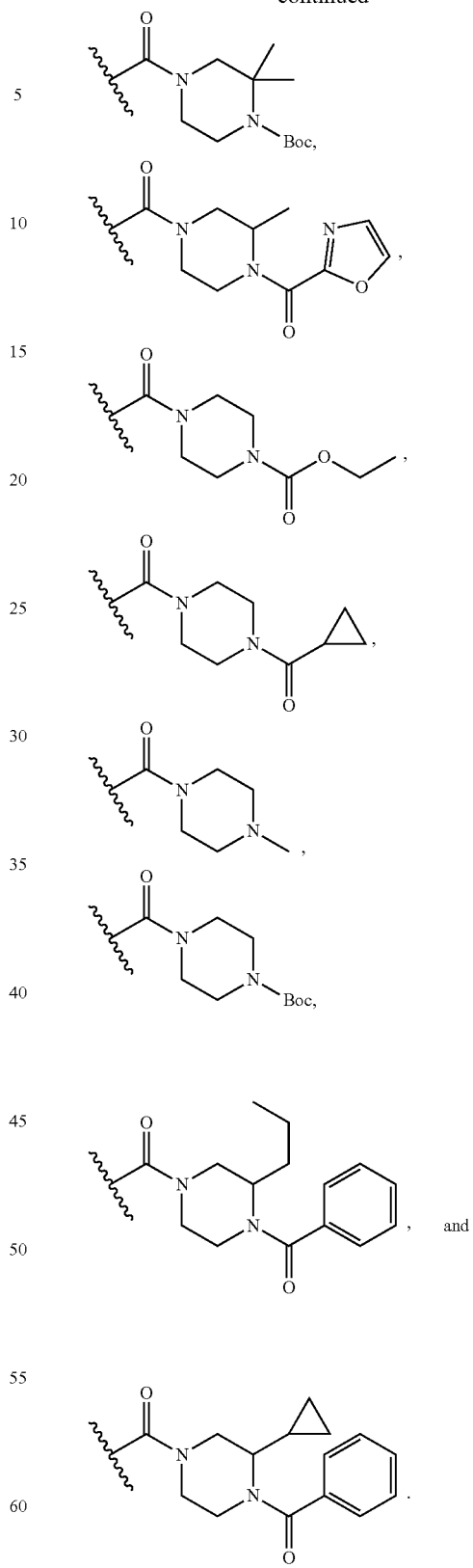
In some embodiments of formula (Ia)-(Ie), the compound is of Table 1, or a pharmaceutically acceptable salt, a solvate, a hydrate, a prodrug, or a stereoisomer thereof.

TABLE 1

| Cmpd | Structure | Name |
|---|---|---|
| 1 | 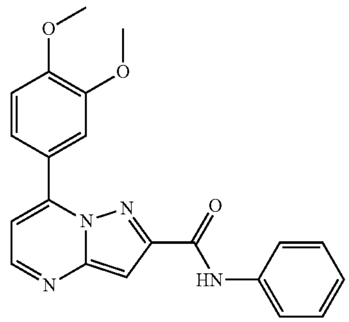 [SMILES: COc1ccc(-c2ccnc3cc(C(=O)Nc4ccccc4)nn23)cc1OC] | 7-(3,4-dimethoxyphenyl)-N-phenylpyrazolo[1,5-a]pyrimidine-2-carboxamide |
| 2 | 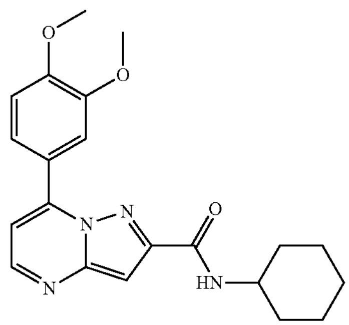 [SMILES: COc1ccc(-c2ccnc3cc(C(=O)NC4CCCCC4)nn23)cc1OC] | N-cyclohexyl-7-(3,4-dimethoxyphenyl)pyrazolo[1,5-a]pyrimidine-2-carboxamide |
| 4 | 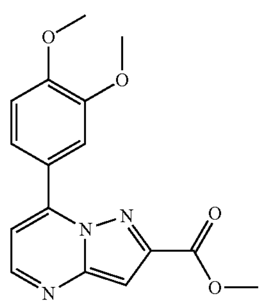 [SMILES: COC(=O)c1cc2nccc(-c3ccc(OC)c(OC)c3)n2n1] | methyl 7-(3,4-dimethoxyphenyl)pyrazolo[1,5-pyrimidine-2-carboxylate |
| 6 | 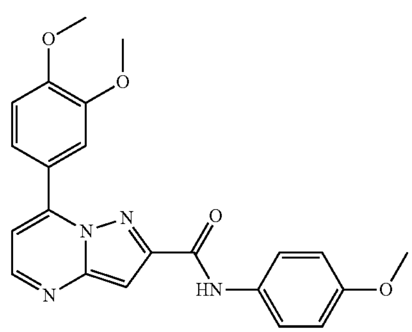 [SMILES: COc1ccc(NC(=O)c2cc3nccc(-c4ccc(OC)c(OC)c4)n3n2)cc1] | 7-(3,4-dimethoxyphenyl)-N-(4-methoxyphenyl)pyrazolo[1,5-a]pyrimidine-2-carboxamide |

TABLE 1-continued

Exemplary compounds

| Cmpd | Structure | Name |
|---|---|---|
| 7 | 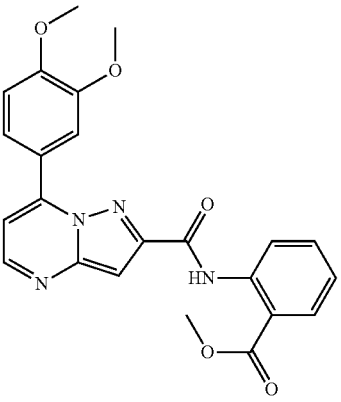 [SMILES: COC(=O)c1ccccc1NC(=O)c1cc2nccc(-c3ccc(OC)c(OC)c3)n2n1] | methyl 2-(7-(3,4-dimethoxyphenyl)pyrazolo[1,5-a]pyrimidine-2-carboxamido)benzoate |
| 8 | 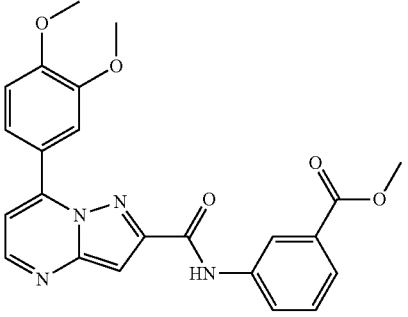 [SMILES: COC(=O)c1cccc(NC(=O)c2cc3nccc(-c4ccc(OC)c(OC)c4)n3n2)c1] | methyl 3-(7-(3,4-dimethoxyphenyl)pyrazolo[1,5-a]pyrimidine-2-carboxamido)benzoate |
| 9 | 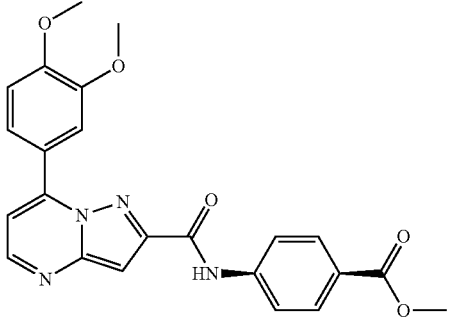 | methyl (1S,4S)-4-(7-(3,4-dimethoxyphenyl)pyrazolo[1,5-a]pyrimidine-2-carboxamido)cyclohexane-1-carboxylate |
| 10 | 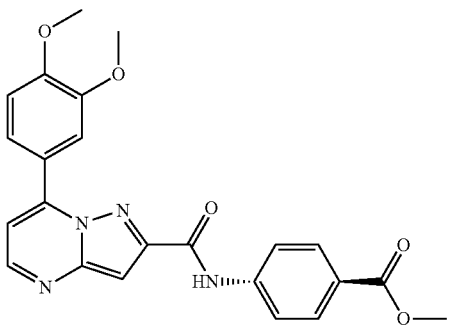 | methyl (1r,4r)-4-(7-(3,4-dimethoxyphenyl)pyrazolo[1,5-a]pyrimidine-2-carboxamido)cylohexane-1-carboxylate |

TABLE 1-continued

| Cmpd | Structure | Name |
|---|---|---|
| 12 | 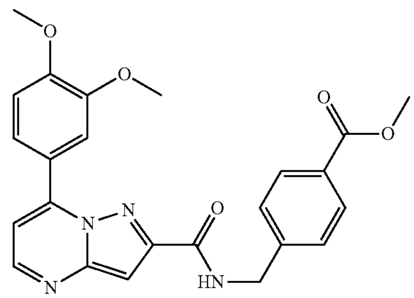 [SMILES: COC(=O)c1ccc(CNC(=O)c2cc3nccc(-c4ccc(OC)c(OC)c4)n3n2)cc1] | methyl 4-((7-(3,4-dimethoxyphenyl)pyrazolo[1,5-a]pyrimidine-2-carboxamido)methyl)benzoate |
| 13 | 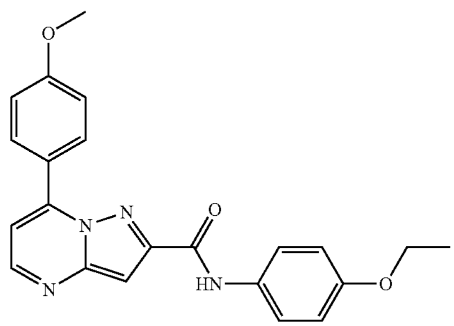 [SMILES: CCOc1ccc(NC(=O)c2cc3nccc(-c4ccc(OC)cc4)n3n2)cc1] | N-(4-ethoxyphenyl)-7-(4-methoxyphenyl)pyrazolo[1,5-a]pyrimidine-2-carboxamide |
| 14 | 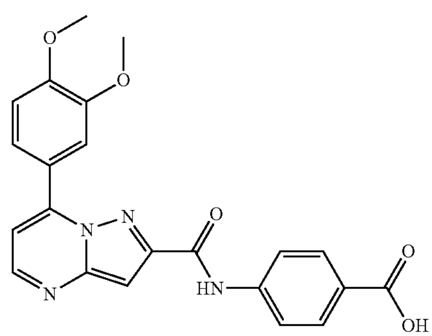 [SMILES: COc1ccc(-c2ccnc3cc(C(=O)Nc4ccc(C(=O)O)cc4)nn23)cc1OC] | 4-(7-(3,4-dimethoxyphenyl)pyrazolo[1,5-a]pyrimidine-2-carboxamido)benzoic acid |
| 15 | 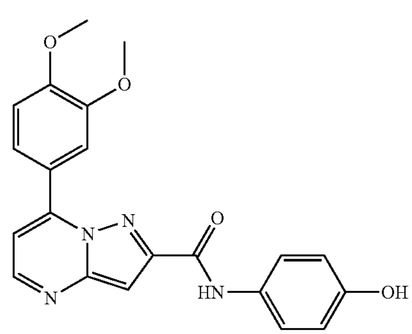 [SMILES: COc1ccc(-c2ccnc3cc(C(=O)Nc4ccc(O)cc4)nn23)cc1OC] | 7-(3,4-dimethoxyphenyl)-N-(4-hydroxyphenyl)pyrazolo[1,5-a]pyrimidine-2-carboxamide |

TABLE 1-continued

Exemplary compounds

| Cmpd | Structure | Name |
|---|---|---|
| 16 | 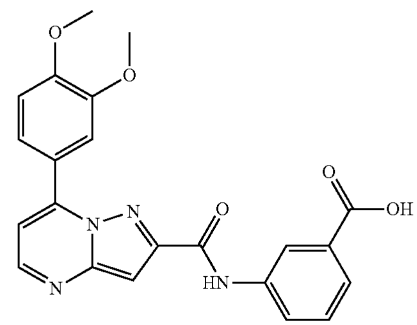 [SMILES: COc1ccc(-c2ccnc3cc(C(=O)Nc4cccc(C(=O)O)c4)nn23)cc1OC] | 3-(7-(3,4-dimethoxyphenyl)pyrazolo[1,5-a]pyrimidine-2-carboxamido)benzoic acid |
| 17 | 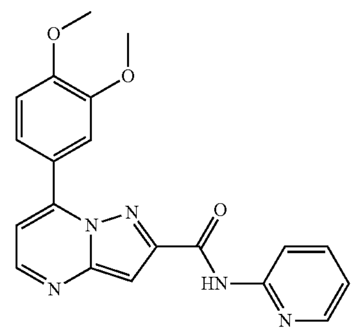 [SMILES: COc1ccc(-c2ccnc3cc(C(=O)Nc4ccccn4)nn23)cc1OC] | 7-(3,4-dimethoxyphenyl)-N-(pyridin-2-yl)pyrazolo[1,5-a]pyrimidine-2-carboxamide |
| 18 | 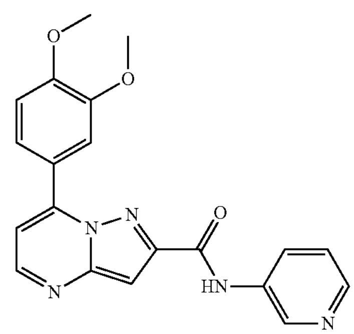 [SMILES: COc1ccc(-c2ccnc3cc(C(=O)Nc4cccnc4)nn23)cc1OC] | 7-(3,4-dimethoxyphenyl)-N-(pyridin-3-yl)pyrazolo[1,5-a]pyrimidine-2-carboxamide |
| 19 | 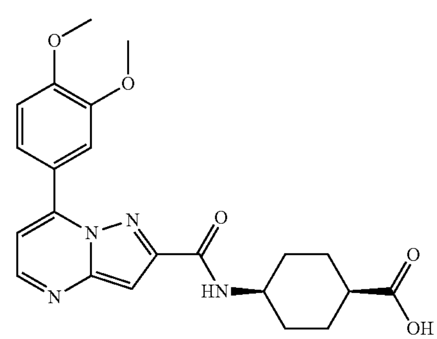 [SMILES: COc1ccc(-c2ccnc3cc(C(=O)N[C@H]4CC[C@@H](C(=O)O)CC4)nn23)cc1OC] | (1S,4S)-4-(7-(3,4-dimethoxyphenyl)pyrazolo[1,5-a]pyrimidine-2-carboxamido)cyclohexane-1-carboxylic acid |

TABLE 1-continued

Exemplary compounds

| Cmpd | Structure | Name |
|---|---|---|
| 20 | 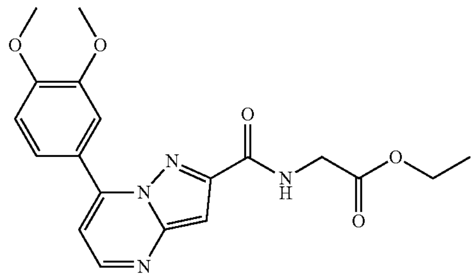 [SMILES: CCOC(=O)CNC(=O)c1cc2nccc(-c3ccc(OC)c(OC)c3)n2n1] | ethyl (7-(3,4-dimethoxyphenyl)pyrazolo[1,5-a]pyrimidine-2-carbonyl)glycinate |
| 21 | 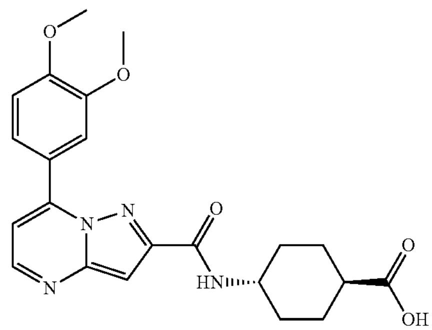 [SMILES: COc1ccc(-c2ccnc3cc(C(=O)N[C@H]4CC[C@H](C(=O)O)CC4)nn23)cc1OC] | (1R,4R)-4-(7-(3,4-dimethoxyphenyl)pyrazolo[1,5-a]pyrimidine-2-carboxamido)cyclohexane-1-carboxylic acid |
| 22 | 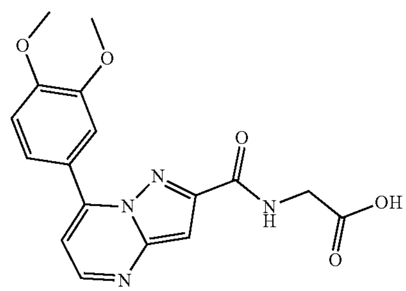 [SMILES: COc1ccc(-c2ccnc3cc(C(=O)NCC(=O)O)nn23)cc1OC] | (7-(3,4-dimethoxyphenyl)pyrazolo[1,5-a]pyrimidine-2-carbonyl)glycine |
| 23 | 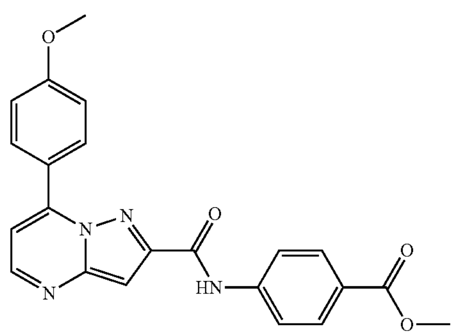 [SMILES: COC(=O)c1ccc(NC(=O)c2cc3nccc(-c4ccc(OC)cc4)n3n2)cc1] | methyl 4-(7-(4-methoxyphenyl)pyrazolo[1,5-a]pyrimidine-2-carboxamido)benzoate |
| 24 | 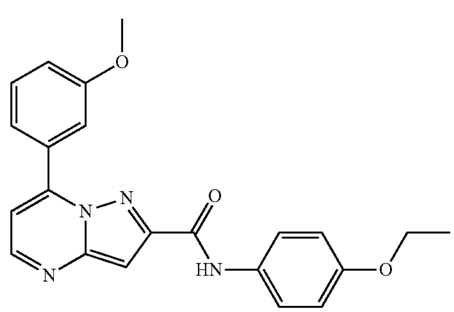 [SMILES: CCOc1ccc(NC(=O)c2cc3nccc(-c4cccc(OC)c4)n3n2)cc1] | N-(4-ethoxyphenyl)-7-(3-methoxyphenyl)pyrazolo[1,5-a]pyrimidine-2-carboxamide |

TABLE 1-continued

Exemplary compounds

| Cmpd | Structure | Name |
|---|---|---|
| 25 | 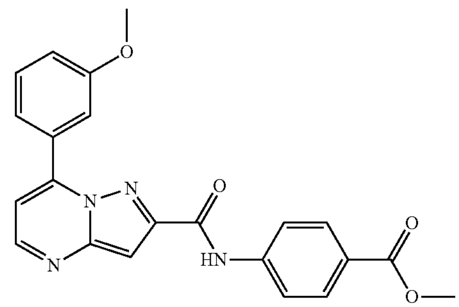 [SMILES: COC(=O)c1ccc(NC(=O)c2cc3nccc(-c4cccc(OC)c4)n3n2)cc1] | methyl 4-(7-(3-methoxyphenyl)pyrazolo[1,5-a]pyrimidine-2-carboxamido)benzoate |
| 26 | 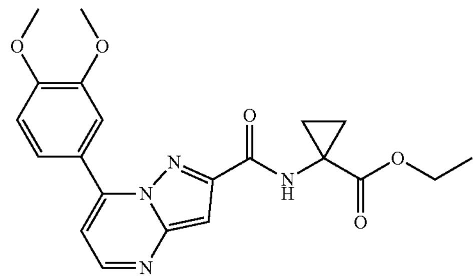 [SMILES: CCOC(=O)C1(NC(=O)c2cc3nccc(-c4ccc(OC)c(OC)c4)n3n2)CC1] | ethyl 1-(7-(3,4-dimethoxyphenyl)pyrazolo[1,5-a]pyrimidine-2-carboxamido)cyclopropane-1-carboxylate |
| 27 | 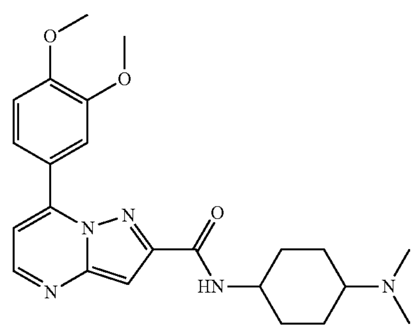 [SMILES: COc1ccc(-c2ccnc3cc(C(=O)NC4CCC(N(C)C)CC4)nn23)cc1OC] | 7-(3,4-dimethoxyphenyl)-N-(4-(dimethylamino)cyclohexyl)pyrazolo[1,5-a]pyrimidine-2-carboxamide |
| 28 | 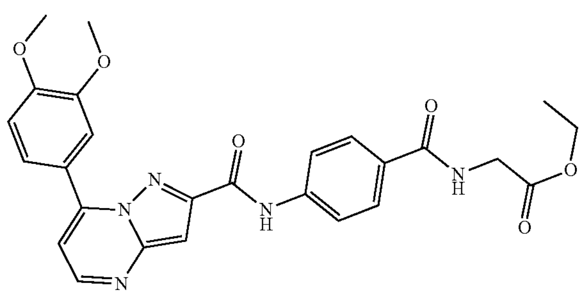 [SMILES: CCOC(=O)CNC(=O)c1ccc(NC(=O)c2cc3nccc(-c4ccc(OC)c(OC)c4)n3n2)cc1] | ethyl (4-(7-(3,4-dimethoxyphenyl)pyrazolo[1,5-a]pyrimidine-2-carboxamido)benzoyl)glycinate |
| 29 | 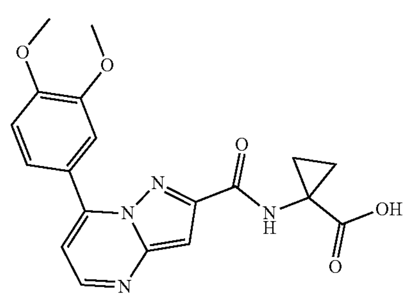 [SMILES: COc1ccc(-c2ccnc3cc(C(=O)NC4(C(=O)O)CC4)nn23)cc1OC] | 1-(7-(3,4-dimethoxyphenyl)pyrazolo[1,5-a]pyrimidine-2-carboxamido)cyclopropane-1-carboxylic acid |

TABLE 1-continued

Exemplary compounds

| Cmpd | Structure | Name |
|---|---|---|
| 30 | 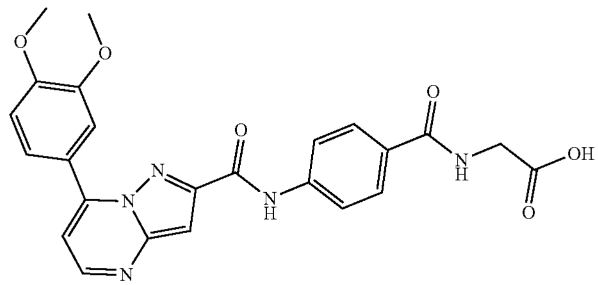 [SMILES: COc1ccc(-c2ccnc3cc(C(=O)Nc4ccc(C(=O)NCC(=O)O)cc4)nn23)cc1OC] | (4-(7-(3,4-dimethoxyphenyl)pyrazolo[1,5-a]pyrimidine-2-carboxamido)benzoyl)glycine |
| 31 | 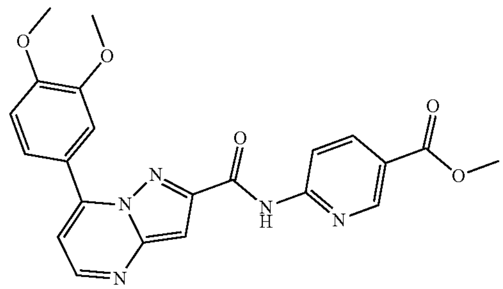 [SMILES: COC(=O)c1ccc(NC(=O)c2cc3nccc(-c4ccc(OC)c(OC)c4)n3n2)nc1] | methyl 6-(7-(3,4-dimethoxyphenyl)pyrazolo[1,5-a]pyrimidine-2-carboxamido)nicotinate |
| 32 | 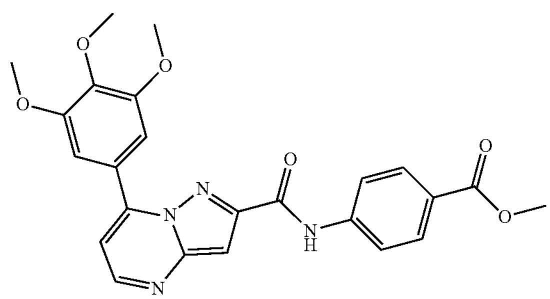 | methyl 4-(7-(3,4,5-trimethoxyphenyl)pyrazolo[1,5-a]pyrimidine-2-carboxamido)benzoate |
| 33 | 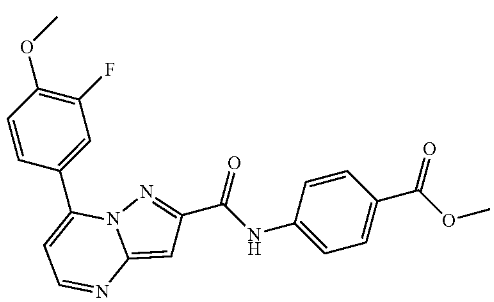 [SMILES: COC(=O)c1ccc(NC(=O)c2cc3nccc(-c4ccc(OC)c(F)c4)n3n2)cc1] | methyl 4-(7-(3-fluoro-4-methoxyphenyl)pyrazolo[1,5-a]pyrimidine-2-carboxamido)benzoate |
| 34 | 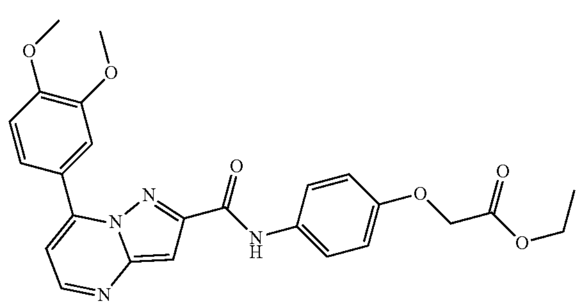 [SMILES: CCOC(=O)COc1ccc(NC(=O)c2cc3nccc(-c4ccc(OC)c(OC)c4)n3n2)cc1] | ethyl 2-(4-(7-(3,4-dimethoxyphenyl)pyrazolo[1,5-a]pyrimidine-2-carboxamido)phenoxy)acetate |

TABLE 1-continued

| Cmpd | Structure | Name |
|---|---|---|
| 35 | 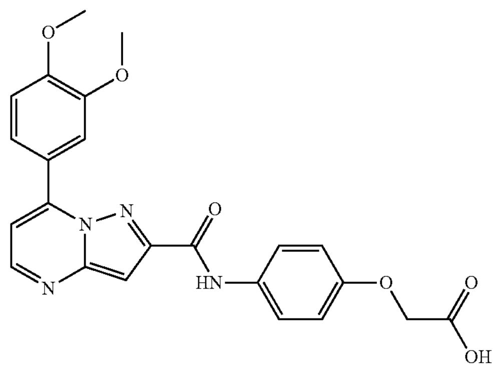 [SMILES: COc1ccc(-c2ccnc3cc(C(=O)Nc4ccc(OCC(=O)O)cc4)nn23)cc1OC] | 2-(4-(7-(3,4-dimethoxyphenyl)pyrazolo[1,5-a]pyrimidine-2-carboxamido)phenoxy)acetic acid |
| 36 | 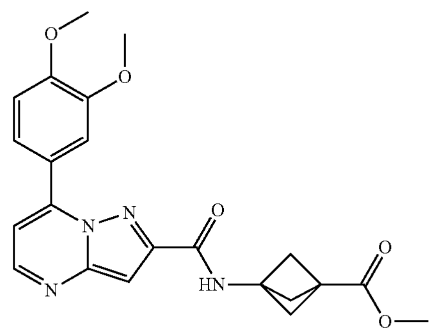 [SMILES: COC(=O)C12CC(NC(=O)c3cc4nccc(-c5ccc(OC)c(OC)c5)n4n3)(C1)C2] | methyl 3-(7-(3,4-dimethoxyphenyl)pyrazolo[1,5-a]pyrimidine-2-carboxamido)bicyclo[1.1.1]pentane-1-carboxylate |
| 37 | 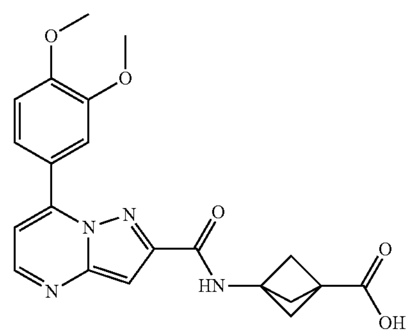 [SMILES: COc1ccc(-c2ccnc3cc(C(=O)NC45CC(C(=O)O)(C4)C5)nn23)cc1OC] | 3-(7-(3,4-dimethoxyphenyl)pyrazolo[1,5-a]pyrimidine-2-carboxamido)bicyclo[1.1.1]pentane-1-carboxylic acid |
| 38 | 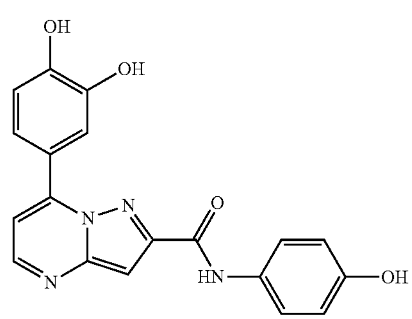 [SMILES: O=C(Nc1ccc(O)cc1)c1cc2nccc(-c3ccc(O)c(O)c3)n2n1] | 7-(3,4-dihydroxyphenyl)-N-(4-hydroxyphenyl)pyrazolo[1,5-a]pyrimidine-2-carboxamide |

TABLE 1-continued

Exemplary compounds

| Cmpd | Structure | Name |
|---|---|---|
| 39 | 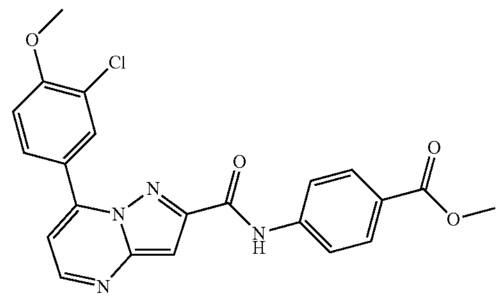 | methyl 4-(7-(3-chloro-4-methoxyphenyl)pyrazolo[1,5-a]pyrimidine-2-carboxamido)benzoate |
| 40 | 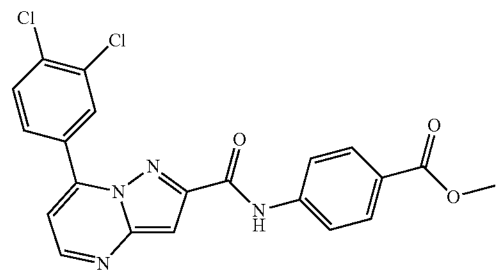 [SMILES: COC(=O)c1ccc(NC(=O)c2cc3nccc(-c4ccc(Cl)c(Cl)c4)n3n2)cc1] | methyl 4-(7-(3,4-dichlorophenyl)pyrazolo[1,5-a]pyrimidine-2-carboxamido)benzoate |
| 41 | 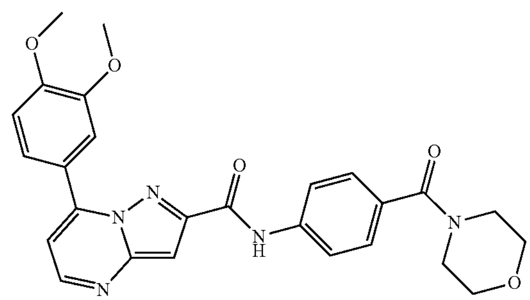 [SMILES: COc1ccc(-c2ccnc3cc(C(=O)Nc4ccc(C(=O)N5CCOCC5)cc4)nn23)cc1OC] | 7-(3,4-dimethoxyphenyl)-N-(4-(morpholine-4-carbonyl)phenyl)pyrazolo[1,5-a]pyrimidine-2-carboxamide |
| 42 | 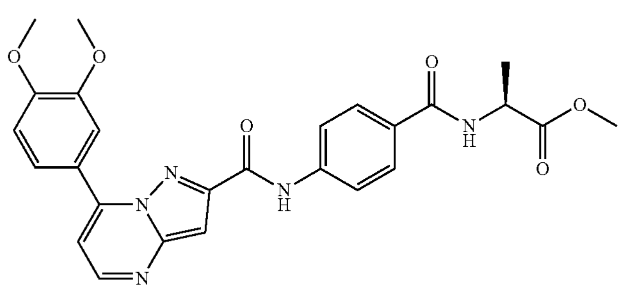 [SMILES: COC(=O)[C@H](C)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-alaninate |
| 43 | 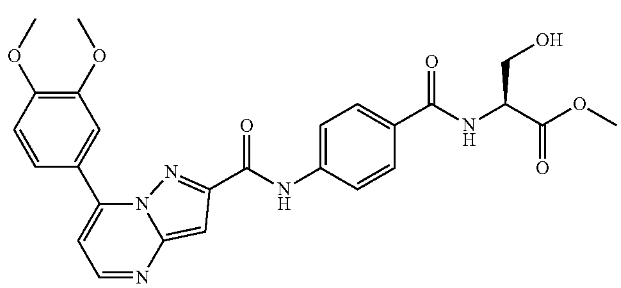 [SMILES: COC(=O)[C@H](CO)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-serinate |

TABLE 1-continued

Exemplary compounds

| Cmpd | Structure | Name |
|---|---|---|
| 44 | 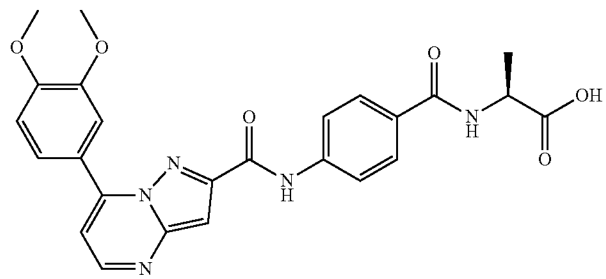 [SMILES: COc1ccc(-c2ccnc3cc(C(=O)Nc4ccc(C(=O)N[C@@H](C)C(=O)O)cc4)nn23)cc1OC] | (4-(7-(3,4-dimethoxyphenyl)pyrazolo[1,5-a]pyrimidine-2-carboxamido)benzoyl)-L-alanine |
| 45 | 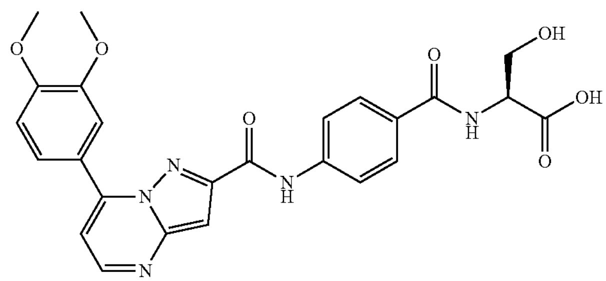 [SMILES: COc1ccc(-c2ccnc3cc(C(=O)Nc4ccc(C(=O)N[C@@H](CO)C(=O)O)cc4)nn23)cc1OC] | (4-(7-(3,4-dimethoxyphenyl)pyrazolo[1,5-a]pyrimidine-2-carboxamido)benzoyl)-L-serine |
| 46 | 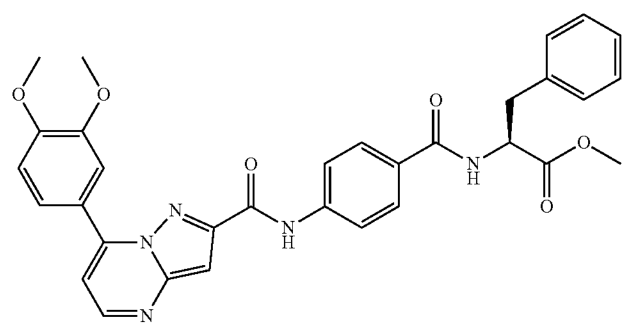 [SMILES: COC(=O)[C@H](Cc1ccccc1)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-phenylalaninate |
| 47 | 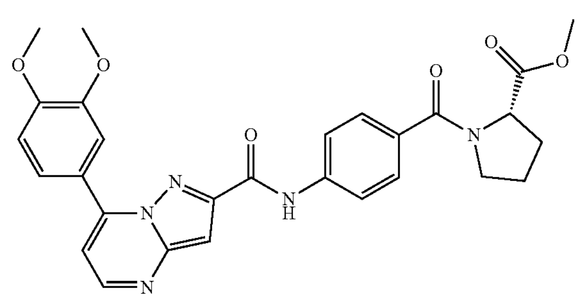 [SMILES: COC(=O)[C@@H]1CCCN1C(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-prolinate |
| 48 | 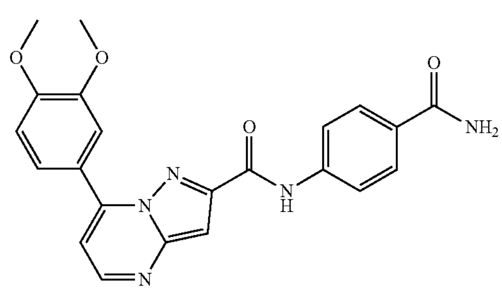 [SMILES: COc1ccc(-c2ccnc3cc(C(=O)Nc4ccc(C(N)=O)cc4)nn23)cc1OC] | N-(4-carbamoylphenyl)-7-(3,4-dimethoxyphenyl)pyrazolo[1,5-a]pyrimidine-2-carboxamide |

TABLE 1-continued

Exemplary compounds

| Cmpd | Structure | Name |
|---|---|---|
| 49 | 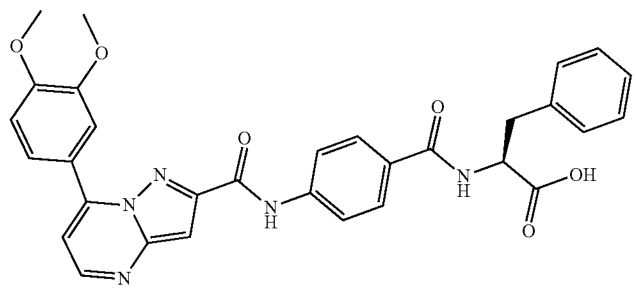 [SMILES: COc1ccc(-c2ccnc3cc(C(=O)Nc4ccc(C(=O)N[C@@H](Cc5ccccc5)C(=O)O)cc4)nn23)cc1OC] | (4-(7-(3,4-dimethoxyphenyl) pyrazolo[1,5-a]pyrimidine-2-carboxamido) benzoyl)-L-phenylalanine |
| 50 | 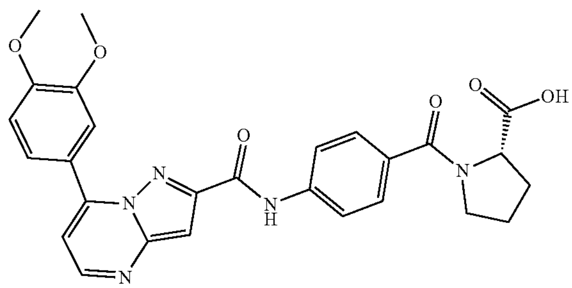 [SMILES: COc1ccc(-c2ccnc3cc(C(=O)Nc4ccc(C(=O)N5CCC[C@H]5C(=O)O)cc4)nn23)cc1OC] | (4-(7-(3,4-dimethoxyphenyl) pyrazolo[1,5-a]pyrimidine-2-carboxamido) benzoyl)-L-proline |
| 51 | 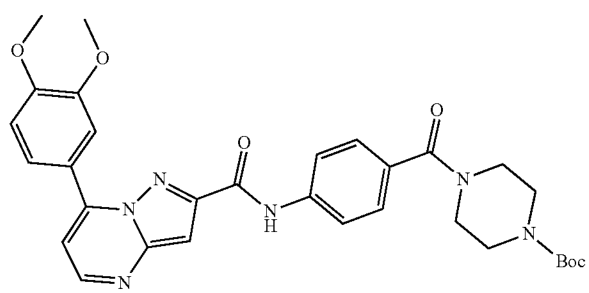 [SMILES: COc1ccc(-c2ccnc3cc(C(=O)Nc4ccc(C(=O)N5CCN(C(=O)OC(C)(C)C)CC5)cc4)nn23)cc1OC] | tert-butyl 4-(4-(7-(3,4-dimethoxyphenyl)pyrazolo [1,5-a]pyrimidine-2-carboxamido)benzoyl) piperazine-1-carboxylate |
| 52 | 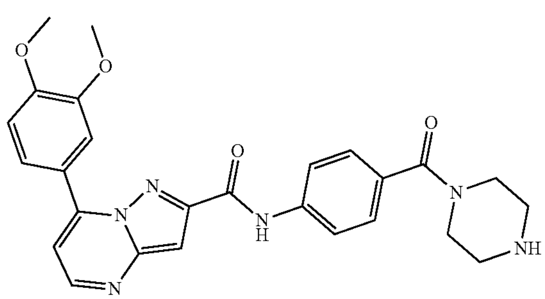 [SMILES: COc1ccc(-c2ccnc3cc(C(=O)Nc4ccc(C(=O)N5CCNCC5)cc4)nn23)cc1OC] | 7-(3,4-dimethoxyphenyl)-N-(4-(piperazine-1-carbonyl)phenyl)pyrazolo [1,5-a]pyrimidine-2-carboxamide |
| 53 | 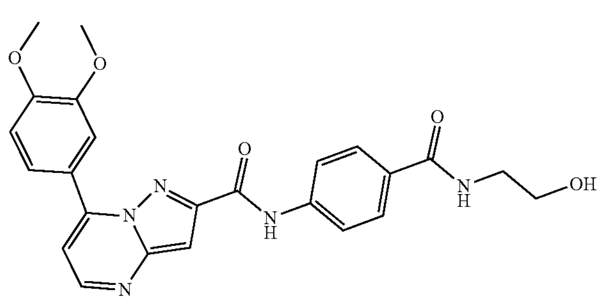 [SMILES: COc1ccc(-c2ccnc3cc(C(=O)Nc4ccc(C(=O)NCCO)cc4)nn23)cc1OC] | 7-(3,4-dimethoxyphenyl)-N-(4-((2-hydroxyethyl)carbamoyl) phenyl)pyrazolo[1,5-a]pyrimidine-2-carboxamide |

TABLE 1-continued

Exemplary compounds

| Cmpd | Structure | Name |
|---|---|---|
| 54 | 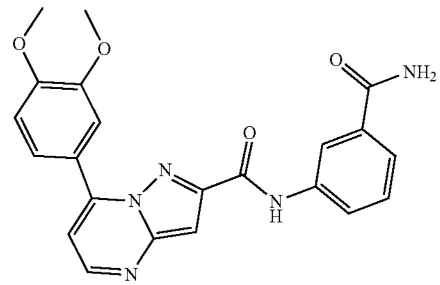 [SMILES: COc1ccc(-c2ccnc3cc(C(=O)Nc4cccc(C(N)=O)c4)nn23)cc1OC] | N-(3-carbamoylphenyl)-7-(3,4-dimethoxyphenyl)pyrazolo[1,5-a]pyrimidine-2-carboxamide |
| 55 | 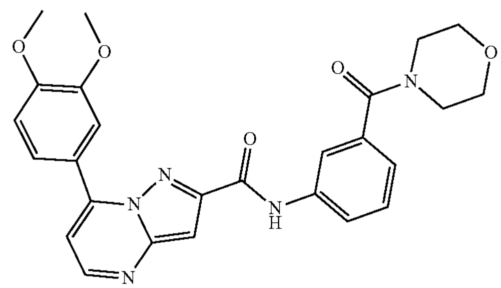 [SMILES: COc1ccc(-c2ccnc3cc(C(=O)Nc4cccc(C(=O)N5CCOCC5)c4)nn23)cc1OC] | 7-(3,4-dimethoxyphenyl)-N-(3-(morpholine-4-carbonyl)phenyl)pyrazolo[1,5-a]pyrimidine-2-carboxamide |
| 56 | 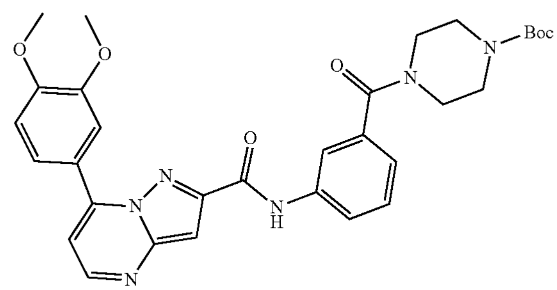 [SMILES: COc1ccc(-c2ccnc3cc(C(=O)Nc4cccc(C(=O)N5CCN(C(=O)OC(C)(C)C)CC5)c4)nn23)cc1OC] | tert-butyl 4-(3-(7-(3,4-dimethoxyphenyl)pyrazolo[1,5-a]pyrimidine-2-carboxamido)benzoyl)piperazine-1-carboxylate |
| 57 | 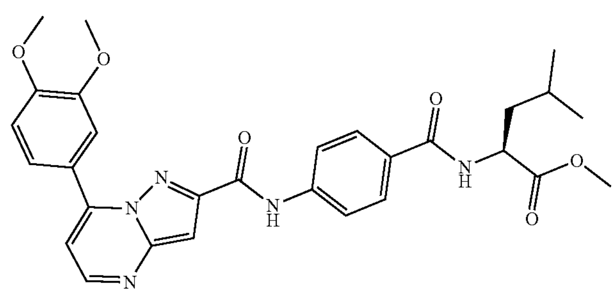 [SMILES: COC(=O)[C@H](CC(C)C)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-leucinate |
| 58 | 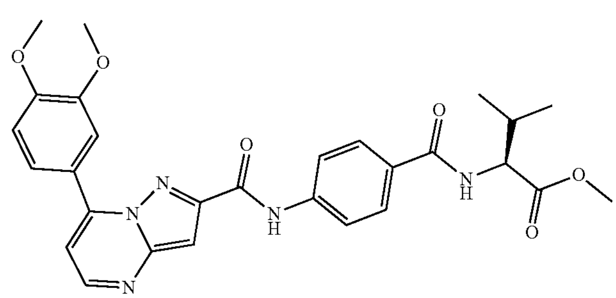 [SMILES: COC(=O)[C@@H](NC(=O)c1ccc(NC(=O)c2cc3nccc(-c4ccc(OC)c(OC)c4)n3n2)cc1)C(C)C] | methyl (4-(7-(3,4-dimethoxyphenyl)pyrazolo[1,5-a]pyrimidine-2-carboxamido)benzoyl)-L-valinate |

TABLE 1-continued

Exemplary compounds

| Cmpd | Structure | Name |
|---|---|---|
| 59 | 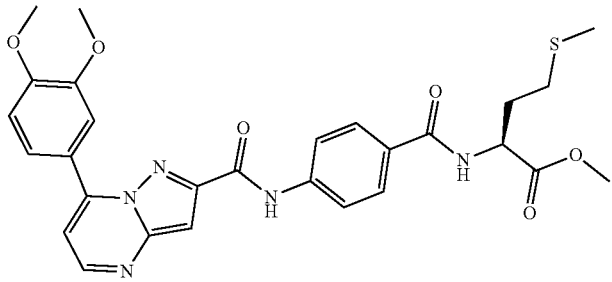 [SMILES: COC(=O)[C@H](CCSC)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-L-methioninate |
| 60 | 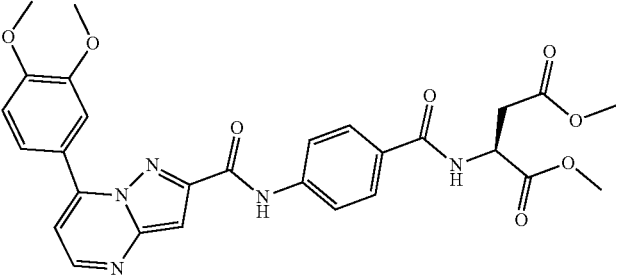 [SMILES: COC(=O)C[C@H](NC(=O)c1ccc(NC(=O)c2cc3nccc(-c4ccc(OC)c(OC)c4)n3n2)cc1)C(=O)OC] | dimethyl (4-(7-(3,4-dimethoxyphenyl)pyrazolo[1,5-a]pyrimidine-2-carboxamido)benzoyl)-L-aspartate |
| 61 | 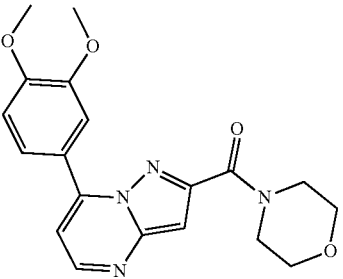 [SMILES: COc1ccc(-c2ccnc3cc(C(=O)N4CCOCC4)nn23)cc1OC] | (7-(3,4-dimethoxyphenyl)pyrazolo[1,5-a]pyrimidine-2-yl)(morpholino)methanone |
| 62 | 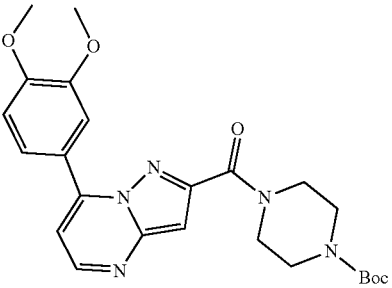 [SMILES: COc1ccc(-c2ccnc3cc(C(=O)N4CCN(C(=O)OC(C)(C)C)CC4)nn23)cc1OC] | tert-butyl 4-(7-(3,4-dimethoxyphenyl)pyrazolo[1,5-a]pyrimidine-2-carbonyl)piperazine-1-carboxylate |
| 63 | 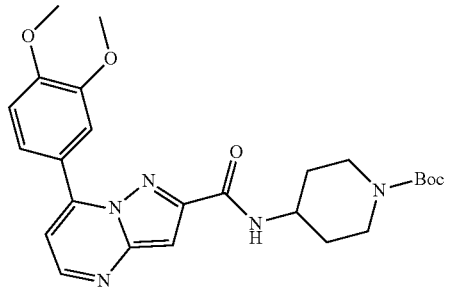 [SMILES: COc1ccc(-c2ccnc3cc(C(=O)NC4CCN(C(=O)OC(C)(C)C)CC4)nn23)cc1OC] | tert-butyl 4-(7-(3,4-dimethoxyphenyl)pyrazolo[1,5-a]pyrimidine-2-carboxamido)piperidine-1-carboxylate |

TABLE 1-continued

| Cmpd | Structure | Name |
|---|---|---|
| 64 | 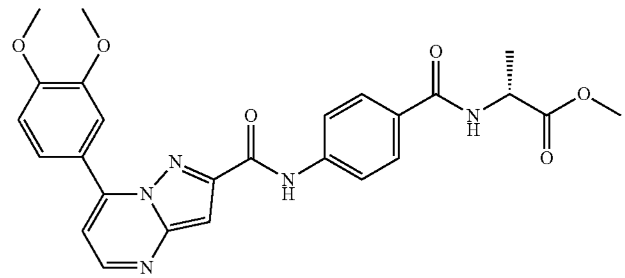 [SMILES: COC(=O)[C@@H](C)NC(=O)c1ccc(NC(=O)c2cc3nccc(-c4ccc(OC)c(OC)c4)n3n2)cc1] | methyl (4-(7-(3,4-dimethoxyphenyl)pyrazolo[1,5-a]pyrimidine-2-carboxamido)benzoyl)-D-alaninate |
| 65 | 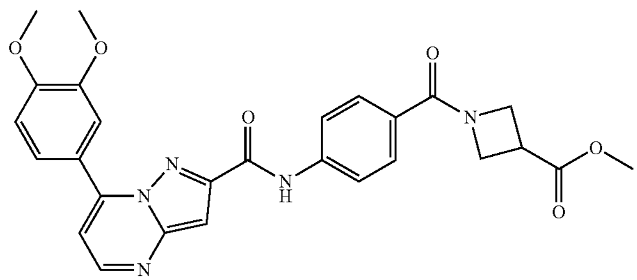 [SMILES: COC(=O)C1CN(C(=O)c2ccc(NC(=O)c3cc4nccc(-c5ccc(OC)c(OC)c5)n4n3)cc2)C1] | methyl 1-(4-(7-(3,4-dimethoxyphenyl)pyrazolo[1,5-a]pyrimidine-2-carboxamido)benzoyl)azetidine-3-carboxylate |
| 66 | 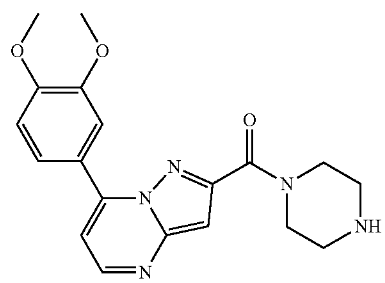 [SMILES: COc1ccc(-c2ccnc3cc(C(=O)N4CCNCC4)nn23)cc1OC] | (7-(3,4-dimethoxyphenyl)pyrazolo[1,5-a]pyrimidin-2-yl)(piperazin-1-yl)methanone |
| 67 | 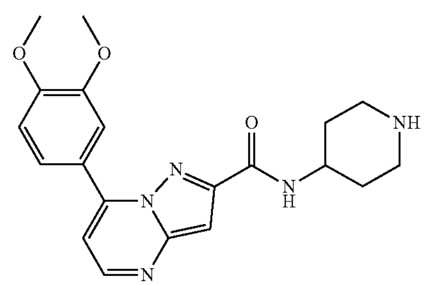 [SMILES: COc1ccc(-c2ccnc3cc(C(=O)NC4CCNCC4)nn23)cc1OC] | 7-(3,4-dimethoxyphenyl)-N-(piperidin-4-yl)pyrazolo[1,5-a]pyrimidine-2-carboxamide |
| 68 | 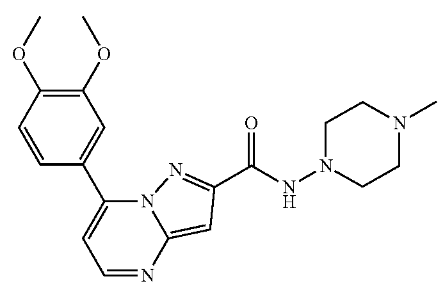 [SMILES: COc1ccc(-c2ccnc3cc(C(=O)NN4CCN(C)CC4)nn23)cc1OC] | 7-(3,4-dimethoxyphenyl)-N-(4-methylpiperazin-1-yl)pyrazolo[1,5-a]pyrimidine-2-carboxamide |

TABLE 1-continued

Exemplary compounds

| Cmpd | Structure | Name |
|---|---|---|
| 69 | 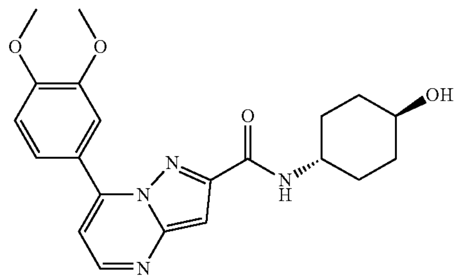 [SMILES: COc1ccc(-c2ccnc3cc(C(=O)N[C@H]4CC[C@H](O)CC4)nn23)cc1OC] | 7-(3,4-dimethoxyphenyl)-N-((1R,4R)-4-hydroxycyclohexyl)pyrazolo[1,5-a]pyrimidine-2-carboxamide |
| 70 | 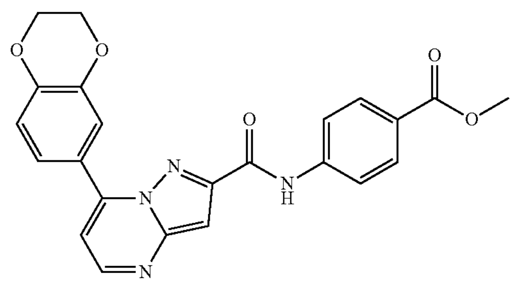 [SMILES: COC(=O)c1ccc(NC(=O)c2cc3nccc(-c4ccc5c(c4)OCCO5)n3n2)cc1] | methyl 4-(7-(2,3-dihydrobenzo[b][1,4]dioxin-6-yl)pyrazolo[1,5-a]pyrimidine-2-carboxamido)benzoate |
| 71 | 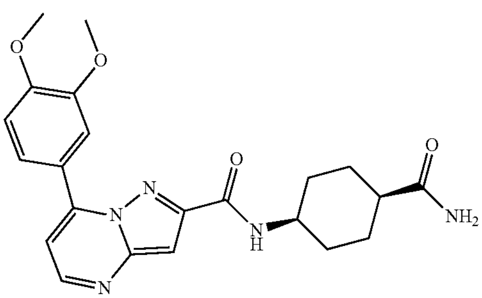 [SMILES: COc1ccc(-c2ccnc3cc(C(=O)N[C@H]4CC[C@@H](C(N)=O)CC4)nn23)cc1OC] | N-((1S,4S)-4-carbamoyl-cyclohexyl)-7-(3,4-dimethoxyphenyl)pyrazolo[1,5-a]pyrimidine-2-carboxamide |
| 72 | 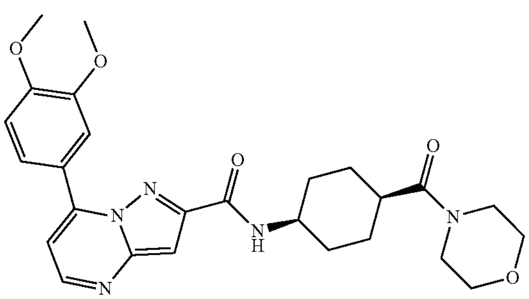 [SMILES: COc1ccc(-c2ccnc3cc(C(=O)N[C@H]4CC[C@@H](C(=O)N5CCOCC5)CC4)nn23)cc1OC] | 7-(3,4-dimethoxyphenyl)-N-((1S,4S)-4-(morpholine-4-carbonyl)cyclohexyl)pyrazolo[1,5-a]pyrimidine-2-carboxamide |
| 73 | 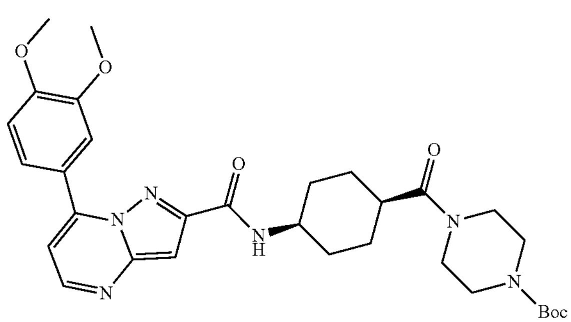 [SMILES: COc1ccc(-c2ccnc3cc(C(=O)N[C@H]4CC[C@@H](C(=O)N5CCN(C(=O)OC(C)(C)C)CC5)CC4)nn23)cc1OC] | tert-butyl 4-((1S,4S)-4-(7-(3,4-dimethoxyphenyl)pyrazolo[1,5-a]pyrimidine-2-carboxamido)cyclohexane-1-carbonyl)piperazine-1-carboxylate |

TABLE 1-continued

Exemplary compounds

| Cmpd | Structure | Name |
|---|---|---|
| 74 | 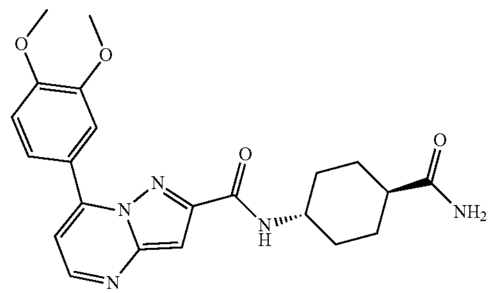 [SMILES: COc1ccc(-c2ccnc3cc(C(=O)N[C@H]4CC[C@H](C(N)=O)CC4)nn23)cc1OC] | N-((1R,4R)-4-carbamoyl-cyclohexyl)-7-(3,4-dimethoxyphenyl)pyrazolo[1,5-a]pyrimidine-2-carboxamide |
| 75 | 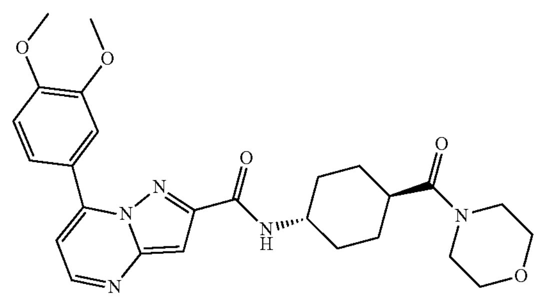 [SMILES: COc1ccc(-c2ccnc3cc(C(=O)N[C@H]4CC[C@H](C(=O)N5CCOCC5)CC4)nn23)cc1OC] | 7-(3,4-dimethoxyphenyl)-N-((1R,4R)-4-(morpholine-4-carbonyl)cyclohexyl)pyrazolo[1,5-a]pyrimidine-2-carboxamide |
| 76 | 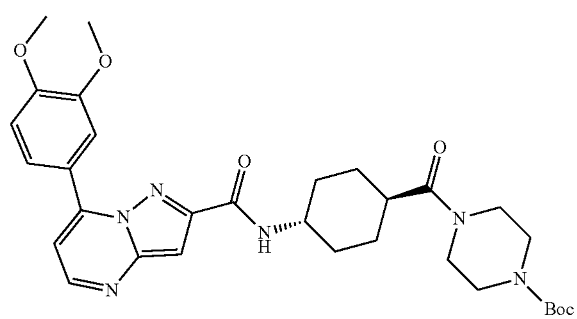 [SMILES: COc1ccc(-c2ccnc3cc(C(=O)N[C@H]4CC[C@H](C(=O)N5CCN(C(=O)OC(C)(C)C)CC5)CC4)nn23)cc1OC] | tert-butyl 4-((1R,4R)-4-(7-(3,4-dimethoxyphenyl)pyrazolo[1,5-a]pyrimidine-2-carboxamido)cyclohexane-1-carbonyl)piperazine-1-carboxylate |
| 77 | 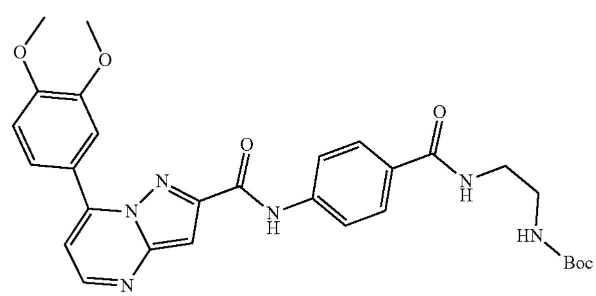 [SMILES: COc1ccc(-c2ccnc3cc(C(=O)Nc4ccc(C(=O)NCCNC(=O)OC(C)(C)C)cc4)nn23)cc1OC] | tert-butyl (2-(4-(7-(3,4-dimethoxyphenyl)pyrazolo[1,5-a]pyrimidine-2-carboxamido)benzamido)ethyl)carbamate |
| 78 | 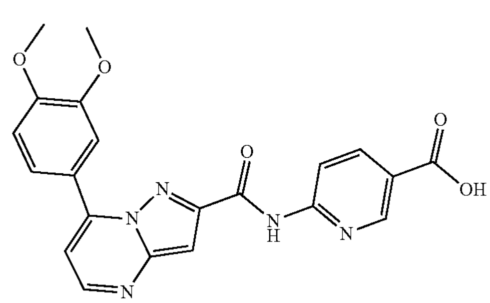 [SMILES: COc1ccc(-c2ccnc3cc(C(=O)Nc4ccc(C(=O)O)cn4)nn23)cc1OC] | 6-(7-(3,4-dimethoxyphenyl)pyrazolo[1,5-a]pyrimidine-2-carboxamido)nicotinic acid |

TABLE 1-continued

Exemplary compounds

| Cmpd | Structure | Name |
|---|---|---|
| 79 | 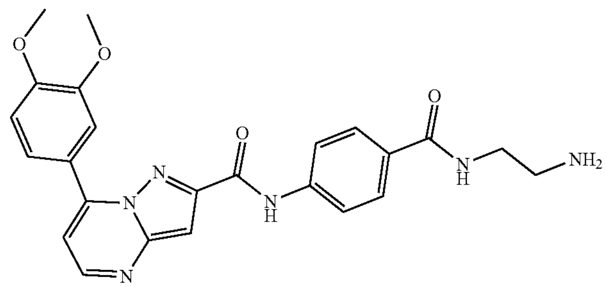 [SMILES: COc1ccc(-c2ccnc3cc(C(=O)Nc4ccc(C(=O)NCCN)cc4)nn23)cc1OC] | N-(4-((2-aminoethyl)carbamoyl)phenyl)-7-(3,4-dimethoxyphenyl)pyrazolo[1,5-a]pyrimidine-2-carboxamide |
| 80 | 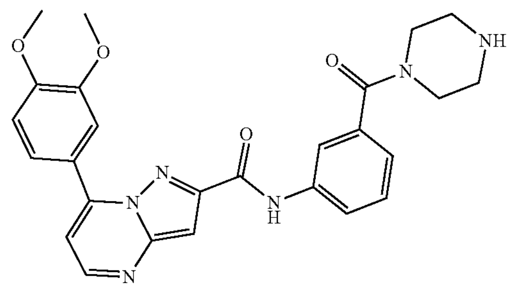 [SMILES: COc1ccc(-c2ccnc3cc(C(=O)Nc4cccc(C(=O)N5CCNCC5)c4)nn23)cc1OC] | 7-(3,4-dimethoxyphenyl)-N-(3-(piperazine-1-carbonyl)phenyl)pyrazolo[1,5-a]pyrimidine-2-carboxamide |
| 81 | 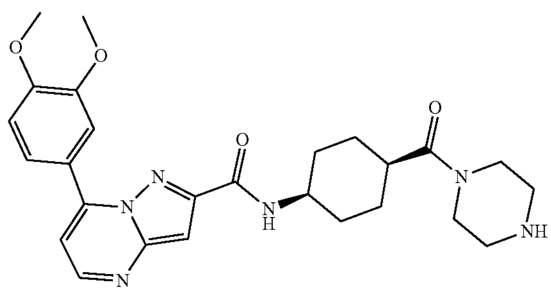 [SMILES: COc1ccc(-c2ccnc3cc(C(=O)N[C@H]4CC[C@@H](C(=O)N5CCNCC5)CC4)nn23)cc1OC] | 7-(3,4-dimethoxyphenyl)-N-((1S,4S)-4-(piperazine-1-carbonyl)cyclohexyl)pyrazolo[1,5-a]pyrimidine-2-carboxamide |
| 82 | 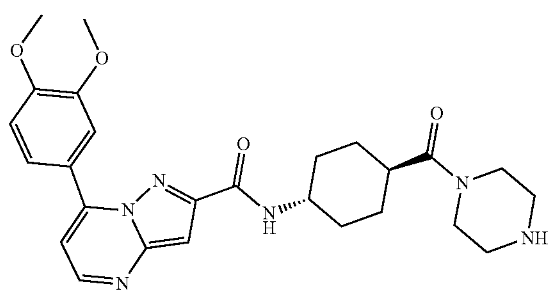 [SMILES: COc1ccc(-c2ccnc3cc(C(=O)N[C@H]4CC[C@H](C(=O)N5CCNCC5)CC4)nn23)cc1OC] | 7-(3,4-dimethoxyphenyl)-N-((1R,4R)-4-(piperazine-1-carbonyl)cyclohexyl)pyrazolo[1,5-a]pyrimidine-2-carboxamide |
| 83 | 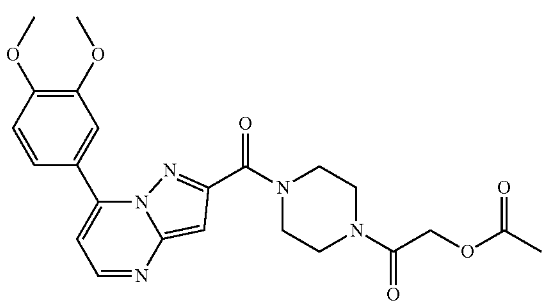 [SMILES: COc1ccc(-c2ccnc3cc(C(=O)N4CCN(C(=O)COC(C)=O)CC4)nn23)cc1OC] | 2-(4-(7-(3,4-dimethoxyphenyl)pyrazolo[1,5-a]pyrimidine-2-carbonyl)piperazin-1-yl)-2-oxoethyl acetate |

TABLE 1-continued

Exemplary compounds

| Cmpd | Structure | Name |
| --- | --- | --- |
| 84 | 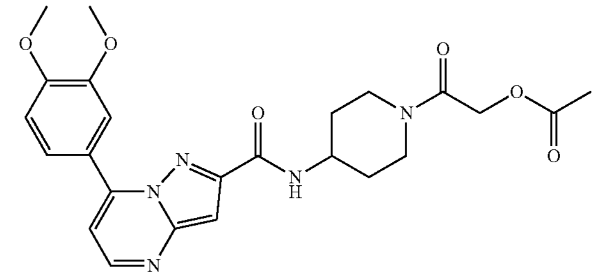 [SMILES: COc1ccc(-c2ccnc3cc(C(=O)NC4CCN(C(=O)COC(C)=O)CC4)nn23)cc1OC] | 2-(4-(7-(3,4-dimethoxy-phenyl)pyrazolo[1,5-a]pyrimidine-2-carboxamido)piperidin-1-yl)-2-oxoethyl acetate |
| 85 | 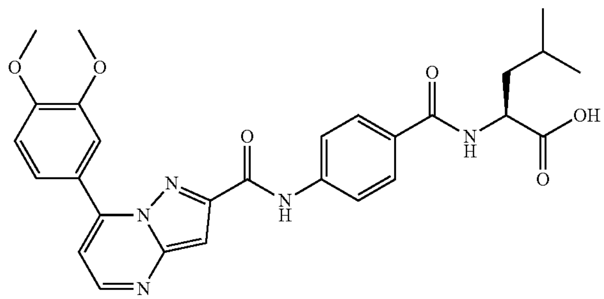 [SMILES: COc1ccc(-c2ccnc3cc(C(=O)Nc4ccc(C(=O)N[C@@H](CC(C)C)C(=O)O)cc4)nn23)cc1OC] | (4-(7-(3,4-dimethoxy-phenyl)pyrazolo[1,5-a]pyrimidine-2-carboxamido)benzoyl)-L-leucine |
| 86 | 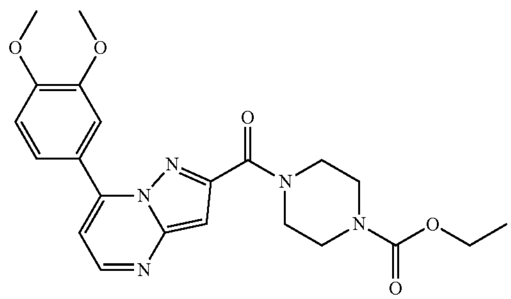 [SMILES: CCOC(=O)N1CCN(C(=O)c2cc3nccc(-c4ccc(OC)c(OC)c4)n3n2)CC1] | ethyl 4-(7-(3,4-dimethoxy-phenyl)pyrazolo[1,5-a]pyrimidine-2-carbonyl)piperazine-1-carboxylate |
| 87 | 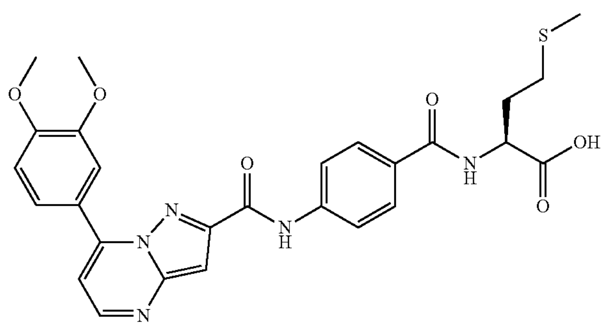 [SMILES: COc1ccc(-c2ccnc3cc(C(=O)Nc4ccc(C(=O)N[C@@H](CCSC)C(=O)O)cc4)nn23)cc1OC] | (4-(7-(3,4-dimethoxy-phenyl)pyrazolo[1,5-a]pyrimidine-2-carboxamido)benzoyl)-L-methionine |
| 88 | 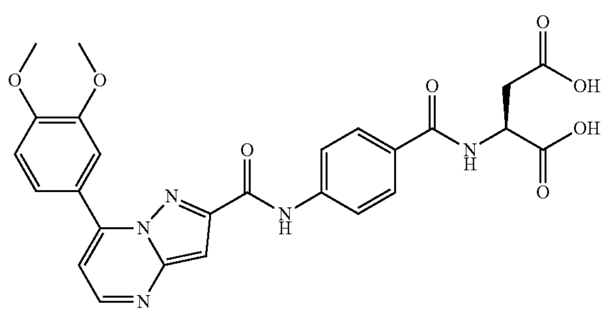 [SMILES: COc1ccc(-c2ccnc3cc(C(=O)Nc4ccc(C(=O)N[C@@H](CC(=O)O)C(=O)O)cc4)nn23)cc1OC] | (4-(7-(3,4-dimethoxy-phenyl)pyrazolo[1,5-a]pyrimidine-2-carboxamido)benzoyl)-L-aspartic acid |

TABLE 1-continued

Exemplary compounds

| Cmpd | Structure | Name |
|---|---|---|
| 89 | 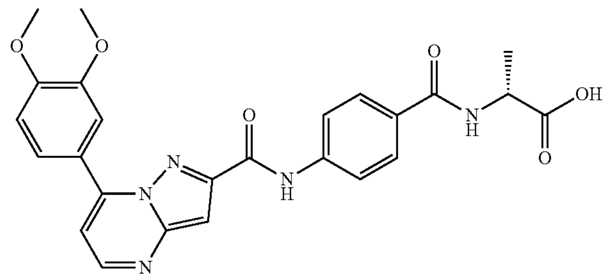 [SMILES: COc1ccc(-c2ccnc3cc(C(=O)Nc4ccc(C(=O)N[C@H](C)C(=O)O)cc4)nn23)cc1OC] | (4-(7-(3,4-dimethoxy-phenyl)pyrazolo[1,5-a]pyrimidine-2-carboxamido)benzoyl)-D-alanine |
| 90 | 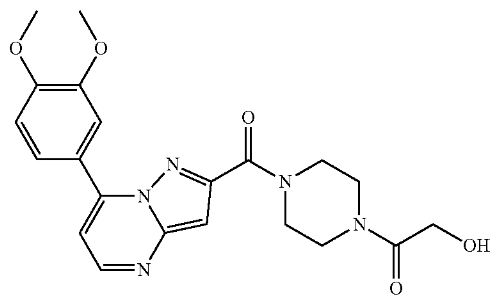 [SMILES: COc1ccc(-c2ccnc3cc(C(=O)N4CCN(C(=O)CO)CC4)nn23)cc1OC] | 1-(4-(7-(3,4-dimethoxy-phenyl)pyrazolo[1,5-a]pyrimidine-2-carbonyl)piperazin-1-yl)-2-hydroxyethan-1-one |
| 91 | 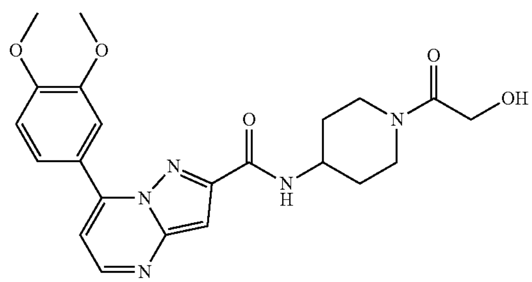 [SMILES: COc1ccc(-c2ccnc3cc(C(=O)NC4CCN(C(=O)CO)CC4)nn23)cc1OC] | 7-(3,4-dimethoxyphenyl)-N-(1-(2-hydroxyacetyl)piperidin-4-yl)pyrazolo[1,5-a]pyrimidine-2-carboxamide |
| 92 | 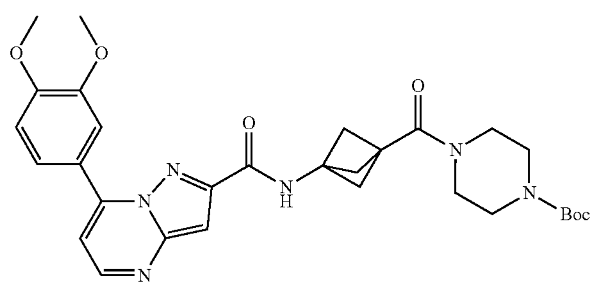 [SMILES: COc1ccc(-c2ccnc3cc(C(=O)NC45CC(C(=O)N6CCN(C(=O)OC(C)(C)C)CC6)(C4)C5)nn23)cc1OC] | tert-butyl 4-(3-(7-(3,4-dimethoxyphenyl)pyrazolo[1,5-a]pyrimidine-2-carboxamido)bicyclo[1.1.1]pentane-1-carbonyl)piperazine-1-carboxylate |
| 93 | 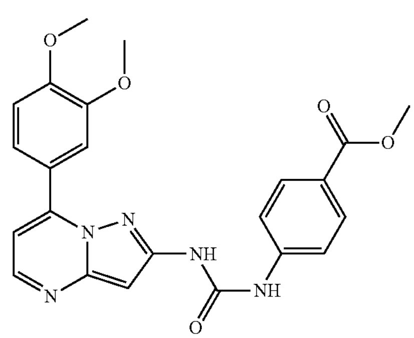 [SMILES: COC(=O)c1ccc(NC(=O)Nc2cc3nccc(-c4ccc(OC)c(OC)c4)n3n2)cc1] | methyl 4-(3-(7-(3,4-dimethoxyphenyl)pyrazolo[1,5-a]pyrimidin-2-yl)ureido)benzoate |

TABLE 1-continued

Exemplary compounds

| Cmpd | Structure | Name |
| --- | --- | --- |
| 94 | 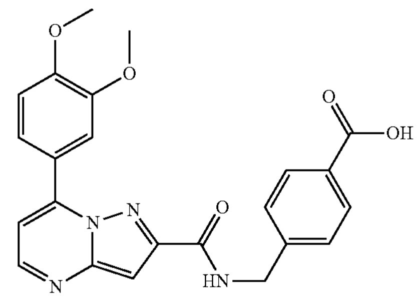 [SMILES: COc1ccc(-c2ccnc3cc(C(=O)NCc4ccc(C(=O)O)cc4)nn23)cc1OC] | 4-((7-(3,4-dimethoxy-phenyl)pyrazolo[1,5-a]pyrimidine-2-carboxamido)methyl) benzoic acid |
| 95 | 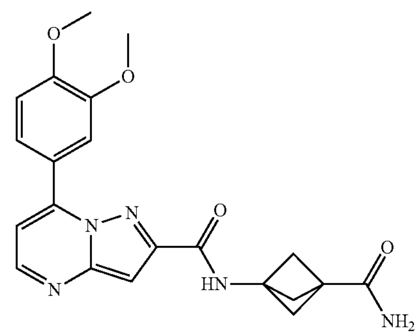 [SMILES: COc1ccc(-c2ccnc3cc(C(=O)NC45CC(C(N)=O)(C4)C5)nn23)cc1OC] | N-(3-carbamoylbicyclo [1.1.1]pentan-1-yl)-7-(3,4-dimethoxyphenyl) pyrazolo[1,5-a]pyrimidine-2-carboxamide |
| 96 | 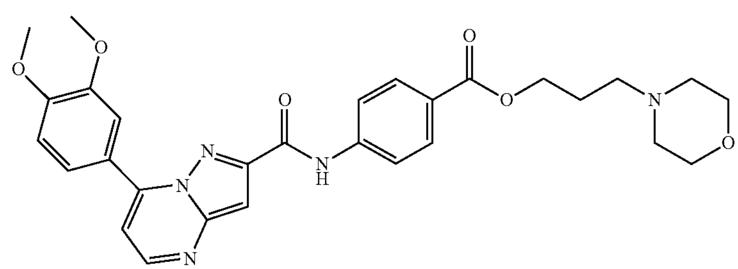 | 3-morpholinopropyl 4-(7-(3,4-dimethoxyphenyl)pyrazolo [1,5-a]pyrimidine-2-carboxamido)benzoate |
| 97 | 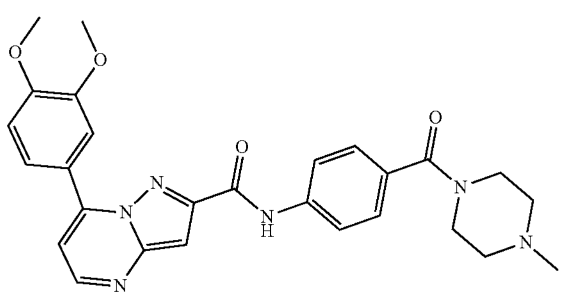 [SMILES: COc1ccc(-c2ccnc3cc(C(=O)Nc4ccc(C(=O)N5CCN(C)CC5)cc4)nn23)cc1OC] | 7-(3,4-dimethoxyphenyl)-N-(4-(4-methylpiperazine-1-carbonyl)phenyl)pyrazolo [1,5-a]pyrimidine-2-carboxamide |
| 98 | 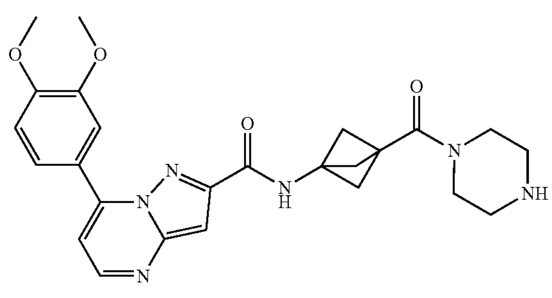 [SMILES: COc1ccc(-c2ccnc3cc(C(=O)NC45CC(C(=O)N6CCNCC6)(C4)C5)nn23)cc1OC] | 7-(3,4-dimethoxyphenyl)-N-(3-(piperazine-1-carbonyl)bicyclo [1.1.1]pentan-1-yl)pyrazolo[1,5-a] pyrimidine-2-carboxamide |

TABLE 1-continued

Exemplary compounds

| Cmpd | Structure | Name |
|---|---|---|
| 99 | 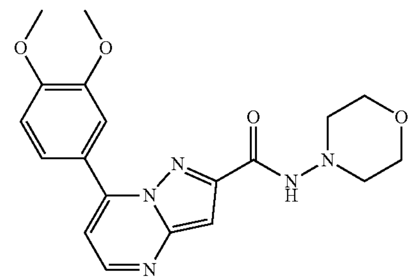 [SMILES: COc1ccc(-c2ccnc3cc(C(=O)NN4CCOCC4)nn23)cc1OC] | 7-(3,4-dimethoxyphenyl)-N-morpholinopyrazolo[1,5-a]pyrimidine-2-carboxamide |
| 100 | 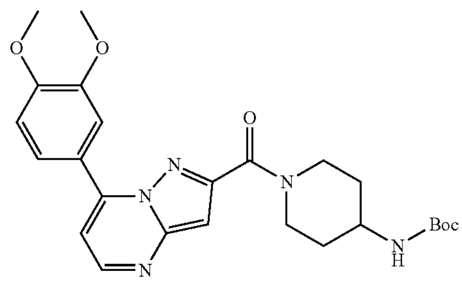 [SMILES: COc1ccc(-c2ccnc3cc(C(=O)N4CCC(NC(=O)OC(C)(C)C)CC4)nn23)cc1OC] | tert-butyl (1-(7-(3,4-dimethoxyphenyl)pyrazolo[1,5-a]pyrimidine-2-carbonyl)piperidin-4-yl)carbamate |
| 101 | 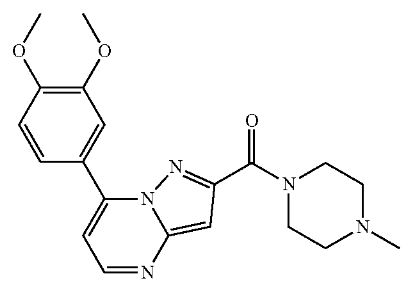 [SMILES: COc1ccc(-c2ccnc3cc(C(=O)N4CCN(C)CC4)nn23)cc1OC] | (7-(3,4-dimethoxyphenyl)pyrazolo[1,5-a]pyrimidin-2-yl)(4-methylpiperazin-1-yl)methanone |
| 102 | 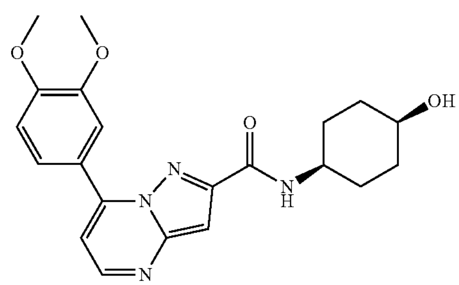 [SMILES: COc1ccc(-c2ccnc3cc(C(=O)N[C@H]4CC[C@@H](O)CC4)nn23)cc1OC] | 7-(3,4-dimethoxyphenyl)-N-((1S,4S)-4-hydroxycyclohexyl)pyrazolo[1,5-a]pyrimidine-2-carboxamide |
| 103 | 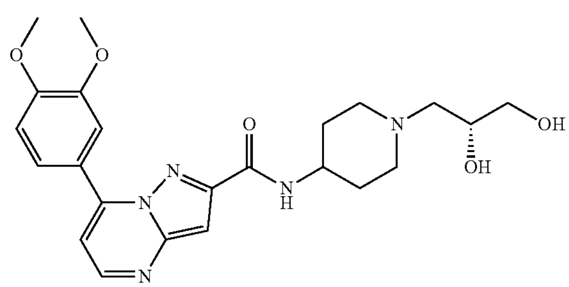 [SMILES: COc1ccc(-c2ccnc3cc(C(=O)NC4CCN(C[C@@H](O)CO)CC4)nn23)cc1OC] | (R)-N-(1-(2,3-dihydroxypropyl)piperidin-4-yl)-7-(3,4-dimethoxyphenyl)pyrazolo[1,5-a]pyrimidine-2-carboxamide |

TABLE 1-continued

Exemplary compounds

| Cmpd | Structure | Name |
|---|---|---|
| 104 | 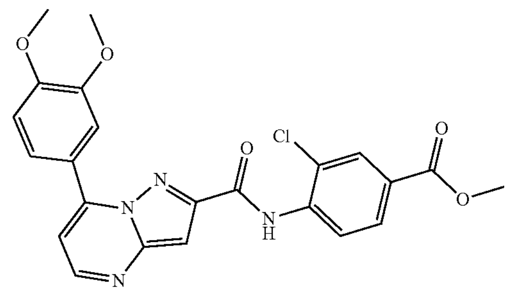 [SMILES: COC(=O)c1ccc(NC(=O)c2cc3nccc(-c4ccc(OC)c(OC)c4)n3n2)c(Cl)c1] | methyl 3-chloro-4-(7-(3,4-dimethoxyphenyl)pyrazolo[1,5-a]pyrimidine-2-carboxamido)benzoate |
| 105 | 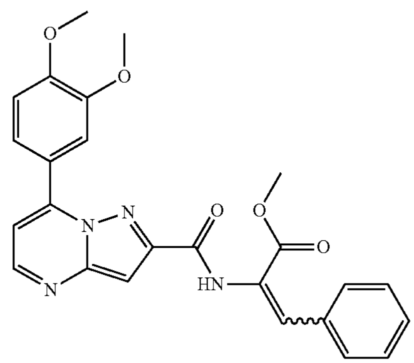 [SMILES: COC(=O)C(=Cc1ccccc1)NC(=O)c1cc2nccc(-c3ccc(OC)c(OC)c3)n2n1] | methyl 2-(7-(3,4-dimethoxyphenyl)pyrazolo[1,5-a]pyrimidine-2-carboxamido) 3-phenylacrylate |
| 106 | 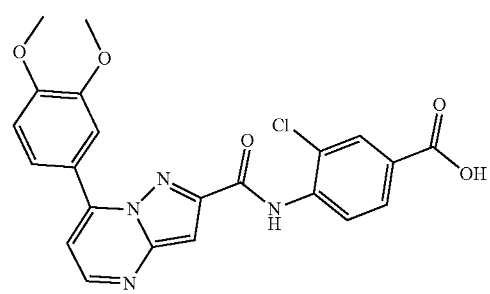 [SMILES: COc1ccc(-c2ccnc3cc(C(=O)Nc4ccc(C(=O)O)cc4Cl)nn23)cc1OC] | 3-chloro-4-(7-(3,4-dimethoxyphenyl)pyrazolo[1,5-a]pyrimidine-2-carboxamido)benzoic acid |
| 107 | 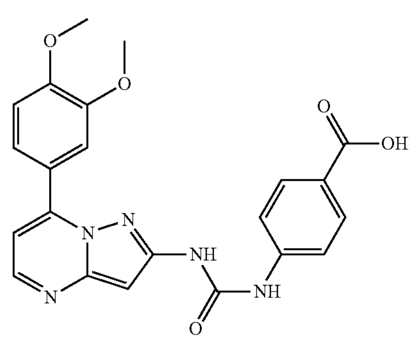 [SMILES: COc1ccc(-c2ccnc3cc(NC(=O)Nc4ccc(C(=O)O)cc4)nn23)cc1OC] | 4-(3-(7-(3,4-dimethoxyphenyl)pyrazolo[1,5-a]pyrimidin-2-yl)ureido)benzoic acid |

TABLE 1-continued

| Cmpd | Structure | Name |
|---|---|---|
| 108 | 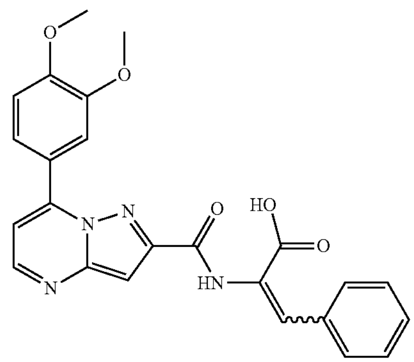 [SMILES: COc1ccc(-c2ccnc3cc(C(=O)NC(=Cc4ccccc4)C(=O)O)nn23)cc1OC] | 2-(7-(3,4-dimethoxy-phenyl)pyrazolo[1,5-a]pyrimidine-2-carboxamido)-3-phenylacrylic acid |
| 109 | 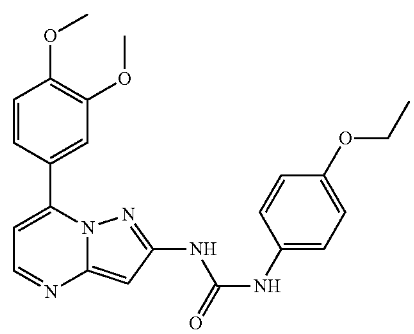 [SMILES: CCOc1ccc(NC(=O)Nc2cc3nccc(-c4ccc(OC)c(OC)c4)n3n2)cc1] | 1-(7-(3,4-dimethoxy-phenyl)pyrazolo[1,5-a]pyrimidine-2-yl)-3-(4-ethoxyphenyl)urea |
| 110 | 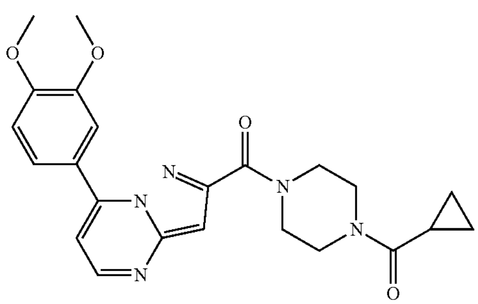 [SMILES: COc1ccc(C2=CC=N/C(=C/C(=N)C(=O)N3CCN(C(=O)C4CC4)CC3)N2)cc1OC] | (4-(cyclopropane-carbonyl)piperazin-1-yl)(7-(3,4-dimethoxyphenyl)pyrazolo[1,5-a]pyrimidin-2-yl)methanone |
| 111 | 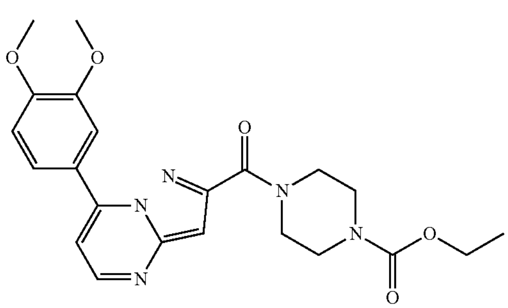 [SMILES: CCOC(=O)N1CCN(C(=O)C(=N)/C=C2/N=CC=C(c3ccc(OC)c(OC)c3)N2)CC1] | ethyl 4-(7-(3,4-dimethoxy-phenyl)pyrazolo[1,5-a]pyrimidine-2-carbonyl)piperazine-1-carboxylate |

TABLE 1-continued

Exemplary compounds

| Cmpd | Structure | Name |
|---|---|---|
| 112 | 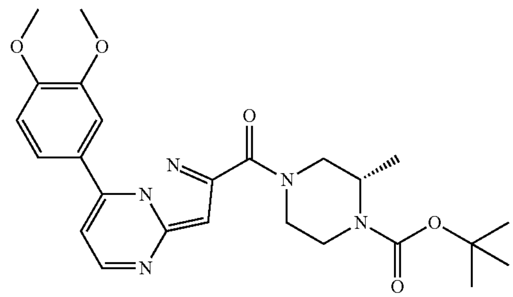 [SMILES: COc1ccc(C2=CC=N/C(=C/C(=N)C(=O)N3CCN(C(=O)OC(C)(C)C)[C@@H](C)C3)N2)cc1OC] | tert-butyl (S)-4-(7-(3,4-dimethoxyphenyl)pyrazolo[1,5-a]pyrimidine-2-carbonyl)-2-methylpiperazine-1-carboxylate |
| 113 | 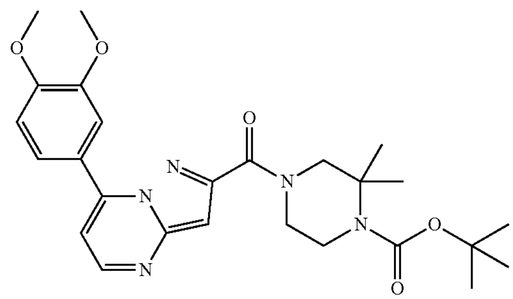 [SMILES: COc1ccc(C2=CC=N/C(=C/C(=N)C(=O)N3CCN(C(=O)OC(C)(C)C)C(C)(C)C3)N2)cc1OC] | tert-butyl 4-(7-(3,4-dimethoxyphenyl)pyrazolo[1,5-a]pyrimidine-2-carbonyl)-2,2-dimethyl-piperazine-1-carboxylate |
| 114 | 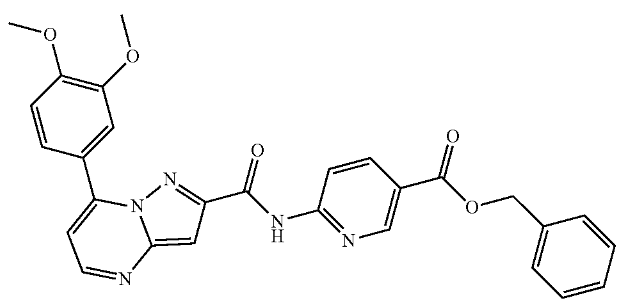 [SMILES: COc1ccc(-c2ccnc3cc(C(=O)Nc4ccc(C(=O)OCc5ccccc5)cn4)nn23)cc1OC] | benzyl 6-(7-(3,4-dimethoxyphenyl)pyrazolo[1,5-a]pyrimidine-2-carboxamido)nicotinate |
| 115 | 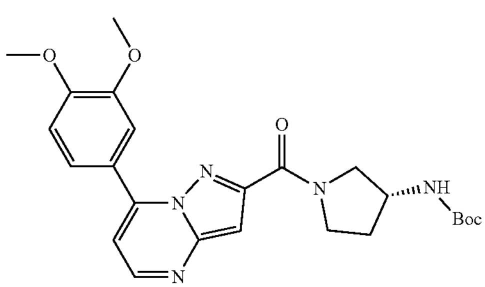 [SMILES: COc1ccc(-c2ccnc3cc(C(=O)N4CC[C@@H](NC(=O)OC(C)(C)C)C4)nn23)cc1OC] | tert-butyl (R)-(1-(7-(3,4-dimethoxyphenyl)pyrazolo[1,5-a]pyrimidine-2-carbonyl)pyrrolidin-3-yl)carbamate |
| 116 | 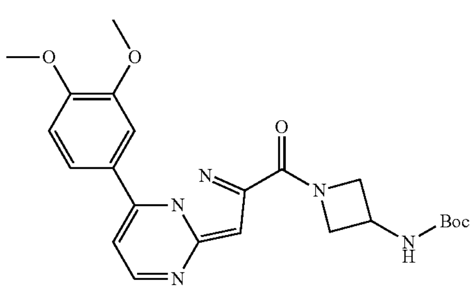 [SMILES: COc1ccc(C2=CC=N/C(=C/C(=N)C(=O)N3CC(NC(=O)OC(C)(C)C)C3)N2)cc1OC] | tert-butyl (1-(7-(3,4-dimethoxyphenyl)pyrazolo[1,5-a]pyrimidine-2-carbonyl)azetidin-3-yl)carbamate |

TABLE 1-continued

Exemplary compounds

| Cmpd | Structure | Name |
|---|---|---|
| 117 | 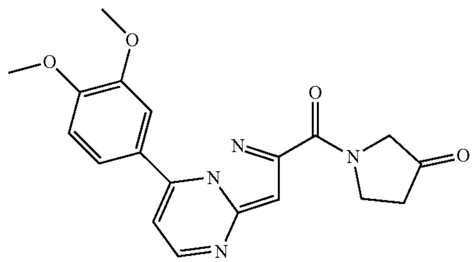 [SMILES: COc1ccc(C2=CC=N/C(=C/C(=N)C(=O)N3CCC(=O)C3)N2)cc1OC] | 1-(7-(3,4-dimethoxyphenyl) pyrazolo[1,5-a]pyrimidine-2-carbonyl) pyrrolidin-3-one |
| 118 | 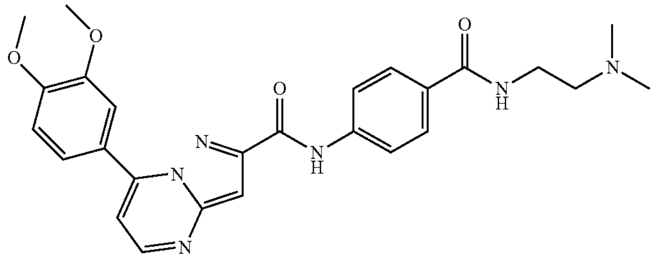 [SMILES: COc1ccc(C2=CC=N/C(=C/C(=N)C(=O)Nc3ccc(C(=O)NCCN(C)C)cc3)N2)cc1OC] | 7-(3,4-dimethoxyphenyl)-N-(4-((2-(dimethylamino)ethyl) carbamoyl)phenyl) pyrazolo[1,5-a]pyrimidine-2-carboxamide |
| 119 | 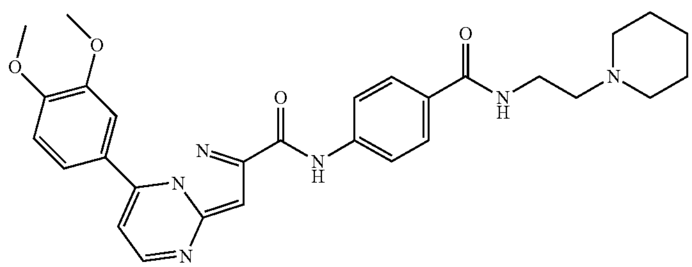 [SMILES: COc1ccc(C2=CC=N/C(=C/C(=N)C(=O)Nc3ccc(C(=O)NCCN4CCCCC4)cc3)N2)cc1OC] | 7-(3,4-dimethoxyphenyl)-N-(4-((2-(piperidin-1-yl)ethyl)carbamoyl)phenyl) pyrazolo[1,5-a]pyrimidine-2-carboxamide |
| 120 | 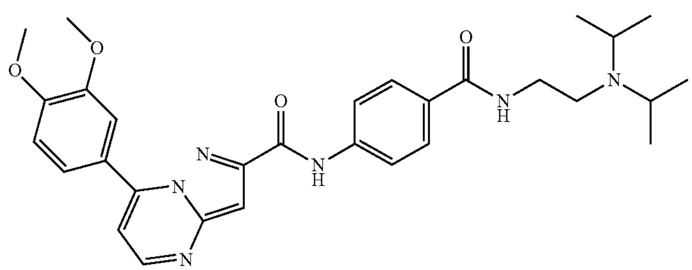 [SMILES: COc1ccc(C2=CC=N/C(=C/C(=N)C(=O)Nc3ccc(C(=O)NCCN(C(C)C)C(C)C)cc3)N2)cc1OC] | N-(4-((2-(diisopropylamino)ethyl) carbamoyl)phenyl)-7-(3,4-dimethoxyphenyl) pyrazolo[1,5-a]pyrimidine-2-carboxamide |
| 121 | 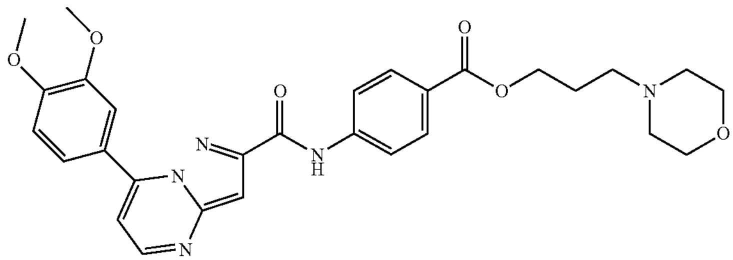 [SMILES: COc1ccc(C2=CC=N/C(=C/C(=N)C(=O)Nc3ccc(C(=O)OCCCN4CCOCC4)cc3)N2)cc1OC] | 3-morpholinopropyl 4-(7-(3,4-dimethoxyphenyl)pyrazolo [1,5-a]pyrimidine-2-carboxamido)benzoate |

TABLE 1-continued

Exemplary compounds

| Cmpd | Structure | Name |
| --- | --- | --- |
| 122 | 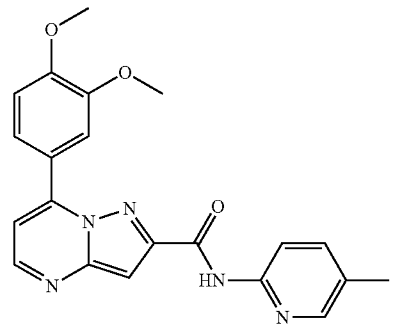 [SMILES: COc1ccc(-c2ccnc3cc(C(=O)Nc4ccc(C)cn4)nn23)cc1OC] | 7-(3,4-dimethoxyphenyl)-N-(5-methylpyridin-2-yl)pyrazolo[1,5-a]pyrimdine-2-carboxamide |
| 123 | 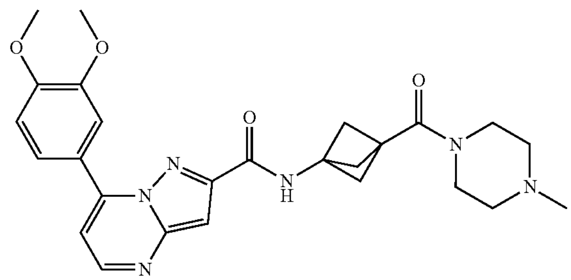 [SMILES: COc1ccc(-c2ccnc3cc(C(=O)NC45CC(C(=O)N6CCN(C)CC6)(C4)C5)nn23)cc1OC] | 7-(3,4-dimethoxyphenyl)-N-(3-(4-methylpiperazine-1-carbonyl)bicyclo[1.1.1]pentan-1-yl)pyrazolo[1,5-a]pyrimidine-2-carboxamide |
| 124 | 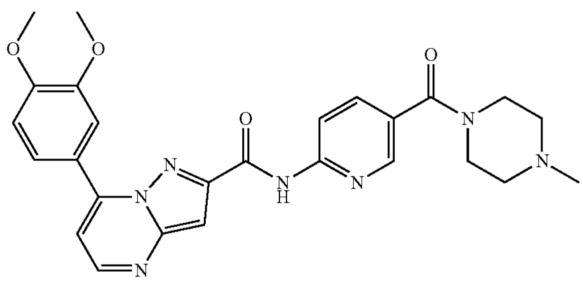 [SMILES: COc1ccc(-c2ccnc3cc(C(=O)Nc4ccc(C(=O)N5CCN(C)CC5)cn4)nn23)cc1OC] | 7-(3,4-dimethoxyphenyl)-N-(5-(4-methylpiperazine-1-carbonyl)pyridin-2-yl)pyrazolo[1,5-a]pyrimidine-2-carboxamide |
| 125 | 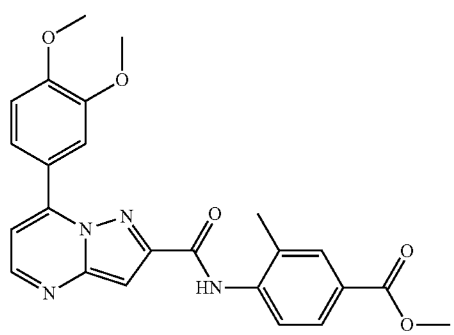 | methyl 4-(7-(3,4-dimethoxyphenyl)pyrazolo[1,5-a]pyrimidine-2-carboxamido)-3-methylbenzoate |
| 126 | 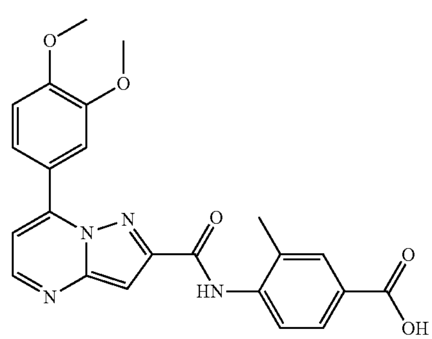 | 4-(7-(3,4-dimethoxyphenyl)pyrazolo[1,5-a]pyrimidine-2-carboxamido)-3-methylbenzoic acid |

TABLE 1-continued

Exemplary compounds

| Cmpd | Structure | Name |
|---|---|---|
| 127 | 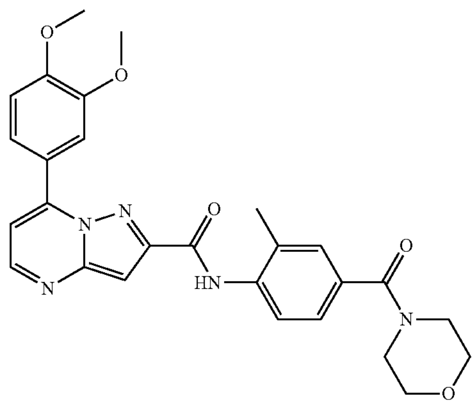 [SMILES: COc1ccc(-c2ccnc3cc(C(=O)Nc4ccc(C(=O)N5CCOCC5)cc4C)nn23)cc1OC] | 7-(3,4-dimethoxyphenyl)-N-(2-methyl-4-(morpholine-4-carbonyl)phenyl)pyrazolo[1,5-a]pyrimidine-2-carboxamide |
| 128 | 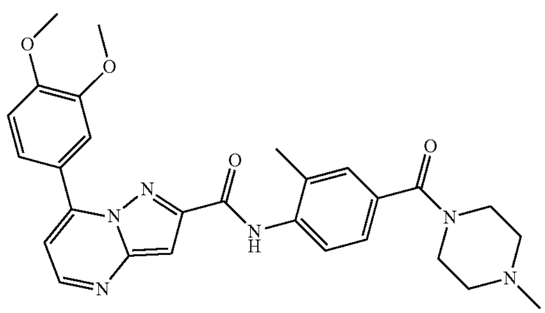 [SMILES: COc1ccc(-c2ccnc3cc(C(=O)Nc4ccc(C(=O)N5CCN(C)CC5)cc4C)nn23)cc1OC] | 7-(3,4-dimethoxyphenyl)-N-(2-methyl-4-(4-methylpiperazine-1-carbonyl)phenyl)pyrazolo[1,5-a]pyrimidine-2-carboxamide |
| 129 | 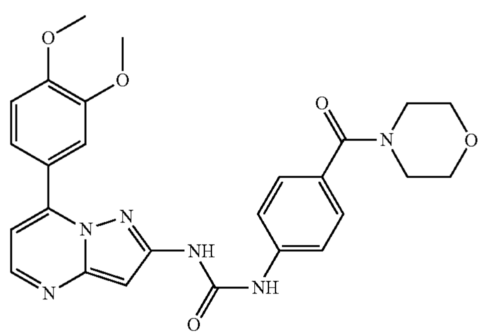 [SMILES: COc1ccc(-c2ccnc3cc(NC(=O)Nc4ccc(C(=O)N5CCOCC5)cc4)nn23)cc1OC] | 1-(7-(3,4-dimethoxyphenyl)pyrazolo[1,5-a]pyrimidin-2-yl)-3-(4-(morpholine-4-carbonyl)phenyl)urea |
| 130 | 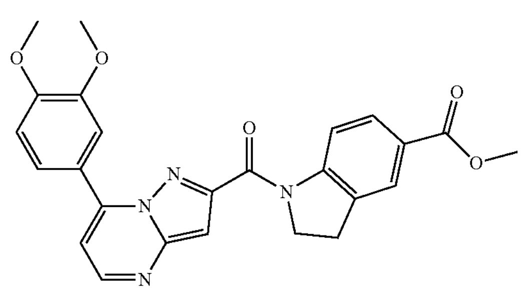 [SMILES: COC(=O)c1ccc2c(c1)CCN2C(=O)c1cc2nccc(-c3ccc(OC)c(OC)c3)n2n1] | methyl 1-(7-(3,4-dimethoxyphenyl)pyrazolo[1,5-a]pyrimidine-2-carbonyl)indoline-5-carboxylate |

TABLE 1-continued

Exemplary compounds

| Cmpd | Structure | Name |
|---|---|---|
| 131 | 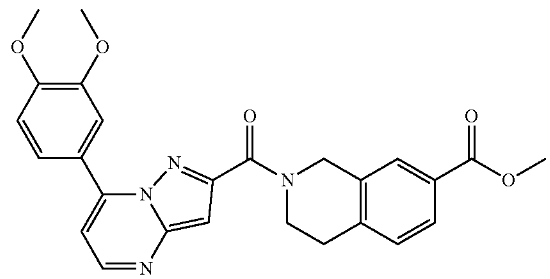 [SMILES: COC(=O)c1ccc2c(c1)CN(C(=O)c1cc3nccc(-c4ccc(OC)c(OC)c4)n3n1)CC2] | methyl 2-(7-(3,4-dimethoxyphenyl)pyrazolo[1,5-a]pyrimidine-2-carbonyl)-1,2,3,4-tetrahydroisoquinoline-7-carboxylate |
| 132 | 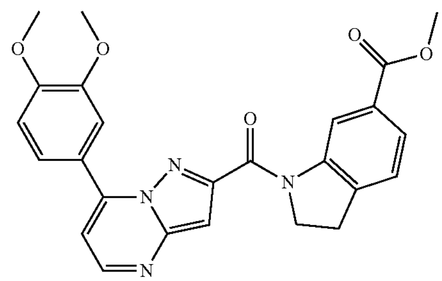 [SMILES: COC(=O)c1ccc2c(c1)N(C(=O)c1cc3nccc(-c4ccc(OC)c(OC)c4)n3n1)CC2] | methyl 1-(7-(3,4-dimethoxyphenyl)pyrazolo[1,5-a]pyrimidine-2-carbonyl)indoline-6-carboxylate |
| 133 | 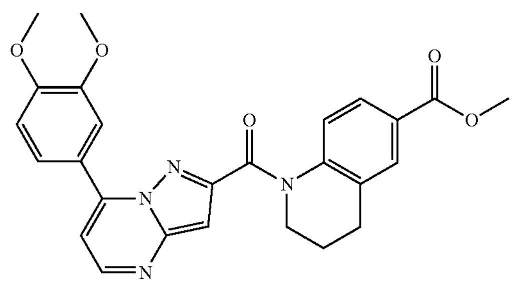 [SMILES: COC(=O)c1ccc2c(c1)CCCN2C(=O)c1cc2nccc(-c3ccc(OC)c(OC)c3)n2n1] | methyl 1-(7-(3,4-dimethoxyphenyl)pyrazolo[1,5-a]pyrimidine-2-carbonyl)-1,2,3,4-tetrahydroquinoline-6-carboxylate |
| 134 | 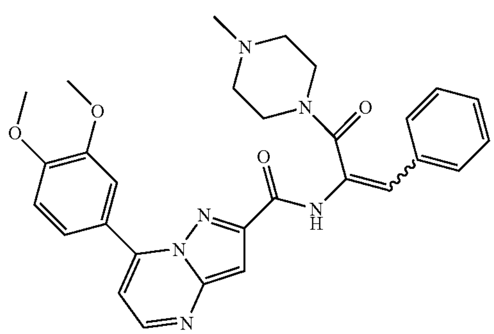 [SMILES: COc1ccc(-c2ccnc3cc(C(=O)NC(=Cc4ccccc4)C(=O)N4CCN(C)CC4)nn23)cc1OC] | 7-(3,4-dimethoxyphenyl)-N-(3-(4-methylpiperazin-1-yl)-3-oxo-1-phenylprop-1-en-2-yl)pyrazolo[1,5-a]pyrimidine-2-carboxamide |
| 135 | 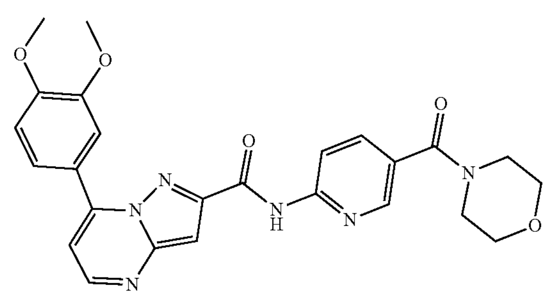 [SMILES: COc1ccc(-c2ccnc3cc(C(=O)Nc4ccc(C(=O)N5CCOCC5)cn4)nn23)cc1OC] | 7-(3,4-dimethoxyphenyl)-N-(5-(morpholine-4-carbonyl)pyridin-2-yl)pyrazolo[1,5-a]pyrimidine-2-carboxamide |

TABLE 1-continued

Exemplary compounds

| Cmpd | Structure | Name |
|---|---|---|
| 136 | 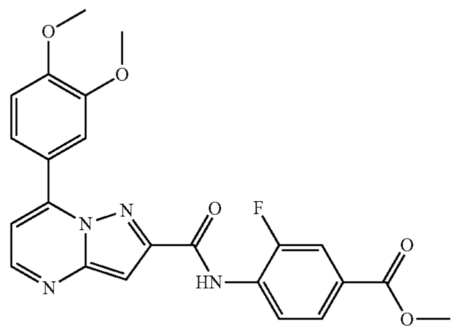 | methyl 4-(7-(3,4-dimethoxyphenyl)pyrazolo[1,5-a]pyrimidine-2-carboxamido)-3-fluorobenzoate |
| 137 | 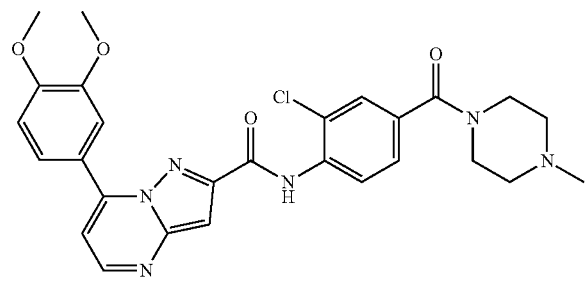 [SMILES: COc1ccc(-c2ccnc3cc(C(=O)Nc4ccc(C(=O)N5CCN(C)CC5)cc4Cl)nn23)cc1OC] | N-(2-chloro-4-(4-methylpiperazine-1-carbonyl)phenyl)-7-(3,4-dimethoxyphenyl)pyrazolo[1,5-a]pyrimidine-2-carboxamide |
| 138 | 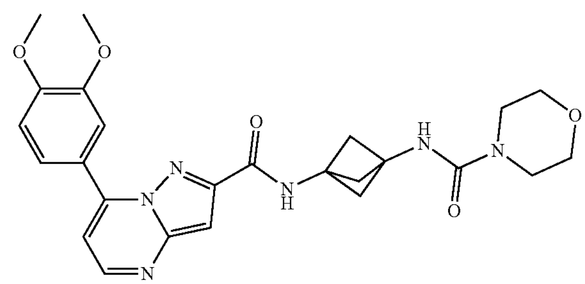 [SMILES: COc1ccc(-c2ccnc3cc(C(=O)NC45CC(NC(=O)N6CCOCC6)(C4)C5)nn23)cc1OC] | N-(3-(7-(3,4-dimethoxyphenyl)pyrazolo[1,5-a]pyrimidine-2-carboxamido)bicyclo[1.1.1]pentan-1-yl)morpholine-4-carboxamide |
| 139 | 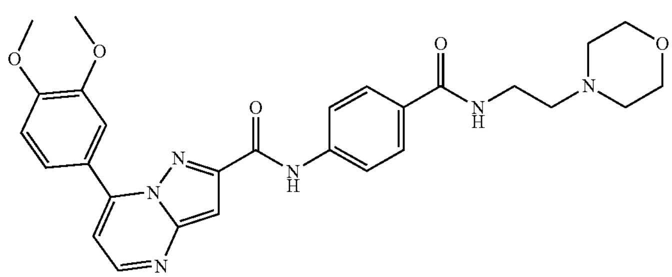 [SMILES: COc1ccc(-c2ccnc3cc(C(=O)Nc4ccc(C(=O)NCCN5CCOCC5)cc4)nn23)cc1OC] | 7-(3,4-dimethoxyphenyl)-N-(4-((2-morpholinoethyl)carbamoyl)phenyl)pyrazolo[1,5-a]pyrimidine-2-carboxamide |
| 140 | 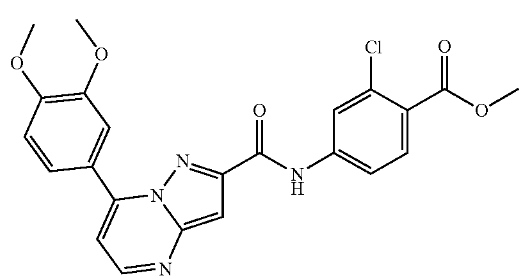 [SMILES: COC(=O)c1ccc(NC(=O)c2cc3nccc(-c4ccc(OC)c(OC)c4)n3n2)cc1Cl] | methyl 2-chloro-4-(7-(3,4-dimethoxyphenyl)pyrazolo[1,5-a]pyrimidine-2-carboxamido)benzoate |

TABLE 1-continued

Exemplary compounds

| Cmpd | Structure | Name |
|---|---|---|
| 141 | 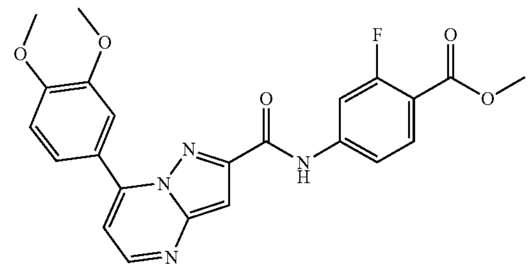 [SMILES: COC(=O)c1ccc(NC(=O)c2cc3nccc(-c4ccc(OC)c(OC)c4)n3n2)cc1F] | methyl 4-(7-(3,4-dimethoxyphenyl)pyrazolo[1,5-a]pyrimidine-2-carboxamido)-2-fluorobenzoate |
| 142 | 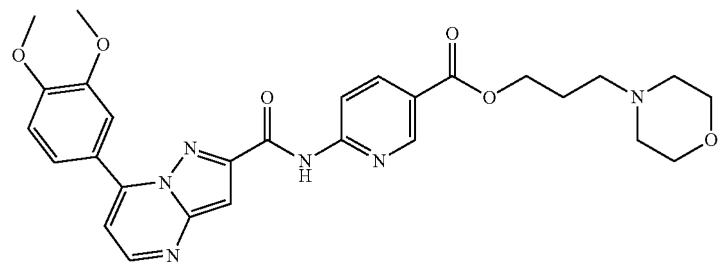 [SMILES: COc1ccc(-c2ccnc3cc(C(=O)Nc4ccc(C(=O)OCCCN5CCOCC5)cn4)nn23)cc1OC] | 3-morpholinopropyl 6-(7-(3,4-dimethoxyphenyl)pyrazolo[1,5-a]pyrimidine-2-carboxamido)nicotinate |
| 143 | 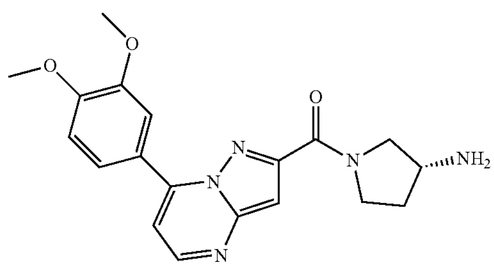 [SMILES: COc1ccc(-c2ccnc3cc(C(=O)N4CC[C@@H](N)C4)nn23)cc1OC] | (R)-(3-aminopyrrolidin-1-yl)(7-(3,4-dimethoxyphenyl)pyrazolo[1,5-a]pyrimidin-2-yl)methanone |
| 144 | 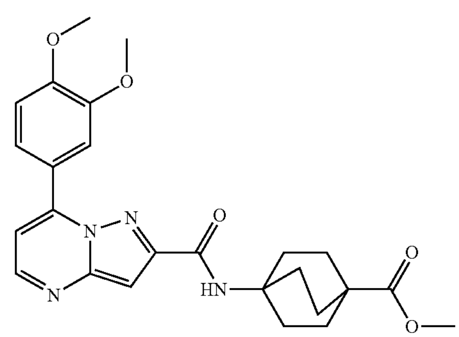 [SMILES: COC(=O)C12CCC(NC(=O)c3cc4nccc(-c5ccc(OC)c(OC)c5)n4n3)(CC1)CC2] | methyl 4-(7-(3,4-dimethoxyphenyl)pyrazolo[1,5-a]pyrimidine-2-carboxamido)bicyclo[2.2.2]octane-1-carboxylate |
| 145 | 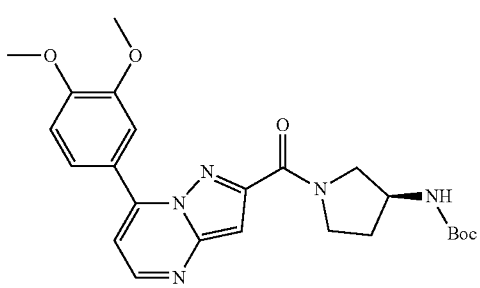 [SMILES: COc1ccc(-c2ccnc3cc(C(=O)N4CC[C@H](NC(=O)OC(C)(C)C)C4)nn23)cc1OC] | tert-butyl (S)-(1-(7-(3,4-dimethoxyphenyl)pyrazolo[1,5-a]pyrimidine-2-carbonyl)pyrrolidine-3-yl)carbamate |

TABLE 1-continued

| Cmpd | Structure | Name |
|---|---|---|
| 146 | 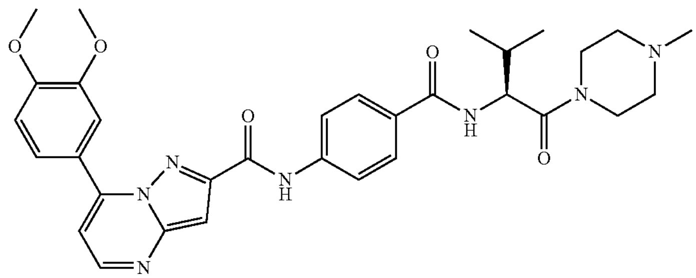 [SMILES: COc1ccc(-c2ccnc3cc(C(=O)Nc4ccc(C(=O)N[C@H](C(=O)N5CCN(C)CC5)C(C)C)cc4)nn23)cc1OC] | (S)-7-(3,4-dimethoxyphenyl)-N-(4-((3-methyl-1-(4-methylpiperazin-1-yl)-1-oxobutan-2-yl)carbamoyl)phenyl)pyrazolo[1,5-a]pyrimidine-2-carboxamide |
| 147 | 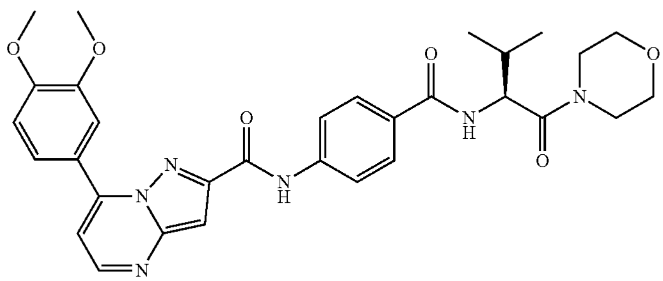 [SMILES: COc1ccc(-c2ccnc3cc(C(=O)Nc4ccc(C(=O)N[C@H](C(=O)N5CCOCC5)C(C)C)cc4)nn23)cc1OC] | (S)-7-(3,4-dimethoxyphenyl)-N-(4-((3-methyl-1-morpholino-1-oxobutan-2-yl)carbamoyl)phenyl)pyrazolo[1,5-a]pyrimidine-2-carboxamide |
| 148 | 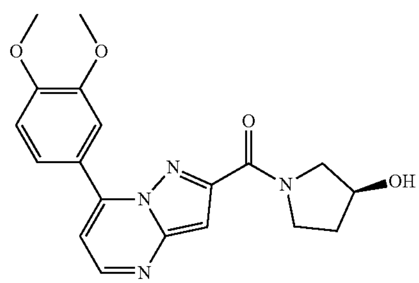 [SMILES: COc1ccc(-c2ccnc3cc(C(=O)N4CC[C@H](O)C4)nn23)cc1OC] | (S)-(7-(3,4-dimethoxyphenyl)pyrazolo[1,5-a]pyrimidin-2-yl)(3-hydroxypyrrolidin-1-yl)methanone |
| 149 | 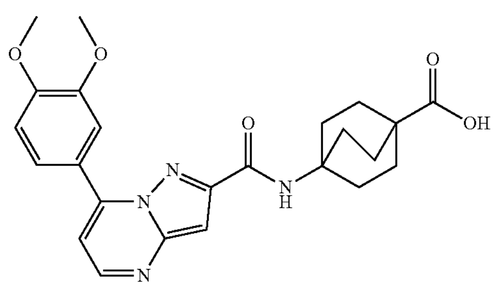 [SMILES: COc1ccc(-c2ccnc3cc(C(=O)NC45CCC(C(=O)O)(CC4)CC5)nn23)cc1OC] | 4-(7-(3,4-dimethoxyphenyl)pyrazolo[1,5-a]pyrimidine-2-carboxamido)bicyclo[2.2.2]octane-1-carboxylic acid |
| 150 | 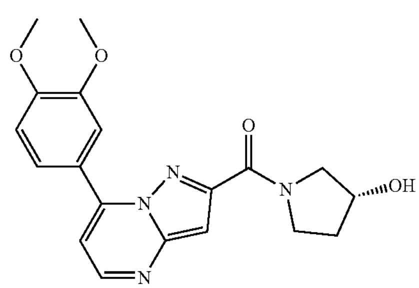 [SMILES: COc1ccc(-c2ccnc3cc(C(=O)N4CC[C@@H](O)C4)nn23)cc1OC] | (R)-(7-(3,4-dimethoxyphenyl)pyrazolo[1,5-a]pyrimidin-2-yl)(3-hydroxypyrrolidin-1-yl)methanone |

TABLE 1-continued

Exemplary compounds

| Cmpd | Structure | Name |
|---|---|---|
| 151 | 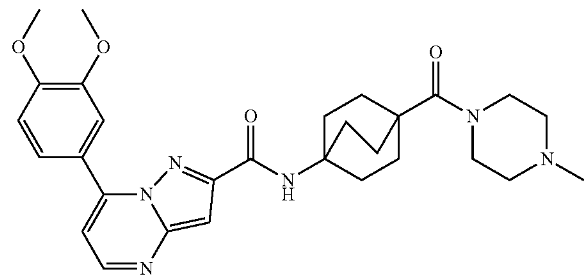 [SMILES: COc1ccc(-c2ccnc3cc(C(=O)NC45CCC(C(=O)N6CCN(C)CC6)(CC4)CC5)nn23)cc1OC] | 7-(3,4-dimethoxyphenyl)-N-(4-(4-methylpiperazine-1-carbonyl)bicyclo[2.2.2]octan-1-yl)pyrazolo[1,5-a]pyrimidine-2-carboxamide |
| 152 | 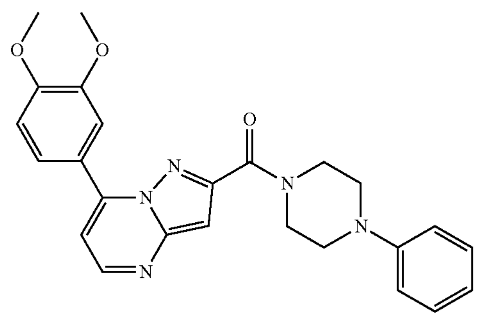 [SMILES: COc1ccc(-c2ccnc3cc(C(=O)N4CCN(c5ccccc5)CC4)nn23)cc1OC] | (7-(3,4-dimethoxyphenyl)pyrazolo[1,5-a]pyrimidin-2-yl)(4-phenylpiperazin-1-yl)methanone |
| 153 | 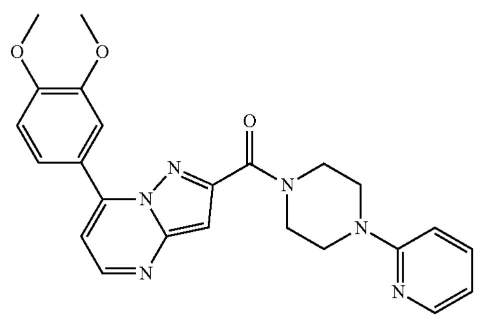 [SMILES: COc1ccc(-c2ccnc3cc(C(=O)N4CCN(c5ccccn5)CC4)nn23)cc1OC] | (7-(3,4-dimethoxyphenyl)pyrazolo[1,5-a]pyrimidin-2-yl)(4-(pyridin-2-yl)piperazin-1-yl)methanone |
| 154 | 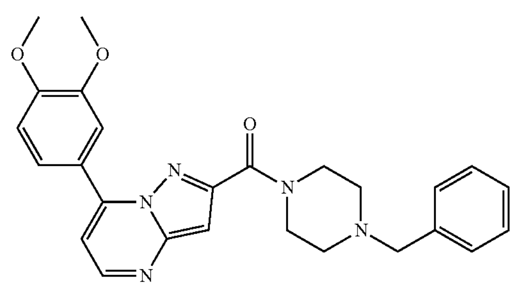 [SMILES: COc1ccc(-c2ccnc3cc(C(=O)N4CCN(Cc5ccccc5)CC4)nn23)cc1OC] | (4-benzylpiperazin-1-yl)(7-(3,4-dimethoxyphenyl)pyrazolo[1,5-a]pyrimidin-2-yl)methanone |
| 155 | 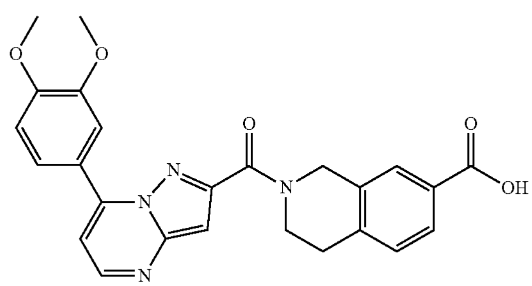 [SMILES: COc1ccc(-c2ccnc3cc(C(=O)N4CCc5ccc(C(=O)O)cc5C4)nn23)cc1OC] | 2-(7-(3,4-dimethoxyphenyl)pyrazolo[1,5-a]pyrimidine-2-carbonyl)-1,2,3,4-tetrahydroisoquinoline-7-carboxylic acid |

TABLE 1-continued

Exemplary compounds

| Cmpd | Structure | Name |
|---|---|---|
| 156 | 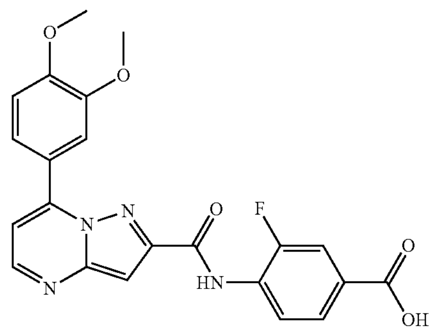 | 4-(7-(3,4-dimethoxyphenyl)pyrazolo[1,5-a]pyrimidine-2-carboxamido)-3-fluorobenzoic acid |
| 157 | 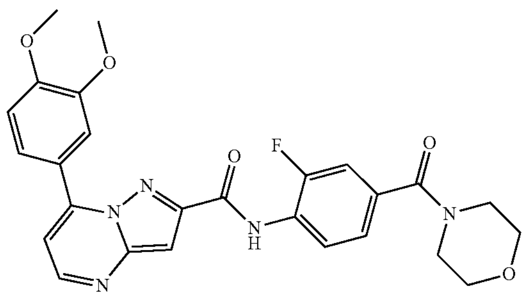 [SMILES: COc1ccc(-c2ccnc3cc(C(=O)Nc4ccc(C(=O)N5CCOCC5)cc4F)nn23)cc1OC] | 7-(3,4-dimethoxyphenyl)-N-(2-fluoro-4-(morpholine-4-carbonyl)phenyl)pyrazolo[1,5-a]pyrimidine-2-carboxamide |
| 158 | 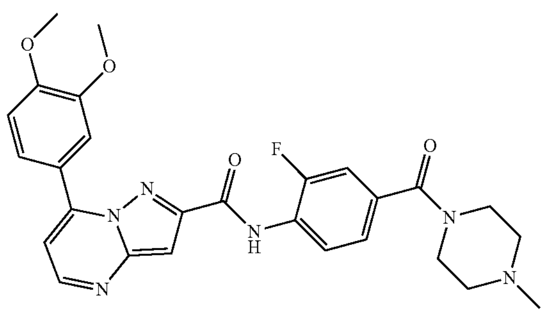 | 7-(3,4-dimethoxyphenyl)-N-(2-fluoro-4-(4-methylpiperazine-1-carbonyl)phenyl)pyrazolo[1,5-a]pyrimidine-2-carboxamide |
| 159 | 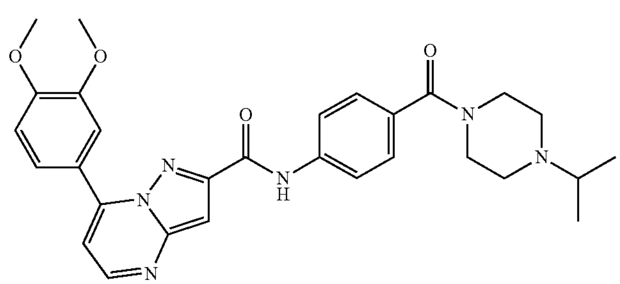 [SMILES: COc1ccc(-c2ccnc3cc(C(=O)Nc4ccc(C(=O)N5CCN(C(C)C)CC5)cc4)nn23)cc1OC] | 7-(3,4-dimethoxyphenyl)-N-(4-(4-isopropylpiperazine-1-carbonyl)phenyl)pyrazolo[1,5-a]pyrimidine-2-carboxamide |
| 160 | 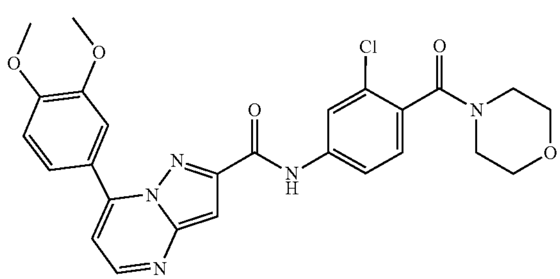 [SMILES: COc1ccc(-c2ccnc3cc(C(=O)Nc4ccc(C(=O)N5CCOCC5)c(Cl)c4)nn23)cc1OC] | N-(3-chloro-4-(morpholine-4-carbonyl)phenyl)-7-(3,4-dimethoxyphenyl)pyrazolo[1,5-a]pyrimidine-2-carboxamide |

TABLE 1-continued

| Cmpd | Structure | Name |
|---|---|---|
| 161 | 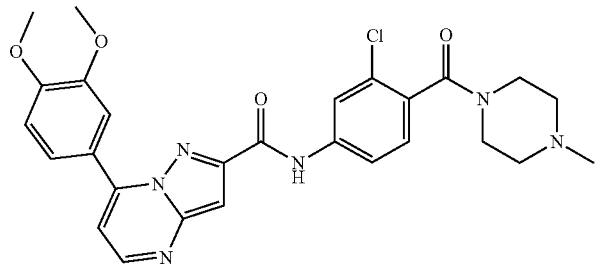 [SMILES: COc1ccc(-c2ccnc3cc(C(=O)Nc4ccc(C(=O)N5CCN(C)CC5)c(Cl)c4)nn23)cc1OC] | N-(3-chloro-4-(4-methylpiperazine-1-carbonyl)phenyl)-7-(3,4-dimethoxyphenyl)pyrazolo[1,5-a]pyrimidine-2-carboxamide |
| 162 | 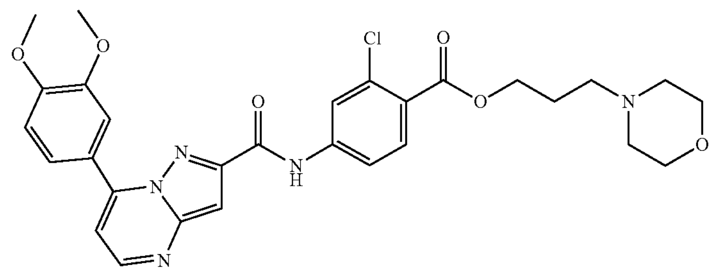 [SMILES: COc1ccc(-c2ccnc3cc(C(=O)Nc4ccc(C(=O)OCCCN5CCOCC5)c(Cl)c4)nn23)cc1OC] | 3-morpholinopropyl 2-chloro-4-(7-(3,4-dimethoxyphenyl)pyrazolo[1,5-a]pyrimidine-2-carboxamido)benzoate |
| 163 | 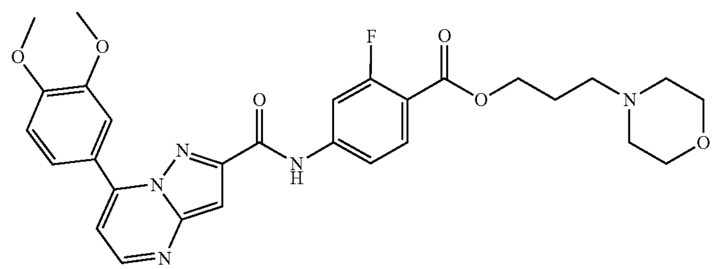 [SMILES: COc1ccc(-c2ccnc3cc(C(=O)Nc4ccc(C(=O)OCCCN5CCOCC5)c(F)c4)nn23)cc1OC] | 3-morpholinopropyl 4-(7-(3,4-dimethoxyphenyl)pyrazolo[1,5-a]pyrimidine-2-carboxamido)-2-fluorobenzoate |
| 164 | 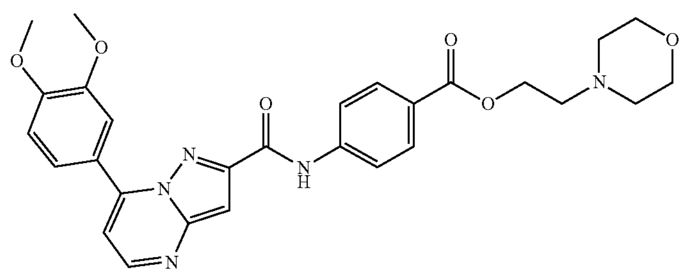 [SMILES: COc1ccc(-c2ccnc3cc(C(=O)Nc4ccc(C(=O)OCCN5CCOCC5)cc4)nn23)cc1OC] | 2-morpholinoethyl 4-(7-(3,4-dimethoxyphenyl)pyrazolo[1,5-a]pyrimidine-2-carboxamido)benzoate |
| 165 | 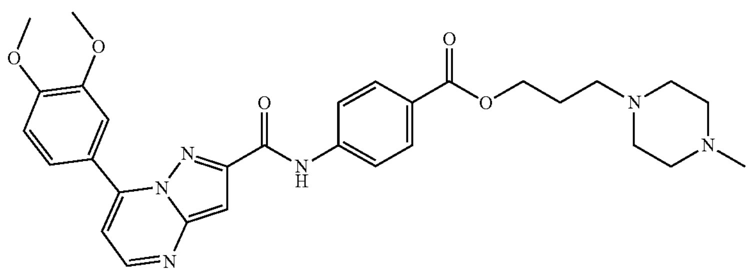 [SMILES: COc1ccc(-c2ccnc3cc(C(=O)Nc4ccc(C(=O)OCCCN5CCN(C)CC5)cc4)nn23)cc1OC] | 3-(4-methylpiperazin-1-yl)propyl 4-(7-(3,4-dimethoxyphenyl)pyrazolo[1,5-a]pyrimidine-2-carboxamido)benzoate |

TABLE 1-continued

Exemplary compounds

| Cmpd | Structure | Name |
|---|---|---|
| 166 | 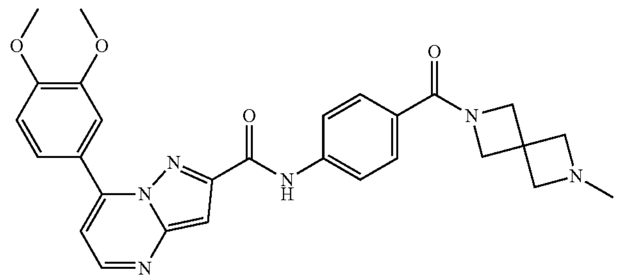 [SMILES: COc1ccc(-c2ccnc3cc(C(=O)Nc4ccc(C(=O)N5CC6(CN(C)C6)C5)cc4)nn23)cc1OC] | 7-(3,4-dimethoxyphenyl)-N-(4-(6-methyl-2,6-diazaspiro[3.3]heptane-2-carbonyl)phenyl)pyrazolo[1,5-a]pyrimidine-2-carboxamide |
| 167 | 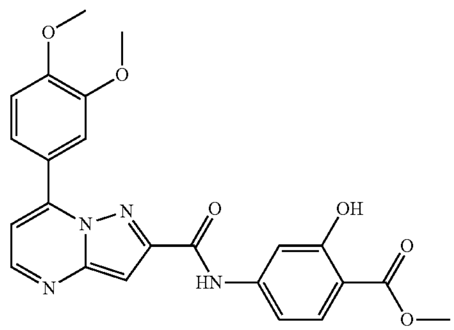 [SMILES: COC(=O)c1ccc(NC(=O)c2cc3nccc(-c4ccc(OC)c(OC)c4)n3n2)cc1O] | methyl 4-(7-(3,4-dimethoxyphenyl)pyrazolo[1,5-a]pyrimidine-2-carboxamido)-2-hydroxybenzoate |
| 168 | 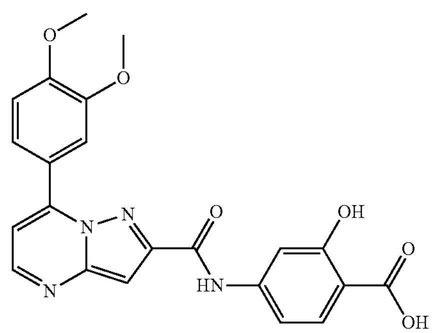 [SMILES: COc1ccc(-c2ccnc3cc(C(=O)Nc4ccc(C(=O)O)c(O)c4)nn23)cc1OC] | 4-(7-(3,4-dimethoxyphenyl)pyrazolo[1,5-a]pyrimidine-2-carboxamido)-2-hydroxybenzoic acid |
| 169 | 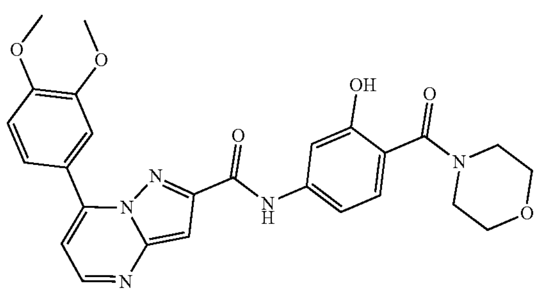 [SMILES: COc1ccc(-c2ccnc3cc(C(=O)Nc4ccc(C(=O)N5CCOCC5)c(O)c4)nn23)cc1OC] | 7-(3,4-dimethoxyphenyl)-N-(3-hydroxy-4-(morpholine-4-carbonyl)phenyl)pyrazolo[1,5-a]pyrimidine-2-carboxamide |
| 170 | 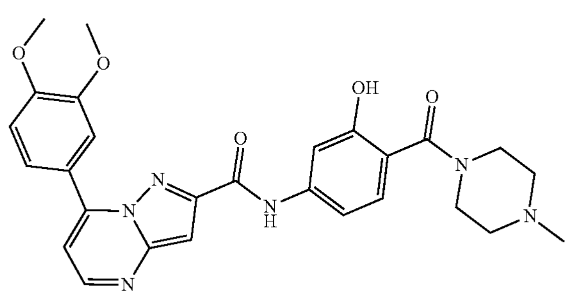 [SMILES: COc1ccc(-c2ccnc3cc(C(=O)Nc4ccc(C(=O)N5CCN(C)CC5)c(O)c4)nn23)cc1OC] | 7-(3,4-dimethoxyphenyl)-N-(3-hydroxy-4-(4-methylpiperazine-1-carbonyl)phenyl)pyrazolo[1,5-a]pyrimidine-2-carboxamide |

TABLE 1-continued

Exemplary compounds

| Cmpd | Structure | Name |
|---|---|---|
| 171 | 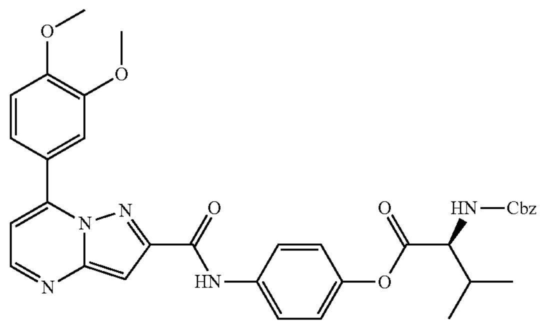 [SMILES: COc1ccc(-c2ccnc3cc(C(=O)Nc4ccc(OC(=O)[C@@H](NC(=O)OCc5ccccc5)C(C)C)cc4)nn23)cc1OC] | 4-(7-(3,4-dimethoxyphenyl) pyrazolo[1,5-a]pyrimidine-2-carboxamido)phenyl ((benzyloxy)carbonyl)-L-valinate |
| 172 | 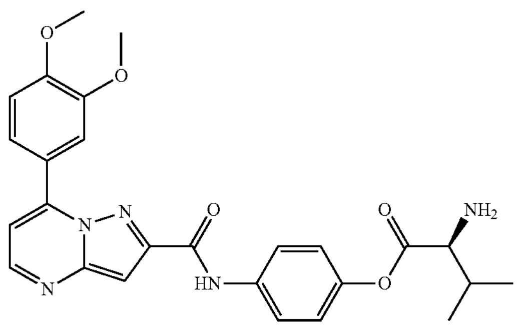 [SMILES: COc1ccc(-c2ccnc3cc(C(=O)Nc4ccc(OC(=O)[C@@H](N)C(C)C)cc4)nn23)cc1OC] | 4-(7-(3,4-dimethoxyphenyl) pyrazolo[1,5-a]pyrimidine-2-carboxamido) phenyl L-valinate |
| 173 | 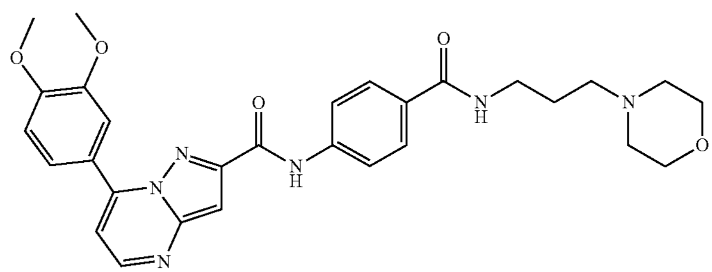 [SMILES: COc1ccc(-c2ccnc3cc(C(=O)Nc4ccc(C(=O)NCCCN5CCOCC5)cc4)nn23)cc1OC] | 7-(3,4-dimethoxyphenyl)-N-(4-((3-morpholinopropyl)carbamoyl) phenyl)pyrazolo [1,5-a]pyrimidine-2-carboxamide |
| 174 | 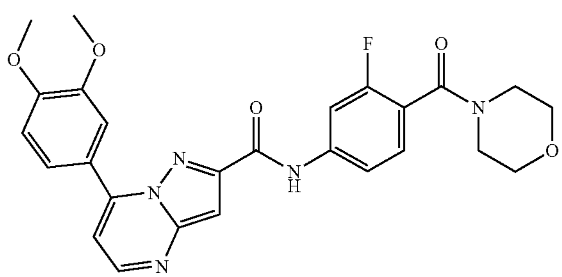 | 7-(3,4-dimethoxyphenyl)-N-(3-fluoro-4-(morpholine-4-carbonyl) phenyl)pyrazolo[1,5-a]pyrimidine-2-carboxamide |
| 175 | 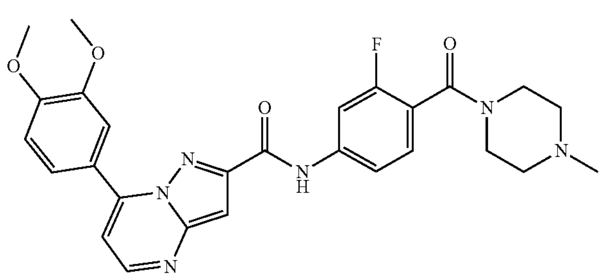 [SMILES: COc1ccc(-c2ccnc3cc(C(=O)Nc4ccc(C(=O)N5CCN(C)CC5)c(F)c4)nn23)cc1OC] | 7-(3,4-dimethoxyphenyl)-N-(3-fluoro-4-(4-methylpiperazine-1-carbonyl)phenyl)pyrazolo [1,5-a]pyrimidine-2-carboxamide |

TABLE 1-continued

Exemplary compounds

| Cmpd | Structure | Name |
|---|---|---|
| 176 | 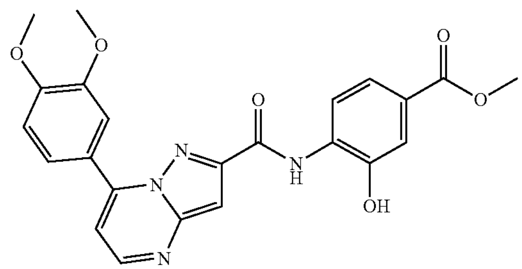 [SMILES: COC(=O)c1ccc(NC(=O)c2cc3nccc(-c4ccc(OC)c(OC)c4)n3n2)c(O)c1] | methyl 4-(7-(3,4-dimethoxyphenyl)pyrazolo[1,5-a]pyrimidine-2-carboxamido)-3-hydroxybenzoate |
| 177 | 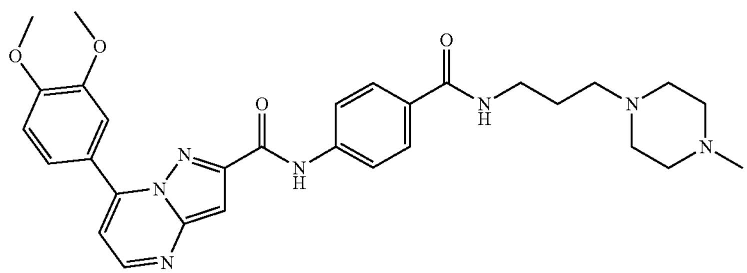 [SMILES: COc1ccc(-c2ccnc3cc(C(=O)Nc4ccc(C(=O)NCCCN5CCN(C)CC5)cc4)nn23)cc1OC] | 7-(3,4-dimethoxyphenyl)-N-(4-((3-(4-methylpiperazin-1-yl)propyl)carbamoyl)phenyl)pyrazolo[1,5-a]pyrimidine-2-carboxamide |
| 178 | 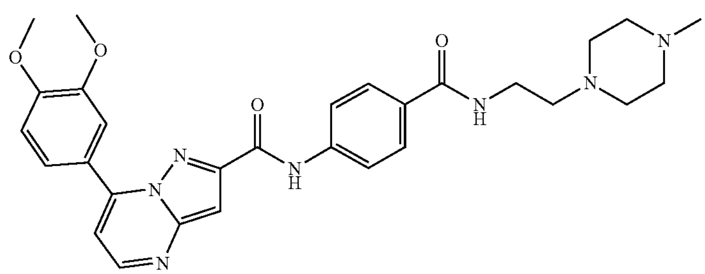 [SMILES: COc1ccc(-c2ccnc3cc(C(=O)Nc4ccc(C(=O)NCCN5CCN(C)CC5)cc4)nn23)cc1OC] | 7-(3,4-dimethoxyphenyl)-N-(4-((2-(4-methylpiperazin-1-yl)ethyl)carbamoyl)phenyl)pyrazolo[1,5-a]pyrimidine-2-carboxamide |
| 179 | 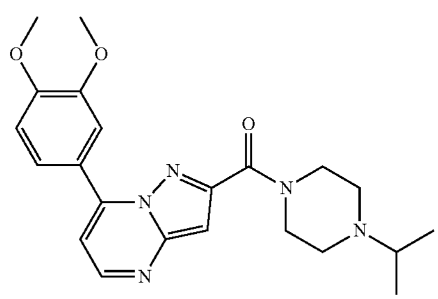 [SMILES: COc1ccc(-c2ccnc3cc(C(=O)N4CCN(C(C)C)CC4)nn23)cc1OC] | (7-(3,4-dimethoxyphenyl)pyrazolo[1,5-a]pyrimidin-2-yl)(4-isopropylpiperazin-1-yl)methanone |
| 180 | 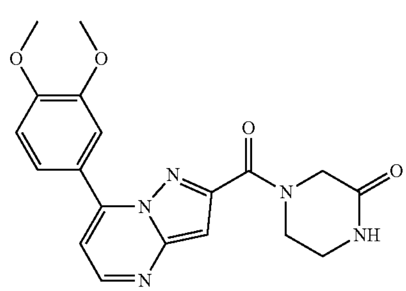 [SMILES: COc1ccc(-c2ccnc3cc(C(=O)N4CCNC(=O)C4)nn23)cc1OC] | 4-(7-(3,4-dimethoxyphenyl)pyrazolo[1,5-a]pyrimidine-2-carbonyl)piperazin-2-one |

TABLE 1-continued

Exemplary compounds

| Cmpd | Structure | Name |
| --- | --- | --- |
| 181 | 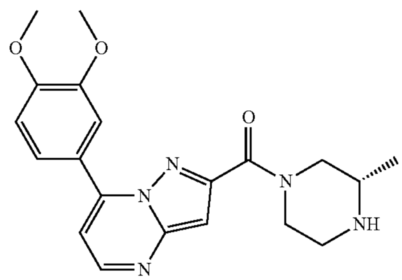 [SMILES: COc1ccc(-c2ccnc3cc(C(=O)N4CCN[C@@H](C)C4)nn23)cc1OC] | (S)-(7-(3,4-dimethoxyphenyl) pyrazolo[1,5-a]pyrimidin-2-yl)(3-methylpiperazin-1-yl)methanone |
| 182 | 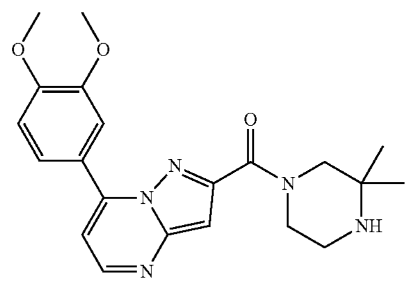 [SMILES: COc1ccc(-c2ccnc3cc(C(=O)N4CCNC(C)(C)C4)nn23)cc1OC] | (7-(3,4-dimethoxyphenyl) pyrazolo[1,5-a]pyrimidin-2-yl)(3,3-dimethylpiperazin-1-yl)methanone |
| 183 | 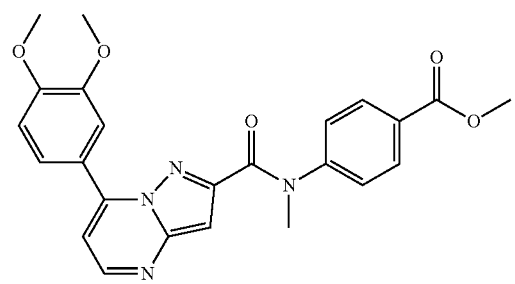 [SMILES: COC(=O)c1ccc(N(C)C(=O)c2cc3nccc(-c4ccc(OC)c(OC)c4)n3n2)cc1] | methyl 4-(7-(3,4-dimethoxyphenyl)-N-methylpyrazolo[1,5-a]pyrimidine-2-carboxamido)benzoate |
| 184 | 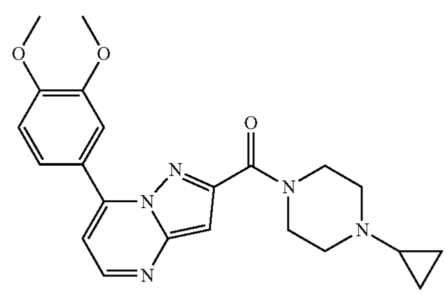 [SMILES: COc1ccc(-c2ccnc3cc(C(=O)N4CCN(C5CC5)CC4)nn23)cc1OC] | (4-cyclopropylpiperazin-1-yl)(7-(3,4-dimethoxyphenyl)pyrazolo[1,5-a]pyrimidin-2-yl)methanone |
| 185 | 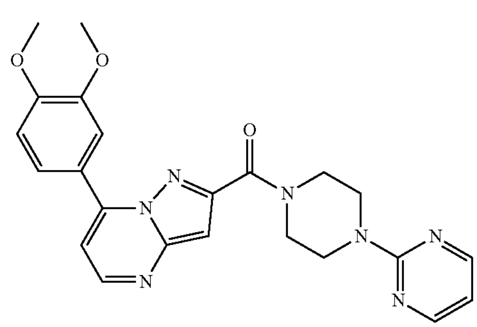 [SMILES: COc1ccc(-c2ccnc3cc(C(=O)N4CCN(c5ncccn5)CC4)nn23)cc1OC] | (7-(3,4-dimethoxyphenyl) pyrazolo[1,5-a]pyrimidin-2-yl)(4-(pyrimidin-2-yl)piperazin-1-yl)methanone |

TABLE 1-continued

| Cmpd | Structure | Name |
|---|---|---|
| 186 | 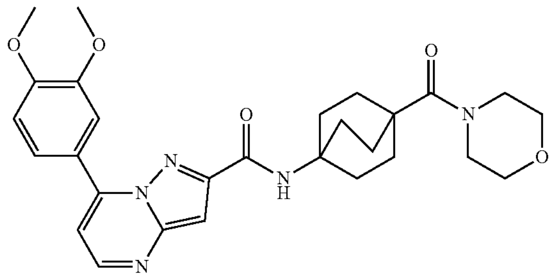 [SMILES: COc1ccc(-c2ccnc3cc(C(=O)NC45CCC(C(=O)N6CCOCC6)(CC4)CC5)nn23)cc1OC] | 7-(3,4-dimethoxyphenyl)-N-(4-(morpholine-4-carbonyl)bicyclo[2.2.2]octan-1-yl)pyrazolo[1,5-a]pyrimidine-2-carboxamide |
| 187 | 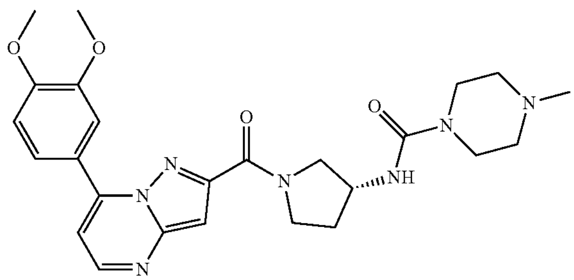 | (R)-N-(1-(7-(3,4-dimethoxyphenyl)pyrazolo[1,5-a]pyrimidine-2-carbonyl)pyrrolidin-3-yl)-1-methylpiperidine-4-carboxamide |
| 188 | 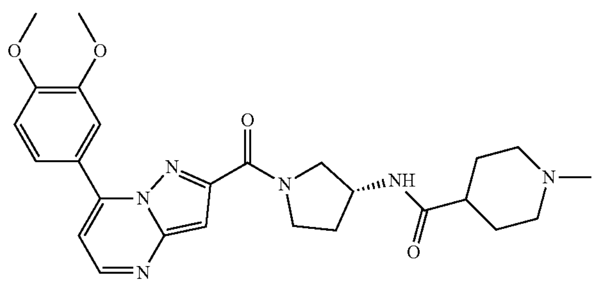 [SMILES: COc1ccc(-c2ccnc3cc(C(=O)N4CC[C@@H](NC(=O)C5CCN(C)CC5)C4)nn23)cc1OC] | (R)-N-(1-(7-(3,4-dimethoxyphenyl)pyrazolo[1,5-a]pyrimidine-2-carbonyl)pyrrolidin-3-yl)-1-methylpiperidine-4-carboxamide |
| 189 | 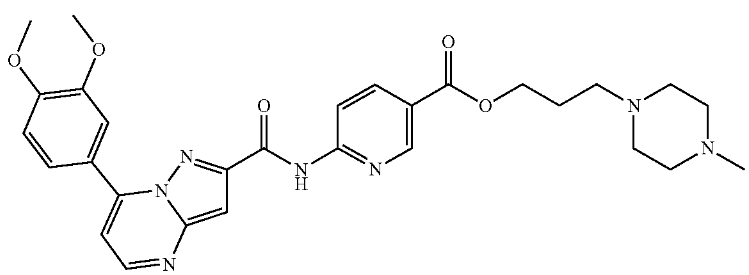 [SMILES: COc1ccc(-c2ccnc3cc(C(=O)Nc4ccc(C(=O)OCCCN5CCN(C)CC5)cn4)nn23)cc1OC] | 3-(4-methylpiperazin-1-yl)propyl 6-(7-(3,4-dimethoxyphenyl)pyrazolo[1,5-a]pyrimidine-2-carboxamido)nicotinate |
| 190 | 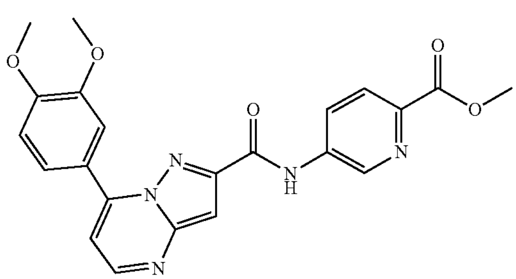 [SMILES: COC(=O)c1ccc(NC(=O)c2cc3nccc(-c4ccc(OC)c(OC)c4)n3n2)cn1] | methyl 5-(7-(3,4-dimethoxyphenyl)pyrazolo[1,5-a]pyrimidine-2-carboxamido)picolinate |

TABLE 1-continued

Exemplary compounds

| Cmpd | Structure | Name |
|---|---|---|
| 191 | 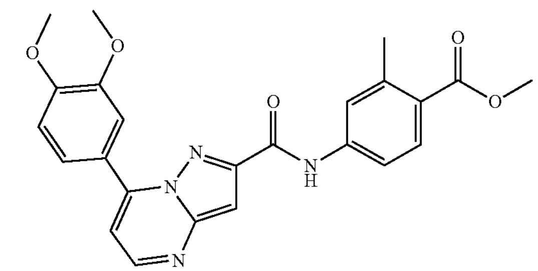 [SMILES: COC(=O)c1ccc(NC(=O)c2cc3nccc(-c4ccc(OC)c(OC)c4)n3n2)cc1C] | methyl 4-(7-(3,4-dimethoxyphenyl)pyrazolo[1,5-a]pyrimidine-2-carboxamido)-2-methylbenzoate |
| 192 | 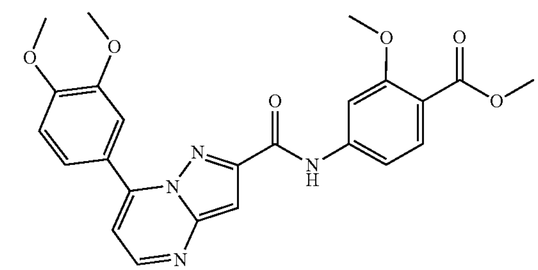 [SMILES: COC(=O)c1ccc(NC(=O)c2cc3nccc(-c4ccc(OC)c(OC)c4)n3n2)cc1OC] | methyl 4-(7-(3,4-dimethoxyphenyl)pyrazolo[1,5-a]pyrimidine-2-carboxamido)-2-methoxybenzoate |
| 193 | 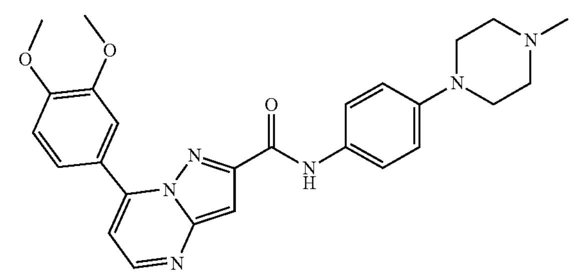 [SMILES: COc1ccc(-c2ccnc3cc(C(=O)Nc4ccc(N5CCN(C)CC5)cc4)nn23)cc1OC] | 7-(3,4-dimethoxyphenyl)-N-(4-(4-methylpiperazin-1-yl)phenyl)pyrazolo[1,5-a]pyrimidine-2-carboxamide |
| 194 | 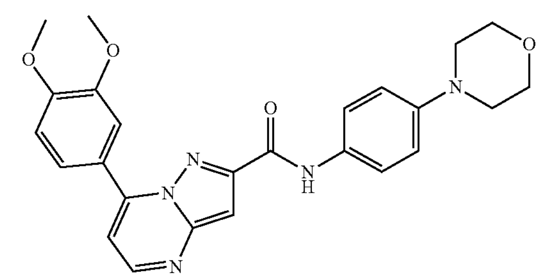 [SMILES: COc1ccc(-c2ccnc3cc(C(=O)Nc4ccc(N5CCOCC5)cc4)nn23)cc1OC] | 7-(3,4-dimethoxyphenyl)-N-(4-morpholinophenyl)pyrazolo[1,5-a]pyrimidine-2-carboxamide |
| 195 | 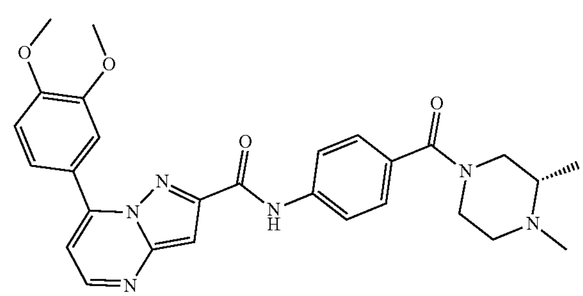 [SMILES: COc1ccc(-c2ccnc3cc(C(=O)Nc4ccc(C(=O)N5CCN(C)[C@@H](C)C5)cc4)nn23)cc1OC] | (S)-7-(3,4-dimethoxyphenyl)-N-(4-(3,4-dimethylpiperazine-1-carbonyl)phenyl)pyrazolo[1,5-a]pyrimidine-2-carboxamide |

TABLE 1-continued

Exemplary compounds

| Cmpd | Structure | Name |
|---|---|---|
| 196 | 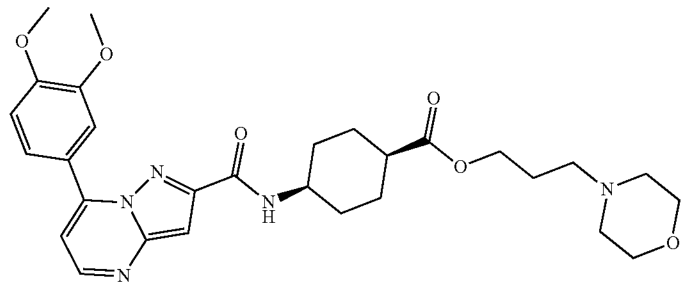 [SMILES: COc1ccc(-c2ccnc3cc(C(=O)N[C@H]4CC[C@@H](C(=O)OCCCN5CCOCC5)CC4)nn23)cc1OC] | 3-morpholinopropyl (1s,4s)-4-(7-(3,4-dimethoxyphenyl)pyrazolo[1,5-a]pyrimidine-2-carboxamido)cyclohexane-1-carboxylate |
| 197 | 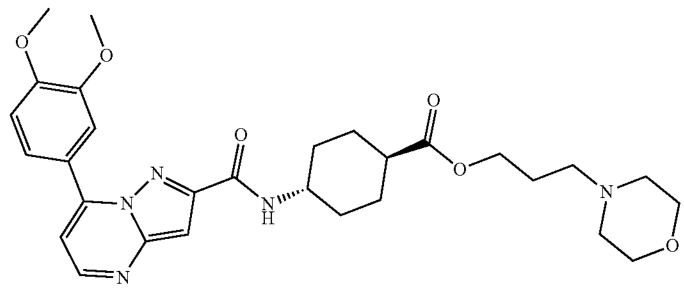 [SMILES: COc1ccc(-c2ccnc3cc(C(=O)N[C@H]4CC[C@H](C(=O)OCCCN5CCOCC5)CC4)nn23)cc1OC] | 3-morpholinopropyl (1r,4r)-4-(7-(3,4-dimethoxyphenyl)pyrazolo[1,5-a]pyrimidine-2-carboxamido)cyclohexane-1-carboxylate |
| 198 | 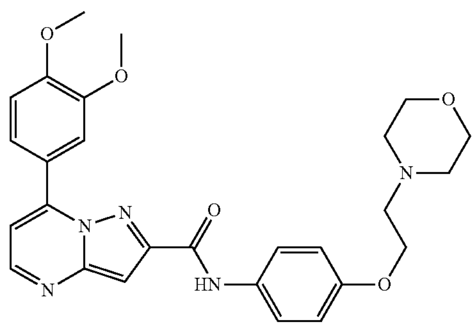 [SMILES: COc1ccc(-c2ccnc3cc(C(=O)Nc4ccc(OCCN5CCOCC5)cc4)nn23)cc1OC] | 7-(3,4-dimethoxyphenyl)-N-(4-(2-morpholinoethoxy)phenyl)pyrazolo[1,5-a]pyrimidine-2-carboxamide |
| 199 | 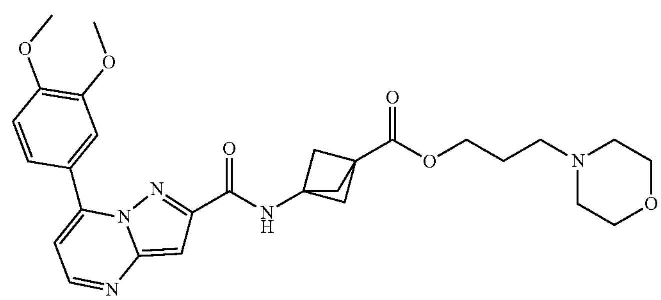 [SMILES: COc1ccc(-c2ccnc3cc(C(=O)NC45CC(C(=O)OCCCN6CCOCC6)(C4)C5)nn23)cc1OC] | 3-morpholinopropyl 3-(7-(3,4-dimethoxyphenyl)pyrazolo[1,5-a]pyrimidine-2-carboxamido)bicyclo[1.1.1]pentane-1-carboxylate |
| 200 | 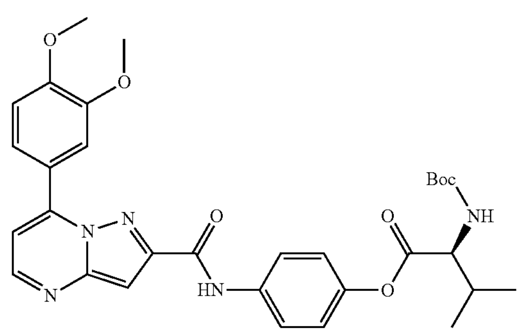 [SMILES: COc1ccc(-c2ccnc3cc(C(=O)Nc4ccc(OC(=O)[C@@H](NC(=O)OC(C)(C)C)C(C)C)cc4)nn23)cc1OC] | 4-(7-(3,4-dimethoxyphenyl)pyrazolo[1,5-a]pyrimidine-2-carboxamido)phenyl (tert-butoxycarbonyl)-L-valinate |

TABLE 1-continued

Exemplary compounds

| Cmpd | Structure | Name |
|---|---|---|
| 201 | 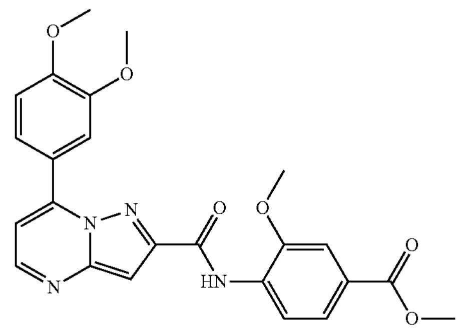 [SMILES: COC(=O)c1ccc(NC(=O)c2cc3nccc(-c4ccc(OC)c(OC)c4)n3n2)c(OC)c1] | methyl 4-(7-(3,4-dimethoxyphenyl)pyrazolo[1,5-a]pyrimidine-2-carboxamido)-3-methoxybenzoate |
| 202 | 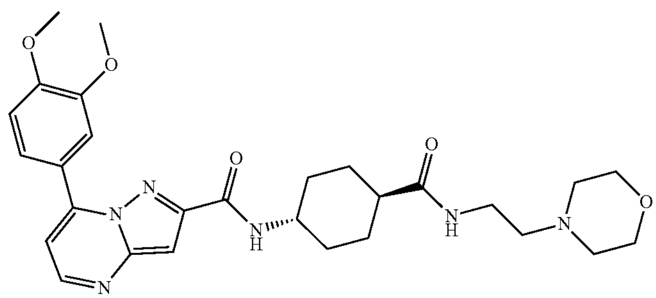 [SMILES: COc1ccc(-c2ccnc3cc(C(=O)N[C@H]4CC[C@H](C(=O)NCCN5CCOCC5)CC4)nn23)cc1OC] | 7-(3,4-dimethoxyphenyl)-N-((1r,4r)-4-((2-morpholinoethyl)carbamoyl)cyclohexyl)pyrazolo[1,5-a]pyrimidine-2-carboxamide |
| 203 | 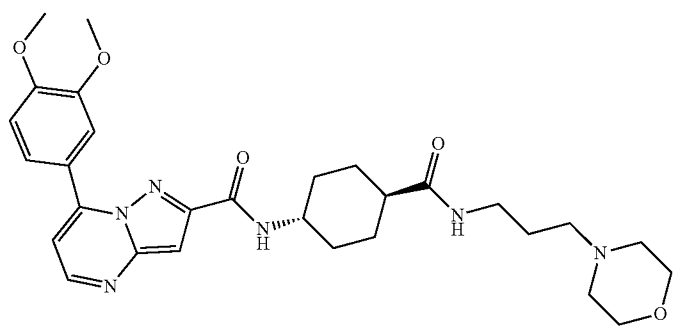 [SMILES: COc1ccc(-c2ccnc3cc(C(=O)N[C@H]4CC[C@H](C(=O)NCCCN5CCOCC5)CC4)nn23)cc1OC] | 7-(3,4-dimethoxyphenyl)-N-((1r,4r)-4-((3-morpholinopropyl)carbamoyl)cyclohexyl)pyrazolo[1,5-a]pyrimidine-2-carboxamide |
| 204 | 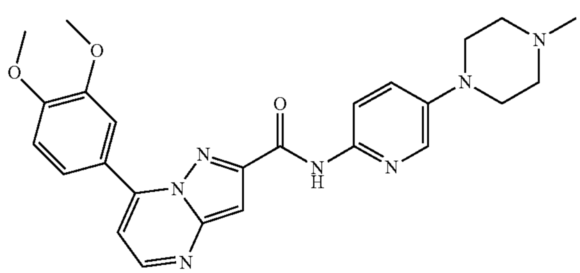 [SMILES: COc1ccc(-c2ccnc3cc(C(=O)Nc4ccc(N5CCN(C)CC5)cn4)nn23)cc1OC] | 7-(3,4-dimethoxyphenyl)-N-(5-(4-methylpiperazin-1-yl)pyridin-2-yl)pyrazolo[1,5-a]pyrimidine-2-carboxamide |
| 205 | 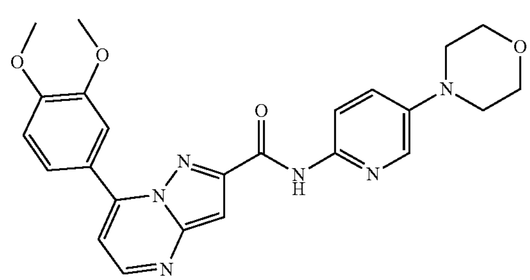 [SMILES: COc1ccc(-c2ccnc3cc(C(=O)Nc4ccc(N5CCOCC5)cn4)nn23)cc1OC] | 7-(3,4-dimethoxyphenyl)-N-(5-morpholinopyridin-2-yl)pyrazolo[1,5-a]pyrimidine-2-carboxamide |

TABLE 1-continued

Exemplary compounds

| Cmpd | Structure | Name |
|---|---|---|
| 206 | 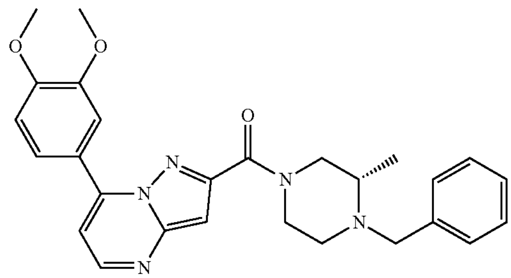 [SMILES: COc1ccc(-c2ccnc3cc(C(=O)N4CCN(Cc5ccccc5)[C@@H](C)C4)nn23)cc1OC] | (S)-(4-benzyl-3-methylpiperazin-1-yl)(7-(3,4-dimethoxyphenyl)pyrazolo[1,5-a]pyrimidin-2-yl)methanone |
| 207 | 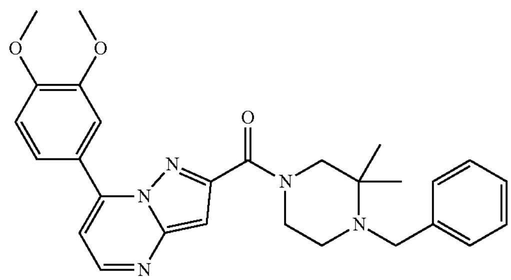 [SMILES: COc1ccc(-c2ccnc3cc(C(=O)N4CCN(Cc5ccccc5)C(C)(C)C4)nn23)cc1OC] | (4-benzyl-3,3-dimethylpiperazin-1-yl)(7-(3,4-dimethoxyphenyl)pyrazolo[1,5-a]pyrimidin-2-yl)methanone |
| 208 | 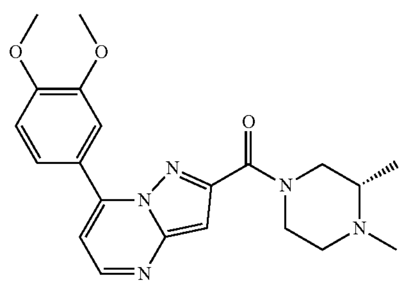 [SMILES: COc1ccc(-c2ccnc3cc(C(=O)N4CCN(C)[C@@H](C)C4)nn23)cc1OC] | (S)-(7-(3,4-dimethoxyphenyl)pyrazolo[1,5-a]pyrimidin-2-yl)(3,4-dimethylpiperazin-1-yl)methanone |
| 209 | 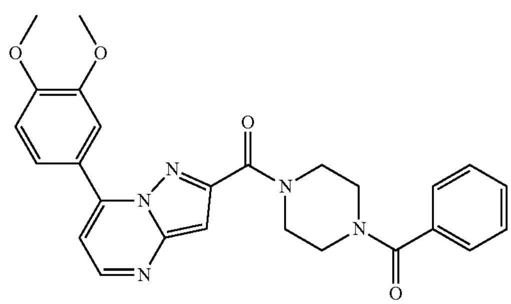 [SMILES: COc1ccc(-c2ccnc3cc(C(=O)N4CCN(C(=O)c5ccccc5)CC4)nn23)cc1OC] | (4-benzoylpiperazin-1-yl)(7-(3,4-dimethoxyphenyl)pyrazolo[1,5-a]pyrimidin-2-yl)methanone |
| 210 | 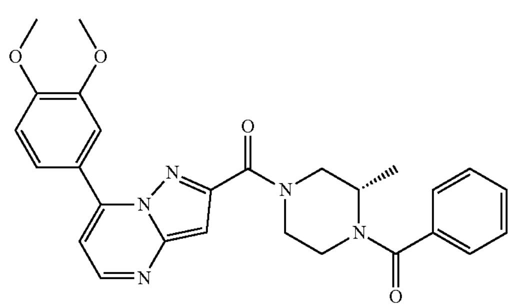 | (S)-(4-benzoyl-3-methylpiperazin-1-yl)(7-(3,4-dimethoxyphenyl)pyrazolo[1,5-a]pyrimidin-2-yl)methanone |

TABLE 1-continued

Exemplary compounds

| Cmpd | Structure | Name |
|---|---|---|
| 211 | 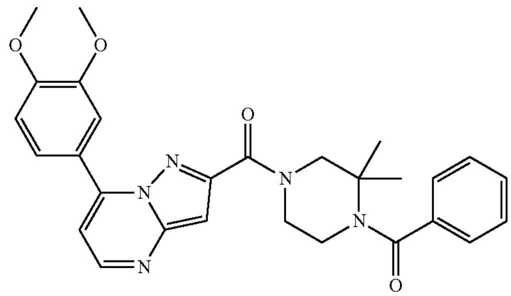 | (4-benzoyl-3,3-dimethylpiperazin-1-yl)(7-(3,4-dimethoxyphenyl)pyrazolo[1,5-a]pyrimidin-2-yl)methanone |
| 212 | 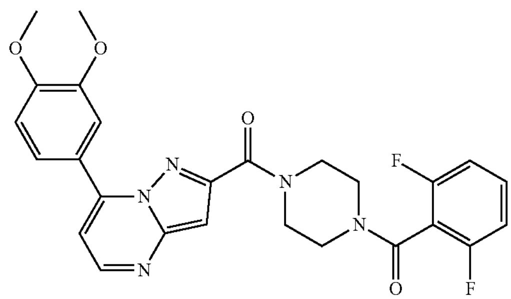 [SMILES: COc1ccc(-c2ccnc3cc(C(=O)N4CCN(C(=O)c5c(F)cccc5F)CC4)nn23)cc1OC] | (4-(2,6-difluorobenzyl)piperazin-1-yl)(7-(3,4-dimethoxyphenyl)pyrazolo[1,5-a]pyrimidin-2-yl)methanone |
| 213 | 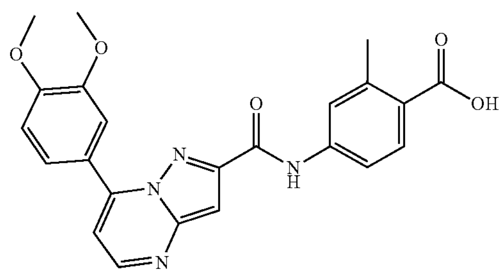 [SMILES: COc1ccc(-c2ccnc3cc(C(=O)Nc4ccc(C(=O)O)c(C)c4)nn23)cc1OC] | 4-(7-(3,4-dimethoxyphenyl)pyrazolo[1,5-a]pyrimidine-2-carboxamido)-2-methylbenzoic acid |
| 214 | 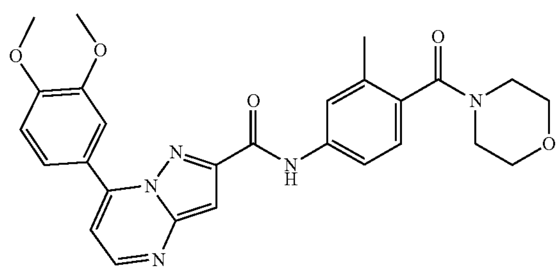 [SMILES: COc1ccc(-c2ccnc3cc(C(=O)Nc4ccc(C(=O)N5CCOCC5)c(C)c4)nn23)cc1OC] | 7-(3,4-dimethoxyphenyl)-N-(3-methyl-4-(morpholine-4-carbonyl)phenyl)pyrazolo[1,5-a]pyrimidine-2-carboxamide |
| 215 | 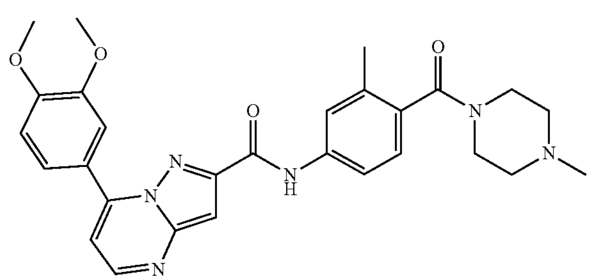 [SMILES: COc1ccc(-c2ccnc3cc(C(=O)Nc4ccc(C(=O)N5CCN(C)CC5)c(C)c4)nn23)cc1OC] | 7-(3,4-dimethoxyphenyl)-N-(3-methyl-4-(4-methylpiperazine-1-carbonyl)phenyl)pyrazolo[1,5-a]pyrimidine-2-carboxamide |

TABLE 1-continued

Exemplary compounds

| Cmpd | Structure | Name |
|---|---|---|
| 216 | 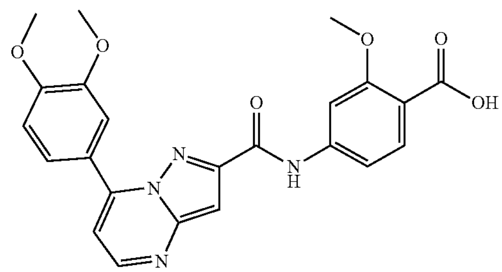 [SMILES: COc1ccc(-c2ccnc3cc(C(=O)Nc4ccc(C(=O)O)c(OC)c4)nn23)cc1OC] | 4-(7-(3,4-dimethoxyphenyl)pyrazolo[1,5-a]pyrimidine-2-carboxamido)-2-methoxybenzoic acid |
| 217 | 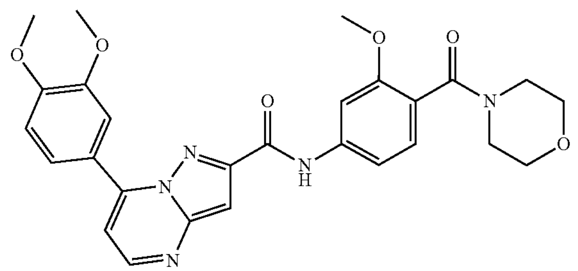 [SMILES: COc1ccc(-c2ccnc3cc(C(=O)Nc4ccc(C(=O)N5CCOCC5)c(OC)c4)nn23)cc1OC] | 7-(3,4-dimethoxyphenyl)-N-(3-methoxy-4-(morpholine-4-carbonyl)phenyl)pyrazolo[1,5-a]pyrimidine-2-carboxamide |
| 218 | 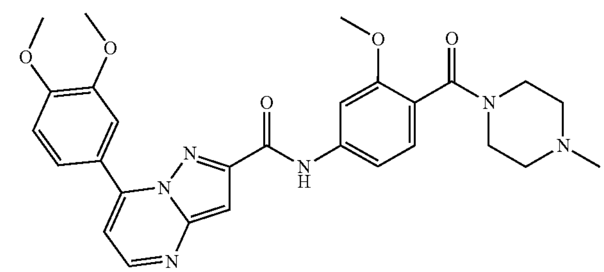 [SMILES: COc1ccc(-c2ccnc3cc(C(=O)Nc4ccc(C(=O)N5CCN(C)CC5)c(OC)c4)nn23)cc1OC] | 7-(3,4-dimethoxyphenyl)-N-(3-methoxy-4-(4-methylpiperazine-1-carbonyl)phenyl)pyrazolo[1,5-a]pyrimidine-2-carboxamide |
| 219 | 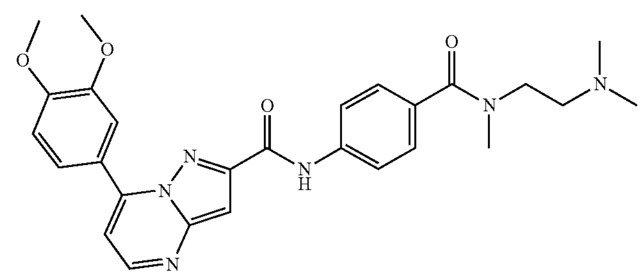 [SMILES: COc1ccc(-c2ccnc3cc(C(=O)Nc4ccc(C(=O)N(C)CCN(C)C)cc4)nn23)cc1OC] | 7-(3,4-dimethoxyphenyl)-N-(4-((2-(dimethylamino)ethyl)(methyl)carbamoyl)phenyl)pyrazolo[1,5-a]pyrimidine-2-carboxamide |
| 220 | 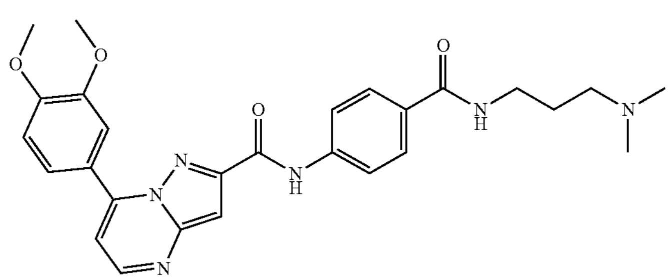 [SMILES: COc1ccc(-c2ccnc3cc(C(=O)Nc4ccc(C(=O)NCCCN(C)C)cc4)nn23)cc1OC] | 7-(3,4-dimethoxyphenyl)-N-(4-((3-(dimethylamino)propyl)carbamoyl)phenyl)pyrazolo[1,5-a]pyrimidine-2-carboxamide |

TABLE 1-continued

| Cmpd | Structure | Name |
|---|---|---|
| 221 | 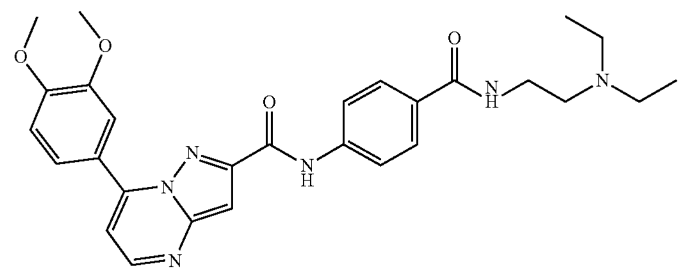 [SMILES: CCN(CC)CCNC(=O)c1ccc(NC(=O)c2cc3nccc(-c4ccc(OC)c(OC)c4)n3n2)cc1] | N-(4-((2-(diethylamino)ethyl)carbamoyl)phenyl)-7-(3,4-dimethoxyphenyl)pyrazolo[1,5-a]pyrimidine-2-carboxamide |
| 222 | 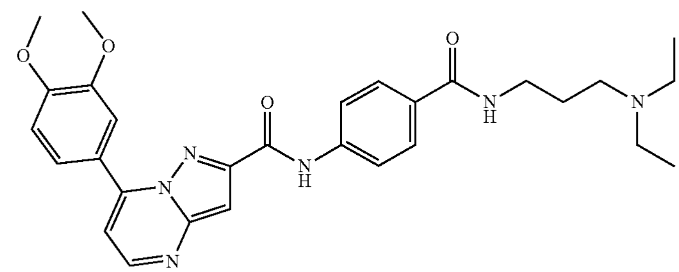 [SMILES: CCN(CC)CCCNC(=O)c1ccc(NC(=O)c2cc3nccc(-c4ccc(OC)c(OC)c4)n3n2)cc1] | N-(4-((3-(diethylamino)propyl)carbamoyl)phenyl)-7-(3,4-dimethoxyphenyl)pyrazolo[1,5-a]pyrimidine-2-carboxamide |
| 223 | 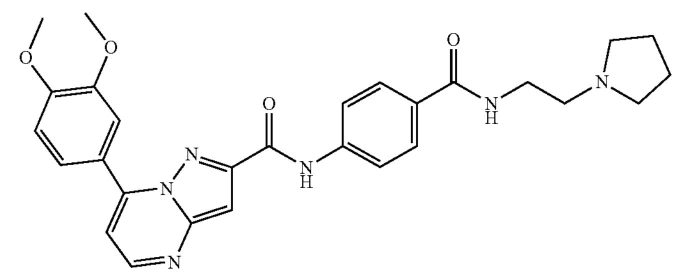 [SMILES: COc1ccc(-c2ccnc3cc(C(=O)Nc4ccc(C(=O)NCCN5CCCC5)cc4)nn23)cc1OC] | 7-(3,4-dimethoxyphenyl)-N-(4-((2-(pyrrolidin-1-yl)ethyl)carbamoyl)phenyl)pyrazolo[1,5-a]pyrimidine-2-carboxamide |
| 224 | 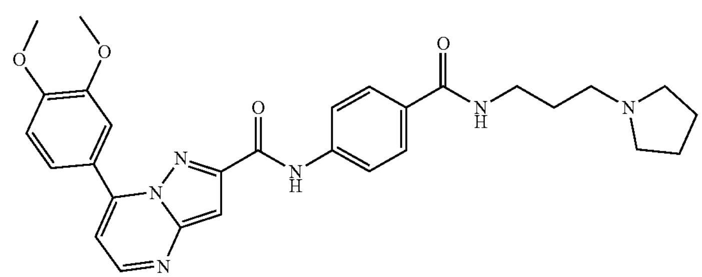 [SMILES: COc1ccc(-c2ccnc3cc(C(=O)Nc4ccc(C(=O)NCCCN5CCCC5)cc4)nn23)cc1OC] | 7-(3,4-dimethoxyphenyl)-N-(4-((3-(pyrrolidin-1-yl)propyl)carbamoyl)phenyl)pyrazolo[1,5-a]pyrimidine-2-carboxamide |
| 225 | 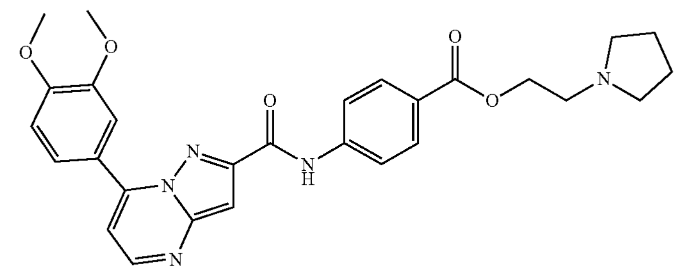 [SMILES: COc1ccc(-c2ccnc3cc(C(=O)Nc4ccc(C(=O)OCCN5CCCC5)cc4)nn23)cc1OC] | 2-(pyrrolidin-1-yl)ethyl 4-(7-(3,4-dimethoxyphenyl)pyrazolo[1,5-a]pyrimidine-2-carboxamido)benzoate |

TABLE 1-continued

Exemplary compounds

| Cmpd | Structure | Name |
|---|---|---|
| 226 | 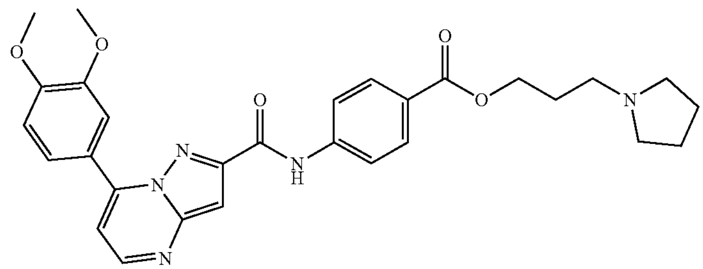 [SMILES: COc1ccc(-c2ccnc3cc(C(=O)Nc4ccc(C(=O)OCCCN5CCCC5)cc4)nn23)cc1OC] | 3-(pyrrolidin-1-yl)propyl 4-(7-(3,4-dimethoxyphenyl)pyrazolo[1,5-a]pyrimidine-2-carboxamido)benzoate |
| 227 | 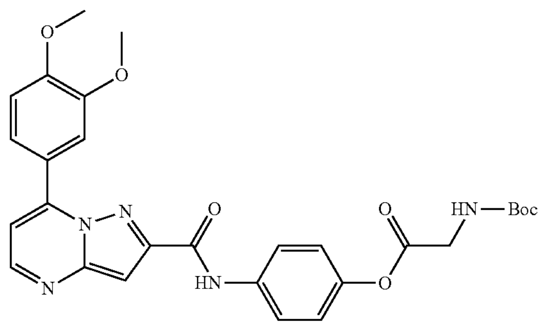 | 4-(7-(3,4-dimethoxyphenyl)pyrazolo[1,5-a]pyrimidine-2-carboxamido)phenyl (tert-butoxycarbonyl)glycinate |
| 228 | 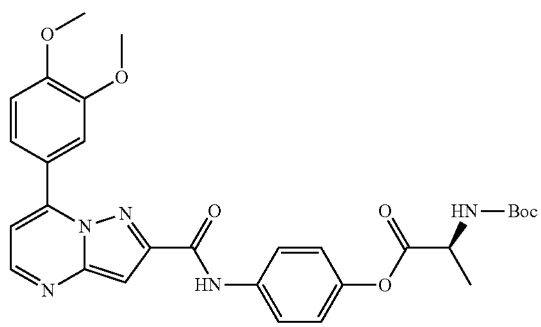 | 4-(7-(3,4-dimethoxyphenyl)pyrazolo[1,5-a]pyrimidine-2-carboxamido)phenyl (tert-butoxycarbonyl)-L-alaninate |
| 229 | 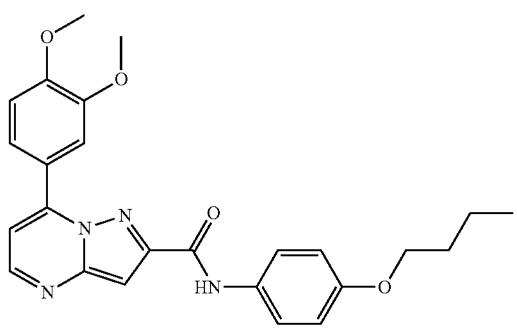 [SMILES: CCCCOc1ccc(NC(=O)c2cc3nccc(-c4ccc(OC)c(OC)c4)n3n2)cc1] | N-(4-butoxyphenyl)-7-(3,4-dimethoxyphenyl)pyrazolo[1,5-a]pyrimidine-2-carboxamide |
| 230 | 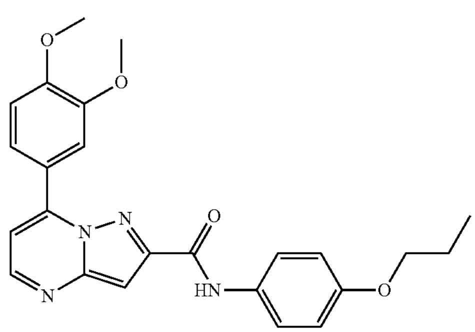 [SMILES: CCCOc1ccc(NC(=O)c2cc3nccc(-c4ccc(OC)c(OC)c4)n3n2)cc1] | 7-(3,4-dimethoxyphenyl)-N-(4-propoxyphenyl)pyrazolo[1,5-a]pyrimidine-2-carboxamide |

TABLE 1-continued

Exemplary compounds

| Cmpd | Structure | Name |
|---|---|---|
| 231 | 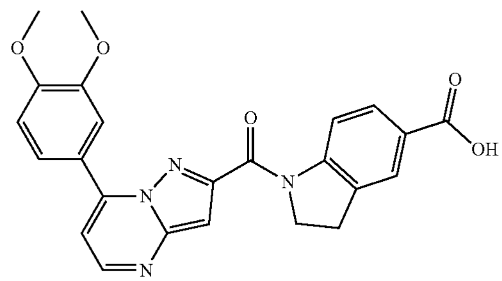 [SMILES: COc1ccc(-c2ccnc3cc(C(=O)N4CCc5cc(C(=O)O)ccc54)nn23)cc1OC] | 1-(7-(3,4-dimethoxyphenyl)pyrazolo[1,5-a]pyrimidine-2-carbonyl)indoline-5-carboxylic acid |
| 232 | 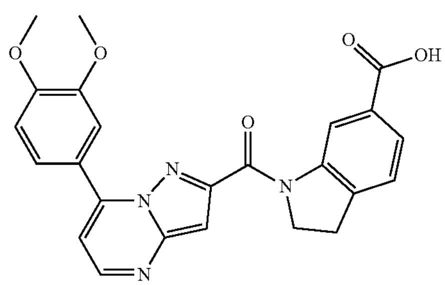 [SMILES: COc1ccc(-c2ccnc3cc(C(=O)N4CCc5ccc(C(=O)O)cc54)nn23)cc1OC] | 1-(7-(3,4-dimethoxyphenyl)pyrazolo[1,5-a]pyrimidine-2-carbonyl)indoline-6-carboxylic acid |
| 233 | 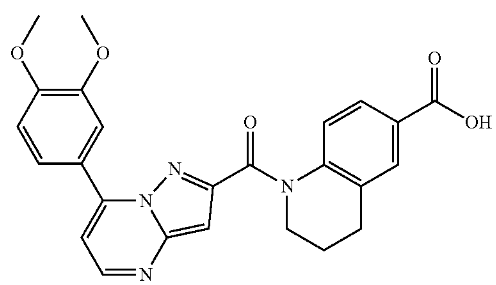 [SMILES: COc1ccc(-c2ccnc3cc(C(=O)N4CCCc5cc(C(=O)O)ccc54)nn23)cc1OC] | 1-(7-(3,4-dimethoxyphenyl)pyrazolo[1,5-a]pyrimidine-2-carbonyl)-1,2,3,4-tetrahydroquinoline-6-carboxylic acid |
| 234 | 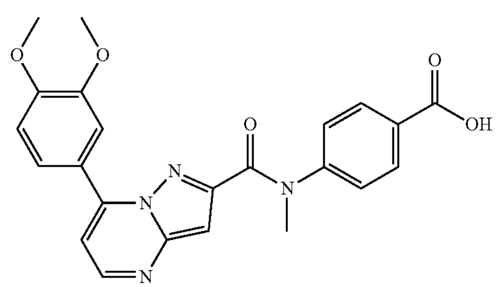 [SMILES: COc1ccc(-c2ccnc3cc(C(=O)N(C)c4ccc(C(=O)O)cc4)nn23)cc1OC] | 4-(7-(3,4-dimethoxyphenyl)-N-methylpyrazolo[1,5-a]pyrimidine-2-carboxamido)benzoic acid |
| 235 | 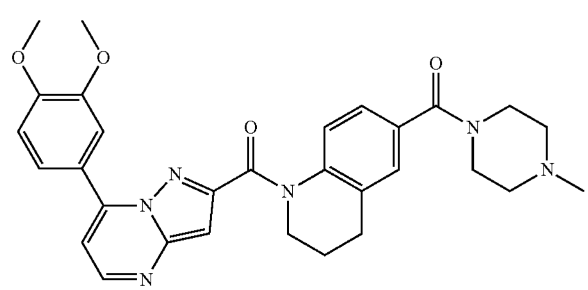 [SMILES: COc1ccc(-c2ccnc3cc(C(=O)N4CCCc5cc(C(=O)N6CCN(C)CC6)ccc54)nn23)cc1OC] | (7-(3,4-dimethoxyphenyl)pyrazolo[1,5-a]pyrimidin-2-yl)(6-(4-methylpiperazine-1-carbonyl)-3,4-dihydroquinolin-1(2H)-yl)methanone |

TABLE 1-continued

Exemplary compounds

| Cmpd | Structure | Name |
|---|---|---|
| 236 | 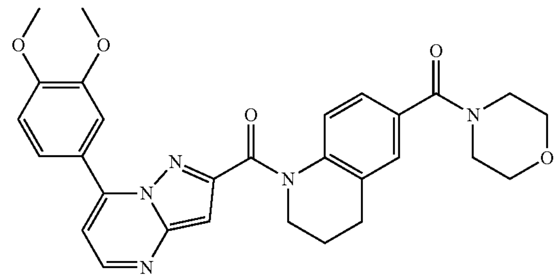 [SMILES: COc1ccc(-c2ccnc3cc(C(=O)N4CCCc5cc(C(=O)N6CCOCC6)ccc54)nn23)cc1OC] | (7-(3,4-dimethoxyphenyl) pyrazolo[1,5-a]pyrimidin-2-yl)(6-(morpholine-4-carbonyl)-3,4-dihydroquinolin-1(2H)-yl)methanone |
| 237 | 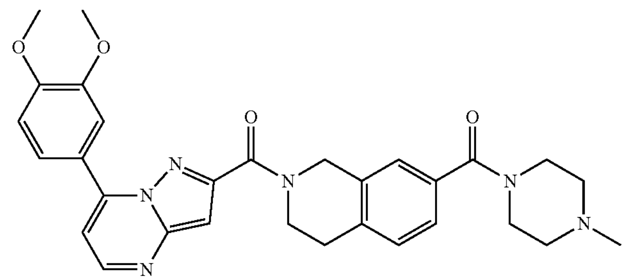 [SMILES: COc1ccc(-c2ccnc3cc(C(=O)N4CCc5ccc(C(=O)N6CCN(C)CC6)cc5C4)nn23)cc1OC] | (7-(3,4-dimethoxyphenyl) pyrazolo[1,5-a]pyrimidin-2-yl)(7-(4-methylpiperazine-1-carbonyl)-3,4-dihyroisoquinolin-2(1H)-yl)methanone |
| 238 | 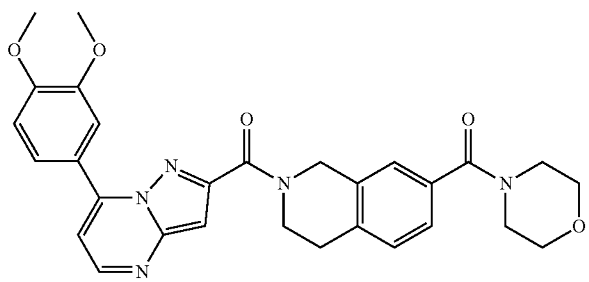 [SMILES: COc1ccc(-c2ccnc3cc(C(=O)N4CCc5ccc(C(=O)N6CCOCC6)cc5C4)nn23)cc1OC] | (7-(3,4-dimethoxyphenyl) pyrazolo[1,5-a]pyrimidin-2-yl)(7-(morpholine-4-carbonyl)-3,4-dihydroisoquinolin-2(1H)-yl)methanone |
| 239 | 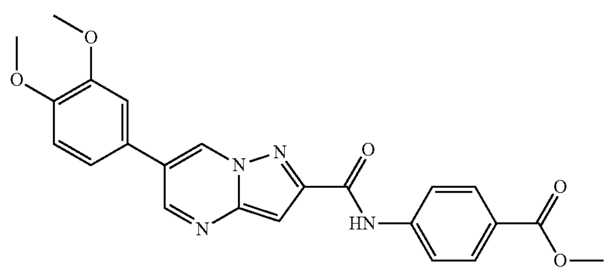 | 7-(3,4-dimethoxyphenyl)-N-((1S,4S)-4-(4-methylpiperazine-1-carbonyl)cyclohexyl) pyrazolo[1,5-a]pyrimidine-2-carboxamide |
| 240 | 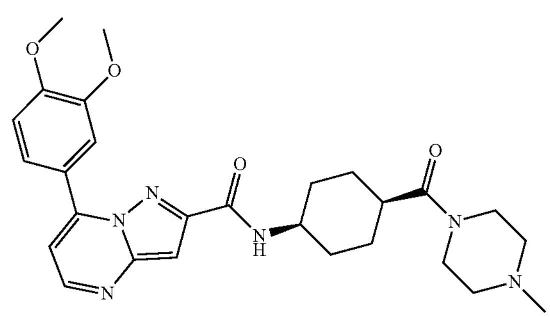 [SMILES: COc1ccc(-c2ccnc3cc(C(=O)N[C@H]4CC[C@@H](C(=O)N5CCN(C)CC5)CC4)nn23)cc1OC] | 7-(3,4-dimethoxyphenyl)-N-((1S,4S)-4-(4-methylpiperazine-1-carbonyl)cyclohexyl) pyrazolo[1,5-a]pyrimidine-2-carboxamide |

TABLE 1-continued

| Cmpd | Structure | Name |
|---|---|---|
| 241 | 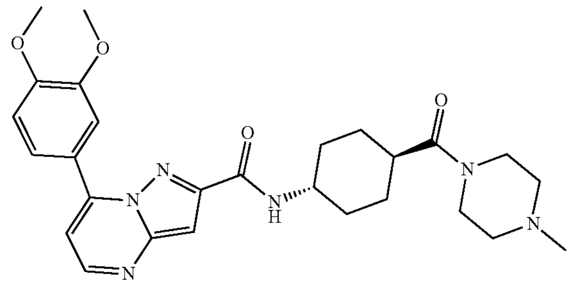 [SMILES: COc1ccc(-c2ccnc3cc(C(=O)N[C@H]4CC[C@H](C(=O)N5CCN(C)CC5)CC4)nn23)cc1OC] | 7-(3,4-dimethoxyphenyl)-N-((1r,4r)-4-(4-methylpiperazine-1-carbonyl)cyclohexyl)pyrazolo[1,5-a]pyrimidine-2-carboxamide |
| 242 | 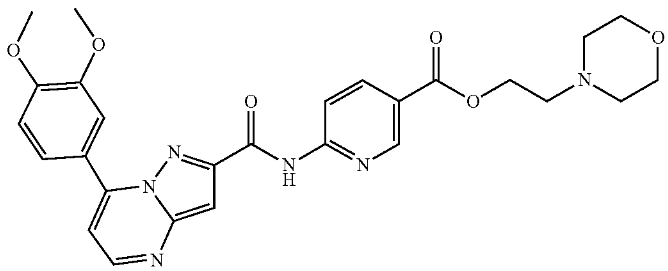 [SMILES: COc1ccc(-c2ccnc3cc(C(=O)Nc4ccc(C(=O)OCCN5CCOCC5)cn4)nn23)cc1OC] | 2-morpholinoethyl 6-(7-(3,4-dimethoxyphenyl)pyrazolo[1,5-a]pyrimidine-2-carboxamido)nicotinate |
| 243 | 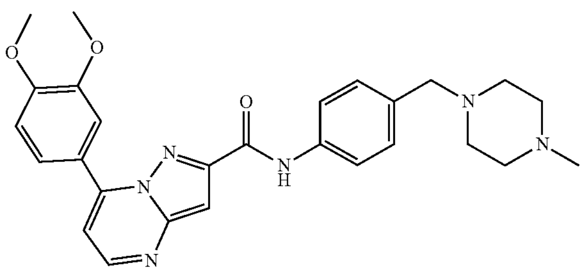 [SMILES: COc1ccc(-c2ccnc3cc(C(=O)Nc4ccc(CN5CCN(C)CC5)cc4)nn23)cc1OC] | 7-(3,4-dimethoxyphenyl)-N-(4-((4-methylpiperazin-1-yl)methyl)phenyl)pyrazolo[1,5-a]pyrimidine-2-carboxamide |
| 244 | 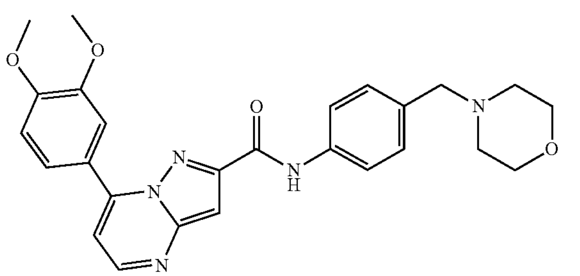 [SMILES: COc1ccc(-c2ccnc3cc(C(=O)Nc4ccc(CN5CCOCC5)cc4)nn23)cc1OC] | 7-(3,4-dimethoxyphenyl)-N-(4-(morpholinomethyl)phenyl)pyrazolo[1,5-a]pyrimidine-2-carboxamide |
| 245 | 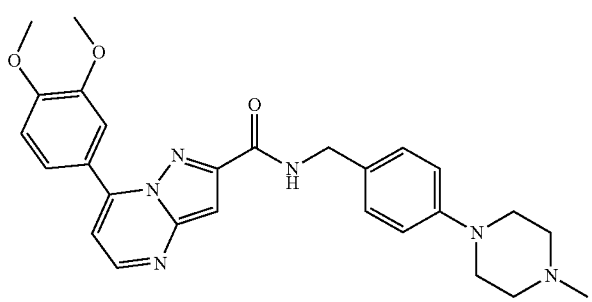 [SMILES: COc1ccc(-c2ccnc3cc(C(=O)NCc4ccc(N5CCN(C)CC5)cc4)nn23)cc1OC] | 7-(3,4-dimethoxyphenyl)-N-(4-(4-methylpiperazin-1-yl)benzyl)pyrazolo[1,5-a]pyrimidine-2-carboxamide |

TABLE 1-continued

Exemplary compounds

| Cmpd | Structure | Name |
|---|---|---|
| 246 | 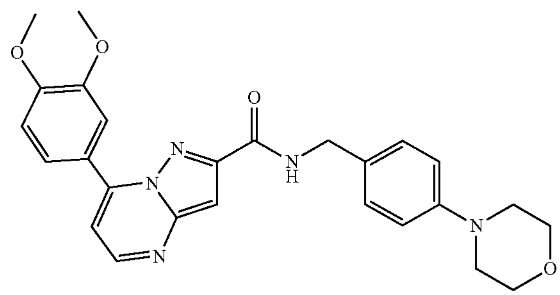 [SMILES: COc1ccc(-c2ccnc3cc(C(=O)NCc4ccc(N5CCOCC5)cc4)nn23)cc1OC] | 7-(3,4-dimethoxyphenyl)-N-(4-morpholinobenzyl)pyrazolo[1,5-a]pyrimidine-2-carboxamide |
| 247 | 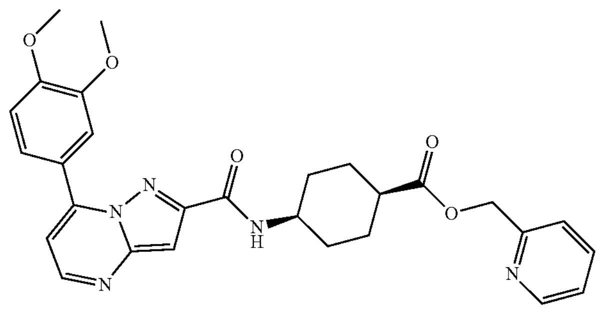 [SMILES: COc1ccc(-c2ccnc3cc(C(=O)N[C@H]4CC[C@@H](C(=O)OCc5ccccn5)CC4)nn23)cc1OC] | pyridin-2-ylmethyl (1S,4S)-4-(7-(3,4-dimethoxyphenyl)pyrazolo[1,5-a]pyrimidine-2-carboxamido)cyclohexane-1-carboxylate |
| 248 | 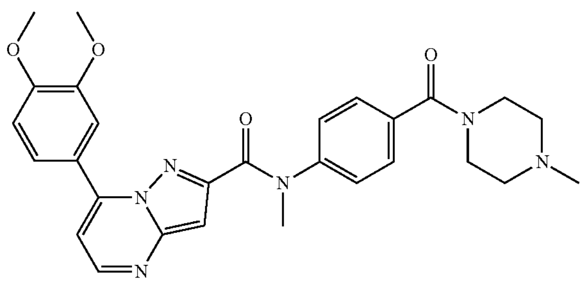 [SMILES: COc1ccc(-c2ccnc3cc(C(=O)N(C)c4ccc(C(=O)N5CCN(C)CC5)cc4)nn23)cc1OC] | 7-(3,4-dimethoxyphenyl)-N-methyl-N-(4-(4-methylpiperazine-1-carbonyl)phenyl)pyrazolo[1,5-a]pyrimidine-2-carboxamide |
| 249 | 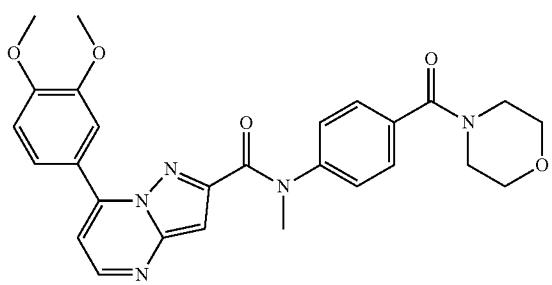 [SMILES: COc1ccc(-c2ccnc3cc(C(=O)N(C)c4ccc(C(=O)N5CCOCC5)cc4)nn23)cc1OC] | 7-(3,4-dimethoxyphenyl)-N-methyl-N-(4-(morpholine-4-carbonyl)phenyl)pyrazolo[1,5-a]pyrimidine-2-carboxamide |
| 250 | 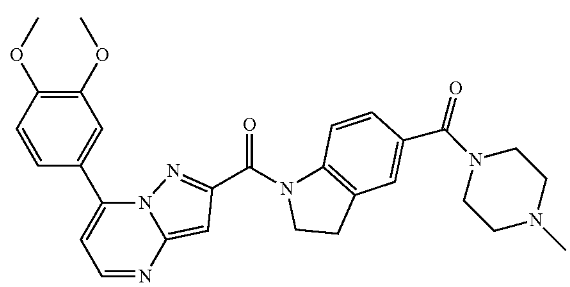 [SMILES: COc1ccc(-c2ccnc3cc(C(=O)N4CCc5cc(C(=O)N6CCN(C)CC6)ccc54)nn23)cc1OC] | (7-(3,4-dimethoxyphenyl)pyrazolo[1,5-a]pyrimidin-2-yl)(5-(4-methylpiperazine-1-carbonyl)indolin-1-yl)methanone |

TABLE 1-continued

Exemplary compounds

| Cmpd | Structure | Name |
| --- | --- | --- |
| 251 | 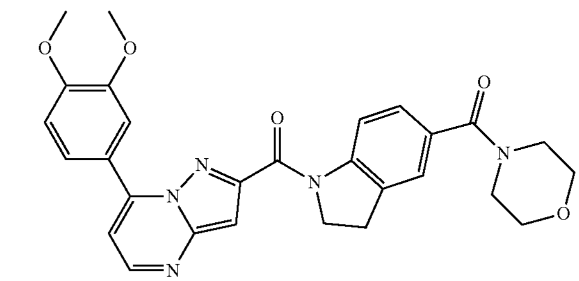 [SMILES: COc1ccc(-c2ccnc3cc(C(=O)N4CCc5cc(C(=O)N6CCOCC6)ccc54)nn23)cc1OC] | (7-(3,4-dimethoxyphenyl) pyrazolo[1,5-a]pyrimidin-2-yl)(5-(morpholine-4-carbonyl)indolin-1-yl) methanone |
| 252 | 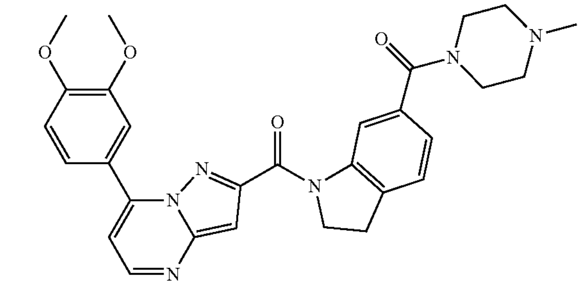 [SMILES: COc1ccc(-c2ccnc3cc(C(=O)N4CCc5ccc(C(=O)N6CCN(C)CC6)cc54)nn23)cc1OC] | (7-(3,4-dimethoxyphenyl) pyrazolo[1,5-a]pyrimidin-2-yl)(6-(4-methylpiperazine-1-carbonyl)indolin-1-yl)methanone |
| 253 | 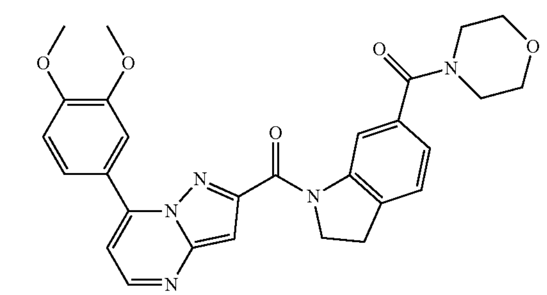 [SMILES: COc1ccc(-c2ccnc3cc(C(=O)N4CCc5ccc(C(=O)N6CCOCC6)cc54)nn23)cc1OC] | (7-(3,4-dimethoxyphenyl) pyrazolo[1,5-a]pyrimidin-2-yl)(6-(morpholine-4-carbonyl)indolin-1-yl) methanone |
| 254 | 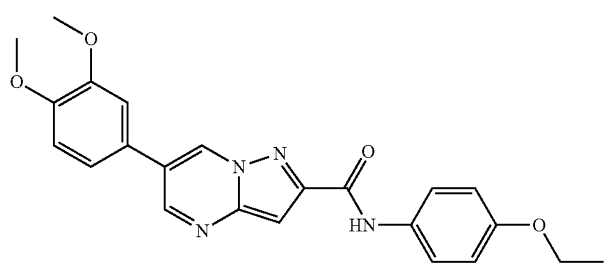 [SMILES: CCOc1ccc(NC(=O)c2cc3ncc(-c4ccc(OC)c(OC)c4)cn3n2)cc1] | 6-(3,4-dimethoxyphenyl)-N-(4-ethoxyphenyl)pyrazolo[1,5-a]pyrimidine-2-carboxamide |
| 255 | 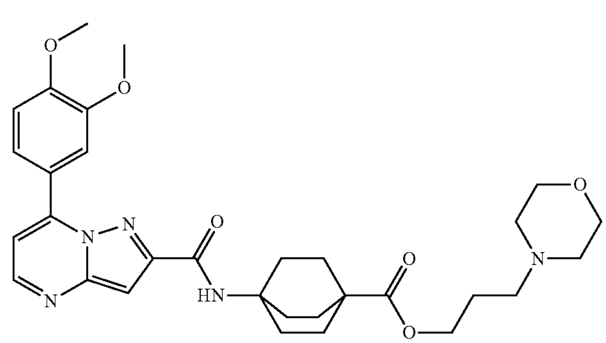 [SMILES: COc1ccc(-c2ccnc3cc(C(=O)NC45CCC(C(=O)OCCCN6CCOCC6)(CC4)CC5)nn23)cc1OC] | 3-morpholinopropyl 4-(7-(3,4-dimethoxyphenyl)pyrazolo[1,5-a]pyrimidine-2-carboxamido)bicyclo[2.2.2]octane-1-carboxylate |

TABLE 1-continued

Exemplary compounds

| Cmpd | Structure | Name |
|---|---|---|
| 256 | 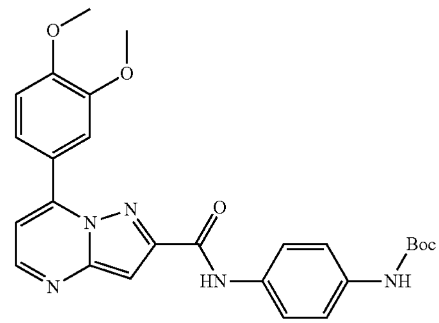 [SMILES: COc1ccc(-c2ccnc3cc(C(=O)Nc4ccc(NC(=O)OC(C)(C)C)cc4)nn23)cc1OC] | tert-butyl (4-(7-(3,4-dimethoxyphenyl)pyrazolo[1,5-a]pyrimidine-2-carboxamido)phenyl)carbamate |
| 257 | 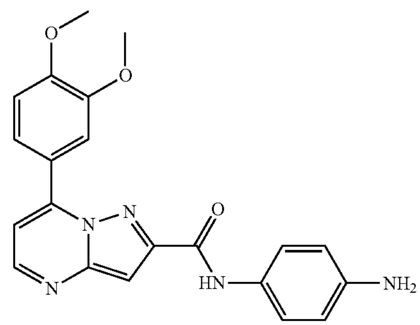 [SMILES: COc1ccc(-c2ccnc3cc(C(=O)Nc4ccc(N)cc4)nn23)cc1OC] | N-(4-aminophenyl)-7-(3,4-dimethoxyphenyl)pyrazolo[1,5-a]pyrimidine-2-carboxamide |
| 258 | 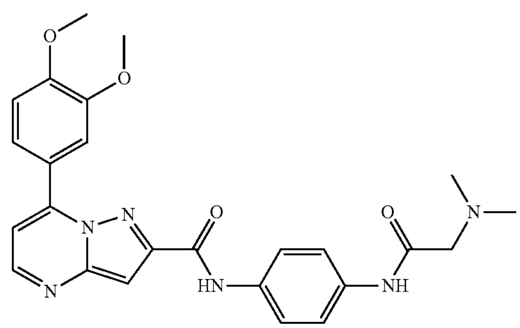 [SMILES: COc1ccc(-c2ccnc3cc(C(=O)Nc4ccc(NC(=O)CN(C)C)cc4)nn23)cc1OC] | 7-(3,4-dimethoxyphenyl)-N-(4-(2-(dimethylamino)acetamido)phenyl)pyrazolo[1,5-a]pyrimidine-2-carboxamide |
| 259 | 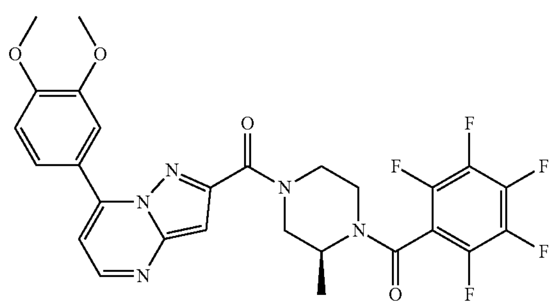 [SMILES: COc1ccc(-c2ccnc3cc(C(=O)N4CCN(C(=O)c5c(F)c(F)c(F)c(F)c5F)[C@@H](C)C4)nn23)cc1OC] | (S)-(7-(3,4-dimethoxyphenyl)pyrazolo[1,5-a]pyrimidin-2-yl)(3-methyl-4-(perfluorobenzoyl)piperazin-1-yl)methanone |

TABLE 1-continued

Exemplary compounds

| Cmpd | Structure | Name |
|---|---|---|
| 260 | 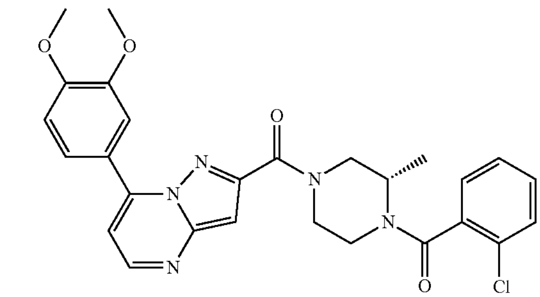 | (S)-(4-(2-chlorobenzoyl)-3-methylpiperazin-1-yl)(7-(3,4-dimethoxyphenyl)pyrazolo[1,5-a]pyrimidin-2-yl)methanone |
| 261 | 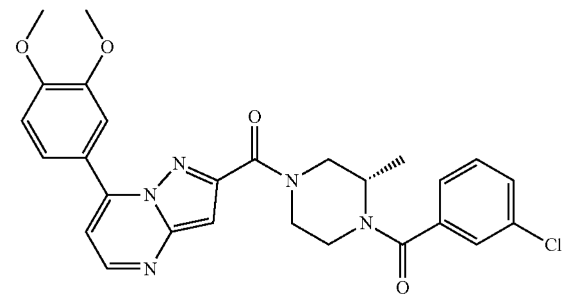 [SMILES: COc1ccc(-c2ccnc3cc(C(=O)N4CCN(C(=O)c5cccc(Cl)c5)[C@@H](C)C4)nn23)cc1OC] | (S)-(4-(3-chlorobenzoyl)-3-methylpiperazin-1-yl)(7-(3,4-dimethoxyphenyl)pyrazolo[1,5-a]pyrimidin-2-yl)methanone |
| 262 | 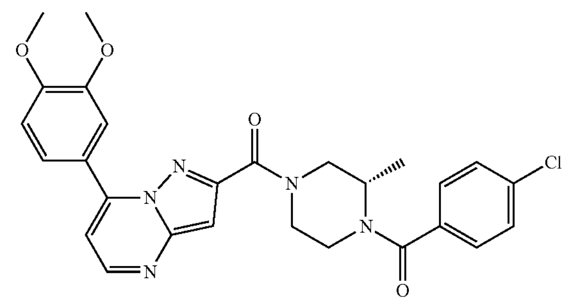 [SMILES: COc1ccc(-c2ccnc3cc(C(=O)N4CCN(C(=O)c5ccc(Cl)cc5)[C@@H](C)C4)nn23)cc1OC] | (S)-(4-(4-chlorobenzoyl)-3-methylpiperazin-1-yl)(7-(3,4-dimethoxyphenyl)pyrazolo[1,5-a]pyrimidin-2-yl)methanone |
| 263 | 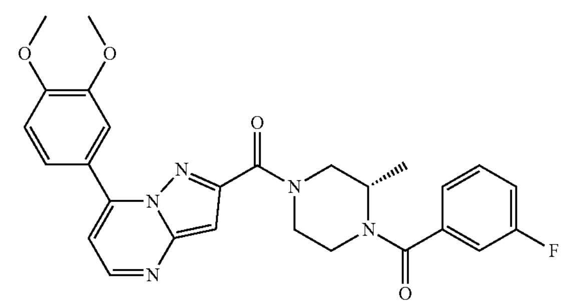 [SMILES: COc1ccc(-c2ccnc3cc(C(=O)N4CCN(C(=O)c5cccc(F)c5)[C@@H](C)C4)nn23)cc1OC] | (S)-(7-(3,4-dimethoxyphenyl)pyrazolo[1,5-a]pyrimidin-2-yl)(4-(3-fluorobenzoyl)-3-methylpiperazin-1-yl)methanone |
| 264 | 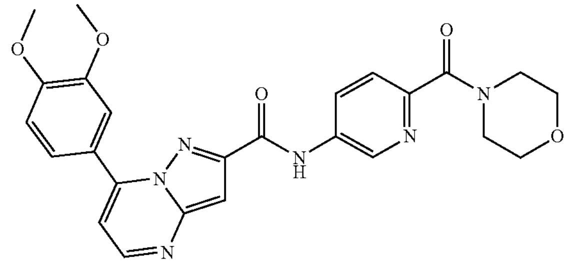 [SMILES: COc1ccc(-c2ccnc3cc(C(=O)Nc4ccc(C(=O)N5CCOCC5)nc4)nn23)cc1OC] | 7-(3,4-dimethoxyphenyl)-N-(6-(morpholine-4-carbonyl)pyridin-3-yl)pyrazolo[1,5-a]pyrimidine-2-carboxamide |

TABLE 1-continued

Exemplary compounds

| Cmpd | Structure | Name |
| --- | --- | --- |
| 265 | 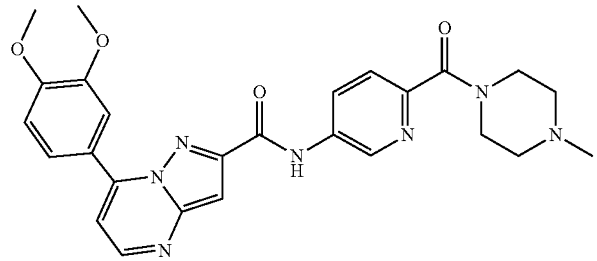 [SMILES: COc1ccc(-c2ccnc3cc(C(=O)Nc4ccc(C(=O)N5CCN(C)CC5)nc4)nn23)cc1OC] | 7-(3,4-dimethoxyphenyl)-N-(6-(4-methylpiperazine-1-carbonyl)pyridin-3-yl)pyrazolo[1,5-a]pyrimidine-2-carboxamide |
| 266 | 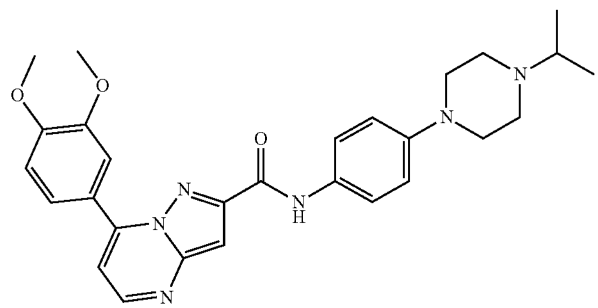 [SMILES: COc1ccc(-c2ccnc3cc(C(=O)Nc4ccc(N5CCN(C(C)C)CC5)cc4)nn23)cc1OC] | 7-(3,4-dimethoxyphenyl)-N-(4-(4-isopropylpiperazin-1-yl)phenyl)pyrazolo[1,5-a]pyrimidine-2-carboxamide |
| 268 | 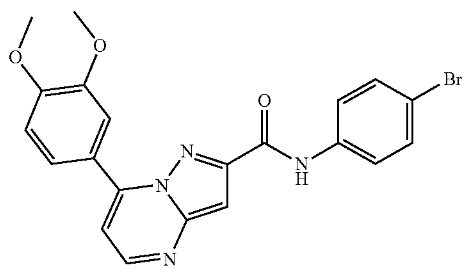 [SMILES: COc1ccc(-c2ccnc3cc(C(=O)Nc4ccc(Br)cc4)nn23)cc1OC] | N-(4-bromophenyl)-7-(3,4-dimethoxyphenyl)pyrazolo[1,5-a]pyrimidine-2-carboxamide |
| 269 | 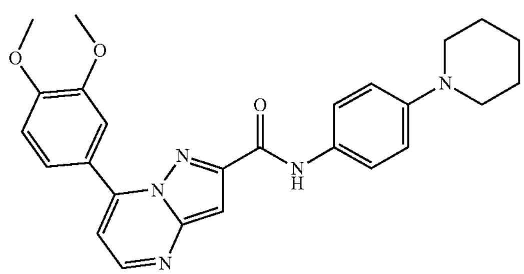 [SMILES: COc1ccc(-c2ccnc3cc(C(=O)Nc4ccc(N5CCCCC5)cc4)nn23)cc1OC] | 7-(3,4-dimethoxyphenyl)-N-(4-(piperidin-1-yl)phenyl)pyrazolo[1,5-a]pyrimidine-2-carboxamide |
| 270 | 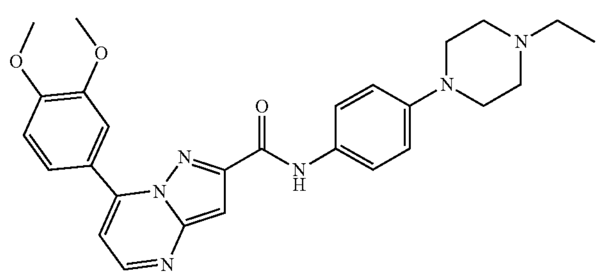 [SMILES: CCN1CCN(c2ccc(NC(=O)c3cc4nccc(-c5ccc(OC)c(OC)c5)n4n3)cc2)CC1] | 7-(3,4-dimethoxyphenyl)-N-(4-(4-ethylpiperazin-1-yl)phenyl)pyrazolo[1,5-a]pyrimidine-2-carboxamide |

TABLE 1-continued

Exemplary compounds

| Cmpd | Structure | Name |
|---|---|---|
| 271 | 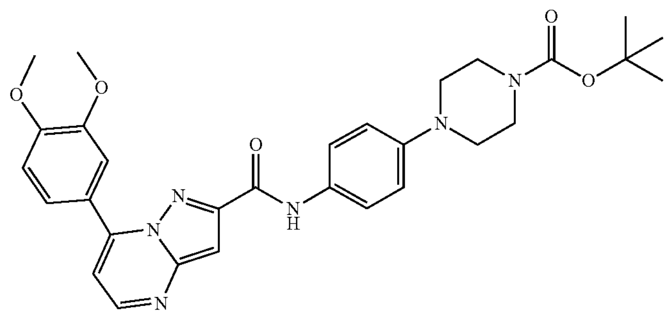 [SMILES: COc1ccc(-c2ccnc3cc(C(=O)Nc4ccc(N5CCN(C(=O)OC(C)(C)C)CC5)cc4)nn23)cc1OC] | tert-butyl 4-(4-(7-(3,4-dimethoxyphenyl)pyrazolo[1,5-a]pyrimidine-2-carboxamido)phenyl)piperazine-1-carboxylate |
| 272 | 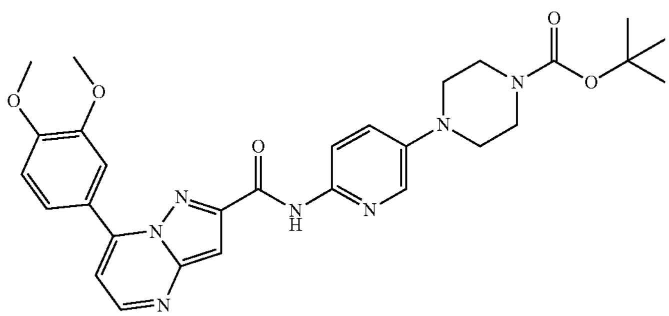 [SMILES: COc1ccc(-c2ccnc3cc(C(=O)Nc4ccc(N5CCN(C(=O)OC(C)(C)C)CC5)cn4)nn23)cc1OC] | tert-butyl 4-(6-(7-(3,4-dimethoxyphenyl)pyrazolo[1,5-a]pyrimidine-2-carboxamido)pyridin-3-yl)piperazine-1-carboxylate |
| 273 | 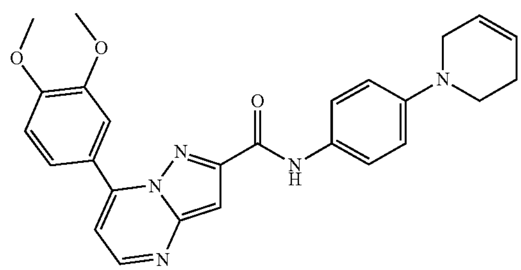 [SMILES: COc1ccc(-c2ccnc3cc(C(=O)Nc4ccc(N5CC=CCC5)cc4)nn23)cc1OC] | N-(4-(3,6-dihydropyridin-1(2H)-yl)phenyl)-7-(3,4-dimethoxyphenyl)pyrazolo[1,5-a]pyrimidine-2-carboxamide |
| 274 | 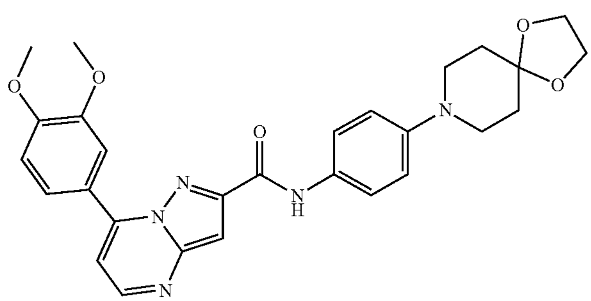 [SMILES: COc1ccc(-c2ccnc3cc(C(=O)Nc4ccc(N5CCC6(CC5)OCCO6)cc4)nn23)cc1OC] | N-(4-(1,4-dioxa-8-azaspiro[4.5]decan-8-yl)phenyl)-7-(3,4-dimethoxyphenyl)pyrazolo[1,5-a]pyrimidine-2-carboxamide |
| 275 | 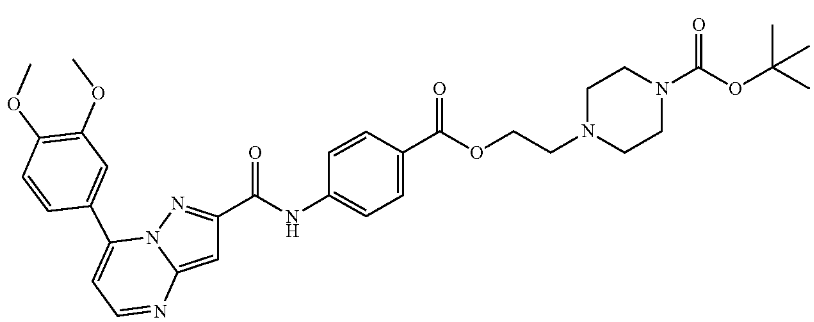 [SMILES: COc1ccc(-c2ccnc3cc(C(=O)Nc4ccc(C(=O)OCCN5CCN(C(=O)OC(C)(C)C)CC5)cc4)nn23)cc1OC] | tert-butyl 4-(2-((4-(7-(3,4-dimethoxyphenyl)pyrazolo[1,5-a]pyrimidine-2-carboxamido)benzoyl)oxy)ethyl)piperazine-1-carboxylate |

TABLE 1-continued

Exemplary compounds

| Cmpd | Structure | Name |
|---|---|---|
| 276 | 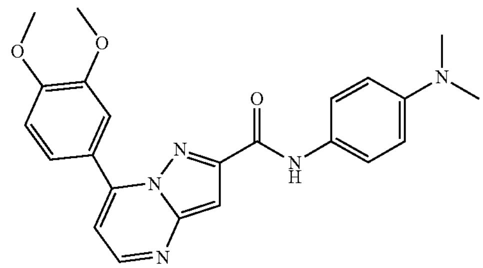 [SMILES: COc1ccc(-c2ccnc3cc(C(=O)Nc4ccc(N(C)C)cc4)nn23)cc1OC] | 7-(3,4-dimethoxyphenyl)-N-(4-(dimethylamino)phenyl)pyrazolo[1,5-a]pyrimidine-2-carboxamide |
| 277 | 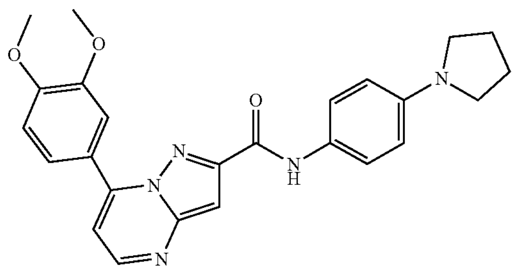 [SMILES: COc1ccc(-c2ccnc3cc(C(=O)Nc4ccc(N5CCCC5)cc4)nn23)cc1OC] | 7-(3,4-dimethoxyphenyl)-N-(4-(pyrrolidin-1-yl)phenyl)pyrazolo[1,5-a]pyrimidine-2-carboxamide |
| 278 | 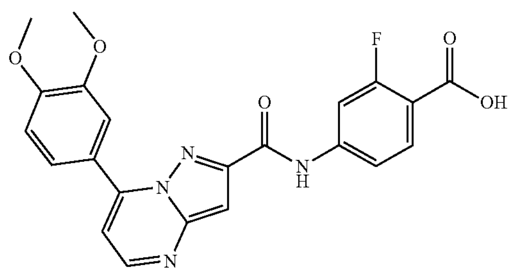 [SMILES: COc1ccc(-c2ccnc3cc(C(=O)Nc4ccc(C(=O)O)c(F)c4)nn23)cc1OC] | 4-(7-(3,4-dimethoxyphenyl)pyrazolo[1,5-a]pyrimidine-2-carboxamido)-2-fluorobenzoic acid |
| 279 | 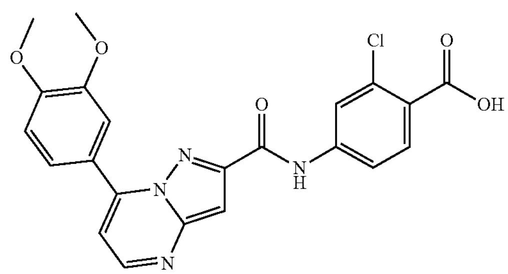 [SMILES: COc1ccc(-c2ccnc3cc(C(=O)Nc4ccc(C(=O)O)c(Cl)c4)nn23)cc1OC] | 2-chloro-4-(7-(3,4-dimethoxyphenyl)pyrazolo[1,5-a]pyrimidine-2-carboxamido)benzoic acid |
| 280 | 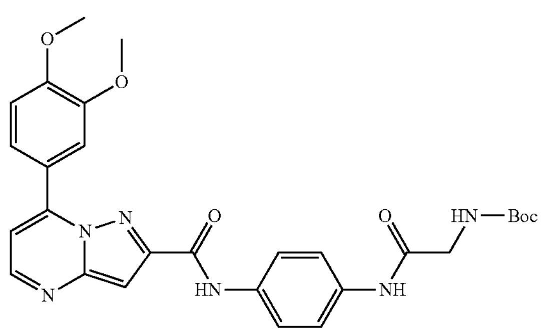 [SMILES: COc1ccc(-c2ccnc3cc(C(=O)Nc4ccc(NC(=O)CNC(=O)OC(C)(C)C)cc4)nn23)cc1OC] | tert-butyl (2-((4-(7-(3,4-dimethoxyphenyl)pyrazolo[1,5-a]pyrimidine-2-carboxamido)phenyl)amino)-2-oxoethyl)carbamate |

TABLE 1-continued

| Cmpd | Structure | Name |
|---|---|---|
| 281 | 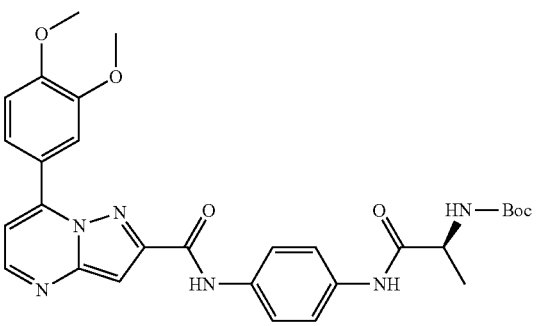 [SMILES: COc1ccc(-c2ccnc3cc(C(=O)Nc4ccc(NC(=O)[C@H](C)NC(=O)OC(C)(C)C)cc4)nn23)cc1OC] | tert-butyl (S)-1-((4-(7-(3,4-dimethoxyphenyl)pyrazolo[1,5-a]pyrimidine-2-carboxamido)phenyl)amino)-1-oxopropan-2-yl)carbamate |
| 282 | 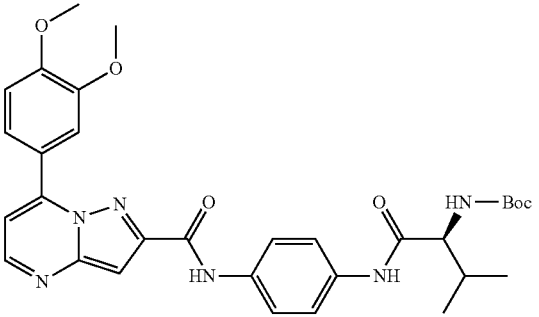 | tert-butyl (S)-(1-((4-(7-(3,4-dimethoxyphenyl)pyrazolo[1,5-a]pyrimidine-2-carboxamido)phenyl)amino)-3-methyl-1-oxobutan-2-yl)carbamate |
| 283 | 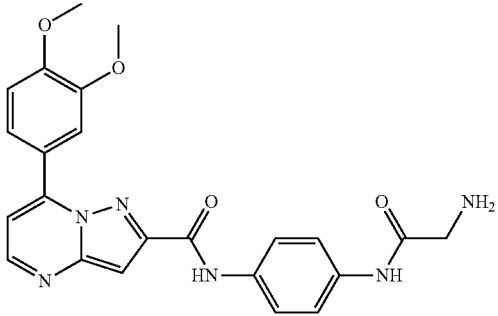 [SMILES: COc1ccc(-c2ccnc3cc(C(=O)Nc4ccc(NC(=O)CN)cc4)nn23)cc1OC] | N-(4-(2-aminoacetamido)phenyl)-7-(3,4-dimethoxyphenyl)pyrazolo[1,5-a]pyrimidine-2-carboxamide |
| 284 | 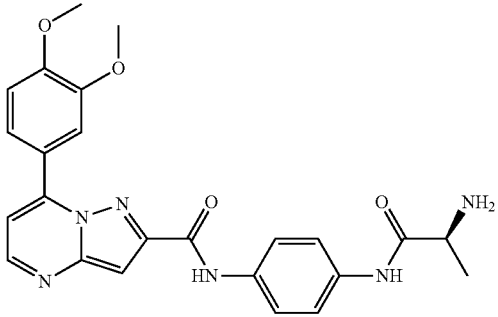 [SMILES: COc1ccc(-c2ccnc3cc(C(=O)Nc4ccc(NC(=O)[C@H](C)N)cc4)nn23)cc1OC] | (S)-N-(4-(2-aminopropanamido)phenyl)-7-(3,4-dimethoxyphenyl)pyrazolo[1,5-a]pyrimidine-2-carboxamide |

TABLE 1-continued

Exemplary compounds

| Cmpd | Structure | Name |
|---|---|---|
| 285 | 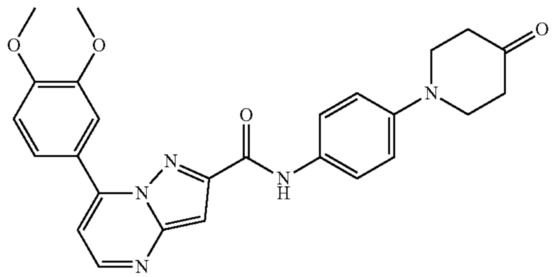 [SMILES: COc1ccc(-c2ccnc3cc(C(=O)Nc4ccc(N5CCC(=O)CC5)cc4)nn23)cc1OC] | 7-(3,4-dimethoxyphenyl)-N-(4-(4-oxopiperidin-1-yl)phenyl)pyrazolo[1,5-a]pyrimidine-2-carboxamide |
| 286 | 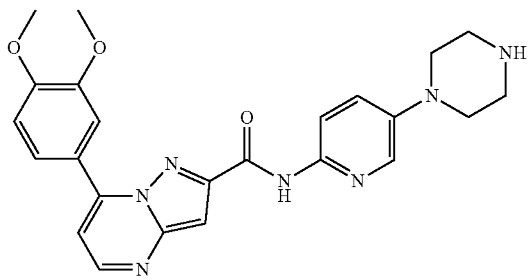 [SMILES: COc1ccc(-c2ccnc3cc(C(=O)Nc4ccc(N5CCNCC5)cn4)nn23)cc1OC] | 7-(3,4-dimethoxyphenyl)-N-(5-(piperazin-1-yl)pyridin-2-yl)pyrazolo[1,5-a]pyrimidine-2-carboxamide |
| 287 | 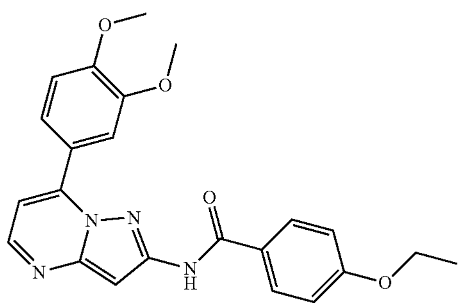 [SMILES: CCOc1ccc(C(=O)Nc2cc3nccc(-c4ccc(OC)c(OC)c4)n3n2)cc1] | N-(7-(3,4-dimethoxyphenyl)pyrazolo[1,5-a]pyrimidin-2-yl)-4-ethoxybenzamide |
| 288 | 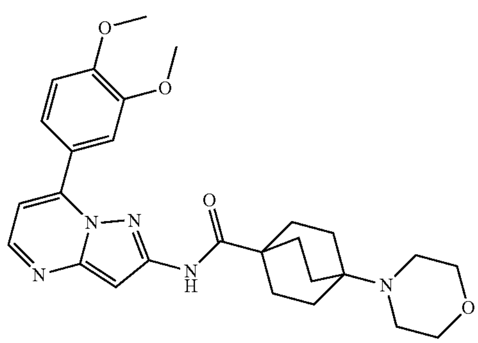 [SMILES: COc1ccc(-c2ccnc3cc(NC(=O)C45CCC(N6CCOCC6)(CC4)CC5)nn23)cc1OC] | N-(7-(3,4-dimethoxyphenyl)pyrazolo[1,5-a]pyrimidin-2-yl)-4-morpholinobicyclo[2.2.2]octane-1-carboxamide |
| 289 | 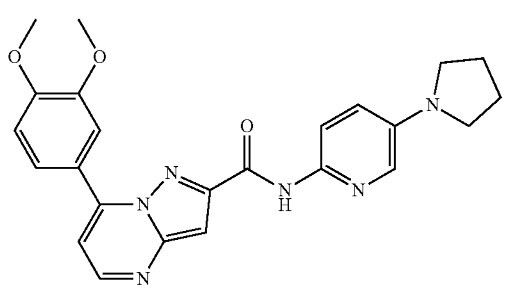 [SMILES: COc1ccc(-c2ccnc3cc(C(=O)Nc4ccc(N5CCCC5)cn4)nn23)cc1OC] | 7-(3,4-dimethoxyphenyl)-N-(5-(pyrrolidin-1-yl)pyridin-2-yl)pyrazolo[1,5-a]pyrimidine-2-carboxamide |

TABLE 1-continued

| Cmpd | Structure | Name |
|---|---|---|
| 290 | 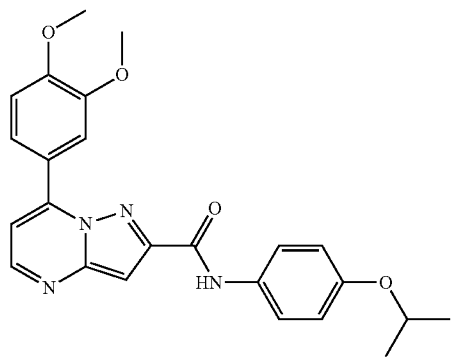 [SMILES: COc1ccc(-c2ccnc3cc(C(=O)Nc4ccc(OC(C)C)cc4)nn23)cc1OC] | 7-(3,4-dimethoxyphenyl)-N-(4-isopropoxyphenyl)pyrazolo[1,5-a]pyrimidine-2-carboxamide |
| 291 | 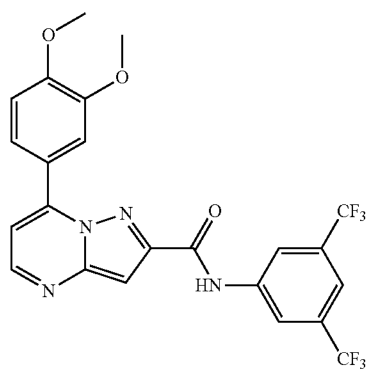 [SMILES: COc1ccc(-c2ccnc3cc(C(=O)Nc4cc(C(F)(F)F)cc(C(F)(F)F)c4)nn23)cc1OC] | N-(3,5-bis(trifluoromethyl)phenyl)-7-(3,4-dimethoxyphenyl)pyrazolo[1,5-a]pyrimidine-2-carboxamide |
| 292 | 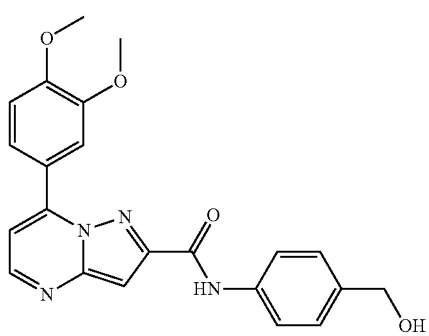 [SMILES: COc1ccc(-c2ccnc3cc(C(=O)Nc4ccc(CO)cc4)nn23)cc1OC] | 7-(3,4-dimethoxyphenyl)-N-(4-(hydroxymethyl)phenyl)pyrazolo[1,5-a]pyrimidine-2-carboxamide |
| 293 | 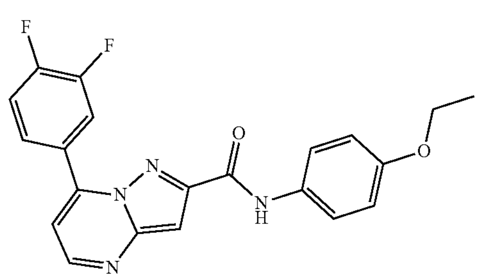 [SMILES: CCOc1ccc(NC(=O)c2cc3nccc(-c4ccc(F)c(F)c4)n3n2)cc1] | 7-(3,4-dimethoxyphenyl)-N-(4-ethoxyphenyl)pyrazolo[1,5-a]pyrimidine-2-carboxamide |

TABLE 1-continued

Exemplary compounds

| Cmpd | Structure | Name |
|---|---|---|
| 294 | 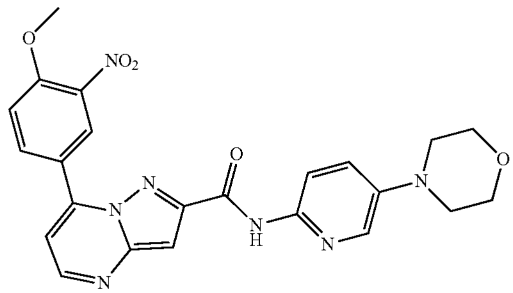 [SMILES: COc1ccc(-c2ccnc3cc(C(=O)Nc4ccc(N5CCOCC5)cn4)nn23)cc1[N+](=O)[O-]] | 7-(4-methoxy-3-nitrophenyl)-N-(5-morpholinopyridin-2-yl)pyrazolo[1,5-a]pyrimidine-2-carboxamide |
| 295 | 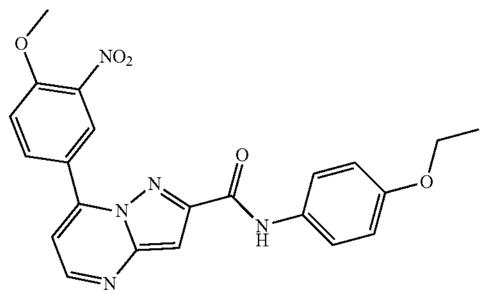 [SMILES: CCOc1ccc(NC(=O)c2cc3nccc(-c4ccc(OC)c([N+](=O)[O-])c4)n3n2)cc1] | N-(4-ethoxyphenyl)-7-(4-methoxy-3-nitrophenyl)pyrazolo[1,5-a]pyrimidine-2-carboxamide |
| 296 | 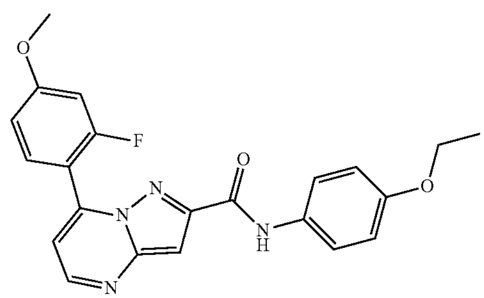 [SMILES: CCOc1ccc(NC(=O)c2cc3nccc(-c4ccc(OC)cc4F)n3n2)cc1] | N-(4-ethoxyphenyl)-7-(2-fluoro-4-methoxyphenyl)pyrazolo[1,5-a]pyrimidine-2-carboxamide |
| 297 | 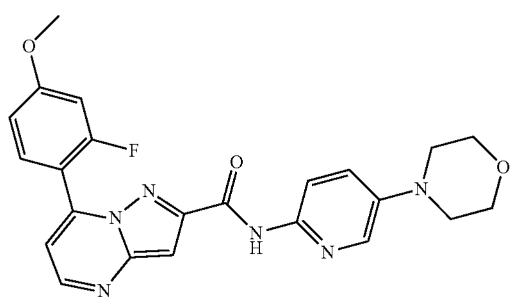 [SMILES: COc1ccc(-c2ccnc3cc(C(=O)Nc4ccc(N5CCOCC5)cn4)nn23)c(F)c1] | 7-(2-fluoro-4-methoxyphenyl)-N-(5-morpholinopyridin-2-yl)pyrazolo[1,5-a]pyrimidine-2-carboxamide |
| 298 | 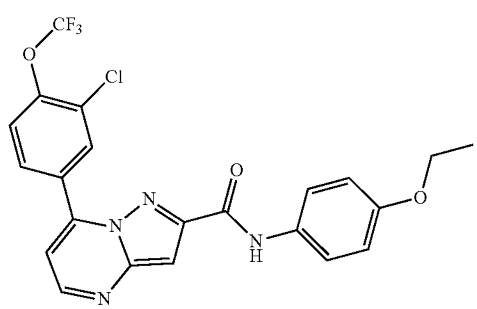 [SMILES: CCOc1ccc(NC(=O)c2cc3nccc(-c4ccc(OC(F)(F)F)c(Cl)c4)n3n2)cc1] | 7-(3-chloro-4-(trifluoromethoxy)phenyl)-N-(4-ethoxyphenyl)pyrazolo[1,5-a]pyrimidine-2-carboxamide |

TABLE 1-continued

Exemplary compounds

| Cmpd | Structure | Name |
|---|---|---|
| 299 | 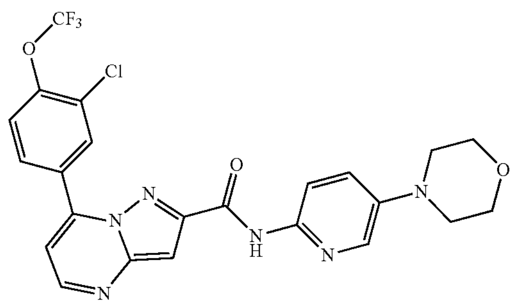 [SMILES: O=C(Nc1ccc(N2CCOCC2)cn1)c1cc2nccc(-c3ccc(OC(F)(F)F)c(Cl)c3)n2n1] | 7-(3-chloro-4-(trifluoromethoxy)phenyl)-N-(5-morpholinopyridin-2-yl)pyrazolo[1,5-a]pyrimidine-2-carboxamide |
| 301 | 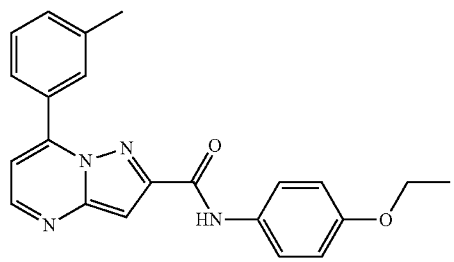 [SMILES: CCOc1ccc(NC(=O)c2cc3nccc(-c4cccc(C)c4)n3n2)cc1] | N-(4-ethoxyphenyl)-7-(m-tolyl)pyrazolo[1,5-a]pyrimidine-2-carboxamide |
| 302 | 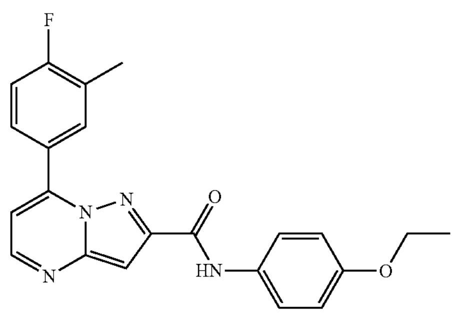 [SMILES: CCOc1ccc(NC(=O)c2cc3nccc(-c4ccc(F)c(C)c4)n3n2)cc1] | N-(4-ethoxyphenyl)-7-(4-fluoro-3-methylphenyl)pyrazolo[1,5-a]pyrimidine-2-carboxamide |
| 303 | 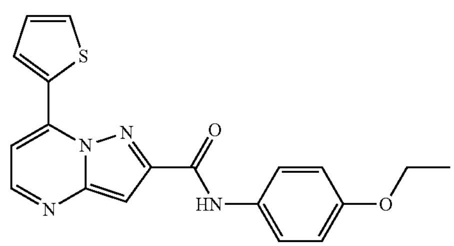 [SMILES: CCOc1ccc(NC(=O)c2cc3nccc(-c4cccs4)n3n2)cc1] | N-(4-ethoxyphenyl)-7-(thiophen-2-yl)pyrazolo[1,5-a]pyrimidine-2-carboxamide |
| 304 | 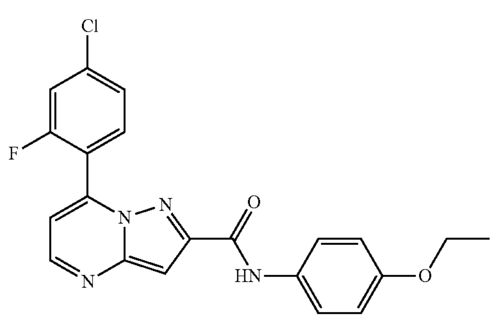 [SMILES: CCOc1ccc(NC(=O)c2cc3nccc(-c4ccc(Cl)cc4F)n3n2)cc1] | 7-(4-chloro-2-fluorophenyl)-N-(4-ethoxyphenyl)pyrazolo[1,5-a]pyrimidine-2-carboxamide |

TABLE 1-continued

Exemplary compounds

| Cmpd | Structure | Name |
|---|---|---|
| 306 | 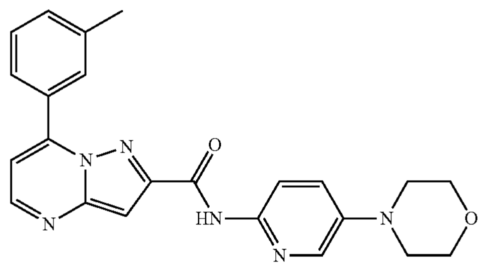 [SMILES: Cc1cccc(-c2ccnc3cc(C(=O)Nc4ccc(N5CCOCC5)cn4)nn23)c1] | N-(5-morpholinopyridin-2-yl)-7-(m-tolyl)pyrazolo[1,5-a]pyrimidine-2-carboxamide |
| 307 | 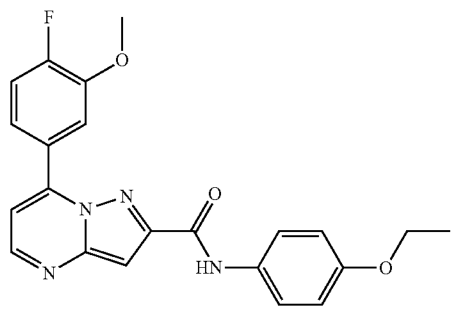 [SMILES: CCOc1ccc(NC(=O)c2cc3nccc(-c4ccc(F)c(OC)c4)n3n2)cc1] | N-(4-ethoxyphenyl)-7-(4-fluoro-3-methoxyphenyl)pyrazolo[1,5-a]pyrimidine-2-carboxamide |
| 308 | 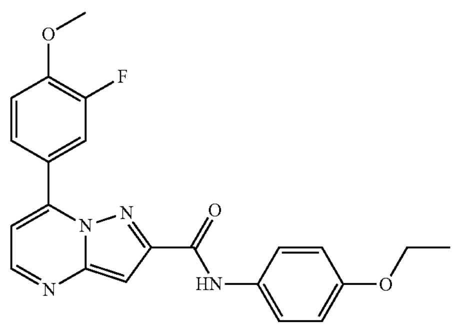 [SMILES: CCOc1ccc(NC(=O)c2cc3nccc(-c4ccc(OC)c(F)c4)n3n2)cc1] | N-(4-ethoxyphenyl)-7-(3-fluoro-4-methoxyphenyl)pyrazolo[1,5-a]pyrimidine-2-carboxamide |
| 309 | 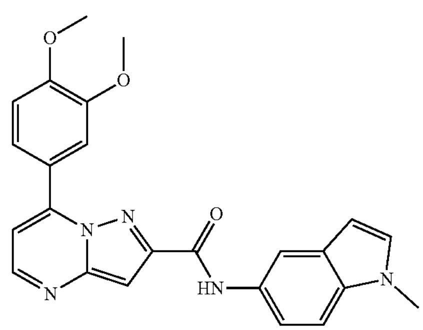 [SMILES: COc1ccc(-c2ccnc3cc(C(=O)Nc4ccc5c(ccn5C)c4)nn23)cc1OC] | 7-(3,4-dimethoxyphenyl)-N-(1-methyl-1H-indol-5-yl)pyrazolo[1,5-a]pyrimidine-2-carboxamide |
| 311 | 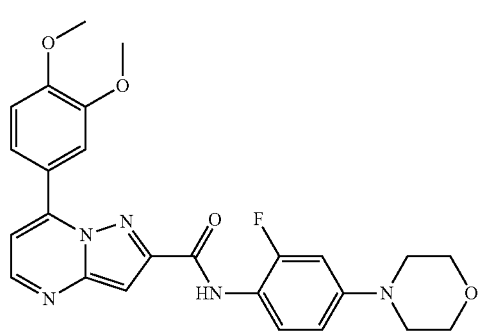 [SMILES: COc1ccc(-c2ccnc3cc(C(=O)Nc4ccc(N5CCOCC5)cc4F)nn23)cc1OC] | 7-(3,4-dimethoxyphenyl)-N-(2-fluoro-4-morpholinophenyl)pyrazolo[1,5-a]pyrimidine-2-carboxamide |

TABLE 1-continued

Exemplary compounds

| Cmpd | Structure | Name |
| --- | --- | --- |
| 312 | 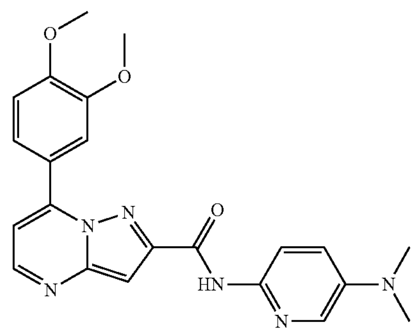 [SMILES: COc1ccc(-c2ccnc3cc(C(=O)Nc4ccc(N(C)C)cn4)nn23)cc1OC] | 7-(3,4-dimethoxyphenyl)-N-(5-(dimethylamino)pyridin-2-yl)pyrazolo[1,5-a]pyrimidine-2-carboxamide |
| 313 | 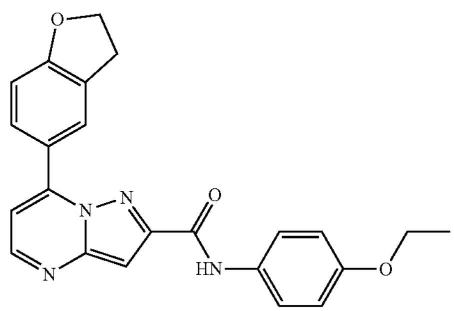 [SMILES: CCOc1ccc(NC(=O)c2cc3nccc(-c4ccc5c(c4)CCO5)n3n2)cc1] | 7-(2,3-dihydrobenzofuran-5-yl)-N-(4-ethoxyphenyl)pyrazolo[1,5-a]pyrimidine-2-carboxamide |
| 314 | 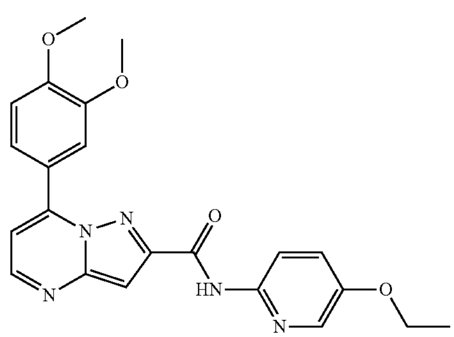 [SMILES: CCOc1ccc(NC(=O)c2cc3nccc(-c4ccc(OC)c(OC)c4)n3n2)nc1] | 7-(3,4-dimethoxyphenyl)-N-(5-ethoxypyridin-2-yl)pyrazolo[1,5-a]pyrimidine-2-carboxamide |
| 315 | 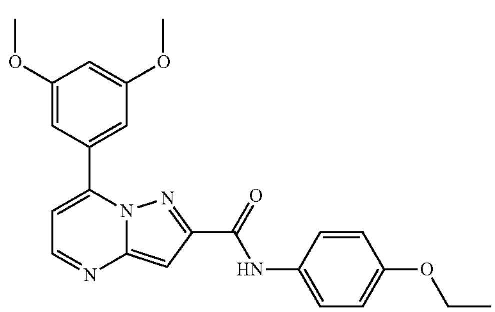 [SMILES: CCOc1ccc(NC(=O)c2cc3nccc(-c4cc(OC)cc(OC)c4)n3n2)cc1] | 7-(3,5-dimethoxyphenyl)-N-(4-ethoxyphenyl)pyrazolo[1,5-a]pyrimidine-2-carboxamide |

TABLE 1-continued

Exemplary compounds

| Cmpd | Structure | Name |
|---|---|---|
| 316 | 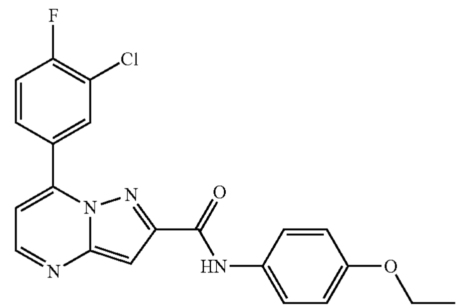 [SMILES: CCOc1ccc(NC(=O)c2cc3nccc(-c4ccc(F)c(Cl)c4)n3n2)cc1] | 7-(3-chloro-4-fluorophenyl)-N-(4-ethoxyphenyl)pyrazolo[1,5-a]pyrimidine-2-carboxamide |
| 317 | 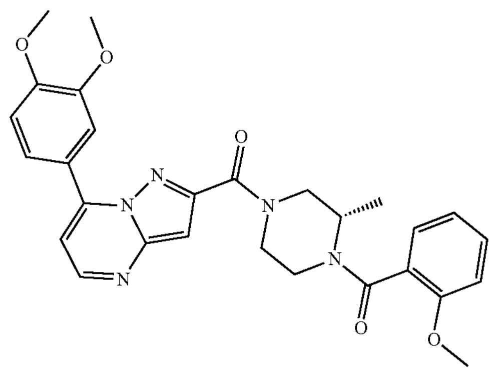 [SMILES: COc1ccc(-c2ccnc3cc(C(=O)N4CCN(C(=O)c5ccccc5OC)[C@@H](C)C4)nn23)cc1OC] | (S)-(7-(3,4-dimethoxyphenyl)pyrazolo[1,5-a]pyrimidin-2-yl)(4-(2-methoxybenzoyl)-3-methylpiperazin-1-yl)methanone |
| 318 | 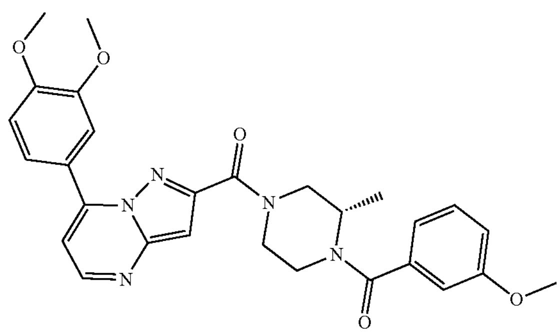 [SMILES: COc1cccc(C(=O)N2CCN(C(=O)c3cc4nccc(-c5ccc(OC)c(OC)c5)n4n3)C[C@@H]2C)c1] | (S)-(7-(3,4-dimethoxyphenyl)pyrazolo[1,5-a]pyrimidin-2-yl)(4-(3-methoxybenzoyl)-3-methylpiperazin-1-yl)methanone |
| 319 | 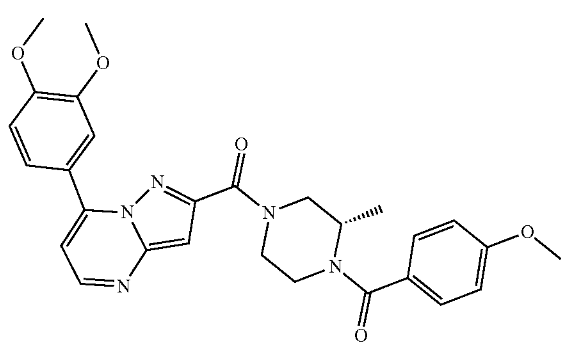 [SMILES: COc1ccc(C(=O)N2CCN(C(=O)c3cc4nccc(-c5ccc(OC)c(OC)c5)n4n3)C[C@@H]2C)cc1] | (S)-(7-(3,4-dimethoxyphenyl)pyrazolo[1,5-a]pyrimidin-2-yl)(4-(4-methoxybenzoyl)-3-methylpiperazin-1-yl)methanone |

TABLE 1-continued

Exemplary compounds

| Cmpd | Structure | Name |
|---|---|---|
| 320 | 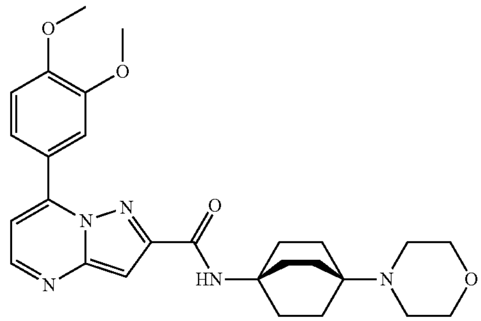 | 7-(3,4-dimethoxyphenyl)-N-(4-morpholinobicyclo[2.2.2]octan-1-yl)pyrazolo[1,5-a]pyrimidine-2-carboxamide |
| 321 | 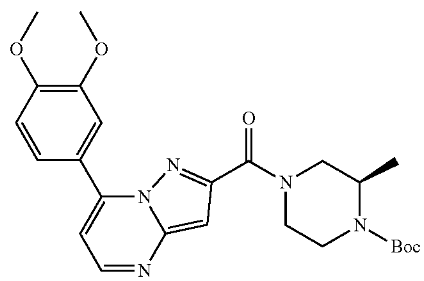 [SMILES: COc1ccc(-c2ccnc3cc(C(=O)N4CCN(C(=O)OC(C)(C)C)[C@H](C)C4)nn23)cc1OC] | tert-butyl (R)-4-(7-(3,4-dimethoxyphenyl)pyrazolo[1,5-a]pyrimidine-2-carbonyl)-2-methylpiperazine-1-carboxylate |
| 322 | 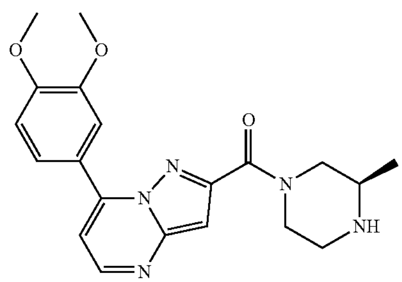 [SMILES: COc1ccc(-c2ccnc3cc(C(=O)N4CCN[C@H](C)C4)nn23)cc1OC] | (R)-(7-(3,4-dimethoxyphenyl)pyrazolo[1,5-a]pyrimidin-2-yl)(3-methylpiperazin-1-yl)methanone |
| 323 | 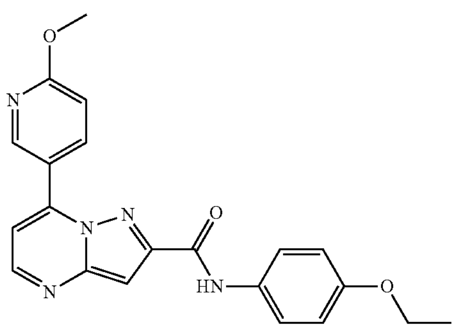 [SMILES: CCOc1ccc(NC(=O)c2cc3nccc(-c4ccc(OC)nc4)n3n2)cc1] | N-(4-ethoxyphenyl)-7-(6-methoxypyridin-3-yl)pyrazolo[1,5-a]pyrimidine-2-carboxamide |
| 324 | 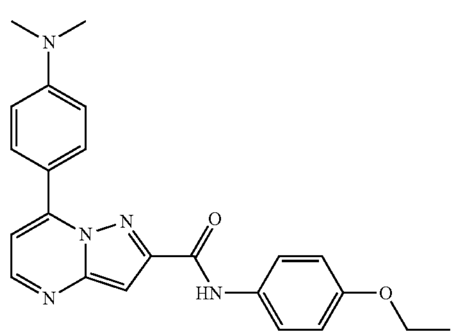 [SMILES: CCOc1ccc(NC(=O)c2cc3nccc(-c4ccc(N(C)C)cc4)n3n2)cc1] | 7-(4-(dimethylamino)phenyl)-N-(4-ethoxyphenyl)pyrazolo[1,5-a]pyrimidine-2-carboxamide |

TABLE 1-continued

Exemplary compounds

| Cmpd | Structure | Name |
|---|---|---|
| 325 | 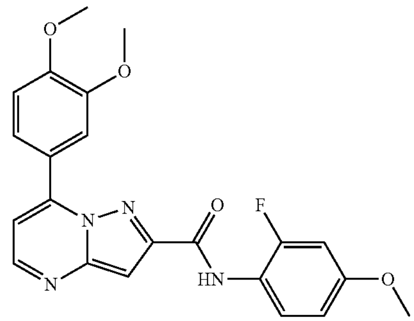 [SMILES: COc1ccc(NC(=O)c2cc3nccc(-c4ccc(OC)c(OC)c4)n3n2)c(F)c1] | 7-(3,4-dimethoxyphenyl)-N-(2-fluoro-4-methoxyphenyl)pyrazolo[1,5-a]pyrimidine-2-carboxamide |
| 326 | 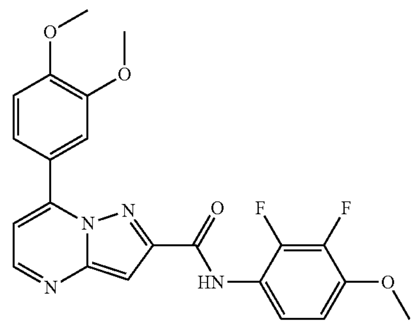 [SMILES: COc1ccc(-c2ccnc3cc(C(=O)Nc4ccc(OC)c(F)c4F)nn23)cc1OC] | N-(2,3-difluoro-4-methoxyphenyl)-7-(3,4-dimethoxyphenyl)pyrazolo[1,5-a]pyrimidine-2-carboxamide |
| 327 | 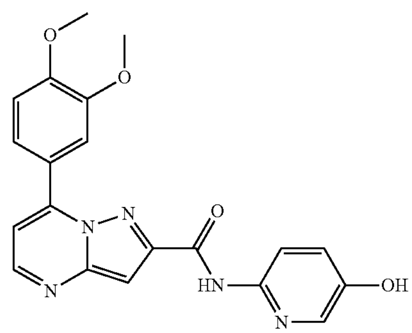 [SMILES: COc1ccc(-c2ccnc3cc(C(=O)Nc4ccc(O)cn4)nn23)cc1OC] | 7-(3,4-dimethoxyphenyl)-N-(5-hydroxypyridin-2-yl)pyrazolo[1,5-a]pyrimidine-2-carboxamide |
| 328 | 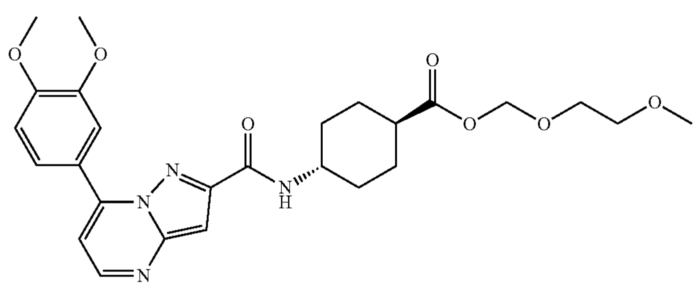 [SMILES: COCCOCOC(=O)[C@H]1CC[C@H](NC(=O)c2cc3nccc(-c4ccc(OC)c(OC)c4)n3n2)CC1] | (2-methoxyethoxy)methyl (1R,4R)-4-(7-(3,4-dimethoxyphenyl)pyrazolo[1,5-a]pyrimidine-2-carboxamido)cyclohexane-1-carboxylate |
| 329 | 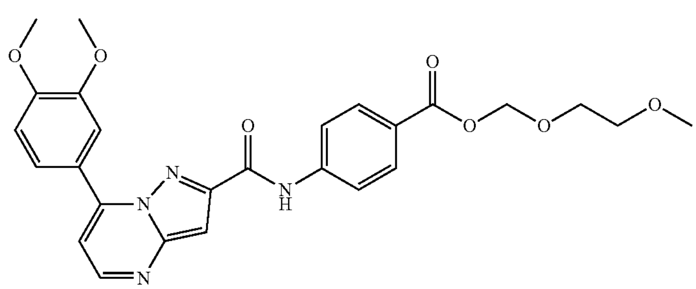 [SMILES: COCCOCOC(=O)c1ccc(NC(=O)c2cc3nccc(-c4ccc(OC)c(OC)c4)n3n2)cc1] | (2-methoxyethoxy)methyl 4-(7-(3,4-dimethoxyphenyl)pyrazolo[1,5-a]pyrimidine-2-carboxamido)benzoate |

TABLE 1-continued

Exemplary compounds

| Cmpd | Structure | Name |
|---|---|---|
| 330 | 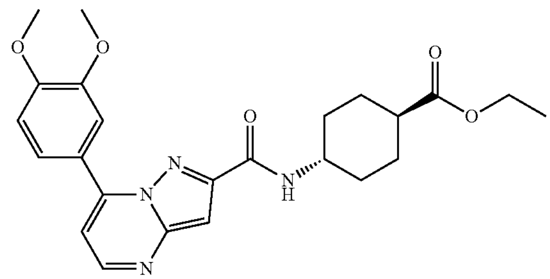 [SMILES: CCOC(=O)[C@H]1CC[C@H](NC(=O)c2cc3nccc(-c4ccc(OC)c(OC)c4)n3n2)CC1] | ethyl (1R,4R)-4-(7-(3,4-dimethoxyphenyl)pyrazolo[1,5-a]pyrimidine-2-carboxamido)cyclohexane-1-carboxylate |
| 331 | 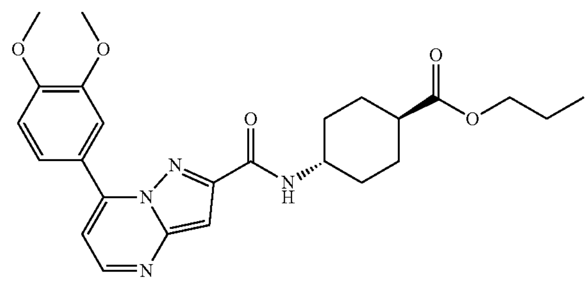 [SMILES: CCCOC(=O)[C@H]1CC[C@H](NC(=O)c2cc3nccc(-c4ccc(OC)c(OC)c4)n3n2)CC1] | propyl (1R,4R)-4-(7-(3,4-dimethoxyphenyl)pyrazolo[1,5-a]pyrimidine-2-carboxamido)cyclohexane-1-carboxylate |
| 332 | 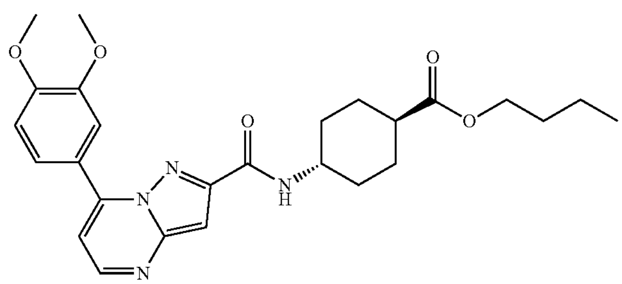 [SMILES: CCCCOC(=O)[C@H]1CC[C@H](NC(=O)c2cc3nccc(-c4ccc(OC)c(OC)c4)n3n2)CC1] | butyl (1r,4r)-4-(7-(3,4-dimethoxyphenyl)pyrazolo[1,5-a]pyrimidine-2-carboxamido)cyclohexane-1-carboxylate |
| 333 | 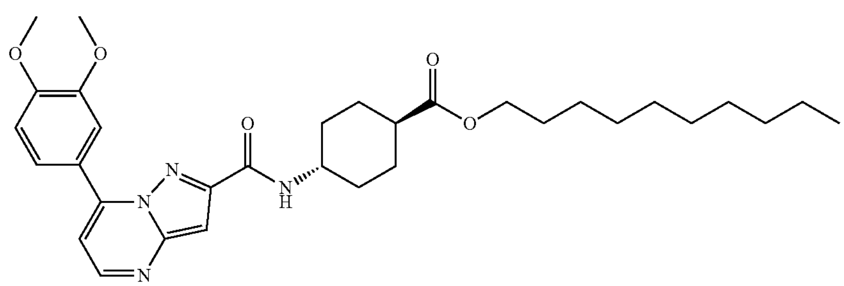 [SMILES: CCCCCCCCCCOC(=O)[C@H]1CC[C@H](NC(=O)c2cc3nccc(-c4ccc(OC)c(OC)c4)n3n2)CC1] | decyl (1r,4r)-4-(7-(3,4-dimethoxyphenyl)pyrazolo[1,5-a]pyrimidine-2-carboxamido)cyclohexane-1-carboxylate |
| 335 | 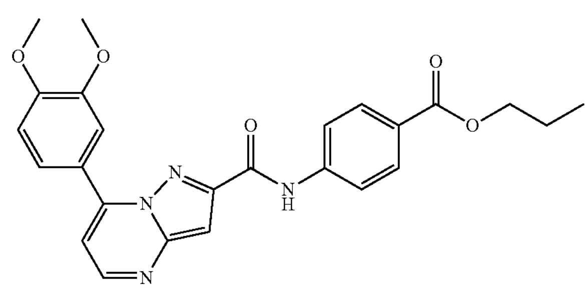 [SMILES: CCCOC(=O)c1ccc(NC(=O)c2cc3nccc(-c4ccc(OC)c(OC)c4)n3n2)cc1] | propyl 4-(7-(3,4-dimethoxyphenyl)pyrazolo[1,5-a]pyrimidine-2-carboxamido)benzoate |

TABLE 1-continued

Exemplary compounds

| Cmpd | Structure | Name |
|---|---|---|
| 336 | 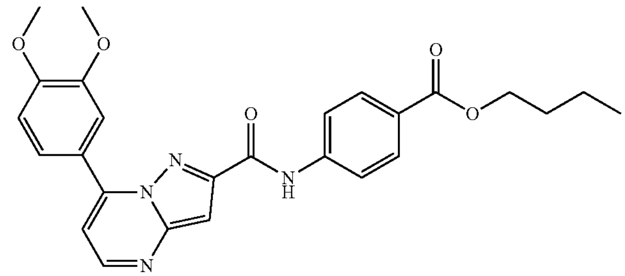 [SMILES: CCCCOC(=O)c1ccc(NC(=O)c2cc3nccc(-c4ccc(OC)c(OC)c4)n3n2)cc1] | butyl 4-(7-(3,4-dimethoxyphenyl)pyrazolo[1,5-a]pyrimidine-2-carboxamido)benzoate |
| 337 | 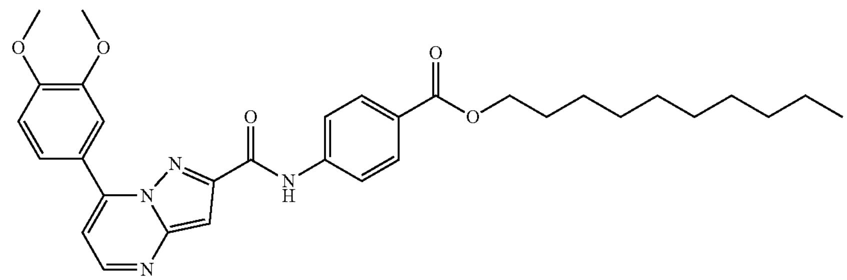 [SMILES: CCCCCCCCCCOC(=O)c1ccc(NC(=O)c2cc3nccc(-c4ccc(OC)c(OC)c4)n3n2)cc1] | decyl 4-(7-(3,4-dimethoxyphenyl)pyrazolo[1,5-a]pyrimidine-2-carboxamido)benzoate |
| 338 | 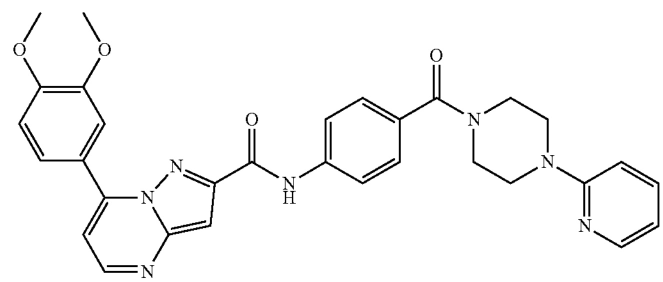 [SMILES: COc1ccc(-c2ccnc3cc(C(=O)Nc4ccc(C(=O)N5CCN(c6ccccn6)CC5)cc4)nn23)cc1OC] | 7-(3,4-dimethoxyphenyl)-N-(4-(4-(pyridin-2-yl)piperazine-1-carbonyl)phenyl)pyrazolo[1,5-a]pyrimidine-2-carboxamide |
| 339 | 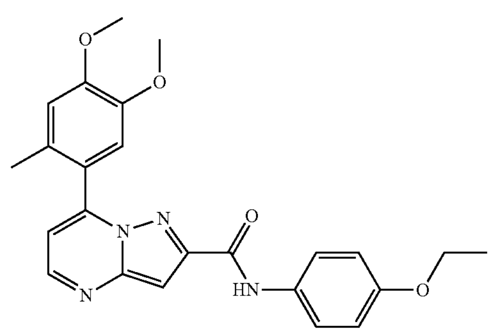 [SMILES: CCOc1ccc(NC(=O)c2cc3nccc(-c4cc(OC)c(OC)cc4C)n3n2)cc1] | 7-(4,5-dimethoxy-2-methylphenyl)-N-(4-ethoxyphenyl)pyrazolo[1,5-a]pyrimidine-2-carboxamide |
| 340 | 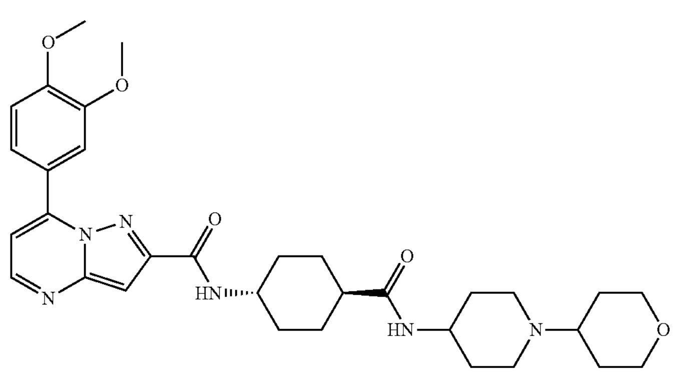 [SMILES: COc1ccc(-c2ccnc3cc(C(=O)N[C@H]4CC[C@H](C(=O)NC5CCN(C6CCOCC6)CC5)CC4)nn23)cc1OC] | 7-(3,4-dimethoxyphenyl)-N-((1R,4R)-4-((1-(tetrahydro-2H-pyran-4-yl)piperidin-4-yl)carbamoyl)cyclohexyl)pyrazolo[1,5-a]pyrimidine-2-carboxamide |

TABLE 1-continued

Exemplary compounds

| Cmpd | Structure | Name |
|---|---|---|
| 341 | 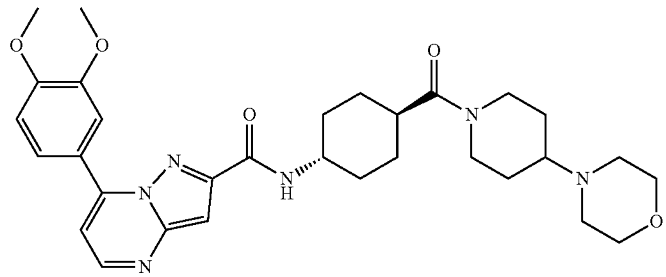 [SMILES: COc1ccc(-c2ccnc3cc(C(=O)N[C@H]4CC[C@H](C(=O)N5CCC(N6CCOCC6)CC5)CC4)nn23)cc1OC] | 7-(3,4-dimethoxyphenyl)-N-((1R,4R)-4-(4-morpholinopiperidine-1-carbonyl)cyclohexyl)pyrazolo[1,5-a]pyrimidine-2-carboxamide |
| 342 | 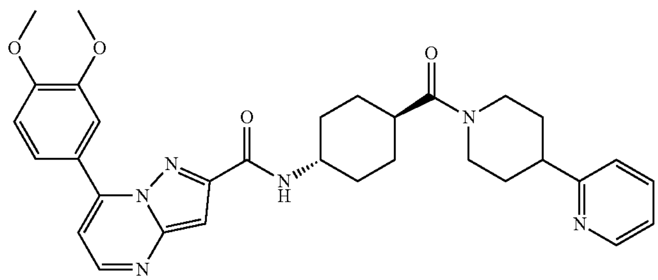 [SMILES: COc1ccc(-c2ccnc3cc(C(=O)N[C@H]4CC[C@H](C(=O)N5CCC(c6ccccn6)CC5)CC4)nn23)cc1OC] | 7-(3,4-dimethoxphenyl)-N-((1R,4R)-4-(4-(pyridin-2-yl)piperazine-1-carbonyl)cyclohexyl)pyrazolo[1,5-a]pyrimidine-2-carboxamide |
| 343 | 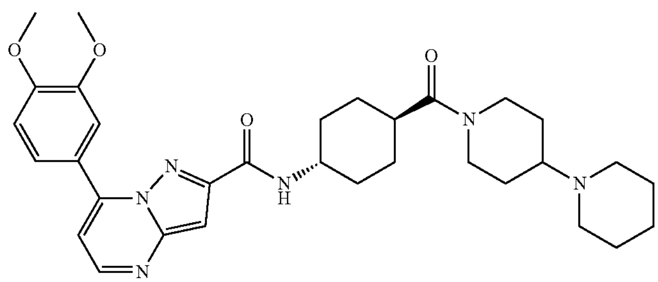 [SMILES: COc1ccc(-c2ccnc3cc(C(=O)N[C@H]4CC[C@H](C(=O)N5CCC(N6CCCCC6)CC5)CC4)nn23)cc1OC] | N-((1R,4R)-4-([1,4'-bipiperidine]-1'-carbonyl)cyclohexyl)-7-(3,4-dimethoxyphenyl)pyrazolo[1,5-a]pyrimidine-2-carboxamide |
| 344 | 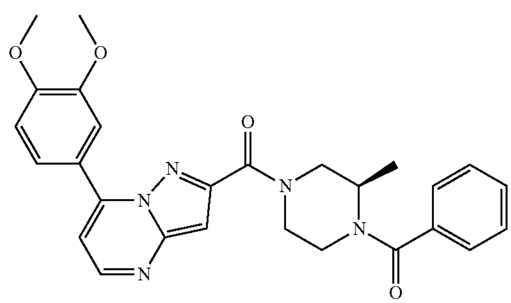 [SMILES: COc1ccc(-c2ccnc3cc(C(=O)N4CCN(C(=O)c5ccccc5)[C@H](C)C4)nn23)cc1OC] | (R)-(4-benzoyl-3-methylpiperazin-1-yl)(7-(3,4-dimethoxyphenyl)pyrazolo[1,5-a]pyrimidine-2-yl)methanone |
| 345 | 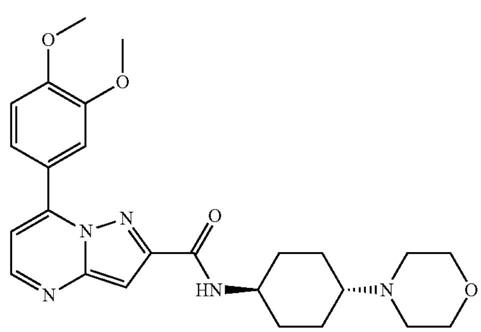 [SMILES: COc1ccc(-c2ccnc3cc(C(=O)N[C@H]4CC[C@H](N5CCOCC5)CC4)nn23)cc1OC] | 7-(3,4-dimethoxyphenyl)-N-((1R,4R)-4-morpholinocyclohexyl)pyrazolo[1,5-a]pyrimidine-2-carboxamide |

TABLE 1-continued

Exemplary compounds

| Cmpd | Structure | Name |
|---|---|---|
| 346 | 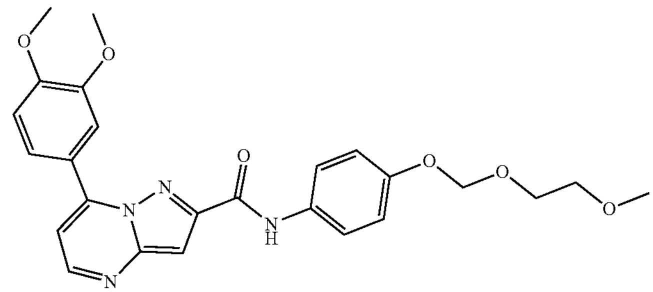 [SMILES: COCCOCOc1ccc(NC(=O)c2cc3nccc(-c4ccc(OC)c(OC)c4)n3n2)cc1] | 7-(3,4-dimethoxyphenyl)-N-(4-((2-methoxyethoxy)methoxy)phenyl)pyrazolo[1,5-a]pyrimidine-2-carboxamide |
| 347 | 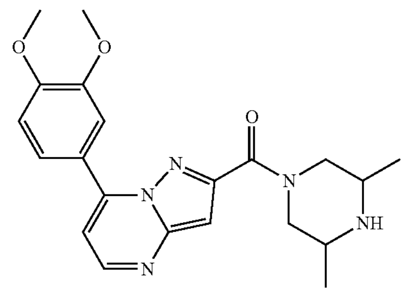 [SMILES: COc1ccc(-c2ccnc3cc(C(=O)N4CC(C)NC(C)C4)nn23)cc1OC] | (7-(3,4-dimethoxyphenyl)pyrazolo[1,5-a]pyrimidin-2-yl)(3,5-dimethylpiperazin-1-yl)methanone |
| 348 | 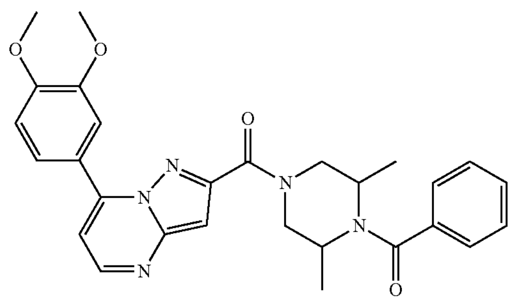 [SMILES: COc1ccc(-c2ccnc3cc(C(=O)N4CC(C)N(C(=O)c5ccccc5)C(C)C4)nn23)cc1OC] | (4-benzoyl-3,5-dimethylpiperazin-1-yl)(7-(3,4-dimethoxyphenyl)pyrazolo[1,5-a]pyrimidine-2-yl)methanone |
| 349 | 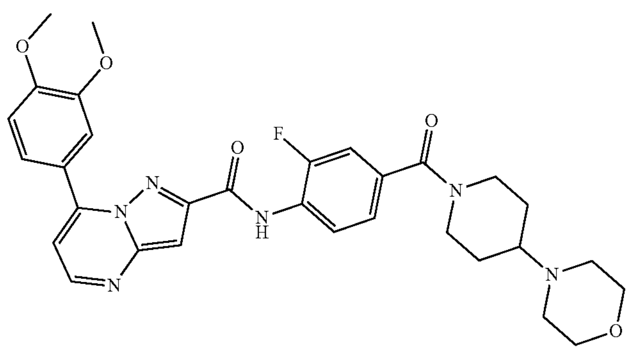 [SMILES: COc1ccc(-c2ccnc3cc(C(=O)Nc4ccc(C(=O)N5CCC(N6CCOCC6)CC5)cc4F)nn23)cc1OC] | 7-(3,4-dimethoxyphenyl)-N-(2-fluoro-4-(4-morpholinopiperidine-1-carbonyl)phenyl)pyrazolo[1,5-a]pyrimidine-2-carboxamide |
| 350 | 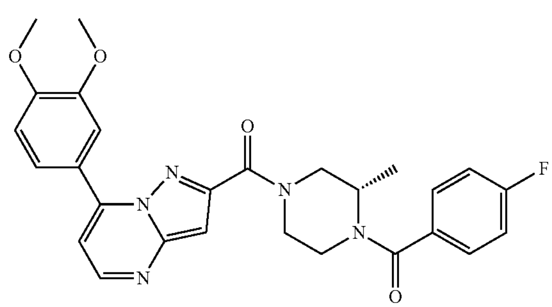 [SMILES: COc1ccc(-c2ccnc3cc(C(=O)N4CCN(C(=O)c5ccc(F)cc5)[C@@H](C)C4)nn23)cc1OC] | (S)-(7-(3,4-dimethoxyphenyl)pyrazolo[1,5-a]pyrimidin-2-yl)(4-(4-fluorobenzoyl)-3-methylpiperazin-1-yl)methanone |

TABLE 1-continued

Exemplary compounds

| Cmpd | Structure | Name |
|---|---|---|
| 351 | 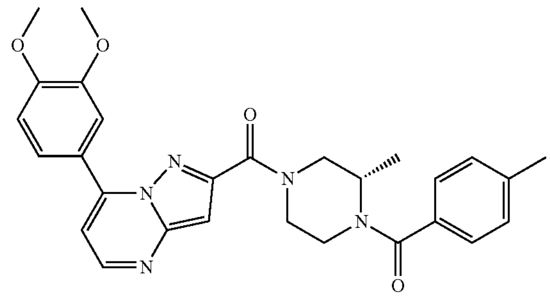 [SMILES: COc1ccc(-c2ccnc3cc(C(=O)N4CCN(C(=O)c5ccc(C)cc5)[C@@H](C)C4)nn23)cc1OC] | (S)-(7-(3,4-dimethoxyphenyl) pyrazolo[1,5-a]pyrimidin-2-yl)(3-methyl-4-(4-methylbenzoyl)piperazin-1-yl)methanone |
| 352 | 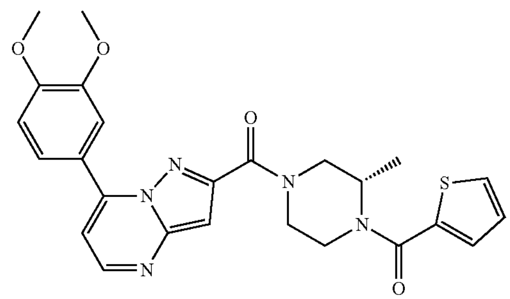 | (S)-(7-(3,4-dimethoxyphenyl) pyrazolo[1,5-a]pyrimidin-2-yl)(3-methyl-4-(thiophene-2-carbonyl)piperazin-1-yl) methanone |
| 353 | 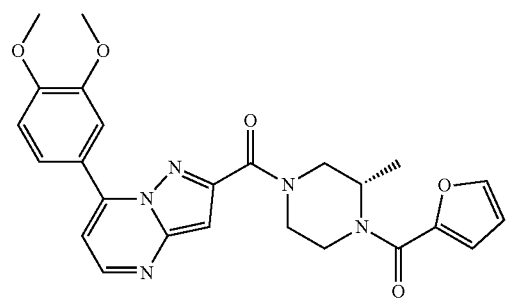 | (S)-(7-(3,4-dimethoxyphenyl) pyrazolo[1,5-a]pyrimidin-2-yl)(4-(furan-2-carbonyl)-3-methylpiperazin-1-yl)methanone |
| 354 | 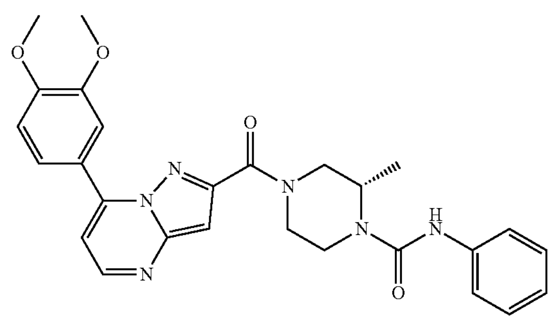 [SMILES: COc1ccc(-c2ccnc3cc(C(=O)N4CCN(C(=O)Nc5ccccc5)[C@@H](C)C4)nn23)cc1OC] | (S)-4-(7-(3,4-dimethoxy-phenyl)pyrazolo[1,5-a]pyrimidine-2-carbonyl)-2-methyl-N-phenylpiperazine-1-carboxamide |
| 355 | 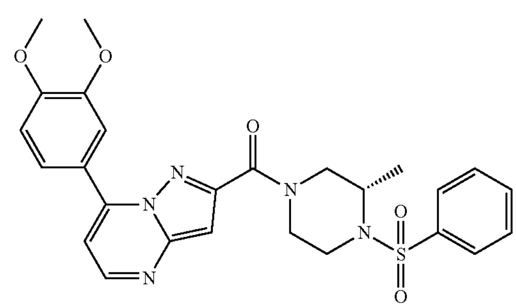 [SMILES: COc1ccc(-c2ccnc3cc(C(=O)N4CCN(S(=O)(=O)c5ccccc5)[C@@H](C)C4)nn23)cc1OC] | (S)-(7-(3,4-dimethoxy-phenyl)pyrazolo[1,5-a]pyrimidin-2-yl)(3-methyl-4-(phenylsulfonyl)piperazin-1-yl)methanone |

TABLE 1-continued

Exemplary compounds

| Cmpd | Structure | Name |
|---|---|---|
| 356 | 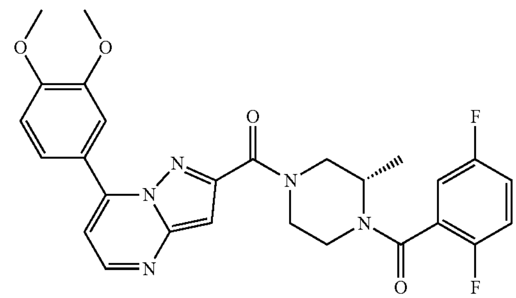 | (S)-4-(2,5-difluorobenzoyl)-3-methylpiperazin-1-yl)(7-(3,4-dimethoxyphenyl)pyrazolo[1,5-a]pyrimidin-2-yl)methanone |
| 357 | 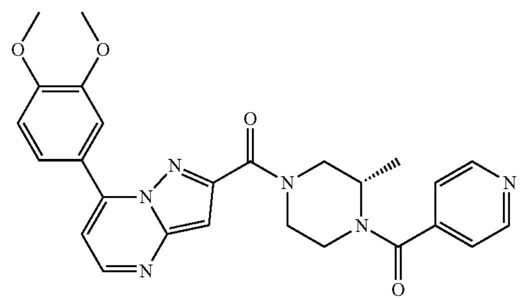 [SMILES: COc1ccc(-c2ccnc3cc(C(=O)N4CCN(C(=O)c5ccncc5)[C@@H](C)C4)nn23)cc1OC] | (S)-(7-(3,4-dimethoxyphenyl)pyrazolo[1,5-a]pyrimidin-2-yl)(4-isonicotinoyl-3-methylpiperazin-1-yl)methanone |
| 358 | 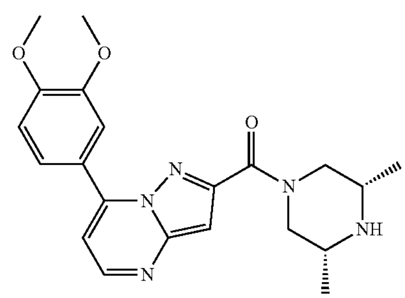 [SMILES: COc1ccc(-c2ccnc3cc(C(=O)N4C[C@@H](C)N[C@@H](C)C4)nn23)cc1OC] | (7-(3,4-dimethoxyphenyl)pyrazolo[1,5-a]pyrimidin-2-yl)((3R,5S)-3,5-dimethylpiperazin-1-yl)methanone |
| 359 | 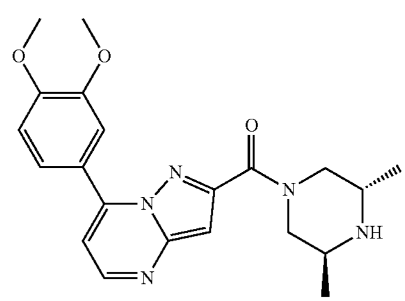 [SMILES: COc1ccc(-c2ccnc3cc(C(=O)N4C[C@H](C)N[C@@H](C)C4)nn23)cc1OC] | (7-(3,4-dimethoxyphenyl)pyrazolo[1,5-a]pyrimidin-2-yl)((3S,5S)-3,5-dimethylpiperazin-1-yl)methanone |
| 360 | 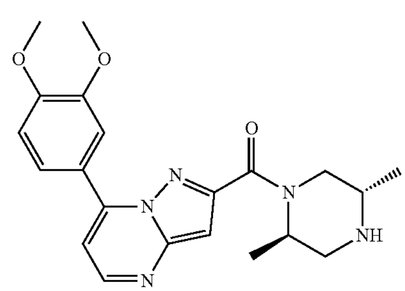 [SMILES: COc1ccc(-c2ccnc3cc(C(=O)N4C[C@H](C)NC[C@H]4C)nn23)cc1OC] | (7-(3,4-dimethoxyphenyl)pyrazolo[1,5-a]pyrimidin-2-yl)((2R,5S)-2,5-dimethylpiperazin-1-yl)methanone |

TABLE 1-continued

Exemplary compounds

| Cmpd | Structure | Name |
|---|---|---|
| 361 | 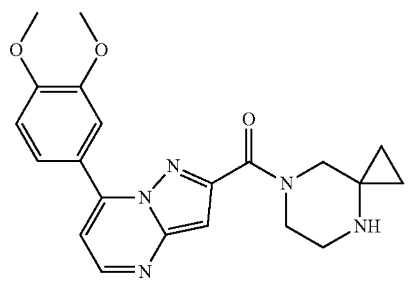 [SMILES: COc1ccc(-c2ccnc3cc(C(=O)N4CCNC5(CC5)C4)nn23)cc1OC] | (7-(3,4-dimethoxyphenyl) pyrazolo[1,5-a]pyrimidin-2-yl)(4,7-diazaspiro[2.5]octan-7-yl)methanone |
| 362 | 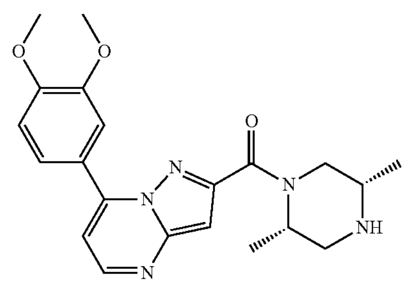 [SMILES: COc1ccc(-c2ccnc3cc(C(=O)N4C[C@H](C)NC[C@@H]4C)nn23)cc1OC] | (7-(3,4-dimethoxyphenyl) pyrazolo[1,5-a]pyrimidin-2-yl) ((2S,5S)-2,5-dimethylpiperazin-1-yl)methanone |
| 363 | 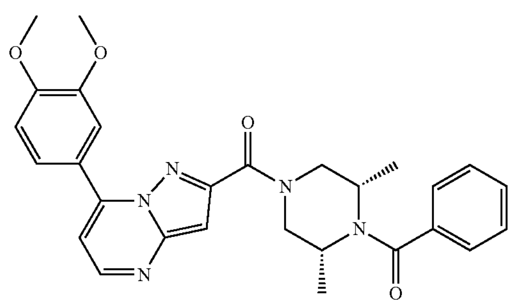 | ((3R,5S)-4-benzoyl-3,5-dimethylpiperazin-1-yl)(7-(3,4-dimethoxyphenyl) pyrazolo[1,5-a]pyrimidin-2-yl) methanone |
| 364 | 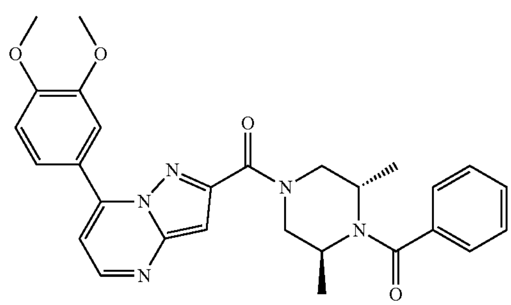 [SMILES: COc1ccc(-c2ccnc3cc(C(=O)N4C[C@H](C)N(C(=O)c5ccccc5)[C@@H](C)C4)nn23)cc1OC] | ((3S,5S)-4-benzoyl-3,5-dimethylpiperazin-1-yl)(7-(3,4-dimethoxyphenyl) pyrazolo[1,5-a]pyrimidin-2-yl)methanone |
| 365 | 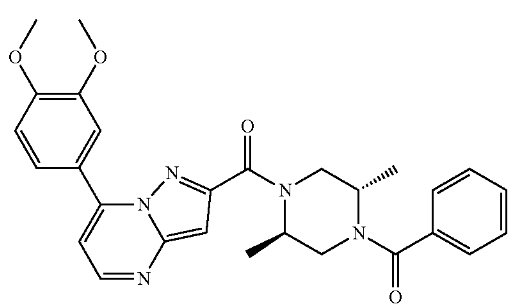 [SMILES: COc1ccc(-c2ccnc3cc(C(=O)N4C[C@H](C)N(C(=O)c5ccccc5)C[C@H]4C)nn23)cc1OC] | ((2R,5S)-4-benzoyl-2,5-dimethylpiperazin-1-yl)(7-(3,4-dimethoxyphenyl) pyrazolo[1,5-a]pyrimidin-2-yl)methanone |

TABLE 1-continued

Exemplary compounds

| Cmpd | Structure | Name |
|---|---|---|
| 366 | 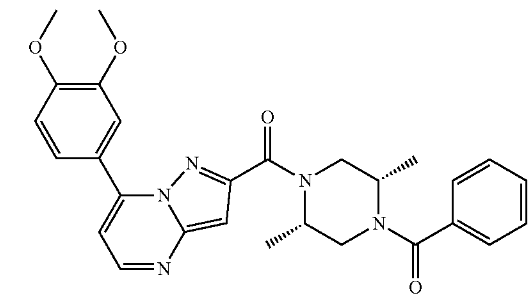 [SMILES: COc1ccc(-c2ccnc3cc(C(=O)N4C[C@H](C)N(C(=O)c5ccccc5)C[C@@H]4C)nn23)cc1OC] | ((2S,5S)-4-benzoyl-2,5-dimethylpiperazin-1-yl)(7-(3,4-dimethoxyphenyl)pyrazolo[1,5-a]pyrimidin-2-yl)methanone |
| 367 | 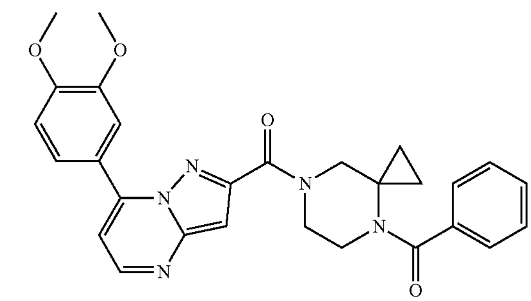 [SMILES: COc1ccc(-c2ccnc3cc(C(=O)N4CCN(C(=O)c5ccccc5)C5(CC5)C4)nn23)cc1OC] | (4-benzoyl-4,7-diazaspiro[2.5]octan-7-yl)(7-(3,4-dimethoxyphenyl)pyrazolo[1,5-a]pyrimidin-2-yl)methanone |
| 368 | 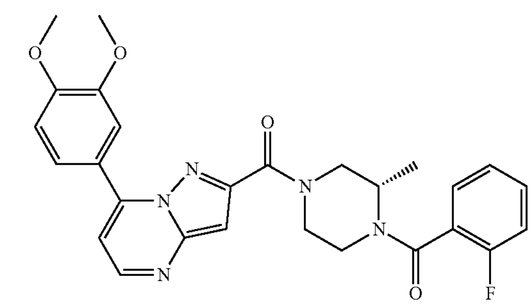 [SMILES: COc1ccc(-c2ccnc3cc(C(=O)N4CCN(C(=O)c5ccccc5F)[C@@H](C)C4)nn23)cc1OC] | (S)-(7-(3,4-dimethoxyphenyl)pyrazolo[1,5-a]pyrimidin-2-yl)(4-(2-fluorobenzoyl)-3-methylpiperazin-1-yl)methanone |
| 369 | 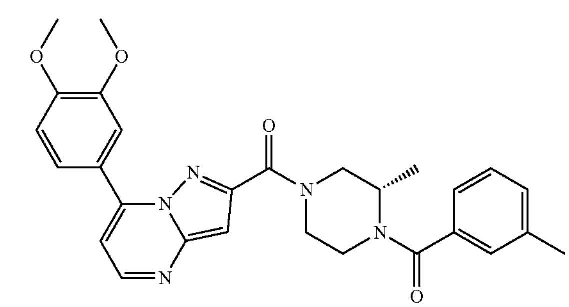 [SMILES: COc1ccc(-c2ccnc3cc(C(=O)N4CCN(C(=O)c5cccc(C)c5)[C@@H](C)C4)nn23)cc1OC] | (S)-(7-(3,4-dimethoxyphenyl)pyrazolo[1,5-a]pyrimidin-2-yl)(3-methyl-4-(3-methylbenzoyl)piperazin-1-yl)methanone |
| 370 | 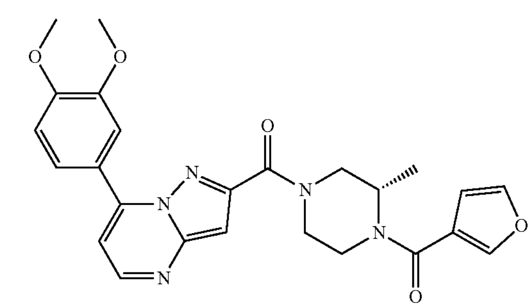 [SMILES: COc1ccc(-c2ccnc3cc(C(=O)N4CCN(C(=O)c5ccoc5)[C@@H](C)C4)nn23)cc1OC] | (S)-(7-(3,4-dimethoxyphenyl)pyrazolo[1,5-a]pyrimidin-2-yl)(4-(furan-3-carbonyl)-3-methylpiperazin-1-yl)methanone |

TABLE 1-continued

Exemplary compounds

| Cmpd | Structure | Name |
|---|---|---|
| 371 | 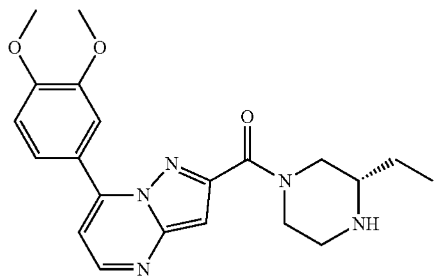 [SMILES: CC[C@H]1CN(C(=O)c2cc3nccc(-c4ccc(OC)c(OC)c4)n3n2)CCN1] | (S)-(7-(3,4-dimethoxyphenyl)pyrazolo[1,5-a]pyrimidin-2-yl)(3-ethylpiperazin-1-yl)methanone |
| 372 | 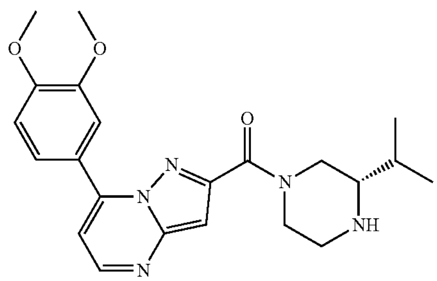 [SMILES: COc1ccc(-c2ccnc3cc(C(=O)N4CCN[C@@H](C(C)C)C4)nn23)cc1OC] | (S)-(7-(3,4-dimethoxyphenyl)pyrazolo[1,5-a]pyrimidin-2-yl)(3-isopropylpiperazin-1-yl)methanone |
| 373 | 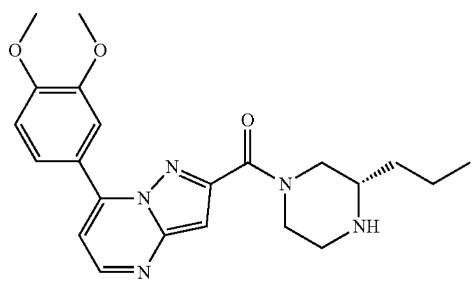 [SMILES: CCC[C@H]1CN(C(=O)c2cc3nccc(-c4ccc(OC)c(OC)c4)n3n2)CCN1] | (S)-(7-(3,4-dimethoxyphenyl)pyrazolo[1,5-a]pyrimidin-2-yl)(3-propylpiperazin-1-yl)methanone |
| 374 | 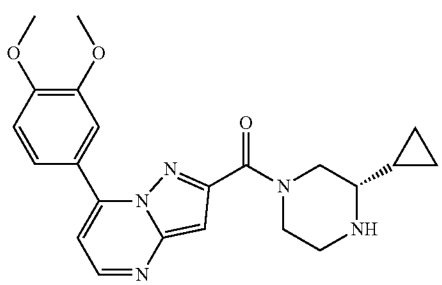 [SMILES: COc1ccc(-c2ccnc3cc(C(=O)N4CCN[C@@H](C5CC5)C4)nn23)cc1OC] | (S)-(3-cyclopropylpiperazin-1-yl)(7-(3,4-dimethoxyphenyl)pyrazolo[1,5-a]pyrimidin-2-yl)methanone |
| 375 | 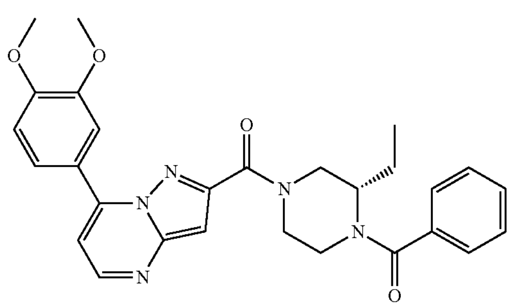 [SMILES: CC[C@H]1CN(C(=O)c2cc3nccc(-c4ccc(OC)c(OC)c4)n3n2)CCN1C(=O)c1ccccc1] | (S)-(4-benzoyl-3-ethylpiperazin-1-yl)(7-(3,4-dimethoxyphenyl)pyrazolo[1,5-a]pyrimidin-2-yl)methanone |

TABLE 1-continued

Exemplary compounds

| Cmpd | Structure | Name |
|---|---|---|
| 376 | 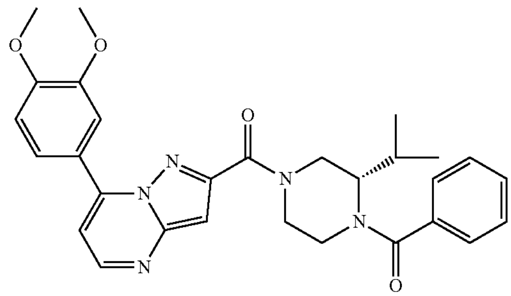 [SMILES: COc1ccc(-c2ccnc3cc(C(=O)N4CCN(C(=O)c5ccccc5)[C@@H](C(C)C)C4)nn23)cc1OC] | (S)-(4-benzoyl-3-isopropylpiperazin-1-yl)(7-(3,4-dimethoxyphenyl)pyrazolo[1,5-a]pyrimidin-2-yl)methanone |
| 377 | 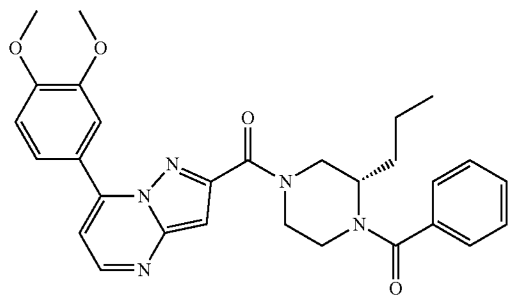 [SMILES: CCC[C@H]1CN(C(=O)c2cc3nccc(-c4ccc(OC)c(OC)c4)n3n2)CCN1C(=O)c1ccccc1] | (S)-(4-benzoyl-3-propylpiperazin-1-yl)(7-(3,4-dimethoxyphenyl)pyrazolo[1,5-a]pyrimidin-2-yl)methanone |
| 378 | 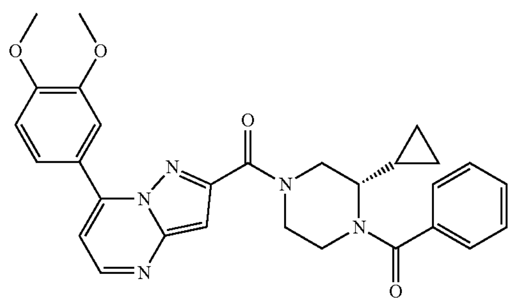 [SMILES: COc1ccc(-c2ccnc3cc(C(=O)N4CCN(C(=O)c5ccccc5)[C@@H](C5CC5)C4)nn23)cc1OC] | (S)-(4-benzoyl-3-cyclopropylpiperazin-1-yl)(7-(3,4-dimethoxyphenyl)pyrazolo[1,5-a]pyrimidin-2-yl)methanone |
| 379 | 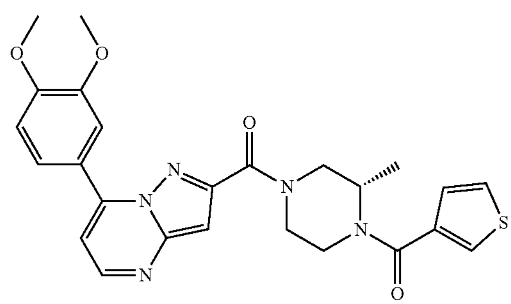 [SMILES: COc1ccc(-c2ccnc3cc(C(=O)N4CCN(C(=O)c5ccsc5)[C@@H](C)C4)nn23)cc1OC] | (S)-(7-(3,4-dimethoxyphenyl)pyrazolo[1,5-a]pyrimidin-2-yl)(3-methyl-4-(thiophene-3-carbonyl)piperazin-1-yl)methanone |
| 380 | 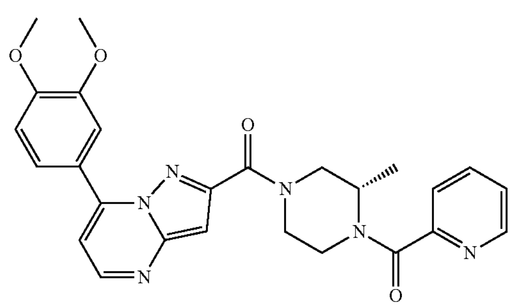 [SMILES: COc1ccc(-c2ccnc3cc(C(=O)N4CCN(C(=O)c5ccccn5)[C@@H](C)C4)nn23)cc1OC] | (S)-(7-(3,4-dimethoxyphenyl)pyrazolo[1,5-a]pyrimidin-2-yl)(3-methyl-4-picolinoylpiperazin-1-yl)methanone |

TABLE 1-continued

Exemplary compounds

| Cmpd | Structure | Name |
|---|---|---|
| 381 | 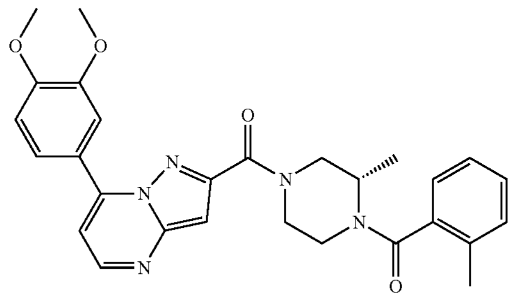 | (S)-(7-(3,4-dimethoxyphenyl)pyrazolo[1,5-a]pyrimidin-2-yl)(3-methyl-4-(2-methylbenzoyl)piperazin-1-yl)methanone |
| 382 | 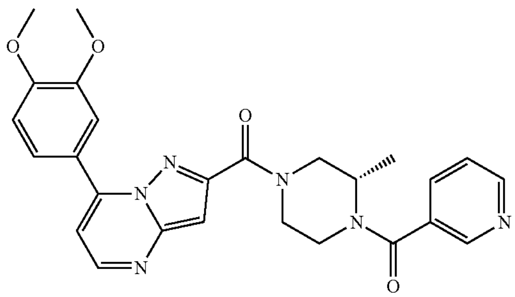 [SMILES: COc1ccc(-c2ccnc3cc(C(=O)N4CCN(C(=O)c5cccnc5)[C@@H](C)C4)nn23)cc1OC] | (S)-(7-(3,4-dimethoxyphenyl)pyrazolo[1,5-a]pyrimidin-2-yl)(3-methyl-4-nicotinoylpiperazin-1-yl)methanone |
| 383 | 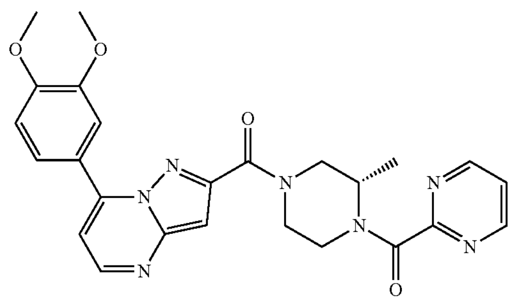 | (S)-(7-(3,4-dimethoxyphenyl)pyrazolo[1,5-a]pyrimidin-2-yl)(3-methyl-4-(pyrimidine-2-carbonyl)piperazin-1-yl)methanone |
| 384 | 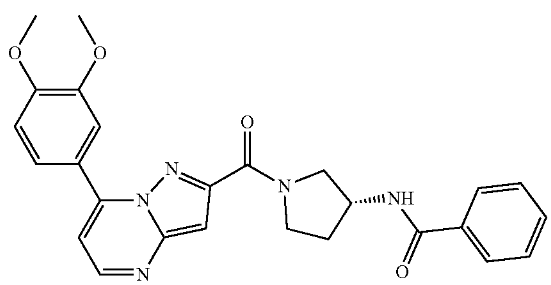 [SMILES: COc1ccc(-c2ccnc3cc(C(=O)N4CC[C@@H](NC(=O)c5ccccc5)C4)nn23)cc1OC] | (R)-N-(1-(7-(3,4-dimethoxyphenyl)pyrazolo[1,5-a]pyrimidine-2-carbonyl)pyrrolidin-3-yl)benzamide |
| 385 | 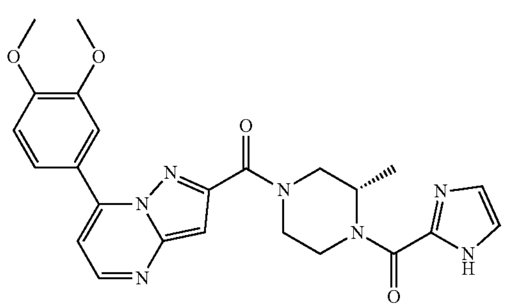 [SMILES: COc1ccc(-c2ccnc3cc(C(=O)N4CCN(C(=O)c5ncc[nH]5)[C@@H](C)C4)nn23)cc1OC] | (S)-(4-(1H-imidazole-2-carbonyl)-3-methylpiperazin-1-yl)(7-(3,4-dimethoxyphenyl)pyrazolo[1,5-a]pyrimidin-2-yl)methanone |

US 11,827,640 B2

TABLE 1-continued

Exemplary compounds

| Cmpd | Structure | Name |
|---|---|---|
| 386 | 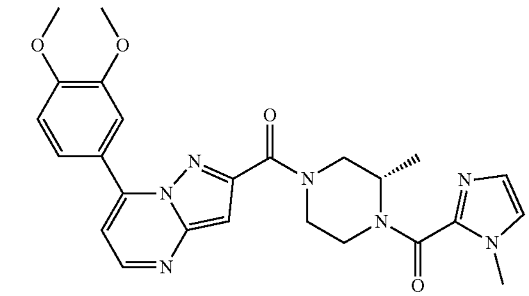 [SMILES: COc1ccc(-c2ccnc3cc(C(=O)N4CCN(C(=O)c5nccn5C)[C@@H](C)C4)nn23)cc1OC] | (S)-(7-(3,4-dimethoxy-phenyl)pyrazolo[1,5-a]pyrimidin-2-yl)(3-methyl-4-(1-methyl-1H-imidazole-2-carbonyl)piperazin-1-yl)methanone |
| 387 | 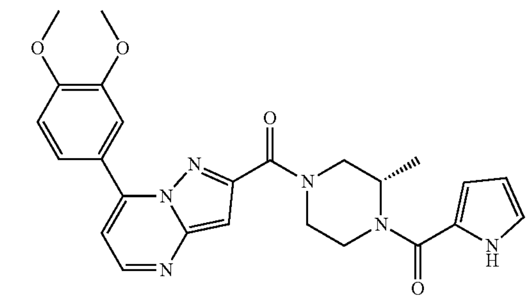 [SMILES: COc1ccc(-c2ccnc3cc(C(=O)N4CCN(C(=O)c5ccc[nH]5)[C@@H](C)C4)nn23)cc1OC] | (S)-(7-(3,4-dimethoxy-phenyl)pyrazolo[1,5-a]pyrimidin-2-yl)(3-methyl-4-(1H-pyrrole-2-carbonyl)piperazin-1-yl)methanone |
| 388 | 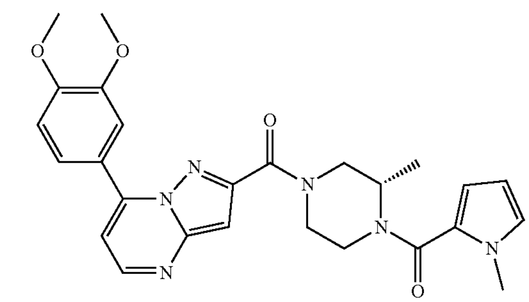 [SMILES: COc1ccc(-c2ccnc3cc(C(=O)N4CCN(C(=O)c5cccn5C)[C@@H](C)C4)nn23)cc1OC] | (S)-(7-(3,4-dimethoxy-phenyl)pyrazolo[1,5-a]pyrimidin-2-yl)(3-methyl-4-(1-methyl-1H-pyrrole-2-carbonyl)piperazin-1-yl)methanone |
| 389 | 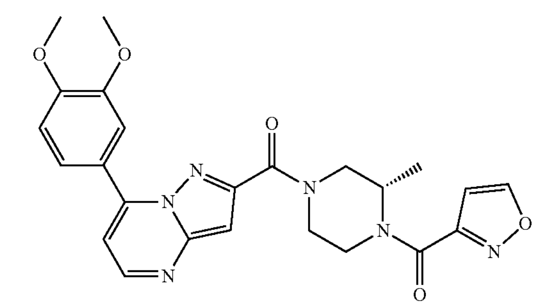 [SMILES: COc1ccc(-c2ccnc3cc(C(=O)N4CCN(C(=O)c5ccon5)[C@@H](C)C4)nn23)cc1OC] | (S)-(7-(3,4-dimethoxy-phenyl)pyrazolo[1,5-a]pyrimidin-2-yl)(4-(isoxazole-3-carbonyl)-3-methylpiperazin-1-yl)methanone |
| 390 | 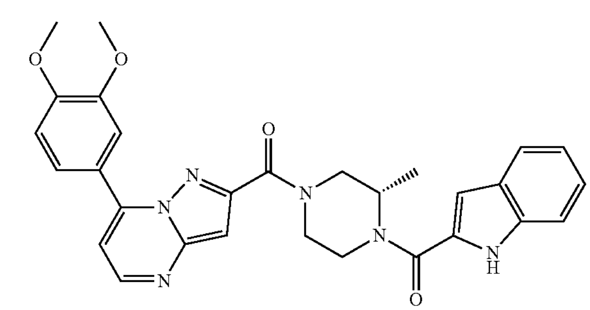 [SMILES: COc1ccc(-c2ccnc3cc(C(=O)N4CCN(C(=O)c5cc6ccccc6[nH]5)[C@@H](C)C4)nn23)cc1OC] | (S)-(4-(1H-indole-2-carbonyl)-3-methylpiperazin-1-yl)(7-(3,4-dimethoxyphenyl)pyrazolo[1,5-a]pyrimidin-2-yl)methanone |

TABLE 1-continued

| Cmpd | Structure | Name |
|---|---|---|
| 391 | 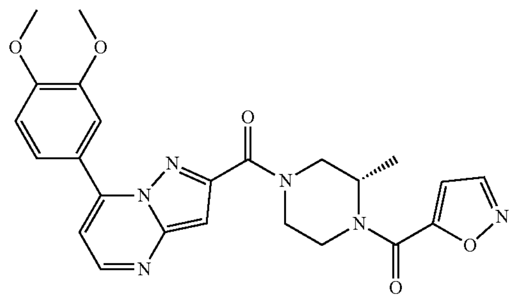 [SMILES: COc1ccc(-c2ccnc3cc(C(=O)N4CCN(C(=O)c5ccno5)[C@@H](C)C4)nn23)cc1OC] | (S)-(7-(3,4-dimethoxyphenyl)pyrazolo[1,5-a]pyrimidin-2-yl)(4-(isoxazole-5-carbonyl)-3-methylpiperazin-1-yl)methanone |
| 392 | 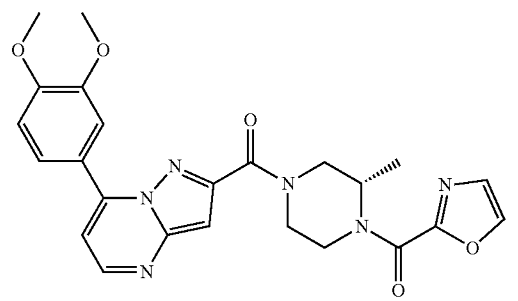 [SMILES: COc1ccc(-c2ccnc3cc(C(=O)N4CCN(C(=O)c5ncco5)[C@@H](C)C4)nn23)cc1OC] | (S)-(7-(3,4-dimethoxyphenyl)pyrazolo[1,5-a]pyrimidin-2-yl)(3-methyl-4-(oxazole-2-carbonyl)piperazin-1-yl)methanone |
| 393 | 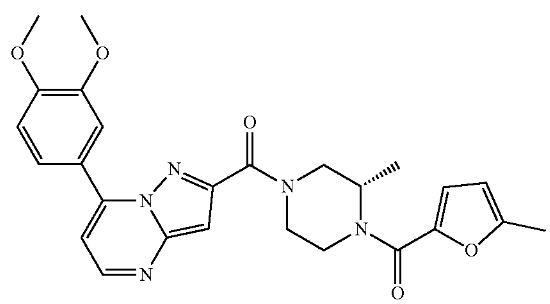 [SMILES: COc1ccc(-c2ccnc3cc(C(=O)N4CCN(C(=O)c5ccc(C)o5)[C@@H](C)C4)nn23)cc1OC] | (S)-(7-(3,4-dimethoxyphenyl)pyrazolo[1,5-a]pyrimidin-2-yl)(3-methyl-4-(5-methylfuran-2-carbonyl)piperazin-1-yl)methanone |
| 394 | 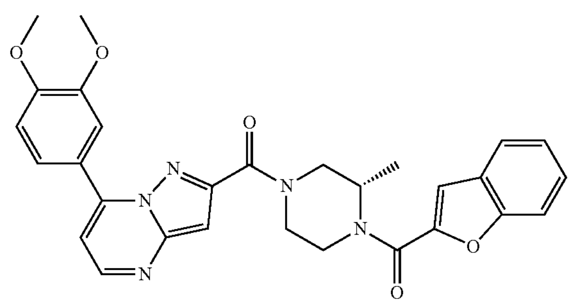 [SMILES: COc1ccc(-c2ccnc3cc(C(=O)N4CCN(C(=O)c5cc6ccccc6o5)[C@@H](C)C4)nn23)cc1OC] | (S)-(4-(benzofuran-2-carbonyl)-3-methylpiperazin-1-yl)(7-(3,4-dimethoxyphenyl)pyrazolo[1,5-a]pyrimidine-2-yl)methanone |
| 395 | 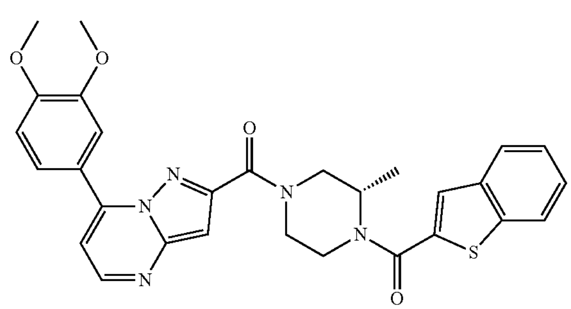 [SMILES: COc1ccc(-c2ccnc3cc(C(=O)N4CCN(C(=O)c5cc6ccccc6s5)[C@@H](C)C4)nn23)cc1OC] | (S)-benzo[b]thiophen-2-yl(4-(7-(3,4-dimethoxyphenyl)pyrazolo[1,5-a]pyrimidine-2-carbonyl)-2-methylpiperazin-1-yl)methanone |

In some embodiments of formula (Ia), the compound is of Table 2, or a pharmaceutically acceptable salt, a solvate, a hydrate, a prodrug, or a stereoisomer thereof.

In some embodiments of formula (Ia), the compound is NOT a compound of Table 2, or a pharmaceutically acceptable salt, a solvate, a hydrate, a prodrug, or a stereoisomer thereof.

In some embodiments of formula (Ia), when $R^1$ and $R^9$ are H, $R^4$ is

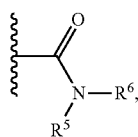

$R^5$ is H, and $R^6$ is substituted aryl; then $R^2$ is not 4-fluoro-phenyl. In some embodiments of formula (Ia), when $R^1$ and $R^9$ are H, $R^4$ is

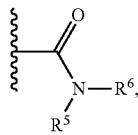

$R^5$ is H, and $R^6$ is substituted aryl; then $R^2$ is not para-toluene. In some embodiments of formula (Ia), when $R^1$ and $R^9$ are H, $R^4$ is

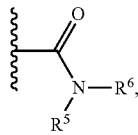

$R^5$ is H, and $R^6$ is substituted aryl; then $R^2$ is not 3,5-dichloro-phenyl. In some embodiments of formula (Ia), when $R^1$ and $R^9$ are H, $R^4$ is

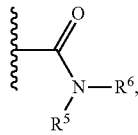

$R^5$ is H, and $R^6$ is optionally substituted aryl; then $R^2$ is not phenyl.

In some embodiments of formula (Ia), when $R^1$ and $R^9$ are H, and $R^4$ is any one of the following:

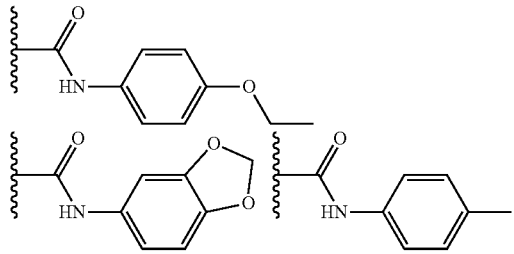

-continued

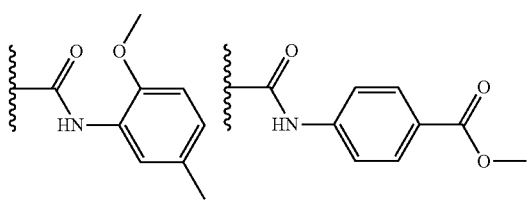

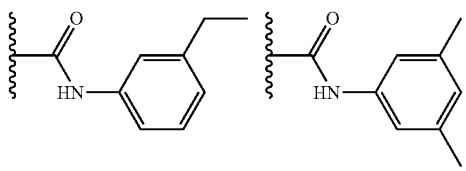

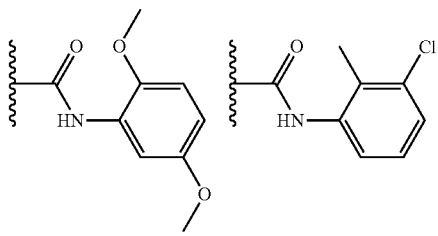

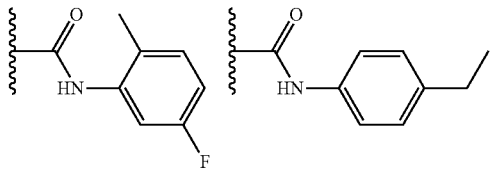

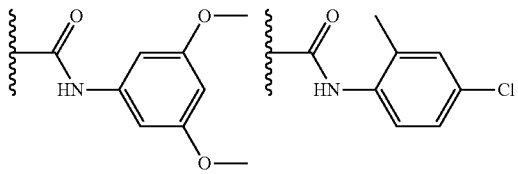

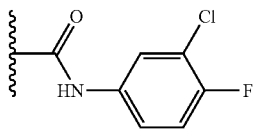

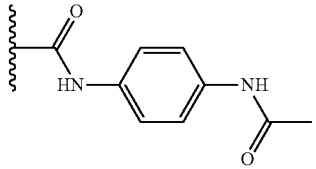

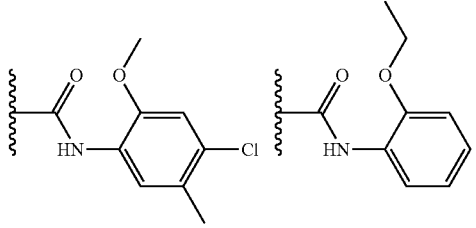

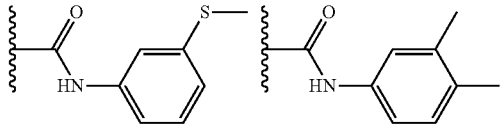

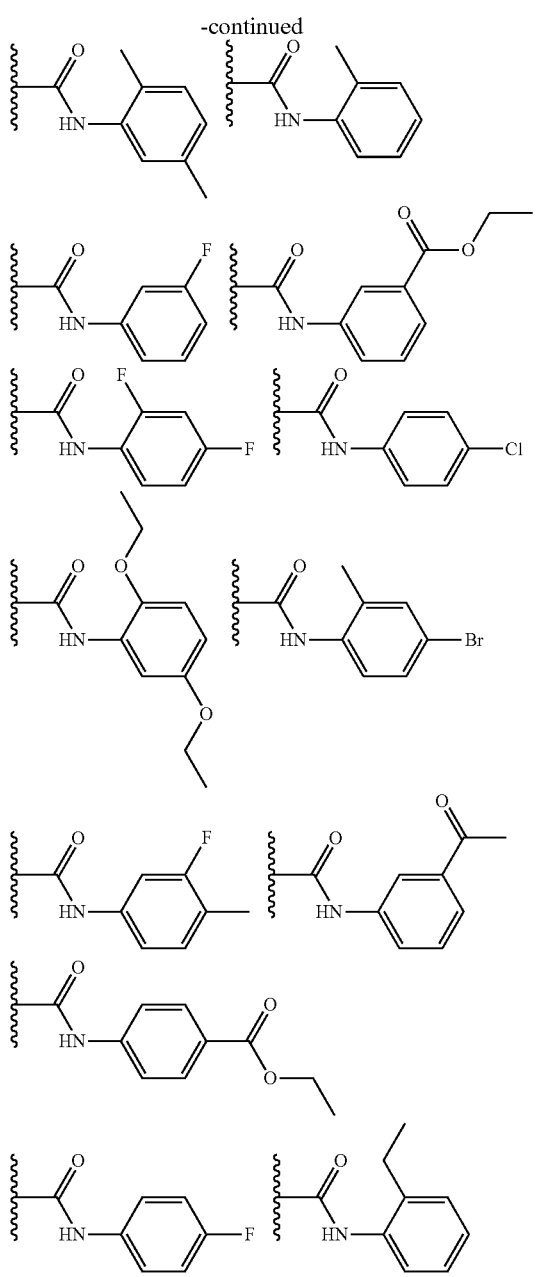
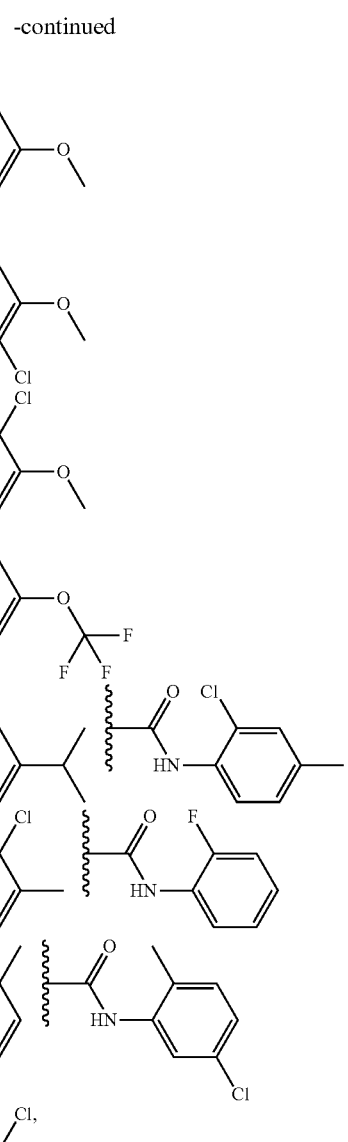

then $R^2$ is not 3,4-dimethoxy-phenyl.

TABLE 2

Exemplary Compounds

| Cmpd | Name |
|---|---|
| 3 | 7-(3,4-dimethoxyphenyl)-N-(4-ethoxyphenyl)pyrazolo[1,5-a]pyrimidine-2-carboxamide |
| 5 | 7-(3,4-dimethoxyphenyl)pyrazolo[1,5-a]pyrimidine-2-carboxylic acid |
| 11 | methyl 4-(7-(3,4-dimethoxyphenyl)pyrazolo[1,5-a]pyrimidine-2-carboxamido)benzoate |
| 267 | 7-(3,4-dimethoxyphenyl)-N-(4-fluorophenyl)pyrazolo[1,5-a]pyrimidine-2-carboxamide |
| 300 | N-(4-ethoxyphenyl)-7-phenylpyrazolo[1,5-a]pyrimidine-2-carboxamide |
| 305 | methyl 4-(7-phenylpyrazolo[1,5-a]pyrimidine-2-carboxamido)benzoate |
| 310 | N-(benzo[d][1,3]dioxol-5-yl)-7-(3,4-dimethoxyphenyl)pyrazolo[1,5-a]pyrimidine-2-carboxamide |
| 334 | ethyl 4-(7-(3,4-dimethoxyphenyl)pyrazolo[1,5-a]pyrimidine-2-carboxamido)benzoate |
| 396 | 7-(3,4-dimethoxyphenyl)-N-(p-tolyl)pyrazolo[1,5-a]pyrimidine-2-carboxamide |

TABLE 2-continued

Exemplary Compounds

| Cmpd | Name |
|---|---|
| 397 | N-(4-chlorophenyl)-7-(3,4-dimethoxyphenyl)pyrazolo[1,5-a]pyrimidine-2-carboxamide |
| 398 | 7-(3,4-dimethoxyphenyl)-N-(4-ethylphenyl)pyrazolo[1,5-a]pyrimidine-2-carboxamide |
| 399 | 7-(3,4-dimethoxyphenyl)-N-(4-(trifluoromethoxy)phenyl)pyrazolo[1,5-a]pyrimidine-2-carboxamide |
| 400 | 7-(3,4-dimethoxyphenyl)-N-(4-isopropylphenyl)pyrazolo[1,5-a]pyrimidine-2-carboxamide |
| 401 | N-(2-chloro-4-methylphenyl)-7-(3,4-dimethoxyphenyl)pyrazolo[1,5-a]pyrimidine-2-carboxamide |
| 402 | N-(3-chloro-4-methylphenyl)-7-(3,4-dimethoxyphenyl)pyrazolo[1,5-a]pyrimidine-2-carboxamide |
| 403 | N-(3-chloro-4-methoxyphenyl)-7-(3,4-dimethoxyphenyl)pyrazolo[1,5-a]pyrimidine-2-carboxamide |
| 404 | 7-(3,4-dimethoxyphenyl)-N-(3-fluoro-4-methylphenyl)pyrazolo[1,5-a]pyrimidine-2-carboxamide |
| 405 | 7-(3,4-dimethoxyphenyl)-N-(3,4-dimethylphenyl)pyrazolo[1,5-a]pyrimidine-2-carboxamide |
| 406 | N-(3-chloro-4-fluorophenyl)-7-(3,4-dimethoxyphenyl)pyrazolo[1,5-a]pyrimidine-2-carboxamide |
| 407 | N-(4-acetamidophenyl)-7-(3,4-dimethoxyphenyl)pyrazolo[1,5-a]pyrimidine-2-carboxamide |
| 408 | N-(4-chloro-2-methylphenyl)-7-(3,4-dimethoxyphenyl)pyrazolo[1,5-a]pyrimidine-2-carboxamide |
| 409 | N-(2,4-difluorophenyl)-7-(3,4-dimethoxyphenyl)pyrazolo[1,5-a]pyrimidine-2-carboxamide |
| 410 | N-(4-bromo-2-methylphenyl)-7-(3,4-dimethoxyphenyl)pyrazolo[1,5-a]pyrimidine-2-carboxamide |
| 411 | N-(2,4-dimethoxyphenyl)-7-(3,4-dimethoxyphenyl)pyrazolo[1,5-a]pyrimidine-2-carboxamide |
| 412 | N-(5-chloro-2,4-dimethoxyphenyl)-7-(3,4-dimethoxyphenyl)pyrazolo[1,5-a]pyrimidine-2-carboxamide |
| 413 | N-(4-chloro-2-methoxy-5-methylphenyl)-7-(3,4-dimethoxyphenyl)pyrazolo[1,5-a]pyrimidine-2-carboxamide |
| 414 | 7-(3,4-dimethoxyphenyl)-N-(2-methoxy-5-methylphenyl)pyrazolo[1,5-a]pyrimidine-2-carboxamide |
| 415 | 7-(3,4-dimethoxyphenyl)-N-(2,5-dimethylphenyl)pyrazolo[1,5-a]pyrimidine-2-carboxamide |
| 416 | N-(2,5-diethoxyphenyl)-7-(3,4-dimethoxyphenyl)pyrazolo[1,5-a]pyrimidine-2-carboxamide |
| 417 | N-(5-chloro-2-methylphenyl)-7-(3,4-dimethoxyphenyl)pyrazolo[1,5-a]pyrimidine-2-carboxamide |
| 418 | N-(2,5-dimethoxyphenyl)-7-(3,4-dimethoxyphenyl)pyrazolo[1,5-a]pyrimidine-2-carboxamide |
| 419 | 7-(3,4-dimethoxyphenyl)-N-(5-fluoro-2-methylphenyl)pyrazolo[1,5-a]pyrimidine-2-carboxamide |
| 420 | 7-(3,4-dimethoxyphenyl)-N-(2-ethoxyphenyl)pyrazolo[1,5-a]pyrimidine-2-carboxamide |
| 421 | 7-(3,4-dimethoxyphenyl)-N-(o-tolyl)pyrazolo[1,5-a]pyrimidine-2-carboxamide |
| 422 | 7-(3,4-dimethoxyphenyl)-N-(2-ethylphenyl)pyrazolo[1,5-a]pyrimidine-2-carboxamide |
| 423 | 7-(3,4-dimethoxyphenyl)-N-(2-fluorophenyl)pyrazolo[1,5-a]pyrimidine-2-carboxamide |
| 424 | 7-(3,4-dimethoxyphenyl)-N-(2,3-dimethylphenyl)pyrazolo[1,5-a]pyrimidine-2-carboxamide |
| 425 | N-(3-chloro-2-methylphenyl)-7-(3,4-dimethoxyphenyl)pyrazolo[1,5-a]pyrimidine-2-carboxamide |
| 426 | N-(3-chlorophenyl)-7-(3,4-dimethoxyphenyl)pyrazolo[1,5-a]pyrimidine-2-carboxamide |
| 427 | N-(4-(4-chloro-1H-pyrazol-1-yl)phenyl)-7-(3,5-dichlorophenyl)pyrazolo[1,5-a]pyrimidine-2-carboxamide |
| 428 | 7-(3,4-dimethoxyphenyl)-N-(3-fluorophenyl)pyrazolo[1,5-a]pyrimidine-2-carboxamide |
| 429 | 7-(3,4-dimethoxyphenyl)-N-(3-ethylphenyl)pyrazolo[1,5-a]pyrimidine-2-carboxamide |
| 430 | 7-(3,4-dimethoxyphenyl)-N-(3-(methylthio)phenyl)pyrazolo[1,5-a]pyrimidine-2-carboxamide |
| 431 | N-(3-acetylphenyl)-7-(3,4-dimethoxyphenyl)pyrazolo[1,5-a]pyrimidine-2-carboxamide |
| 432 | ethyl 3-(7-(3,4-dimethoxyphenyl)pyrazolo[1,5-a]pyrimidine-2-carboxamido)benzoate |
| 433 | 7-(3,4-dimethoxyphenyl)-N-(3,5-dimethylphenyl)pyrazolo[1,5-a]pyrimidine-2-carboxamide |
| 434 | 7-(3,4-dimethoxyphenyl)-N-(3,5-dimethoxyphenyl)pyrazolo[1,5-a]pyrimidine-2-carboxamide |
| 435 | N-(2,5-dimethoxyphenyl)-7-phenylpyrazolo[1,5-a]pyrimidine-2-carboxamide |

TABLE 2-continued

Exemplary Compounds

| Cmpd | Name |
|---|---|
| 436 | N-(2,4-dimethoxyphenyl)-7-phenylpyrazolo[1,5-a]pyrimidine-2-carboxamide |
| 437 | N-(4-methoxy-2-methylphenyl)-7-phenylpyrazolo[1,5-a]pyrimidine-2-carboxamide |
| 438 | N-(4-fluoro-2-methylphenyl)-7-phenylpyrazolo[1,5-a]pyrimidine-2-carboxamide |
| 439 | N-(2,4-difluorophenyl)-7-phenylpyrazolo[1,5-a]pyrimidine-2-carboxamide |
| 440 | N-(3-methoxyphenyl)-7-phenylpyrazolo[1,5-a]pyrimidine-2-carboxamide |
| 441 | N-(2-methoxyphenyl)-7-phenylpyrazolo[1,5-a]pyrimidine-2-carboxamide |
| 442 | N-(2-ethoxyphenyl)-7-phenylpyrazolo[1,5-a]pyrimidine-2-carboxamide |
| 443 | N-(4-methoxyphenyl)-7-phenylpyrazolo[1,5-a]pyrimidine-2-carboxamide |
| 445 | N-(4-fluorophenyl)-7-phenylpyrazolo[1,5-a]pyrimidine-2-carboxamide |
| 446 | N-(2-fluorophenyl)-7-phenylpyrazolo[1,5-a]pyrimidine-2-carboxamide |
| 447 | N-(3-fluorophenyl)-7-phenylpyrazolo[1,5-a]pyrimidine-2-carboxamide |
| 448 | N-(3-fluoro-4-methylphenyl)-7-phenylpyrazolo[1,5-a]pyrimidine-2-carboxamide |
| 449 | N-(3,4-difluorophenyl)-7-phenylpyrazolo[1,5-a]pyrimidine-2-carboxamide |
| 450 | N-(2-ethoxyphenyl)-7-phenylpyrazolo[1,5-a]pyrimidine-2-carboxamide |
| 451 | N-(3-chloro-4-methoxyphenyl)-7-phenylpyrazolo[1,5-a]pyrimidine-2-carboxamide |
| 452 | N-(3-chloro-4-fluorophenyl)-7-phenylpyrazolo[1,5-a]pyrimidine-2-carboxamide |
| 453 | N-(5-chloro-2-methoxyphenyl)-7-phenylpyrazolo[1,5-a]pyrimidine-2-carboxamide |
| 454 | N-(2-methoxy-5-methylphenyl)-7-phenylpyrazolo[1,5-a]pyrimidine-2-carboxamide |
| 455 | N-(5-fluoro-2-methylphenyl)-7-phenylpyrazolo[1,5-a]pyrimidine-2-carboxamide |
| 456 | N-(2-fluoro-5-methylphenyl)-7-phenylpyrazolo[1,5-a]pyrimidine-2-carboxamide |
| 457 | N-(2,5-difluorophenyl)-7-phenylpyrazolo[1,5-a]pyrimidine-2-carboxamide |
| 458 | N-(4-acetamidophenyl)-7-phenylpyrazolo[1,5-a]pyrimidine-2-carboxamide |
| 459 | 7-phenyl-N-(4-(trifluoromethoxy)phenyl)pyrazolo[1,5-a]pyrimidine-2-carboxamide |
| 460 | indolin-1-yl(7-phenylpyrazolo[1,5-a]pyrimidin-2-yl)methanone |
| 461 | 7-(4-fluorophenyl)-N-(3-methoxyphenyl)pyrazolo[1,5-a]pyrimidine-2-carboxamide |
| 462 | 7-(4-fluorophenyl)-N-(2-methoxyphenyl)pyrazolo[1,5-a]pyrimidine-2-carboxamide |
| 463 | N-(2-ethoxyphenyl)-7-(4-fluorophenyl)pyrazolo[1,5-a]pyrimidine-2-carboxamide |
| 464 | N-(3,4-dimethoxyphenyl)-7-(4-fluorophenyl)pyrazolo[1,5-a]pyrimidine-2-carboxamide |
| 465 | 7-(4-fluorophenyl)-N-(4-methoxy-2-methylphenyl)pyrazolo[1,5-a]pyrimidine-2-carboxamide |
| 466 | N-(2,5-difluorophenyl)-7-(4-fluorophenyl)pyrazolo[1,5-a]pyrimidine-2-carboxamide |
| 467 | N-(4-acetylphenyl)-7-(4-fluorophenyl)pyrazolo[1,5-a]pyrimidine-2-carboxamide |
| 468 | N-(2,4-difluorophenyl)-7-(4-fluorophenyl)pyrazolo[1,5-a]pyrimidine-2-carboxamide |
| 469 | N-(5-fluoro-2-methylphenyl)-7-(4-fluorophenyl)pyrazolo[1,5-a]pyrimidine-2-carboxamide |
| 470 | N-(4-fluoro-2-methylphenyl)-7-(4-fluorophenyl)pyrazolo[1,5-a]pyrimidine-2-carboxamide |
| 471 | N-(4-ethoxyphenyl)-7-(4-fluorophenyl)pyrazolo[1,5-a]pyrimidine-2-carboxamide |
| 472 | N-(4-(dimethylamino)phenyl)-7-(4-fluorophenyl)pyrazolo[1,5-a]pyrimidine-2-carboxamide |
| 473 | N-(4-acetamidophenyl)-7-(4-fluorophenyl)pyrazolo[1,5-a]pyrimidine-2-carboxamide |
| 474 | N-(4-carbamoylphenyl)-7-(4-fluorophenyl)pyrazolo[1,5-a]pyrimidine-2-carboxamide |
| 475 | N-(2-fluorophenyl)-7-(4-fluorophenyl)pyrazolo[1,5-a]pyrimidine-2-carboxamide |
| 476 | 7-(4-fluorophenyl)-N-(o-tolyl)pyrazolo[1,5-a]pyrimidine-2-carboxamide |
| 474 | 7-(4-fluorophenyl)-N-(m-tolyl)pyrazolo[1,5-a]pyrimidine-2-carboxamide |
| 478 | 7-(4-fluorophenyl)-N-phenylpyrazolo[1,5-a]pyrimidine-2-carboxamide |
| 479 | N-(3-acetylphenyl)-7-(4-fluorophenyl)pyrazolo[1,5-a]pyrimidine-2-carboxamide |
| 480 | N-(4-fluoro-3-nitrophenyl)-7-(4-fluorophenyl)pyrazolo[1,5-a]pyrimidine-2-carboxamide |
| 481 | (7-(4-fluorophenyl)pyrazolo[1,5-a]pyrimidin-2-yl)(indolin-1-yl)methanone |
| 482 | N-mesityl-7-(p-tolyl)pyrazolo[1,5-a]pyrimidine-2-carboxamide |
| 483 | N-(4-methoxy-2-methylphenyl)-7-(p-tolyl)pyrazolo[1,5-a]pyrimidine-2-carboxamide |
| 484 | N-(2-chloro-6-methylphenyl)-7-(p-tolyl)pyrazolo[1,5-a]pyrimidine-2-carboxamide |
| 485 | N-(4-(4-chloro-1H-pyrazol-1-yl)phenyl)-7-(3,5-dichlorophenyl)pyrazolo[1,5-a]pyrimidine-2-carboxamide |

It is understood that all variations of salts, solvates, hydrates, prodrugs and/or stereoisomers of the compounds described herein are meant to be encompassed by the present disclosure.

5.1.1. Isotopically Labelled Analogs

The present disclosure also encompasses isotopically-labeled compounds which are identical to those compounds as described herein, except that one or more atoms are replaced by an atom having an atomic mass or mass number different from the atomic mass or mass number usually found in nature ("isotopologues"). The compounds of the present disclosure may also contain unnatural proportions of atomic isotopes at one or more atoms that constituted such compounds. Examples of isotopes that can be incorporated into compounds described herein include isotopes of hydrogen, carbon, nitrogen, oxygen, phosphorus, fluorine and chlorine, such as $^{2}H$ ("D"), $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound described herein can have one or more H atoms replaced with deuterium.

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$ and $^{35}S$ are thus within the scope of the present technology. Procedures for inserting such labels into the compounds of the present technology will be readily apparent to those skilled in the art based on the disclosure herein.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

In some embodiments, certain isotopically-labeled compounds, such as those labeled with $^{3}H$ and $^{14}C$, can be useful in compound and/or substrate tissue distribution assays. Tritiated ($^{3}H$) and carbon-14 ($^{14}C$) isotopes can be particularly preferred for their ease of preparation and detectability. Further, substitution with heavier isotopes such as deuterium can afford certain therapeutic advantages resulting from greater metabolic stability, such as increased in vivo half-life or reduced dosage requirements, and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

In some embodiments, the compounds disclosed in the present disclosure are deuterated analogs of any of the compounds, or a pharmaceutically acceptable salt, a solvate, a hydrate, a prodrug, or a stereoisomer thereof, as described herein. A deuterated analog of a compound of formula (Ia)-(Ie) is a compound where one or more hydrogen atoms are substituted with a deuterium. In some embodiments, the deuterated analog is a compound of formula (Ia) that includes a deuterated $R^x$ group, e.g., $R^1$-$R^9$ group. In some embodiments of a deuterated analog of a compound of formula (Ia), wherein the optional substituent is an optionally substituted heterocycloalkyl including at least one deuterium atom

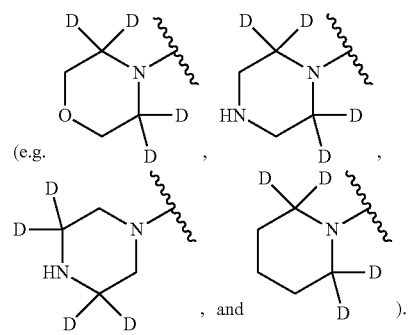

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

5.1.2. Fluorinated Analogs

In some embodiments, the compounds disclosed in the present disclosure are fluorinated analogs of any of the compounds, or a pharmaceutically acceptable salt, a solvate, a hydrate, a prodrug, or a stereoisomer thereof, as described herein. A fluorinated analog of a compound of formula (Ia)-(Ie) is a compound where one or more hydrogen atoms or substituents are substituted with a fluorine atom. In some embodiments, the fluorinated analog is a compound of formula (Ia)-(Ie) that includes a fluorinated $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^7$, $R^{18}$, $R^{19}$, $R^{20}$, $R^{31}$, $R^{32}$ group, or other substituent R group. In some embodiments of a fluorinated analog of a compound of formula (Ia)-(Ie), the hydrogen atom of an aliphatic or an aromatic C—H bond is replaced by a fluorine atom. In some embodiments of a fluorinated analog of a compound of formula (Ia)-(Ie), at least one hydrogen of an optionally substituted aryl or an optionally substituted heteroaryl is replaced by a fluorine atom. In some embodiments of a fluorinated analog of a compound of formula (Ia)-(Ie), a hydroxyl substituent (—OH) or an amino substituent (—NH$_2$) is replaced by a fluorine atom.

5.1.3. Isomers

The term "compound", as used herein, is meant to include all stereoisomers, geometric isomers, tautomers, and isotopes of the structures depicted.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. In some embodiments, the compounds described herein have one or more chiral centers. It is understood that if an absolute stereochemistry is not expressly indicated, then each chiral center may independently be of the R-configuration or the S-configuration or a mixture thereof. Thus, compounds described herein include enriched or resolved optical isomers at any or all asymmetric atoms as are apparent from the depictions. Racemic mixtures of R-enantiomer and S-enantiomer, and enantio-enriched stereomeric mixtures comprising of R- and S-enantiomers, as well as the individual optical isomers can be isolated or synthesized so as to be substantially free of their enantiomeric or diastereomeric partners, and these stereoisomers are all within the scope of the present technology.

Compounds of the present disclosure containing an asymmetrically substituted atom may be isolated in optically active or racemic forms. It is well known in the art how to prepare optically active forms, such as by resolution of racemic forms, by synthesis from optically active starting materials, or through use of chiral auxiliaries.

Geometric isomers, resulting from the arrangement of substituents around a carbon-carbon double bond or arrangement of substituents around a cycloalkyl or heterocyclic ring, can also exist in the compounds of the present disclosure. Geometric isomers of olefins, C=N double bonds, or other types of double bonds may be present in the compounds described herein, and all such stable isomers are included in the present disclosure. Specifically, cis and trans geometric isomers of the compounds of the present disclosure may also exist and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

5.1.4. Salts and Other Forms

In some embodiments, the compounds described herein are present in a salt form. In some embodiments, the compounds are provided in the form of pharmaceutically acceptable salts.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, chloride.

Compounds containing an amine functional group or a nitrogen-containing heteroaryl group may be basic in nature and may react with a variety of inorganic and organic acids to form the corresponding salts. The compounds could be used in the form of a pharmaceutically acceptable salt derived from inorganic acid or organic acid. In some embodiments, the pharmaceutically acceptable salt could be a salt derived from hydrochloric acid (i.e., a hydrochloride salt of a compound as described herein), or the like.

The pharmaceutically acceptable salts of the compounds of this disclosure could be produced by dissolving the compound in a water-miscible organic solvent, such as acetone, methanol, ethanol, or acetonitrile, and so on, and adding excessive amount of organic acid or inorganic acid aqueous solution and precipitating or crystalizing. Then, it is possible to obtain additional salt by evaporating the solvent or excessive acid from this mixture and then drying it or by produce salt by filtering extracted salt.

Other examples of salts include anions of the compounds of the present disclosure compounded with a suitable cation. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

Compounds included in the present compositions that are acidic in nature are capable of forming base salts with various pharmacologically acceptable cations. Examples of such salts include alkali metal or alkaline earth metal salts.

Compounds that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds described herein can be present in various forms including crystalline, powder and amorphous forms of those compounds, pharmaceutically acceptable salts, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

In some embodiments, the compounds described herein are present in a solvate form. In some embodiments, the compounds described herein are present in a hydrate form when the solvent component of the solvate is water.

5.1.5. Prodrugs

Aspects of this disclosure include prodrug forms of any of the compounds described herein. Any convenient prodrug forms of the subject compounds can be prepared, for example, according to the strategies and methods described by Rautio et al. ("Prodrugs: design and clinical applications", Nature Reviews Drug Discovery 7, 255-270 (February 2008)).

The term "prodrug" refers to an agent which is converted into a biologically active drug in vivo by some physiological or chemical process. In some embodiments, a prodrug is converted to the desired drug form, when subjected to a biological system at physiological pH. In some embodiments, a prodrug is enzymatically converted to the desired drug form, when subjected to a biological system.

Prodrugs forms of any of the compounds described herein can be useful, for example, to provide particular therapeutic benefits as a consequence of an extension of the half-life of the resulting compound in the body, or a reduction in the active dose required.

Pro-drugs can also be useful in some situations, as they may be easier to administer than the parent drug. They may, for instance, be bioavailable by oral administration whereas the parent drug is not. The pro-drug may also have improved solubility in pharmacological compositions over the parent drug.

Prodrug forms or derivatives of a compound of this disclosure generally include a promoiety substituent at a suitable labile site of the compound. The promoiety refers to the group that can be removed by enzymatic or chemical reactions, when a prodrug is converted to the drug ill vivo.

In some embodiments, the promoiety is a group (e.g., a optionally substituted C1-6 alkanoyl, or an optionally substituted C1-6 alkyl) attached via an ester linkage to a hydroxyl group or a carboxylic acid group of the compound or drug.

5.2. Compound Synthesis

Compounds of the present disclosure may be synthesized according to standard methods known in the art [see, e.g. Morrison and Boyd in "Organic Chemistry", $6^{th}$ edition, Prentice Hall (1992)]. Some compounds and/or intermediates of the present disclosure may be commercially available, known in the literature, or readily obtainable by those skilled in the art using standard procedures. Some compounds of the present disclosure may be synthesized using schemes, examples, or intermediates described herein. Where the synthesis of a compound, intermediate or variant thereof is not fully described, those skilled in the art can recognize that the reaction time, number of equivalents of reagents and/or temperature may be modified from reactions described herein to prepare compounds presented or intermediates or variants thereof and that different work-up and/or purification techniques may be necessary or desirable to prepare such compounds, intermediates, or variants.

Synthesized compounds may be validated for proper structure by methods known to those skilled in the art, for example by nuclear magnetic resonance (NMR) spectroscopy and/or mass spectrometry.

In various embodiments, the compound as described herein is represented by the structure of one of the compounds in Table 3A-3B of Example 2 below. The present disclosure is meant to encompass a compound of any one of Tables 1-2, or a salt, a single stereoisomer, a mixture of stereoisomers and/or an isotopically labelled form thereof.

5.3. Pharmaceutical Compositions

Compounds of the present disclosure may be included in a pharmaceutical composition that includes one or more compounds and at least one excipient (e.g., a pharmaceutically acceptable excipient). Such compositions may include a CFTR modulator and/or PDE4 inhibitor compound of formula (Ia)-(Ie), or a pharmaceutically acceptable salt, a solvate, a hydrate, a prodrug, or a stereoisomer thereof, e.g., as described herein.

The compounds described herein can find use in pharmaceutical compositions for administration to a subject in need thereof in a variety of therapeutic applications where modulation of CFTR, or inhibition of PDE4, is desirable.

Accordingly, another aspect of the present disclosure provides pharmaceutical compositions comprising at least one compound described herein, a pharmaceutically acceptable salt thereof, or a prodrug, a solvate, a hydrate, or a stereoisomer thereof, and at least one pharmaceutically acceptable excipient.

The phrase "pharmaceutically acceptable excipient," refers any ingredient other than the compounds of this disclosure described herein (for example, a vehicle capable of suspending or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing, or dispersing agents, sweeteners, and waters of hydration. In some embodiments, the pharmaceutical composition comprises a compound as described herein, a pharmaceutically acceptable salt thereof, or a prodrug, a solvate, a hydrate, or a stereoisomer thereof in a therapeutically effective amount.

5.3.1.1. Ophthalmic Compositions

In some embodiments, the pharmaceutical compositions are formulated for ophthalmic administration. In some embodiments, the pharmaceutical compositions are ophthalmic compositions formulated for topical administration, e.g., to the eye of a human subject. In some embodiments of the ophthalmic composition, the composition is an aqueous solution.

Thus, the present disclosure provides an ophthalmic composition including a therapeutically effective amount of a compound described herein or a pharmaceutically acceptable salt, a solvate, a hydrate, a prodrug, or a stereoisomer thereof as described herein, and a physiologically compatible ophthalmic vehicle.

5.3.1.2. Other Compositions

The pharmaceutical compositions of this disclosure may be formulated according to any convenient methods, and may also be prepared in various forms for oral administration such as tablets, pills, powders, nanoparticles, capsules, syrups, suspensions, emulsions and microemulsions, or in forms for non-oral administration such as preparations for intramuscular, intravenous or subcutaneous administration.

In a specific example, the pharmaceutical composition could contain a pharmaceutically allowed carrier, excipient, or additive. The pharmaceutical composition could be produced as medicine in the conventional method, and could be produced as various oral medicine such as tablet, pill, powder, capsule, syrup, emulsion, micro-emulsion, and so on, or could be produced as non-oral medicine such as muscular injection, vascular injection, or subcutaneous injection.

If the pharmaceutical composition is produced in the form of an oral medicine, examples of the used additive or carrier could include cellulose, silicic calcium, corn starch, lactose, sucrose, dextrose, phosphoric acid calcium, stearic acid, stearic acid magnesium, stearic acid calcium, gelatin, talc, surfactant, suspension, emulsifying agent, diluting agent, and so on.

If the pharmaceutical composition of this disclosure is produced in the form of an injection, the additives or carrier could include water, saline water, glucose aqueous solution, similar sugar-soluble solution, alcohol, glycol, ether (e.g., polyethylene glycol 400), oil, fatty acid, fatty acid ester, glyceride, surfactant, suspension, emulsifying agent, and so on.

In some embodiments, the pharmaceutical compositions are formulated for parenteral administration to a subject in need thereof. In some parenteral embodiments, the pharmaceutical compositions are formulated for intravenous administration to a subject in need thereof. In some parenteral embodiments, the pharmaceutical compositions are formulated for subcutaneous administration to a subject in need thereof.

5.4. Methods of Modulating CFTR

Aspects of the present disclosure include methods of modulating CFTR with compounds as described herein. Such methods may include methods of modulating CFTR in biological systems by contacting such systems with CFTR modulator compounds (e.g., CFTR modulator compounds having structures according to any of those of Table 1 or a pharmaceutically acceptable salt, a solvate, a hydrate, a prodrug, or a stereoisomer thereof). Biological systems may include, but are not limited to, cells, tissues, organs, bodily fluids, organisms, non-mammalian subjects, and mammalian subjects (e.g., humans). A method of contacting biological systems with CFTR modulator compounds may be performed by administering the compounds to subjects.

The term "modulator" refers to a compound or composition that increases the level of a target or the function of a target, which may be, but is not limited to, CFTR. In some embodiments, the modulator compound can agonize or activate a target, such as CFTR, and increase the level of the target or the function of the target. In this respect, the method of modulating CFTR comprises a method of activating CFTR or the function of CFTR.

In some embodiments, the CFTR modulator compounds described herein are CFTR activator compounds that are capable of activating CFTR proteins and increasing the level of the function of the CFTR proteins. In another embodiment, the CFTR activator compounds described herein are capable of modulating or activating downstream function(s) resulting from CFTR activation.

In some embodiments, the method of modulating CFTR includes contacting a biological system or sample comprising CFTR with an effective amount of any of the CFTR modulating compounds or a pharmaceutically acceptable salt, a solvate, a hydrate, a prodrug, or a stereoisomer thereof as described herein, or a pharmaceutical composition including same as described herein to modulate CFTR. In certain embodiments, the biological system or sample is in vitro. In another embodiment, the biological system or sample is in vivo.

The CFTR modulators may modulate the enzymatic activity of CFTR in a sample. For example, yellow fluorescent protein (YFP)-based binding assay, as described in Example 4, can be used to measure CFTR function. Using such assay, the CFTR function is assessed from the time course of cell fluorescence in response to extracellular addition of iodide ions followed by forskolin that results in decrease YFP fluorescence due to CFTR-mediated iodide entry. CFTR activity can also be assessed by the assay described in Example 5. CFTR modulators according to such method may exhibit $EC_{50}$ values for modulation of CFTR function (e.g. as assessed by short-circuit current measurement assay of Example 5) of less than 2000 nM, such as 200 nM or less. Biological systems may include subjects (e.g., human subjects).

In some embodiments, the present disclosure provides methods of modulating CFTR activity in a subject. In some cases, the percentage of CFTR activity modulated in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%. In some embodiments, the CFTR activity is increased, e.g., at least 10% or more, as compared to a baseline level of CFTR activity measured in a sample of the subject.

In some embodiments, compounds of the present disclosure may be used in assays to assess CFTR modulation activity. Some assays may include diagnostic assays. In some cases, compounds may be included in methods of drug discovery. In some embodiments, methods of the present disclosure include use of CFTR modulating compounds of the present disclosure to assess CFTR modulation by other compounds. Such methods may include conjugating CFTR modulating compounds with one or more detectable labels (e.g., fluorescent dyes) and measuring CFTR dissociation (via detectable label detection) in the presence of the other compounds. The detectable labels may include fluorescent compounds.

5.5. Methods of Inhibiting PDE4

Aspects of the present disclosure include methods of inhibiting activity of PDE4 in a biological system or sample by contacting with a compound which exhibit PDE4 inhibiting activity, (e.g., PDE4 inhibitor compounds having structures according to any of those of Tables 1-2, or a pharmaceutically acceptable salt, a solvate, a hydrate, a prodrug, or a stereoisomer thereof). A method of contacting biological systems with CFTR modulator compounds may be performed by administering the compounds to subjects.

Biological systems may include, but are not limited to, cells, tissues, organs, bodily fluids, organisms, non-mammalian subjects, and mammalian subjects (e.g., humans). In certain embodiments, the biological system or sample is in vitro. In another embodiment, the biological system or sample is in vivo. In some instances, the sample is a cellular sample.

In some embodiments, the present disclosure provides methods of inhibiting PDE4 activity in a subject. In some cases, the percentage of PDE4 activity inhibited in a subject may be at least 10%, at least 20%, at least 30%, at least 40%, at least 50%, at least 60%, at least 70%, at least 80%, at least, 85%, at least 90%, at least 95%, at least 96%, at least 97%, at least 98%, at least 99%, at least 99.5%, or at least 99.9%. In some cases, this level of inhibition and/or maximum inhibition of PDE4 activity may be achieved by from about 1 hour after administration to about 3 hours after administration, from about 2 hours after administration to about 4 hours after administration, from about 3 hours after administration to about 10 hours after administration, from about 5 hours after administration to about 20 hours after administration, or from about 12 hours after administration to about 24 hours after administration. Inhibition of PDE4 activity may continue throughout a period of at least 1 day, of at least 2 days, of at least 3 days, of at least 4 days, of at least 5 days, of at least 6 days, of at least 7 days, of at least 2 weeks, of at least 3 weeks, of at least 4 weeks, of at least 8 weeks, of at least 3 months, of at least 6 months, or at least 1 year. In some cases, this level of inhibition may be achieved through daily administration. Such daily administration may include administration for at least 2 days, for at least 3 days, for at least 4 days, for at least 5 days, for at least 6 days, for at least 7 days, for at least 2 weeks, for at least 3 weeks, for at least 4 weeks, for at least 2 months, for at least 4 months, for at least 6 months, for at least 1 year, or for at least 5 years. In some cases, subjects may be administered compounds or compositions of the present disclosure for the life of such subjects.

5.6. Therapeutic Indications

Methods of the present disclosure include methods of treating therapeutic indications using compounds and/or compositions disclosed herein. The term "therapeutic indication" refers to any symptom, condition, disorder, or disease that may be alleviated, stabilized, improved, cured, or otherwise addressed by some form of treatment or other therapeutic intervention (e.g., through CFTR modulator or PDE4 inhibitor administration).

5.6.1. CFTR-Related Indications

Therapeutic indications associated with CFTR activity and/or dysfunction are referred to herein as "CFTR-related indications." In some embodiments, methods of the present disclosure may include treating CFTR-related indications by administering compounds and/or compositions disclosed herein (e.g., CFTR modulator compounds).

The terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

5.6.1.1. Eye Disease or Disorder

In another aspect, the present disclosure provides a method of treating an eye disease or disorder, including administering to an eye of a subject a therapeutically effective amount of an ophthalmic composition as described herein. In some embodiments, the subject is human. In some embodiments of the method, the eye disease or disorder is dry eye disease.

Dry eye disease is a heterogeneous tear film disorder that results in eye discomfort, visual disturbance, and ocular surface pathology. CFTR is a major prosecretory chloride channel at the ocular surface. Activators of ocular surface CFTR activity can lead to increased tear fluid secretion after topical delivery and be useful for treating dry eye disease.

In some embodiments, the method further includes identifying a subject suffering from dry eye disease. In some embodiments, the method further includes identifying an underlying disease or condition associated with the dry eye disease.

In some embodiments, the dry eye disease is caused by one or more disease or condition of the group consisting of allergic conjunctivitis, keratoconjunctivitis sicca, age-related dry eye, Stevens-Johnson syndrome, Sjogren's syndrome, ocular cicatrical pemphigoid, corneal injury, infection, Riley-Day syndrome, congenital alacrima, nutritional disorders or deficiencies, pharmacologic side effects, contact lens intolerance, eye stress resulting in glandular and tissue destruction, autoimmune disorders, immuno-deficient disorders, comatose patients who are unable to blink, or environmental exposure to smog, smoke, excessively dry air, airborne particulates, lacrimal deficiency, lacrimal gland duct obstruction, Meibomian oil deficiency, a disorder of eyelid aperture, and ocular surface disease (OSD).

In some embodiments, the dry eye disease is caused by keratoconjunctivitis sicca, age-related dry eye, Stevens-Johnson syndrome, Sjogren's syndrome, ocular cicatrical pemphigoid, corneal injury, Riley-Day syndrome, or congenital alacrima.

In some embodiments, the eye disease or disorder treated according to the method of this disclosure is Sjogren's syndrome.

In some embodiments, the dry eye disease is caused by nutritional disorders or deficiencies, contact lens intolerance, autoimmune disorders, immuno-deficient disorders, comatose patients who are unable to blink, or environmental exposure to smog, smoke, excessively dry air, or airborne particulates.

In some embodiments, the eye disease or disorder treated according to the method of this disclosure is conjunctivitis. In some embodiments, the conjunctivitis is allergic conjunctivitis or keratoconjunctivitis.

In some embodiments, the eye disease or disorder is keratitis.

In some embodiments, one or more symptoms of the dry eye disease are reduced or alleviated in the subject after administration of compounds or compositions disclosed herein.

In some embodiments, one or more symptoms of the dry eye disease are selected from dryness, burning, ocular itching, photophobia, foreign body sensation, and grittiness.

In some embodiments, the method further comprises assessing restoration of the natural tear film in the eye after administration.

In some embodiments, the ophthalmic composition is topically administered to the eye daily or as needed. In certain embodiments, the ophthalmic composition is a solution.

A tear volume reduction mouse model for dry eye disease can be used to assess the abilities of the compounds of the present disclosure to modulate tear volume in subjects induced with Scopolamine. In some embodiments, the administration of the compounds of the present disclosure can cause significant changes in tear volume as illustrated by Example 6.

5.6.1.2. Other Diseases or Disorders

Other CFTR-related indications which can be targeted for treatment include, but are not limited to, chronic obstructive pulmonary disease (COPD), asthma, bronchitis, bronchiectasis, celiac disease, constipation, cholestatic liver disease, chronic rhinosinusitis, and hepatic impairment.

CFTR dysfunction or CFTR hypofunction can be acquired in chronic obstructive pulmonary disease (COPD) and can contribute to other diseases that share clinical features such as asthma, bronchitis and bronchiectasis. The diseases of chronic obstructive pulmonary disease (COPD), and chronic bronchitis are characterized by mucus-congested and inflamed airways. In some embodiments, the compounds of this disclosure can act as anti-inflammatory agents that simultaneously restore or enhance mucociliary clearance through CFTR activation.

In some embodiments, the CFTR-related indication is COPD.

In some embodiments, the CFTR-related indication is bronchitis.

In some embodiments, the CFTR-related indication is bronchiectasis.

In some embodiments, the CFTR-related indication is asthma.

In some embodiments, the CFTR-related indication is constipation. Constipation is a common clinical complaint in adults and children that negatively impacts quality of life. In some embodiments, the constipation is opioid-induced constipation, chronic idiopathic constipation or irritable bowel syndrome with constipation predominance. In some embodiments, the CFTR modulating compounds of this disclosure can stimulate intestinal fluid secretion and normalized stool output to treat the constipation.

In some embodiments, the CFTR-related indication is celiac disease. In celiac disease, an intolerance to dietary gluten/gliadin, antigenic gliadin peptides trigger an HLADQ2/DQ8-restricted adaptive Th1 immune response. CFTR acts as membrane receptor for the gluten/gliadin-derived peptide (P31-43) which inhibits CFTR in intestinal epithelial cells, causing a local stress response that contributes to the immunopathology of celiac disease. In some embodiments, stimulation of CFTR function with CFTR activating compounds of this disclosure can attenuate the autophagy-inhibition and pro-inflammatory effects of gliadin, and provide for treatment of celiac disease.

In some embodiments, the CFTR-related indication is cholestatic liver disease.

In some embodiments, the CFTR-related indication is chronic rhinosinusitis.

In some embodiments, the CFTR-related indication is hepatic impairment.

5.6.2. PDE4-Related Indications

Aspects of the present disclosure include methods of treating therapeutic indications of interest using compounds and/or compositions disclosed herein. Therapeutic indications associated with PDE4 activity and/or dysfunction are referred to herein as "PDE4-related indications." In some embodiments, methods of the present disclosure may include treating PDE4-related indications by administering compounds and/or compositions disclosed herein (e.g., PDE4 inhibitor compounds).

PDE4 inhibitors are a well characterized class of agent having a variety of anti-inflammatory activities. A human phosphodiesterase 4 (PDE4) inhibition assay in host cells can be used to assess the abilities of the compounds of the present disclosure to inhibit target PDE4. In some embodiments, the administration of the compounds of the present disclosure can cause significant changes PDE4 activity as illustrated by Example 7.

In some embodiments, the PDE4 inhibiting compounds of this disclosure have board anti-inflammatory effects such as the inhibition of TNF-alpha production and several other mediators. PDE4 is a therapeutic target for the treatment of diverse pulmonary, dermatological, and severe neurological diseases.

In some embodiments of the method, the PDE4-related indication is an inflammatory disease or disorder. In some embodiments, inflammatory disease or disorder is a chronic inflammatory disease or disorder. In some embodiments, inflammatory disease or disorder is an acute inflammatory disease or disorder. In some embodiments of the method, the PDE4-related indication is an autoimmune disease.

In some embodiments of the method, the PDE4-related indication is an inflammatory lung disease. In some embodiments, the inflammatory lung disease is chronic obstructive pulmonary disease (COPD), asthma, pulmonary fibrosis or an inflammatory airway disease.

In some embodiments of the method, the PDE4-related indication is an inflammatory skin disease. In some embodiments, the inflammatory skin disease is psoriasis or a psoriatic disorder, such as psoriatic arthritis. In some embodiments, the inflammatory skin disease is atopic dermatitis.

In some embodiments of the method, the PDE4-related indication is inflammatory bowel disease (IBD).

In some embodiments of the method, the PDE4-related indication is rheumatoid arthritis.

In some embodiments of the method, the PDE4-related indication is ankylosing spondylitis.

In some embodiments of the method, the PDE4-related indication is a neurological disease, such as neuroinflammation.

In some embodiments of the method, the PDE4-related indication is conjunctivitis. In some embodiments, the conjunctivitis is allergic conjunctivitis or keratoconjunctivitis.

In some embodiments, the PDE4-related indication is keratitis.

Accordingly, PDE4-related indications of interest which can be targeted for treatment according to the methods of this disclosure include, but are not limited to, COPD, asthma, inflammatory airway disease, psoriasis, psoriatic disorder, atopic dermatitis, inflammatory bowel disease (IBD), rheumatoid arthritis, ankylosing spondylitis, neuroinflammation, and allergic conjunctivitis.

5.6.3. Administration Methods

In some embodiments, the method includes oral administration of the subject compound or composition. The administration dose may be administrated orally or non-orally depending on the purpose, in an amount effective at prevention or therapy in the individual or patient in question. When administering orally, the compound may be administered so that 0.01 to 1000 mg, more specifically 0.1 to 300 mg of the active agent is administered per 1 kg body weight, and when administering non-orally, the compound may be administered so that 0.01 to 100 mg, more specifically 0.1 to 50 mg of the active ingredient is administered per 1 kg body weight. The dose may be administered at one time or over multiple administrations. The administration dose for a specific individual or patient should be decided based on various related factors such as the body weight, age, sex, health, diet, administration intervals, method of administration and severity of the illness, and may be appropriately increased or reduced by an expert. The administration doses stated above are not intended to limit the scope of the present invention in any manner. A physician or veterinarian have ordinary skill in related art may readily decide and prescribe an effective required dose for the pharmaceutical composition. For example, a physician or veterinarian may, beginning at levels less than that required for achieving the target therapeutic effect, gradually increase the dose of the compound of the present invention in a pharmaceutical composition until the intended effect is achieved.

The compounds and compositions of the present disclosure may be administered alone, in combination with a compound according to another example of the present disclosure, or in simultaneous, separate or sequential concomitant administration with at least one other therapeutic agent, for example with other pharmaceutical active ingre-

5.7. Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

The symbol "━━━" refers to a covalent bond that is a single or a double bond.

The term "$C_x$-$C_y$" when used in conjunction with a chemical moiety, such as alkyl, alkenyl, or alkynyl is meant to include groups that contain from x toy carbons in the chain. For example, the term "$C_1$-$C_6$ alkyl" refers to substituted or unsubstituted saturated hydrocarbon groups, including straight-chain alkyl and branched-chain alkyl groups that contain from 1 to 6 carbons. In some embodiments, the term "($C_x$-$C_y$)alkylene" refers to a substituted or unsubstituted alkylene chain with from x to y carbons in the alkylene chain. For example "($C_x$-$C_y$)alkylene may be selected from methylene, ethylene, propylene, butylene, pentylene, and hexylene, any one of which is optionally substituted.

The term "alkyl" refers to an unbranched or branched saturated hydrocarbon chain. In some embodiments, alkyl as used herein has 1 to 20 carbon atoms (($C_1$-$C_{20}$)alkyl), 1 to 10 carbon atoms (($C_1$-$C_{10}$)alkyl), 1 to 8 carbon atoms (($C_1$-$C_8$)alkyl), 1 to 6 carbon atoms (($C_1$-$C_6$)alkyl), 1 to 5 carbon atoms (($C_1$-$C_5$)alkyl) or 1 to 3 carbon atoms (($C_1$-$C_3$)alkyl). Examples include, but are not limited to, methyl, ethyl, n-propyl, isopropyl, n-butyl, sec-butyl, tert-butyl, n-pentyl, 2-pentyl, isopentyl, neopentyl, n-hexyl, 2-hexyl, 3-hexyl, and 3-methyl pentyl. When an alkyl residue having a specific number of carbons is named, all geometric isomers having that number of carbons may be encompassed. For example, "butyl" can include n-butyl, sec-butyl, isobutyl and t-butyl, and "propyl" can include n-propyl and isopropyl. Unless stated otherwise specifically in the specification, an alkyl chain is optionally substituted by one or more substituents such as those substituents described herein.

The term "alkoxy" refers to an unbranched or branched alkyl group attached to an oxygen atom (alkyl-O—). In some embodiments, alkoxy as used herein has 1 to 20 carbon atoms (($C_1$-$C_{20}$)alkoxy), 1 to 10 carbon atoms (($C_1$-$C_{10}$) alkoxy), 1 to 8 carbon atoms (($C_1$-$C_8$)alkoxy), 1 to 6 carbon atoms (($C_1$-$C_6$)alkoxy), 1 to 5 carbon atoms (($C_1$-$C_5$)alkoxy) or 1 to 3 carbon atoms (($C_1$-$C_3$)alkoxy). Examples include, but are not limited to, methoxy, ethoxy, n-propoxy, and butoxy. When an alkoxy residue having a specific number of carbons is named, all geometric isomers having that number of carbons may be encompassed, such as isopropoxy, isobutoxy, and t-butoxy. Unless stated otherwise specifically in the specification, an alkoxy chain is optionally substituted by one or more substituents such as those substituents described herein.

The term "alkylene" refers to a straight divalent hydrocarbon chain linking the rest of the molecule to a radical group, consisting solely of carbon and hydrogen, containing no unsaturation, and preferably having from 1 to 20 carbon atoms (($C_1$-$C_{20}$)alkylene), 1 to 10 carbon atoms (($C_1$-$C_{10}$) alkylene), 1 to 6 carbon atoms (($C_1$-$C_6$)alkylene), or 1 to 5 carbon atoms (($C_1$-$C_5$)alkylene). Examples include, but are not limited to, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. Unless stated otherwise specifically in the specification, an alkylene chain is optionally substituted by one or more substituents such as those substituents described herein. Examples include methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—($CH_2$)$_6$—) and the like.

The term "alkenyl" refers to an aliphatic hydrocarbon group containing at least one carbon-carbon double bond including straight-chain, branched-chain and cyclic alkenyl groups.

In some embodiments, the alkenyl group has 2-10 carbon atoms (($C_2$-$C_{10}$) alkenyl). In another embodiment, the alkenyl group has 2-4 carbon atoms in the chain (($C_2$-$C_4$) alkenyl). Exemplary alkenyl groups include, but are not limited to, ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl The term "alkynyl" refers to straight or branched monovalent hydrocarbyl groups having from 2 to 6 carbon atoms and preferably 2 to 3 carbon atoms and having at least 1 and preferably from 1 to 2 sites of acetylenic (C≡C—) unsaturation. Examples of such alkynyl groups include, but are not limited to, acetylenyl (C≡CH), and propargyl ($CH_2$C≡CH).

The term "aryl" refers to a monocyclic or poly cyclic group having at least one hydrocarbon aromatic ring, wherein all of the ring atoms of the at least one hydrocarbon aromatic ring are carbon. Aryl may include groups with a single aromatic ring (e.g., phenyl) and multiple fused aromatic rings (e.g., naphthyl, anthryl). Aryl may further include groups with one or more aromatic hydrocarbon rings fused to one or more non-aromatic hydrocarbon rings (e.g., fluorenyl; 2,3-dihydro-1H-indene; 1,2,3,4-tetrahydronaphthalene). In certain embodiments, aryl includes groups with an aromatic hydrocarbon ring fused to a non-aromatic ring, wherein the non-aromatic ring comprises at least one ring heteroatom independently selected from the group consisting of N, O, and S. For example, in some embodiments, aryl includes groups with a phenyl ring fused to a non-aromatic ring, wherein the non-aromatic ring comprises at least one ring heteroatom independently selected from the group consisting of N, O, and S (e.g., chromane; thiochromane; 2,3-dihydrobenzofuran; indoline). In some embodiments, aryl as used herein has from 6 to 14 carbon atoms (($C_6$-$C_{14}$) aryl), or 6 to 10 carbon atoms (($C_6$-$C_{10}$)aryl). Where the aryl includes fused rings, the aryl may connect to one or more substituents or moieties of the formulae described herein through any atom of the fused ring for which valency permits.

The term "cycloalkyl" refers to a monocyclic or polycyclic saturated hydrocarbon. In some embodiments, cycloalkyl has 3 to 20 carbon atoms (($C_3$-$C_{20}$)cycloalkyl), 3 to 8 carbon atoms (($C_3$-$C_8$)cycloalkyl), 3 to 6 carbon atoms (($C_3$-$C_6$)cycloalkyl), or 3 to 5 carbon atoms (($C_3$-$C_5$)cycloalkyl). In some embodiments, cycloalkyl has 3 to 8 carbon atoms having single or multiple cyclic rings including fused, bridged, and spiro ring systems. Examples of suitable cycloalkyl groups include, but are not limited to, adamantyl, cyclopropyl, cyclobutyl, cyclopentyl, cyclooctyl, octahydropentalenyl, octahydro-1H-indene, decahydronaphthalene, cubane, bicyclo[3.1.0]hexane, and bicyclo[1.1.1]pentane, and the like.

The term "carbocycle" refers to a saturated, unsaturated or aromatic ring system in which each atom of the ring system is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl.

The term "haloalkyl" refers to a mono haloalkyl or a polyhaloalkyl group that can be further substituted or unsubstituted.

The term "heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems.

The term "heteroaryl" refers to an aromatic group of from 4 to 10 carbon atoms and 1 to 4 heteroatoms within the ring(s)(e.g., oxygen, nitrogen and/or sulfur). Such heteroaryl groups can have a single ring (i.e., pyridinyl or furyl) or multiple condensed rings (i.e., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Examples of monocyclic heteroaryl include pyrazolyl, pyrrolyl, thiazolyl, oxazolyl, thiophenyl, furanyl, imidazolyl, isoxazolyl, triazolyl, thiadiazolyl, tetrazolyl, oxadiazolyl, pyridinyl, pyridazinyl, pyrimidinyl, pyrazinyl, thiazolyl, and similar groups, but are not limited to the aforementioned. Examples of bicyclic heteroaryl include indolyl, benzothiophenyl, benzofuranyl, benzimidazolyl, benzoxazolyl, benzisoxazolyl, benzothiazolyl, benzothiadiazole, benzotriazolyl, quinolinyl, isoquinolinyl, purinyl, furopyridinyl, oxocromen, dioxoisoindolin, pyrazolopyridinyl, pyrazolo [1, 5-a] pyridinyl, and similar groups, but are not restricted to the aforementioned. Preferred heteroaryls include 5 or 6 membered heteroaryls such as pyridinyl, pyrrolyl, indolyl, thiophenyl, and furanyl.

The term "heteroalkyl" refers to an alkyl substituent in which one or more of the carbon atoms and any attached hydrogen atoms are independently replaced with the same or different heteroatomic group. For example, 1, 2, or 3 carbon atoms may be independently replaced with the same or different heteroatomic substituent.

The term "heterocycloalkyl" refers to substituted or unsubstituted monocyclic alkyl containing one or more hetero atoms (e.g., B, N, O, S, P(=O), Si or P). Examples include piperidinyl, piperazinyl, morpholinyl, pyrrolidinyl, thiomorpholinyl, imidazolidinyl, tetrahydrofurfuryl, and similar groups, but are not restricted to the aforementioned.

The term "substituted" refers to moieties having substituents replacing a hydrogen on one or more carbons or substitutable heteroatoms, e.g., NH or NH$_2$, of a compound. It will be understood that "substitution" or "substituted with" includes the implicit proviso that such substitution is in accordance with permitted valence of the substituted atom and the substituent, and that the substitution results in a stable compound. For example, stable compounds include, but is not limited to, compounds which do not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. The term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants, unless specified otherwise.

When referring to compound features, the phrase "optionally substituted" may be used interchangeably with the phrase "unsubstituted or substituted" and refers to when a non-hydrogen substituent may or may not be present on a given atom or group, and, thus, the description includes structures where a non-hydrogen substituent is present and structures where a non-hydrogen substituent is not present. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible and/or inherently unstable.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$N(R$^a$)S(O)$_t$NR$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2). In another exemplary embodiment, substituents include alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo, thioxo, cyano, nitro, imino, oximo, hydrazine, —$R^bOR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$N$R^a$ (where t is 1 or 2), —$R^b$—S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2); and wherein each $R^a$, $R^b$, and $R^c$ are independently selected from hydrogen, alkyl, cycloalkyl, cycloalkylalkyl, aryl, aralkyl, heterocycloalkyl, heterocycloalkylalkyl, heteroaryl, and heteroarylalkyl; and wherein each $R^a$, $R^b$, and $R^c$, valence permitting, may be optionally substituted with alkyl, alkenyl, alkynyl, halogen, haloalkyl, haloalkenyl, haloalkynyl, oxo, thioxo, cyano, nitro, imino, oximo, hydrazine, —$R^bOR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$N$R^a$ (where t is 1 or 2), —$R^b$—S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2).

The term "isomers" refers to two or more compounds comprising the same numbers and types of atoms, groups or components, but with different structural arrangement and connectivity of the atoms.

The term "tautomer" refers to one of two or more structural isomers which readily convert from one isomeric form to another and which exist in equilibrium.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposable mirror images of one another.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their respective enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, Classics in Stereoselective Synthesis, Wiley-VCH: Weinheim, 2009.

The symbol ═ denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituent on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compound wherein the substituents are disposed on both the same and opposite sides of the plane of the ring are designated "cis/trans."

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

A dash ("-") symbol that is not between two letters or symbols refers to a point of bonding or attachment for a substituent. For example, —NH$_2$ is attached through the nitrogen atom.

The term "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts.

The terms "pharmaceutically acceptable excipient," "pharmaceutically acceptable diluent," "pharmaceutically acceptable carrier," and "pharmaceutically acceptable adjuvant" are used interchangeably and refer to an excipient, diluent, carrier, or adjuvant that is useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. The phrase "pharmaceutically acceptable excipient" includes both one and more than one such excipient, diluent, carrier, and/or adjuvant.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal, intramuscular, subcutaneous, and the like.

The terms "individual" and "subject" are used interchangeably and refer to a subject requiring treatment of a disease. More specifically, what is referred to is a human or non-human primate, mouse, dog, cat, horse, cow, rabbit, rat, or other mammal.

5.8. Exemplary Embodiments

As described herein, the text refers to various embodiments of the present compounds, compositions, and methods. The various embodiments described are meant to provide a variety of illustrative examples and should not be construed as descriptions of alternative species.

Rather, it should be noted that the descriptions of various embodiments provided herein may be of overlapping scope. The embodiments discussed herein are merely illustrative and are not meant to limit the scope of the present technology.

Notwithstanding the appended claims, aspects of the present disclosure are illustrated by the following clauses.

Clause 1. A compound of formula (Ia):

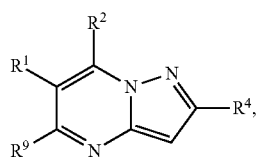

(Ia)

or a pharmaceutically acceptable salt, a solvate, a hydrate, a prodrug, or a stereoisomer thereof, wherein:

$R^1$ is selected from H, halogen, optionally substituted aryl, optionally substituted $(C_1-C_{10})$alkyl, and optionally substituted $(C_1-C_{10})$alkoxy;

$R^2$ is selected from H, optionally substituted $(C_1-C_{10})$ alkyl, optionally substituted cycloalkyl, optionally substituted aryl, optionally substituted heteroaryl, and optionally substituted heterocycle, and the optional substituents on aryl, heteroaryl, and heterocycle are independently selected from: H, OH, $NH_2$, $NO_2$, $OCF_3$, $CF_3$ halogen, optionally substituted amino, optionally substituted $(C_1-C_5)$alkyl, and optionally substituted $(C_1-C_5)$alkoxy;

$R^4$ is selected from

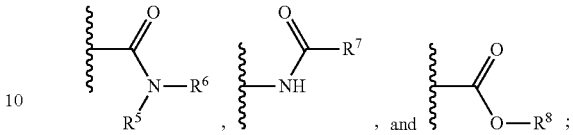

$R^5$ and $R^6$ are independently selected from H, optionally substituted $(C_1-C_{10})$alkyl, optionally substituted $(C_1-C_{10})$ alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted $(C_1-C_{10})$alkyl, optionally substituted $(C_1-C_{10})$alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$ alkyl; and $R^9$ is selected from H and halogen.

Clause 2. The compound of clause 1, wherein the $R^2$ is a substituted aryl with 1 to 3 substituents or a substituted heteroaryl with 1 to 3 substituents.

Clause 3. The compound of clause 1, wherein the $R^2$ is an optionally substituted phenyl or an optionally substituted heteroaryl.

Clause 4. The compound of clause 3, wherein the compound is of formula (Ib):

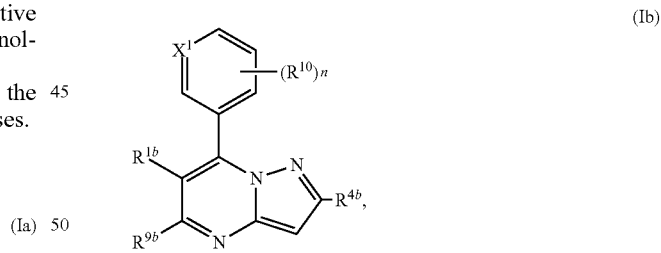

(Ib)

wherein:

$X^1$ is $CR^{10'}$ or N;

$R^{1b}$ is selected from H, halogen, optionally substituted aryl, optionally substituted $(C_1-C_{10})$alkyl, and optionally substituted $(C_1-C_{10})$alkoxy;

$R^{4b}$ is selected from

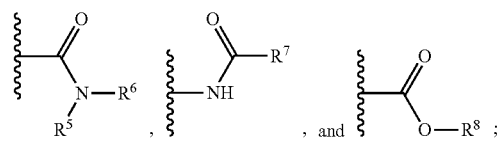

$R^5$ and $R^6$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted $(C_1-C_{10})$alkyl, optionally substituted $(C_1-C_{10})$alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted $(C_1-C_{10})$alkyl;

$R^{9b}$ is selected from H and halogen;

each $R^{10}$ and $R^{10'}$ is independently selected from H, OH, $NH_2$, $NO_2$, halogen, optionally substituted $(C_1-C_6)$alkyl, optionally substituted $(C_1-C_6)$alkoxy, and substituted amino; and n is 0 to 4.

Clause 5. The compound of clause 4, wherein each $R^{10}$ and $R^{10'}$ is independently selected from H, OH, $CH_3$, $CF_3$, $OCF_3$, $OCH_3$, $NO_2$, F, and Cl, and dimethylamine.

Clause 6. The compound of any one of clauses 3-5, wherein $R^2$ is selected from:

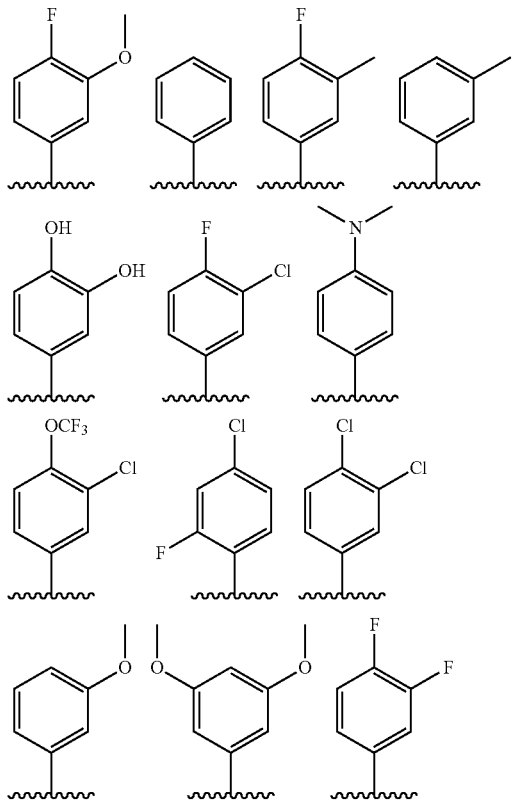

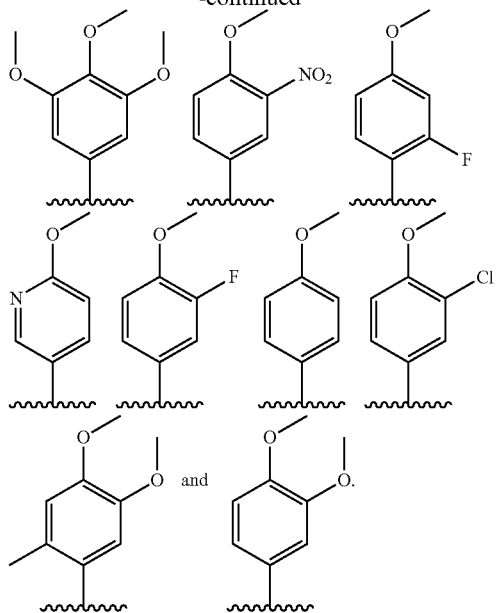

Clause 7. The compound of clause 5 or 6, wherein the compound is of formula (Ic):

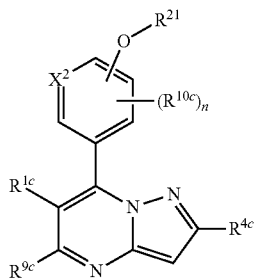

(Ic)

wherein:

$X^2$ is $CR^{10c'}$ or N;

$R^{21}$ is selected from H, and optionally substituted $(C_1-C_{10})$alkyl; optionally substituted acyl; optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

$R^{1c}$ is selected from H, halogen, optionally substituted aryl, optionally substituted $(C_1-C_{10})$alkyl, and optionally substituted $(C_1-C_{10})$alkoxy;

$R^{4c}$ is selected from

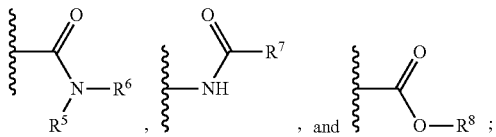

$R^5$ and $R^6$ are independently selected from H, optionally substituted $(C_1-C_{10})$alkyl, optionally substituted $(C_1-C_{10})$alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle; or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted ($C_1$-$C_{10}$)alkyl, optionally substituted ($C_1$-$C_{10}$)alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted ($C_1$-$C_{10}$) alkyl;

$R^{9c}$ is selected from H and halogen;

each $R^{10c}$ and $R^{10c'}$ is independently selected from H, OH, $NH_2$, $NO_2$, halogen, optionally substituted ($C_1$-$C_6$)alkyl, optionally substituted ($C_1$-$C_6$)alkoxy, and substituted amino; and n is 0 to 3.

Clause 8. The compound of clause 7, wherein the compound is of formula (Id):

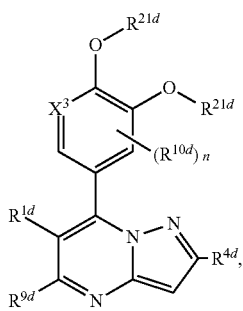

wherein:

$X^3$ is $CR^{10d'}$ or N;

each $R^{21d}$ is independently selected from H, and optionally substituted ($C_1$-$C_{10}$)alkyl; optionally substituted acyl; optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

$R^{1d}$ is selected from H, halogen, optionally substituted aryl, optionally substituted ($C_1$-$C_{10}$)alkyl, and optionally substituted ($C_1$-$C_{10}$)alkoxy;

$R^{4d}$ is selected from

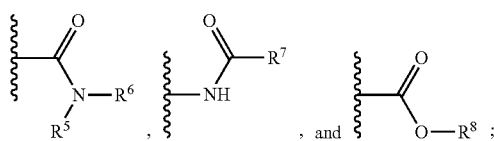

$R^5$ and $R^6$ are independently selected from H, optionally substituted ($C_1$-$C_{10}$)alkyl, optionally substituted ($C_1$-$C_{10}$) alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^5$ and $R^6$ together with the nitrogen atom to which they are attached are cyclically linked to form an optionally substituted monocyclic or bicyclic heterocycle;

$R^7$ is selected from $NR^5R^6$, optionally substituted ($C_1$-$C_{10}$)alkyl, optionally substituted ($C_1$-$C_{10}$)alkoxy, optionally substituted aryl, optionally substituted heteroaryl, optionally substituted arylalkyl, optionally substituted cycloalkyl, and optionally substituted heterocycloalkyl;

$R^8$ is selected from H and optionally substituted ($C_1$-$C_{10}$) alkyl;

$R^{9d}$ is selected from H and halogen;

each $R^{10d}$ and $R^{10d'}$ is independently selected from H, OH, $NH_2$, $NO_2$, halogen, optionally substituted ($C_1$-$C_6$)alkyl, optionally substituted ($C_1$-$C_6$)alkoxy, and substituted amino; and n is 0 to 2.

Clause 9. The compound of clause 7 or 8, wherein $R^{21}$, or $R^{21d}$ is methyl.

Clause 10. The compound of any one of clauses 1 to 9, wherein any of $R^4$-$R^{4d}$ is

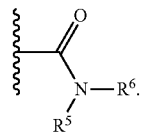

Clause 11. The compound of clause 10, wherein $R^5$ and $R^6$ together with the nitrogen atom to which they are attached are cyclically linked to provide an optionally substituted monocyclic or bicyclic ($C_4$-$C_{10}$)heterocycle.

Clause 12. The compound of clause 10 or 11, wherein $R^4$ is

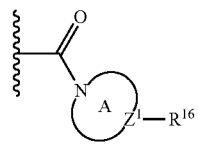

wherein:

ring A is an optionally substituted monocyclic or bicyclic ($C_4$-$C_{10}$)heterocycle;

$Z^1$ is $CR^{14}$ or N, where $R^{14}$ is selected from H, OH, $NH_2$, CN, $CF_3$, $OCF_3$, $CH_2NH_2$, halogen, optionally substituted ($C_1$-$C_5$)alkyl, optionally substituted ($C_1$-$C_5$)alkoxy, optionally substituted cycloalkyl, optionally substituted heterocycloalkyl, optionally substituted carbocycle, and optionally substituted heterocycle; and $R^{16}$ is selected from H, halogen, $-OR^{22a}$, $-C(O)R^{22b}$, $-CO_2R^{22c}$, and $-C(O)NR^{50}R^{60}$, $-NR^{50}R^{60}$, optionally substituted aryl, optionally substituted heteroaryl, optionally substituted carbocycle, optionally substituted heterocycle, optionally substituted ($C_1$-$C_5$)alkyl, and optionally substituted ($C_1$-$C_5$)alkoxy;

$R^{22a}$, $R^{22b}$, and $R^{22c}$ are independently selected from H, optionally substituted ($C_1$-$C_{10}$) alkyl, optionally substituted cycloalkyl, optionally substituted aryl, optionally substituted heteroaryl, and optionally substituted heterocycle; and $R^{50}$ and $R^{60}$ are independently selected from H, optionally substituted ($C_1$-$C_{10}$)alkyl, optionally substituted ($C_1$-$C_{10}$) alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^{50}$ and $R^{60}$ together with the nitrogen atom to which they are attached are cyclically linked to form an optionally substituted heterocycle, or an optionally substituted heteroaryl.

Clause 13. The compound of clause 12, wherein when the A ring is piperidine, then R16 comprises at least one cyclic group selected from optionally substituted aryl, optionally substituted heteroaryl, optionally substituted carbocycle, optionally substituted heterocycle.

Clause 14. The compound of clause 12, wherein the A ring is an optionally substituted piperazine, pyrrolidine, or azetidine.

Clause 15. The compound of clause 14, wherein the A ring is:

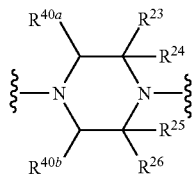

wherein:

$R^{23}$-$R^{26}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$)alkoxy, optionally substituted cycloalkyl, optionally substituted aryl, optionally substituted heteroaryl, and optionally substituted heterocycle; or one or both of $R^{23}$-$R^{24}$ and $R^{25}$-$R^{26}$ together with the carbon atom to which they are attached are cyclically linked to form an optionally substituted carbocycle or an optionally substituted heterocycle; and $R^{40a}$ and $R^{40b}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$)alkoxy, optionally substituted cycloalkyl, optionally substituted aryl, optionally substituted heteroaryl, and optionally substituted heterocycle.

Clause 16. The compound of clause 15, wherein:

$R^{23}$ is selected from optionally substituted ($C_1$-$C_6$)alkyl, optionally substituted cycloalkyl; and $R^{24}$-$R^{26}$, $R^{40a}$ and $R^{40b}$ are each H.

Clause 17. The compound of clause 15, wherein:

two of $R^{23}$, $R^{25}$, and $R^{40b}$ are independently selected from optionally substituted ($C_1$-$C_6$)alkyl, optionally substituted cycloalkyl;

the other one of $R^{23}$, $R^{25}$ and $R^{40b}$ is H; and $R^{24}$, $R^{26}$ and $R^{40a}$ are each H.

Clause 18. The compound of clause 15, wherein:

$R^{23}$ and $R^{24}$ together with the carbon atom to which they are attached are cyclically linked to form a carbocycle or $R^{23}$ and $R^{24}$ are each independently selected from optionally substituted ($C_1$-$C_6$)alkyl and optionally substituted cycloalkyl; and $R^{25}$-$R^{26}$, $R^{40a}$ and $R^{40b}$ are each H.

Clause 19. The compound of anyone of clauses 14-18, wherein the A ring is selected from:

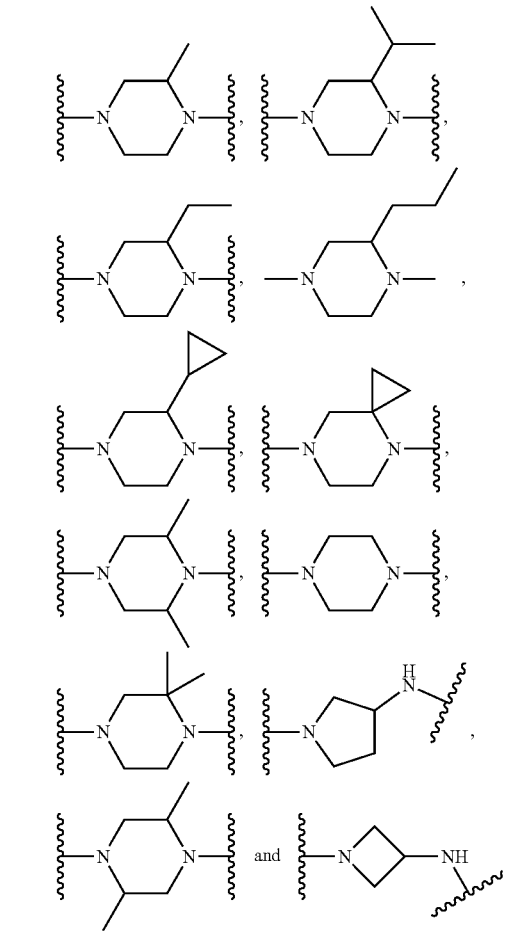

Clause 20. The compound of any one of clauses 12-19, wherein $R^{16}$ is:

—$(R^{110})_n R^{210}$ wherein:

each $R^{110}$ is independently selected from optionally substituted ($C_1$-$C_6$)alkyl,

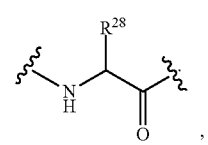

—$C(O)(R^{110a})n^1$, —$C(O)O(R^{110b})n^2$, —$S(O)(R^{110c})n^3$, —$SO_2(R^{110d})n^4$, and —$C(O)NR^{27}(R^{110e})n^5$; where $R^{110a}$-$R^{110e}$ are each independently optionally substituted ($C_1$-$C_6$)alkyl,

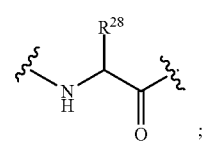

$R^{27}$-$R^{28}$ are each independently selected from H and optionally substituted ($C_1$-$C_6$)alkyl; and n-$n^5$ are each independently 0 to 3; and $R^{210}$ is selected from optionally substituted aryl, optionally substituted heteroaryl, optionally substituted carbocycle and optionally substituted heterocycle.

Clause 21. The compound of clause 20, wherein:

$R^{110}$ is selected from —C(O)—, —C(O)O—, —C(O)NH—, —S(O)—, and —SO$_2$—; and $R^{210}$ is selected from optionally substituted aryl and optionally substituted heteroaryl.

Clause 22. The compound of clause 20 or 21, wherein $R^{210}$ is selected from:

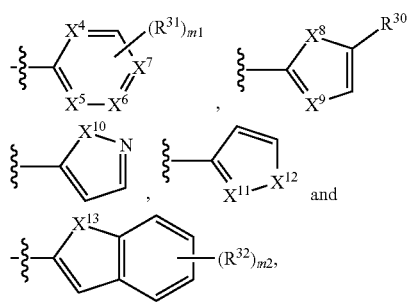

wherein:

$X^4$-$X^7$, $X^9$, and $X^{11}$ are each independently selected from CH, $CR^{31}$, S, O, and N;

$X^8$, $X^{10}$, $X^{12}$ and $X^{13}$ are each independently selected from S, O, and $NR^{29}$;

$R^{29}$ is selected from H and optionally substituted ($C_1$-$C_6$) alkyl;

$R^{30}$-$R^{32}$ are each independently selected from H, halogen, OH, $NO_2$, $OCF_3$, $CF_3$, optionally substituted amino, optionally substituted ($C_1$-$C_6$)alkyl, optionally substituted ($C_1$-$C_6$) alkoxy, optionally substituted cycloalkyl, optionally substituted aryl, optionally substituted heteroaryl, and optionally substituted heterocycle; and $m^1$-$m^2$ are each independently 0 to 5.

Clause 23. The compound of clause 12, wherein any of $R^4$-$R^{4d}$ is selected from:

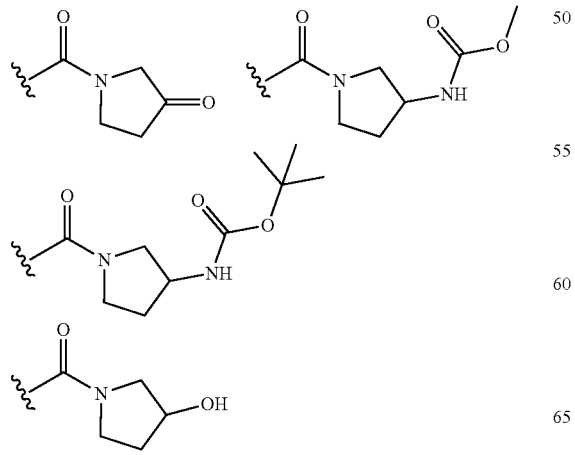

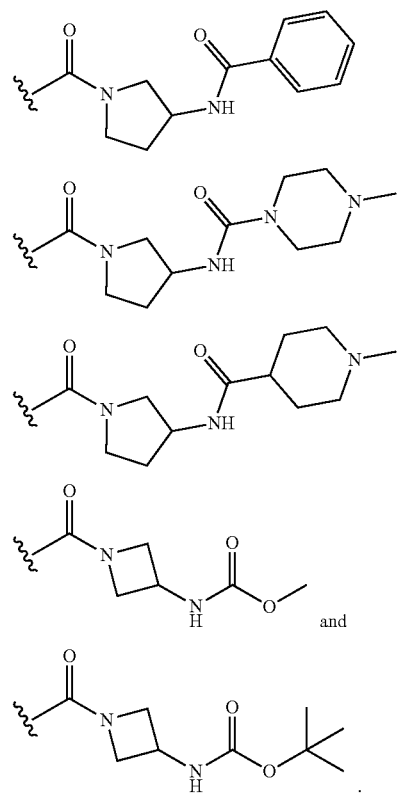

Clause 24. The compound of cause 12, wherein any of $R^4$-$R^{4d}$ is selected from:

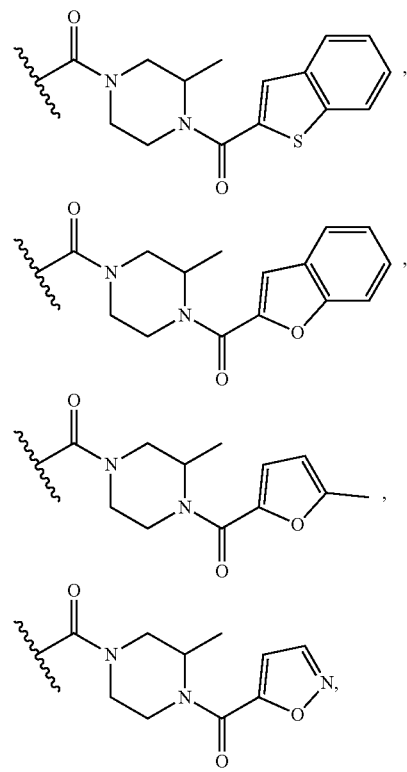

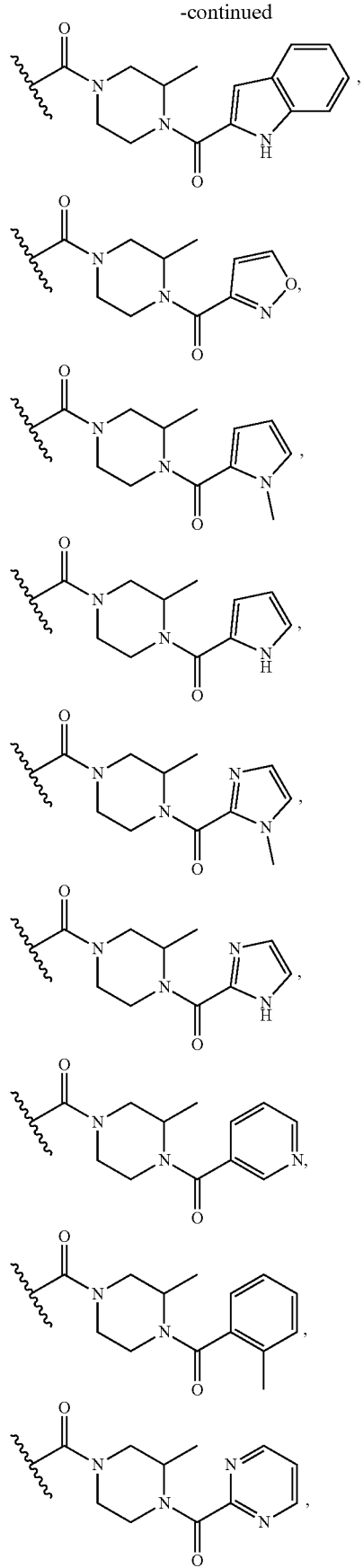
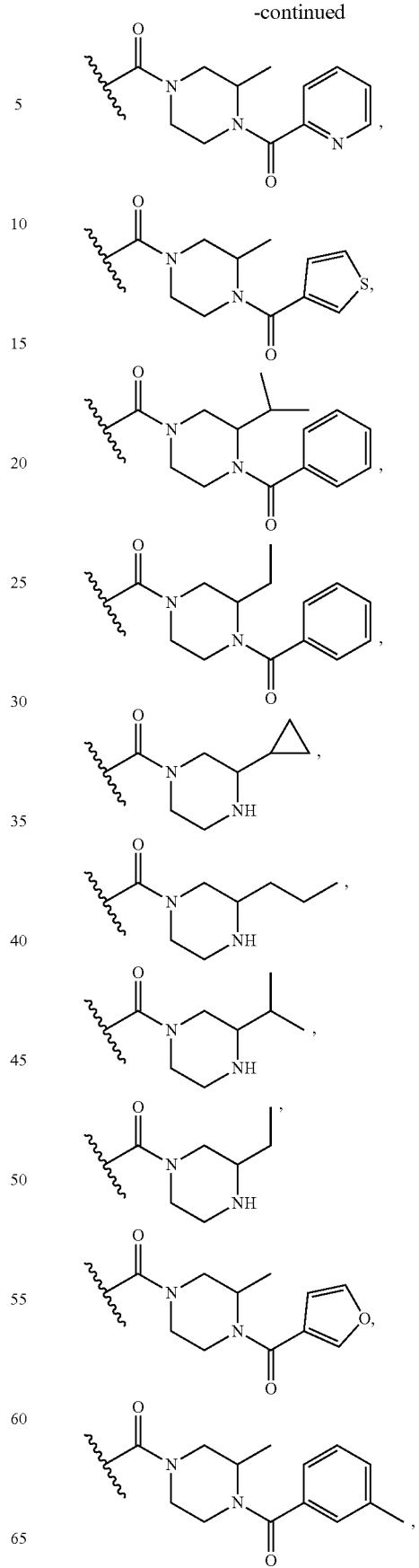

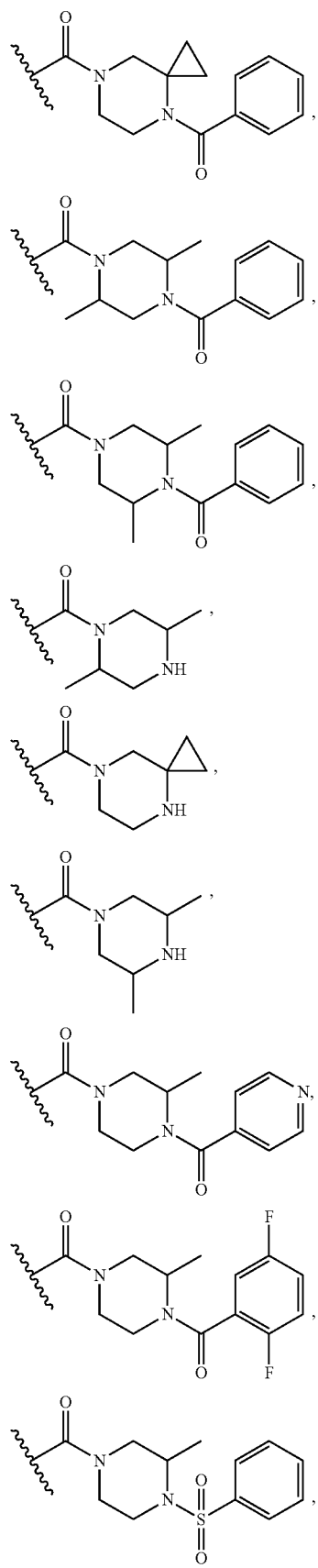
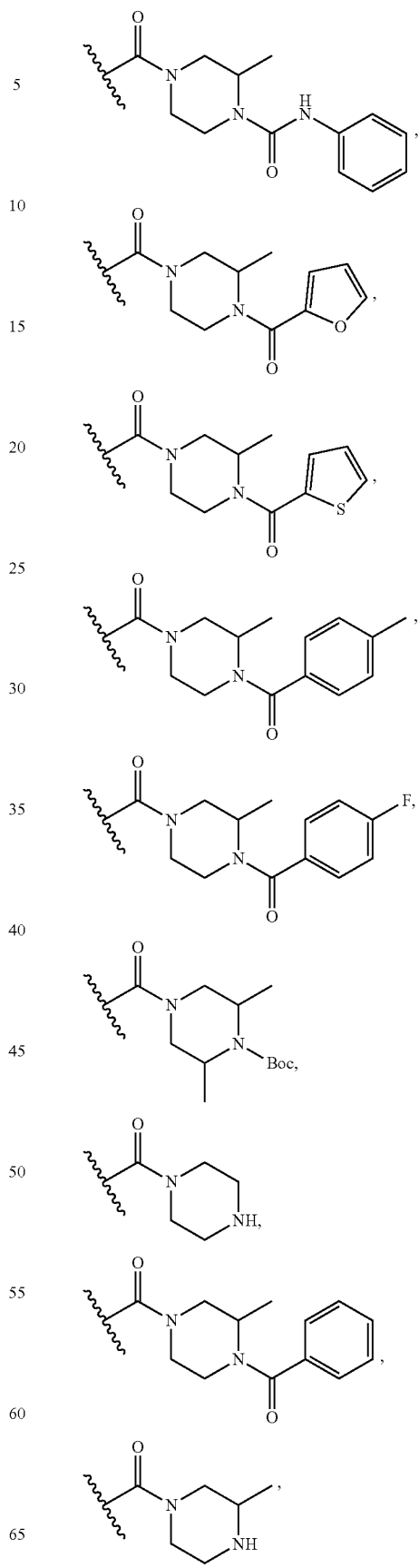

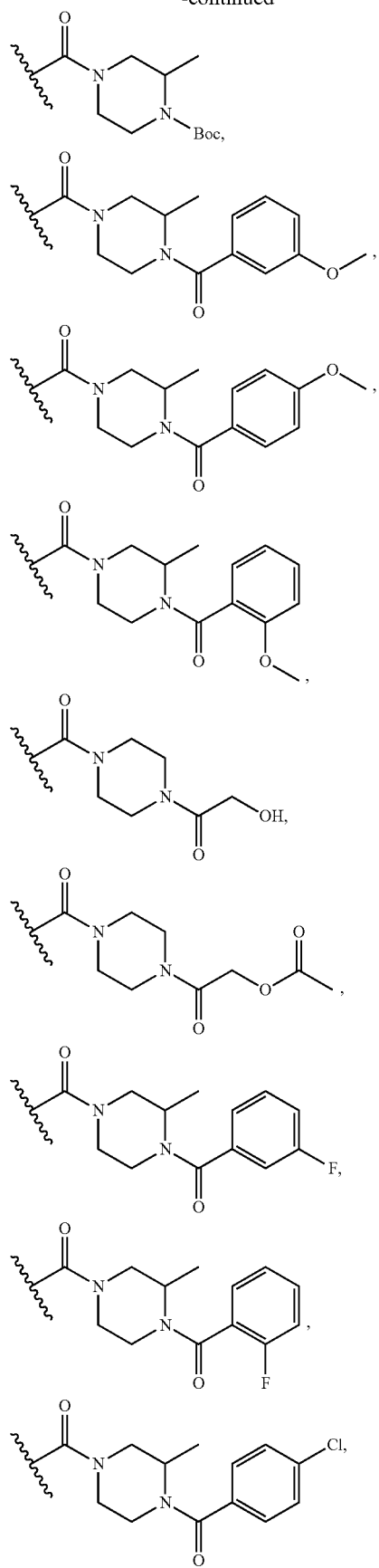
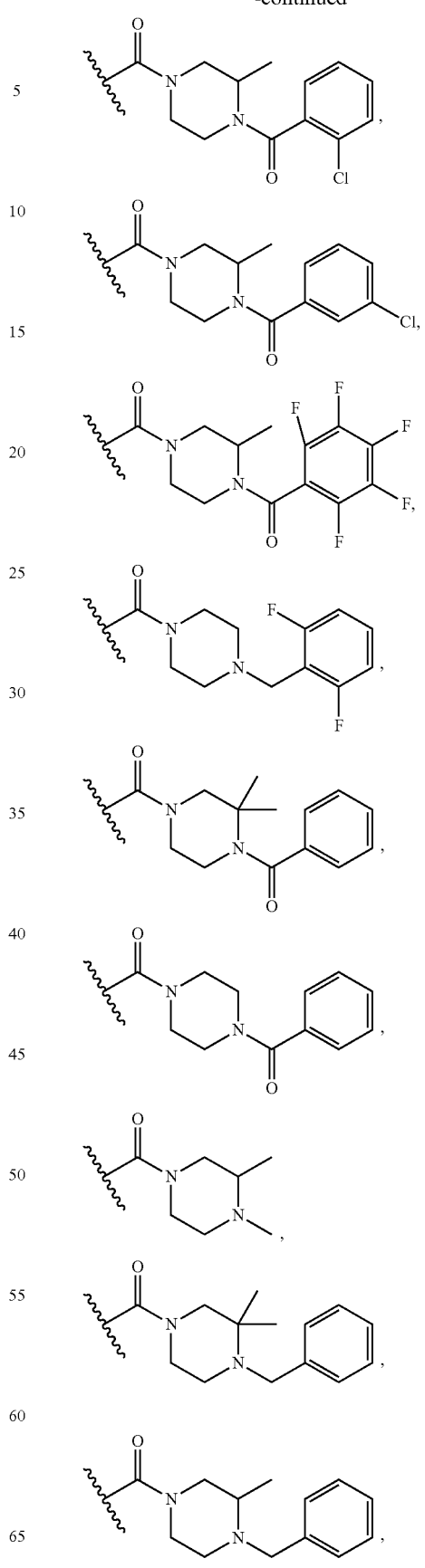

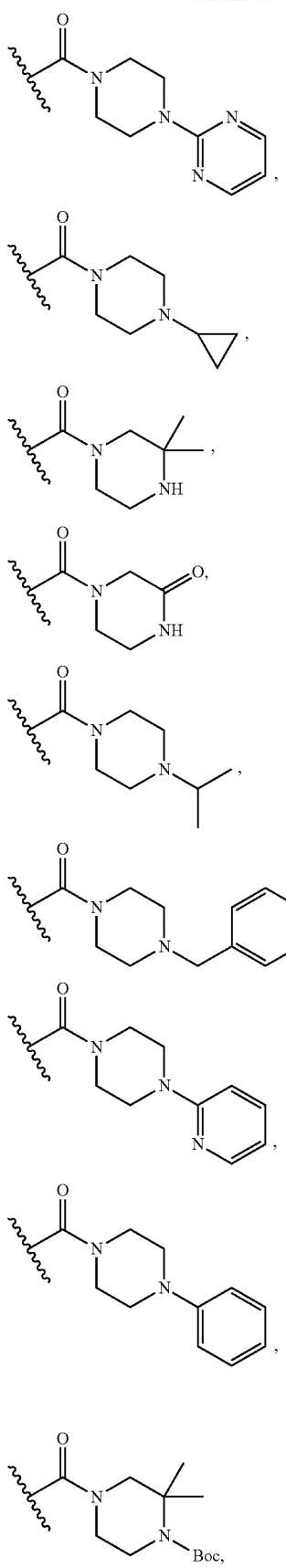
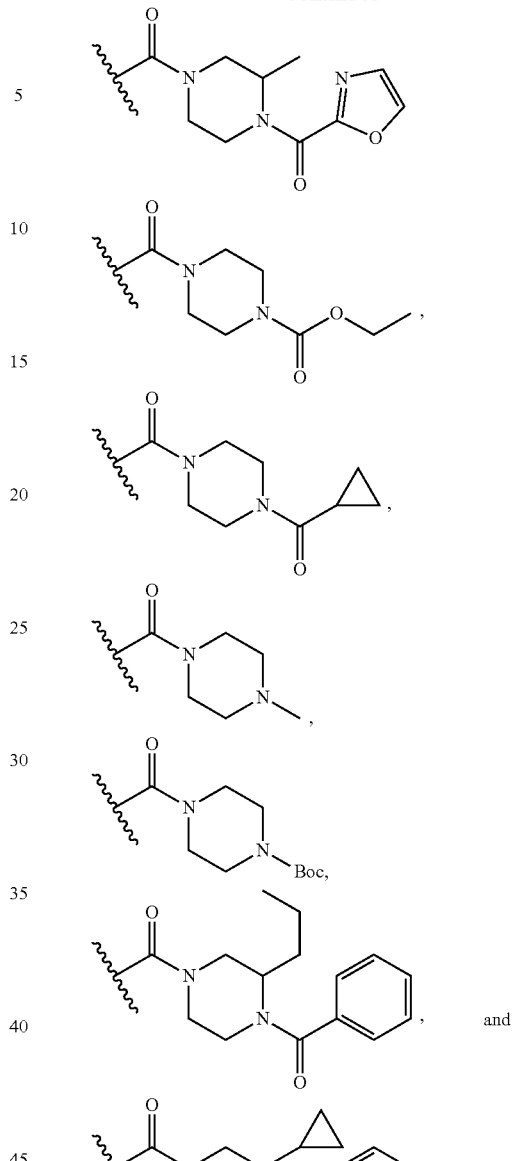
Clause 25. The compound of clause 10, wherein $R^5$ is H or Me, and $R^6$ is selected from:
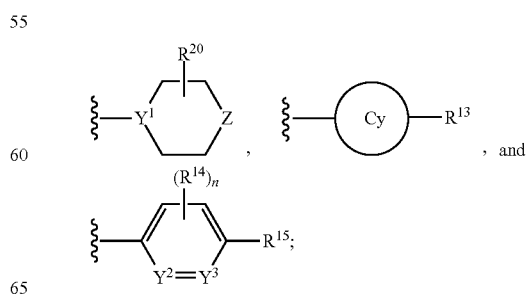

wherein:

$Y^1$, $Y^2$, and $Y^3$ are independently selected from $CR^{14}$ and N;

Z is selected from O, S, $CHR^{11}$, and $NR^{12}$;

n is 0 to 4;

$R^{11}$ is selected from H, $NH_2$, CN, $CH_2NH_2$, $NO_2$, halogen, $OR^{2a}$, $C(O)R^{2b}$, $CO_2R^{2c}$, $C(O)NR^5R^6$, optionally substituted amino, optionally substituted ($C_1$-$C_5$)alkyl, and optionally substituted ($C_1$-$C_5$)alkoxy, and optionally substituted heterocycle;

$R^{12}$ is selected from H, $NH_2$, halogen, $C(O)R^{2d}$, $CO_2R^{2e}$, $C(O)NR^5R^6$, and optionally substituted ($C_1$-$C_5$)alkyl;

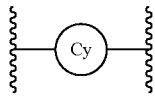

is selected from optionally substituted ($C_1$-$C_6$)alkyl-cycloalkyl, optionally substituted heterocycloalkyl, optionally substituted monocyclic or bicyclic ($C_4$-$C_{10}$)carbocycle, and optionally substituted monocyclic or bicyclic ($C_4$-$C_{10}$)heterocycle;

$R^{13}$ is selected from H, $NH_2$, CN, $CH_2NH_2$, $NO_2$, halogen, $OR^{2f}$, $C(O)R^{2g}$, $CO_2R^{2h}$, $C(O)NR^5R^6$, $NR^5R^6$, NHC$(O)R^2$, optionally substituted ($C_1$-$C_5$)alkyl, and optionally substituted ($C_1$-$C_5$)alkoxy, and optionally substituted heterocycle;

$R^{14}$ is selected from H, OH, $NH_2$, CN, $CF_3$, $OCF_3$, $CH_2NH_2$, halogen, $CO_2R^2$, $C(O)NR^5R^6$, optionally substituted ($C_1$-$C_5$)alkyl, optionally substituted ($C_1$-$C_5$)alkoxy, optionally substituted cycloalkyl, optionally substituted heterocycloalkyl, optionally substituted carbocycle, and optionally substituted heterocycle;

$R^{15}$ is selected from H, halogen, $NHC(O)R^{2i}$, $OR^{2j}$, $C(O)R^{2k}$, $OC(O)R^{2l}$ $CO_2R^{2m}$, $C(O)NR^5R^6$, $NR^5R^6$ optionally substituted ($C_1$-$C_5$)alkyl, optionally substituted ($C_1$-$C_5$)alkoxy, optionally substituted cycloalkyl, and optionally substituted heterocycle;

$R^{20}$ is selected from H, halogen, optionally substituted ($C_1$-$C_5$)alkyl, optionally substituted ($C_1$-$C_5$)alkoxy, optionally substituted carbocycle, and optionally substituted heterocycle; and $R^{2a}$-$R^{2m}$ are independently selected from H, optionally substituted ($C_1$-$C_{10}$) alkyl, optionally substituted cycloalkyl, optionally substituted aryl, optionally substituted heteroaryl, and optionally substituted heterocycle, and the optional substituents on alkyl, cycloalkyl, aryl, heteroaryl, and heterocycle are independently selected from: H, OH, $NH_2$, $NO_2$, $OCF_3$, $CF_3$, halogen, heterocycle, heteroaryl, optionally substituted amino, optionally substituted ($C_1$-$C_5$)alkyl, and optionally substituted ($C_1$-$C_5$)alkoxy.

Clause 26. The compound of clause 25, wherein $R^6$ is selected from:

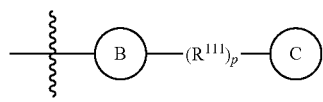

wherein:

ring B and ring C are each independently selected from optionally substituted aryl, optionally substituted heteroaryl, optionally substituted carbocycle and optionally substituted heterocycle;

each $R^{111}$ is independently selected from optionally substituted ($C_1$-$C_6$)alkyl,

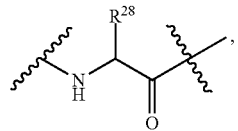

—$C(O)(R^{111a})p^1$, —$C(O)O(R^{111b})p^2$, —$S(O)(R^{111c})p^3$, —$SO_2(R^{111d})p^4$, and —$C(O)NR^{27}(R^{111e})p^5$; where $R^{111a}$-$R^{111e}$ are each independently optionally substituted ($C_1$-$C_6$) alkyl,

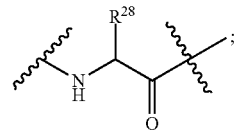

$R^{27}$-$R^{28}$ are each independently selected from H and optionally substituted ($C_1$-$C_6$)alkyl; and p-$p^5$ are each independently 0 to 3.

Clause 27. The compound of clause 26, wherein one or both of the B ring and the C ring are optionally substituted piperazine.

Clause 28. The compound of clause 26, wherein $R^6$ is

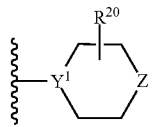

and is selected from:

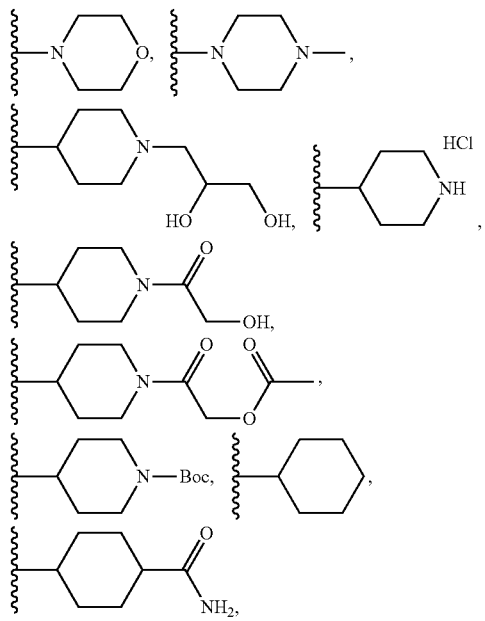

291
-continued
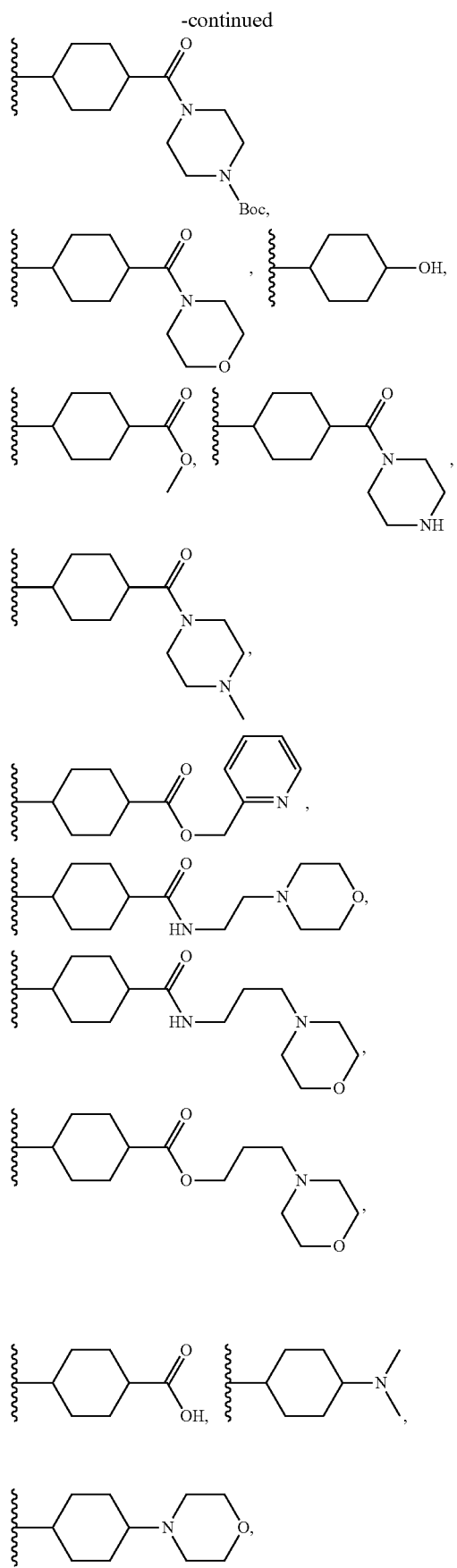
292
-continued
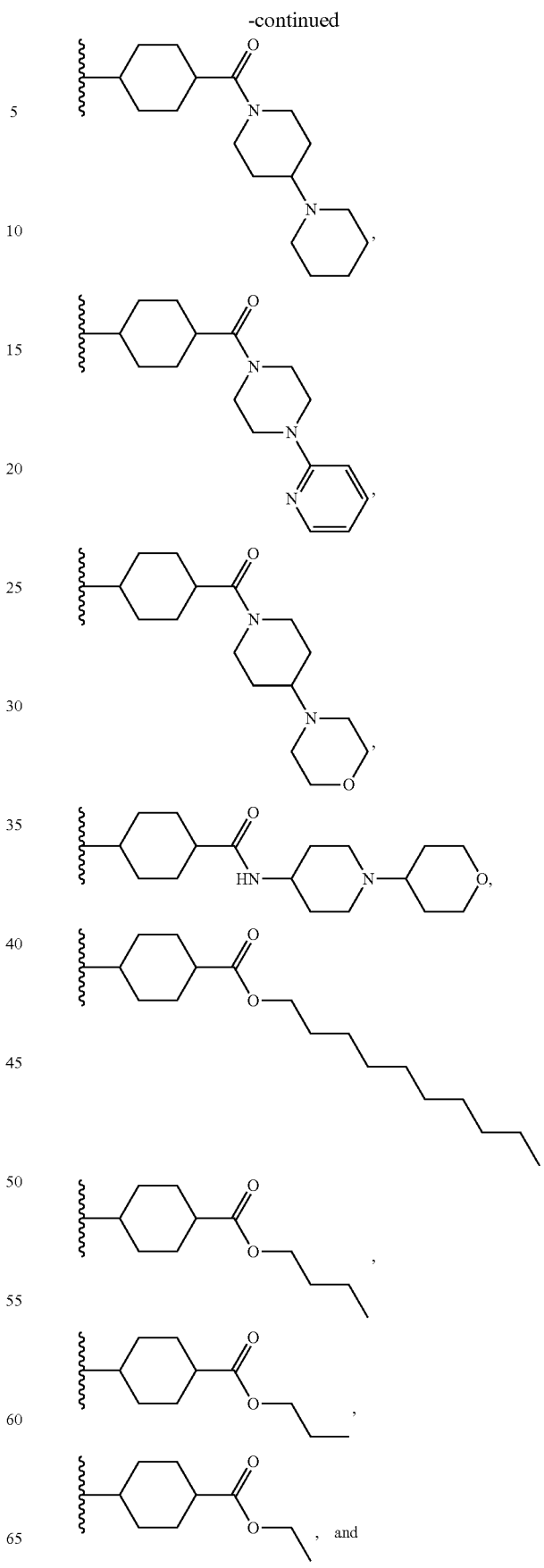

-continued

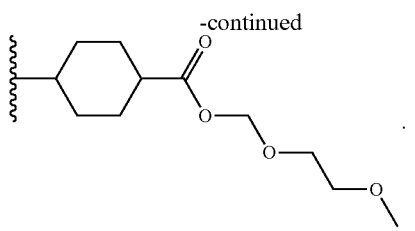

Clause 29. The compound of clause 25, wherein $R^6$ is

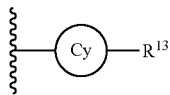

and is selected from:

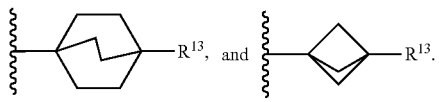

Clause 30. The compound of clause 29, wherein $R^{13}$ is —C(O)OR$^{41a}$, —NHC(O)R$^{41b}$, —C(O)NHR$^{41c}$, C(O)R$^{41d}$, C(O)NH$_2$, heterocycle (e.g., morpholine), wherein R$^{41a}$-R$^{41d}$ are independently selected from H, optionally substituted (C$_1$-C$_6$)alkyl, optionally substituted heterocycle (e.g., morpholine, piperidine, morpholine-3-one), and optionally substituted (C$_1$-C$_6$)alkyl-heterocycle.

Clause 31. The compound of clause 29 or 30, wherein $R^{13}$ is selected from:

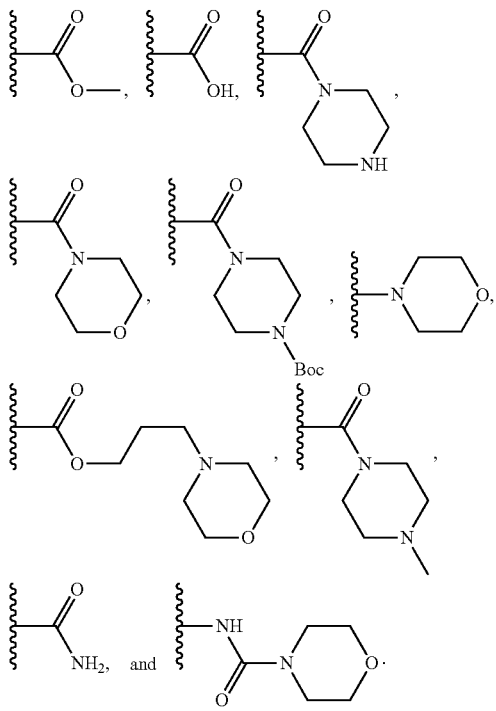

Clause 32. The compound of clause 25, wherein $R^6$ is

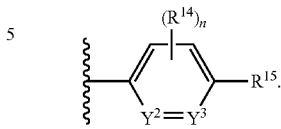

Clause 33. The compound of clause 32, wherein $Y^2$ and $Y^3$ are each CR$^{14}$.

Clause 34. The compound of clause 32 or 33, wherein:

each R$^{14}$ is independently selected from H, OH, NH$_2$, CN, CF$_3$, OCF$_3$, CH$_2$NH$_2$, halogen, —C(O)R$^{42f}$, —OC(O)R$^{42g}$, optionally substituted (C$_1$-C$_5$)alkyl, and optionally substituted (C$_1$-C$_5$)alkoxy; and R$^{15}$ is selected from H, halogen, —OC(O)R$^{42a}$, —C(O)R$^{42b}$, —C(O)NHR$^{42c}$, R$^{42d}$ or —OR$^{42e}$, wherein R$^{42a}$ to R$^{42g}$ are independently selected from —OH, optionally substituted amino, optionally substituted (C$_1$-C$_6$)alkyl, optionally substituted cycloalkyl, optionally substituted (C$_1$-C$_{10}$)alkoxy, optionally substituted heterocycle, optionally substituted —O—(C$_1$-C$_6$)alkyl-heterocycle, and amino acid.

Clause 35. The compound of anyone of clauses 32 to 34, wherein $R^6$ is selected from:

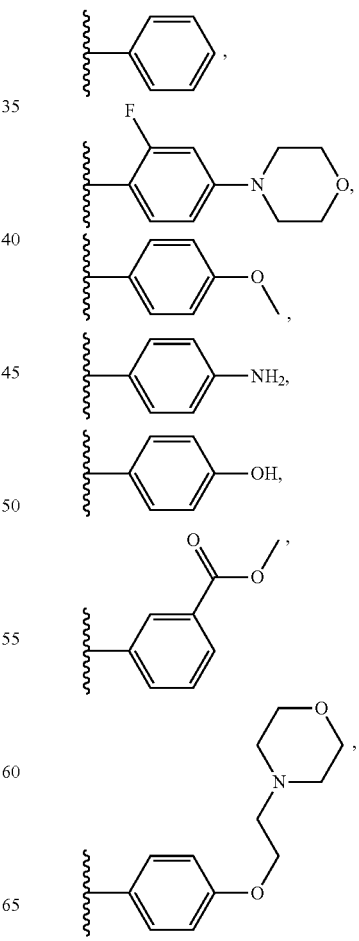

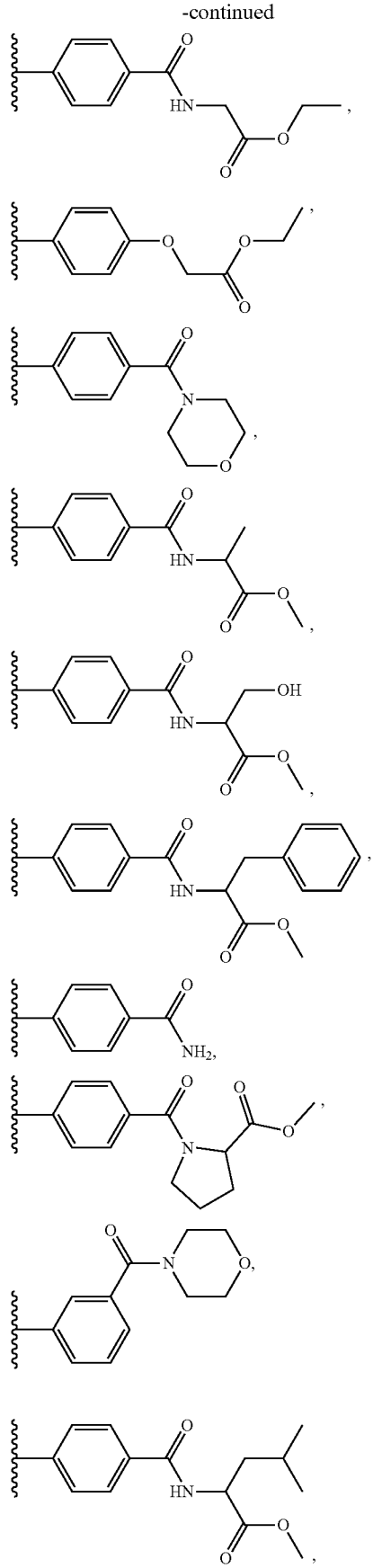

297
-continued
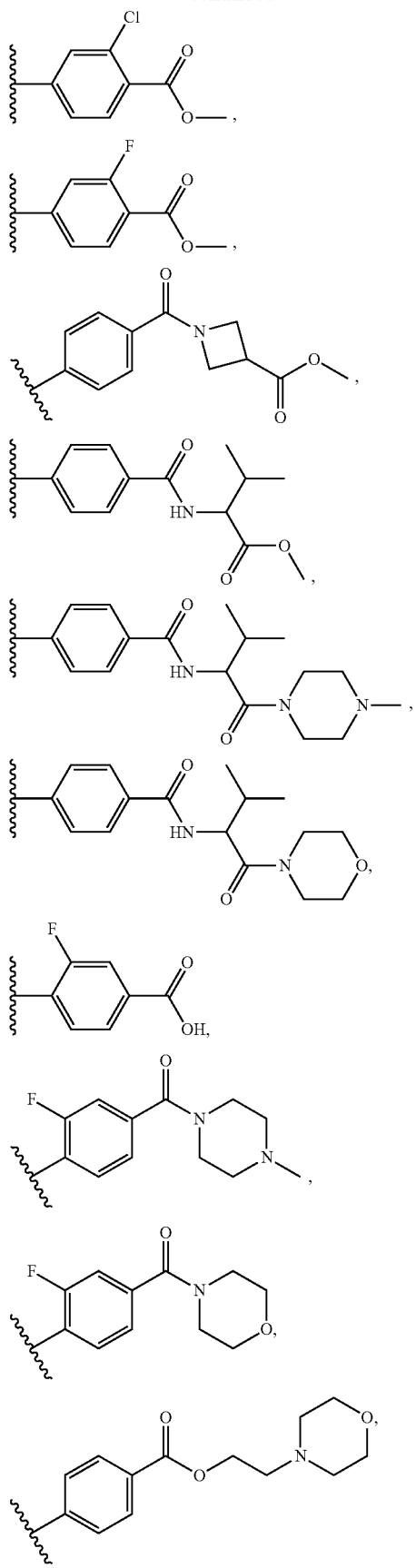
298
-continued
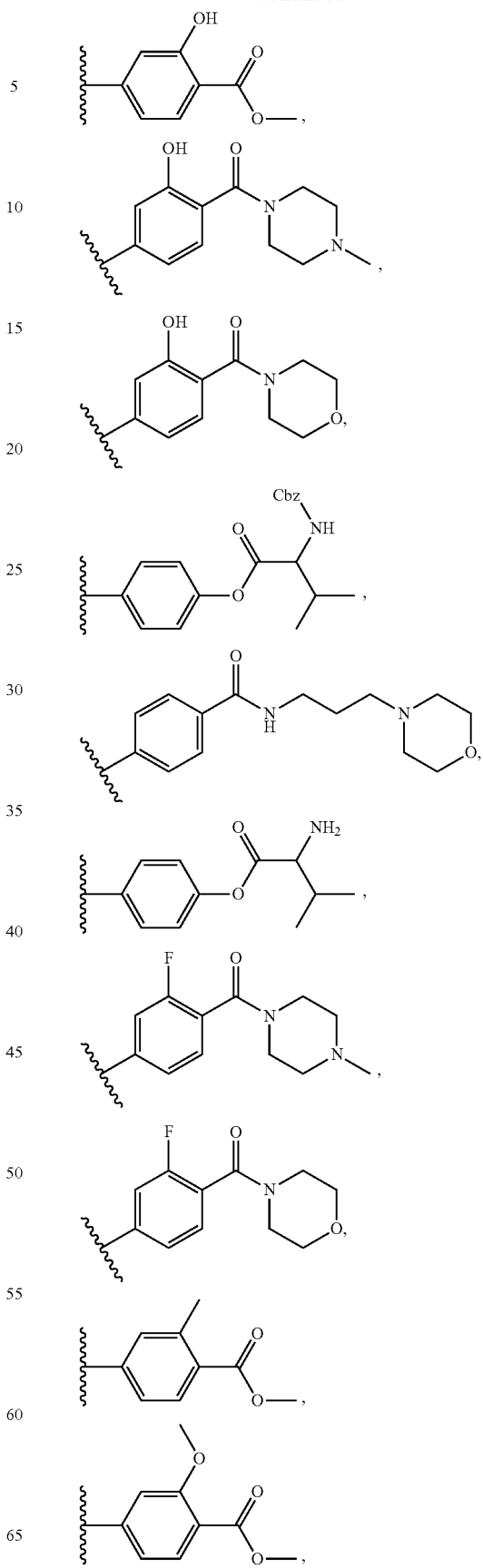

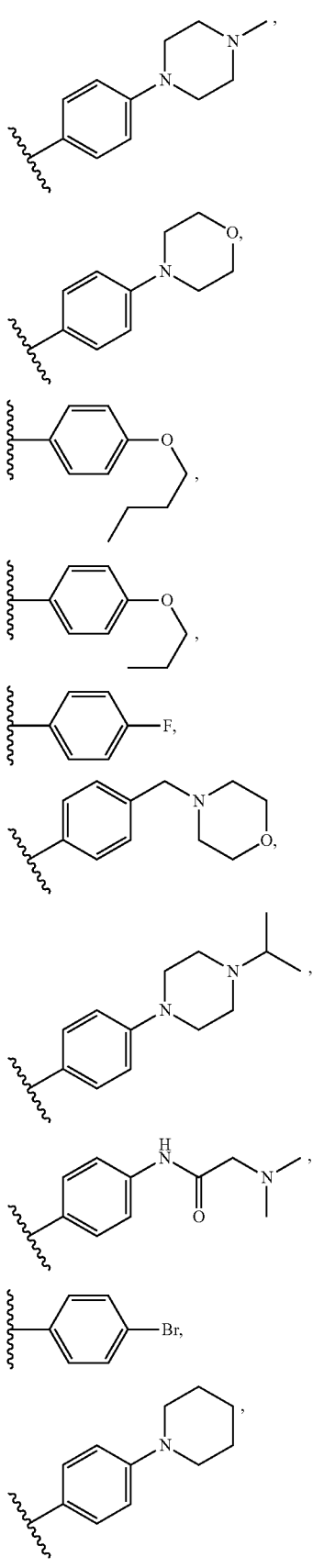
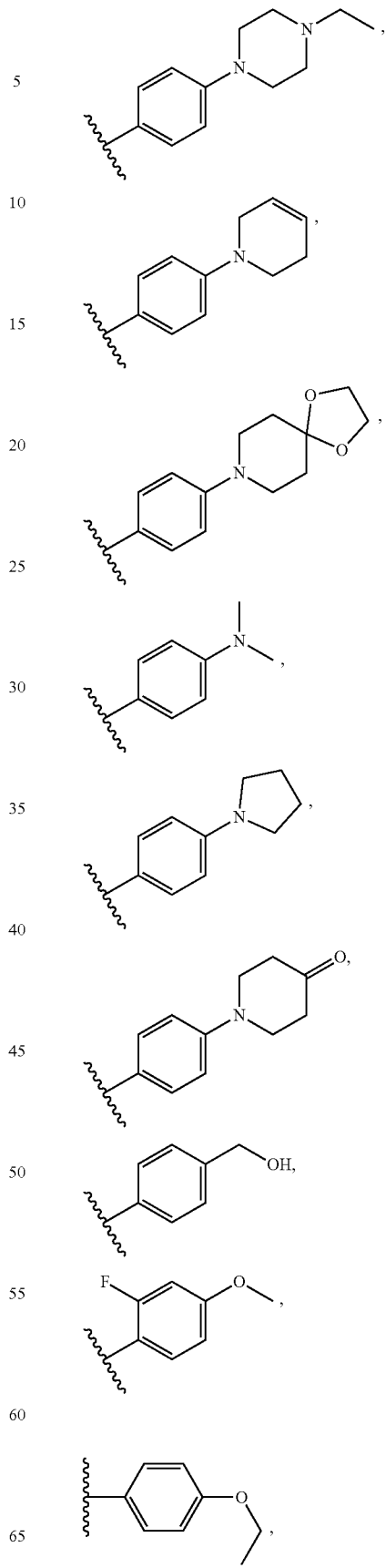

301
-continued
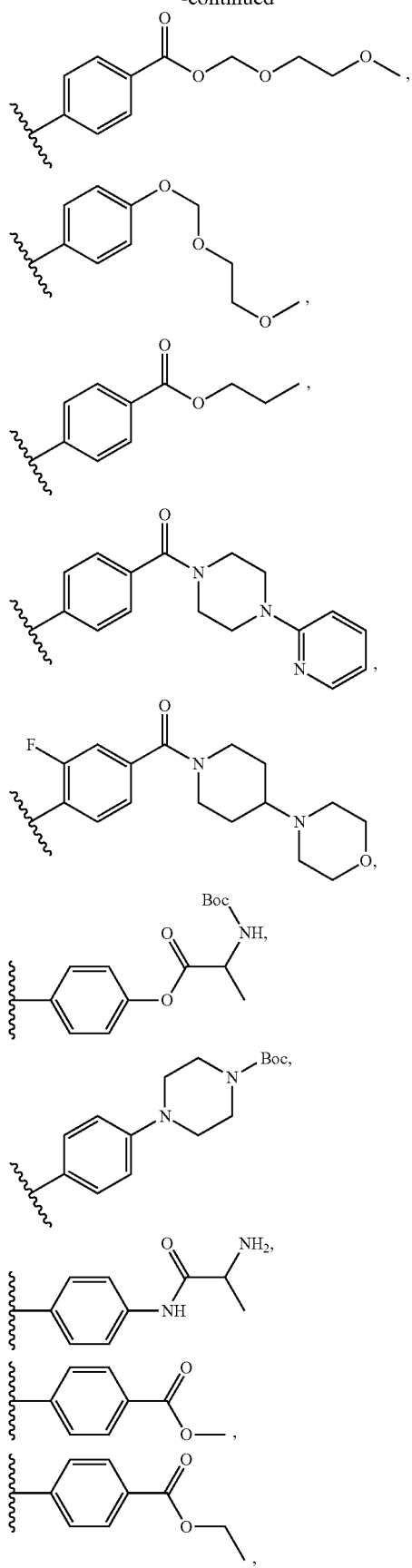
302
-continued
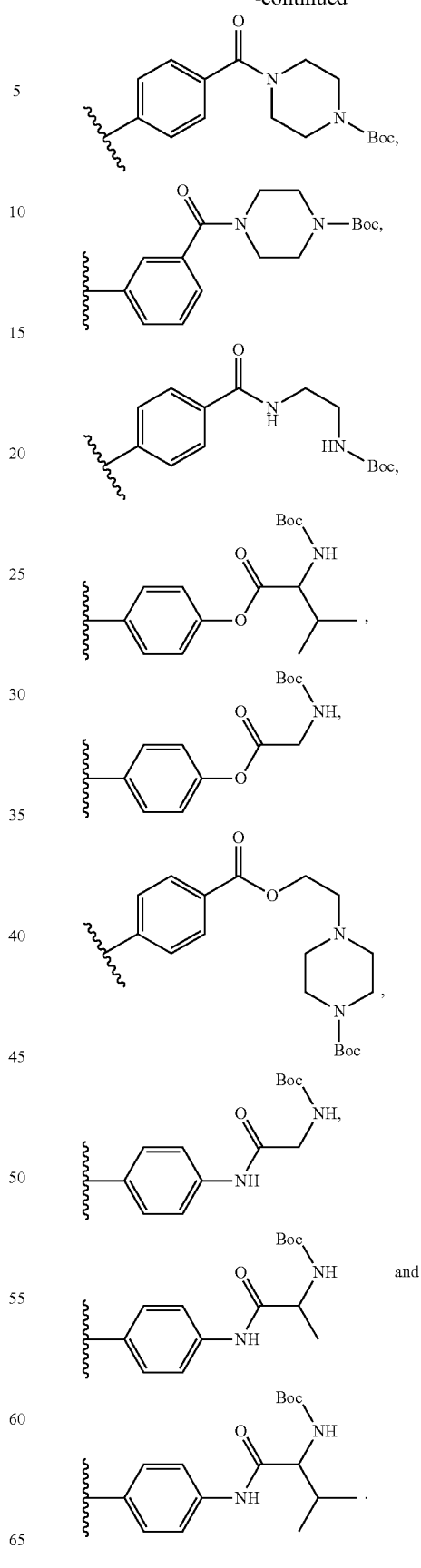

Clause 36. The compound of clause 25, wherein $R^6$ is
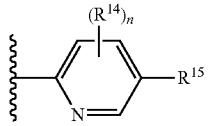
and n is 0 to 3.
Clause 37. The compound of clause 36, wherein $R^6$ is selected from:
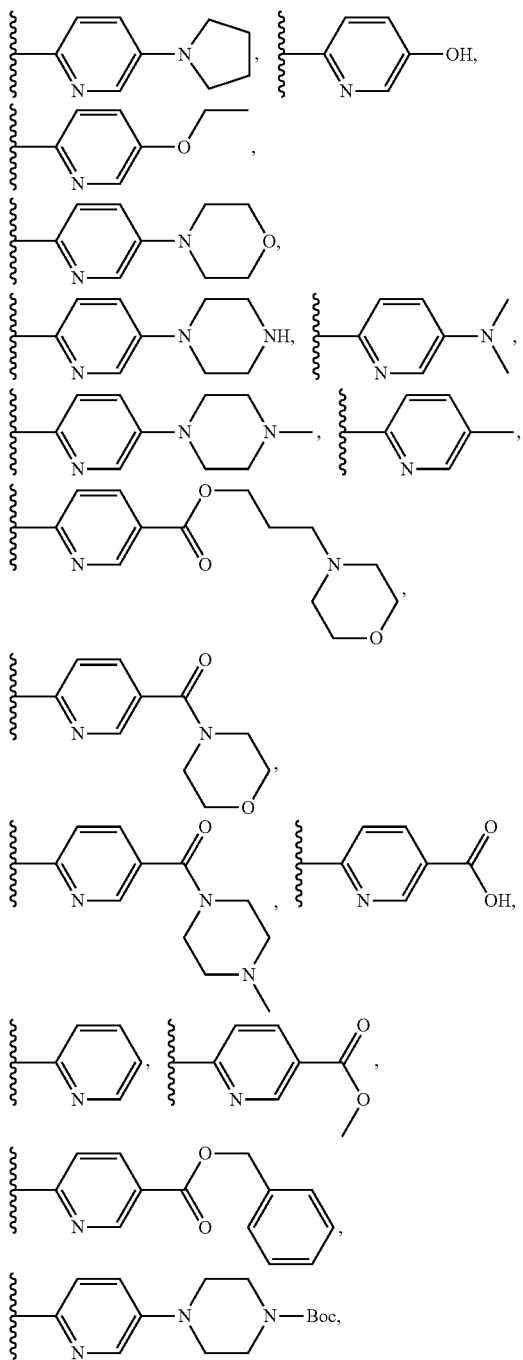
Clause 38. The compound of clause 25, wherein $R^6$ is
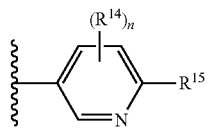
and n is 0 to 3.
Clause 39. The compound of clause 38, wherein $R^6$ is selected from:
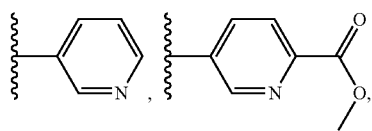
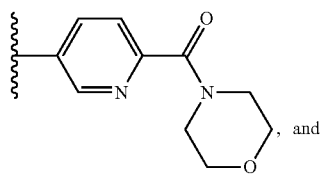
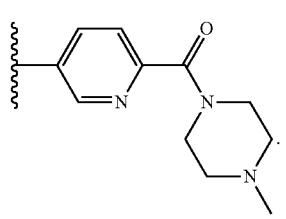
Clause 40. The compound of any one of clauses 1 to 10, wherein $R^5$ is H or Me, and $R^6$ is selected from:
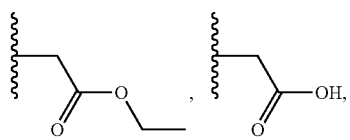

-continued

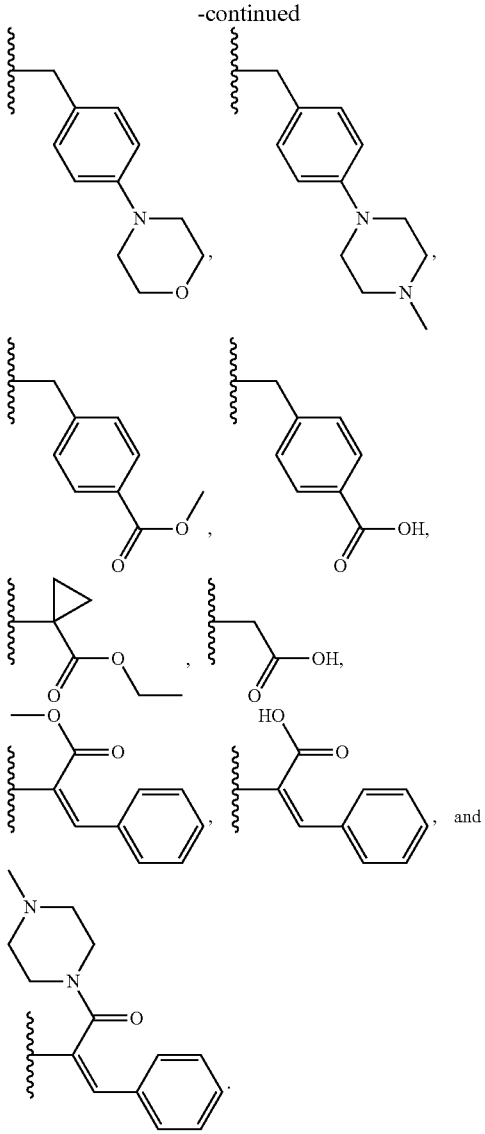

Clause 41. The compound of anyone of clauses 1-40, wherein the compound is of formula (Ie):

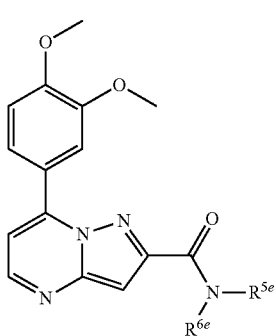

wherein:

$R^{5e}$ and $R^{6e}$ are independently selected from H, optionally substituted $(C_1-C_{10})$alkyl, optionally substituted $(C_1-C_{10})$ alkenyl, optionally substituted aryl, optionally substituted heteroaryl, optionally substituted arylalkyl, optionally substituted cycloalkyl, optionally substituted heterocycloalkyl, optionally substituted monocyclic or bicyclic carbocycle, and optionally substituted monocyclic or bicyclic heterocycle;

or $R^{5e}$ and $R^{6e}$ together with the nitrogen atom to which they are attached are cyclically linked to form an optionally substituted monocyclic or bicyclic heterocycle.

Clause 42. The compound of any one of clause 1 to 9, wherein any of $R^4$-$R^{4d}$ is

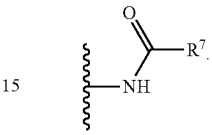

Clause 43. The compound of clause 42, wherein $R^7$ is selected from optionally substituted N-anilino, optionally substituted phenyl and optionally substituted bicyclic carbocycle.

Clause 44. The compound of clause 42, wherein $R^7$ is selected from:

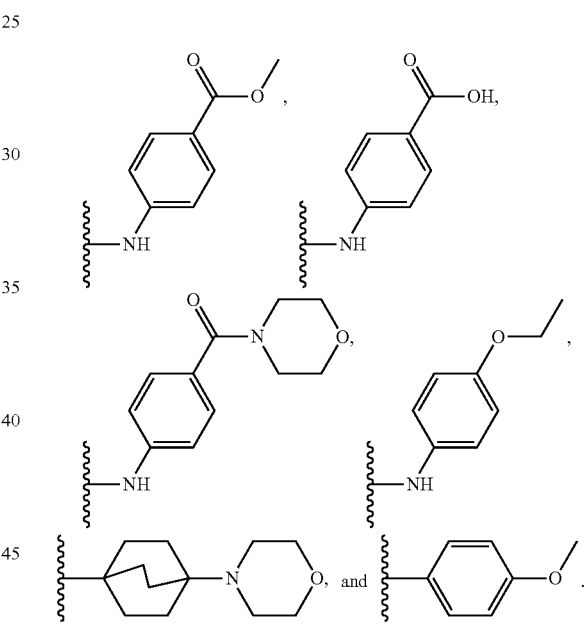

Clause 45. The compound of anyone of clauses 1 to 44, wherein the compound is of Table 1.

Clause 46. The compound of anyone of clauses 1 to 44, wherein the compound is not a compound of Table 2.

Clause 47. The compound of any one of clauses 1 to 46, wherein:

when $R^1$ and $R^9$ are H, $R^4$ is

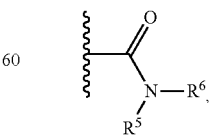

$R^5$ is H, and $R^6$ is optionally substituted aryl; then $R^2$ is not 4-fluoro-phenyl, p-toluene, 3,5-dichloro-phenyl, or phenyl; or when R¹ and R⁹ are H, and R⁴ is any one of the following:
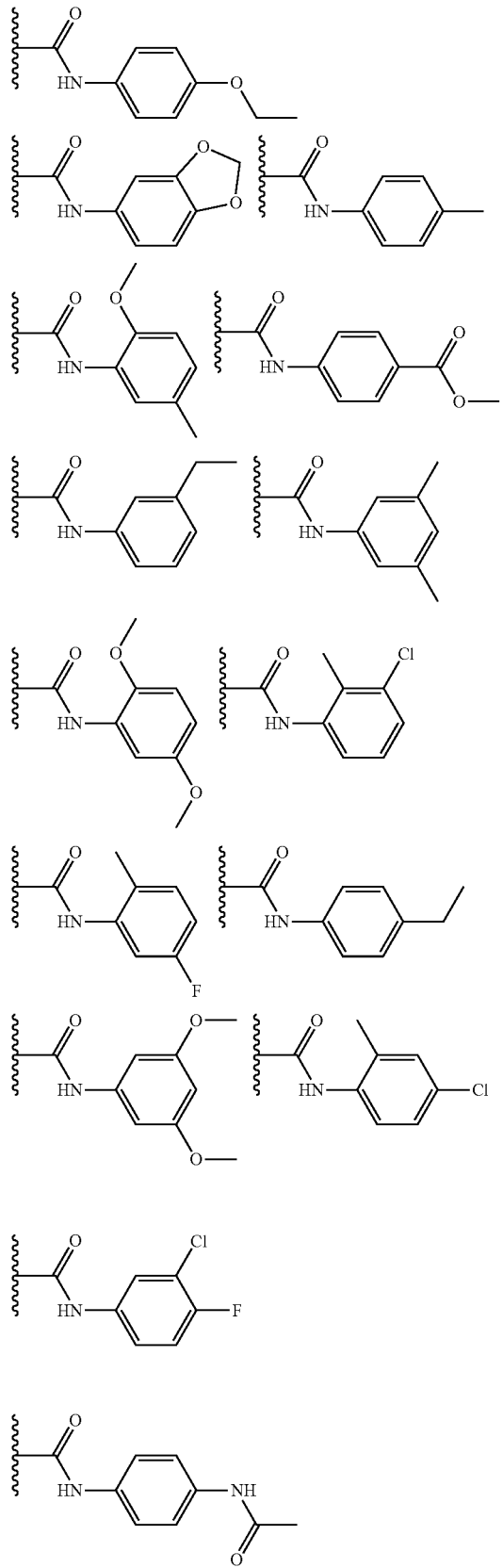
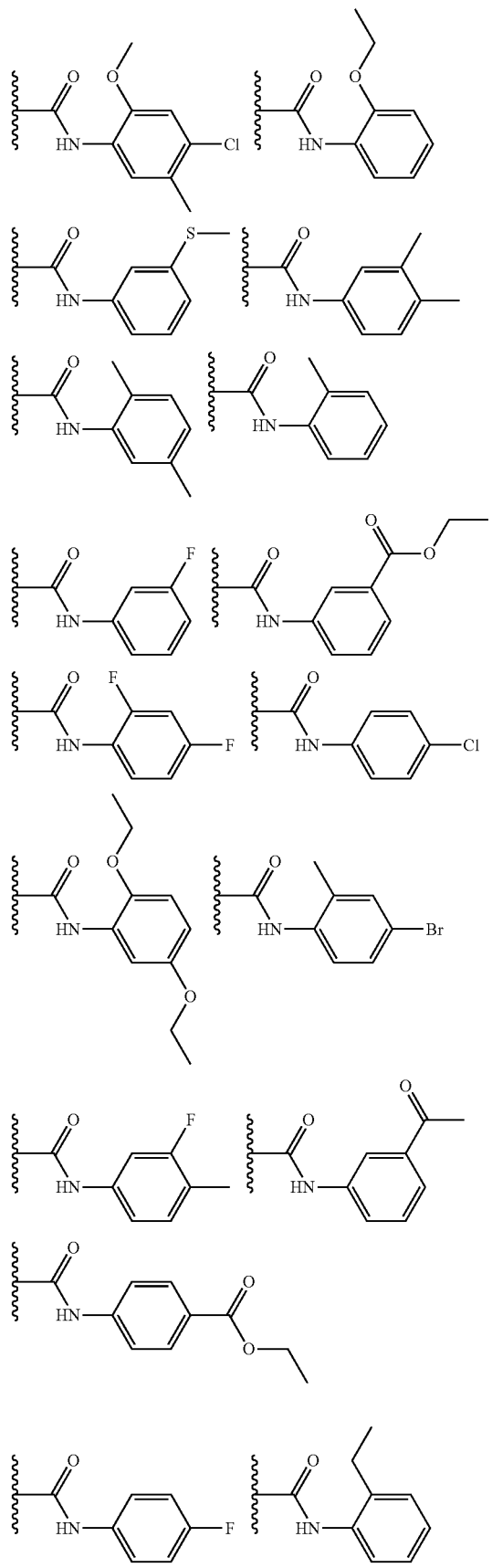

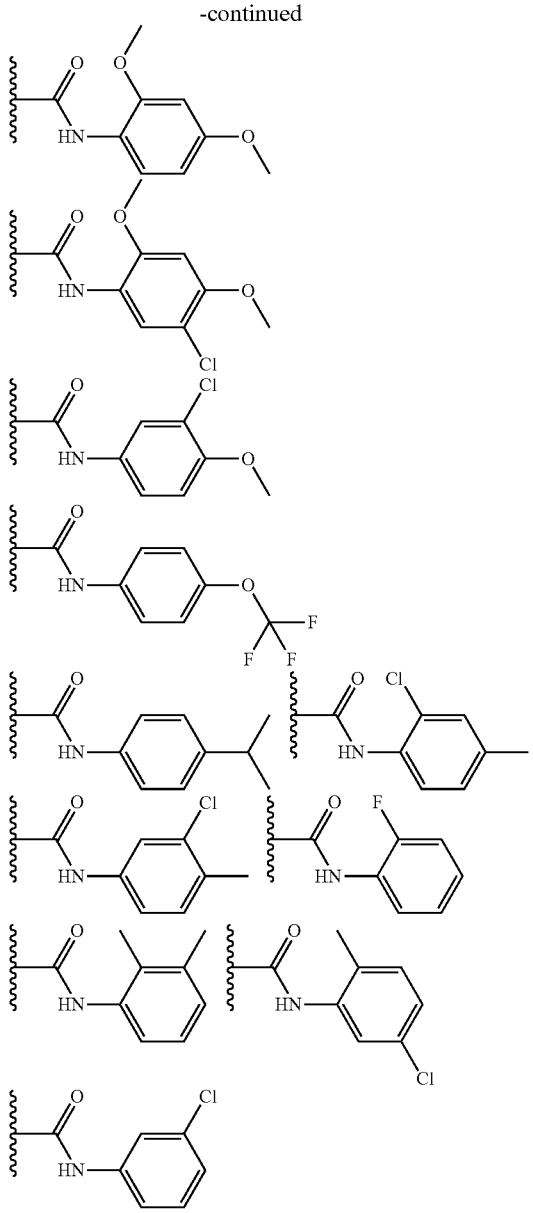

then R² is not 3,4-dimethoxy-phenyl.

Clause 48. A pharmaceutical composition comprising:
a therapeutically effective amount of a compound of formula (Ia), or a pharmaceutically acceptable salt, a solvate, a hydrate, a prodrug, or a stereoisomer thereof, according to clause 1; and
a pharmaceutically acceptable excipient.

Clause 49. The pharmaceutical composition of clause 48, wherein the compound of formula (Ia) is a compound or a pharmaceutically acceptable salt, a solvate, a hydrate, a prodrug, or a stereoisomer thereof according to any one of clauses 2 to 47.

Clause 50. The pharmaceutical composition of anyone of clauses 48 to 49, wherein the composition is an ophthalmic composition, and comprises a physiologically compatible ophthalmic vehicle.

Clause 51. The pharmaceutical composition of anyone of clauses 48 to 50, wherein the composition is an aqueous solution.

Clause 52. A compound for use in modulating cystic fibrosis transmembrane conductance regulator (CFTR), wherein the compound is according to any one of clauses 1 to 47.

Clause 53. A pharmaceutical composition for use in modulating CFTR, wherein the pharmaceutical composition is according to any one of clauses 48 to 51.

Clause 54. A compound for use in inhibiting phosphodiesterase 4 (PDE4), wherein the compound is according to any one of clauses 1 to 47.

Clause 55. A pharmaceutical composition for use in inhibiting PDE4, wherein the pharmaceutical composition is according to any one of clauses 48 to 51.

Clause 56. A method of modulating CFTR, the method comprising contacting a sample or biological system with an effective amount of a compound to modulate the CFTR, wherein the compound is of formula (Ia), or a pharmaceutically acceptable salt, a solvate, a hydrate, a prodrug, or a stereoisomer thereof, according to clause 1.

Clause 57. A method of inhibiting PDE4, the method comprising contacting a sample or biological system with an effective amount of a PDE inhibiting compound to inhibit PDE4, wherein the compound is of formula (Ia), or a pharmaceutically acceptable salt, a solvate, a hydrate, a prodrug, or a stereoisomer thereof, according to clause 1.

Clause 58. The method of clause 56 or 57, wherein the sample is in vitro.

Clause 59. The method of clause 56 or 57, wherein the biological system is in vivo.

Clause 60. A method of treating dry eye disease, the method comprising administering to an eye of a subject a therapeutically effective amount of a compound according to any one of clauses 1 to 47 or a therapeutically effective amount of an ophthalmic composition according to clause 50.

Clause 61. The method of clause 60, further comprising identifying a subject suffering from dry eye disease.

Clause 62. The method of clause 60, further comprising identifying an underlying disease or condition associated with the dry eye disease.

Clause 63. The method of clause 60, wherein the dry eye disease is caused by one or more disease or condition of the group consisting of keratoconjunctivitis sicca, age-related dry eye, Stevens-Johnson syndrome, Sjogren's syndrome, ocular cicatrical pemphigoid, corneal injury, infection, Riley-Day syndrome, congenital alacrima, nutritional disorders or deficiencies, pharmacologic side effects, contact lens intolerance, eye stress resulting in glandular and tissue destruction, autoimmune disorders, immuno-deficient disorders, comatose patients who are unable to blink, or environmental exposure to smog, smoke, excessively dry air, airborne particulates, lacrimal deficiency, lacrimal gland duct obstruction, Meibomian oil deficiency, a disorder of eyelid aperture, and ocular surface disease (OSD).

Clause 64. The method of clause 60, wherein said dry eye disease is caused by keratoconjunctivitis sicca, age-related dry eye, Stevens-Johnson syndrome, Sjogren's syndrome, ocular cicatrical pemphigoid, corneal injury, Riley-Day syndrome, or congenital alacrima.

Clause 65. The method of clause 60, wherein said dry eye disease is caused by nutritional disorders or deficiencies, contact lens intolerance, autoimmune disorders, immuno-deficient disorders, comatose patients who are unable to blink, or environmental exposure to smog, smoke, excessively dry air, or airborne particulates.

Clause 66. The method of any one of clauses 60 to 65, whereby one or more dry eye symptoms are reduced or alleviated in the subject after administration.

Clause 67. The method of clause 66, wherein the one or more dry eye symptoms are selected from dryness, burning, ocular itching, photophobia, foreign body sensation, and grittiness.

Clause 68. The method of any one of clauses 60 to 67, further comprising assessing restoration of the natural tear film in the eye after administration.

Clause 69. The method of any one of clauses 60 to 68, wherein the compound or the ophthalmic composition is topically administered to the eye.

Clause 70. A method of treating an inflammatory disease, comprising administering to a subject a therapeutically effective amount compound, wherein the compound is of formula (Ia), or a pharmaceutically acceptable salt, a solvate, a hydrate, a prodrug, or a stereoisomer thereof, according to clause 1.

Clause 71. The method of clause 70, wherein the subject has an inflammatory disease.

Clause 72. The method of clause 70 or 71, wherein the inflammatory disease is a chronic inflammatory disease.

Clause 73. The method of clause 70 or 71, wherein the inflammatory disease is an acute inflammatory disease.

Clause 74. The method of any one of clauses 70 to 73, wherein the inflammatory disease is selected from chronic obstructive pulmonary disease (COPD), asthma, inflammatory airway disease, psoriasis, psoriatic disorder, atopic dermatitis, inflammatory bowel disease (IBD), rheumatoid arthritis, ankylosing spondylitis, neuroinflammation, and conjunctivitis.

Clause 75. The method of any one of clauses 70 to 73, wherein the inflammatory disease is an inflammatory skin disease.

Clause 76. A method of treating a CFTR-related indication, comprising administering to a subject in need thereof a therapeutically effective amount of compound, wherein the compound is of formula (Ia), or a pharmaceutically acceptable salt, a solvate, a hydrate, a prodrug, or a stereoisomer thereof, according to clause 1.

Clause 77. The method of clause 76, wherein the CFTR-related indication is selected from chronic obstructive pulmonary disease (COPD), asthma, bronchitis, bronchiectasis, celiac disease, constipation, cholestatic liver disease, chronic rhinosinusitis, and hepatic impairment.

Clause 78. The method of any one of clauses 56 to 77, wherein the compound of formula (Ia) or a pharmaceutically acceptable salt, a solvate, a hydrate, a prodrug, or a stereoisomer thereof, is according to any one of clauses 1 to 47.

Clause 79. The method of clause 78, wherein the compound of formula (Ia) is a compound of Table 1 or Table 2, or a pharmaceutically acceptable salt, a solvate, a hydrate, a prodrug, or a stereoisomer thereof.

Clause 80. The method of clause 78, wherein the compound of formula (Ia) is a compound of Table 1, or a pharmaceutically acceptable salt, a solvate, a hydrate, a prodrug, or a stereoisomer thereof.

As described herein, the text refers to various embodiments of the present compounds, compositions, and methods. The various embodiments described are meant to provide a variety of illustrative examples and should not be construed as descriptions of alternative species.

Rather, it should be noted that the descriptions of various embodiments provided herein may be of overlapping scope. The embodiments discussed herein are merely illustrative and are not meant to limit the scope of the present technology.

6. EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

All experiments conformed to the ethical guidelines for investigation in conscious animals and in full compliance with the central Israeli animal care commission.

In the examples below, if an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
$Cs_2CO_3$=cesium carbonate
NaH=sodium hydride
o/n=overnight
HATU=1-[Bis(dimethylamino)methylene]-1H-1,2,3-trI zolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
DIEA=diisopropylethylamine
equiv.=equivalent
EtOAc or EA=ethyl acetate
EtOH=ethanol
EDCI=1-ethyl-3-(3-dimethylaminopropyl)carbodiimide
g=gram
h=hours
HCl=hydrochloric acid
HPLC=high-performance liquid chromatography
HOAc=acetic acid
HBTU=O-benzotriazole-N,N,N',N'-tetramethyluronium-hexafluorophosphate
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
ppm=parts per million
TFA=trifluoroacetic acid
TLC=thin layer chromatography SCOP=scopolamine TsOH=p-Toluenesulfonic acid UV=ultraviolet wt %=weight percent μM=micromolar General Synthetic Methods Final compounds were confirmed by HPLC/MS analysis and determined to be >90% pure by weight. $^1$H and $^{13}$C NMR spectra were recorded in CDCl$_3$ (residual internal standard CHCl$_3$=δ 7.26), DMSO-d$_6$ (residual internal standard CD$_3$SOCD$_2$H=δ 2.50), methanol-d$_4$ (residual internal standard CD$_2$HOD=δ 3.20), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Example 1—Synthesis of Common Intermediates

Method A—Synthesis of 7-substituted pyrazolo[1,5-a]pyrimidine-2-carboxylic acid (Formula II-a)

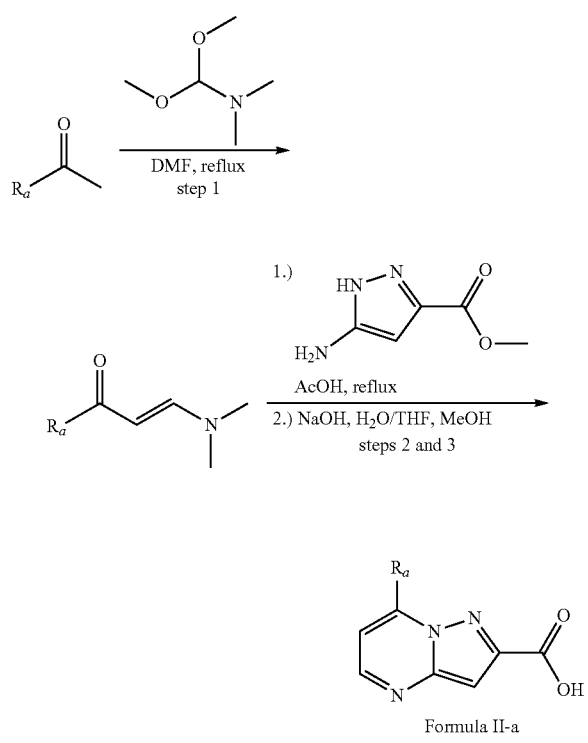

Formula II-a

Synthesis of 7-phenylpyrazolo[1,5-a]pyrimidine-2-carboxylic acid

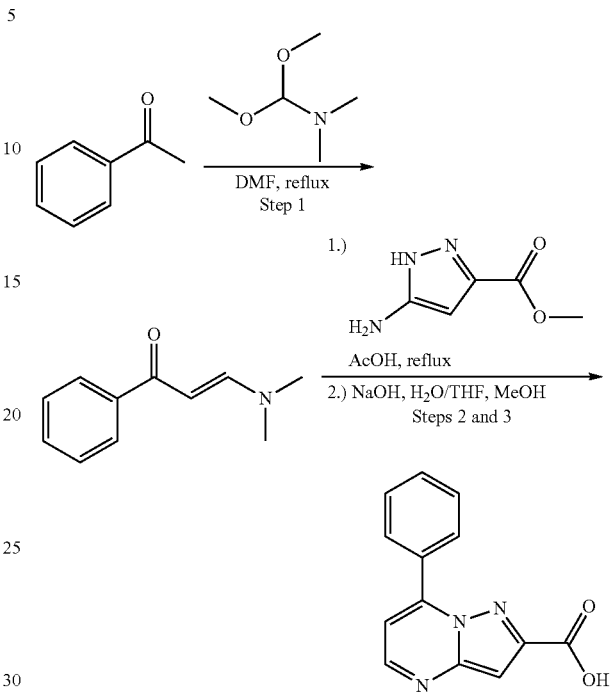

Step 1

Acetophenone (0.29 mL, 2.5 mmol) and DMF-DMA (1.33 mL, 10 mmol) were combined in DMF (2.5 mL) and heated to reflux for 17 hr. The reaction mixture was extracted by DCM and aq. NH$_4$Cl. The organic layer was dried over anhydrous MgSO$_4$ and concentrated. The mixture was extracted by EA and aq. NH$_4$Cl to give (E)-3-(dimethylamino)-1-phenylprop-2-en-1-one (193 mg, 43%) as a yellow solid. $^1$H NMR (400 MHz, DMSO-d$_6$) δ 7.94-7.85 (m, 2H), 7.72 (d, J=12.3 Hz, 1H), 7.55-7.38 (m, 3H), 5.83 (d, J=12.3 Hz, 1H), 3.15 (s, 3H), 2.91 (s, 3H).

Step 2

(E)-3-(dimethylamino)-1-phenylprop-2-en-1-one (190 mg, 1.08 mmol) and methyl 5-amino-1H-pyrazole-3-carboxylate (152 mg, 1.08 mmol) were dissolved in acetic acid (5.4 mL) and heated to reflux for 2.5 hr. The reaction mixture was extracted by DCM and aq. NaHCO$_3$. The organic layer was dried over anhydrous MgSO$_4$ and concentrated. The reaction mixture was purified by MPLC. The crude mixture was solidified by using DCM and hexane to give methyl 7-phenylpyrazolo[1,5-a]pyrimidine-2-carboxylate (87.8 mg, 32%) as a white solid. $^1$H NMR (400 MHz, DMSO-d$_6$) δ 8.75 (d, J=4.3 Hz, 1H), 8.14-8.04 (m, 2H), 7.71-7.61 (m, 3H), 7.41 (d, J=4.3 Hz, 1H), 7.31 (s, 1H), 3.90 (s, 3H).

Step 3

Methyl 7-phenylpyrazolo[1,5-a]pyrimidine-2-carboxylate (87 mg, 0.34 mmol) was dissolved in H$_2$O/THF/MeOH (1.4/2.2/1.1 mL), followed up by addition of sodium hydroxide in H$_2$O (1 N, 0.68 mL) and stirred at 60° C. for 2 hr. After cooling at 0° C., the mixture was acidified by adding 1 N HCl. Then the precipitated crystals were filtered out by using H$_2$O to give 7-phenylpyrazolo[1,5-a]pyrimidine-2-carboxylic acid (65.5 mg, 80%) as a yellow solid. $^1$H NMR (400

MHz, DMSO-d$_6$) δ 13.3 (bs, 1H), 8.72 (d, J=4.3 Hz, 1H), 8.16-8.05 (m, 2H), 7.73-7.60 (m, 3H), 7.39 (d, J=4.3 Hz, 1H), 7.23 (s, 1H).

Synthesis of 7-(3,4-dimethoxyphenyl)pyrazolo[1,5-a]pyrimidine-2-carboxylic acid

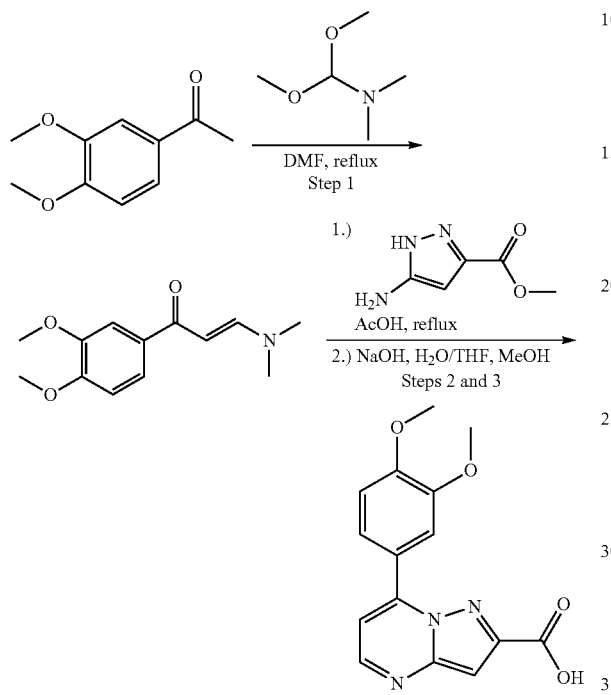

Step 1
3',4'-Dimethoxyacetophenone (1 g, 5.55 mmol) and DMF-DMA (2.95 mL, 22.2 mmol) were combined in DMF (5.55 mL) and heated to reflux for 18 hr. The mixture was extracted by DCM and aq. NH$_4$Cl. The reaction mixture was solidified by using diethyl ether to give (E)-1-(3,4-dimethoxyphenyl)-3-(dimethylamino)prop-2-en-1-one (797 mg, 61%) as an orange solid. $^1$H NMR (400 MHz, DMSO-d$_6$) δ 7.66 (d, J=12.4 Hz, 1H), 7.54 (dd, J=8.4, 2.0 Hz, 1H), 7.45-7.44 (m, 1H), 6.98 (d, J=8.4 Hz, 1H), 5.82 (d, J=12.4 Hz, 1H), 3.82-3.80 (m, 6H), 3.13 (s, 3H), 2.91 (s, 3H).
Step 2
(E)-1-(3,4-dimethoxyphenyl)-3-(dimethylamino)prop-2-en-1-one (790 mg, 3.35 mmol) and methyl 5-amino-1H-pyrazole-3-carboxylate (473 mg, 3.35 mmol) were dissolved in acetic acid (15 mL) and heated to reflux for 2 hr. After evaporating acetic acid, the mixture was solidified by using diethyl ether to give Methyl 7-(3,4-dimethoxyphenyl)pyrazolo[1,5-a]pyrimidine-2-carboxylate (919 mg, 88%) as a white solid. $^1$H NMR (400 MHz, DMSO-d$_6$): δ 8.69 (d, J=4.4 Hz, 1H), 7.87 (dd, J=8.6 Hz, 2.4 Hz, 1H), 7.78 (d, J=2.4 Hz, 1H), 7.46 (d, J=4.4 Hz, 1H), 7.25 (s, 1H), 7.21 (d, J=8.8 Hz, 1H), 3.91 (s, 3H), 3.89 (s, 3H), 3.87 (s, 3H).
Step 3
Methyl 7-(3,4-dimethoxyphenyl)pyrazolo[1,5-a]pyrimidine-2-carboxylate (915 mg, 2.92 mmol) was dissolved in H$_2$O/THF/MeOH (12/20/10 mL), followed up by addition of sodium hydroxide in H$_2$O (1 N, 5.84 mL) and stirred at 60° C. for 2 hr. After cooling at 0° C., the mixture was acidified by adding 1 N HCl. Then the precipitated crystals were filtered out by using H$_2$O to give 7-(3,4-dimethoxyphenyl)pyrazolo[1,5-a]pyrimidine-2-carboxylic acid (980 mg, >99%) as a pale yellow solid. $^1$H NMR (400 MHz, DMSO-d$_6$): δ 13.35 (s, 1H), 8.68 (d, J=4.4 Hz, 1H), 7.90 (dd, J=8.4 Hz, 2.0 Hz, 1H), 7.80 (d, J=2.0 Hz, 1H), 7.44 (d, J=4.4 Hz, 1H), 7.22-7.20 (m, 2H), 3.89 (s, 3H), 3.87 (s, 3H).

Synthesis of 7-(4-fluoro-3-methoxyphenyl)pyrazolo[1,5-a]pyrimidine-2-carboxylic acid

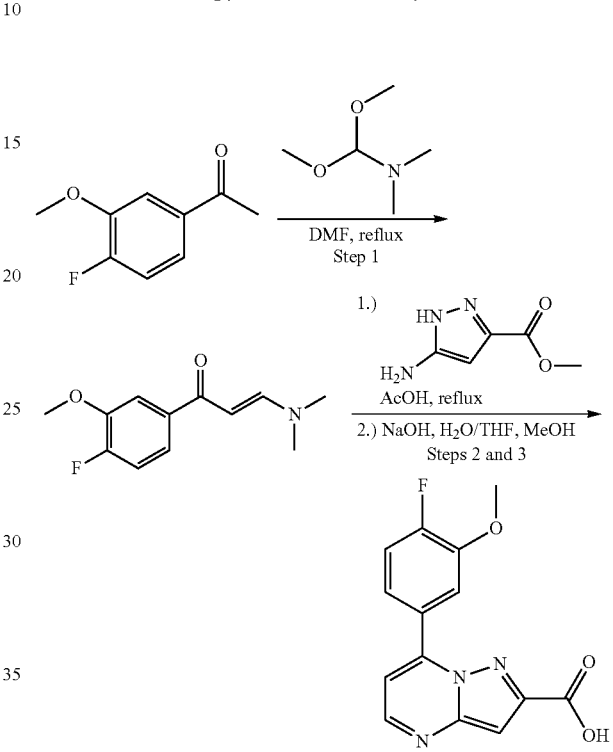

Step 1
1-(4-Fluoro-3-methoxyphenyl)ethan-1-one (500 mg, 2.97 mmol) and DMF-DMA (1.58 mL, 11.9 mmol) were combined in DMF (2.97 mL) and heated to reflux for 21 hr. The mixture was extracted by DCM and aq. NH$_4$Cl. The reaction mixture was solidified by using DCM and hexane to give (E)-3-(dimethylamino)-1-(4-fluoro-3-methoxyphenyl)prop-2-en-1-one (516 mg, 77%) as an orange solid. $^1$H NMR (400 MHz, DMSO-d$_6$) δ 7.71 (d, J=12.2 Hz, 1H), 7.60 (dd, J=8.7, 2.0 Hz, 1H), 7.56-7.49 (m, 1H), 7.29-7.20 (m, 1H), 5.82 (d, J=12.2 Hz, 1H), 3.89 (s, 3H), 3.15 (s, 3H), 2.92 (s, 3H).
Step 2
(E)-3-(dimethylamino)-1-(4-fluoro-3-methoxyphenyl)prop-2-en-1-one (515 mg, 2.3 mmol) and methyl 5-amino-1H-pyrazole-3-carboxylate (325 mg, 2.3 mmol) were dissolved in acetic acid (12 mL) and heated to reflux for 2 hr. The reaction mixture was extracted by DCM and aq. NaHCO$_3$. The organic layer was dried over anhydrous MgSO$_4$ and concentrated. The crude mixture was solidified by using DCM and hexane to give methyl 7-(4-fluoro-3-methoxyphenyl)pyrazolo[1,5-a]pyrimidine-2-carboxylate (1950 mg, >99%) as a white solid. $^1$H NMR (400 MHz, DMSO-d$_6$) δ 8.75 (d, J=4.4 Hz, 1H), 7.92 (dd, J=8.4, 2.1 Hz, 1H), 7.80-7.74 (m, 1H), 7.55-7.45 (m, 2H), 7.31 (s, 1H), 3.94 (s, 3H), 3.91 (s, 3H).
Step 3
Methyl 7-(4-fluoro-3-methoxyphenyl)pyrazolo[1,5-a]pyrimidine-2-carboxylate (693 mg, 2.3 mmol) was dissolved in H₂O/THF/MeOH (9/15/8 mL), followed up by addition of sodium hydroxide in H₂O (1 N, 4.6 mL) and stirred at 60° C. for 4 hr. After cooling at 0° C., the mixture was acidified by adding 1 N HCl. Then the precipitated crystals were filtered out by using H₂O to give 7-(4-fluoro-3-methoxyphenyl)pyrazolo[1,5-a]pyrimidine-2-carboxylic acid (521 mg, 79%) as a yellow solid. ¹H NMR (400 MHz, DMSO-d₆) δ 13.40 (s, 1H), 8.73 (d, J=4.4 Hz, 1H), 7.93 (dd, J=8.4, 2.1 Hz, 1H), 7.83-7.76 (m, 1H), 7.56-7.42 (m, 2H), 7.23 (s, 1H), 3.94 (s, 3H).

Synthesis of 7-(3,4-difluorophenyl)pyrazolo[1,5-a]pyrimidine-2-carboxylic acid

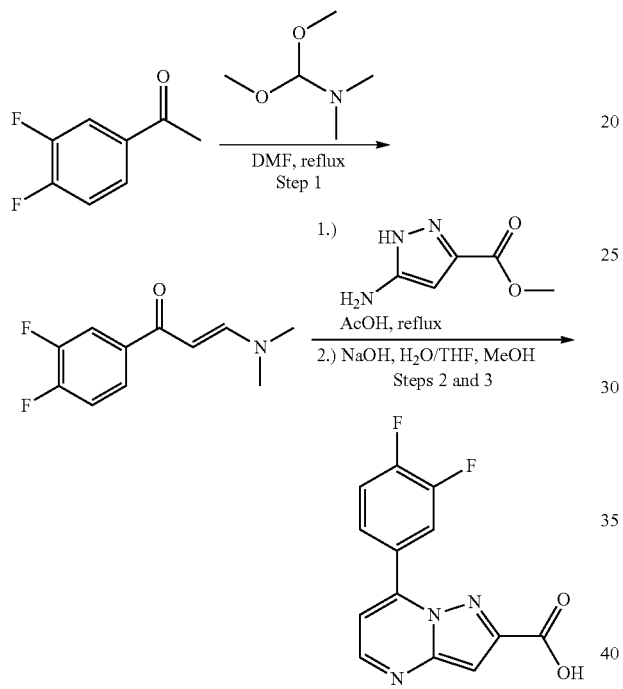

Step 1

1-(3,4-difluorophenyl)ethan-1-one (1000 mg, 6.41 mmol) and DMF-DMA (3.40 mL, 25.62 mmol) were combined in DMF (3 mL) and heated to reflux for 22 hr. The mixture was extracted by DCM and aq. NH₄Cl. The organic layer was dried over anhydrous MgSO₄ and concentrated to give (E)-1-(3,4-difluorophenyl)-3-(dimethylamino)prop-2-en-1-one (1275.4 mg, >99%) as an orange solid. ¹H NMR (400 MHz, DMSO-d₆) δ 7.96-7.88 (m, 1H), 7.82-7.77 (m, 1H), 7.74 (d, J=12.2 Hz, 1H), 7.53-7.45 (m, 1H), 5.85 (d, J=12.2 Hz, 1H), 3.15 (s, 3H), 2.93 (s, 3H).

Step 2

(E)-1-(3,4-difluorophenyl)-3-(dimethylamino)prop-2-en-1-one (1275 mg, 6.04 mmol) and methyl 5-amino-1H-pyrazole-3-carboxylate (852 mg, 6.04 mmol) were dissolved in acetic acid (30 mL) and heated to reflux for 1 hr. The reaction mixture was extracted by DCM and aq. NaHCO₃. The organic layer was dried over anhydrous MgSO₄ and concentrated. The crude mixture was solidified by using DCM and hexane to give methyl 7-(3,4-difluorophenyl)pyrazolo[1,5-a]pyrimidine-2-carboxylate (1188 mg, 68%) as a yellow solid. ¹H NMR (400 MHz, DMSO-d₆) δ 8.76 (d, J=4.4 Hz, 1H), 8.32-8.23 (m, 1H), 8.05-7.97 (m, 1H), 7.80-7.70 (m, 1H), 7.48 (d, J=4.4 Hz, 1H), 7.33 (s, 1H), 3.90 (s, 3H).

Step 3

Methyl 7-(3,4-difluorophenyl)pyrazolo[1,5-a]pyrimidine-2-carboxylate (1188 mg, 4.11 mmol) was dissolved in H₂O/THF/MeOH (16/20/10 mL), followed up by addition of sodium hydroxide in H₂O (1 N, 8.22 mL) and stirred at 60° C. for 2 hr. After cooling at 0° C., the mixture was acidified by adding 1 N HCl. Then the precipitated crystals were filtered out by using H₂O to give 7-(3,4-difluorophenyl) pyrazolo[1,5-a]pyrimidine-2-carboxylic acid (280 mg, 25%) as a pale orange solid. ¹H NMR (400 MHz, DMSO-d₆) δ 13.45 (s, 1H), 8.74 (d, J=4.4 Hz, 1H), 8.36-8.27 (m, 1H), 8.09-8.01 (m, 1H), 7.79-7.70 (m, 1H), 7.46 (d, J=4.4 Hz, 1H), 7.25 (s, 1H).

Synthesis of 7-(2-fluoro-4-methoxyphenyl)pyrazolo[1,5-a]pyrimidine-2-carboxylic acid

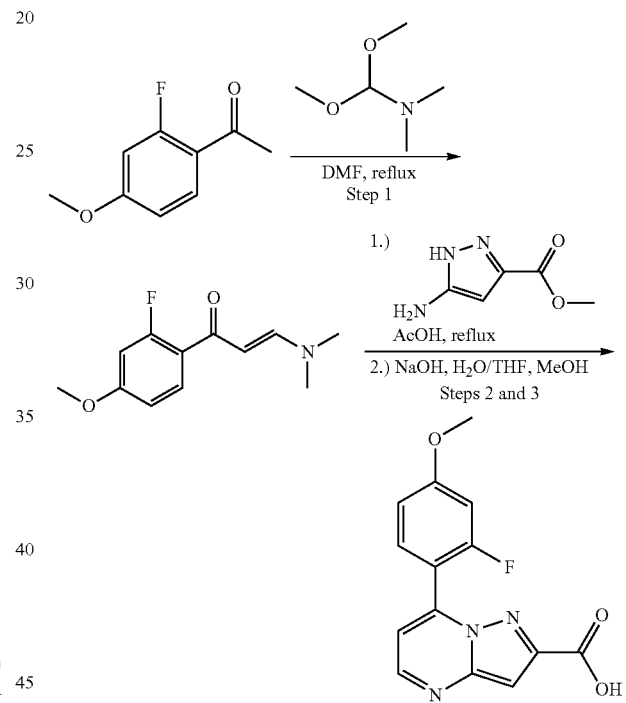

Step 1

1-(2-fluoro-4-methoxyphenyl)ethan-1-one (1000 mg, 5.95 mmol) and DMF-DMA (3.2 mL, 23.8 mmol) were combined in DMF (6 mL) and heated to reflux for 18 hr. The mixture was extracted by DCM and aq. NH₄Cl. After evaporating DCM, the mixture was extracted by EA and aq. NH₄Cl. The reaction mixture was solidified by using diethyl ether to give (E)-3-(dimethylamino)-1-(2-fluoro-4-methoxyphenyl)prop-2-en-1-one (1057 mg, 80%) as an orange solid. ¹H NMR (400 MHz, DMSO-d₆) δ 7.69-7.57 (m, 2H), 6.87-6.77 (m, 2H), 6.99 (d, J=12.2 Hz, 1H), 3.80 (s, 3H), 3.12 (s, 3H), 2.84 (s, 3H).

Step 2

(E)-3-(dimethylamino)-1-(2-fluoro-4-methoxyphenyl) prop-2-en-1-one (1057 mg, 4.74 mmol) and methyl 5-amino-1H-pyrazole-3-carboxylate (668 mg, 4.74 mmol) were dissolved in acetic acid (24 mL) and heated to reflux for 8 hr. After evaporating acetic acid, the mixture was extracted by EA and aq. NaOH to give methyl 7-(2-fluoro-4-methoxyphenyl)pyrazolo[1,5-a]pyrimidine-2-carboxylate (972 mg, 68%) as a pale orange solid. $^1$H NMR (400 MHz, DMSO-$d_6$) δ 8.73 (d, J=4.3 Hz, 1H), 7.77 (t, J=8.5 Hz, 1H), 7.32 (dd, J=4.3, 0.7 Hz, 1H), 7.30 (s, 1H), 7.14 (dd, J=12.4, 2.4 Hz, 1H), 7.04 (dd, J=8.7, 2.5 Hz, 1H), 3.89 (s, 3H), 3.87 (s, 3H).

Step 3

Methyl 7-(2-fluoro-4-methoxyphenyl)pyrazolo[1,5-a]pyrimidine-2-carboxylate (970 mg, 3.22 mmol) was dissolved in H$_2$O/THF/MeOH (12/20/10 mL), followed up by addition of sodium hydroxide in H$_2$O (1 N, 6.44 mL) and stirred at 60° C. for 4 hr. After cooling at 0° C., the mixture was acidified by adding 1 N HCl. Then the precipitated crystals were filtered out by using H$_2$O to give 7-(2-fluoro-4-methoxyphenyl)pyrazolo[1,5-a]pyrimidine-2-carboxylic acid (790 mg, 85%) as a white solid. $^1$H NMR (400 MHz, DMSO-$d_6$) δ 13.38 (s, 1H), 8.70 (d, J=4.3 Hz, 1H), 7.78 (t, J=8.5 Hz, 1H), 7.29 (dd, J=4.2, 0.7 Hz, 1H), 7.22 (s, 1H), 7.13 (dd, J=12.4, 2.4 Hz, 1H), 7.03 (dd, J=8.7, 2.5 Hz, 1H), 3.89 (s, 3H).

Method B—Synthesis of 6-substituted pyrazolo[1,5-a]pyrimidine-2-carboxylic acid (Formula II-b)

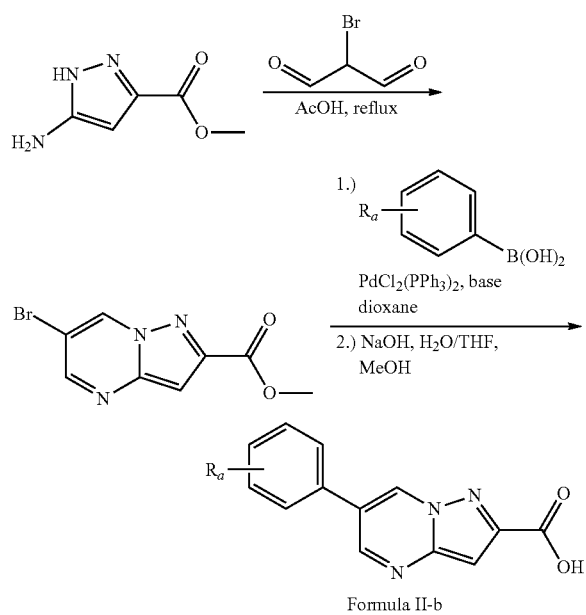

Formula II-b

Synthesis of 6-(3,4-dimethoxyphenyl)pyrazolo[1,5-a]pyrimidine-2-carboxylic acid

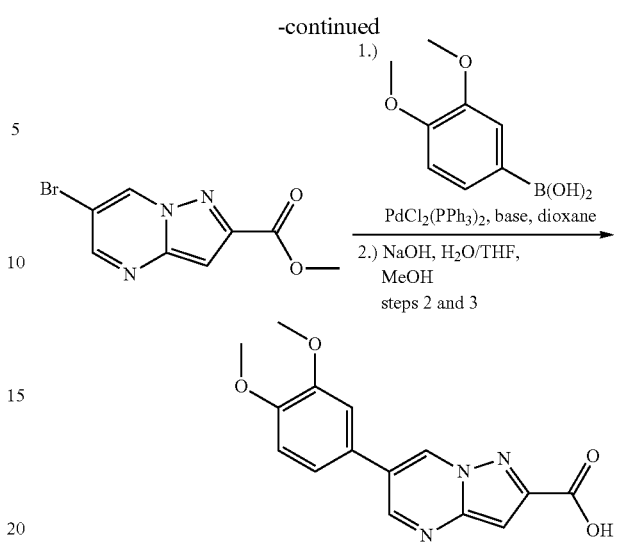

Step 1

2-Bromomalonaldehyde (200 mg, 1.32 mmol) and methyl 5-amino-1H-pyrazole-3-carboxylate (187 mg, 1.32 mmol) were dissolved in acetic acid (13 mL) and heated to reflux for 22 hr. After evaporating acetic acid, the mixture was extracted by DCM and aq. HCl. The reaction mixture was purified by MPLC to give a product, methyl 6-bromopyrazolo[1,5-a]pyrimidine-2-carboxylate (138 mg, 41%) as a white solid. $^1$H NMR (400 MHz, DMSO-$d_6$) δ 9.72 (dd, J=2.2, 0.9 Hz, 1H), 8.77 (d, J=2.2 Hz, 1H), 7.28 (d, J=0.8 Hz, 1H), 3.91 (s, 3H).

Step 2 and 3 methyl 6-bromopyrazolo[1,5-a]pyrimidine-2-carboxylate (130 mg, 0.508 mmol) and PdCl$_2$(PPh$_3$)$_2$ (4 mg, 0.01 mmol) were purged in vacuo. After 40 min, the reagents were dissolved in dioxane (5 mL). To a solution, sodium carbonate (2 M, 2.29 mL) in water was added and heated to 90° C. After 0.5 hr, a solution of 3,4-dimethoxyphenylboronic acid in dioxane (2 mL) was added and stirred for 1 hr. The organic layer was dried over anhydrous MgSO$_4$ and concentrated. The reaction mixture was dissolved in H$_2$O/THF/MeOH (2/4/2 mL), followed up by addition of sodium hydroxide in H$_2$O (1 N, 1.1 mL) and stirred at 60° C. for 4 hr. After cooling at 0° C., the mixture was acidified by adding 1 N HCl. Then the precipitated crystals were filtered out by using H$_2$O to give 6-(3,4-dimethoxyphenyl)pyrazolo[1,5-a]pyrimidine-2-carboxylic acid (90 mg, 59%) as white solid. $^1$H NMR (400 MHz, DMSO-$d_6$) δ 13.23 (s, 1H), 9.54 (s, 1H), 9.08 (d, J=2.2 Hz, 1H), 7.48-7.45 (m, 1H), 7.43 (d, J=8.3 Hz, 1H), 7.16 (s, 1H), 7.11 (d, J=8.4 Hz, 1H), 3.89 (s, 3H), 3.83 (s, 3H).

Method C—Synthesis of 7-substituted pyrazolo[1,5-a]pyrimidine-2-carbonyl chloride (Formula II-c)

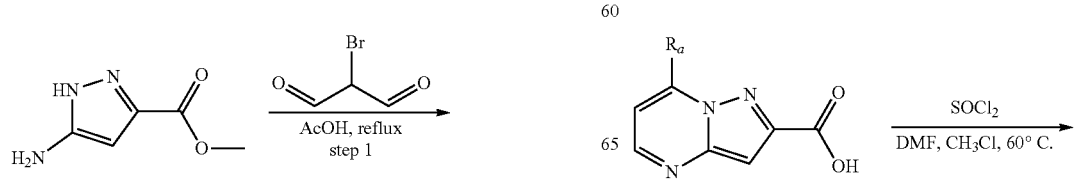

Synthesis of 7-(3,4-dimethoxyphenyl)pyrazolo[1,5-a]pyrimidine-2-carbonyl chloride

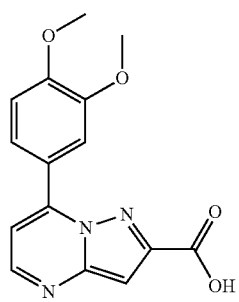

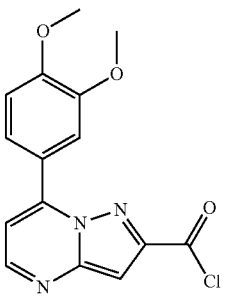

To a solution of 7-(3,4-dimethoxyphenyl)pyrazolo[1,5-a]pyrimidine-2-carboxylic acid (70 mg, 0.23 mmol) in chloroform (2.3 mL), DMF (catalytic amount) and SOCl$_2$ (0.084 mL, 1.15 mmol) were added and stirred at 60° C. for 2 hr. The mixture was concentrated and used in the next step without further purification. $^1$H NMR (400 MHz, DMSO-d$_6$) δ 8.68 (d, J=4.4 Hz, 1H), 7.90 (d, J=8.5 Hz, 1H), 7.81-7.76 (m, 1H), 7.45 (d, J=4.4 Hz, 1H), 7.24-7.16 (m, 2H), 3.89 (s, 3H), 3.86 (s, 3H).

Method D—Synthesis of 7-substituted pyrazolo[1,5-a]pyrimidin-2-amine (Formula II-d)

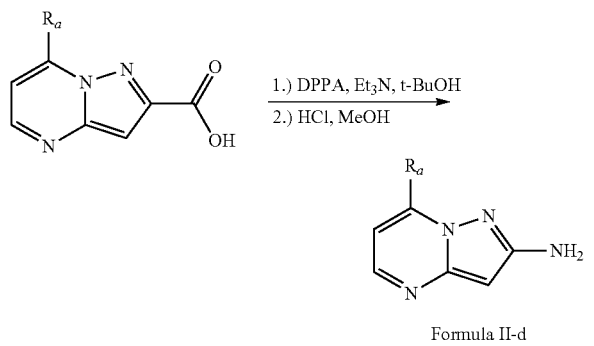

Synthesis of 7-(3,4-dimethoxyphenyl)pyrazolo[1,5-a]pyrimidin-2-amine

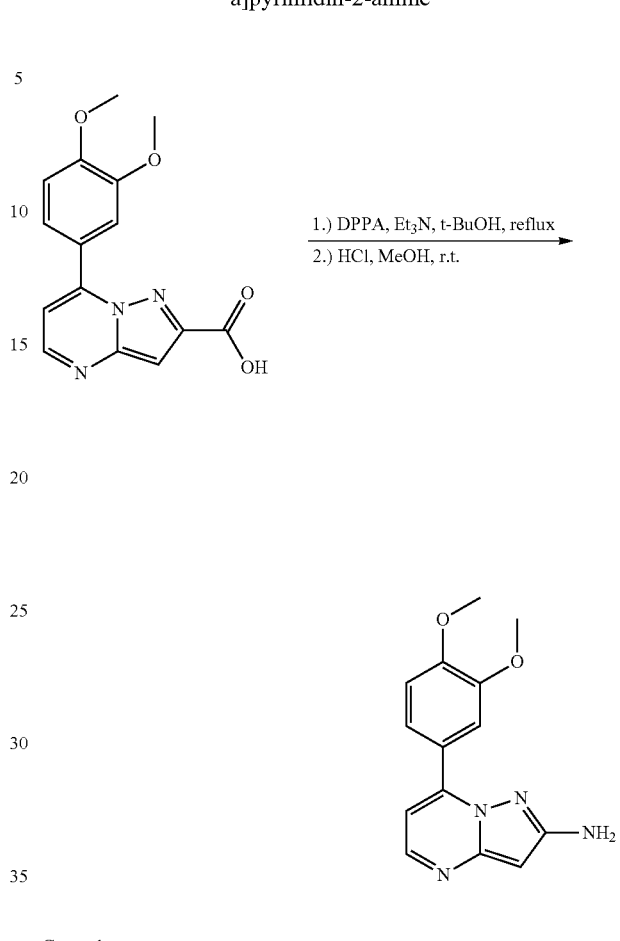

Step 1

7-(3,4-dimethoxyphenyl)pyrazolo[1,5-a]pyrimidine-2-carboxylic acid (1 g, 3.34 mmol), DPPA (0.79 mL, 3.68 mmol), TEA (5.17 mL, 3.68 mmol) were combined in t-BuOH (0.2 M, 15 mL) and heated to reflux for 18.5 hr. After evaporation, the reaction mixture was extracted by DCM and aq. NaHCO$_3$. The mixture was purified by MPLC. The crude mixture was solidified by using DCM and hexane to give a product, tert-butyl (7-(3,4-dimethoxyphenyl)pyrazolo[1,5-a]pyrimidin-2-yl)carbamate (260 mg, 21%) as a white solid. $^1$H NMR (400 MHz, DMSO-d$_6$) δ 10.25 (s, 1H), 8.45 (d, J=4.6 Hz, 1H), 7.97 (d, J=2.1 Hz, 1H), 7.74 (dd, J=8.5, 2.2 Hz, 1H), 7.18-7.13 (m, 2H), 6.71 (s, 1H), 3.88 (s, 3H), 3.86 (s, 3H), 1.49 (s, 9H).

Step 2

Tert-Butyl (7-(3,4-dimethoxyphenyl)pyrazolo[1,5-a]pyrimidin-2-yl)carbamate (250 mg, 0.675 mmol) was dissolved in methanol (6 mL), then hydrochloride (4 N, 3 mL) in dioxane was added at r.t. After 16.5 hr, the mixture was basified by adding 1 N NaOH and extracted by DCM. The mixture was purified by MPLC. The crude mixture was solidified by using DCM and hexane to give a product 7-(3,4-dimethoxyphenyl)pyrazolo[1,5-a]pyrimidin-2-amine (157 mg, 86%) as a yellow solid. $^1$H NMR (400 MHz, DMSO-d$_6$) δ 8.23 (d, J=4.6 Hz, 1H), 7.81-7.75 (m, 2H), 7.13 (d, J=8.5 Hz, 1H), 6.87 (d, J=4.6 Hz, 1H), 5.76 (s, 1H), 5.70 (s, 2H), 3.85 (s, 3H), 3.84 (s, 3H).

Example 2—Synthesis of Compounds of Formulae (Ia)-(Ic)

General Method A

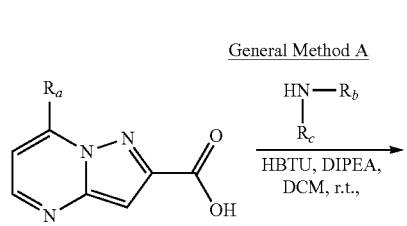

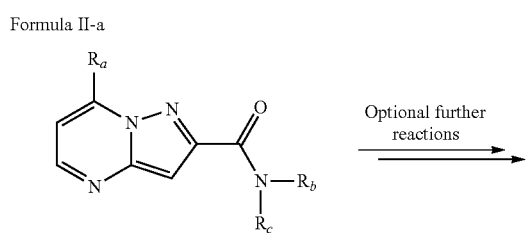

Synthesis of Compound 2

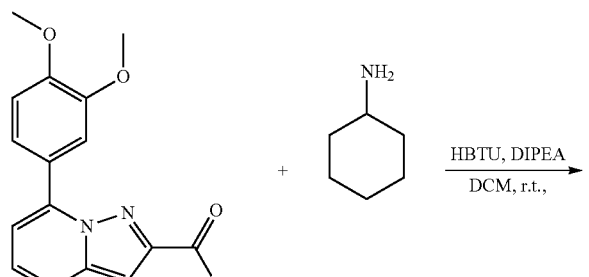

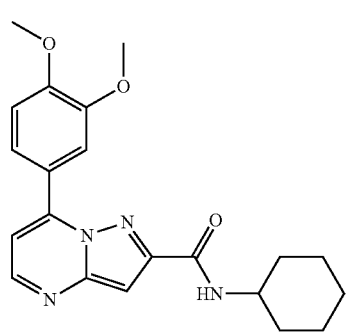

Compound 2

7-(3,4-dimethoxyphenyl)pyrazolo[1,5-a]pyrimidine-2-carboxylic acid (50 mg, 0.17 mmol), cyclohexylamine (0.022 mL, 0.18 mmol), HBTU (70 mg, 0.18 mmol), diisopropylethylamine (0.057 mL, 0.33 mmol) were combined in DCM. After stirring for 1 hr at r.t., the reaction mixture was extracted by DCM and aq. NaHCO₃. The reaction mixture was purified by MPLC. The crude mixture was solidified using DCM and hexane to give compound 2, N-cyclohexyl-7-(3,4-dimethoxyphenyl)pyrazolo[1,5-a]pyrimidine-2-carboxamide (34.8 mg, 55% yield) as a white solid.

Synthesis of Compound 10

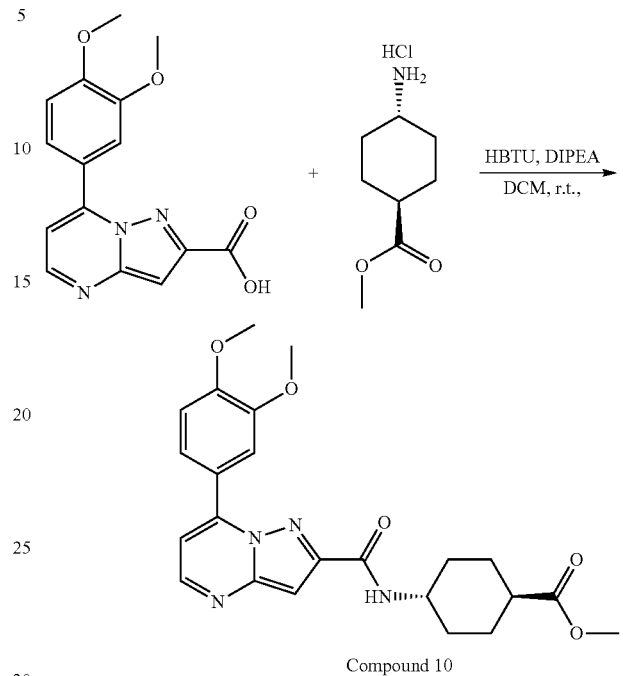

Compound 10

7-(3,4-dimethoxyphenyl)pyrazolo[1,5-a]pyrimidine-2-carboxylic acid (100 mg, 0.33 mmol), methyl trans-4-aminocyclohexanecarboxylate hydrochloride (71.3 mg, 0.37 mmol), HBTU (140 mg, 0.37 mmol), diisopropylethylamine (0.17 mL, 1 mmol) were combined in DCM. After stirring for 1 hr at r.t., the reaction mixture was extracted by DCM and aq. NaHCO₃. The reaction mixture was purified by MPLC. The crude mixture was solidified using DCM and hexane to give compound 10, methyl (1r,4r)-4-(7-(3,4-dimethoxyphenyl)pyrazolo[1,5-a]pyrimidine-2-carboxamido)cyclohexane-1-carboxylate (135 mg, 92% yield) as a pale yellow solid.

Synthesis of Compound 144

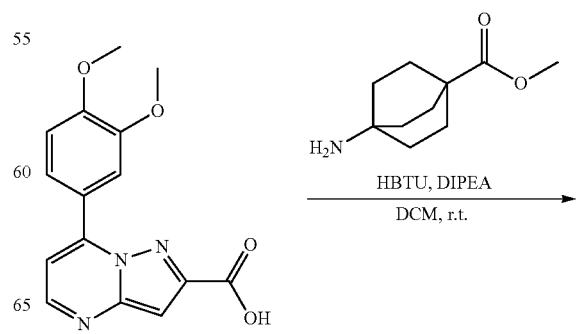

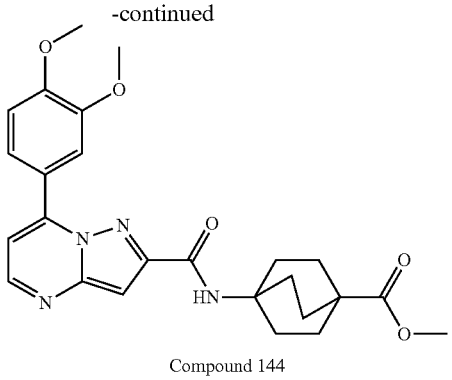

Compound 144

7-(3,4-dimethoxyphenyl)pyrazolo[1,5-a]pyrimidine-2-carboxylic acid (1688 mg, 5.639 mmol), 4-aminobicylo[2,2,2]octane-1-carboxylic acid methyl ester (1033.1 mg, 5.639 mmol), HBTU (2352 mg, 6.203 mmol), diisopropylethylamine (1.943 mL, 11.278 mmol) were combined in DCM. After stirring for 2 hr at r.t., the reaction mixture was extracted by DCM and aq. NaHCO$_3$. The reaction mixture was purified by MPLC. The crude mixture was solidified using DCM and hexane to give compound 144, methyl 4-(7-(3,4-dimethoxyphenyl)pyrazolo[1,5-a]pyrimidine-2-carboxamido)bicyclo[2.2.2]octane-1-carboxylate (3167.6 mg, >99% yield) as a yellow solid.

Synthesis of Compound 149

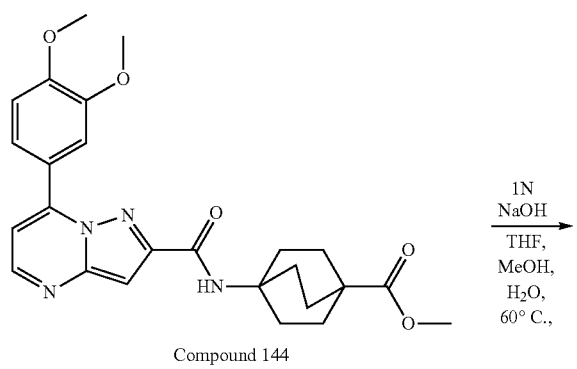

Compound 144

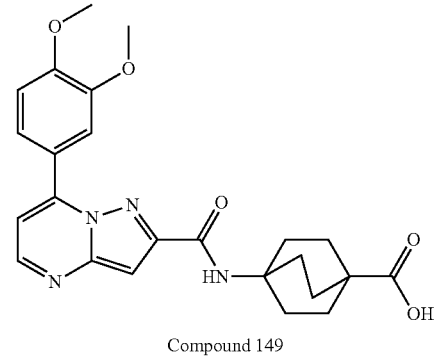

Compound 149

Compound 144 (3167.6 mg, 6.819 mmol) was dissolved in H$_2$O/THF/MeOH (27/22/11 mL), followed up by addition of sodium hydroxide in H$_2$O (1 N, 13.638 mL) and stirred at 60° C. for 2 hr. After cooling at 0° C., the mixture was acidified by adding 1 N HCl. Then the solid was filtered by using H$_2$O to give compound 149, 4-(7-(3,4-dimethoxyphenyl)pyrazolo[1,5-a]pyrimidine-2-carboxamido)bicyclo[2.2.2]octane-1-carboxylic acid (1989 mg, 65%) as a pale yellow solid.

Synthesis of Compound 151

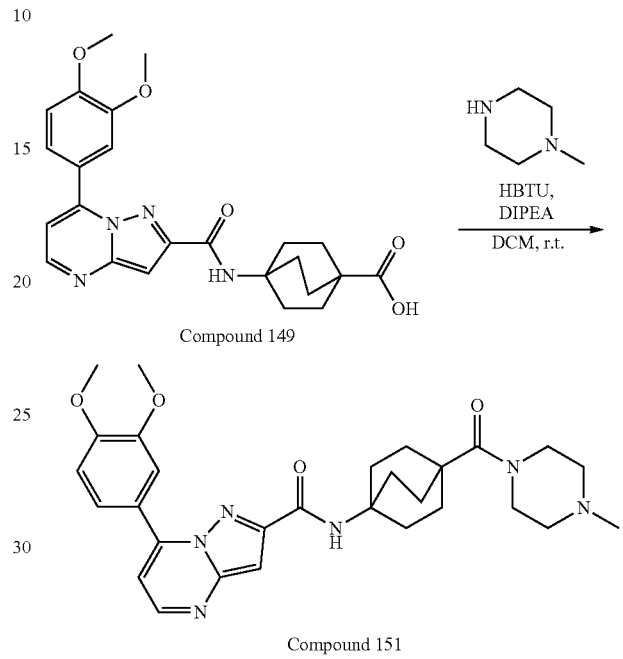

Compound 149

Compound 151

Compound 149 (1000 mg, 2.220 mmol), 1-methylpiperazine (0.271 mL, 2.442 mmol), HBTU (926 mg, 2.442 mmol), diisopropylethylamine (0.765 mL, 4.440 mmol) were combined in DCM. After stirring for 4 hr at r.t., the reaction mixture was extracted by DCM and aq. NaHCO$_3$ and purified by MPLC. The crude mixture was solidified using DCM and diethyl ether to give compound 151, 7-(3,4-dimethoxyphenyl)-N-(4-(4-methylpiperazine-1-carbonyl)bicyclo[2.2.2]octan-1-yl)pyrazolo[1,5-a]pyrimidine-2-carboxamide (961.6 mg, 81% yield) as a white solid.

General Method B

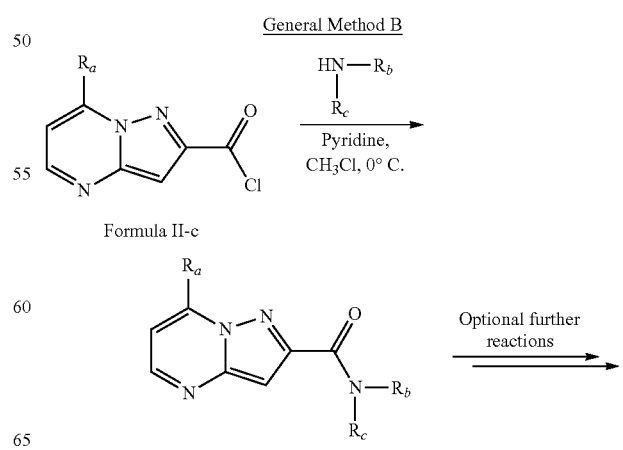

Formula II-c

Synthesis of Compound 36

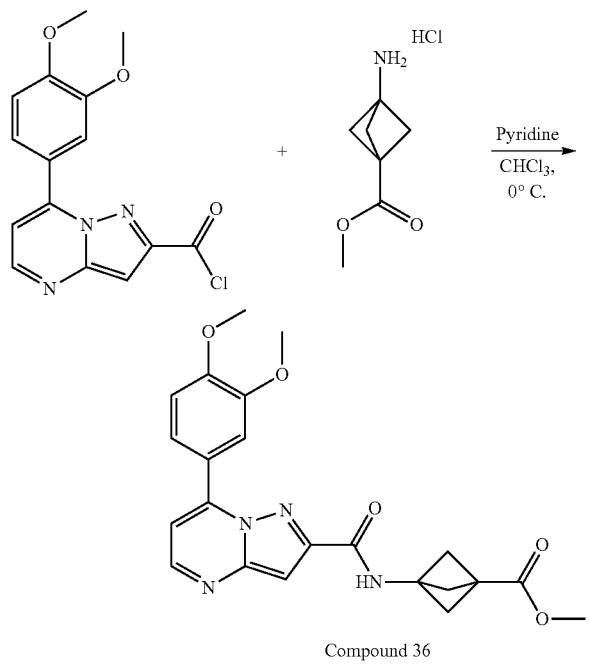

Compound 36

To a solution of methyl 3-aminobicyclo[1.1.1]pentane-1-carboxylate hydrochloride (47.5 mg, 0.267 mmol) and pyridine (0.136 mL, 1.67 mmol) in chloroform, 7-(3,4-dimethoxyphenyl)pyrazolo[1,5-a]pyrimidine-2-carbonyl chloride (106 mg, 0.334 mmol) dissolved in chloroform was added dropwise and stirred for 1 hr at 0° C. The reaction mixture was extracted by DCM and aq. NH₄Cl. The reaction mixture was purified by MPLC. The crude mixture was solidified by using DCM and hexane to give compound 36, methyl 3-(7-(3,4-dimethoxyphenyl)pyrazolo[1,5-a]pyrimidine-2-carboxamido)bicyclo[1.1.1]pentane-1-carboxylate (40.7 mg, 29%) as a white solid.

Synthesis of Compound 37

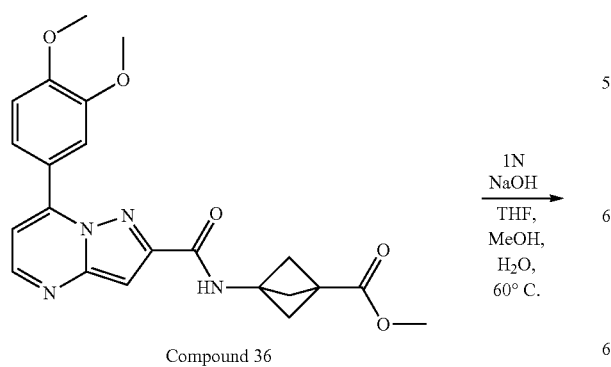

Compound 36

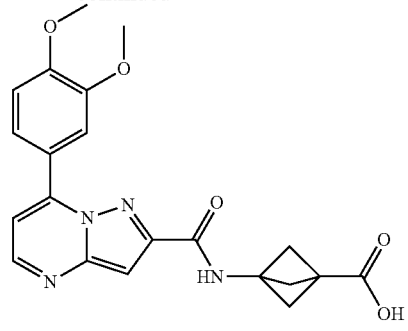

Compound 37

Compound 36 (60 mg, 0.142 mmol) was dissolved in H₂O/THF/MeOH (0.6/1/0.5 mL), followed up by addition of sodium hydroxide in H₂O (1 N, 0.284 mL) and stirred at 30° C. for 2 hr. After cooling at 0° C., the mixture was acidified by adding 1 N HCl. The mixture was extracted by DCM and H₂O. The crude mixture was solidified by using DCM and hexane to give compound 37, 3-(7-(3,4-dimethoxyphenyl)pyrazolo[1,5-a]pyrimidine-2-carboxamido)bicyclo[1.1.1]pentane-1-carboxylic acid (36.8 mg, 63%) as a yellow solid.

Synthesis of Compound 96

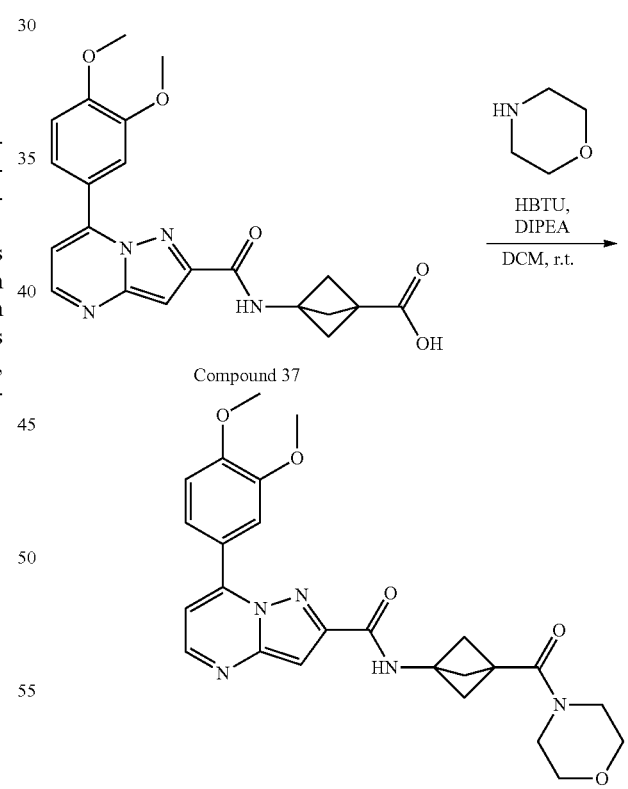

Compound 37

Compound 96

Compound 37 (874 mg, 2.140 mmol), morpholine (0.205 mL, 2.354 mmol), HBTU (893 mg, 2.354 mmol), diisopropylethylamine (0.746 mL, 4.280 mmol) were combined in DCM. After stirring for 4 hr at r.t., the reaction mixture was extracted by DCM and aq. NaHCO₃ and purified by MPLC. The crude mixture was solidified using DCM and n-heptane to give compound 96, 7-(3,4-dimethoxyphenyl)-N-(3-(morpholine-4-carbonyl)bicyclo[1.1.1]pentan-1-yl)pyrazolo[1,5-a]pyrimidine-2-carboxamide (728.9 mg, 71% yield) as a white solid.

Synthesis of Compound 140

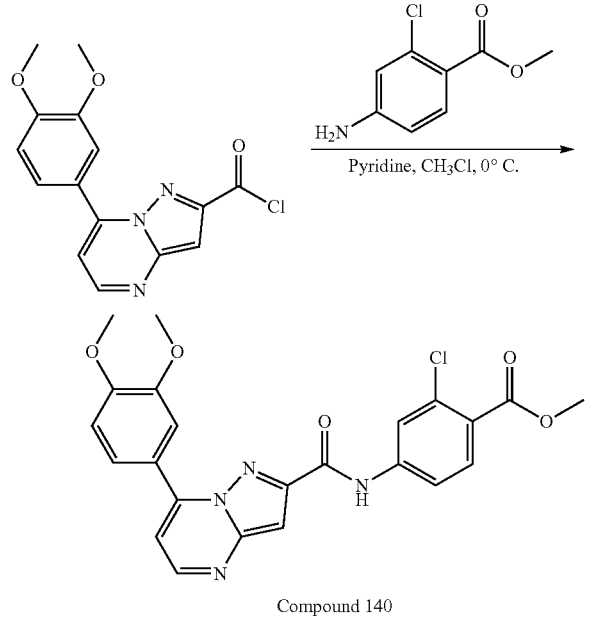

Compound 140

To a solution of methyl 4-amino-2-chlorobenzoate (278 mg, 1.5 mmol) and pyridine (0.25 mL, 3 mmol) in chloroform, 7-(3,4-dimethoxyphenyl)pyrazolo[1,5-a]pyrimidine-2-carbonyl chloride (318 mg, 1 mmol) dissolved in chloroform was added dropwise and stirred for 17 hr at 0° C. The reaction mixture was extracted by DCM and aq. NH$_4$Cl. The organic layer was dried over anhydrous MgSO$_4$ and concentrated. The reaction mixture was purified by MPLC. The crude mixture was solidified by using DCM and hexane to give compound 140, methyl 2-chloro-4-(7-(3,4-dimethoxyphenyl)pyrazolo[1,5-a]pyrimidine-2-carboxamido)benzoate (353 mg, 76%) as a white solid.

Synthesis of Compound 136

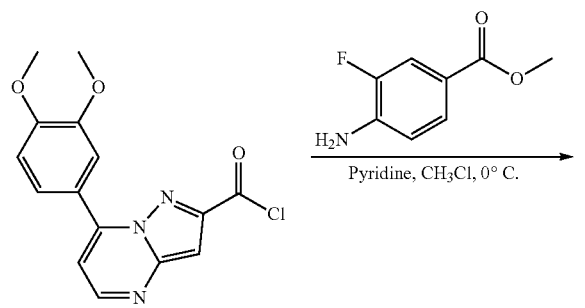

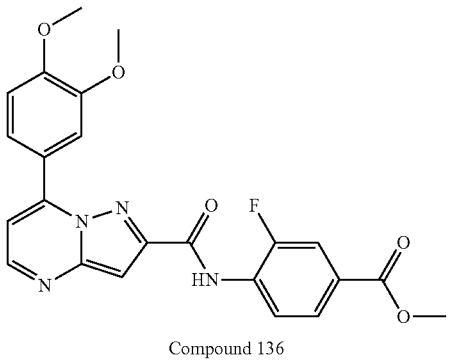

Compound 136

To a solution of methyl 4-amino-3-fluorobenzoate (339 mg, 2.01 mmol) and pyridine (0.33 mL, 4.01 mmol) in chloroform, 7-(3,4-dimethoxyphenyl)pyrazolo[1,5-a]pyrimidine-2-carbonyl chloride (637 mg, 2.01 mmol) dissolved in chloroform was added dropwise and stirred for 2 hr at 0° C. The reaction mixture was extracted by DCM and aq. NH$_4$Cl. The mixture was purified by MPLC to give compound 136, methyl 4-(7-(3,4-dimethoxyphenyl)pyrazolo[1,5-a]pyrimidine-2-carboxamido)-3-fluorobenzoate (684 mg, 76%) as a white solid.

Synthesis of Compound 156

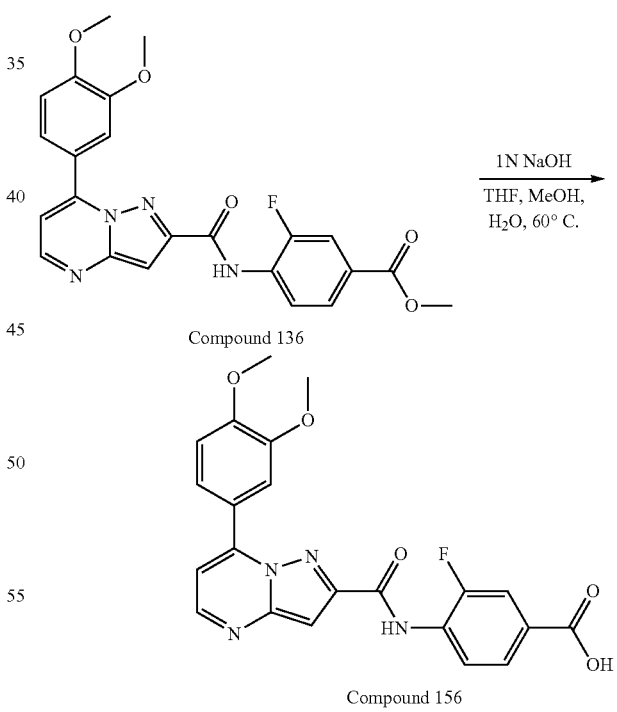

Compound 156

Compound 136 (550 mg, 1.22 mmol) was dissolved in H$_2$O/THF/MeOH (5/8/4 mL), followed up by addition of sodium hydroxide in H$_2$O (1 N, 2.44 mL) and stirred at 60° C. for 30 hr. After cooling at 0° C., the mixture was acidified by adding 1 N HCL. Then the solid was filtered by using H$_2$O. The crude mixture was purified by MPLC to give compound 156, 4-(7-(3,4-dimethoxyphenyl)pyrazolo[1,5-a]pyrimidine-2-carboxamido)-3-fluorobenzoic acid (175 mg, 20%) as a white solid.

Synthesis of Compound 158

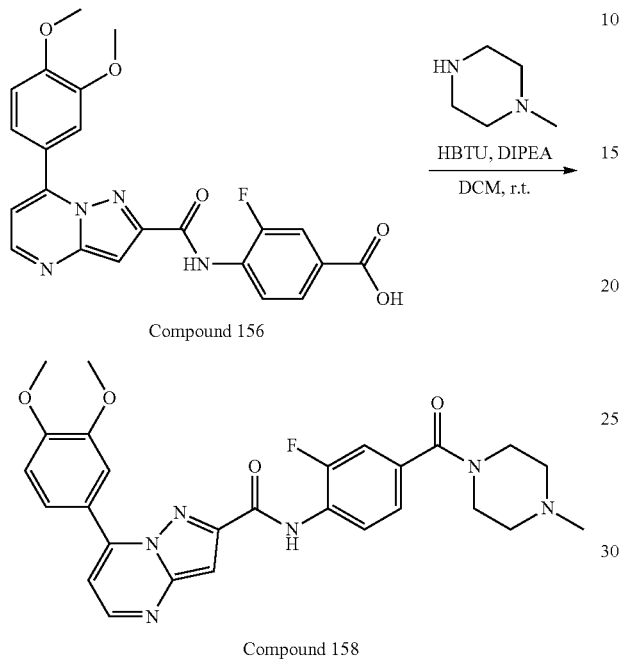

Compound 156

Compound 158

Compound 156 (80 mg, 0.183 mmol), 1-methylpiperazine (0.022 mL, 0.202 mmol), HBTU (77 mg, 0.202 mmol), diisopropylethylamine (0.063 mL, 0.366 mmol) were combined in DCM. After stirring for 1 hr at r.t., the reaction mixture was extracted by DCM and aq. NaHCO₃ and purified by MPLC. The crude mixture was solidified using DCM and hexane to give compound 158, 7-(3,4-dimethoxyphenyl)-N-(2-fluoro-4-(4-methylpiperazine-1-carbonyl)phenyl)pyrazolo[1,5-a]pyrimidine-2-carboxamide (43.8 mg, 46% yield) as a white solid.

Synthesis of Compound 289

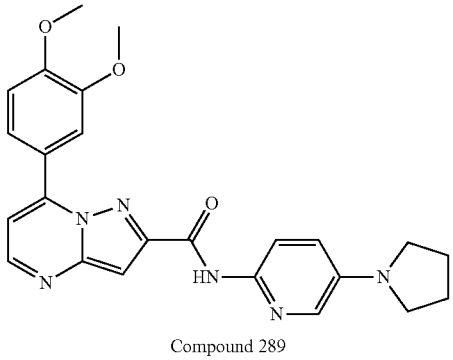

Compound 289

To a solution of 5-(pyrrolidin-1-yl)pyridin-2-amine (108 mg, 0.66 mmol) and pyridine (0.183 mL, 0.99 mmol) in chloroform, 7-(3,4-dimethoxyphenyl)pyrazolo[1,5-a]pyrimidine-2-carbonyl chloride (210 mg, 0.66 mmol) dissolved in chloroform was added dropwise and stirred for 17.5 hr at 0° C. The reaction mixture was extracted by DCM and aq. NaHCO₃ and purified by MPLC. The crude mixture was solidified using DCM and hexane to give compound 289, 7-(3,4-dimethoxyphenyl)-N-(5-(pyrrolidin-1-yl)pyridin-2-yl)pyrazolo[1,5-a]pyrimidine-2-carboxamide (43.5 mg, 14%) as a brown solid.

General Method C

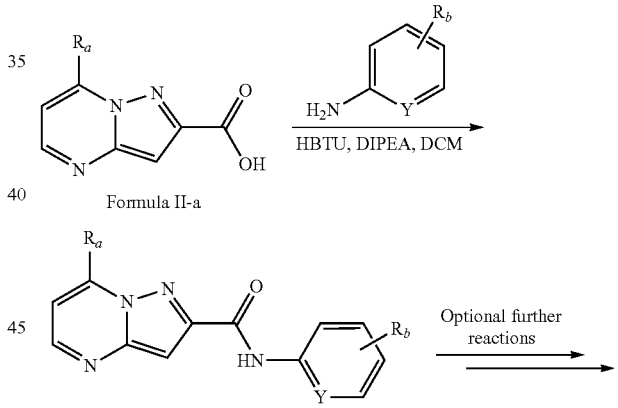

Formula II-a

Synthesis of Compound 6

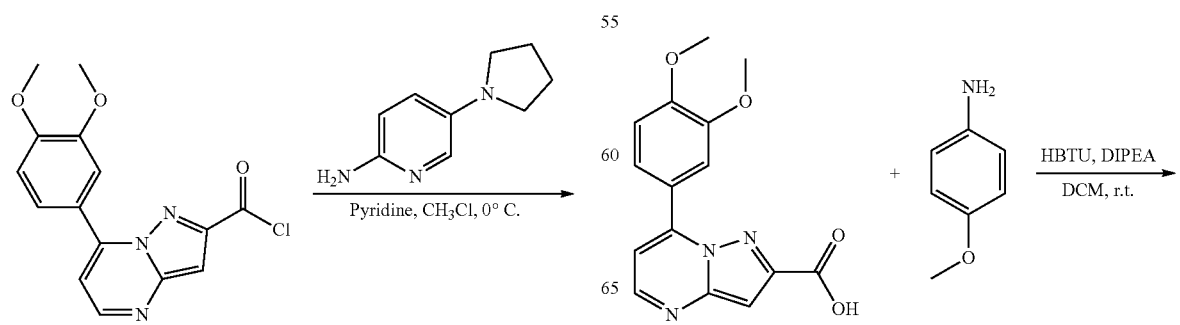

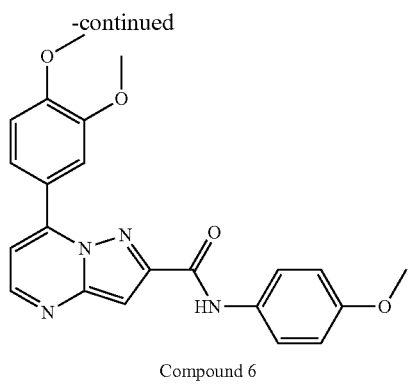

Compound 6

7-(3,4-dimethoxyphenyl)pyrazolo[1,5-a]pyrimidine-2-carboxylic acid (50 mg, 0.167 mmol), p-anisidine (22.7 mg, 0.184 mmol), HBTU (70 mg, 0.184 mmol), diisopropylethylamine (0.057 mL, 0.334 mmol) were combined in DCM. After stirring for 1 hr at r.t., the reaction mixture was extracted by DCM and aq. NaHCO$_3$. The reaction mixture was purified by MPLC. The crude mixture was solidified using DCM and hexane to give compound 6, 7-(3,4-dimethoxyphenyl)-N-(4-methoxyphenyl)pyrazolo[1,5-a]pyrimidine-2-carboxamide (56.3 mg, 83% yield) as a white solid.

Synthesis of Compound 15

Step 1

4-aminophenol (3 g, 27.49 mmol), imidazole (2.246 g, 32.988 mmol), DMAP (34 mg, 0.275 mmol) and TBDMSCl (4.972 g, 32.988 mmol) were combined in DCM. After stirring for 21 hr at r.t., the reaction mixture was filtered by using H$_2$O, and then extracted by DCM and H$_2$O. The crude mixture was purified by MPLC to give a product 4-((tert-butyldimethylsilyl)oxy)aniline (2709.5 mg, 44% yield) as a liquid.

Step 2

7-(3,4-dimethoxyphenyl)pyrazolo[1,5-a]pyrimidine-2-carboxylic acid (3.629 g, 12.127 mmol), 4-((tert-butyldimethylsilyl)oxy)aniline (2.709 g, 12.127 mmol), HBTU (5.059 g, 13.340 mmol), diisopropylethylamine (4.214 mL, 24.454 mmol) were combined in DCM. After stirring for 5 hr at r.t., the reaction mixture was extracted by DCM and aq. NaHCO$_3$. The mixture was purified by MPLC to give N-(4-((tert-butyldimethylsilyl)oxy)phenyl)-7-(3,4-dimethoxyphenyl)pyrazolo[1,5-a]pyrimidine-2-carboxamide (5409.7 mg, 88% yield) as a white solid.

Step 3

N-(4-((tert-butyldimethylsilyl)oxy)phenyl)-7-(3,4-dimethoxyphenyl)pyrazolo[1,5-a]pyrimidine-2-carboxamide (5.409 g, 10.718 mmol) was dissolved in THF (50 mL) at 0° C., and then TBAF (1 M, 10.718 mL) in THF was added. After 15 min, the reaction mixture was quenched by using H$_2$O (50 mL) and extracted by EA. The mixture was purified by MPLC. The crude mixture was solidified using DCM and

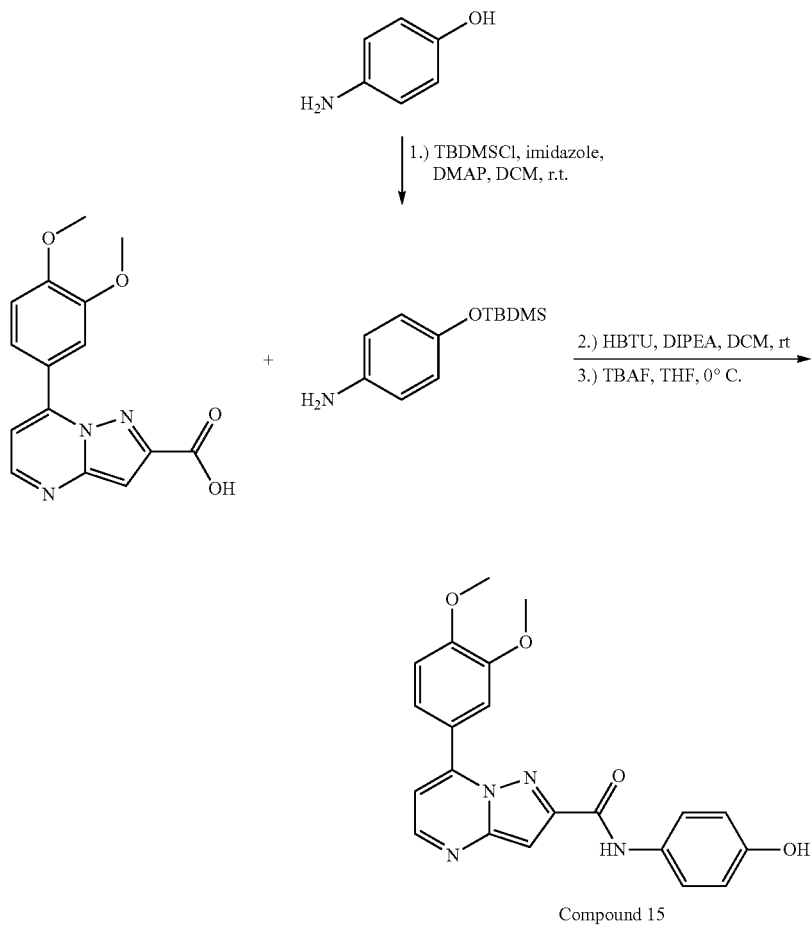

Compound 15 diethyl ether to give compound 15, 7-(3,4-dimethoxyphenyl)-N-(4-hydroxyphenyl)pyrazolo[1,5-a]pyrimidine-2-carboxamide (2805.6 mg, 67% yield) as a white solid.

Synthesis of Compound 11

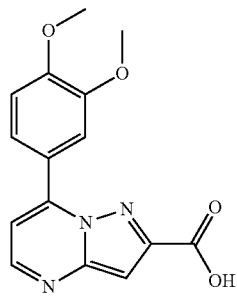

+

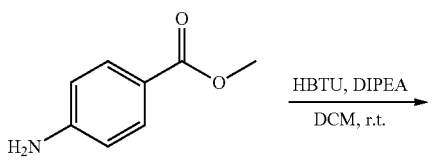

Synthesis of Compound 14

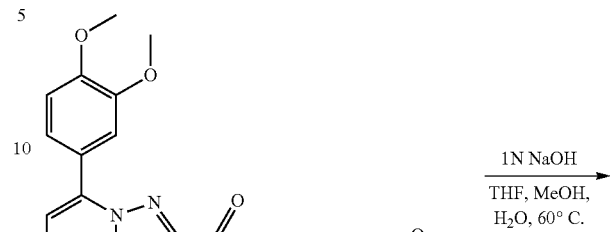

Compound 11

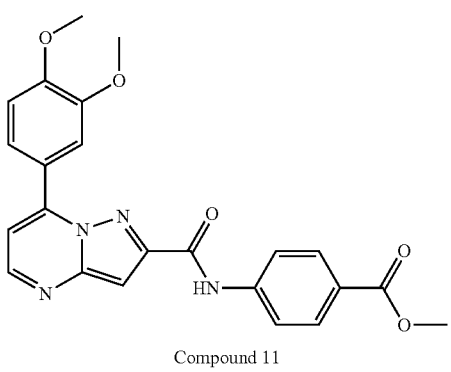

Compound 11

7-(3,4-dimethoxyphenyl)pyrazolo[1,5-a]pyrimidine-2-carboxylic acid (100 mg, 0.334 mmol), methyl 4-aminobenzoate (55.64 mg, 0.368 mmol), HBTU (140 mg, 0.368 mmol), diisopropylethylamine (0.114 mL, 0.668 mmol) were combined in DCM. After stirring for 1 hr at r.t., the reaction mixture was extracted by DCM and aq. NaHCO$_3$. The reaction mixture was purified by MPLC. The crude mixture was solidified using DCM and hexane to give compound 11, methyl 4-(7-(3,4-dimethoxyphenyl)pyrazolo[1,5-a]pyrimidine-2-carboxamido)benzoate (75 mg, 52% yield) as a pale yellow solid.

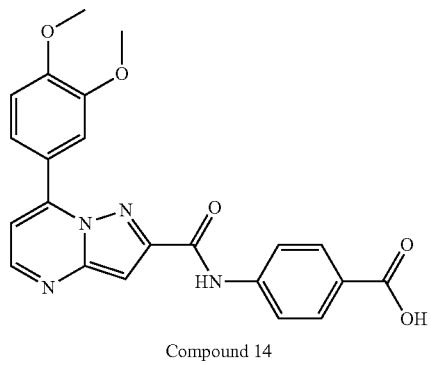

Compound 14

Compound 11 (550 mg, 1.22 mmol) was dissolved in H2O/THF/MeOH (5/8/4 mL), followed up by addition of sodium hydroxide in H$_2$O (1 N, 2.44 mL) and stirred at 60° C. for 30 hr. After cooling at 0° C., the mixture was acidified by adding 1 N HCl. Then the solid was filtered by using H$_2$O. The reaction mixture was purified by MPLC to give compound 14, 4-(7-(3,4-dimethoxyphenyl)pyrazolo[1,5-a]pyrimidine-2-carboxamido)benzoic acid (464 mg, 91%) as a yellow solid.

Synthesis of Compound 97

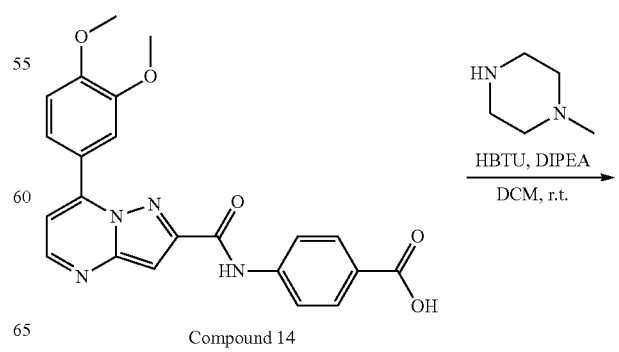

Compound 14

337

-continued

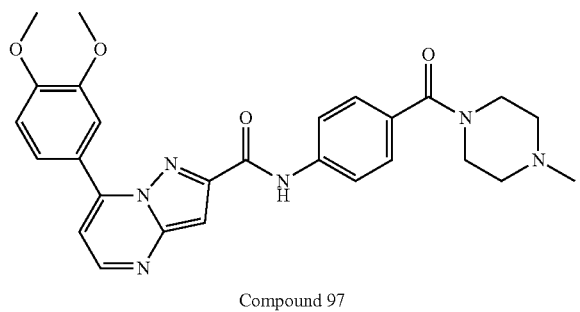

Compound 97

Compound 14(80 mg, 0.183 mmol), 1-methylpiperazine (0.022 mL, 0.202 mmol), HBTU (77 mg, 0.202 mmol), diisopropylethylamine (0.063 mL, 0.366 mmol) were combined in DCM. After stirring for 24 hr at r.t., the reaction mixture was extracted by DCM and aq. NaHCO$_3$ and purified by MPLC. The crude mixture was solidified using DCM and hexane to give compound 97, 7-(3,4-dimethoxyphenyl)-N-(4-(4-methylpiperazine-1-carbonyl)phenyl)pyrazolo[1,5-a]pyrimidine-2-carboxamide (43.8 mg, 46% yield) as a white solid.

Synthesis of Compound 159

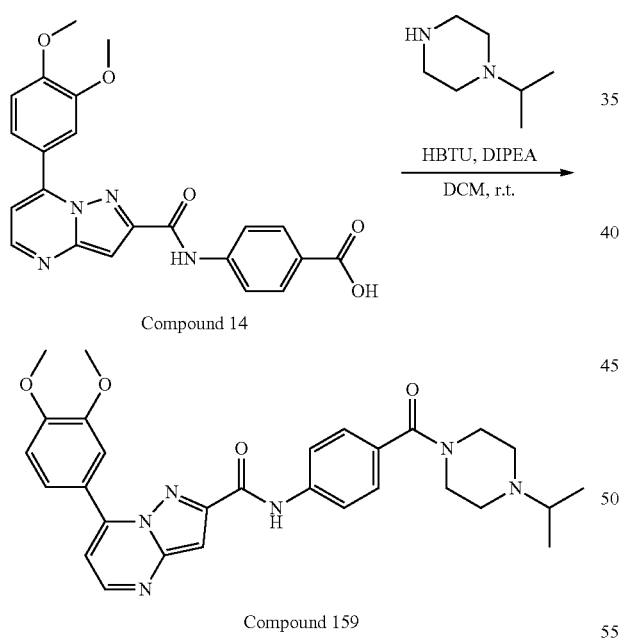

Compound 159

Compound 14 (1700 mg, 4.063 mmol), 1-isopropylpiperazine (0.637 mL, 4.469 mmol). HBTU (1695 mg, 4.469 mmol), diisopropylethylamine (1.4 mL, 8.126 mmol) were combined in DCM. After stirring for 26 hr at r.t., the reaction mixture was extracted by DCM and aq. NaHCO$_3$ and purified by MPLC. The crude mixture was solidified using DCM and diethyl ether to give compound 159, 7-(3,4-dimethoxyphenyl)-N-(4-(4-isopropylpiperazine-1-carbonyl)phenyl)pyrazolo[1,5-a]pyrimidine-2-carboxamide (1641.6 mg, 76% yield) as a white solid.

338

Synthesis of Compound 165

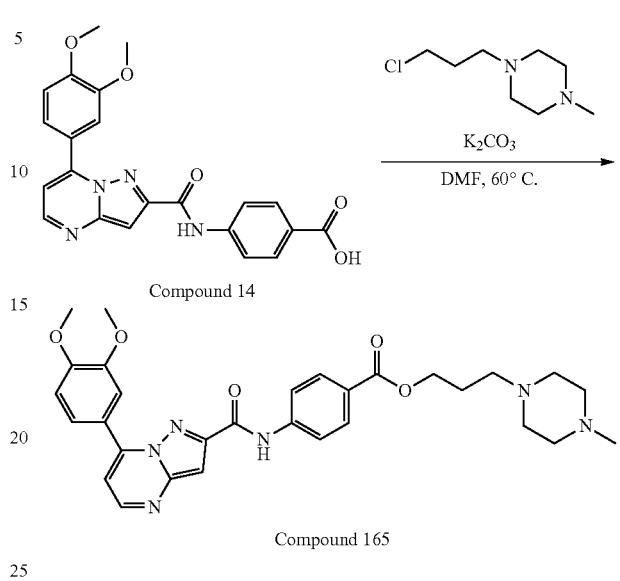

Compound 165

Compound 14(180 mg, 0.43 mmol), 1-(3-chloropropyl)-4-methylpiperazine (0.15 mL, 0.86 mmol) and potassium carbonate (178 mg, 1.29 mmol) were combined in DMF and heated to 60° C. for 26 hr. The reaction mixture was extracted by DCM and aq. NH$_4$Cl and purified by MPLC. The crude mixture was solidified using DCM and hexane to give compound 165, 3-(4-methylpiperazin-1-yl)propyl 4-(7-(3,4-dimethoxyphenyl)pyrazolo[1,5-a]pyrimidine-2-carboxamido)benzoate (15.31 mg, 6% yield) as a white solid.

Synthesis of Compound 204

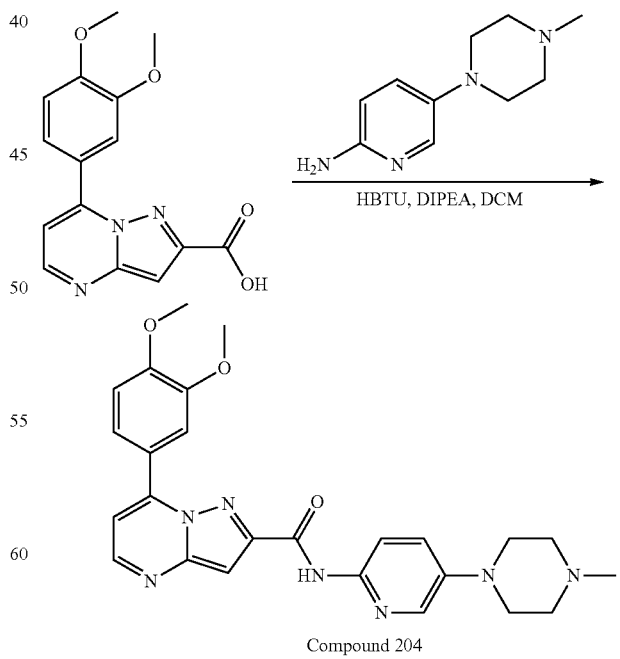

Compound 204

7-(3,4-dimethoxyphenyl)pyrazolo[1,5-a]pyrimidine-2-carboxylic acid (114 mg, 0.38 mmol), 5-(4-methylpiperazin- 1-yl)pyridin-2-amine (80 mg, 0.42 mmol), HBTU (159 mg, 0.42 mmol), diisopropylethylamine (0.196 mL, 1.14 mmol) were combined in DCM. After stirring for 22 hr at r.t., the reaction mixture was extracted by DCM and aq. NaHCO$_3$. The reaction mixture was purified by MPLC. The crude mixture was solidified using DCM and hexane to give compound 204, 7-(3,4-dimethoxyphenyl)-N-(5-(4-methylpiperazin-1-yl)pyridin-2-yl)pyrazolo[1,5-a]pyrimidine-2-carboxamide (120 mg, 67% yield) as a yellow solid.

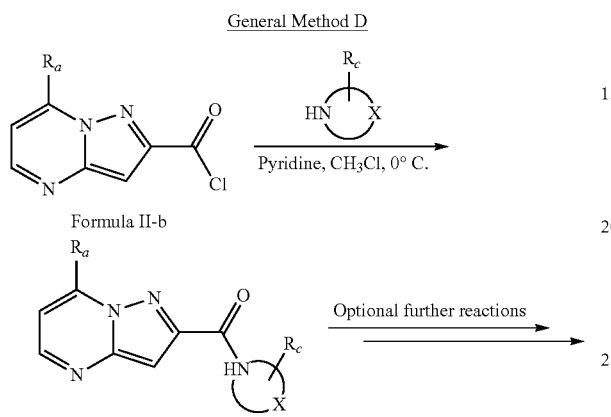

General Method D

Formula II-b

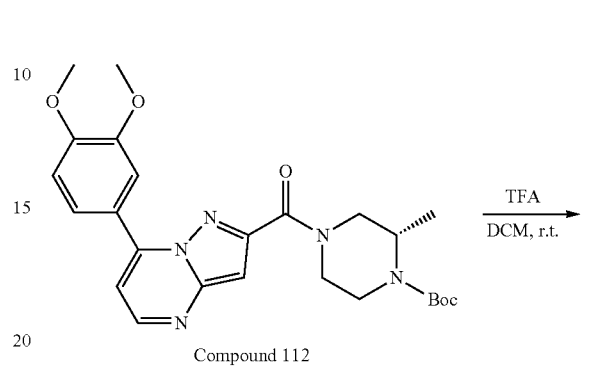

Synthesis of Compound 112

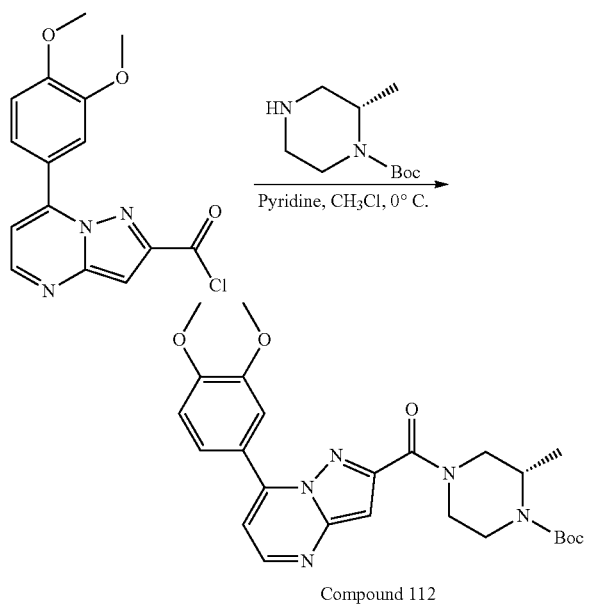

Compound 112

To a solution of ((S)-1-N-Boc-2-methylpiperazine)(1205 mg, 6.014 mmol) and pyridine (2.724 mL, 33.410 mmol) in chloroform (66.82 mL), 7-(3,4-dimethoxyphenyl)pyrazolo[1,5-a]pyrimidine-2-carbonyl chloride (2123 mg, 6.682 mmol) dissolved in chloroform (134 mL) was added dropwise and stirred for 4.5 hr at 0° C. The reaction mixture was extracted by EA and aq. NaHCO$_3$. The organic layer was dried over anhydrous MgSO$_4$ and concentrated. The crude mixture was solidified using DCM, hexane and diethyl ether to give compound 112, tert-butyl (S)-4-(7-(3,4-dimethoxy-phenyl)pyrazolo[1,5-a]pyrimidine-2-carbonyl)-2-methylpiperazine-1-carboxylate. (2335.6 mg, 73%) as a beige solid.

Synthesis of Compound 181

Compound 112

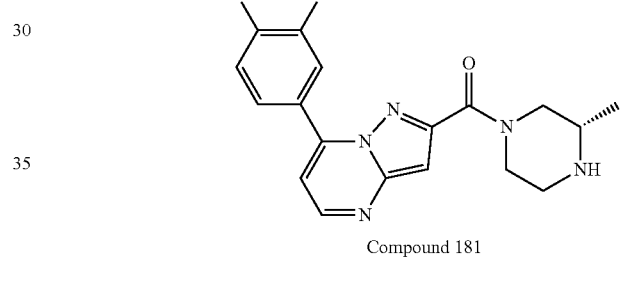

Compound 181

Compound 112 (2335 mg, 4.849 mmol), TFA (3.614 ml, 48.489 mmol) were combined in DCM (48.489 mL) at r.t. for 20 hr. After evaporation, the reaction mixture was extracted by DCM and aq. NaHCO$_3$. The organic layer was dried over anhydrous MgSO$_4$ and concentrated in vacuo to give compound 181, (S)-(7-(3,4-dimethoxyphenyl)pyrazolo[1,5-a]pyrimidin-2-yl)(3-methylpiperazin-1-yl)methanone (1784 mg, 97%) as a yellow solid.

Synthesis of Compound 210

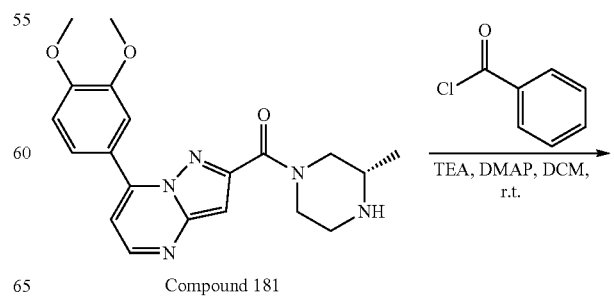

Compound 181

-continued

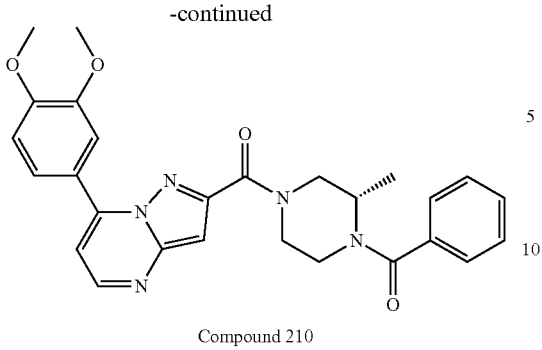

Compound 210

Compound 181 (1784 mg, 4.688 mmol), benzoyl chloride (986 mg, 7.016 mmol), TEA (2366 mg, 23.385 mmol), DMAP (6 mg, 0.01 eq) were combined in DCM at r.t. for 14 hr. The reaction mixture was extracted by DCM and aq. NaHCO₃. The organic layer was dried over anhydrous MgSO₄ and concentrated. The reaction mixture was purified by MPLC. The crude mixture was solidified using DCM and isopropyl ether to give compound 210, (S)-(4-benzoyl-3-methylpiperazin-1-yl)(7-(3,4-dimethoxyphenyl)pyrazolo[1,5-a]pyrimidin-2-yl)methanone (1689 mg, 74% yield) as a yellow solid.

Synthesis of Compound 185

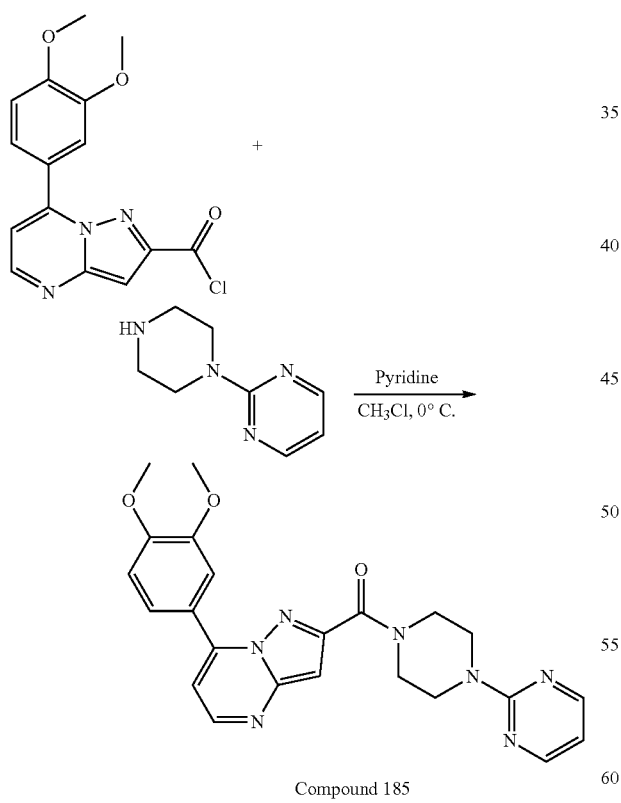

Compound 185

To a solution of 2-(piperazin-1-yl)pyrimidine (36 mg, 0.22 mmol) and pyridine (0.036 mL, 0.44 mmol) in chloroform (2 mL), 7-(3,4-dimethoxyphenyl)pyrazolo[1,5-a]pyrimidine-2-carbonyl chloride (70 mg, 0.22 mmol) dissolved in chloroform (2 mL) was added dropwise and stirred for 2 hr at 0° C. The reaction mixture was extracted by EA and aq. NaHCO₃. The organic layer was dried over anhydrous MgSO₄ and concentrated. The crude mixture was solidified using DCM, hexane and diethyl ether to give compound 185, (7-(3,4-dimethoxyphenyl)pyrazolo[1,5-a]pyrimidin-2-yl)(4-(pyrimidin-2-yl)piperazin-1-yl)methanone (50 mg, 51%) as a white solid.

General Method E

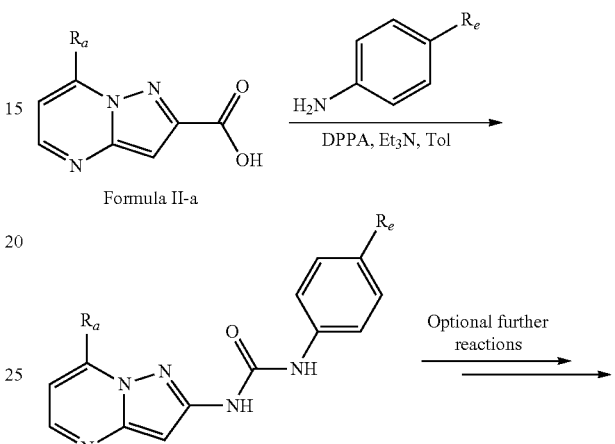

Synthesis of Compound 109

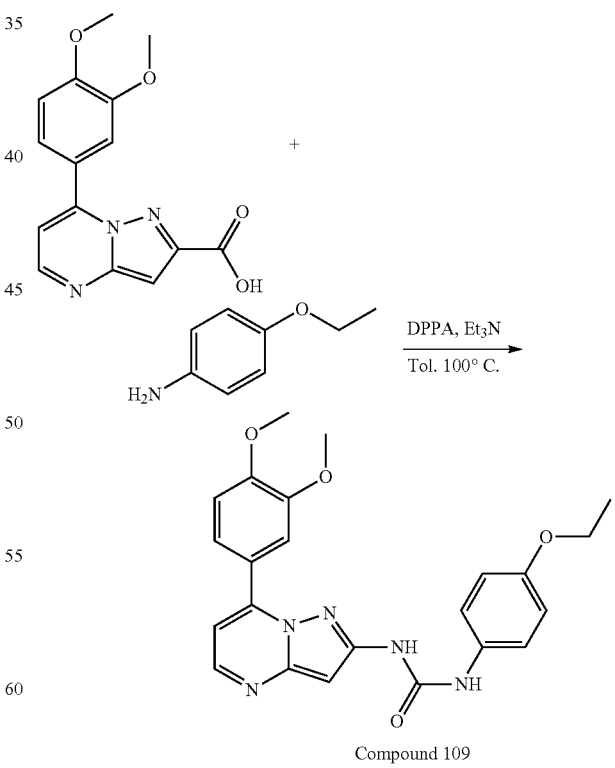

Compound 109

7-(3,4-dimethoxyphenyl)pyrazolo[1,5-a]pyrimidine-2-carboxylic acid (80 mg, 0.267 mmol), p-phenetidine (0.023 mL, 0.178 mmol), DPPA (0.046 mL, 0.214 mmol), TEA (0.075 mL, 0.534 mmol) were combined in toluene (1 mL). The mixture was stirred in microwave at 100° C. for 25 min. The reaction mixture was extracted by DCM and aq. NaHCO₃. The reaction mixture was purified by MPLC. The crude mixture was solidified using DCM and hexane to give compound 109, 1-(7-(3,4-dimethoxyphenyl)pyrazolo[1,5-a]pyrimidin-2-yl)-3-(4-ethoxyphenyl)urea (25 mg, 22% yield) as a pale grey solid.

Synthesis of Compound 93

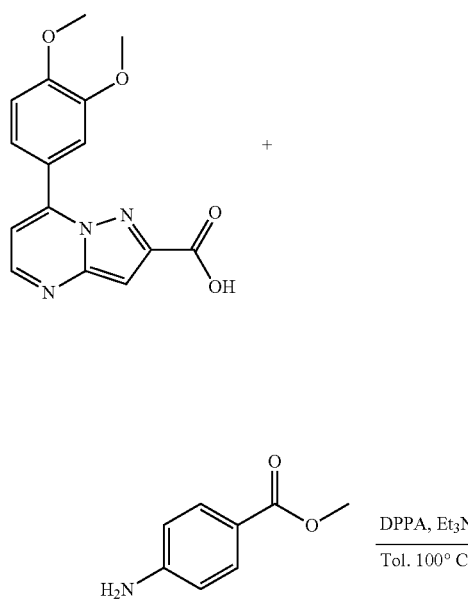

Synthesis of Compound 107

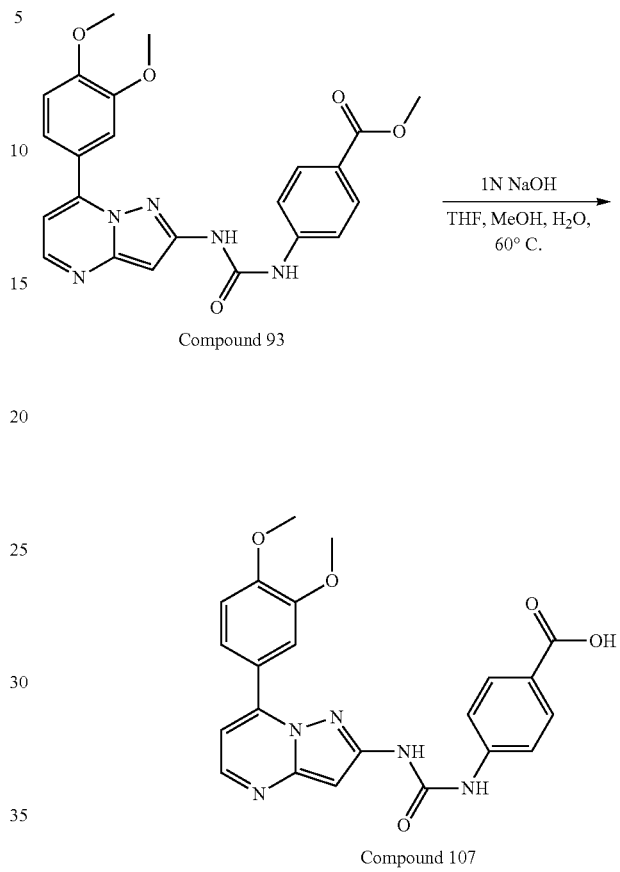

7-(3,4-dimethoxyphenyl)pyrazolo[1,5-a]pyrimidine-2-carboxylic acid (80 mg, 0.267 mmol), methyl 4-aminobenzoate (30.3 mg, 0.200 mmol), DPPA (0.047 mL, 0.216 mmol), TEA (0.083 mL, 0.594 mmol) were combined in toluene (1 mL). The mixture was stirred in microwave at 100° C. for 15 min. The reaction mixture was extracted by DCM and aq. NaHCO₃. The reaction mixture was purified by MPLC. The crude mixture was solidified using DCM, methanol and hexane to give compound 93, methyl 4-(3-(7-(3,4-dimethoxyphenyl)pyrazolo[1,5-a]pyrimidin-2-yl)ureido)benzoate (55.5 mg, 42% yield) as a pale yellow solid.

Compound 93 (55 mg, 0.123 mmol) was dissolved in H₂O/THF/MeOH (0.5/0.8/0.4 mL), followed up by addition of sodium hydroxide in H₂O (1 N, 0.246 mL) and stirred at 60° C. for 7 hr. After cooling at 0° C., the mixture was acidified by adding 1 N HCl. Then the solid was filtered by using H₂O to give compound 107, 4-(3-(7-(3,4-dimethoxyphenyl)pyrazolo[1,5-a]pyrimidin-2-yl)ureido)benzoic acid (31.4 mg, 59% yield) as an orange solid.

Synthesis of Compound 129

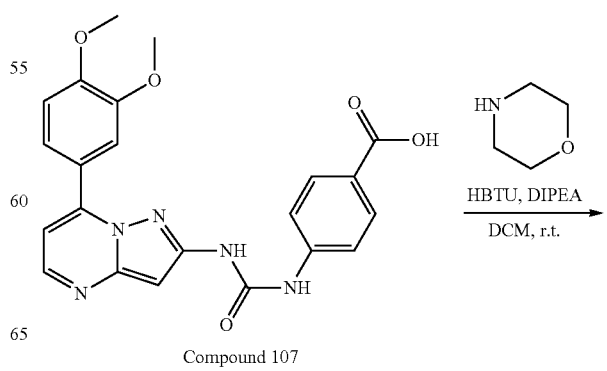

346

Synthesis of Compound 287

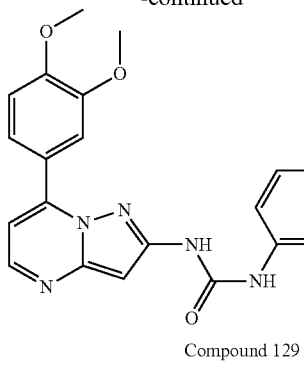

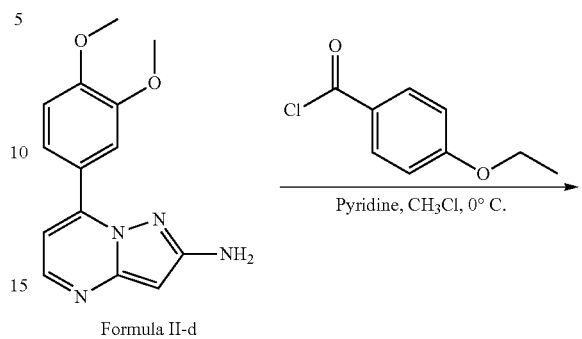

Compound 129

Compound 107 (24 mg, 0.0554 mmol), morpholine (0.005 mL, 0.0609 mmol), HBTU (23 mg, 0.0609 mmol), diisopropylethylamine (0.019 mL, 0.1108 mmol) were combined in DCM. After stirring for 22 hr at r.t., the reaction mixture was extracted by DCM and aq. NaHCO$_3$. The reaction mixture was purified by MPLC. The crude mixture was solidified using DCM and hexane to give compound 129, 1-(7-(3,4-dimethoxyphenyl)pyrazolo[1,5-a]pyrimidin-2-yl)-3-(4-(morpholin-4-carbonyl)phenyl)urea (16 mg, 57% yield) as a pale yellow solid.

General Method F

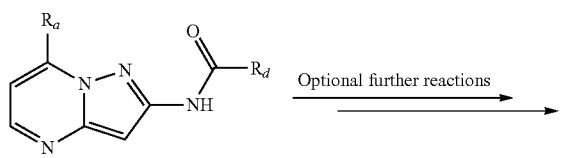

Formula II-d

To a solution of 7-(3,4-dimethoxyphenyl)pyrazolo[1,5-a]pyrimidin-2-amine (31 mg, 0.12 mmol) and pyridine (0.019 mL, 0.23 mmol) in chloroform (1 mL), 4-ethoxybenzoyl chloride (21 mg, 0.12 mmol) dissolved in chloroform (1 mL) was added dropwise and stirred for 2 hr at 0° C. The reaction mixture was extracted by EA and aq. NaHCO$_3$. The organic layer was dried over anhydrous MgSO$_4$ and concentrated. The reaction mixture was purified by MPLC to give compound 287, N-(7-(3,4-dimethoxyphenyl)pyrazolo[1,5-a]pyrimidin-2-yl)-4-ethoxybenzamide as a white solid. (20 mg, 42%)

Synthesis of Compound 288

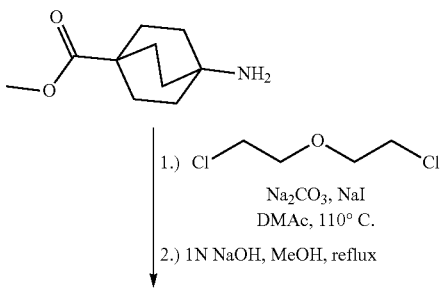

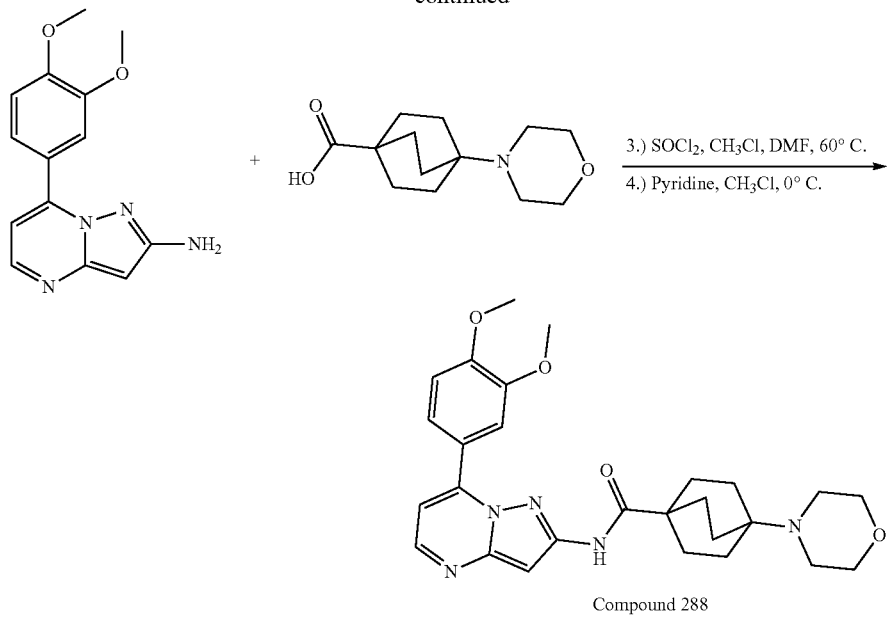

Compound 288

Step 1
Methyl 4-aminobicyclo[2.2.2]octane-1-carboxylate (109 mg, 0.59 mmol), 2-chloro ethyl ether (0.077 mL, 0.65 mmol), sodium carbonate (189 mg, 1.78 mmol) and sodium iodide (178 mg, 0.19 mmol) were combined in N,N-dimethylacetamide (DMAc) (2 mL) and stirred at 110° C. 2-Chloro ethyl ether (0.070 mL) was added twice for every 30 minutes. After 16 hr, the mixture was extracted by DCM and H₂O. The organic layer was dried over anhydrous MgSO₄ and concentrated to give methyl 4-morpholinobicyclo[2.2.2]octane-1-carboxylate (115.5 mg, 77%) as a white solid.

Step 2
Methyl 4-morpholinobicyclo[2.2.2]octane-1-carboxylate (143 mg, 0.56 mmol) was dissolved in MeOH (5 mL), followed up by addition of sodium hydroxide in H₂O (1 N, 1.130 mL) and heated to reflux for 2 hr. The mixture was concentrated to give 4-morpholinobicyclo[2.2.2]octane-1-carboxylic acid (51 mg, 38%) as a pale red solid.

Step 3
To a solution of 4-morpholinobicyclo[2.2.2]octane-1-carboxylic acid (32 mg, 0.13 mmol) in Chloroform (2 mL), DMF (catalytic amount) and SOCl₂ (0.048 mL, 0.67 mmol) were added and stirred at 60° C. for 2 hr. The mixture was concentrated to give 4-morpholinobicyclo[2.2.2]octane-1-carbonyl chloride (34 mg, 99%).

Step 4
To a solution of 2-(piperazin-1-yl)pyrimidine (36 mg, 0.13 mmol) and pyridine (0.054 mL, 0.67 mmol) in chloroform (2 mL), 4-morpholinobicyclo[2.2.2]octane-1-carbonyl chloride (34 mg, 0.13 mmol) dissolved in chloroform (2 mL) was added dropwise and stirred for 2 hr at 0° C. The reaction mixture was extracted by EA and aq. NaHCO₃. The organic layer was dried over anhydrous MgSO₄ and concentrated. The crude mixture was purified by MPLC to give compound 288, N-(7-(3,4-dimethoxyphenyl)pyrazolo[1,5-a]pyrimidin-2-yl)-4-morpholinobicyclo[2.2.2]octane-1-carboxamide (24.1 mg, 37%) as a pale yellow solid.

General Method G

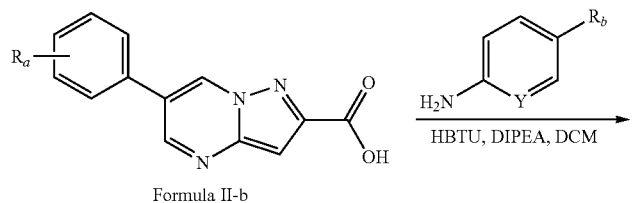

Formula II-b

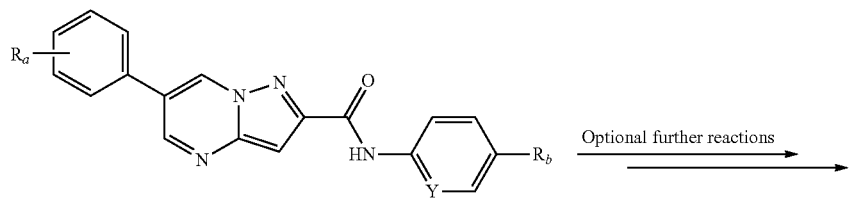

Optional further reactions

349
Synthesis of Compound 239

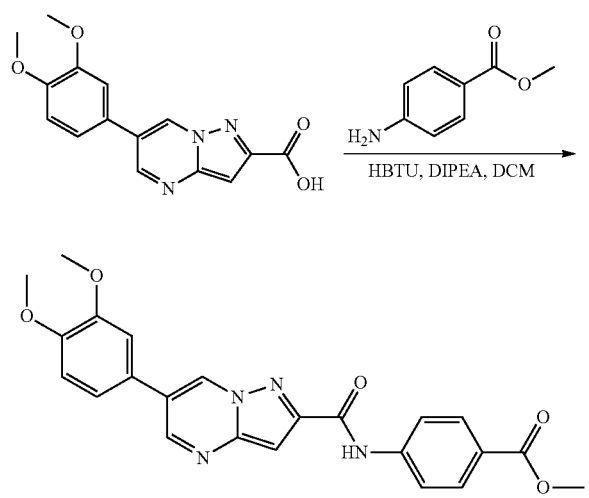

Compound 239

6-(3,4-dimethoxyphenyl)pyrazolo[1,5-a]pyrimidine-2-carboxylic acid (50 mg, 0.0554 mmol), methyl 4-aminobenzoate (28 mg, 0.184 mmol), HBTU (70 mg, 0.184 mmol), diisopropylethylamine (0.058 mL, 0.334 mmol) were combined in DCM. After stirring for 22 hr at r.t., the reaction mixture was extracted by EA and aq. NaHCO$_3$. The reaction mixture was purified by MPLC. The crude mixture was solidified using DCM and hexane to give compound 239, methyl 4-(6-(3,4-dimethoxyphenyl)pyrazolo[1,5-a]pyrimidine-2-carboxamido)benzoate (12 mg, 17% yield) as a white solid.

350
Synthesis of Compound 254

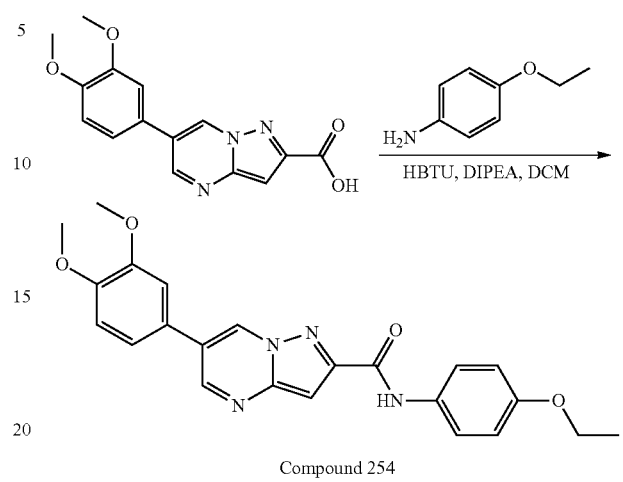

Compound 254

6-(3,4-dimethoxyphenyl)pyrazolo[1,5-a]pyrimidine-2-carboxylic acid (34.4 mg, 0.115 mmol), p-phenetidine (0.016 mL, 0.126 mmol), HBTU (48 mg, 0.126 mmol), diisopropylethylamine (0.040 mL, 0.230 mmol) were combined in DCM. After stirring for 22 hr at r.t., the reaction mixture was extracted by EA and aq. NaHCO$_3$. The reaction mixture was purified by MPLC. The crude mixture was solidified using DCM and hexane to give compound 254, 6-(3,4-dimethoxyphenyl)-N-(4-ethoxyphenyl)pyrazolo[1,5-a]pyrimidine-2-carboxamide (10 mg, 21% yield) as a white solid.

The chemical structures, selected characterizations, and synthetic methods of the compound of the present disclosure are tabulated in Tables 3A and 3B below.

TABLE 3A

Compound Structures, Characterization Data and Synthetic Method

| Cmpd | Structure | Characterization Data | General Method (Ex. 2) |
|---|---|---|---|
| 1 | (structure) | $^1$H NMR (400 MHz, DMSO-d$_6$) δ 10.24 (s, 1H), 8.69 (d, J = 4.5 Hz, 1H), 8.02 (dd, J = 8.5, 2.0 Hz, 1H), 7.96 (d, J = 2.0 Hz, 1H), 7.81 (d, J = 7.8 Hz, 2H), 7.49 (d, J = 4.5 Hz, 1H), 7.38 (t, J = 7.9 Hz, 2H), 7.30 (s, 1H), 7.22 (d, J = 8.6 Hz, 1H), 7.14 (t, J = 7.4 Hz, 1H), 3.93-3.87 (m, 6H). | C |

TABLE 3A-continued

Compound Structures, Characterization Data and Synthetic Method

| Cmpd | Structure | Characterization Data | General Method (Ex. 2) |
|---|---|---|---|
| 2 | 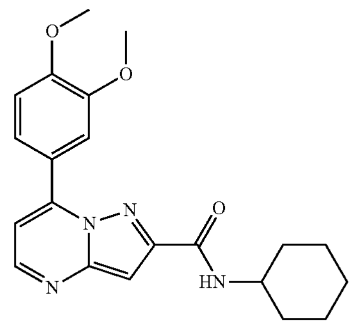 [SMILES: COc1ccc(-c2ccnc3cc(C(=O)NC4CCCCC4)nn23)cc1OC] | $^1$H NMR (400 MHz, DMSO-d$_6$) δ 8.64 (d, J = 4.5 Hz, 1H), 8.05 (d, J = 8.3 Hz, 1H), 7.97 (d, J = 2.1 Hz, 1H), 7.89 (dd, J = 8.5, 2.1 Hz, 1H), 7.42 (d, J = 4.5 Hz, 1H), 7.20 (d, J = 8.6 Hz, 1H), 7.13 (s, 1H), 3.90-3.88 (m, 6H), 3.85-3.76 (m, 1H), 1.90-1.68 (m, 4H), 1.66-1.55 (m, 1H), 1.45-1.24 (m, 4H), 1.21-1.07 (m, 1H). | A |
| 4 | 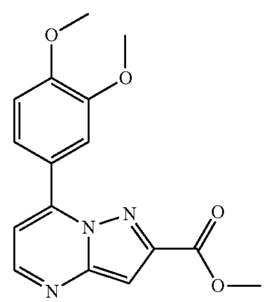 [SMILES: COC(=O)c1cc2nccc(-c3ccc(OC)c(OC)c3)n2n1] | $^1$H NMR (400 MHz, DMSO-d$_6$) δ 8.69 (d, J = 4.4 Hz, 1H), 7.87 (dd, J = 8.6, 2.4 Hz, 1H), 7.78 (d, J = 2.4 Hz, 1H), 7.46 (d, J = 4.4 Hz, 1H), 7.25 (s, 1H), 7.21 (d, J = 8.8 Hz, 1H), 3.91 (s, 3H), 3.89 (s, 3H), 3.87 (s, 3H). | A (Example 11) |
| 6 | 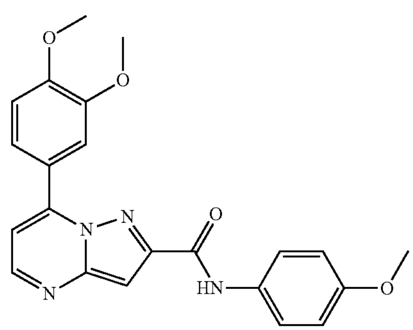 [SMILES: COc1ccc(NC(=O)c2cc3nccc(-c4ccc(OC)c(OC)c4)n3n2)cc1] | $^1$H NMR (400 MHz, DMSO-d$_6$) δ 10.13 (s, 1H), 8.69 (d, J = 4.5 Hz, 1H), 8.02 (dd, J = 8.5, 2.1 Hz, 1H), 7.95 (d, J = 2.1 Hz, 1H), 7.72 (d, J = 9.0 Hz, 2H), 7.48 (d, J = 4.5 Hz, 1H), 7.27 (s, 1H), 7.22 (d, J = 8.6 Hz, 1H), 6.96 (d, J = 9.1 Hz, 2H), 3.92-3.89 (m, 6H), 3.76 (s, 3H). | C |
| 7 | 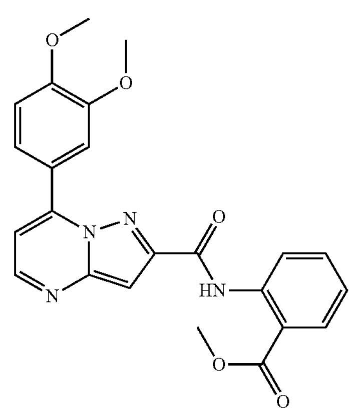 [SMILES: COC(=O)c1ccccc1NC(=O)c1cc2nccc(-c3ccc(OC)c(OC)c3)n2n1] | $^1$H NMR (400 MHz, DMSO-d$_6$) δ 12.52 (s, 1H), 8.87 (d, J = 8.5 Hz, 1H), 8.72 (d, J = 4.5 Hz, 1H), 8.25 (dd, J = 8.5, 2.0 Hz, 1H), 8.09 (d, J = 7.8 Hz, 1H), 7.81 (d, J = 1.9 Hz, 1H), 7.73 (t, J = 7.8 Hz, 1H), 7.55 (d, J = 4.5 Hz, 1H), 7.31 (s, 1H), 7.29-7.21 (m, 2H), 3.95 (s, 3H), 3.92-3.89 (m, 6H). | C |

TABLE 3A-continued

Compound Structures, Characterization Data and Synthetic Method

| Cmpd | Structure | Characterization Data | General Method (Ex. 2) |
|---|---|---|---|
| 8 | 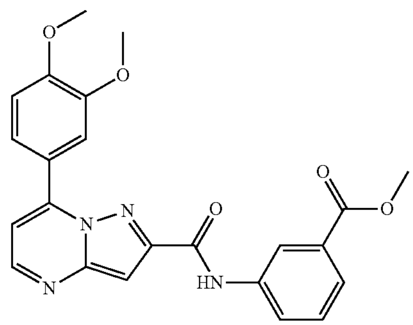 [SMILES: COC(=O)c1cccc(NC(=O)c2cc3nccc(-c4ccc(OC)c(OC)c4)n3n2)c1] | $^1$H NMR (400 MHz, DMSO-d$_6$) δ 10.52 (s, 1H), 8.70 (d, J = 4.5 Hz, 1H), 8.52 (s, 1H), 8.13-8.06 (m, 1H), 8.03 (dd, J = 8.5, 2.1 Hz, 1H), 7.95 (d, J = 2.0 Hz, 1H), 7.74 (d, J = 7.7 Hz, 1H), 7.54 (t, J = 7.9 Hz, 1H), 7.50 (d, J = 4.5 Hz, 1H), 7.33 (s, 1H), 7.23 (d, J = 8.6 Hz, 1H), 3.93-3.87 (m, 9H). | C |
| 9 | 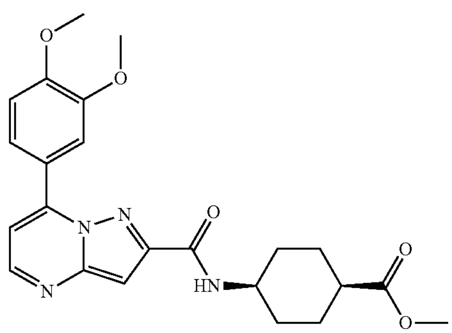 [SMILES: COc1ccc(-c2ccnc3cc(C(=O)N[C@H]4CC[C@@H](C(=O)OC)CC4)nn23)cc1OC] | $^1$H NMR (400 MHz, DMSO-d$_6$) δ 8.64 (d, J = 4.5 Hz, 1H), 8.07 (d, J = 7.9 Hz, 1H), 7.98 (d, J = 2.1 Hz, 1H), 7.90 (dd, J = 8.5, 2.1 Hz, 1H), 7.43 (d, J = 4.5 Hz, 1H), 7.20 (d, J = 8.6 Hz, 1H), 7.14 (s, 1H), 3.99-3.86 (m, 7H), 3.64 (s, 3H), 2.65-2.57 (m, 1H), 2.01-1.88 (m, 2H), 1.74-1.56 (m, 6H). | A |
| 10 | 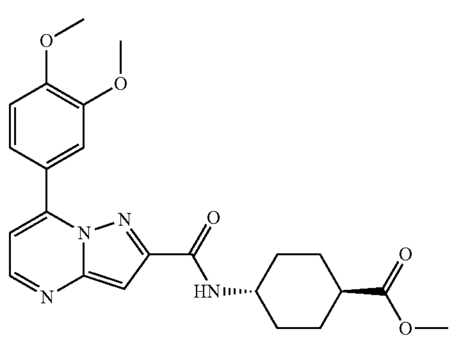 [SMILES: COc1ccc(-c2ccnc3cc(C(=O)N[C@H]4CC[C@H](C(=O)OC)CC4)nn23)cc1OC] | $^1$H NMR (400 MHz, DMSO-d$_6$) δ 8.64 (d, J = 4.5 Hz, 1H), 8.10 (d, J = 8.3 Hz, 1H), 7.96 (d, J = 2.1 Hz, 1H), 7.90 (dd, J = 8.5, 2.1 Hz, 1H), 7.42 (d, J = 4.5 Hz, 1H), 7.20 (d, J = 8.6 Hz, 1H), 7.13 (s, 1H), 3.91-3.88 (m, 6H), 3.86-3.74 (m, 1H), 3.61 (s, 3H), 2.35-2.24 (m, 1H), 2.01-1.83 (m, 4H), 1.52-1.35 (m, 4H). | A |
| 12 | 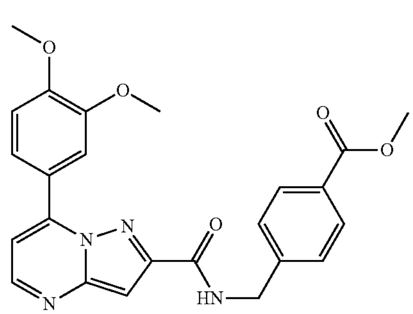 [SMILES: COC(=O)c1ccc(CNC(=O)c2cc3nccc(-c4ccc(OC)c(OC)c4)n3n2)cc1] | $^1$H NMR (400 MHz, DMSO-d$_6$) δ 9.09 (t, J = 6.3 Hz, 1H), 8.66 (dd, J = 4.5, 0.7 Hz, 1H), 7.97-7.90 (m, 3H), 7.86 (d, J = 1.4 Hz, 1H), 7.48 (d, J = 8.1 Hz, 2H), 7.44-7.41 (m, 1H), 7.21-7.15 (m, 2H), 4.60 (d, J = 6.2 Hz, 2H), 3.90-3.83 (m, 9H). | A |

TABLE 3A-continued

Compound Structures, Characterization Data and Synthetic Method

| Cmpd | Structure | Characterization Data | General Method (Ex. 2) |
|---|---|---|---|
| 13 | 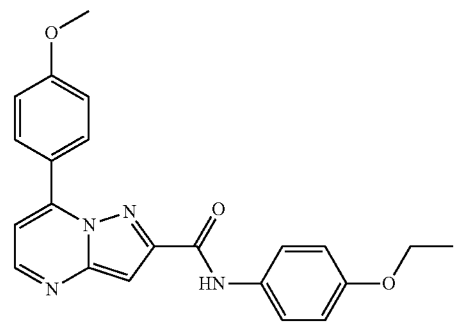 [SMILES: CCOc1ccc(NC(=O)c2cc3nccc(-c4ccc(OC)cc4)n3n2)cc1] | $^1$H NMR (400 MHz, DMSO-d$_6$) δ 10.09 (s, 1H), 8.68 (d, J = 4.5 Hz, 1H), 8.35 (d, J = 9.0 Hz, 2H), 7.69 (d, J = 9.0 Hz, 2H), 7.41 (d, J = 4.5 Hz, 1H), 7.26 (s, 1H), 7.20 (d, J = 9.0 Hz, 2H), 6.94 (d, J = 9.1 Hz, 2H), 4.03 (q, J = 7.0 Hz, 2H), 3.90 (s, 3H), 1.34 (t, J = 7.0 Hz, 3H). | C |
| 14 | 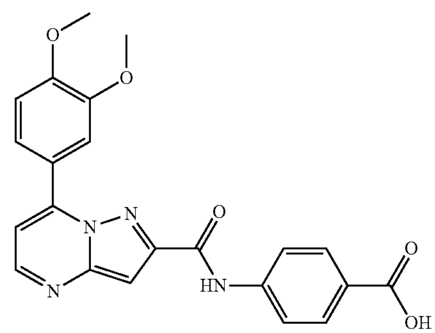 [SMILES: COc1ccc(-c2ccnc3cc(C(=O)Nc4ccc(C(=O)O)cc4)nn23)cc1OC] | $^1$H NMR (400 MHz, DMSO-d$_6$) δ 12.72 (s, 1H), 10.53 (s, 1H), 8.71 (d, J = 4.1 Hz, 1H), 8.09-7.84 (m, 6H), 7.50 (d, J = 4.3 Hz, 1H), 7.34 (s, 1H), 7.23 (d, J = 8.4 Hz, 1H), 4.00-3.82 (m, 6H). | C |
| 15 | 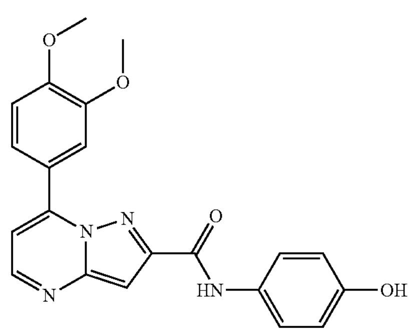 [SMILES: COc1ccc(-c2ccnc3cc(C(=O)Nc4ccc(O)cc4)nn23)cc1OC] | $^1$H NMR (400 MHz, DMSO-d$_6$) δ 10.00 (s, 1H), 9.32 (s, 1H), 8.68 (d, J = 3.4 Hz, 1H), 8.03 (d, J = 8.6 Hz, 1H), 7.93 (s, 1H), 7.57 (d, J = 7.9 Hz, 2H), 7.47 (d, J = 4.3 Hz, 1H), 7.28-7.15 (m, 2H), 6.77 (d, J = 7.7 Hz, 2H), 3.94-3.88 (m, 6H). | C |
| 16 | 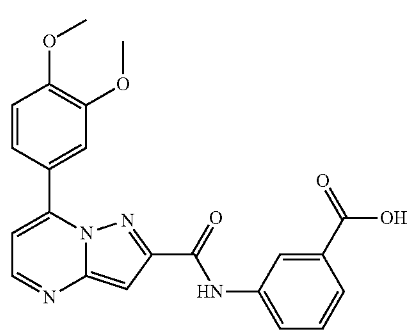 [SMILES: COc1ccc(-c2ccnc3cc(C(=O)Nc4cccc(C(=O)O)c4)nn23)cc1OC] | $^1$H NMR (400 MHz, DMSO-d$_6$) δ 10.47 (s, 1H), 8.70 (d, J = 4.5 Hz, 1H), 8.47-8.44 (m, 1H), 8.10-8.00 (m, 2H), 7.95 (d, J = 2.1 Hz, 1H), 7.71 (d, J = 7.9 Hz, 1H), 7.56-7.47 (m, 2H), 7.33 (s, 1H), 7.23 (d, J = 8.6 Hz, 1H), 3.92-3.89 (m, 6H). | C |

TABLE 3A-continued

Compound Structures, Characterization Data and Synthetic Method

| Cmpd | Structure | Characterization Data | General Method (Ex. 2) |
|---|---|---|---|
| 17 | 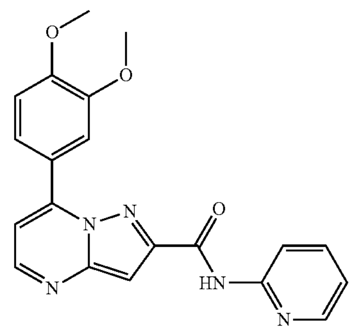 [SMILES: COc1ccc(-c2ccnc3cc(C(=O)Nc4ccccn4)nn23)cc1OC] | ¹H NMR (400 MHz, DMSO-d₆) δ 10.02 (s, 1H), 8.76-8.67 (m, 1H), 8.45-8.37 (m, 1H), 8.25 (d, J = 8.3 Hz, 1H), 7.99-7.87 (m, 3H), 7.53-7.48 (m, 1H), 7.39 (d, J = 3.5 Hz, 1H), 7.30-7.17 (m, 2H), 3.96-3.89 (m, 6H). | C |
| 18 | 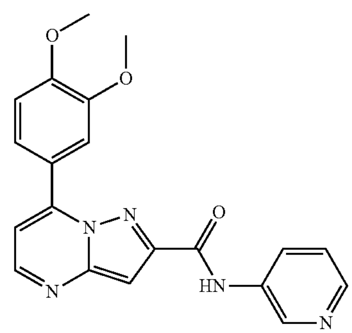 [SMILES: COc1ccc(-c2ccnc3cc(C(=O)Nc4cccnc4)nn23)cc1OC] | ¹H NMR (400 MHz, DMSO-d₆) δ 10.52 (s, 1H), 8.98 (d, J = 2.1 Hz, 1H), 8.70 (d, J = 4.5 Hz, 1H), 8.40-8.33 (m, 1H), 8.29-8.20 (m, 1H), 8.09-7.90 (m, 2H), 7.58-7.39 (m, 2H), 7.33 (s, 1H), 7.22 (d, J = 8.5 Hz, 1H), 4.01-3.88 (m, 6H). | C |
| 19 | 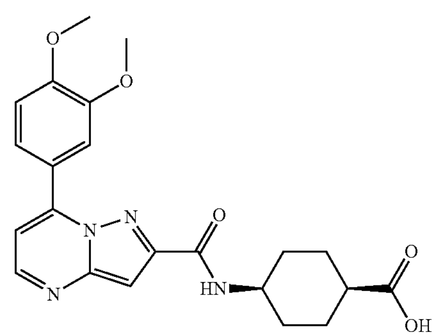 [SMILES: COc1ccc(-c2ccnc3cc(C(=O)N[C@H]4CC[C@@H](C(=O)O)CC4)nn23)cc1OC] | ¹H NMR (400 MHz, DMSO-d₆) δ 8.64 (d, J = 4.5 Hz, 1H), 8.08 (d, J = 7.7 Hz, 1H), 7.98 (d, J = 2.0 Hz, 1H), 7.94-7.88 (m, 1H), 7.43 (d, J = 4.5 Hz, 1H), 7.21 (s, 1H), 7.14 (s, 1H), 3.94-3.86 (m, J = 8.0 Hz, 7H), 2.48-2.43 (m, 1H), 1.99-1.90 (m, 2H), 1.72-1.57 (m, 6H). | A |
| 20 | 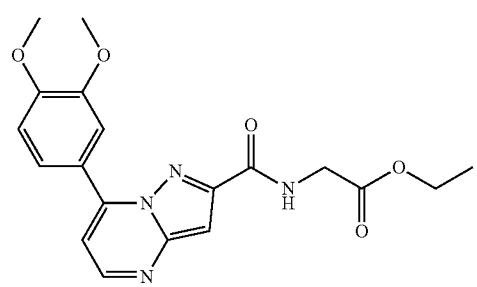 [SMILES: CCOC(=O)CNC(=O)c1cc2nccc(-c3ccc(OC)c(OC)c3)n2n1] | ¹H NMR (400 MHz, DMSO-d₆) δ 8.75 (t, J = 6.0 Hz, 1H), 8.67 (d, J = 4.5 Hz, 1H), 7.93 (dd, J = 8.5, 2.1 Hz, 1H), 7.82 (d, J = 2.1 Hz, 1H), 7.43 (d, J = 4.5 Hz, 1H), 7.20 (d, J = 8.6 Hz, 1H), 7.16 (s, 1H), 4.13 (q, J = 7.1 Hz, 2H), 4.06 (d, J = 6.1 Hz, 2H), 3.91-3.87 (m, 6H), 1.21 (t, J = 7.1 Hz, 3H). | A |

TABLE 3A-continued

Compound Structures, Characterization Data and Synthetic Method

| Cmpd | Structure | Characterization Data | General Method (Ex. 2) |
|---|---|---|---|
| 21 | 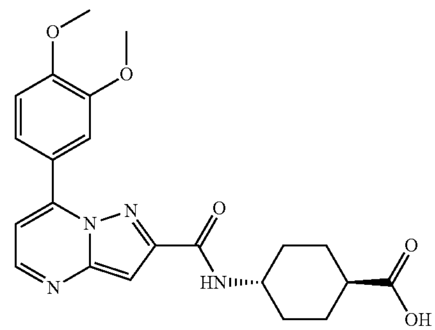 [SMILES: COc1ccc(-c2ccnc3cc(C(=O)N[C@H]4CC[C@H](C(=O)O)CC4)nn23)cc1OC] | ¹H NMR (400 MHz, DMSO-d₆) δ 12.06 (s, 1H), 8.64 (d, J = 4.5 Hz, 1H), 8.10 (d, J = 8.3 Hz, 1H), 7.96 (d, J = 2.1 Hz, 1H), 7.90 (dd, J = 8.5, 2.1 Hz, 1H), 7.43 (d, J = 4.5 Hz, 1H), 7.20 (d, J = 8.6 Hz, 1H), 7.13 (s, 1H), 3.92-3.87 (m, 6H), 3.82-3.73 (m, 1H), 2.22-2.12 (m, 1H), 2.02-1.85 (m, 4H), 1.52-1.35 (m, 4H). | A |
| 22 | 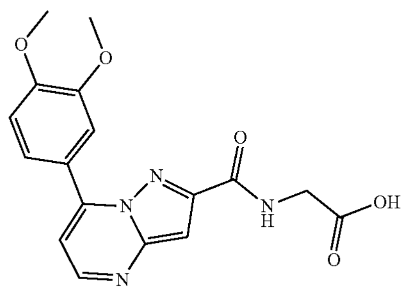 [SMILES: COc1ccc(-c2ccnc3cc(C(=O)NCC(=O)O)nn23)cc1OC] | ¹H NMR (400 MHz, DMSO-d₆) δ 8.67 (d, J = 4.5 Hz, 1H), 8.60 (t, J = 5.4 Hz, 1H), 7.92 (dd, J = 8.5, 2.1 Hz, 1H), 7.85 (d, J = 2.0 Hz, 1H), 7.43 (d, J = 4.5 Hz, 1H), 7.20 (d, J = 8.6 Hz, 1H), 7.15 (d, J = 0.6 Hz, 1H), 3.98 (d, J = 6.0 Hz, 2H), 3.92-3.86 (m, 6H). | A |
| 23 | 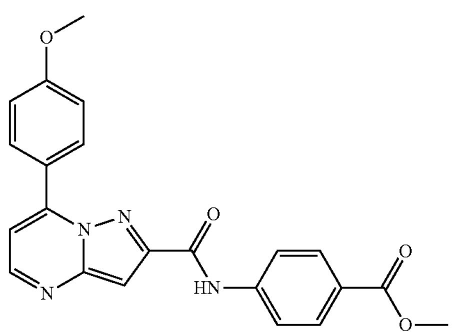 [SMILES: COC(=O)c1ccc(NC(=O)c2cc3nccc(-c4ccc(OC)cc4)n3n2)cc1] | ¹H NMR (400 MHz, DMSO-d₆) δ 10.56 (s, 1H), 8.70 (d, J = 4.5 Hz, 1H), 8.35 (d, J = 8.8 Hz, 2H), 8.00 (s, 4H), 7.43 (d, J = 4.4 Hz, 1H), 7.34 (s, 1H), 7.20 (d, J = 8.8 Hz, 2H), 3.91 (s, 3H), 3.85 (s, 3H). | C |
| 24 | 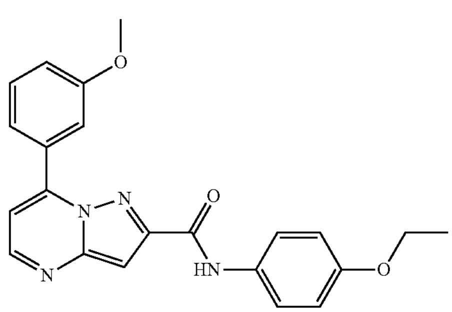 [SMILES: CCOc1ccc(NC(=O)c2cc3nccc(-c4cccc(OC)c4)n3n2)cc1] | ¹H NMR (400 MHz, DMSO-d₆) δ 10.14 (s, 1H), 8.72 (d, J = 4.2 Hz, 1H), 7.86-7.79 (m, 2H), 7.68 (d, J = 8.7 Hz, 2H), 7.56 (t, J = 7.9 Hz, 1H), 7.45 (d, J = 4.3 Hz, 1H), 7.31 (s, 1H), 7.24 (d, J = 7.7 Hz, 1H), 6.93 (d, J = 8.8 Hz, 2H), 4.02 (q, J = 13.9, 6.9 Hz, 2H), 3.88 (s, 3H), 1.33 (t, J = 6.9 Hz, 3H). | C |

TABLE 3A-continued

Compound Structures, Characterization Data and Synthetic Method

| Cmpd | Structure | Characterization Data | General Method (Ex. 2) |
|---|---|---|---|
| 25 | 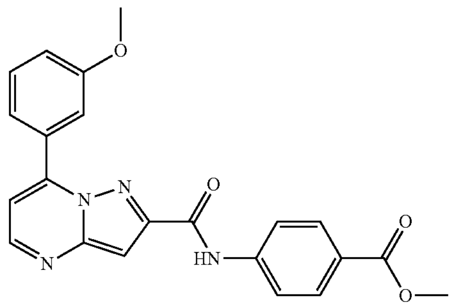 [SMILES: COC(=O)c1ccc(NC(=O)c2cc3nccc(-c4cccc(OC)c4)n3n2)cc1] | ¹H NMR (400 MHz, DMSO-d₆) δ 10.60 (s, 1H), 8.74 (d, J = 4.4 Hz, 1H), 7.98 (s, 4H), 7.86-7.79 (m, 2H), 7.57 (t, J = 8.0 Hz, 1H), 7.47 (d, J = 4.4 Hz, 1H), 7.38 (s, 1H), 7.24 (dd, J = 8.3, 2.5 Hz, 1H), 3.88 (s, 3H), 3.85 (s, 3H). | C |
| 26 | 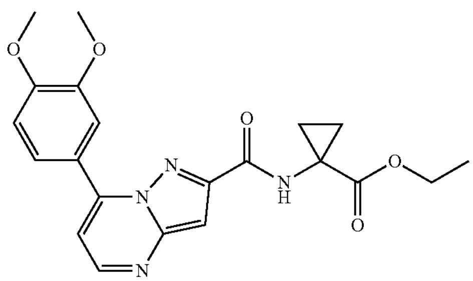 [SMILES: CCOC(=O)C1(NC(=O)c2cc3nccc(-c4ccc(OC)c(OC)c4)n3n2)CC1] | ¹H NMR (400 MHz, DMSO-d₆) δ 9.08 (s, 1H), 8.66 (d, J = 4.5 Hz, 1H), 7.99 (d, J = 8.5, 2.0 Hz, 1H), 7.85 (d, J = 2.0 Hz, 1H), 7.44 (d, J = 4.4 Hz, 1H), 7.23-7.12 (m, 2H), 4.10-4.03 (m, 2H), 3.93-3.87 (m, 6H), 1.51-1.46 (m, 2H), 1.25-1.20 (m, 2H), 1.13 (t, J = 7.1 Hz, 3H). | A |
| 27 | 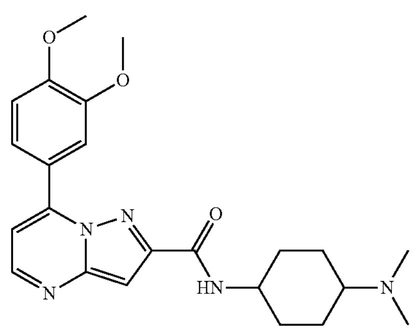 [SMILES: COc1ccc(-c2ccnc3cc(C(=O)NC4CCC(N(C)C)CC4)nn23)cc1OC] | ¹H NMR (400 MHz, DMSO-d₆) δ 8.64 (d, J = 4.5 Hz, 1H), 8.00-7.92 (m, 3H), 7.42 (d, J = 4.5 Hz, 1H), 7.22-7.14 (m, 2H), 4.04-3.94 (m, 1H), 3.93-3.85 (m, 6H), 2.30-2.08 (m, 7H), 1.86-1.68 (m, 4H), 1.65-1.48 (m, 4H). | A |
| 28 | 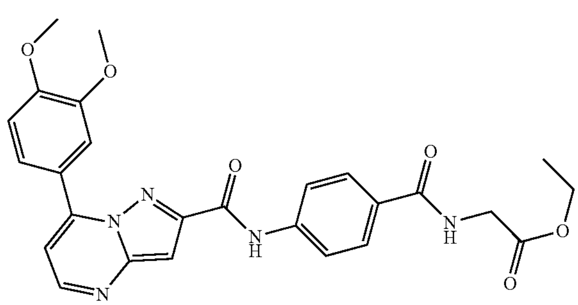 [SMILES: CCOC(=O)CNC(=O)c1ccc(NC(=O)c2cc3nccc(-c4ccc(OC)c(OC)c4)n3n2)cc1] | ¹H NMR (400 MHz, DMSO-d₆) δ 10.50 (s, 1H), 8.89 (t, J = 5.8 Hz, 1H), 8.71 (d, J = 4.5 Hz, 1H), 8.03 (dd, J = 8.5, 2.1 Hz, 1H), 7.97-7.88 (m, 5H), 7.50 (d, J = 4.5 Hz, 1H), 7.33 (s, 1H), 7.23 (d, J = 8.6 Hz, 1H), 4.13 (q, J = 7.1 Hz, 2H), 4.00 (d, J = 5.8 Hz, 2H), 3.95-3.87 (m, 6H), 1.22 (t, J = 7.1 Hz, 3H). | C |

TABLE 3A-continued

Compound Structures, Characterization Data and Synthetic Method

| Cmpd | Structure | Characterization Data | General Method (Ex. 2) |
|---|---|---|---|
| 29 | 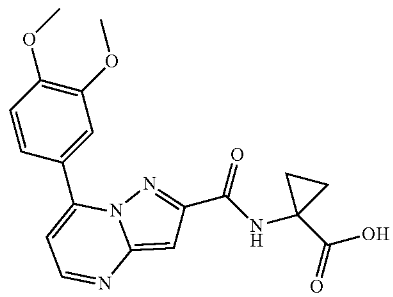 [SMILES: COc1ccc(-c2ccnc3cc(C(=O)NC4(C(=O)O)CC4)nn23)cc1OC] | $^1$H NMR (400 MHz, DMSO-d$_6$) δ 8.97 (s, 1H), 8.65 (d, J = 4.5 Hz, 1H), 7.99 (dd, J = 8.5, 2.2 Hz, 1H), 7.85 (d, J = 2.1 Hz, 1H), 7.44 (d, J = 4.5 Hz, 1H), 7.19 (d, J = 8.6 Hz, 1H), 7.14 (s, 1H), 3.91-3.87 (m, 6H), 1.47-1.39 (m, 2H), 1.22-1.15 (m, 2H). | A |
| 30 | 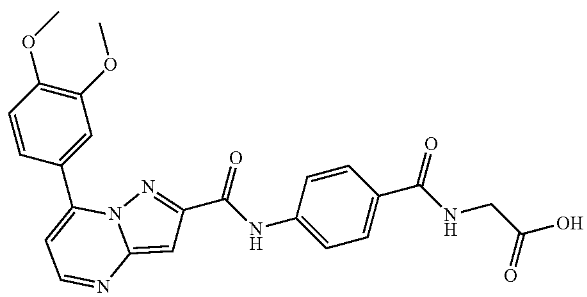 [SMILES: COc1ccc(-c2ccnc3cc(C(=O)Nc4ccc(C(=O)NCC(=O)O)cc4)nn23)cc1OC] | $^1$H NMR (400 MHz, DMSO-d$_6$) δ 12.59 (s, 1H), 10.50 (s, 1H), 8.79 (t, J = 5.9 Hz, 1H), 8.71 (d, J = 4.5 Hz, 1H), 8.03 (dd, J = 8.5, 2.1 Hz, 1H), 7.98-7.87 (m, 5H), 7.50 (d, J = 4.5 Hz, 1H), 7.34 (s, 1H), 7.23 (d, J = 8.6 Hz, 1H), 3.96-3.87 (m, 8H). | C |
| 31 | 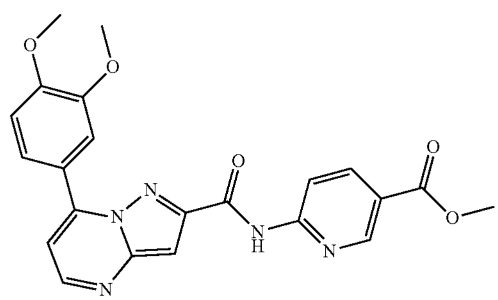 [SMILES: COC(=O)c1ccc(NC(=O)c2cc3nccc(-c4ccc(OC)c(OC)c4)n3n2)nc1] | $^1$H NMR (400 MHz, CDCl$_3$) δ 9.73 (s, 1H), 8.97 (d, J = 2.1 Hz, 1H), 8.63 (d, J = 4.3 Hz, 1H), 8.52 (d, J = 8.7 Hz, 1H), 8.39 (dd, J = 8.7, 2.2 Hz, 1H), 7.80 (d, J = 2.1 Hz, 1H), 7.71 (dd, J = 8.4, 2.1 Hz, 1H), 7.45 (s, 1H), 7.21-7.07 (m, 2H), 4.13-4.03 (m, 6H), 3.97 (s, 3H). | B |
| 32 | 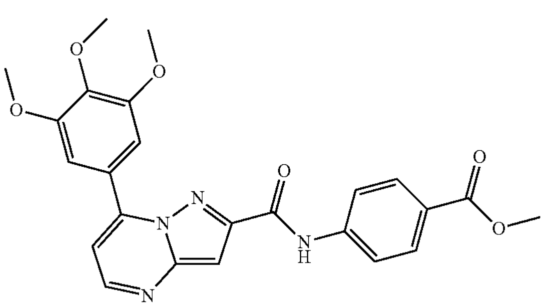 | $^1$H NMR (400 MHz, DMSO-d$_6$) δ 10.64 (s, 1H), 8.74 (d, J = 4.4 Hz, 1H), 8.04-7.92 (m, 4H), 7.67 (s, 2H), 7.57 (d, J = 4.4 Hz, 1H), 7.37 (s, 1H), 3.96-3.88 (m, 6H), 3.85 (s, 3H), 3.80 (s, 3H). | C |

TABLE 3A-continued

Compound Structures, Characterization Data and Synthetic Method

| Cmpd | Structure | Characterization Data | General Method (Ex. 2) |
|---|---|---|---|
| 33 | 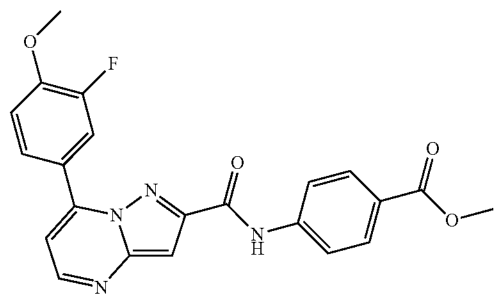 [SMILES: COC(=O)c1ccc(NC(=O)c2cc3nccc(-c4ccc(OC)c(F)c4)n3n2)cc1] | ¹H NMR (400 MHz, DMSO-d₆) δ 10.64 (s, 1H), 8.72 (d, J = 4.5 Hz, 1H), 8.33 (dd, J = 12.8, 2.2 Hz, 1H), 8.24 (d, J = 8.7 Hz, 1H), 8.00 (s, 4H), 7.51 (d, J = 4.5 Hz, 1H), 7.44 (t, J = 8.9 Hz, 1H), 7.37 (s, 1H), 3.99 (s, 3H), 3.85 (s, 3H). | C |
| 34 | 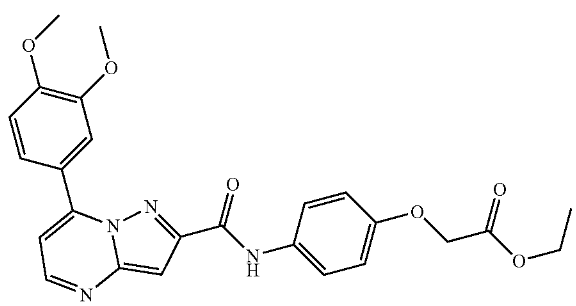 [SMILES: CCOC(=O)COc1ccc(NC(=O)c2cc3nccc(-c4ccc(OC)c(OC)c4)n3n2)cc1] | ¹H NMR (400 MHz, DMSO-d₆) δ 10.18 (s, 1H), 8.68 (d, J = 4.5 Hz, 1H), 8.02 (dd, J = 8.5, 2.1 Hz, 1H), 7.94 (d, J = 2.1 Hz, 1H), 7.71 (d, J = 9.1 Hz, 2H), 7.48 (d, J = 4.5 Hz, 1H), 7.27 (s, 1H), 7.21 (d, J = 8.6 Hz, 1H), 6.95 (d, J = 9.1 Hz, 2H), 4.77 (s, 2H), 4.18 (q, J = 7.1 Hz, 2H), 3.96-3.87 (m, 6H), 1.22 (t, J = 7.1 Hz, 3H). | C |
| 35 | 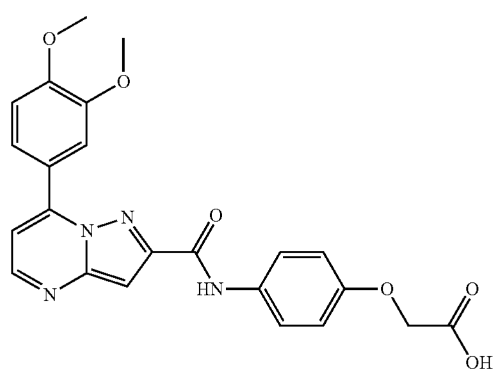 [SMILES: COc1ccc(-c2ccnc3cc(C(=O)Nc4ccc(OCC(=O)O)cc4)nn23)cc1OC] | ¹H NMR (400 MHz, DMSO-d₆) δ 13.07 (s, 1H), 10.16 (s, 1H), 8.68 (d, J = 4.5 Hz, 1H), 8.02 (dd, J = 8.5, 1.9 Hz, 1H), 7.94 (d, J = 1.9 Hz, 1H), 7.70 (d, J = 9.0 Hz, 2H), 7.48 (d, J = 4.5 Hz, 1H), 7.27 (s, 1H), 7.21 (d, J = 8.6 Hz, 1H), 6.93 (d, J = 9.0 Hz, 2H), 4.66 (s, 2H), 3.93-3.87 (m, 6H). | C |
| 36 | 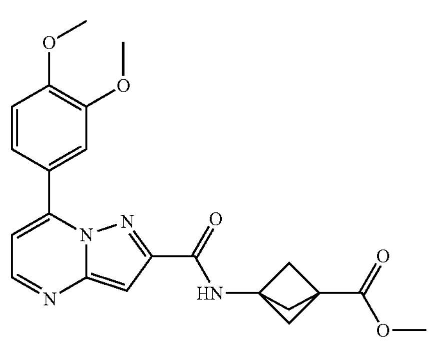 [SMILES: COC(=O)C12CC(NC(=O)c3cc4nccc(-c5ccc(OC)c(OC)c5)n4n3)(C1)C2] | ¹H NMR (400 MHz, DMSO-d₆) δ 9.08 (s, 1H), 8.64 (d, J = 4.5 Hz, 1H), 7.97 (dd, J = 8.5, 2.1 Hz, 1H), 7.80 (d, J = 2.0 Hz, 1H), 7.42 (d, J = 4.5 Hz, 1H), 7.19 (d, J = 8.6 Hz, 1H), 7.12 (s, 1H), 3.91-3.86 (m, 6H), 3.63 (s, 3H), 2.36 (s, 6H). | B |

TABLE 3A-continued

Compound Structures, Characterization Data and Synthetic Method

| Cmpd | Structure | Characterization Data | General Method (Ex. 2) |
|---|---|---|---|
| 37 | 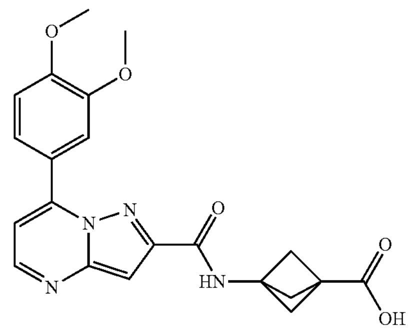 [SMILES: COc1ccc(-c2ccnc3cc(C(=O)NC45CC(C(=O)O)(C4)C5)nn23)cc1OC] | $^1$H NMR (400 MHz, DMSO-d$_6$) δ 12.49 (s, 1H), 9.03 (s, 1H), 8.64 (d, J = 4.5 Hz, 1H), 7.97 (dd, J = 8.5, 2.1 Hz, 1H), 7.80 (d, J = 2.1 Hz, 1H), 7.42 (d, J = 4.5 Hz, 1H), 7.19 (d, J = 8.6 Hz, 1H), 7.12 (s, 1H), 3.93-3.87 (m, 6H), 2.32 (s, 6H). | B |
| 38 | 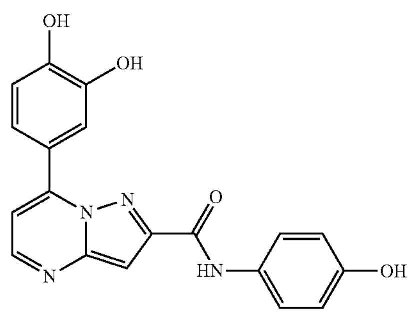 [SMILES: O=C(Nc1ccc(O)cc1)c1cc2nccc(-c3ccc(O)c(O)c3)n2n1] | $^1$H NMR (400 MHz, DMSO-d$_6$) δ 9.89 (s, 1H), 9.74-9.06 (m, 3H), 8.61 (d, J = 4.5 Hz, 1H), 7.82 (d, J = 2.2 Hz, 1H), 7.69 (dd, J = 8.4, 2.3 Hz, 1H), 7.56 (d, J = 8.9 Hz, 2H), 7.29 (d, J = 4.5 Hz, 1H), 7.21 (s, 1H), 6.96 (d, J = 8.4 Hz, 1H), 6.77 (d, J = 8.9 Hz, 2H). | C |
| 39 | 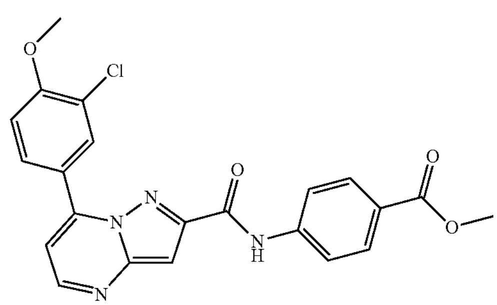 | $^1$H NMR (400 MHz, DMSO-d$_6$) δ 10.60 (s, 1H), 8.71 (d, J = 4.4 Hz, 1H), 8.50-8.33 (m, 2H), 8.09-7.90 (m, 4H), 7.50 (d, J = 4.4 Hz, 1H), 7.42 (d, J = 8.5 Hz, 1H), 7.37 (s, 1H), 4.01 (s, 3H), 3.85 (s, 3H). | C |
| 40 | 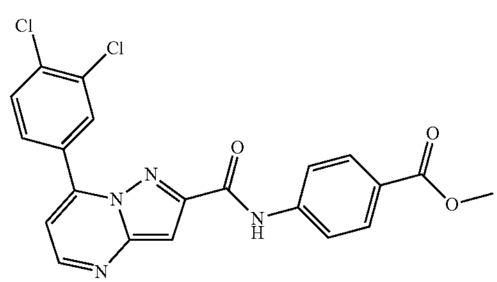 [SMILES: COC(=O)c1ccc(NC(=O)c2cc3nccc(-c4ccc(Cl)c(Cl)c4)n3n2)cc1] | $^1$H NMR (400 MHz, DMSO-d$_6$) δ 10.58 (s, 1H), 8.77 (d, J = 4.4 Hz, 1H), 8.52 (d, J = 2.1 Hz, 1H), 8.31 (dd, J = 8.5, 2.1 Hz, 1H), 7.99 (s, 4H), 7.93 (d, J = 8.5 Hz, 1H), 7.55 (d, J = 4.4 Hz, 1H), 7.41 (s, 1H), 3.85 (s, 3H). | C |

TABLE 3A-continued

Compound Structures, Characterization Data and Synthetic Method

| Cmpd | Structure | Characterization Data | General Method (Ex. 2) |
|---|---|---|---|
| 41 | 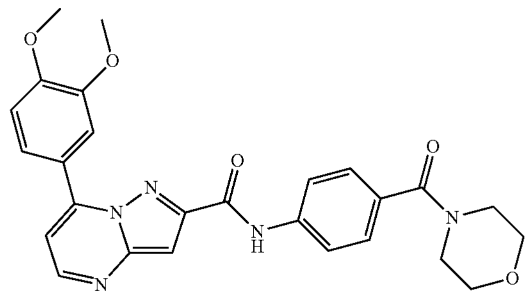 [SMILES: COc1ccc(-c2ccnc3cc(C(=O)Nc4ccc(C(=O)N5CCOCC5)cc4)nn23)cc1OC] | $^1$H NMR (400 MHz, DMSO-d6) δ 10.43 (s, 1H), 8.70 (d, J = 4.5 Hz, 1H), 8.01 (dd, J = 8.5, 2.1 Hz, 1H), 7.96 (d, J = 2.0 Hz, 1H), 7.90 (d, J = 8.56 Hz, 2H), 7.49 (d, J = 4.5 Hz, 1H), 7.45 (d, J = 8.5 Hz, 2H), 7.32 (s, 1H), 7.22 (d, J = 8.6 Hz, 1H), 3.93-3.87 (m, 6H), 3.67-3.39 (m, 8H). | C |
| 42 | 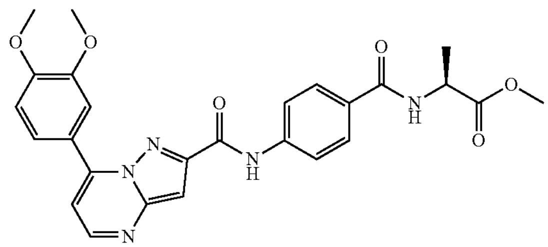 [SMILES: COC(=O)[C@H](C)NC(=O)c1ccc(NC(=O)c2cc3nccc(-c4ccc(OC)c(OC)c4)n3n2)cc1] | $^1$H NMR (400 MHz, DMSO-d$_6$) δ 10.49 (s, 1H), 8.77-8.64 (m, 2H), 8.03 (dd, J = 8.5, 2.1 Hz, 1H), 7.99-7.84 (m, 5H), 7.50 (d, J = 4.5 Hz, 1H), 7.34 (s, 1H), 7.23 (d, J = 8.6 Hz, 1H), 4.57-4.41 (m, 1H), 3.95-3.83 (m, 6H), 3.66 (s, 3H), 1.42 (d, J = 7.3 Hz, 3H). | C |
| 43 | 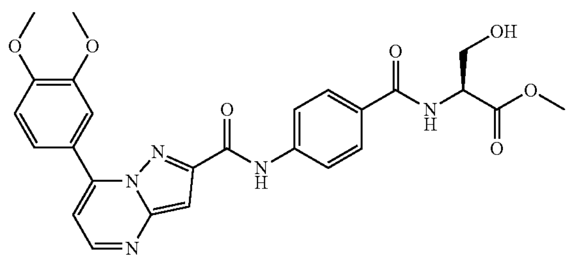 [SMILES: COC(=O)[C@H](CO)NC(=O)c1ccc(NC(=O)c2cc3nccc(-c4ccc(OC)c(OC)c4)n3n2)cc1] | $^1$H NMR (400 MHz, DMSO-d$_6$) δ 10.49 (s, 1H), 8.71 (d, J = 4.4 Hz, 1H), 8.51 (d, J = 7.3 Hz, 1H), 8.09-7.99 (m, 1H), 7.99-7.88 (m, 5H), 7.51 (d, J = 4.5 Hz, 1H), 7.34 (s, 1H), 7.23 (d, J = 8.6 Hz, 1H), 5.07 (t, J = 6.1 Hz, 1H), 4.64-4.40 (m, 1H), 3.98-3.87 (m, 6H), 3.81 (t, J = 5.7 Hz, 2H), 3.67 (s, 3H). | C |
| 44 | 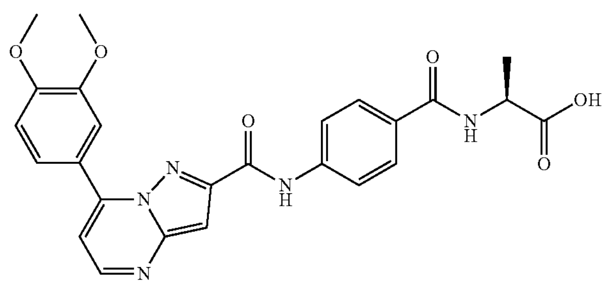 [SMILES: COc1ccc(-c2ccnc3cc(C(=O)Nc4ccc(C(=O)N[C@@H](C)C(=O)O)cc4)nn23)cc1OC] | $^1$H NMR (400 MHz, DMSO-d$_6$) δ 12.53 (s, 1H), 10.47 (s, 1H), 8.71 (d, J = 4.4 Hz, 1H), 8.58 (d, J = 7.2 Hz, 1H), 8.09-8.00 (m, 1H), 8.00-7.84 (m, 5H), 7.50 (d, J = 4.4 Hz, 1H), 7.33 (s, 1H), 7.23 (d, J = 8.6 Hz, 1H), 4.54-4.29 (m, 1H), 4.00-3.71 (m, 6H), 1.41 (d, J = 7.3 Hz, 3H). | C |
| 45 | 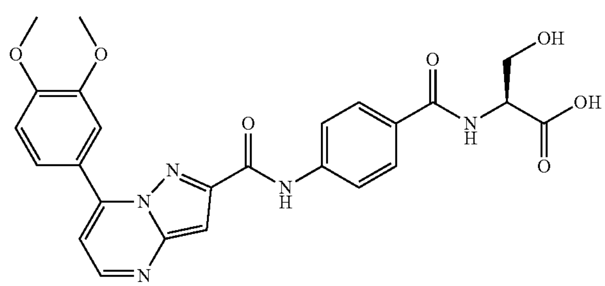 [SMILES: COc1ccc(-c2ccnc3cc(C(=O)Nc4ccc(C(=O)N[C@@H](CO)C(=O)O)cc4)nn23)cc1OC] | $^1$H NMR (400 MHz, DMSO-d$_6$) δ 12.64 (s, 1H), 10.47 (s, 1H), 8.70 (d, J = 4.5 Hz, 1H), 8.32 (d, J = 7.7 Hz, 1H), 8.02 (dd, J = 8.5, 2.1 Hz, 1H), 7.99-7.85 (m, 5H), 7.49 (d, J = 4.5 Hz, 1H), 7.33 (s, 1H), 7.23 (d, J = 8.6 Hz, 1H), 4.98 (s, 1H), 4.56-4.36 (m, 1H), 3.98-3.85 (m, 6H), 3.85-3.67 (m, 2H). | C |

TABLE 3A-continued

Compound Structures, Characterization Data and Synthetic Method

| Cmpd | Structure | Characterization Data | General Method (Ex. 2) |
|---|---|---|---|
| 46 | 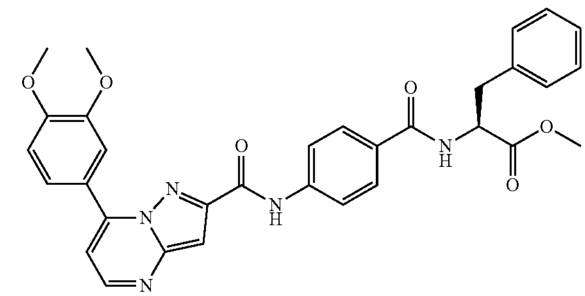 [SMILES: COC(=O)[C@H](Cc1ccccc1)NC(=O)c1ccc(NC(=O)c2cc3nccc(-c4ccc(OC)c(OC)c4)n3n2)cc1] | $^1$H NMR (400 MHz, DMSO-d$_6$) δ 10.48 (s, 1H), 8.79 (d, J = 7.6 Hz, 1H), 8.71 (d, J = 4.2 Hz, 1H), 8.08-7.77 (m, 6H), 7.50 (d, J = 4.3 Hz, 1H), 7.40-7.14 (m, 7H), 4.73-4.57 (m, 1H), 4.02-3.80 (m, 6H), 3.65 (s, 3H), 3.24-3.03 (m, 2H). | C |
| 47 | 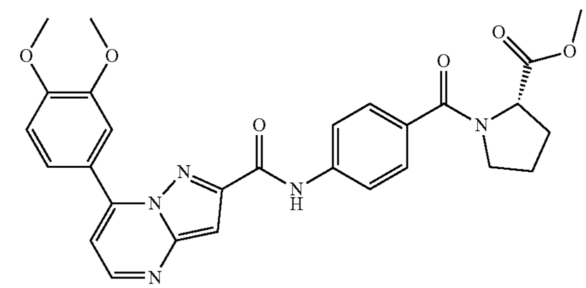 [SMILES: COC(=O)[C@@H]1CCCN1C(=O)c1ccc(NC(=O)c2cc3nccc(-c4ccc(OC)c(OC)c4)n3n2)cc1] | $^1$H NMR (400 MHz, DMSO-d$_6$) δ 10.53-10.31 (m, 1H), 8.71 (d, J = 4.3 Hz, 1H), 8.03 (d, J = 8.3 Hz, 1H), 7.99-7.81 (m, 3H), 7.68-7.36 (m, 3H), 7.33 (s, 1H), 7.23 (d, J = 8.4 Hz, 1H), 4.57-4.42 (m, 1H), 3.99-3.81 (m, 6H), 3.74-3.41 (m, 5H), 2.37-2.21 (m, 1H), 2.03-1.73 (m, 3H). | C |
| 48 | 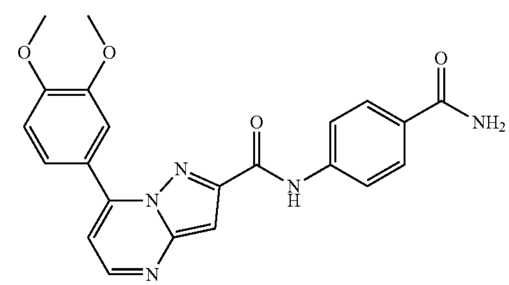 [SMILES: COc1ccc(-c2ccnc3cc(C(=O)Nc4ccc(C(N)=O)cc4)nn23)cc1OC] | $^1$H NMR (400 MHz, DMSO-d$_6$) δ 10.46 (s, 1H), 8.70 (d, J = 4.5 Hz 1H), 8.02 (dd, J = 8.5, 2.1 Hz, 1H), 7.96 (d, J = 2.1 Hz, 1H), 7.94-7.87 (m, 5H), 7.50 (d, J = 4.5 Hz, 1H), 7.34-7.27 (m, 2H), 7.22 (d, J = 8.6 Hz, 1H), 3.94-3.87 (m, 6H). | C |
| 49 | 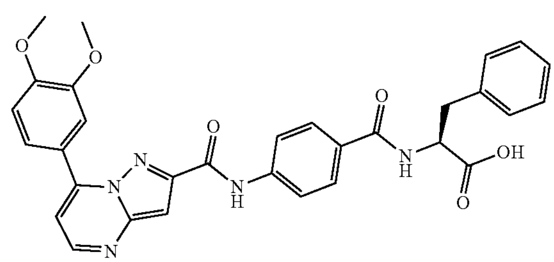 [SMILES: COc1ccc(-c2ccnc3cc(C(=O)Nc4ccc(C(=O)N[C@@H](Cc5ccccc5)C(=O)O)cc4)nn23)cc1OC] | $^1$H NMR (400 MHz, DMSO-d$_6$) δ 12.77 (s, 1H), 10.46 (s, 1H), 8.70 (d, J = 4.4 Hz, 1H), 8.62 (d, J = 8.0 Hz, 1H), 8.12-7.72 (m, 6H), 7.50 (d, J = 4.4 Hz, 1H), 7.39-7.07 (m, 7H), 4.62 (s, 1H), 4.06-3.66 (m, 6H), 3.24-3.04 (m, 2H). | C |
| 50 | 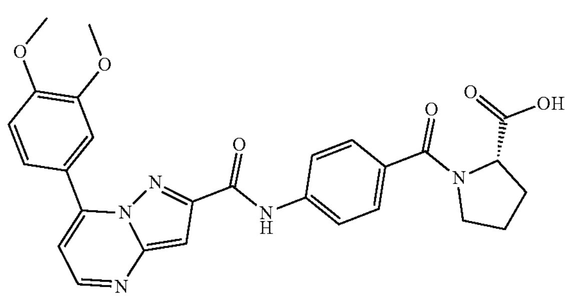 [SMILES: COc1ccc(-c2ccnc3cc(C(=O)Nc4ccc(C(=O)N5CCC[C@H]5C(=O)O)cc4)nn23)cc1OC] | $^1$H NMR (400 MHz, DMSO-d$_6$) δ 12.53 (s, 1H), 10.56-10.40 (m, 1H), 8.70 (d, J = 4.4 Hz, 1H), 8.03 (d, J = 8.4 Hz, 1H), 7.97-7.98 (m, 3H), 7.65-7.37 (m, 3H), 7.33 (s, 1H), 7.23 (d, J = 8.5 Hz, 1H), 4.48-4.35 (m, 1H), 4.05-3.76 (m, 6H), 3.68-3.45 (m, 2H), 2.38-2.10 (m, 1H), 2.05-1.66 (m, 3H). | C |

TABLE 3A-continued

Compound Structures, Characterization Data and Synthetic Method

| Cmpd | Structure | Characterization Data | General Method (Ex. 2) |
|---|---|---|---|
| 51 | 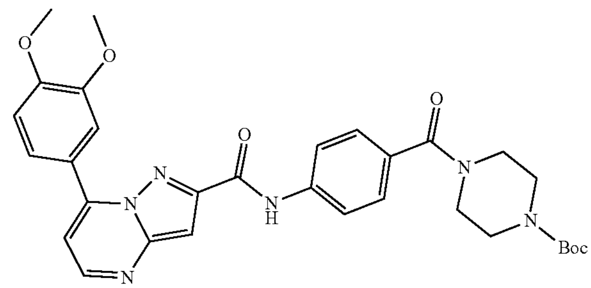 [SMILES: COc1ccc(-c2ccnc3cc(C(=O)Nc4ccc(C(=O)N5CCN(C(=O)OC(C)(C)C)CC5)cc4)nn23)cc1OC] | $^1$H NMR (400 MHz, DMSO-d$_6$) δ 10.45 (s, 1H), 8.70 (d, J = 4.5 Hz, 1H), 8.02 (dd, J = 8.5, 2.1 Hz, 1H), 7.96 (d, J = 2.1 Hz, 1H), 7.90 (d, J = 8.6 Hz, 2H), 7.50 (d, J = 4.5 Hz, 1H), 7.45 (d, J = 8.6 Hz, 2H), 7.32 (s, 1H), 7.22 (d, J = 8.6 Hz, 1H), 3.92-3.88 (m, 6H), 3.61-3.35 (m, 8H), 1.41 (s, 9H). | C |
| 52 | 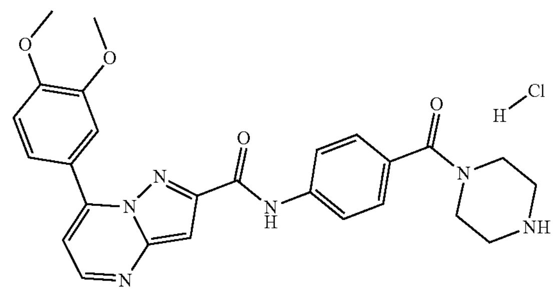 | $^1$H NMR (400 MHz, DMSO-d$_6$) δ 10.49 (s, 1H), 9.46 (s, 2H), 8.70 (d, J = 4.5 Hz, 1H), 8.01 (dd, J = 8.5, 2.1 Hz, 1H), 7.96 (d, J = 2.1 Hz, 1H), 7.93 (d, J = 8.7 Hz, 2H), 7.53-7.48 (m, 3H), 7.35 (s, 1H), 7.22 (d, J = 8.6 Hz, 1H), 3.92-3.86 (m, 6H), 3.81-3.64 (m, 4H), 3.21-3.09 (m, 4H). | C |
| 53 | 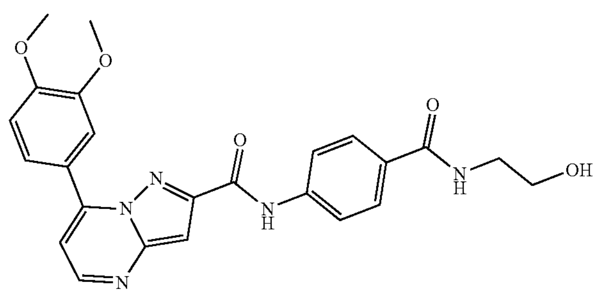 [SMILES: COc1ccc(-c2ccnc3cc(C(=O)Nc4ccc(C(=O)NCCO)cc4)nn23)cc1OC] | $^1$H NMR (400 MHz, CDCl$_3$) δ 9.00 (s, 1H), 8.63 (d, J = 4.4 Hz, 1H), 7.89-7.75 (m, 5H), 7.75-7.67 (m, 2H), 7.41 (s, 1H), 7.14 (d, J = 8.4 Hz, 1H), 7.08 (d, J = 4.4 Hz, 1H), 6.70 (s, 1H), 4.11-4.00 (m, 6H), 3.92-3.85 (m, 2H), 3.71-3.65 (m, 2H). | C |
| 54 | 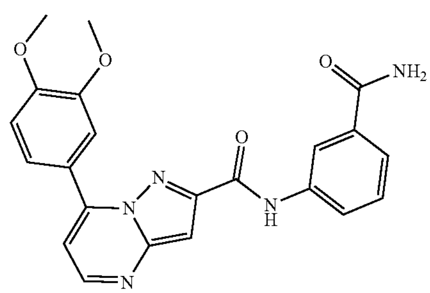 [SMILES: COc1ccc(-c2ccnc3cc(C(=O)Nc4cccc(C(N)=O)c4)nn23)cc1OC] | $^1$H NMR (400 MHz, DMSO-d$_6$) δ 10.28 (s, 1H), 8.61 (d, J = 4.4 Hz, 1H), 8.18 (s, 1H), 8.00-7.92 (m, 1H), 7.91-7.80 (m, 3H), 7.54 (d, J = 7.7 Hz, 1H), 7.42-7.34 (m, 2H), 7.29 (s, 1H), 7.23 (s, 1H), 7.13 (d, J = 8.5 Hz, 1H), 3.83-3.78 (m, 6H). | C |
| 55 | 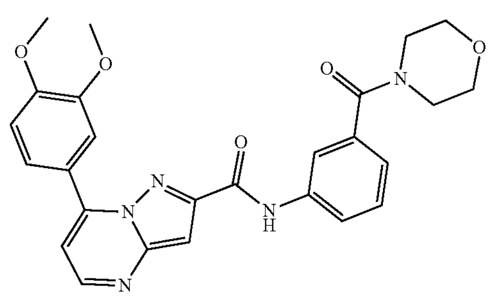 [SMILES: COc1ccc(-c2ccnc3cc(C(=O)Nc4cccc(C(=O)N5CCOCC5)c4)nn23)cc1OC] | $^1$H NMR (400 MHz, DMSO-d$_6$) δ 10.42 (s, 1H), 8.70 (d, J = 4.5 Hz, 1H), 8.03 (dd, J = 8.5, 2.1 Hz, 1H), 7.95 (d, J = 2.1 Hz, 1H), 7.93-7.86 (m, 2H), 7.52-7.43 (m, 2H), 7.32 (s, 1H), 7.22 (d, J = 8.6 Hz, 1H), 7.19-7.16 (m, 1H), 3.94-3.87 (m, 6H), 3.74-3.35 (m, 8H). | C |

TABLE 3A-continued

Compound Structures, Characterization Data and Synthetic Method

| Cmpd | Structure | Characterization Data | General Method (Ex. 2) |
|---|---|---|---|
| 56 | 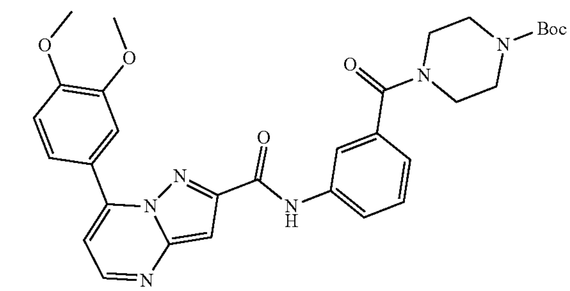 [SMILES: COc1ccc(-c2ccnc3cc(C(=O)Nc4cccc(C(=O)N5CCN(C(=O)OC(C)(C)C)CC5)c4)nn23)cc1OC] | 1H NMR (400 MHz, CDCl3) δ 8.94 (s, 1H), 8.63 (s, 1H), 7.85 (s, 1H), 7.73 (dd, J = 8.4, 2.1 Hz, 2H), 7.62 (d, J = 2.0 Hz, 1H), 7.49-7.41 (m, 2H), 7.21 (d, J = 7.6 Hz, 1H), 7.14 (d, J = 8.5 Hz, 1H), 7.06 (d, J = 4.0 Hz, 1H), 4.06 (s, 3H), 4.01 (s, 3H), 3.87-3.39 (m, 8H), 1.49 (s, 9H). | C |
| 57 | 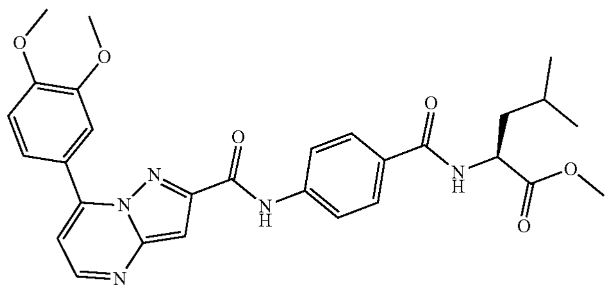 [SMILES: COC(=O)[C@H](CC(C)C)NC(=O)c1ccc(NC(=O)c2cc3nccc(-c4ccc(OC)c(OC)c4)n3n2)cc1] | 1H NMR (400 MHz, DMSO-d6) δ 10.48 (s, 1H), 8.71 (d, J = 4.5 Hz, 1H), 8.65 (d, J = 7.7 Hz, 1H), 8.02 (dd, J = 8.5, 2.1 Hz, 1H), 7.99-7.84 (m, 5H), 7.50 (d, J = 4.5 Hz, 1H), 7.34 (s, 1H), 7.23 (d, J = 8.6 Hz, 1H), 4.59-4.40 (m, 1H), 3.97-3.77 (m, 6H), 3.66 (s, 3H), 1.86-1.66 (m, 2H), 1.63-1.54 (m, 1H), 0.94 (d, J = 6.5 Hz, 3H), 0.90 (d, J = 6.4 Hz, 3H). | C |
| 58 | 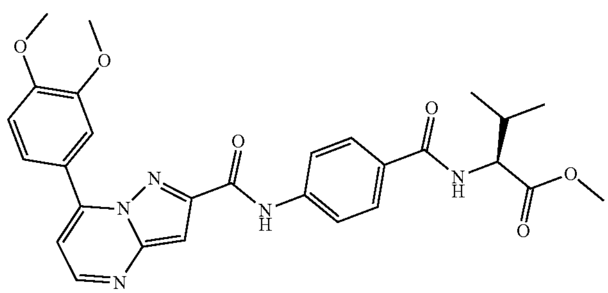 [SMILES: COC(=O)[C@@H](NC(=O)c1ccc(NC(=O)c2cc3nccc(-c4ccc(OC)c(OC)c4)n3n2)cc1)C(C)C] | 1H NMR (400 MHz, DMSO-d6) δ 10.48 (s, 1H), 8.71 (d, J = 4.5 Hz, 1H), 8.52 (d, J = 7.8 Hz, 1H), 8.02 (dd, J = 8.5, 2.1 Hz, 1H), 8.00-7.84 (m, 5H), 7.50 (d, J = 4.5 Hz, 1H), 7.33 (s, 1H), 7.23 (d, J = 8.6 Hz, 1H), 4.30 (t, J = 7.6 Hz, 1H), 3.97-3.82 (m, 6H), 3.67 (s, 3H), 2.27-2.10 (m, 1H), 1.00 (d, J = 6.7 Hz, 3H), 0.95 (d, J = 6.8 Hz, 3H). | C |
| 59 | 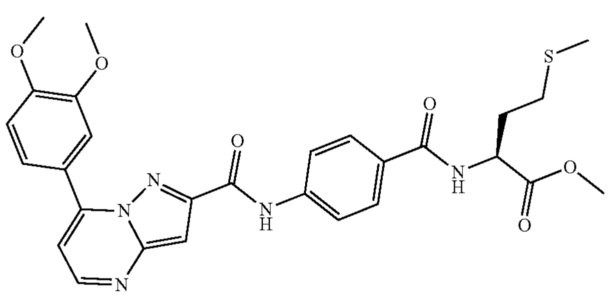 [SMILES: COC(=O)[C@H](CCSC)NC(=O)c1ccc(NC(=O)c2cc3nccc(-c4ccc(OC)c(OC)c4)n3n2)cc1] | 1H NMR (400 MHz, DMSO-d6) δ 10.48 (s, 1H), 8.78-8.62 (m, 2H), 8.10-7.81 (m, 6H), 7.50 (d, J = 4.5 Hz, 1H), 7.34 (s, 1H), 7.34 (d, J = 8.5 Hz, 1H), 4.59 (dd, J = 14.3, 7.2 Hz, 1H), 3.97-3.83 (m, 6H), 3.67 (s, 3H), 2.70-2.53 (m, 2H), 2.12-2.03 (m, 5H). | C |
| 60 | 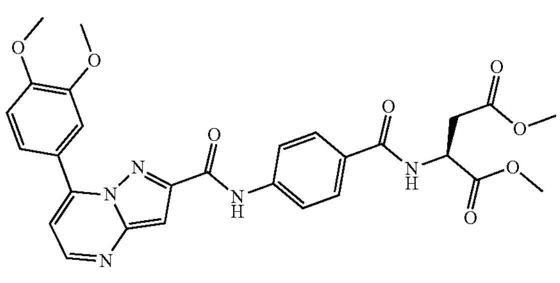 [SMILES: COC(=O)C[C@H](NC(=O)c1ccc(NC(=O)c2cc3nccc(-c4ccc(OC)c(OC)c4)n3n2)cc1)C(=O)OC] | 1H NMR (400 MHz, DMSO-d6) δ 10.49 (s, 1H), 8.85 (d, J = 7.9 Hz, 1H), 8.71 (d, J = 4.5 Hz, 1H), 8.07-7.99 (m, 1H), 7.99-7.91 (m, 3H), 7.91-7.83 (m, 2H), 7.50 (d, J = 4.5 Hz, 1H), 7.33 (s, 1H), 7.23 (d, J = 8.4 Hz, 1H), 4.91-4.77 (m, 1H), 3.96-3.86 (m, 6H), 3.66 (s, 3H), 3.63 (s, 3H), 3.03-2.91 (m, 1H), 2.91-2.76 (m, 1H). | C |

TABLE 3A-continued

Compound Structures, Characterization Data and Synthetic Method

| Cmpd | Structure | Characterization Data | General Method (Ex. 2) |
|---|---|---|---|
| 61 | 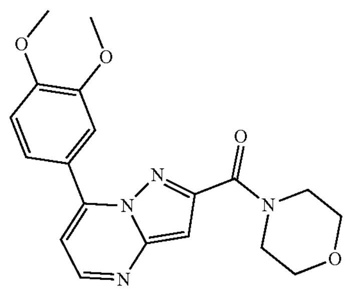 [SMILES: COc1ccc(-c2ccnc3cc(C(=O)N4CCOCC4)nn23)cc1OC] | ¹H NMR (400 MHz, DMSO-d₆) δ 8.66 (d, J = 4.5 Hz, 1H), 7.82 (dd, J = 8.5, 2.1 Hz, 1H), 7.77 (d, J = 2.1 Hz, 1H), 7.39 (d, J = 4.5 Hz, 1H), 7.21 (d, J = 8.6 Hz, 1H), 7.04 (s, 1H), 3.94-3.78 (m, 8H), 3.73-3.64 (m, 4H), 3.63-3.51 (m, 2H). | D |
| 62 | 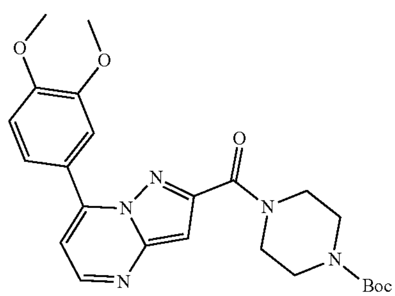 [SMILES: COc1ccc(-c2ccnc3cc(C(=O)N4CCN(C(=O)OC(C)(C)C)CC4)nn23)cc1OC] | ¹H NMR (400 MHz, DMSO-d₆) δ 8.66 (d, J = 4.4 Hz, 1H), 7.83 (dd, J = 8.5, 2.0 Hz, 1H), 7.77 (d, J = 2.0 Hz, 1H), 7.39 (d, J = 4.5 Hz, 1H), 7.21 (d, J = 8.6 Hz, 1H), 7.04 (s, 1H), 3.93-3.78 (m, 8H), 3.73-3.61 (m, 2H), 3.50-3.41 (m, 2H), 3.39-3.34 (m, 2H), 1.42 (s, 9H). | D |
| 63 | 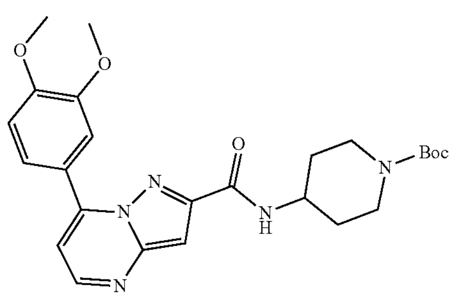 [SMILES: COc1ccc(-c2ccnc3cc(C(=O)NC4CCN(C(=O)OC(C)(C)C)CC4)nn23)cc1OC] | ¹H NMR (400 MHz, DMSO-d₆) δ 8.65 (d, J = 4.5 Hz, 1H), 8.23 (d, J = 8.3 Hz, 1H), 7.96 (d, J = 2.1 Hz, 1H), 7.91 (dd, J = 8.5, 2.2 Hz, 1H), 7.43 (d, J = 4.5 Hz, 1H), 7.20 (d, J = 8.6 Hz, 1H), 7.14 (s, 1H), 4.09-3.83 (m, 9H), 2.99-2.74 (m, 2H), 1.85-1.72 (m, 2H), 1.61-1.32 (m, 11H). | A |
| 64 | 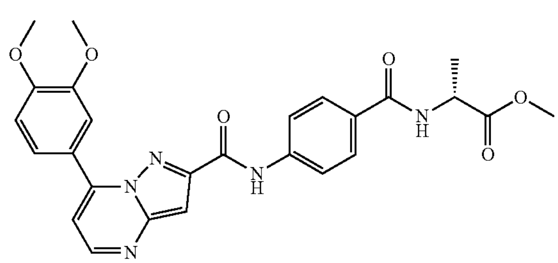 [SMILES: COC(=O)[C@@H](C)NC(=O)c1ccc(NC(=O)c2cc3nccc(-c4ccc(OC)c(OC)c4)n3n2)cc1] | ¹H NMR (400 MHz, DMSO-d₆) δ 10.49 (s, 1H), 8.84-8.56 (m, 2H), 8.19-7.73 (m, 6H), 7.68-7.43 (m, 1H), 7.34 (s, 1H), 7.23 (d, J = 7.4 Hz, 1H), 4.61-4.35 (m, 1H), 4.13-3.78 (m, 6H), 3.66 (s, 3H), 1.42 (d, J = 6.6 Hz, 3H). | C |
| 65 | 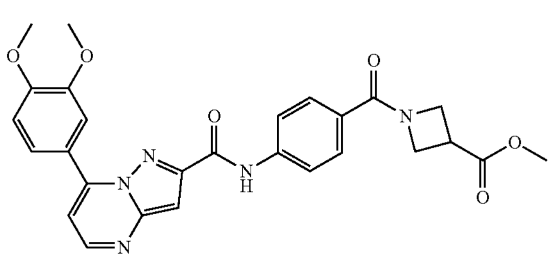 [SMILES: COC(=O)C1CN(C(=O)c2ccc(NC(=O)c3cc4nccc(-c5ccc(OC)c(OC)c5)n4n3)cc2)C1] | ¹H NMR (400 MHz, DMSO-d₆) δ 10.49 (s, 1H), 8.71 (d, J = 4.5 Hz, 1H), 8.10-8.00 (m, 1H), 8.00-7.83 (m, 3H), 7.68 (d, J = 8.6 Hz, 2H), 7.50 (d, J = 4.5 Hz, 1H), 7.33 (s, 1H), 7.23 (d, J = 8.5 Hz, 1H), 4.63-4.48 (m, 1H), 4.48-4.35 (m, 1H), 4.35-4.19 (m, 1H), 4.18-4.00 (m, 1H), 3.97-3.82 (m, 6H), 3.69 (s, 3H), 3.66-3.52 (m, 1H). | C |

TABLE 3A-continued

Compound Structures, Characterization Data and Synthetic Method

| Cmpd | Structure | Characterization Data | General Method (Ex. 2) |
|---|---|---|---|
| 66 | 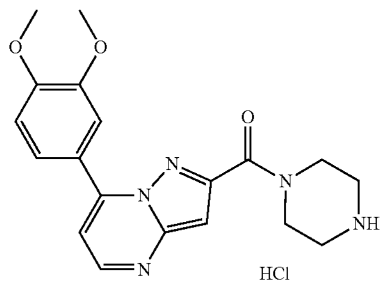 [SMILES: COc1ccc(-c2ccnc3cc(C(=O)N4CCNCC4)nn23)cc1OC ; Cl] | $^1$H NMR (400 MHz, DMSO-d$_6$) δ 9.25 (s, 2H), 8.68 (d, J = 4.4 Hz, 1H), 7.81 (d, J = 8.5 Hz, 1H), 7.76 (s, 1H), 7.41 (d, J = 4.4 Hz, 1H), 7.20 (d, J = 8.6 Hz, 1H), 7.10 (s, 1H), 4.23-4.03 (m, 2H), 3.98-3.76 (m, 8H), 3.36-3.09 (m, 4H). | D |
| 67 | 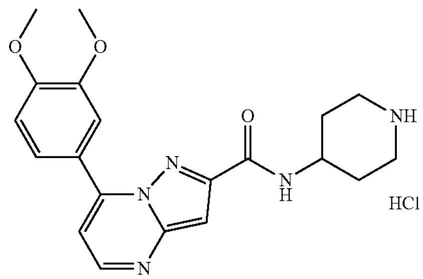 [SMILES: COc1ccc(-c2ccnc3cc(C(=O)NC4CCNCC4)nn23)cc1OC ; Cl] | $^1$H NMR (400 MHz, DMSO-d$_6$) δ 8.98-8.83 (m, 1H), 8.81-8.68 (m, 1H), 8.66 (d, J = 4.5 Hz, 1H), 8.53 (d, J = 7.8 Hz, 1H), 7.99 (d, J = 2.1 Hz, 1H), 7.91 (dd, J = 8.5, 2.1 Hz, 1H), 7.44 (d, J = 4.5 Hz, 1H), 7.20 (d, J = 8.6 Hz, 1H), 7.18 (s, 1H), 4.18-4.04 (m, 1H), 3.93-3.86 (m, 6H), 3.31 (d, J = 12.2 Hz, 2H), 3.09-2.95 (m, 2H), 2.04-1.92 (m, 2H), 1.91-1.76 (m, 2H). | A |
| 68 | 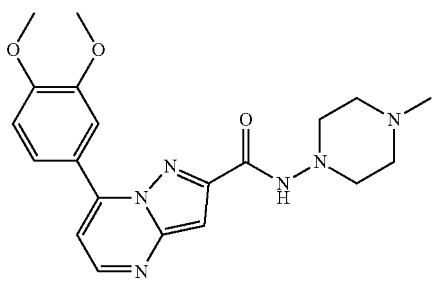 [SMILES: COc1ccc(-c2ccnc3cc(C(=O)NN4CCN(C)CC4)nn23)cc1OC] | $^1$H NMR (400 MHz, DMSO-d$_6$) δ 9.36 (s, 1H), 8.65 (d, J = 4.5 Hz, 1H), 7.97 (d, J = 2.1 Hz, 1H), 7.93 (dd, J = 8.5, 2.2 Hz, 1H)), 7.44 (d, J = 4.5 Hz, 1H), 7.20 (d, J = 8.6 Hz, 1H), 7.12 (s, 1H), 3.95-3.69 (m, 6H), 3.00-2.74 (m, 4H), 2.49-2.34 (m, 4H), 2.19 (s, 3H). | A |
| 69 | 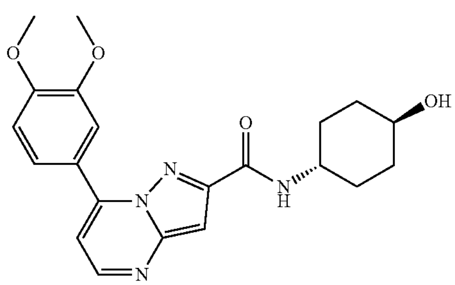 [SMILES: COc1ccc(-c2ccnc3cc(C(=O)N[C@H]4CC[C@H](O)CC4)nn23)cc1OC] | $^1$H NMR (400 MHz, DMSO-d$_6$) δ 8.64 (d, J = 4.4 Hz, 1H), 8.03 (d, J = 8.2 Hz, 1H), 7.96 (d, J = 1.8 Hz, 1H), 7.90 (dd, J = 8.4, 2.0 Hz, 1H), 7.42 (d, J = 4.5 Hz, 1H), 7.20 (d, J = 8.6 Hz, 1H), 7.12 (s, 1H), 4.57 (d, J = 4.4 Hz, 1H), 3.96-3.84 (m, 6H), 3.83-3.67 (m, 1H), 3.50-3.36 (m, 1H), 1.92-1.76 (m, 4H), 1.51-1.37 (m, 2H), 1.34-1.18 (m, 2H). | A |
| 70 | 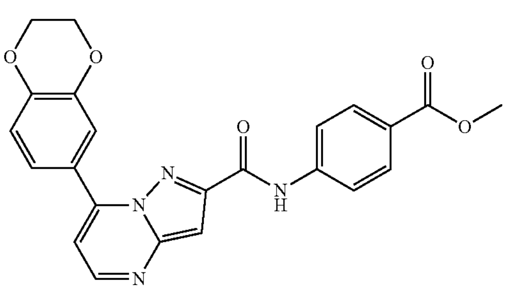 [SMILES: COC(=O)c1ccc(NC(=O)c2cc3nccc(-c4ccc5c(c4)OCCO5)n3n2)cc1] | $^1$H NMR (400 MHz, DMSO-d$_6$) δ 10.59 (s, 1H), 8.68 (d, J = 4.5 Hz, 1H), 8.03-7.92 (m, 4H), 7.91-7.82 (m, 2H), 7.41 (d, J = 4.5 Hz, 1H), 7.34 (s, 1H), 7.12 (d, J = 8.5 Hz, 1H), 4.46-4.14 (m, 4H), 3.86 (s, 3H). | C |

TABLE 3A-continued

Compound Structures, Characterization Data and Synthetic Method

| Cmpd | Structure | Characterization Data | General Method (Ex. 2) |
|---|---|---|---|
| 71 | 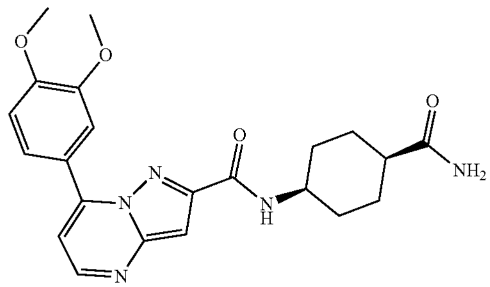 [SMILES: COc1ccc(-c2ccnc3cc(C(=O)N[C@H]4CC[C@@H](C(N)=O)CC4)nn23)cc1OC] | $^1$H NMR (400 MHz, DMSO-d$_6$) δ 8.65 (d, J = 4.5 Hz, 1H), 7.98 (d, J = 2.1 Hz, 1H), 7.95-7.88 (m, 2H), 7.43 (d, J = 4.5 Hz, 1H), 7.25-7.19 (m, 2H), 7.15 (s, 1H), 6.75 (s, 1H), 4.06-3.95 (m, 1H), 3.94-3.85 (m, 6H), 2.31-2.21 (m, 1H), 1.87-1.70 (m, 4H), 1.70-1.48 (m, 4H). | A |
| 72 | 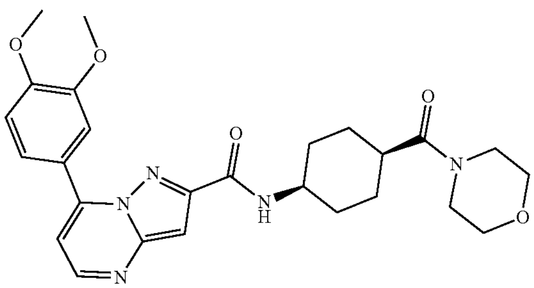 [SMILES: COc1ccc(-c2ccnc3cc(C(=O)N[C@H]4CC[C@@H](C(=O)N5CCOCC5)CC4)nn23)cc1OC] | $^1$H NMR (400 MHz, DMSO-d$_6$) δ 8.65 (d, J = 4.5 Hz, 1H), 7.97 (d, J = 2.1 Hz, 1H), 7.95-7.87 (m, 2H), 7.44 (d, J = 4.5 Hz, 1H), 7.24 (d, J = 8.6 Hz, 1H), 7.16 (s, 1H), 4.11-4.03 (m, 1H), 3.92-3.86 (m, 6H), 3.62-3.40 (m, 8H), 2.78-2.69 (m, 1H), 1.94-1.81 (m, 2H), 1.76-1.63 (m, 4H), 1.61-1.51 (m, 2H). | A |
| 73 | 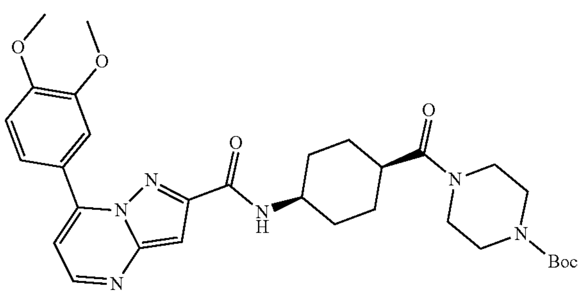 [SMILES: COc1ccc(-c2ccnc3cc(C(=O)N[C@H]4CC[C@@H](C(=O)N5CCN(C(=O)OC(C)(C)C)CC5)CC4)nn23)cc1OC] | $^1$H NMR (400 MHz, DMSO-d$_6$) δ 8.65 (d, J = 4.5 Hz, 1H), 7.97 (d, J = 2.1 Hz, 1H), 7.95-7.85 (m, 2H), 7.44 (d, J = 4.5 Hz, 1H), 7.24 (d, J = 8.6 Hz, 1H), 7.16 (s, 1H), 4.11-4.03 (m, 1H), 3.93-3.86 (m, 6H), 3.52-3.39 (m, 4H), 3.32-3.25 (m, 4H), 2.78-2.71 (m, 1H), 1.92-1.83 (m, 2H), 1.74-1.62 (m, 4H), 1.62-1.51 (m, 2H), 1.42 (s, 9H). | A |
| 74 | 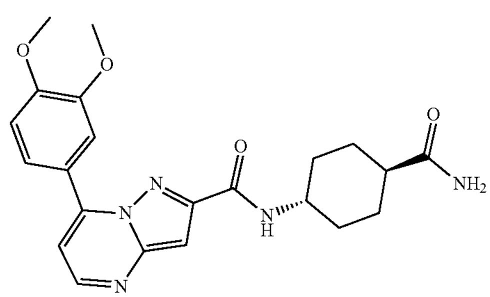 [SMILES: COc1ccc(-c2ccnc3cc(C(=O)N[C@H]4CC[C@H](C(N)=O)CC4)nn23)cc1OC] | $^1$H NMR (400 MHz, DMSO-d$_6$) δ 8.64 (d, J = 4.5 Hz, 1H), 8.12 (d, J = 8.3 Hz, 1H), 7.99 (d, J = 2.1 Hz, 1H), 7.89 (dd, J = 8.5, 2.1 Hz, 1H), 7.43 (d, J = 4.5 Hz, 1H), 7.26-7.17 (m, 2H), 7.13 (s, 1H), 6.71 (s, 1H), 3.94-3.86 (m, 6H), 3.83-3.70 (m, 1H), 2.11-2.00 (m, 1H), 1.95-1.75 (m, 4H), 1.51-1.33 (m, 4H). | A |
| 75 | 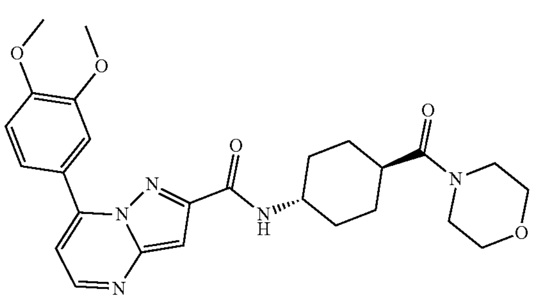 [SMILES: COc1ccc(-c2ccnc3cc(C(=O)N[C@H]4CC[C@H](C(=O)N5CCOCC5)CC4)nn23)cc1OC] | $^1$H NMR (400 MHz, DMSO-d$_6$) δ 8.65 (d, J = 4.5 Hz, 1H), 8.10 (d, J = 8.2 Hz, 1H), 7.98 (d, J = 2.1 Hz, 1H), 7.89 (dd, J = 8.5, 2.2 Hz, 1H), 7.43 (d, J = 4.5 Hz, 1H), 7.20 (d, J = 8.6 Hz, 1H), 7.13 (s, 1H), 3.92-3.87 (m, 6H), 3.87-3.72 (m, 1H), 3.66-3.37 (m, 8H), 2.59-2.52 (m, 1H), 1.99-1.66 (m, 4H), 1.55-1.39 (m, 4H). | A |

TABLE 3A-continued

Compound Structures, Characterization Data and Synthetic Method

| Cmpd | Structure | Characterization Data | General Method (Ex. 2) |
|---|---|---|---|
| 76 | 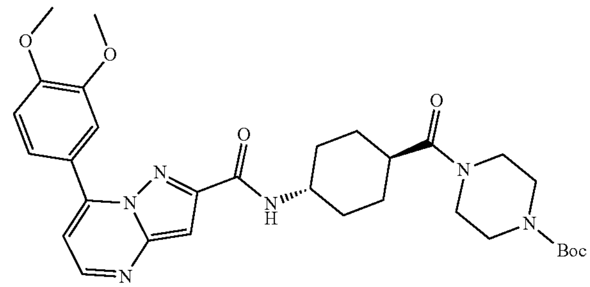 [SMILES: COc1ccc(-c2ccnc3cc(C(=O)N[C@H]4CC[C@H](C(=O)N5CCN(C(=O)OC(C)(C)C)CC5)CC4)nn23)cc1OC] | ¹H NMR (400 MHz, DMSO-d₆) δ 8.65 (d, J = 4.5 Hz, 1H), 8.10 (d, J = 8.2 Hz, 1H), 7.98 (d, J = 2.1 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 3.93-3.87 (m, 6H), 3.86-3.70 (m, 1H), 3.55-3.39 (m, 4H), 3.33-3.24 (m, 4H), 2.60-2.54 (m, 1H), 1.99-1.65 (m, 4H), 1.56-1.45 (m, 4H), 1.42 (s, 9H). | A |
| 77 | 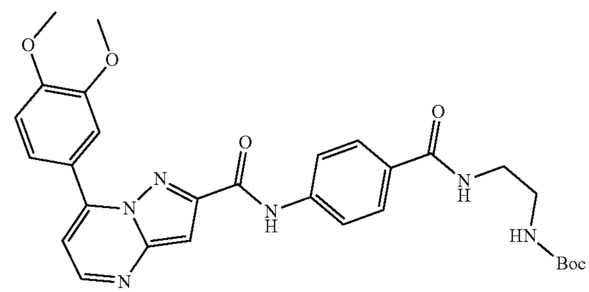 [SMILES: COc1ccc(-c2ccnc3cc(C(=O)Nc4ccc(C(=O)NCCNC(=O)OC(C)(C)C)cc4)nn23)cc1OC] | ¹H NMR (400 MHz, DMSO-d₆) δ 10.45 (s, 1H), 8.70 (d, J = 4.5 Hz, 1H), 8.40 (t, J = 5.5 Hz, 1H), 8.02 (dd, J = 8.5, 2.1 Hz, 1H), 7.96 (d, J = 2.1 Hz, 1H), 7.94-7.82 (m, 4H), 7.50 (d, J = 4.5 Hz, 1H), 7.33 (s, 1H), 7.23 (d, J = 8.6 Hz, 1H), 6.92 (t, J = 5.5 Hz, 1H), 3.93-3.86 (m, 6H), 3.31-3.25 (m, 2H), 3.15-3.07 (m, 2H), 1.39 (s, 9H). | C |
| 78 | 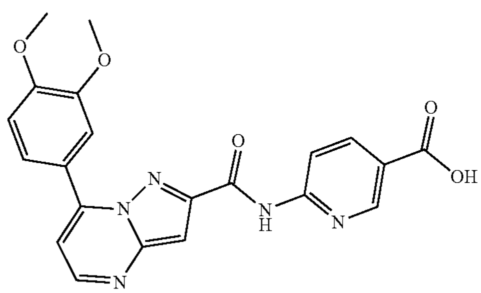 [SMILES: COc1ccc(-c2ccnc3cc(C(=O)Nc4ccc(C(=O)O)cn4)nn23)cc1OC] | ¹H NMR (400 MHz, DMSO-d₆) δ 10.19 (s, 1H), 8.81 (s, 1H), 8.72 (d, J = 4.5 Hz, 1H), 8.31-8.18 (m, 2H), 7.97 (dd, J = 8.5, 2.1 Hz, 1H), 7.92 (d, J = 2.1 Hz, 1H), 7.50 (d, J = 4.5 Hz, 1H), 7.41 (s, 1H), 7.25 (d, J = 8.6 Hz, 1H), 3.95-3.89 (m, 6H). | B |
| 79 | 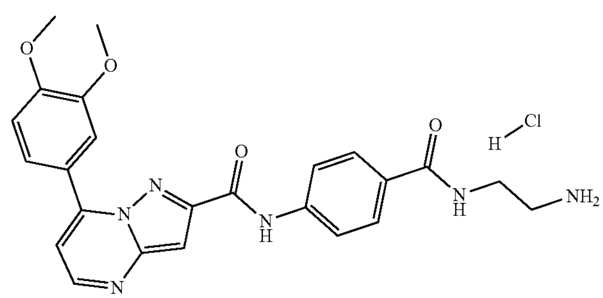 | ¹H NMR (400 MHz, DMSO-d₆) δ 10.50 (s, 1H), 8.73-8.64 (m, 2H), 8.13-7.85 (m, 9H), 7.51 (d, J = 4.5 Hz, 1H), 7.34 (s, 1H), 7.23 (d, J = 8.6 Hz, 1H), 3.93-3.87 (m, 6H), 3.56-3.49 (m, 2H), 3.04-2.96 (m, 2H). | C |
| 80 | 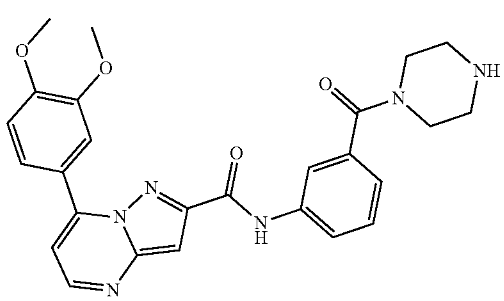 [SMILES: COc1ccc(-c2ccnc3cc(C(=O)Nc4cccc(C(=O)N5CCNCC5)c4)nn23)cc1OC] | ¹H NMR (400 MHz, DMSO-d₆) δ 10.40 (s, 1H), 8.70 (d, J = 4.5 Hz, 1H), 8.03 (dd, J = 8.5, 2.1 Hz, 1H), 7.95 (d, J = 2.1 Hz, 1H), 7.92-7.84 (m, 2H), 7.51-7.42 (m, 2H), 7.32 (s, 1H), 7.22 (d, J = 8.6 Hz, 1H), 7.16-7.09 (m, 1H), 3.93-3.88 (m, 6H), 3.42-3.17 (m, 4H), 2.81-2.59 (m, 4H). | C |

TABLE 3A-continued

Compound Structures, Characterization Data and Synthetic Method

| Cmpd | Structure | Characterization Data | General Method (Ex. 2) |
|---|---|---|---|
| 81 | 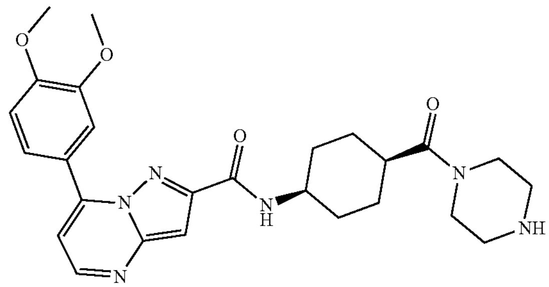 [SMILES: COc1ccc(-c2ccnc3cc(C(=O)N[C@H]4CC[C@@H](C(=O)N5CCNCC5)CC4)nn23)cc1OC] | ¹H NMR (400 MHz, DMSO-d₆) δ 8.65 (d, J = 4.5 Hz, 1H), 8.07 (d, J = 8.1 Hz, 1H), 7.97 (d, J = 2.1 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 3.92-3.84 (m, 6H), 3.84-3.71 (m, 1H), 3.43-3.36 (m, 4H), 2.74-2.58 (m, 4H), 2.57-2.53 (m, 1H), 1.96-1.85 (m, 2H), 1.76-1.66 (m, 2H), 1.54-1.39 (m, 4H). | A |
| 82 | 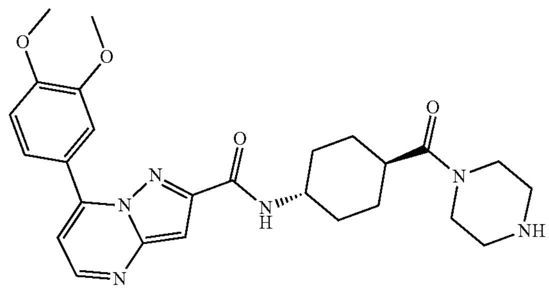 [SMILES: COc1ccc(-c2ccnc3cc(C(=O)N[C@H]4CC[C@H](C(=O)N5CCNCC5)CC4)nn23)cc1OC] | ¹H NMR (400 MHz, DMSO-d₆) δ 8.65 (d, J = 4.5 Hz, 1H), 7.97 (d, J = 2.1 Hz, 1H), 7.92 (dd, J = 8.5, 2.1 Hz, 1H), 7.88 (d, J = 7.4 Hz, 1H), 7.45 (d, J = 4.5 Hz, 1H), 7.25 (d, J = 8.6 Hz, 1H), 7.16 (s, 1H), 4.11-4.03 (m, 1H), 3.92-3.86 (m, 6H), 3.43-3.36 (m, 4H), 2.74-2.58 (m, 5H), 1.91-1.82 (m, 2H), 1.73-1.62 (m, 4H), 1.59-1.48 (m, 2H). | A |
| 83 | 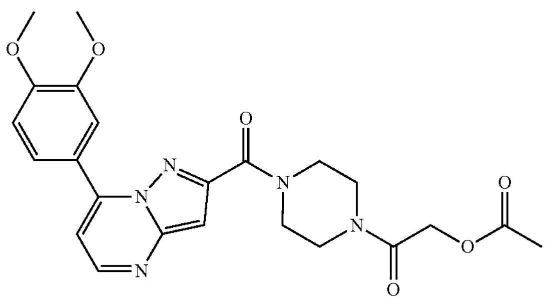 [SMILES: COc1ccc(-c2ccnc3cc(C(=O)N4CCN(C(=O)COC(C)=O)CC4)nn23)cc1OC] | ¹H NMR (400 MHz, DMSO-d₆) δ 8.67 (d, J = 4.5 Hz, 1H), 7.84 (t, J = 9.2 Hz, 1H), 7.76 (d, J = 2.0 Hz, 1H), 7.46-7.34 (m, 1H), 7.21 (d, J = 8.1 Hz, 1H), 7.06 (s, 1H), 4.88-4.71 (m, 2H), 3.89-3.83 (m, 8H), 3.77-3.61 (m, 2H), 3.60-3.45 (m, 4H), 2.09 (s, 3H). | D |
| 84 | 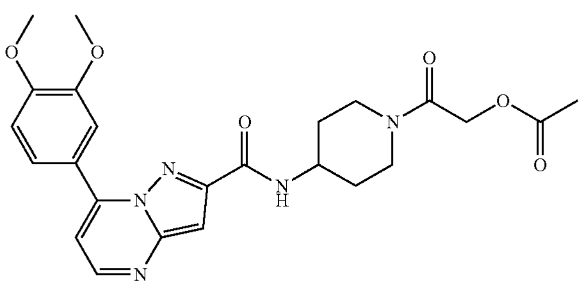 [SMILES: COc1ccc(-c2ccnc3cc(C(=O)NC4CCN(C(=O)COC(C)=O)CC4)nn23)cc1OC] | ¹H NMR (400 MHz, DMSO-d₆) δ 8.65 (d, J = 4.5 Hz, 1H), 8.29 (d, J = 8.2 Hz, 1H), 7.96 (d, J = 2.1 Hz, 1H), 7.92 (dd, J = 8.5, 2.2 Hz, 1H), 7.44 (d, J = 4.5 Hz, 1H), 7.20 (d, J = 8.6 Hz, 1H), 7.15 (s, 1H), 4.90-4.68 (m, 2H), 4.36-4.22 (m, 1H), 4.18-4.05 (m, 1H), 3.92-3.84 (m, 6H), 3.81-3.66 (m, 1H), 3.17-3.07 (m, 1H), 2.82-2.69 (m, 1H), 2.09 (s, 3H), 1.92-1.77 (m, 2H), 1.67-1.40 (m, 2H). | A |
| 85 | 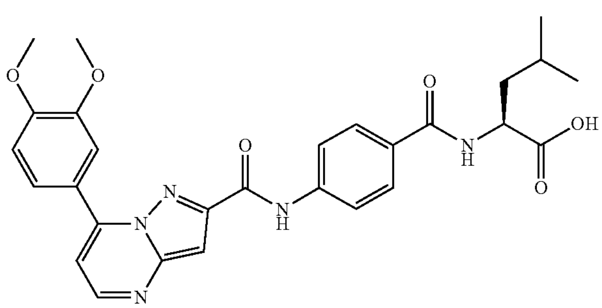 [SMILES: COc1ccc(-c2ccnc3cc(C(=O)Nc4ccc(C(=O)N[C@@H](CC(C)C)C(=O)O)cc4)nn23)cc1OC] | ¹H NMR (400 MHz, DMSO-d₆) δ 12.56 (s, 1H), 10.48 (s, 1H), 8.71 (d, J = 4.5 Hz, 1H), 8.52 (d, J = 7.9 Hz, 1H), 8.02 (dd, J = 8.5, 2.1 Hz, 1H), 7.97 (d, J = 2.1 Hz, 1H), 7.93 (s, 4H), 7.50 (d, J = 4.5 Hz, 1H), 7.34 (s, 1H), 7.23 (d, J = 8.6 Hz, 1H), 4.54-4.32 (m, 1H), 3.99-3.72 (m, 6H), 1.88-1.65 (m, 2H), 1.65-1.51 (m, 1H), 0.94 (d, J = 6.4 Hz, 3H), 0.89 (d, J = 6.4 Hz, 3H). | C |

TABLE 3A-continued

Compound Structures, Characterization Data and Synthetic Method

| Cmpd | Structure | Characterization Data | General Method (Ex. 2) |
|---|---|---|---|
| 86 | 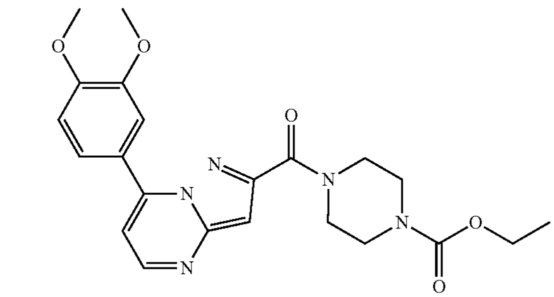 [SMILES: CCOC(=O)N1CCN(C(=O)C(=N)/C=C2/N=CC=C(c3ccc(OC)c(OC)c3)N2)CC1] | ¹H NMR (400 MHz, DMSO-d₆) δ 12.63 (s, 1H), 10.48 (s, 1H), 8.71 (d, J = 4.5 Hz, 1H), 8.32 (d, J = 8.0 Hz, 1H), 8.02 (dd, J = 8.5, 2.1 Hz, 1H), 7.97 (d, J = 2.1 Hz, 1H), 7.95-7.84 (m, 4H), 7.50 (d, J = 4.5 Hz, 1H), 7.34 (s, 1H), 7.23 (d, J = 8.6 Hz, 1H), 4.39-4.10 (m, 1H), 4.00-3.75 (m, 6H), 2.31-1.97 (m, 1H), 1.04-0.92 (m, 6H). | C |
| 87 | 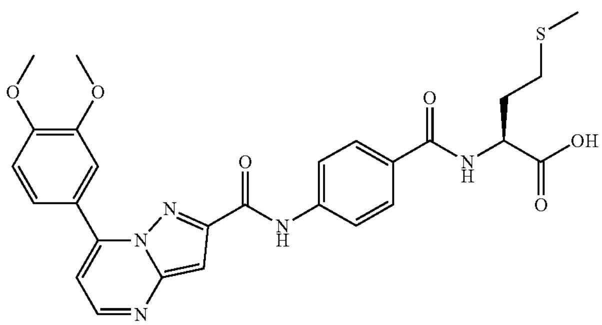 [SMILES: COc1ccc(-c2ccnc3cc(C(=O)Nc4ccc(C(=O)N[C@@H](CCSC)C(=O)O)cc4)nn23)cc1OC] | ¹H NMR (400 MHz, DMSO-d₆) δ 12.67 (s, 1H), 10.49 (s, 1H), 8.71 (d, J = 4.5 Hz, 1H), 8.58 (d, J = 7.7 Hz, 1H), 8.02 (dd, J = 8.5, 2.1 Hz, 1H), 7.99-7.95 (m, 1H), 7.95-7.89 (m, 4H), 7.51 (d, J = 4.5 Hz, 1H), 7.34 (s, 1H), 7.23 (d, J = 8.6 Hz, 1H), 4.53 (dd, J = 14.4, 7.7 Hz, 1H), 3.96-3.85 (m, 6H), 2.67-2.53 (m, 2H), 2.12-2.03 (m, 5H). | C |
| 88 | 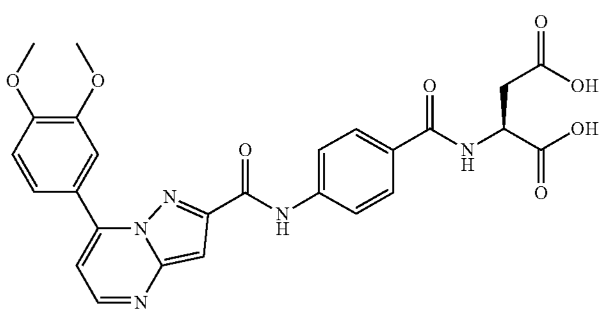 [SMILES: COc1ccc(-c2ccnc3cc(C(=O)Nc4ccc(C(=O)N[C@@H](CC(=O)O)C(=O)O)cc4)nn23)cc1OC] | ¹H NMR (400 MHz, DMSO-d₆) δ 12.69 (s, 2H), 10.49 (s, 1H), 8.71 (d, J = 4.5 Hz, 1H), 8.66 (d, J = 7.4 Hz, 1H), 8.03 (dd, J = 8.5, 2.1 Hz, 1H), 7.98-7.85 (m, 5H), 7.50 (d, J = 4.5 Hz, 1H), 7.33 (s, 1H), 7.29-7.14 (m, 1H), 4.81-4.53 (m, 1H), 4.01-3.70 (m, 6H), 2.93-2.79 (m, 1H), 2.78-2.57 (m, 1H). | C |
| 89 | 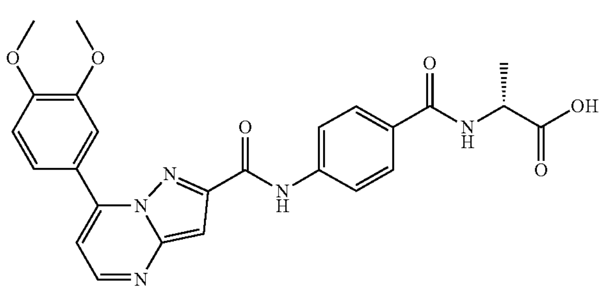 [SMILES: COc1ccc(-c2ccnc3cc(C(=O)Nc4ccc(C(=O)N[C@H](C)C(=O)O)cc4)nn23)cc1OC] | ¹H NMR (400 MHz, DMSO-d₆) δ 12.54 (s, 1H), 10.48 (s, 1H), 8.71 (d, J = 4.5 Hz, 1H), 8.59 (d, J = 7.2 Hz, 1H), 8.03 (dd, J = 8.5, 2.1 Hz, 1H), 7.97 (d, J = 2.1 Hz, 1H), 7.95-7.86 (m, 4H), 7.51 (d, J = 4.5 Hz, 1H), 7.34 (s, 1H), 7.23 (d, J = 8.7 Hz, 1H), 4.50-4.35 (m, 1H), 3.96-3.86 (m, 6H), 1.41 (d, J = 7.3 Hz, 3H). | C |

TABLE 3A-continued

Compound Structures, Characterization Data and Synthetic Method

| Cmpd | Structure | Characterization Data | General Method (Ex. 2) |
|---|---|---|---|
| 90 | 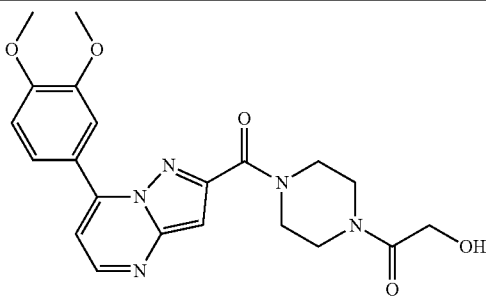 | ¹H NMR (400 MHz, DMSO-$d_6$) δ 8.67 (d, J = 4.5 Hz, 1H), 7.83 (d, J = 7.88 Hz, 1H), 7.77 (d, J = 2.1 Hz, 1H), 7.40 (d, J = 4.4 Hz, 1H), 7.21 (d, J = 8.5 Hz, 1H), 7.06 (s, 1H), 4.68 (t, J = 5.4 Hz, 1H), 4.21-4.05 (m, 2H), 3.95-3.78 (m, 8H), 3.75-3.65 (m, 2H), 3.64-3.56 (m, 1H), 3.56-3.45 (m, 2H), 3.45-3.37 (m, 1H). | D |
| 91 | 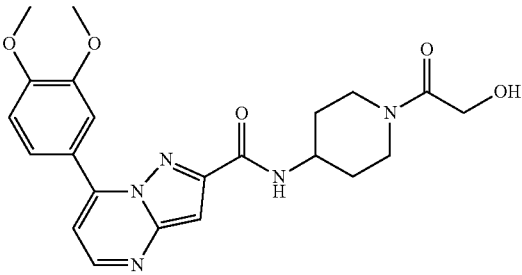 [SMILES: COc1ccc(-c2ccnc3cc(C(=O)NC4CCN(C(=O)CO)CC4)nn23)cc1OC] | ¹H NMR (400 MHz, DMSO-$d_6$) δ 8.65 (d, J = 4.5 Hz, 1H), 8.26 (d, J = 8.1 Hz, 1H), 7.95 (d, J = 2.0 Hz, 1H), 7.92 (dd, J = 8.5, 2.1 Hz, 1H), 7.44 (d, J = 4.5 Hz, 1H), 7.20 (d, J = 8.5 Hz, 1H), 7.14 (s, 1H), 4.53 (t, J = 5.4 Hz, 1H), 4.41-4.26 (m, 1H), 4.20-4.00 (m, 3H), 3.96-3.82 (m, 6H), 3.77-3.63 (m, 1H), 3.14-3.00 (m, 1H), 2.77 (t, J = 12.4 Hz, 1H), 1.84 (d, J = 11.8 Hz, 2H), 1.64-1.41 (m, 2H). | A |
| 92 | 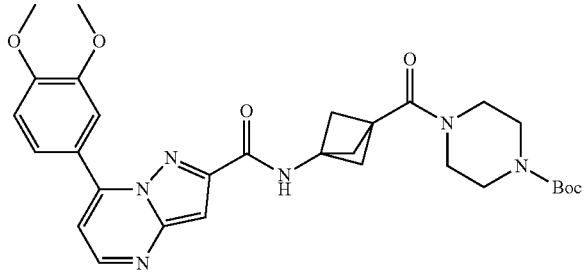 [SMILES: COc1ccc(-c2ccnc3cc(C(=O)NC45CC(C(=O)N6CCN(C(=O)OC(C)(C)C)CC6)(C4)C5)nn23)cc1OC] | ¹H NMR (400 MHz, DMSO-$d_6$) δ 9.04 (s, 1H), 8.65 (d, J = 4.5 Hz, 1H), 7.97 (dd, J = 8.5, 2.1 Hz, 1H), 7.83 (d, J = 2.1 Hz, 1H), 7.43 (d, J = 4.5 Hz, 1H), 7.20 (d, J = 8.7 Hz, 1H), 7.13 (s, 1H), 3.92-3.84 (m, 6H), 3.60-3.52 (m, 2H), 3.46-3.40 (m, 2H), 3.40-3.34 (m, 2H), 3.32-3.25 (m, 2H), 2.41 (s, 6H), 1.42 (s, 9H). | B |
| 93 | 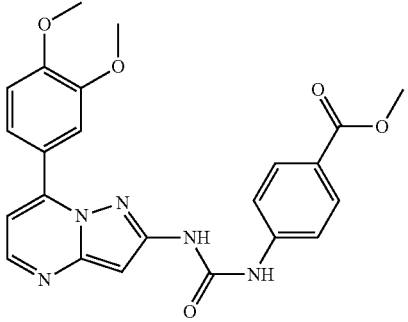 [SMILES: COC(=O)c1ccc(NC(=O)Nc2cc3nccc(-c4ccc(OC)c(OC)c4)n3n2)cc1] | ¹H NMR (400 MHz, DMSO-$d_6$) δ 9.81 (s, 1H), 9.36 (s, 1H), 8.50 (d, J = 4.5 Hz, 1H), 7.92 (d, J = 8.8 Hz, 2H), 7.83 (dd, J = 8.5, 2.1 Hz, 1H), 7.78 (d, J = 2.0 Hz, 1H), 7.61 (d, J = 8.8 Hz, 2H), 7.24-7.13 (m, 2H), 6.80 (s, 1H), 3.92-3.85 (m, 6H), 3.83 (s, 3H). | E |
| 94 | 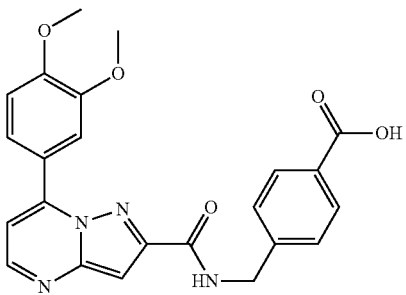 [SMILES: COc1ccc(-c2ccnc3cc(C(=O)NCc4ccc(C(=O)O)cc4)nn23)cc1OC] | ¹H NMR (400 MHz, DMSO-$d_6$) δ 12.87 (s, 1H), 9.08 (t, J = 6.3 Hz, 1H), 8.66 (d, J = 4.5 Hz, 1H), 7.95 (dd, J = 8.5, 2.1 Hz, 1H), 7.91 (d, J = 8.2 Hz, 2H), 7.86 (d, J = 2.1 Hz, 1H), 7.49-7.39 (m, 3H), 7.23-7.14 (m, 2H), 4.59 (d, J = 6.2 Hz, 2H), 3.90-3.84 (m, 6H). | A |

TABLE 3A-continued

Compound Structures, Characterization Data and Synthetic Method

| Cmpd | Structure | Characterization Data | General Method (Ex. 2) |
|---|---|---|---|
| 95 | 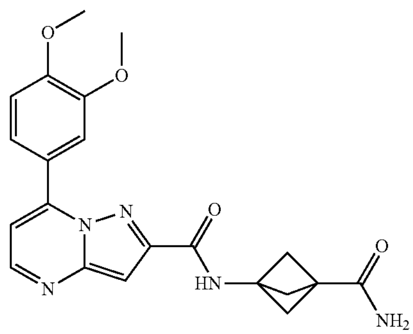 [SMILES: COc1ccc(-c2ccnc3cc(C(=O)NC45CC(C(N)=O)(C4)C5)nn23)cc1OC] | ¹H NMR (400 MHz, DMSO-d₆) δ 8.97 (s, 1H), 8.65 (d, J = 4.5 Hz, 1H), 7.98 (dd, J = 8.5, 2.2 Hz, 1H), 7.82 (d, J = 2.1 Hz, 1H), 7.43 (d, J = 4.5 Hz, 1H), 7.32 (s, 1H), 7.20 (d, J = 8.6 Hz, 1H), 7.12 (s, 1H), 6.98 (s, 1H), 3.92-3.86 (m, 6H), 2.26 (s, 6H). | B |
| 96 | 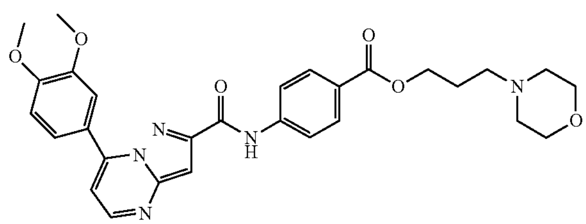 [SMILES: COc1ccc(C2=CC=N/C(=C/C(=N)C(=O)Nc3ccc(C(=O)OCCCN4CCOCC4)cc3)N2)cc1OC] | ¹H NMR (400 MHz, DMSO-d₆) δ 9.03 (s, 1H), 8.65 (d, J = 4.5 Hz, 1H), 7.96 (dd, J = 8.5, 2.1 Hz, 1H), 7.82 (d, J = 2.1 Hz, 1H), 7.42 (d, J = 4.5 Hz, 1H), 7.19 (d, J = 8.6 Hz, 1H), 7.12 (s, 1H), 3.92-3.87 (m, 6H), 3.61-3.53 (m, 6H), 3.48-3.42 (m, 2H), 2.41 (s, 6H). | B |
| 97 | 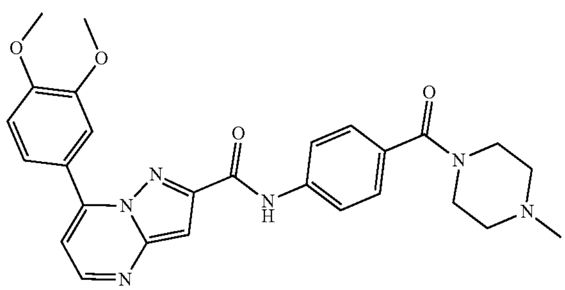 [SMILES: COc1ccc(-c2ccnc3cc(C(=O)Nc4ccc(C(=O)N5CCN(C)CC5)cc4)nn23)cc1OC] | ¹H NMR (400 MHz, DMSO-d₆) δ 10.44 (s, 1H), 8.70 (d, J = 4.5 Hz, 1H), 8.02 (dd, J = 8.5, 2.1 Hz, 1H), 7.96 (d, J = 2.1 Hz, 1H), 7.90 (d, J = 8.6 Hz, 2H), 7.50 (d, J = 4.5 Hz, 1H), 7.43 (d, J = 8.6 Hz, 2H), 7.32 (s, 1H), 7.22 (d, J = 8.6 Hz, 1H), 3.94-3.85 (m, 6H), 3.68-3.37 (m, 4H), 2.44-2.27 (m, 4H), 2.22 (s, 3H). | C |
| 98 | 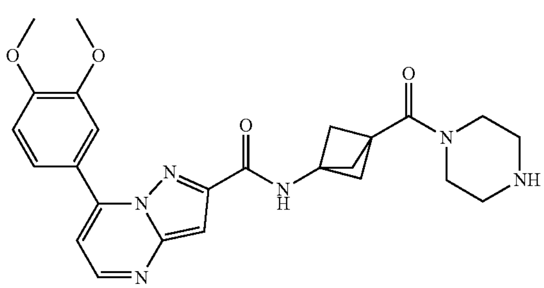 [SMILES: COc1ccc(-c2ccnc3cc(C(=O)NC45CC(C(=O)N6CCNCC6)(C4)C5)nn23)cc1OC] | ¹H NMR (400 MHz, DMSO-d₆) δ 9.03 (s, 1H), 8.65 (d, J = 4.5 Hz, 1H), 7.97 (dd, J = 8.5, 2.2 Hz, 1H), 7.82 (d, J = 2.1 Hz, 1H), 7.43 (d, J = 4.5 Hz, 1H), 7.20 (d, J = 8.6 Hz, 1H), 7.12 (s, 1H), 3.92-3.85 (m, 6H), 3.51-3.35 (m, 4H), 2.70-2.59 (m, 4H), 2.39 (s, 6H). | B |
| 99 | 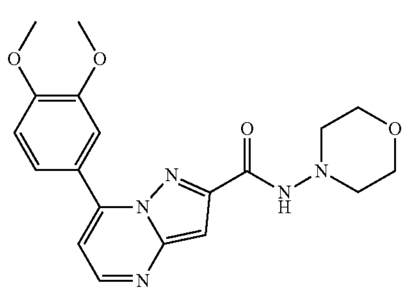 [SMILES: COc1ccc(-c2ccnc3cc(C(=O)NN4CCOCC4)nn23)cc1OC] | ¹H NMR (400 MHz, DMSO-d₆) δ 9.50 (s, 1H), 8.65 (d, J = 4.5 Hz, 1H), 8.01-7.86 (m, 2H), 7.44 (d, J = 4.5 Hz, 1H), 7.20 (d, J = 8.5 Hz, 1H), 7.13 (s, 1H), 3.95-3.80 (m, 6H), 3.74-3.60 (m, 4H), 3.00-2.82 (m, 4H). | A |

TABLE 3A-continued

Compound Structures, Characterization Data and Synthetic Method

| Cmpd | Structure | Characterization Data | General Method (Ex. 2) |
|---|---|---|---|
| 100 | 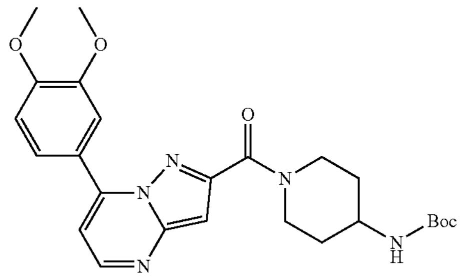 [SMILES: COc1ccc(-c2ccnc3cc(C(=O)N4CCC(NC(=O)OC(C)(C)C)CC4)nn23)cc1OC] | $^1$H NMR (400 MHz, DMSO-d$_6$) δ 8.65 (d, J = 4.5 Hz, 1H), 7.82 (dd, J = 8.5, 2.1 Hz, 1H), 7.76 (d, J = 2.1 Hz, 1H), 7.37 (d, J = 4.5 Hz, 1H), 7.19 (d, J = 8.5 Hz, 1H), 6.99 (s, 1H), 6.92 (d, J = 7.6 Hz, 1H), 4.44-4.24 (m, 2H), 3.88 (s, 3H), 3.85 (s, 3H), 3.65-3.48 (m, 1H), 3.30-3.20 (m, 1H), 3.04-2.92 (m, 1H), 2.91-2.83 (m, 2H), 1.88-1.69 (m, 2H), 1.39 (s, 9H). | D |
| 101 | 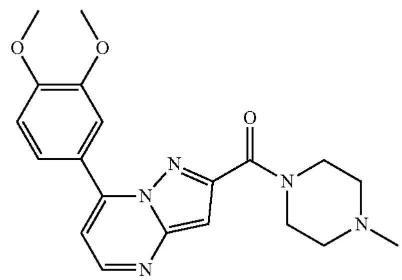 [SMILES: COc1ccc(-c2ccnc3cc(C(=O)N4CCN(C)CC4)nn23)cc1OC] | $^1$H NMR (400 MHz, DMSO-d$_6$) δ 8.65 (d, J = 4.5 Hz, 1H), 7.85-7.74 (m, 2H), 7.38 (d, J = 4.4 Hz, 1H), 7.20 (d, J = 8.2 Hz, 1H), 7.01 (s, 1H), 3.88 (s, 3H), 3.86 (s, 3H), 3.83-3.77 (m, 2H), 3.72-3.61 (m, 2H), 2.43-2.35 (m, 2H), 2.35-2.28 (m, 2H), 2.21 (s, 3H). | D |
| 102 | 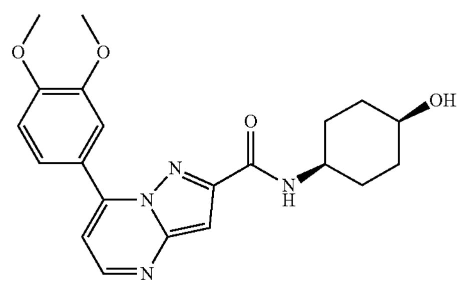 [SMILES: COc1ccc(-c2ccnc3cc(C(=O)N[C@H]4CC[C@@H](O)CC4)nn23)cc1OC] | $^1$H NMR (400 MHz, DMSO-d$_6$) δ 8.64 (d, J = 4.5 Hz, 1H), 8.03-7.95 (m, 2H), 7.92 (dd, J = 8.5, 2.1 Hz, 1H), 7.43 (d, J = 4.5 Hz, 1H), 7.21 (d, J = 8.6 Hz, 1H), 7.15 (s, 1H), 4.41 (d, J = 2.9 Hz, 1H), 3.93-3.79 (m, 7H), 3.79-3.71 (m, 1H), 1.88-1.72 (m, 2H), 1.72-1.46 (m, 6H). | A |
| 103 | 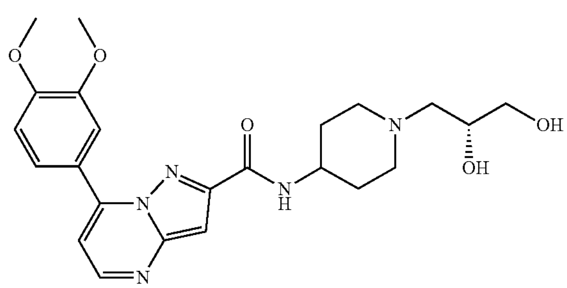 [SMILES: COc1ccc(-c2ccnc3cc(C(=O)NC4CCN(C[C@@H](O)CO)CC4)nn23)cc1OC] | $^1$H NMR (400 MHz, DMSO-d$_6$) δ 8.65 (d, J = 4.5 Hz, 1H), 8.15 (d, J = 8.2 Hz, 1H), 7.98 (d, J = 2.1 Hz, 1H), 7.91 (dd, J = 8.5, 2.2 Hz, 1H), 7.43 (d, J = 4.5 Hz, 1H), 7.20 (d, J = 8.6 Hz, 1H), 7.13 (s, 1H), 4.72 (s, 2H), 3.92-3.86 (m, 6H), 3.86-3.71 (m, 1H), 3.64-3.51 (m, 1H), 2.98-2.78 (m, 2H), 2.42-2.32 (m, 1H), 2.30-2.20 (m, 1H), 2.15-2.01 (m, 2H), 1.84-1.70 (m, 2H), 1.70-1.56 (m, 2H). | A |
| 104 | 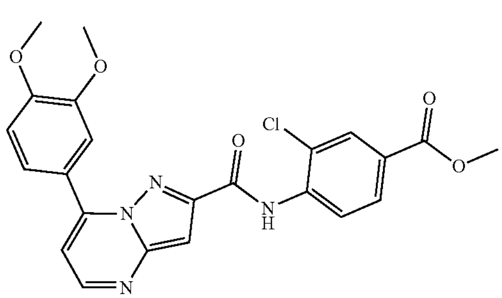 [SMILES: COC(=O)c1ccc(NC(=O)c2cc3nccc(-c4ccc(OC)c(OC)c4)n3n2)c(Cl)c1] | $^1$H NMR (400 MHz, CDCl$_3$) δ 9.92 (s, 1H), 8.81 (d, J = 8.7 Hz, 1H), 8.64 (d, J = 4.4 Hz, 1H), 8.13 (d, J = 1.9 Hz, 1H), 8.04 (dd, J = 8.6, 1.9 Hz, 1H), 7.78 (dd, J = 8.4, 2.1 Hz, 1H), 7.73 (d, J = 2.1 Hz, 1H), 7.45 (s, 1H), 7.12-7.07 (m, 2H), 4.04 (s, 3H), 4.01 (s, 3H), 3.95 (s, 3H). | B |

TABLE 3A-continued

Compound Structures, Characterization Data and Synthetic Method

| Cmpd | Structure | Characterization Data | General Method (Ex. 2) |
|---|---|---|---|
| 105 | 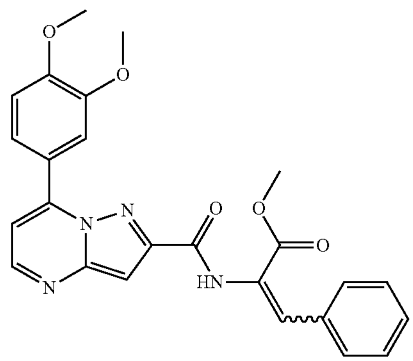 [SMILES: COC(=O)C(=Cc1ccccc1)NC(=O)c1cc2nccc(-c3ccc(OC)c(OC)c3)n2n1] | $^1$H NMR (400 MHz, DMSO-d$_6$) δ 10.05 (s, 1H), 8.70 (d, J = 4.5 Hz, 1H), 7.97 (dd, J = 8.5, 2.1 Hz, 1H), 7.91 (d, J = 2.0 Hz, 1H), 7.78-7.70 (m, 2H), 7.50 (s, 1H), 7.47 (d, J = 4.5 Hz, 1H), 7.40-7.36 (m, 3H), 7.25 (s, 1H), 7.17 (d, J = 8.6 Hz, 1H), 3.88 (s, 3H), 3.83 (s, 3H), 3.75 (s, 3H). | A |
| 106 | 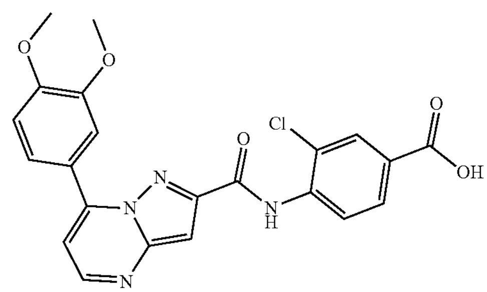 [SMILES: COc1ccc(-c2ccnc3cc(C(=O)Nc4ccc(C(=O)O)cc4Cl)nn23)cc1OC] | $^1$H NMR (400 MHz, DMSO-d$_6$) δ 9.97 (s, 1H), 8.74 (d, J = 4.5 Hz, 1H), 8.38 (d, J = 8.4 Hz, 1H), 8.02 (d, J = 1.7 Hz, 1H), 7.97-7.91 (m, 2H), 7.85 (d, J = 2.1 Hz, 1H), 7.51 (d, J = 4.5 Hz, 1H), 7.35 (s, 1H), 7.22 (d, J = 8.6 Hz, 1H), 3.94-3.86 (m, 6H). | B |
| 107 | 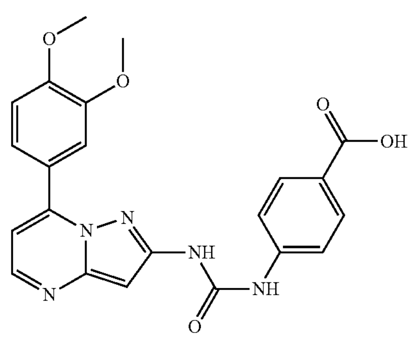 [SMILES: COc1ccc(-c2ccnc3cc(NC(=O)Nc4ccc(C(=O)O)cc4)nn23)cc1OC] | $^1$H NMR (400 MHz, DMSO-d$_6$) δ 9.83 (s, 1H), 9.49 (s, 1H), 8.49 (d, J = 4.6 Hz, 1H), 7.89 (d, J = 8.7 Hz, 2H), 7.85-7.78 (m, 2H), 7.59 (d, J = 8.7 Hz, 2H), 7.22-7.16 (m, 2H), 6.80 (s, 1H), 3.91-3.85 (m, 6H). | E |
| 108 | 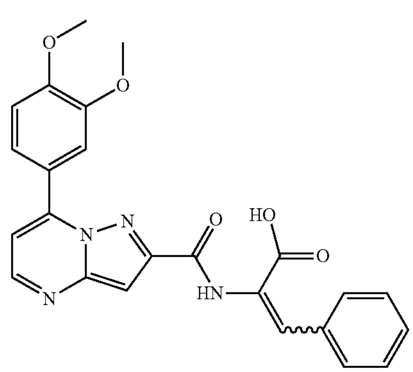 [SMILES: COc1ccc(-c2ccnc3cc(C(=O)NC(=Cc4ccccc4)C(=O)O)nn23)cc1OC] | $^1$H NMR (400 MHz, DMSO-d$_6$) δ 12.88 (s, 1H), 9.88 (s, 1H), 8.69 (d, J = 4.5 Hz, 1H), 7.97 (dd, J = 8.5, 2.1 Hz, 1H), 7.92 (d, J = 2.0 Hz, 1H), 7.74-7.67 (m, 2H), 7.50 (s, 1H), 7.47 (d, J = 4.5 Hz, 1H), 7.38-7.33 (m, 3H), 7.24 (s, 1H), 7.18 (d, J = 8.6 Hz, 1H), 3.88 (s, 3H), 3.84 (s, 3H). | A |

TABLE 3A-continued

Compound Structures, Characterization Data and Synthetic Method

| Cmpd | Structure | Characterization Data | General Method (Ex. 2) |
|---|---|---|---|
| 109 | 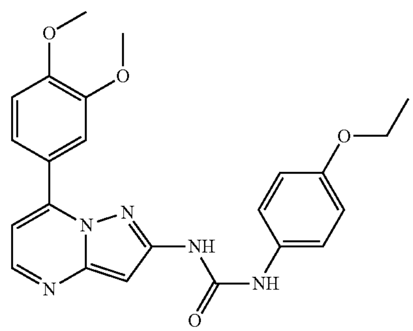 [SMILES: CCOc1ccc(NC(=O)Nc2cc3nccc(-c4ccc(OC)c(OC)c4)n3n2)cc1] | ¹H NMR (400 MHz, DMSO-d₆) δ 9.55 (s, 1H), 8.83 (s, 1H), 8.47 (d, J = 4.6 Hz, 1H), 7.83 (dd, J = 8.5, 2.1 Hz, 1H), 7.76 (d, J = 2.1 Hz, 1H), 7.38-7.32 (m, 2H), 7.21-7.13 (m, 2H), 6.91-6.84 (m, 2H), 6.73 (s, 1H), 3.99 (q, J = 7.0 Hz, 2H), 3.89 (s, 3H), 3.86 (s, 3H), 1.32 (t, J = 7.0 Hz, 3H). | E |
| 110 | 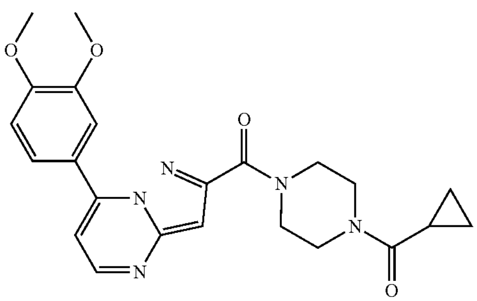 [SMILES: COc1ccc(C2=CC=N/C(=C/C(=N)C(=O)N3CCN(C(=O)C4CC4)CC3)N2)cc1OC] | ¹H NMR (400 MHz, DMSO-d₆) δ 8.67 (d, J = 4.5 Hz, 1H), 7.92-7.80 (m, 1H), 7.77 (s, 1H), 7.43-7.35 (m, 1H), 7.21 (d, J = 8.4 Hz, 1H), 7.06 (s, 1H), 3.98-3.44 (m, 14H), 2.12-1.89 (m, 1H), 0.85-0.59 (m, 4H). | D |
| 111 | 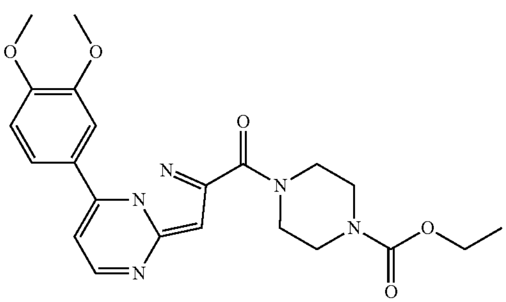 [SMILES: CCOC(=O)N1CCN(C(=O)C(=N)/C=C2/N=CC=C(c3ccc(OC)c(OC)c3)N2)CC1] | ¹H NMR (400 MHz, DMSO-d₆) δ 8.67 (d, J = 4.5 Hz, 1H), 7.83 (dd, J = 8.5, 2.1 Hz, 1H), 7.76 (d, J = 2.1 Hz, 1H), 7.40 (d, J = 4.5 Hz, 1H), 7.21 (d, J = 8.6 Hz, 1H), 7.04 (s, 1H), 4.07 (q, J = 7.1 Hz, 2H), 3.93-3.78 (m, 8H), 3.74-3.61 (m, 2H), 3.53-3.46 (m, 2H), 3.44-3.37 (m, 2H), 1.20 (t, J = 6.8 Hz, 3H). | D |
| 112 | 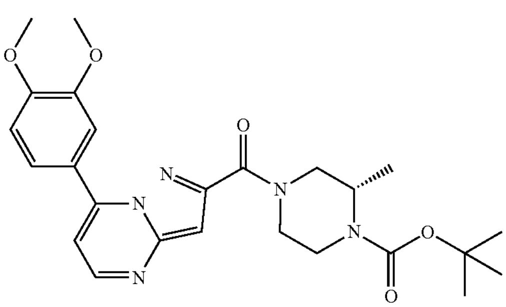 [SMILES: COc1ccc(C2=CC=N/C(=C/C(=N)C(=O)N3CCN(C(=O)OC(C)(C)C)[C@@H](C)C3)N2)cc1OC] | ¹H NMR (400 MHz, DMSO-d₆) δ 8.66 (d, J = 4.4 Hz, 1H), 7.87-7.64 (m, 2H), 7.39 (dd, J = 7.8, 4.5 Hz, 1H), 7.20 (dd, J = 8.4, 4.8 Hz, 1H), 7.05 (d, J = 21.4 Hz, 1H), 4.51-4.02 (m, 3H), 3.93-3.63 (m, 7H), 3.26-2.86 (m, 3H), 1.41 (d, J = 2.2 Hz, 9H), 1.05 (dd, J = 33.4, 6.7 Hz, 3H). | D |

TABLE 3A-continued

Compound Structures, Characterization Data and Synthetic Method

| Cmpd | Structure | Characterization Data | General Method (Ex. 2) |
|---|---|---|---|
| 113 | 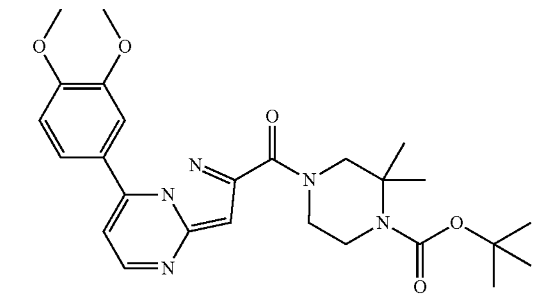 [SMILES: COc1ccc(C2=CC=N/C(=C/C(=N)C(=O)N3CCN(C(=O)OC(C)(C)C)C(C)(C)C3)N2)cc1OC] | ¹H NMR (400 MHz, DMSO-d₆) δ 8.66 (d, J = 4.4 Hz, 1H), 7.95-7.66 (m, 2H), 7.38 (dd, J = 10.5, 4.4 Hz, 1H), 7.19 (dd, J = 11.7, 8.5 Hz, 1H), 7.07 (d, J = 28.1 Hz, 1H), 4.04-3.91 (m, 2H), 3.91-3.80 (m, 6H), 3.78-3.52 (m, 4H), 1.51-1.35 (m, 12H), 1.26 (s, 3H). | D |
| 114 | 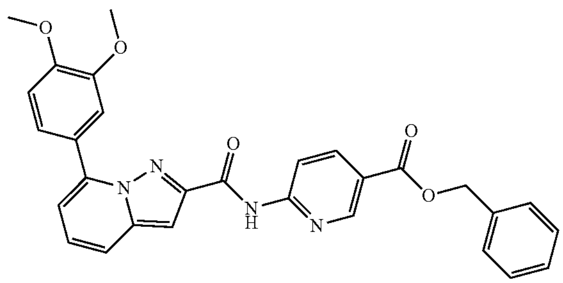 [SMILES: COc1ccc(-c2cccc3cc(C(=O)Nc4ccc(C(=O)OCc5ccccc5)cn4)nn23)cc1OC] | ¹H NMR (400 MHz, CDCl₃) δ 9.69 (s, 1H), 8.98 (d, J = 1.5 Hz, 1H), 8.61 (d, J = 4.4 Hz, 1H), 8.49 (d, J = 8.7 Hz, 1H), 8.39 (dd, J = 8.7, 2.1 Hz, 1H), 7.78 (d, J = 2.0 Hz, 1H), 7.68 (dd, J = 8.4, 2.1 Hz, 1H), 7.56-7.33 (m, 6H), 7.10 (dd, J = 9.8, 6.4 Hz, 2H), 5.39 (s, 2H), 4.16-3.96 (m, 6H). | B |
| 115 | 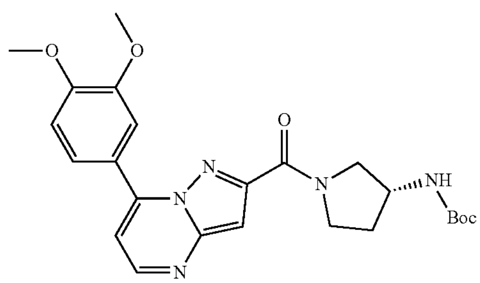 [SMILES: COc1ccc(-c2ccnc3cc(C(=O)N4CC[C@@H](NC(=O)OC(C)(C)C)C4)nn23)cc1OC] | ¹H NMR (400 MHz, DMSO-d₆) δ 8.65 (dd, J = 4.4, 1.2 Hz, 1H), 7.86-7.76 (m, 2H), 7.39 (dd, J = 4.4, 1.2 Hz, 1H), 7.29-7.15 (m, 2H), 7.09 (d, J = 3.8 Hz, 1H), 4.13-3.95 (m, 2H), 3.90-3.82 (m, 6H), 3.77-3.37 (m, 3H), 2.16-1.97 (m, 1H), 1.89-1.74 (m, 1H), 1.46-1.28 (m, 9H). | D |
| 116 | 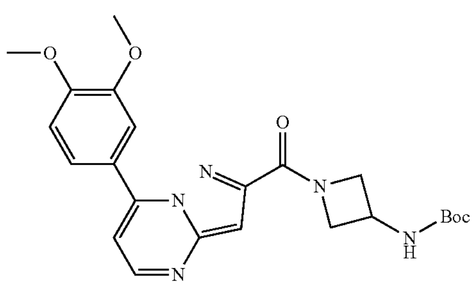 [SMILES: COc1ccc(C2=CC=N/C(=C/C(=N)C(=O)N3CC(NC(=O)OC(C)(C)C)C3)N2)cc1OC] | ¹H NMR (400 MHz, DMSO-d₆) δ 8.66 (d, J = 4.4 Hz, 1H), 7.82 (dd, J = 8.3, 1.7 Hz, 1H), 7.74 (d, J = 1.4 Hz, 1H), 7.65 (d, J = 6.5 Hz, 1H), 7.40 (d, J = 4.4 Hz, 1H), 7.20 (d, J = 8.6 Hz, 1H), 7.10 (s, 1H), 4.89-4.68 (m, 1H), 4.46-4.26 (m, 3H), 3.95-3.82 (m, 7H), 1.39 (s, 9H). | D |
| 117 | 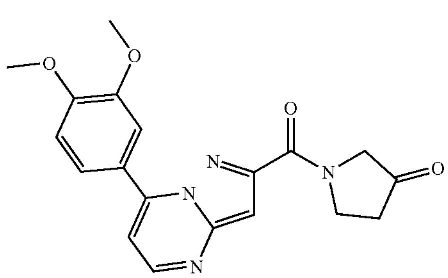 [SMILES: COc1ccc(C2=CC=N/C(=C/C(=N)C(=O)N3CCC(=O)C3)N2)cc1OC] | ¹H NMR (400 MHz, DMSO-d₆) δ 8.72-8.62 (m, 1H), 7.87-7.68 (m, 2H), 7.44-7.36 (m, 1H), 7.24-7.13 (m, 2H), 4.46 (s, 1H), 4.40 (t, J = 7.8 Hz, 1H), 4.01-3.95 (m, 2H), 3.92-3.80 (m, 6H), 2.68 (t, J = 7.8 Hz, 1H), 2.61 (t, J = 8.0 Hz, 1H). | D |

TABLE 3A-continued

Compound Structures, Characterization Data and Synthetic Method

| Cmpd | Structure | Characterization Data | General Method (Ex. 2) |
|---|---|---|---|
| 118 | 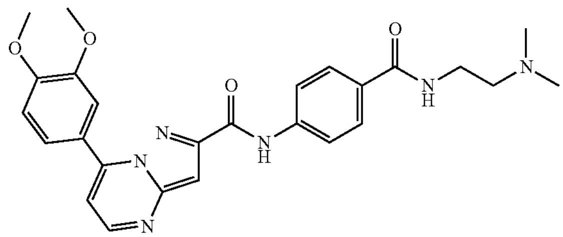 [SMILES: COc1ccc(C2=CC=N/C(=C/C(=N)C(=O)Nc3ccc(C(=O)NCCN(C)C)cc3)N2)cc1OC] | ¹H NMR (400 MHz, DMSO-d₆) δ 10.48 (s, 1H), 8.70 (d, J = 4.5 Hz, 1H), 8.58-8.46 (m, 1H), 8.01 (dd, J = 8.5, 2.1 Hz, 1H), 7.98-7.84 (m, 5H), 7.50 (d, J = 4.5 Hz, 1H), 7.32 (s, 1H), 7.22 (d, J = 8.6 Hz, 1H), 3.92-3.86 (m, 6H), 3.58-3.48 (m, 2H), 3.07-2.94 (m, 2H), 2.65 (s, 6H). | C |
| 119 | 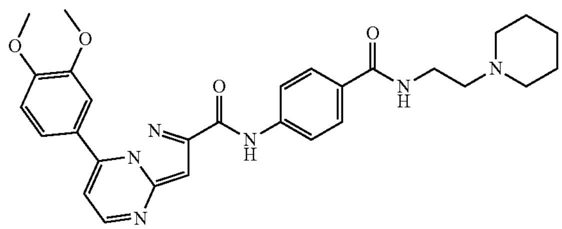 [SMILES: COc1ccc(C2=CC=N/C(=C/C(=N)C(=O)Nc3ccc(C(=O)NCCN4CCCCC4)cc3)N2)cc1OC] | ¹H NMR (400 MHz, DMSO-d₆) δ 10.51 (s, 1H), 9.35 (s, 1H), 8.71 (d, J = 4.5 Hz, 1H), 8.02 (dd, J = 8.5, 2.1 Hz, 1H), 7.98-7.84 (m, 5H), 7.51 (d, J = 4.5 Hz, 1H), 7.34 (s, 1H), 7.23 (d, J = 8.6 Hz, 1H), 3.96-3.86 (m, 6H), 3.73-3.41 (m, 4H), 3.01-2.78 (m, 2H), 1.84-1.32 (m, 8H). | C |
| 120 | 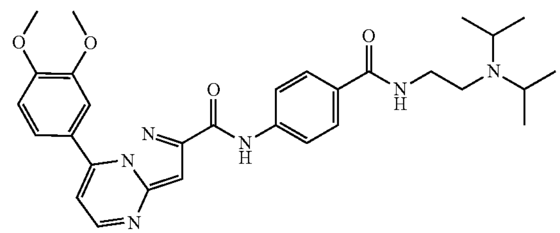 [SMILES: COc1ccc(C2=CC=N/C(=C/C(=N)C(=O)Nc3ccc(C(=O)NCCN(C(C)C)C(C)C)cc3)N2)cc1OC] | ¹H NMR (400 MHz, DMSO-d₆) δ 10.46 (s, 1H), 8.71 (d, J = 4.4 Hz, 1H), 8.34 (s, 1H), 8.03 (d, J = 6.7 Hz, 1H), 8.00-7.74 (m, 5H), 7.50 (d, J = 4.4 Hz, 1H), 7.33 (s, 1H), 7.23 (d, J = 8.5 Hz, 1H), 4.05-3.72 (m, 6H), 3.29-3.10 (m, 2H), 3.10-2.85 (m, 2H), 1.25-0.74 (m, 12H). | C |
| 121 | 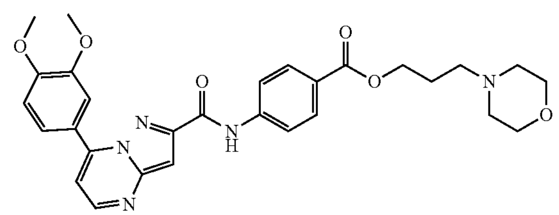 [SMILES: COc1ccc(C2=CC=N/C(=C/C(=N)C(=O)Nc3ccc(C(=O)OCCCN4CCOCC4)cc3)N2)cc1OC] | ¹H NMR (400 MHz, DMSO-d₆) δ 10.61 (s, 1H), 8.71 (d, J = 4.5 Hz, 1H), 8.07-7.88 (m, 6H), 7.51 (d, J = 4.5 Hz, 1H), 7.35 (s, 1H), 7.22 (d, J = 8.6 Hz, 1H), 4.31 (t, J = 6.4 Hz, 2H), 3.98-3.78 (m, 6H), 3.65-3.48 (m, 4H), 2.46-2.27 (m, 6H), 2.00-1.75 (m, 2H). | C |
| 122 | 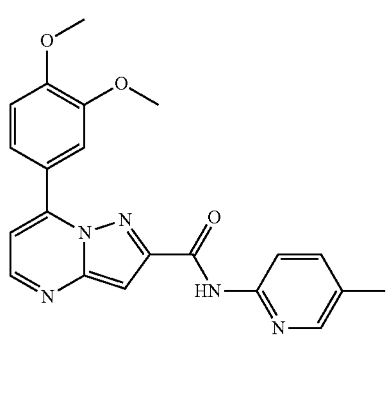 [SMILES: COc1ccc(-c2ccnc3cc(C(=O)Nc4ccc(C)cn4)nn23)cc1OC] | ¹H NMR (400 MHz, DMSO-d₆) δ 9.98 (s, 1H), 8.71 (d, J = 4.5 Hz, 1H), 8.25-8.21 (m, 1H), 8.15 (d, J = 8.5 Hz, 1H), 7.95 (dd, J = 8.5, 2.1 Hz, 1H), 7.91 (d, J = 2.1 Hz, 1H), 7.72 (dd, J = 8.5, 2.2 Hz, 1H), 7.49 (d, J = 4.5 Hz, 1H), 7.38 (s, 1H), 7.24 (d, J = 8.6 Hz, 1H), 3.93-3.89 (m, 6H), 2.30 (s, 3H). | C |

TABLE 3A-continued

Compound Structures, Characterization Data and Synthetic Method

| Cmpd | Structure | Characterization Data | General Method (Ex. 2) |
|---|---|---|---|
| 123 | 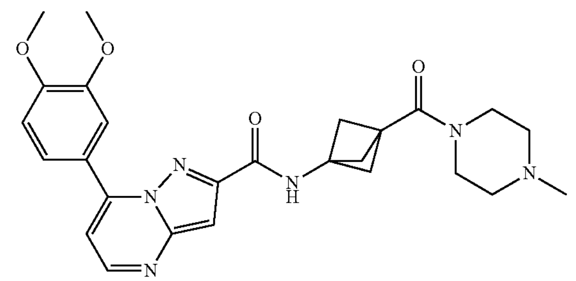 [SMILES: COc1ccc(-c2ccnc3cc(C(=O)NC45CC(C(=O)N6CCN(C)CC6)(C4)C5)nn23)cc1OC] | ¹H NMR (400 MHz, DMSO-d₆) δ 9.05 (s, 1H), 8.65 (d, J = 4.5 Hz, 1H), 7.97 (dd, J = 8.5, 2.1 Hz, 1H), 7.82 (d, J = 2.1 Hz, 1H), 7.43 (d, J = 4.5 Hz, 1H), 7.20 (d, J = 8.6 Hz, 1H), 7.13 (s, 1H), 3.92-3.86 (m, 6H), 3.72-3.40 (m, 4H), 2.75-2.54 (m, 4H), 2.45-2.33 (m, 9H). | B |
| 124 | 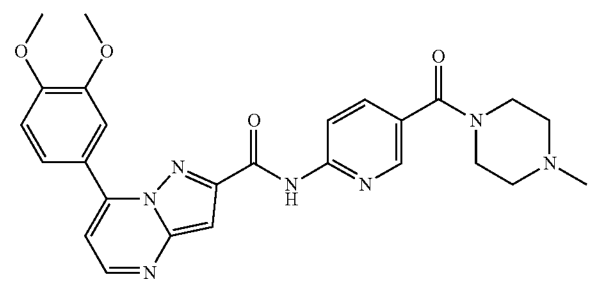 [SMILES: COc1ccc(-c2ccnc3cc(C(=O)Nc4ccc(C(=O)N5CCN(C)CC5)cn4)nn23)cc1OC] | ¹H NMR (400 MHz, DMSO-d₆) δ 10.20 (s, 1H), 8.63 (d, J = 4.5 Hz, 1H), 8.38-8.34 (m, 1H), 8.22 (d, J = 8.5 Hz, 1H), 7.91-7.85 (m, 2H), 7.83 (d, J = 2.1 Hz, 1H), 7.42 (d, J = 4.5 Hz, 1H), 7.34 (s, 1H), 7.15 (d, J = 8.6 Hz, 1H), 3.87-3.80 (m, 6H), 3.61-3.28 (m, 4H), 2.35-2.18 (m, 4H), 2.12 (s, 3H). | B |
| 125 | 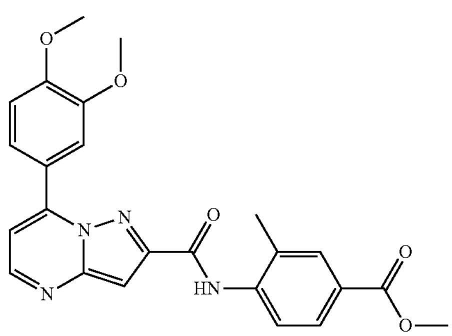 [SMILES: COC(=O)c1ccc(NC(=O)c2cc3nccc(-c4ccc(OC)c(OC)c4)n3n2)c(C)c1] | ¹H NMR (400 MHz, DMSO-d₆) δ 9.85 (s, 1H), 8.71 (d, J = 4.5 Hz, 1H), 8.05-7.99 (m, 2H), 7.92-7.82 (m, 3H), 7.50 (d, J = 4.5 Hz, 1H), 7.31 (s, 1H), 7.20 (d, J = 8.6 Hz, 1H), 3.92-3.82 (m, 9H), 2.38 (s, 3H). | B |
| 126 | 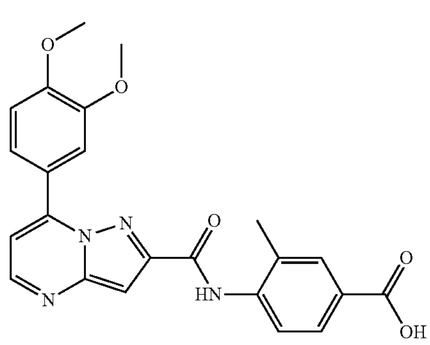 [SMILES: COc1ccc(-c2ccnc3cc(C(=O)Nc4ccc(C(=O)O)cc4C)nn23)cc1OC] | ¹H NMR (400 MHz, DMSO-d₆) δ 12.86 (s, 1H), 9.84 (s, 1H), 8.71 (d, J = 4.5 Hz, 1H), 8.03 (dd, J = 8.5, 2.0 Hz, 1H), 7.97 (d, J = 8.4 Hz, 1H), 7.91-7.81 (m, 3H), 7.50 (d, J = 4.5 Hz, 1H), 7.31 (s, 1H), 7.20 (d, J = 8.6 Hz, 1H), 3.93-3.86 (m, 6H), 2.37 (s, 3H). | B |

TABLE 3A-continued

Compound Structures, Characterization Data and Synthetic Method

| Cmpd | Structure | Characterization Data | General Method (Ex. 2) |
|---|---|---|---|
| 127 | 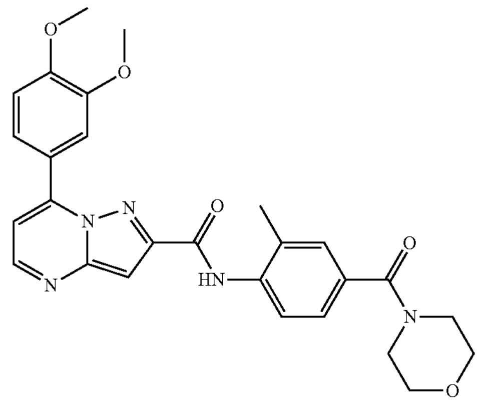 [SMILES: COc1ccc(-c2ccnc3cc(C(=O)Nc4ccc(C(=O)N5CCOCC5)cc4C)nn23)cc1OC] | ¹H NMR (400 MHz, DMSO-d₆) δ 9.84 (s, 1H), 8.71 (d, J = 4.5 Hz, 1H), 8.03 (dd, J = 8.5, 1.9 Hz, 1H), 7.86 (d, J = 2.1 Hz, 1H), 7.79 (d, J = 8.1 Hz, 1H), 7.50 (d, J = 4.5 Hz, 1H), 7.37 (s, 1H), 7.34-7.28 (m, 2H), 7.20 (d, J = 8.6 Hz, 1H), 3.92-3.86 (m, 6H), 3.71-3.37 (m, 8H), 2.33 (s, 3H). | B |
| 128 | 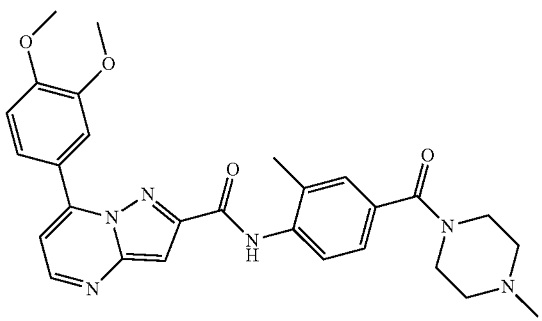 [SMILES: COc1ccc(-c2ccnc3cc(C(=O)Nc4ccc(C(=O)N5CCN(C)CC5)cc4C)nn23)cc1OC] | ¹H NMR (400 MHz, DMSO-d₆) δ 9.83 (s, 1H), 8.71 (d, J = 4.5 Hz, 1H), 8.03 (dd, J = 8.5, 1.9 Hz, 1H), 7.86 (d, J = 2.1 Hz, 1H), 7.78 (d, J = 8.1 Hz, 1H), 7.50 (d, J = 4.5 Hz, 1H), 7.36-7.25 (m, 3H), 7.20 (d, J = 8.6 Hz, 1H), 3.93-3.86 (m, 6H), 3.71-3.38 (m, 4H), 2.43-2.28 (m, 7H), 2.22 (s, 3H). | B |
| 129 | 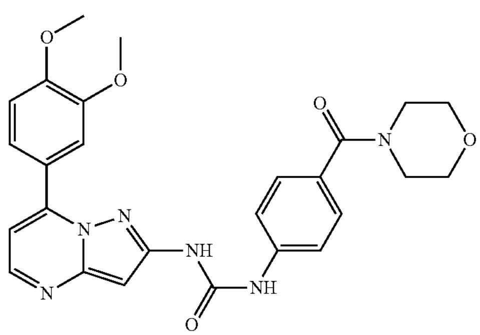 [SMILES: COc1ccc(-c2ccnc3cc(NC(=O)Nc4ccc(C(=O)N5CCOCC5)cc4)nn23)cc1OC] | ¹H NMR (400 MHz, DMSO-d₆) δ 9.76 (s, 1H), 9.24 (s, 1H), 8.40 (d, J = 4.6 Hz, 1H), 7.80-7.68 (m, 2H), 7.45 (d, J = 8.5 Hz, 2H), 7.29 (d, J = 8.5 Hz, 2H), 7.15-7.07 (m, 2H), 6.69 (s, 1H), 3.85-3.74 (m, 6H), 3.58-3.35 (m, 8H). | E |
| 130 | 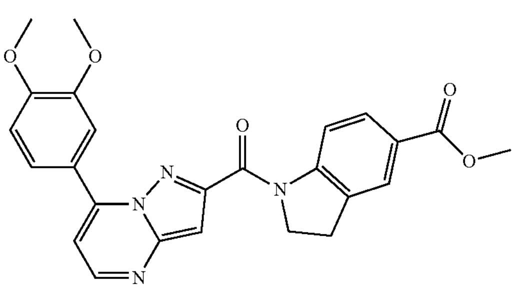 [SMILES: COC(=O)c1ccc2c(c1)CCN2C(=O)c1cc2nccc(-c3ccc(OC)c(OC)c3)n2n1] | ¹H NMR (400 MHz, CDCl₃) δ 8.60 (d, J = 4.4 Hz, 1H), 8.50-8.33 (m, 1H), 8.03-7.93 (m, 1H), 7.91 (d, J = 1.2 Hz, 1H), 7.77-7.59 (m, 2H), 7.37 (s, 1H), 7.12-6.92 (m, 2H), 4.75-4.52 (m, 2H), 4.11-3.80 (m, 9H), 3.22 (t, J = 8.5 Hz, 2H). | D |

TABLE 3A-continued

Compound Structures, Characterization Data and Synthetic Method

| Cmpd | Structure | Characterization Data | General Method (Ex. 2) |
|---|---|---|---|
| 131 | 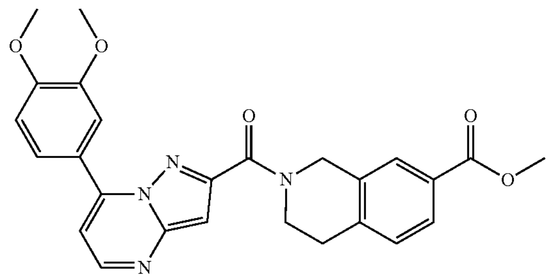 [SMILES: COC(=O)c1ccc2c(c1)CN(C(=O)c1cc3nccc(-c4ccc(OC)c(OC)c4)n3n1)CC2] | $^1$H NMR (400 MHz, DMSO-d$_6$) δ 8.72-8.61 (m, 1H), 7.95-7.65 (m, 4H), 7.48-7.30 (m, 2H), 7.19 (dd, J = 23.1, 8.6 Hz, 1H), 7.07 (d, J = 17.2 Hz, 1H), 5.17 (s, 1H), 4.92 (s, 1H), 4.05 (t, J = 5.8 Hz, 1H), 3.93 (t, J = 6.0 Hz, 1H), 3.90-3.71 (m, 9H), 3.05-2.88 (m, 2H). | D |
| 132 | 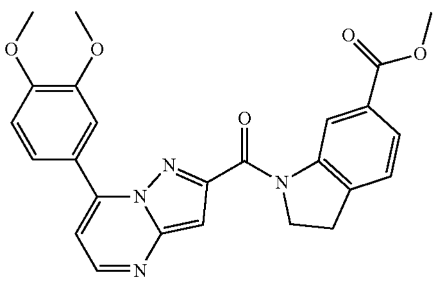 [SMILES: COC(=O)c1ccc2c(c1)N(C(=O)c1cc3nccc(-c4ccc(OC)c(OC)c4)n3n1)CC2] | $^1$H NMR (400 MHz, DMSO-d$_6$) δ 8.86 (s, 1H), 8.71 (d, J = 4.4 Hz, 1H), 7.94-7.79 (m, 2H), 7.74 (d, J = 7.1 Hz, 1H), 7.52-7.40 (m, 2H), 7.28 (s, 1H), 7.22 (d, J = 8.7 Hz, 1H), 4.73-4.56 (m, 2H), 3.95-3.76 (m, 9H), 3.32-3.23 (m, 2H). | D |
| 133 | 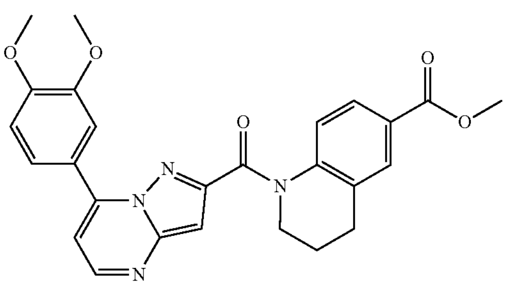 [SMILES: COC(=O)c1ccc2c(c1)CCCN2C(=O)c1cc2nccc(-c3ccc(OC)c(OC)c3)n2n1] | $^1$H NMR (400 MHz, DMSO-d$_6$) δ 8.65 (d, J = 4.5 Hz, 1H), 7.88 (d, J = 1.9 Hz, 1H), 7.58 (dd, J = 9.2, 1.9 Hz, 2H), 7.52-7.43 (m, 1H), 7.40 (d, J = 4.5 Hz, 1H), 7.25 (d, J = 8.1 Hz, 1H), 7.05 (s, 1H), 6.97 (d, J = 8.6 Hz, 1H), 4.00-3.90 (m, 2H), 3.89-3.71 (m, 9H), 2.90 (t, J = 6.6 Hz, 2H), 2.04-1.92 (m, 2H). | D |
| 134 | 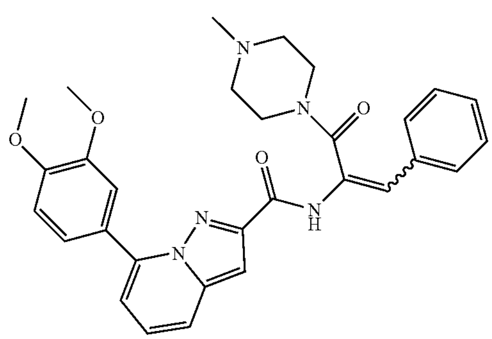 [SMILES: COc1ccc(-c2cccc3cc(C(=O)NC(=Cc4ccccc4)C(=O)N4CCN(C)CC4)nn23)cc1OC] | $^1$H NMR (400 MHz, DMSO-d$_6$) δ 10.04 (s, 1H), 8.70 (d, J = 4.5 Hz, 1H), 8.01 (dd, J = 8.5, 2.1 Hz, 1H), 7.74 (d, J = 2.1 Hz, 1H), 7.64-7.59 (m, 2H), 7.48 (d, J = 4.5 Hz, 1H), 7.38-7.31 (m, 3H), 7.30 (s, 1H), 7.10 (d, J = 8.6 Hz, 1H), 6.33 (s, 1H), 3.88 (s, 3H), 3.76 (s, 3H), 3.70-3.48 (m, 4H), 2.42-2.32 (m, 4H), 2.22 (s, 3H). | A |
| 135 | 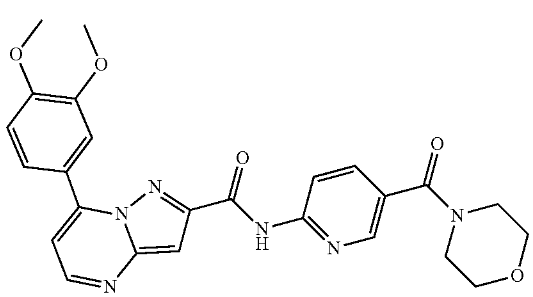 [SMILES: COc1ccc(-c2ccnc3cc(C(=O)Nc4ccc(C(=O)N5CCOCC5)cn4)nn23)cc1OC] | $^1$H NMR (400 MHz, DMSO-d$_6$) δ 10.29 (s, 1H), 8.72 (d, J = 4.5 Hz, 1H), 8.50-8.46 (m, 1H), 8.31 (d, J = 8.5 Hz, 1H), 8.02-7.94 (m, 2H), 7.92 (d, J = 2.1 Hz, 1H), 7.51 (d, J = 4.5 Hz, 1H), 7.43 (s, 1H), 7.24 (d, J = 8.6 Hz, 1H), 3.95-3.88 (m, 6H), 3.74-3.38 (m, 8H). | B |

TABLE 3A-continued

Compound Structures, Characterization Data and Synthetic Method

| Cmpd | Structure | Characterization Data | General Method (Ex. 2) |
|---|---|---|---|
| 136 | 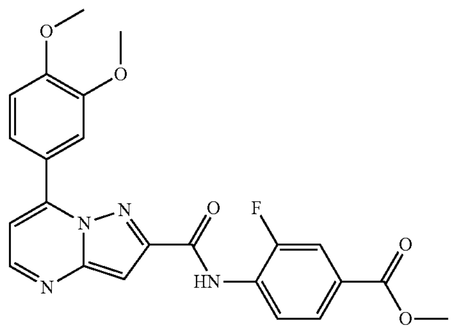 [SMILES: COC(=O)c1ccc(NC(=O)c2cc3nccc(-c4ccc(OC)c(OC)c4)n3n2)c(F)c1] | ¹H NMR (400 MHz, DMSO-d$_6$) δ 10.00 (s, 1H), 8.72 (d, J = 4.5 Hz, 1H), 8.28 (t, J = 8.1 Hz, 1H), 7.95 (d, J = 2.1 Hz, 1H), 7.92-7.80 (m, 3H), 7.50 (d, J = 4.5 Hz, 1H), 7.34 (s, 1H), 7.21 (d, J = 8.6 Hz, 1H), 3.93-3.85 (m, 9H). | B |
| 137 | 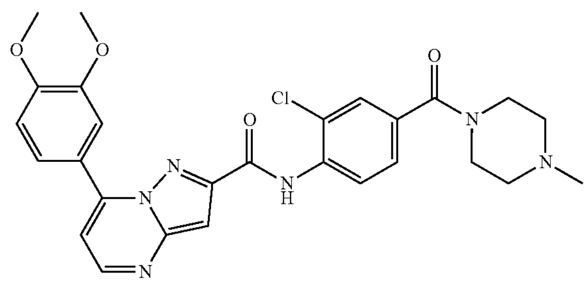 [SMILES: COc1ccc(-c2ccnc3cc(C(=O)Nc4ccc(C(=O)N5CCN(C)CC5)cc4Cl)nn23)cc1OC] | ¹H NMR (400 MHz, DMSO-d$_6$) δ 9.96 (s, 1H), 8.73 (d, J = 4.5 Hz, 1H), 8.34 (d, J = 8.4 Hz, 1H), 7.92 (dd, J = 8.5, 2.1 Hz, 1H), 7.87 (d, J = 2.1 Hz, 1H), 7.66 (d, J = 1.9 Hz, 1H), 7.53-7.46 (m, 2H), 7.35 (s, 1H), 7.21 (d, J = 8.6 Hz, 1H), 3.94-3.82 (m, 6H), 3.77-3.40 (m, 4H), 2.86-2.55 (m, 4H), 2.40 (s, 3H). | B |
| 138 | 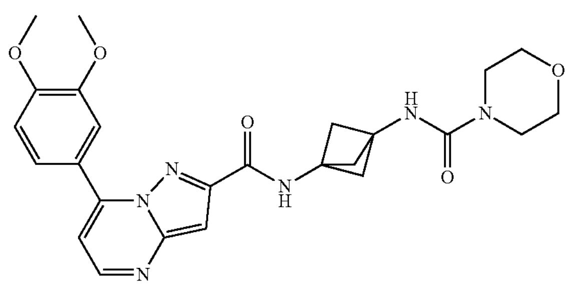 [SMILES: COc1ccc(-c2ccnc3cc(C(=O)NC45CC(NC(=O)N6CCOCC6)(C4)C5)nn23)cc1OC] | ¹H NMR (400 MHz, DMSO-d$_6$) δ 8.94 (s, 1H), 8.65 (d, J = 4.5 Hz, 1H), 7.99 (dd, J = 8.5, 2.1 Hz, 1H), 7.82 (d, J = 2.1 Hz, 1H), 7.43 (d, J = 4.5 Hz, 1H), 7.22-7.15 (m, 2H), 7.12 (s, 1H), 3.93-3.84 (m, 6H), 3.57-3.48 (m, 4H), 3.27-3.21 (m, 4H), 2.28 (s, 6H). | B |
| 139 | 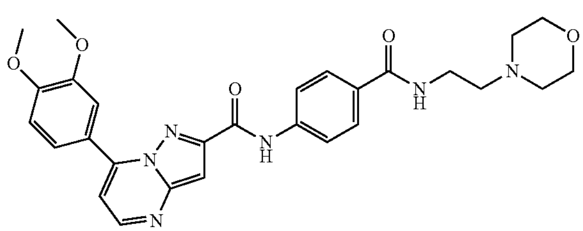 [SMILES: COc1ccc(-c2ccnc3cc(C(=O)Nc4ccc(C(=O)NCCN5CCOCC5)cc4)nn23)cc1OC] | ¹H NMR (400 MHz, DMSO-d$_6$) δ 10.48 (s, 1H), 8.71 (d, J = 4.5 Hz, 1H), 8.37 (t, J = 5.7 Hz, 1H), 8.03 (dd, J = 8.5, 2.1 Hz, 1H), 7.96 (d, J = 2.1 Hz, 1H), 7.94-7.89 (m, 2H), 7.89-7.82 (m, 2H), 7.51 (d, J = 4.5 Hz, 1H), 7.33 (s, 1H), 7.23 (d, J = 8.7 Hz, 1H), 3.93-3.87 (m, 6H), 3.61-3.55 (m, 4H), 3.44-3.35 (m, 2H), 2.50-2.38 (m, 6H). | C |
| 140 | 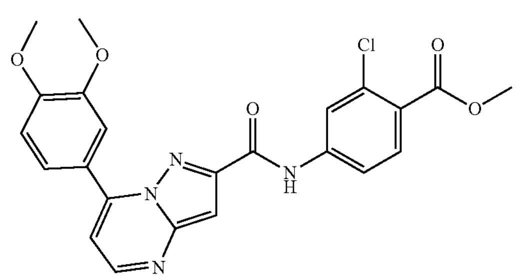 [SMILES: COC(=O)c1ccc(NC(=O)c2cc3nccc(-c4ccc(OC)c(OC)c4)n3n2)cc1Cl] | ¹H NMR (400 MHz, DMSO-d$_6$) δ 10.72 (s, 1H), 8.71 (d, J = 4.5 Hz, 1H), 8.17 (s, 1H), 8.03 (dd, J = 8.5, 2.2 Hz, 1H), 7.96-7.85 (m, 3H), 7.52 (d, J = 4.5 Hz, 1H), 7.35 (s, 1H), 7.23 (d, J = 8.6 Hz, 1H), 3.95-3.88 (m, 6H), 3.86 (s, 3H). | B |

TABLE 3A-continued

Compound Structures, Characterization Data and Synthetic Method

| Cmpd | Structure | Characterization Data | General Method (Ex. 2) |
|---|---|---|---|
| 141 | 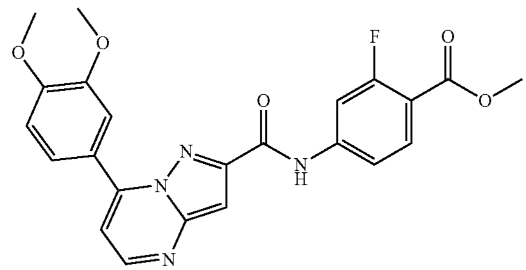 [SMILES: COC(=O)c1ccc(NC(=O)c2cc3nccc(-c4ccc(OC)c(OC)c4)n3n2)cc1F] | ¹H NMR (400 MHz, DMSO-d₆) δ 10.79 (s, 1H), 8.71 (d, J = 4.5 Hz, 1H), 8.02 (dd, J = 8.5, 2.1 Hz, 1H), 7.96-7.84 (m, 3H), 7.77 (dd, J = 8.7, 1.9 Hz, 1H), 7.52 (d, J = 4.5 Hz, 1H), 7.35 (s, 1H), 7.23 (d, J = 8.6 Hz, 1H), 3.94-3.86 (m, 6H), 3.85 (s, 3H). | B |
| 142 | 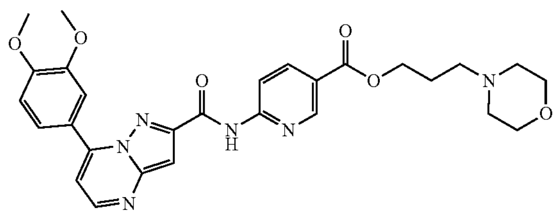 [SMILES: COc1ccc(-c2ccnc3cc(C(=O)Nc4ccc(C(=O)OCCCN5CCOCC5)cn4)nn23)cc1OC] | ¹H NMR (400 MHz, DMSO-d₆) δ 10.49 (s, 1H), 8.95-8.84 (m, 1H), 8.73 (d, J = 4.4 Hz, 1H), 8.46-8.29 (m, 2H), 8.00-7.83 (m, 2H), 7.52 (d, J = 4.5 Hz, 1H), 7.45 (s, 1H), 7.24 (d, J = 8.5 Hz, 1H), 4.35 (t, J = 6.5 Hz, 2H), 3.98-3.77 (m, 6H), 3.56 (t, J = 4.5 Hz, 4H), 2.43 (t, J = 7.1 Hz, 2H), 2.40-2.30 (m, 4H), 1.94-1.85 (m, 2H). | B |
| 143 | 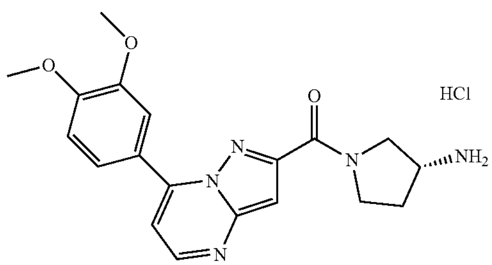 [SMILES: COc1ccc(-c2ccnc3cc(C(=O)N4CC[C@@H](N)C4)nn23)cc1OC ; Cl] | ¹H NMR (400 MHz, DMSO-d₆) δ 8.68 (dd, J = 4.4, 2.5 Hz, 1H), 8.38 (s, 3H), 7.97-7.69 (m, 2H), 7.42 (dd, J = 13.9, 4.4 Hz, 1H), 7.25 (dd, J = 34.4, 8.8 Hz, 1H), 7.14 (s, 1H), 4.21-4.12 (m, 3H), 3.90-3.84 (m, 6H), 3.82-3.63 (m, 2H), 2.33-2.17 (m, 1H), 2.15-1.99 (m, 1H). | D |
| 144 | 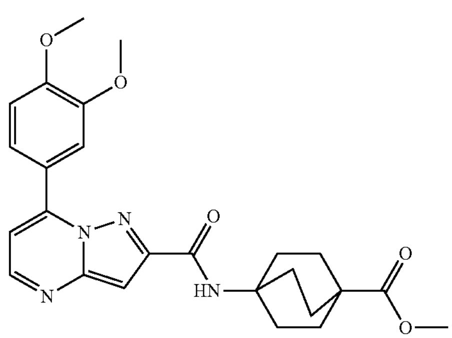 [SMILES: COC(=O)C12CCC(NC(=O)c3cc4nccc(-c5ccc(OC)c(OC)c5)n4n3)(CC1)CC2] | ¹H NMR (400 MHz, DMSO-d₆) δ 8.64 (d, J = 4.5 Hz, 1H), 8.00 (d, J = 2.1 Hz, 1H), 7.85 (dd, J = 8.5, 2.1 Hz, 1H), 7.46-7.40 (m, 2H), 7.19 (d, J = 8.6 Hz, 1H), 7.09 (s, 1H), 3.90-3.87 (m, 6H), 3.58 (s, 3H), 2.05-1.92 (m, 6H), 1.89-1.77 (m, 6H). | A |
| 145 | 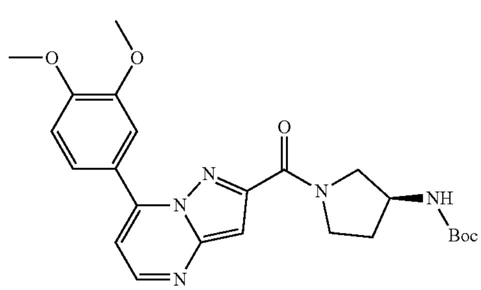 [SMILES: COc1ccc(-c2ccnc3cc(C(=O)N4CC[C@H](NC(=O)OC(C)(C)C)C4)nn23)cc1OC] | ¹H NMR (400 MHz, DMSO-d₆) δ 8.69-8.64 (m, 1H), 7.87-7.76 (m, 2H), 7.41-7.37 (m, 1H), 7.29-7.17 (m, 2H), 7.09 (d, J = 3.8 Hz, 1H), 4.16-4.03 (m, 2H), 3.90-3.82 (m, 6H), 3.81-3.50 (m, 3H), 2.13-2.00 (m, 1H), 1.92-1.78 (m, 1H), 1.45-1.35 (m, 9H). | D |

TABLE 3A-continued

Compound Structures, Characterization Data and Synthetic Method

| Cmpd | Structure | Characterization Data | General Method (Ex. 2) |
|---|---|---|---|
| 146 | 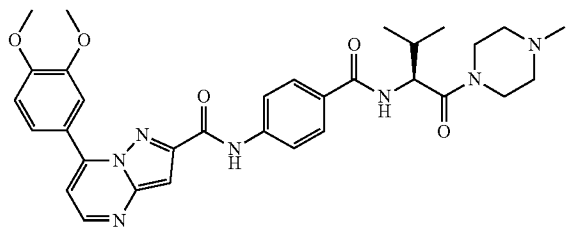 [SMILES: COc1ccc(-c2ccnc3cc(C(=O)Nc4ccc(C(=O)N[C@H](C(=O)N5CCN(C)CC5)C(C)C)cc4)nn23)cc1OC] | ¹H NMR (400 MHz, DMSO-d₆) δ 10.48 (s, 1H), 8.70 (d, J = 4.5 Hz, 1H), 8.43 (d, J = 8.6 Hz, 1H), 8.05-7.99 (m, 1H), 7.99-7.87 (m, 5H), 7.50 (d, J = 4.5 Hz, 1H), 7.33 (s, 1H), 7.22 (d, J = 8.6 Hz, 1H), 4.71 (t, J = 8.6 Hz, 1H), 3.94-3.86 (m, 6H), 3.70-3.59 (m, 2H), 3.55-3.47 (m, 2H), 2.35-2.23 (m, 4H), 2.22-2.14 (m, 4H), 0.96-0.88 (m, 6H). | C |
| 147 | 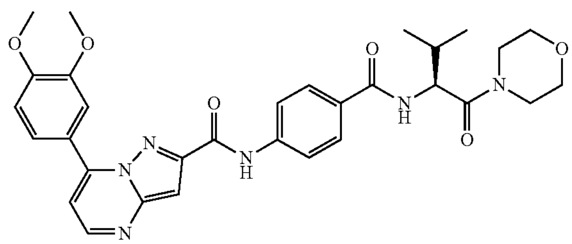 [SMILES: COc1ccc(-c2ccnc3cc(C(=O)Nc4ccc(C(=O)N[C@H](C(=O)N5CCOCC5)C(C)C)cc4)nn23)cc1OC] | ¹H NMR (400 MHz, DMSO-d₆) δ 10.48 (s, 1H), 8.70 (d, J = 4.5 Hz, 1H), 8.48 (d, J = 8.4 Hz, 1H), 8.02 (dd, J = 8.5, 2.1 Hz, 1H), 7.99-7.87 (m, 5H), 7.50 (d, J = 4.5 Hz, 1H), 7.33 (s, 1H), 7.22 (d, J = 8.6 Hz, 1H), 4.69 (t, J = 8.6 Hz, 1H), 3.93-3.88 (m, 6H), 3.73-3.64 (m, 2H), 3.62-3.47 (m, 6H), 2.26-2.10 (m, 1H), 1.00-0.89 (m, 6H). | C |
| 148 | 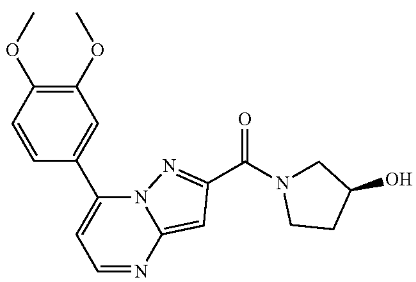 [SMILES: COc1ccc(-c2ccnc3cc(C(=O)N4CC[C@H](O)C4)nn23)cc1OC] | ¹H NMR (400 MHz, DMSO-d₆) δ 8.65 (s, 1H), 7.82 (s, 2H), 7.38 (s, 1H), 7.19 (s, 1H), 7.09 (s, 1H), 5.12-4.87 (m, 1H), 4.49-4.18 (m, 1H), 4.16-3.97 (m, 1H), 3.96-3.72 (m, 7H), 3.70-3.44 (m, 2H), 2.03-1.74 (m, 2H). | D |
| 149 | 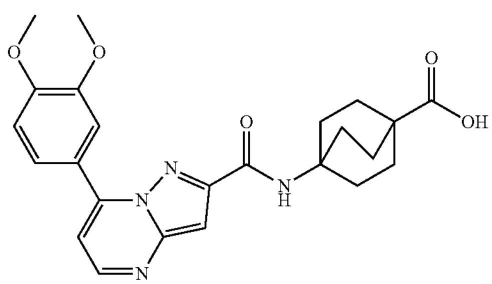 [SMILES: COc1ccc(-c2ccnc3cc(C(=O)NC45CCC(C(=O)O)(CC4)CC5)nn23)cc1OC] | ¹H NMR (400 MHz, DMSO-d₆) δ 12.12 (s, 1H), 8.64 (d, J = 4.4 Hz, 1H), 8.10-7.93 (m, 1H), 7.90-7.78 (m, 1H), 7.52-7.34 (m, 2H), 7.20 (d, J = 8.6 Hz, 1H), 7.09 (s, 1H), 4.04-3.73 (m, 6H), 2.06-1.89 (m, 6H), 1.88-1.70 (m, 6H). | A |
| 150 | 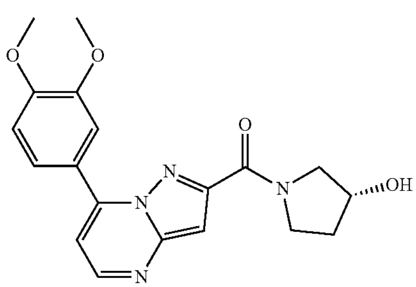 [SMILES: COc1ccc(-c2ccnc3cc(C(=O)N4CC[C@@H](O)C4)nn23)cc1OC] | ¹H NMR (400 MHz, DMSO-d₆) δ 8.66 (d, J = 4.4 Hz, 1H), 7.93-7.74 (m, 2H), 7.39 (d, J = 4.3 Hz, 1H), 7.20 (d, J = 8.3 Hz, 1H), 7.10 (d, J = 3.0 Hz, 1H), 5.14-4.94 (m, 1H), 4.41-4.27 (m, 1H), 4.10-3.82 (m, 8H), 3.70-3.45 (m, 2H), 2.13-1.65 (m, 2H). | D |

TABLE 3A-continued

Compound Structures, Characterization Data and Synthetic Method

| Cmpd | Structure | Characterization Data | General Method (Ex. 2) |
|---|---|---|---|
| 151 | 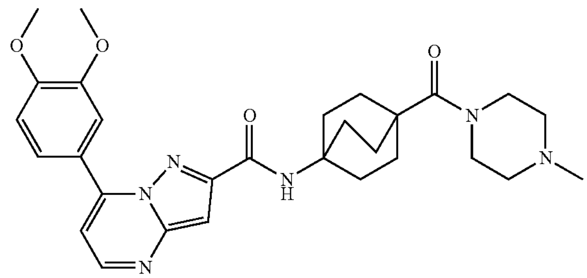 [SMILES: COc1ccc(-c2ccnc3cc(C(=O)NC45CCC(C(=O)N6CCN(C)CC6)(CC4)CC5)nn23)cc1OC] | $^1$H NMR (400 MHz, DMSO-d$_6$) δ 8.64 (d, J = 4.5 Hz, 1H), 8.02 (d, J = 2.1 Hz, 1H), 7.84 (dd, J = 8.5, 2.1 Hz, 1H), 7.46-7.41 (m, 2H), 7.20 (d, J = 8.6 Hz, 1H), 7.10 (s, 1H), 3.92-3.86 (m, 6H), 3.63-3.48 (m, 4H), 2.30-2.20 (m, 4H), 2.17 (s, 3H), 2.03-1.94 (m, 6H), 1.94-1.84 (m, 6H). | A |
| 152 | 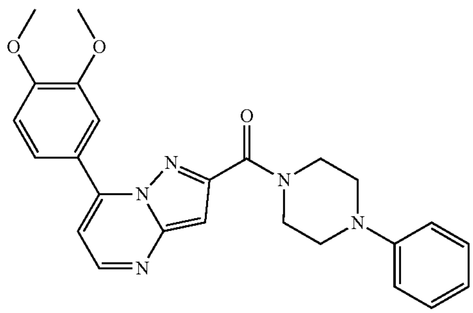 [SMILES: COc1ccc(-c2ccnc3cc(C(=O)N4CCN(c5ccccc5)CC4)nn23)cc1OC] | $^1$H NMR (400 MHz, DMSO-d$_6$) δ 8.67 (d, J = 4.4 Hz, 1H), 7.85 (dd, J = 8.5, 2.1 Hz, 1H), 7.80 (d, J = 2.1 Hz, 1H), 7.41 (d, J = 4.5 Hz, 1H), 7.31-7.15 (m, 3H), 7.07 (s, 1H), 6.97 (d, J = 7.9 Hz, 2H), 6.82 (t, J = 7.3 Hz, 1H), 4.05-3.92 (m, 2H), 3.91-3.78 (m, 8H), 3.28-3.21 (m, 2H), 3.21-3.11 (m, 2H). | D |
| 153 | 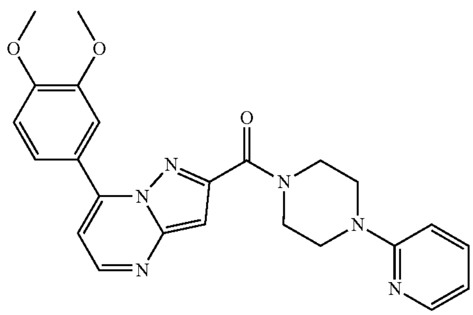 [SMILES: COc1ccc(-c2ccnc3cc(C(=O)N4CCN(c5ccccn5)CC4)nn23)cc1OC] | $^1$H NMR (400 MHz, DMSO-d$_6$) δ 8.67 (d, J = 4.5 Hz, 1H), 8.16-8.09 (m, 1H), 7.85 (dd, J = 8.5, 2.1 Hz, 1H), 7.79 (d, J = 2.1 Hz, 1H), 7.65-7.50 (m, 1H), 7.41 (d, J = 4.5 Hz, 1H), 7.22 (d, J = 8.6 Hz, 1H), 7.07 (s, 1H), 6.87 (d, J = 8.5 Hz, 1H), 6.75-6.62 (m, 1H), 4.00-3.91 (m, 2H), 3.88 (s, 3H), 3.86 (s, 3H), 3.83-3.75 (m, 2H), 3.70-3.59 (m, 2H), 3.59-3.47 (m, 2H). | D |
| 154 | 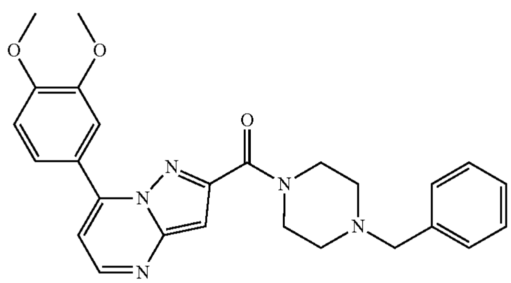 [SMILES: COc1ccc(-c2ccnc3cc(C(=O)N4CCN(Cc5ccccc5)CC4)nn23)cc1OC] | $^1$H NMR (400 MHz, DMSO-d$_6$) δ 8.65 (d, J = 4.5 Hz, 1H), 7.85-7.72 (m, 2H), 7.42-7.30 (m, 5H), 7.30-7.24 (m, 1H), 7.19 (d, J = 8.6 Hz, 1H), 7.01 (s, 1H), 3.88 (s, 3H), 3.86-3.75 (m, 5H), 3.74-3.64 (m, 2H), 3.52 (s, 2H), 2.47-2.42 (m, 2H), 2.42-2.36 (m, 2H). | D |
| 155 | 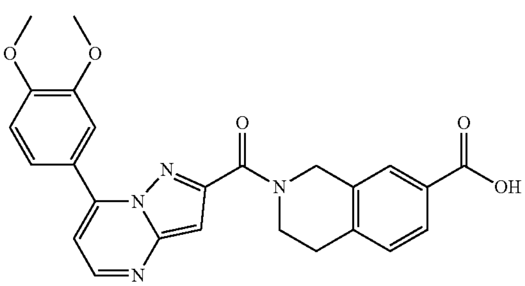 [SMILES: COc1ccc(-c2ccnc3cc(C(=O)N4CCc5ccc(C(=O)O)cc5C4)nn23)cc1OC] | $^1$H NMR (400 MHz, DMSO-d$_6$) δ 12.92 (s, 1H), 8.74-8.55 (m, 1H), 7.93-7.73 (m, 4H), 7.40 (t, J = 3.8 Hz, 1H), 7.33 (dd, J = 7.8, 4.5 Hz, 1H), 7.27-7.14 (m, 1H), 7.07 (d, J = 12.2 Hz, 1H), 5.21 (s, 1H), 4.90 (s, 1H), 4.04 (t, J = 5.8 Hz, 1H), 3.93 (t, J = 5.8 Hz, 1H), 3.85 (m, 6H), 3.02-2.92 (m, 2H). | D |

TABLE 3A-continued

Compound Structures, Characterization Data and Synthetic Method

| Cmpd | Structure | Characterization Data | General Method (Ex. 2) |
|---|---|---|---|
| 156 | 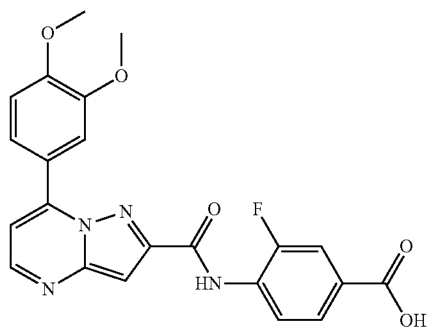 [SMILES: COc1ccc(-c2ccnc3cc(C(=O)Nc4ccc(C(=O)O)cc4F)nn23)cc1OC] | ¹H NMR (400 MHz, DMSO-d₆) δ 9.97 (s, 1H), 8.72 (d, J = 4.5 Hz, 1H), 8.20 (t, J = 8.1 Hz, 1H), 7.95 (d, J = 2.0 Hz, 1H), 7.90 (dd, J = 8.4, 2.0 Hz, 1H), 7.86-7.82 (m, 1H), 7.78 (dd, J = 11.3, 1.6 Hz, 1H), 7.50 (d, J = 4.5 Hz, 1H), 7.34 (s, 1H), 7.22 (d, J = 8.6 Hz, 1H), 3.93-3.88 (m, 6H). | B |
| 157 | 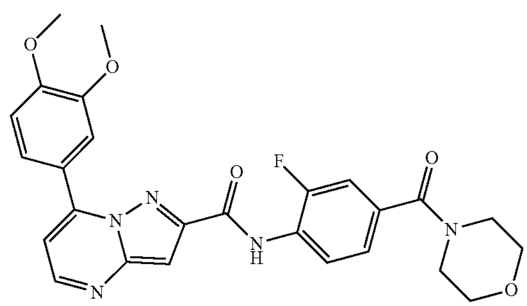 [SMILES: COc1ccc(-c2ccnc3cc(C(=O)Nc4ccc(C(=O)N5CCOCC5)cc4F)nn23)cc1OC] | ¹H NMR (400 MHz, DMSO-d₆) δ 9.97 (s, 1H), 8.72 (d, J = 4.5 Hz, 1H), 8.08 (t, J = 8.0 Hz, 1H), 7.96 (d, J = 2.1 Hz, 1H), 7.91 (dd, J = 8.5, 2.0 Hz, 1H), 7.50 (d, J = 4.5 Hz, 1H), 7.45 (dd, J = 10.9, 1.7 Hz, 1H), 7.36-7.31 (m, 2H), 7.21 (d, J = 8.6 Hz, 1H), 3.94-3.87 (m, 6H), 3.72-3.38 (m, 8H). | B |
| 158 | 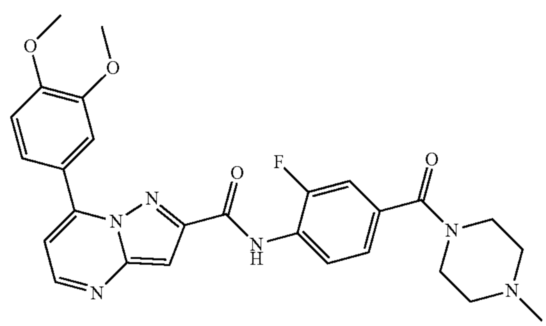 | ¹H NMR (400 MHz, DMSO-d₆) δ 9.96 (s, 1H), 8.72 (d, J = 4.5 Hz, 1H), 8.07 (t, J = 8.0 Hz, 1H), 7.96 (d, J = 2.1 Hz, 1H), 7.91 (dd, J = 8.5, 2.0 Hz, 1H), 7.50 (d, J = 4.5 Hz, 1H), 7.42 (dd, J = 10.8, 1.7 Hz, 1H), 7.35-7.27 (m, 2H), 7.21 (d, J = 8.6 Hz, 1H), 3.92-3.87 (m, 6H), 3.72-3.39 (m, 4H), 2.44-2.27 (m, 4H), 2.22 (s, 3H). | B |
| 159 | 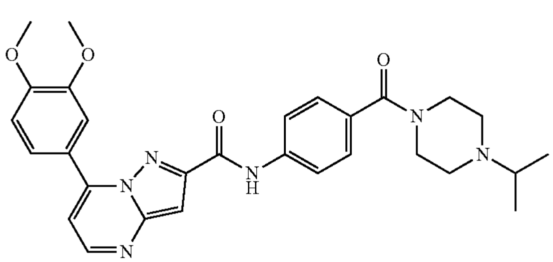 [SMILES: COc1ccc(-c2ccnc3cc(C(=O)Nc4ccc(C(=O)N5CCN(C(C)C)CC5)cc4)nn23)cc1OC] | ¹H NMR (400 MHz, DMSO-d₆) δ 10.45 (s, 1H), 8.71 (d, J = 4.5 Hz, 1H), 8.02 (dd, J = 8.5, 2.1 Hz, 1H), 7.97 (d, J = 2.1 Hz, 1H), 7.90 (d, J = 8.5 Hz, 2H), 7.51 (d, J = 4.5 Hz, 1H), 7.43 (d, J = 8.3 Hz, 2H), 7.33 (s, 1H), 7.22 (d, J = 8.6 Hz, 1H), 3.94-3.88 (m, 6H), 3.71-3.39 (m, 4H), 2.75-2.65 (m, 1H), 2.50-2.38 (m, 4H), 1.07-0.91 (m, 6H). | C |

TABLE 3A-continued

Compound Structures, Characterization Data and Synthetic Method

| Cmpd | Structure | Characterization Data | General Method (Ex. 2) |
|---|---|---|---|
| 160 | 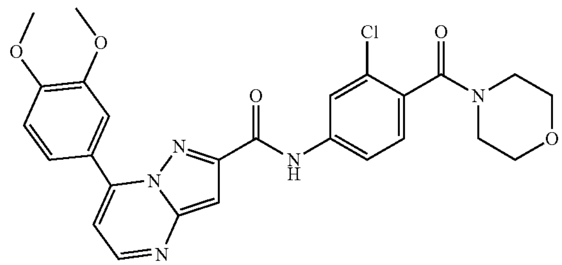 [SMILES: COc1ccc(-c2ccnc3cc(C(=O)Nc4ccc(C(=O)N5CCOCC5)c(Cl)c4)nn23)cc1OC] | $^1$H NMR (400 MHz, DMSO-d$_6$) δ 10.59 (s, 1H), 8.71 (d, J = 4.5 Hz, 1H), 8.10 (s, 1H), 8.02 (d, J = 8.5 Hz, 1H), 7.94 (s, 1H), 7.86 (d, J = 8.3 Hz, 1H), 7.51 (d, J = 4.5 Hz, 1H), 7.41 (d, J = 8.4 Hz, 1H), 7.33 (s, 1H), 7.22 (d, J = 8.6 Hz, 1H), 3.99-3.84 (m, 6H), 3.75-3.61 (m, 4H), 3.60-3.50 (m, 2H), 3.24-3.13 (m, 2H). | B |
| 161 | 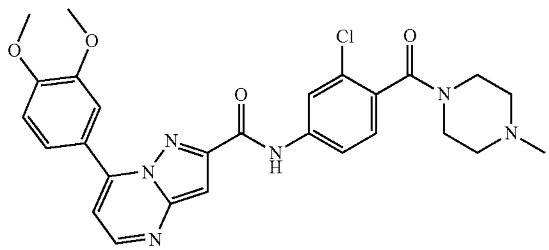 [SMILES: COc1ccc(-c2ccnc3cc(C(=O)Nc4ccc(C(=O)N5CCN(C)CC5)c(Cl)c4)nn23)cc1OC] | $^1$H NMR (400 MHz, DMSO-d$_6$) δ 10.59 (s, 1H), 8.71 (d, J = 4.4 Hz, 1H), 8.10 (s, 1H), 8.02 (d, J = 8.4 Hz, 1H), 7.94 (s, 1H), 7.86 (d, J = 7.9 Hz, 1H), 7.51 (d, J = 4.5 Hz, 1H), 7.38 (d, J = 8.4 Hz, 1H), 7.33 (s, 1H), 7.23 (d, J = 8.6 Hz, 1H), 3.95-3.84 (m, 6H), 3.76-3.51 (m, 2H), 3.23-3.08 (m, 2H), 2.47-2.38 (m, 2H), 2.38-2.29 (m, 2H), 2.29-2.14 (m, 3H). | B |
| 162 | 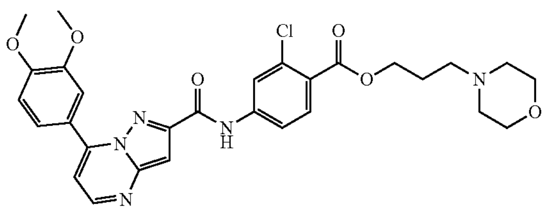 [SMILES: COc1ccc(-c2ccnc3cc(C(=O)Nc4ccc(C(=O)OCCCN5CCOCC5)c(Cl)c4)nn23)cc1OC] | $^1$H NMR (400 MHz, DMSO-d$_6$) δ 10.72 (s, 1H), 8.70 (d, J = 4.5 Hz, 1H), 8.15 (s, 1H), 8.01 (dd, J = 8.5, 2.1 Hz, 1H), 7.95-7.83 (m, 3H), 7.50 (d, J = 4.5 Hz, 1H), 7.34 (s, 1H), 7.22 (d, J = 8.6 Hz, 1H), 4.30 (t, J = 6.4 Hz, 2H), 3.98-3.78 (m, 6H), 3.56 (t, J = 4.5 Hz, 4H), 2.42 (t, J = 7.0 Hz, 2H), 2.40-2.28 (m, 4H), 1.91-1.78 (m, 2H). | B |
| 163 | 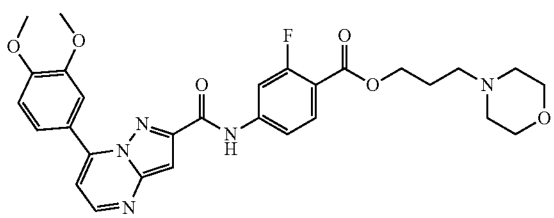 [SMILES: COc1ccc(-c2ccnc3cc(C(=O)Nc4ccc(C(=O)OCCCN5CCOCC5)c(F)c4)nn23)cc1OC] | $^1$H NMR (400 MHz, DMSO-d$_6$) δ 10.79 (s, 1H), 8.72 (d, J = 4.4 Hz, 1H), 8.01 (d, J = 8.5 Hz, 1H), 7.98-7.85 (m, 3H), 7.77 (d, J = 8.6 Hz, 1H), 7.52 (d, J = 4.4 Hz, 1H), 7.36 (s, 1H), 7.23 (d, J = 8.6 Hz, 1H), 4.31 (t, J = 6.4 Hz, 2H), 3.96-3.81 (m, 6H), 3.63-3.47 (m, 4H), 2.45-2.26 (m, 6H), 1.97-1.75 (m, 2H). | B |
| 164 | 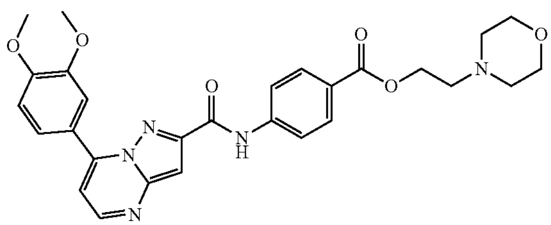 [SMILES: COc1ccc(-c2ccnc3cc(C(=O)Nc4ccc(C(=O)OCCN5CCOCC5)cc4)nn23)cc1OC] | $^1$H NMR (400 MHz, DMSO-d$_6$) δ 10.61 (s, 1H), 8.71 (d, J = 4.5 Hz, 1H), 8.08-7.90 (m, 6H), 7.51 (d, J = 4.4 Hz, 1H), 7.35 (s, 1H), 7.22 (d, J = 8.5 Hz, 1H), 4.38 (t, J = 5.6 Hz, 2H), 3.99-3.83 (m, 6H), 3.65-3.49 (m, 4H), 2.70 (t, J = 5.8 Hz, 2H), 2.49-2.36 (m, 4H). | C |
| 165 | 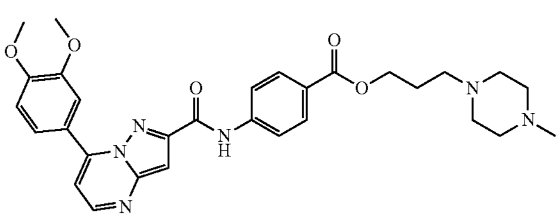 [SMILES: COc1ccc(-c2ccnc3cc(C(=O)Nc4ccc(C(=O)OCCCN5CCN(C)CC5)cc4)nn23)cc1OC] | $^1$H NMR (400 MHz, DMSO-d$_6$) δ 10.60 (s, 1H), 8.71 (d, J = 4.3 Hz, 1H), 8.11-7.83 (m, 6H), 7.51 (d, J = 4.4 Hz, 1H), 7.34 (s, 1H), 7.22 (d, J = 8.6 Hz, 1H), 4.29 (t, J = 6.3 Hz, 2H), 3.97-3.87 (m, 6H), 2.50-2.21 (m, 10H), 2.16 (s, 3H), 1.94-1.74 (m, 2H). | C |

TABLE 3A-continued

Compound Structures, Characterization Data and Synthetic Method

| Cmpd | Structure | Characterization Data | General Method (Ex. 2) |
|---|---|---|---|
| 166 | 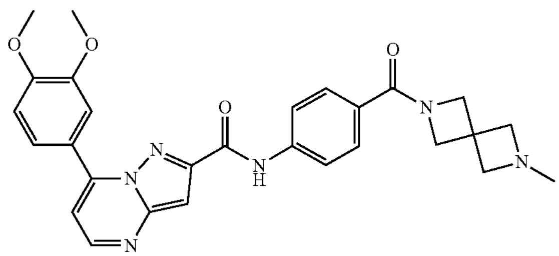 [SMILES: COc1ccc(-c2ccnc3cc(C(=O)Nc4ccc(C(=O)N5CC6(CN(C)C6)C5)cc4)nn23)cc1OC] | $^1$H NMR (400 MHz, DMSO-d$_6$) δ 10.49 (s, 1H), 8.71 (d, J = 4.5 Hz, 1H), 8.02 (dd, J = 8.5, 2.1 Hz, 1H), 7.96 (d, J = 2.1 Hz, 1H), 7.91 (d, J = 8.7 Hz, 2H), 7.66 (d, J = 8.7 Hz, 2H), 7.51 (d, J = 4.5 Hz, 1H), 7.33 (s, 1H), 7.22 (d, J = 8.6 Hz, 1H), 4.41 (s, 2H), 4.12 (d, J = 19.2 Hz, 2H), 3.95-3.86 (m, 6H), 3.26 (s, 4H), 2.17 (s, 3H). | C |
| 167 | 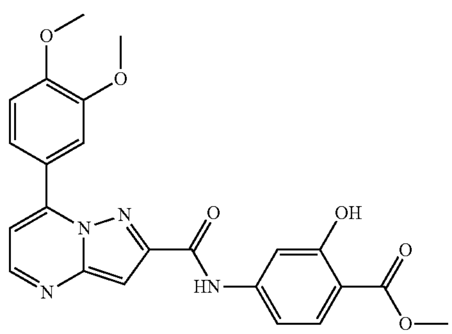 [SMILES: COC(=O)c1ccc(NC(=O)c2cc3nccc(-c4ccc(OC)c(OC)c4)n3n2)cc1O] | $^1$H NMR (400 MHz, DMSO-d$_6$) δ 10.73-10.48 (m, 2H), 8.71 (d, J = 4.5 Hz, 1H), 8.02 (dd, J = 8.5, 2.1 Hz, 1H), 7.96 (d, J = 2.1 Hz, 1H), 7.80 (d, J = 8.8 Hz, 1H), 7.63 (d, J = 2.0 Hz, 1H), 7.51 (d, J = 4.5 Hz, 1H), 7.41 (dd, J = 8.8, 2.0 Hz, 1H), 7.34 (s, 1H), 7.23 (d, J = 8.6 Hz, 1H), 3.93-3.87 (m, 9H). | B |
| 168 | 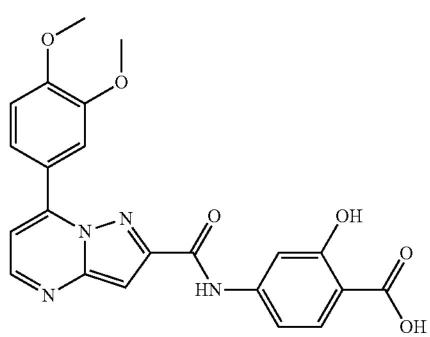 [SMILES: COc1ccc(-c2ccnc3cc(C(=O)Nc4ccc(C(=O)O)c(O)c4)nn23)cc1OC] | $^1$H NMR (400 MHz, DMSO-d$_6$) δ 13.79 (s, 1H), 11.47 (s, 1H), 10.50 (s, 1H), 8.71 (d, J = 4.5 Hz, 1H), 8.02 (dd, J = 8.5, 2.1 Hz, 1H), 7.96 (d, J = 2.1 Hz, 1H), 7.79 (d, J = 8.7 Hz, 1H), 7.58 (d, J = 2.0 Hz, 1H), 7.51 (d, J = 4.5 Hz, 1H), 7.43-7.31 (m, 2H), 7.23 (d, J = 8.6 Hz, 1H), 3.93-3.87 (m, 6H). | B |
| 169 | 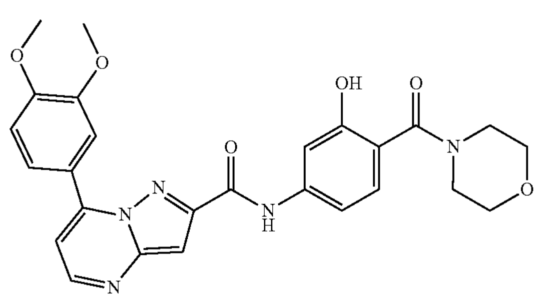 [SMILES: COc1ccc(-c2ccnc3cc(C(=O)Nc4ccc(C(=O)N5CCOCC5)c(O)c4)nn23)cc1OC] | $^1$H NMR (400 MHz, DMSO-d$_6$) δ 10.28 (s, 1H), 10.03 (s, 1H), 8.70 (d, J = 4.5 Hz, 1H), 8.04-7.96 (m, 2H), 7.58 (d, J = 1.7 Hz, 1H), 7.50 (d, J = 4.5 Hz, 1H), 7.31 (s, 1H), 7.25-7.19 (m, 2H), 7.14 (d, J = 8.3 Hz, 1H), 3.93-3.88 (m, 6H), 3.68-3.36 (m, 8H). | B |

TABLE 3A-continued

Compound Structures, Characterization Data and Synthetic Method

| Cmpd | Structure | Characterization Data | General Method (Ex. 2) |
|---|---|---|---|
| 170 | 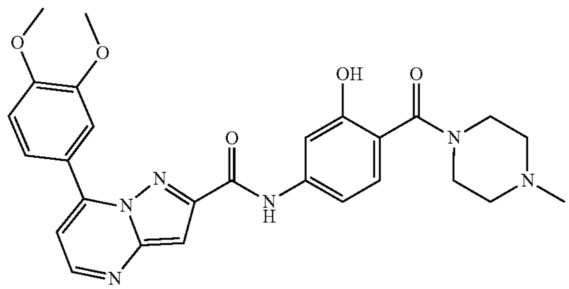 [SMILES: COc1ccc(-c2ccnc3cc(C(=O)Nc4ccc(C(=O)N5CCN(C)CC5)c(O)c4)nn23)cc1OC] | $^1$H NMR (400 MHz, DMSO-d$_6$) δ 10.27 (s, 1H), 9.97 (s, 1H), 8.70 (d, J = 4.5 Hz, 1H), 8.03-7.95 (m, 2H), 7.57 (d, J = 1.8 Hz, 1H), 7.50 (d, J = 4.5 Hz, 1H), 7.31 (s, 1H), 7.22 (d, J = 8.5 Hz, 2H), 7.11 (d, J = 8.3 Hz, 1H), 3.94-3.87 (m, 6H), 3.65-3.35 (m, 4H), 2.38-2.24 (m, 4H), 2.19 (s, 3H). | B |
| 171 | 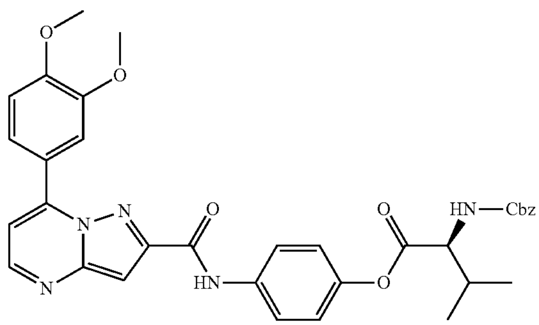 [SMILES: COc1ccc(-c2ccnc3cc(C(=O)Nc4ccc(OC(=O)[C@@H](NC(=O)OCc5ccccc5)C(C)C)cc4)nn23)cc1OC] | $^1$H NMR (400 MHz, DMSO-d$_6$) δ 10.38 (s, 1H), 8.70 (d, J = 4.5 Hz, 1H), 8.02 (dd, J = 8.5, 2.0 Hz, 1H), 7.98-7.92 (m, 2H), 7.86 (d, J = 8.6 Hz, 2H), 7.50 (d, J = 4.5 Hz, 1H), 7.42-7.30 (m, 6H), 7.22 (d, J = 8.6 Hz, 1H), 7.09 (d, J = 8.9 Hz, 2H), 5.12-5.07 (m, 2H), 4.20-4.14 (m, 1H), 3.94-3.87 (m, 6H), 2.30-2.14 (m, 1H), 1.03 (d, J = 6.7 Hz, 6H). | C |
| 172 | 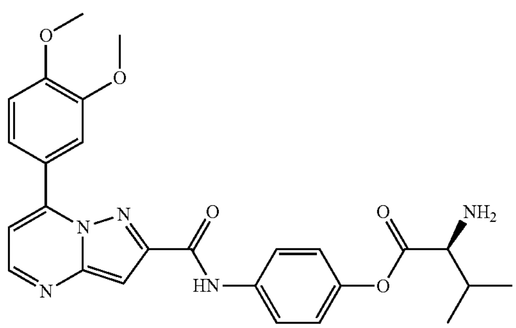 [SMILES: COc1ccc(-c2ccnc3cc(C(=O)Nc4ccc(OC(=O)[C@@H](N)C(C)C)cc4)nn23)cc1OC] | $^1$H NMR (400 MHz, DMSO-d$_6$) δ 10.37 (s, 1H), 8.70 (d, J = 4.5 Hz, 1H), 8.02 (dd, J = 8.5, 2.0 Hz, 1H), 7.96 (s, 1H), 7.86 (d, J = 8.9 Hz, 2H), 7.50 (d, J = 4.5 Hz, 1H), 7.31 (s, 1H), 7.22 (d, J = 8.6 Hz, 1H), 7.13 (d, J = 8.9 Hz, 2H), 3.93-3.88 (m, 6H), 3.73-3.71 (m, 1H), 2.09-1.98 (m, 1H), 1.94-1.78 (m, 2H), 1.01 (d, J = 6.8 Hz, 3H), 0.96 (d, J = 6.8 Hz, 3H). | C |
| 173 | 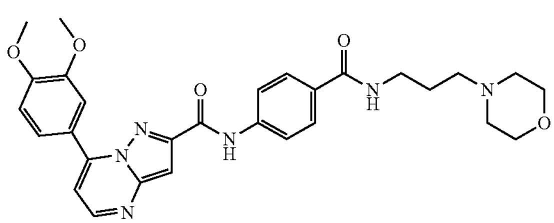 [SMILES: COc1ccc(-c2ccnc3cc(C(=O)Nc4ccc(C(=O)NCCCN5CCOCC5)cc4)nn23)cc1OC] | $^1$H NMR (400 MHz, DMSO-d$_6$) δ 10.47 (s, 1H), 8.71 (d, J = 4.4 Hz, 1H), 8.50-8.36 (m, 1H), 8.02 (d, J = 8.5 Hz, 1H), 7.99-7.77 (m, 5H), 7.51 (d, J = 4.4 Hz, 1H), 7.33 (s, 1H), 7.23 (d, J = 8.6 Hz, 1H), 4.02-3.77 (m, 6H), 3.64-3.47 (m, 4H), 3.31-3.22 (m, 2H), 2.44-2.18 (m, 6H), 1.76-1.58 (m, 2H). | C |
| 174 | 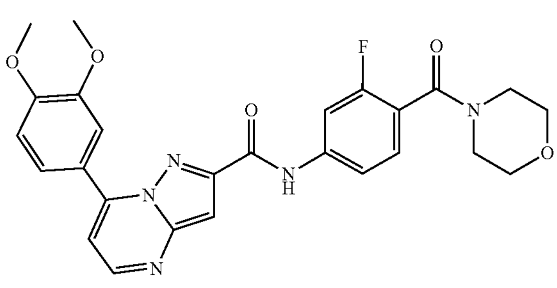 [SMILES: COc1ccc(-c2ccnc3cc(C(=O)Nc4ccc(C(=O)N5CCOCC5)c(F)c4)nn23)cc1OC] | $^1$H NMR (400 MHz, DMSO-d$_6$) δ 10.65 (s, 1H), 8.71 (d, J = 4.3 Hz, 1H), 8.01 (d, J = 8.4 Hz, 1H), 7.96 (s, 1H), 7.89 (d, J = 12.3 Hz, 1H), 7.72 (d, J = 7.9 Hz, 1H), 7.51 (d, J = 4.2 Hz, 1H), 7.44 (t, J = 8.0 Hz, 1H), 7.34 (s, 1H), 7.23 (d, J = 8.7 Hz, 1H), 3.95-3.80 (m, 6H), 3.73-3.58 (m, 4H), 3.60-3.46 (m, 2H), 3.32-3.20 (m, 2H). | B |

TABLE 3A-continued

Compound Structures, Characterization Data and Synthetic Method

| Cmpd | Structure | Characterization Data | General Method (Ex. 2) |
|---|---|---|---|
| 175 | 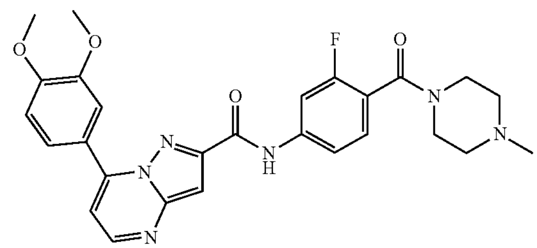 [SMILES: COc1ccc(-c2ccnc3cc(C(=O)Nc4ccc(C(=O)N5CCN(C)CC5)c(F)c4)nn23)cc1OC] | ¹H NMR (400 MHz, DMSO-d₆) δ 10.64 (s, 1H), 8.71 (d, J = 4.5 Hz, 1H), 8.01 (d, J = 8.6 Hz, 1H), 7.95 (s, 1H), 7.89 (d, J = 12.4 Hz, 1H), 7.71 (d, J = 8.4 Hz, 1H), 7.51 (d, J = 4.5 Hz, 1H), 7.41 (t, J = 8.2 Hz, 1H), 7.34 (s, 1H), 7.23 (d, J = 8.6 Hz, 1H), 3.96-3.86 (m, 6H), 3.74-3.55 (m, 2H), 3.31-3.22 (m, 2H), 2.47-2.39 (m, 2H), 2.39-2.30 (m, 2H), 2.26 (s, 3H). | B |
| 176 | 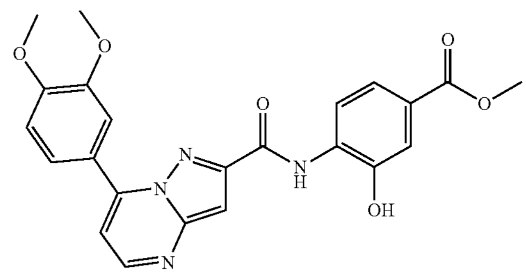 [SMILES: COC(=O)c1ccc(NC(=O)c2cc3nccc(-c4ccc(OC)c(OC)c4)n3n2)c(O)c1] | ¹H NMR (400 MHz, DMSO-d₆) δ 11.00 (s, 1H), 9.82 (s, 1H), 8.72 (d, J = 4.3 Hz, 1H), 8.48 (d, J = 8.3 Hz, 1H), 8.00 (s, 1H), 7.73 (d, J = 8.4 Hz, 1H), 7.57-7.38 (m, 3H), 7.31 (s, 1H), 7.21 (d, J = 8.4 Hz, 1H), 3.95-3.85 (m, 6H), 3.82 (s, 3H). | B |
| 177 | 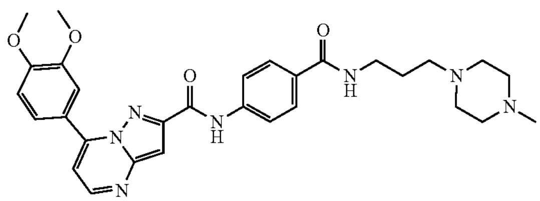 [SMILES: COc1ccc(-c2ccnc3cc(C(=O)Nc4ccc(C(=O)NCCCN5CCN(C)CC5)cc4)nn23)cc1OC] | ¹H NMR (400 MHz, DMSO-d₆) δ 10.47 (s, 1H), 8.70 (d, J = 4.4 Hz, 1H), 8.57-8.36 (m, 1H), 8.02 (d, J = 8.3 Hz, 1H), 7.98-7.75 (m, 5H), 7.50 (d, J = 4.4 Hz, 1H), 7.33 (s, 1H), 7.22 (d, J = 8.7 Hz, 1H), 3.98-3.79 (m, 6H), 3.31-3.20 (m, 2H), 2.50-2.27 (m, 10H), 2.24 (s, 3H), 1.75-1.58 (m, 2H). | C |
| 178 | 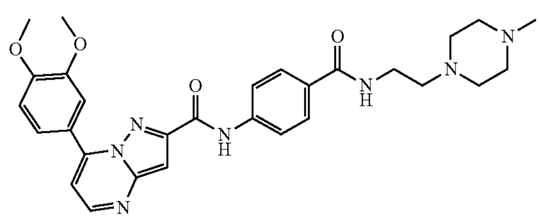 [SMILES: COc1ccc(-c2ccnc3cc(C(=O)Nc4ccc(C(=O)NCCN5CCN(C)CC5)cc4)nn23)cc1OC] | ¹H NMR (400 MHz, DMSO-d₆) δ 10.47 (s, 1H), 8.70 (d, J = 4.0 Hz, 1H), 8.40-8.32 (m, 1H), 8.10-7.70 (m, 6H), 7.51 (d, J = 3.5 Hz, 1H), 7.33 (s, 1H), 7.22 (d, J = 8.5 Hz, 1H), 4.0-3.8 (m, 6H), 3.42-3.36 (m, 2H), 2.48-2.00 (m, 13H). | C |
| 179 | 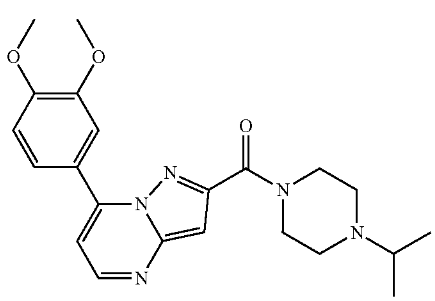 [SMILES: COc1ccc(-c2ccnc3cc(C(=O)N4CCN(C(C)C)CC4)nn23)cc1OC] | ¹H NMR (400 MHz, DMSO-d₆) δ 8.65 (d, J = 4.5 Hz, 1H), 7.86-7.72 (m, 2H), 7.38 (d, J = 4.5 Hz, 1H), 7.20 (d, J = 8.4 Hz, 1H), 7.00 (s, 1H), 3.88 (s, 3H), 3.85 (s, 3H), 3.81-3.71 (m, 2H), 3.71-3.59 (m, 2H), 2.77-2.60 (m, 1H), 2.46-2.39 (m, 2H), 0.97 (d, J = 6.5 Hz, 6H). | D |

TABLE 3A-continued

Compound Structures, Characterization Data and Synthetic Method

| Cmpd | Structure | Characterization Data | General Method (Ex. 2) |
|---|---|---|---|
| 180 | 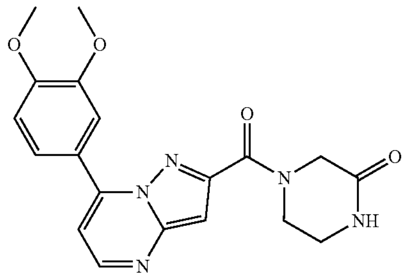 [SMILES: COc1ccc(-c2ccnc3cc(C(=O)N4CCNC(=O)C4)nn23)cc1OC] | ¹H NMR (400 MHz, DMSO-d₆) δ 8.67 (d, J = 4.4 Hz, 1H), 8.21-8.07 (m, 1H), 7.88-7.69 (m, 2H), 7.45-7.32 (m, 1H), 7.26-7.13 (m, 1H), 7.09 (d, J = 8.9 Hz, 1H), 4.55 (s, 1H), 4.17 (s, 1H), 4.10-3.97 (m, 1H), 3.92-3.72 (m, 7H), 3.32-3.21 (m, 2H). | D |
| 181 | 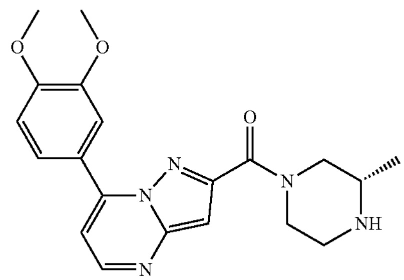 [SMILES: COc1ccc(-c2ccnc3cc(C(=O)N4CCN[C@@H](C)C4)nn23)cc1OC] | ¹H NMR (400 MHz, DMSO-d₆) δ 8.65 (d, J = 4.4 Hz, 1H), 7.87-7.69 (m, 2H), 7.44-7.32 (m, 1H), 7.18 (t, J = 8.3 Hz, 1H), 6.99 (s, 1H), 4.43-4.18 (m, 2H), 3.87 (s, 3H), 3.85 (s, 3H), 3.15-2.90 (m, 1H), 2.87-2.56 (m, 4H), 2.47-2.36 (m, 1H), 1.05-0.80 (m, 3H). | D |
| 182 | 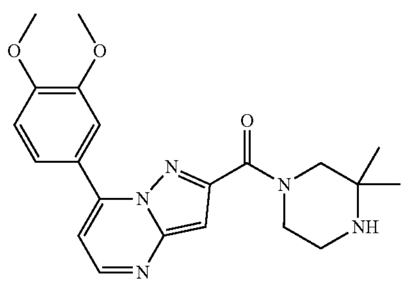 [SMILES: COc1ccc(-c2ccnc3cc(C(=O)N4CCNC(C)(C)C4)nn23)cc1OC] | ¹H NMR (400 MHz, DMSO-d₆) δ 8.64 (dd, J = 4.4, 2.0 Hz, 1H), 7.85-7.70 (m, 2H), 7.37 (dd, J = 11.6, 4.5 Hz, 1H), 7.18 (t, J = 8.4 Hz, 1H), 6.98 (d, J = 20.0 Hz, 1H), 3.90-3.83 (m, 6H), 3.68-3.59 (m, 1H), 3.59-3.52 (m, 1H), 3.51 (s, 1H), 3.40 (s, 1H), 2.85-2.70 (m, 2H), 2.27-1.95 (m, 1H), 1.06 (s, 3H), 0.93 (s, 3H). | D |
| 183 | 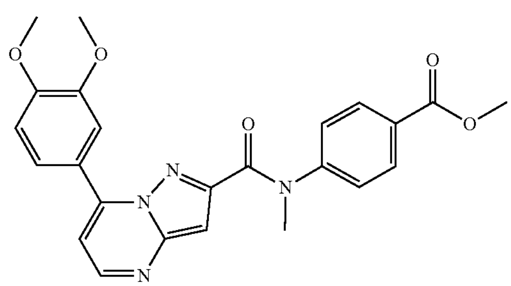 [SMILES: COC(=O)c1ccc(N(C)C(=O)c2cc3nccc(-c4ccc(OC)c(OC)c4)n3n2)cc1] | ¹H NMR (400 MHz, DMSO-d₆) δ 8.58 (d, J = 4.5 Hz, 1H), 7.98-7.84 (m, 2H), 7.47-7.35 (m, 3H), 7.32 (d, J = 4.5 Hz, 1H), 7.06 (d, J = 8.4 Hz, 1H), 6.96 (s, 1H), 6.86 (d, J = 8.6 Hz, 1H), 3.88 (s, 3H), 3.85-3.77 (m, 6H), 3.48 (s, 3H). | B |
| 184 | 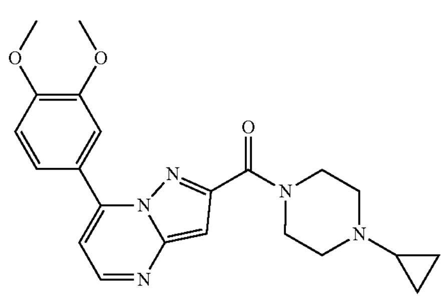 [SMILES: COc1ccc(-c2ccnc3cc(C(=O)N4CCN(C5CC5)CC4)nn23)cc1OC] | ¹H NMR (400 MHz, DMSO-d₆) δ 8.65 (d, J = 4.5 Hz, 1H), 7.84-7.74 (m, 2H), 7.38 (d, J = 4.5 Hz, 1H), 7.20 (d, J = 8.4 Hz, 1H), 7.01 (s, 1H), 3.88 (s, 3H), 3.85 (s, 3H), 3.78-3.70 (m, 2H), 3.69-3.58 (m, 2H), 2.65-2.57 (m, 2H), 2.55-2.52 (m, 2H), 1.71-1.57 (m, 1H), 0.48-0.40 (m, 2H), 0.37-0.28 (m, 2H). | D |

TABLE 3A-continued

Compound Structures, Characterization Data and Synthetic Method

| Cmpd | Structure | Characterization Data | General Method (Ex. 2) |
|---|---|---|---|
| 185 | 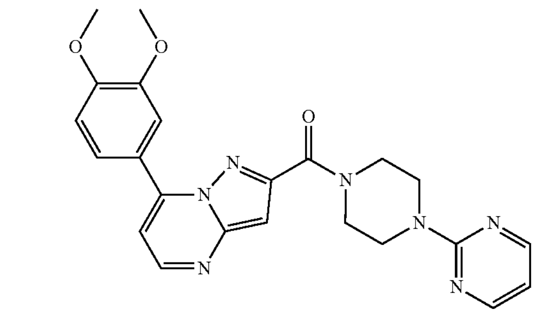 [SMILES: COc1ccc(-c2ccnc3cc(C(=O)N4CCN(c5ncccn5)CC4)nn23)cc1OC] | $^1$H NMR (400 MHz, DMSO-d$_6$) δ 8.67 (d, J = 4.4 Hz, 1H), 8.40 (d, J = 4.7 Hz, 1H), 7.88-7.81 (m, 1H), 7.79 (s, 1H), 7.40 (d, J = 4.5 Hz, 1H), 7.21 (d, J = 8.5 Hz, 1H), 7.07 (s, 1H), 6.68 (t, J = 4.7 Hz, 1H), 3.97-3.90 (m, 2H), 3.89-3.81 (m, 8H), 3.81-3.69 (m, 4H). | D |
| 186 | 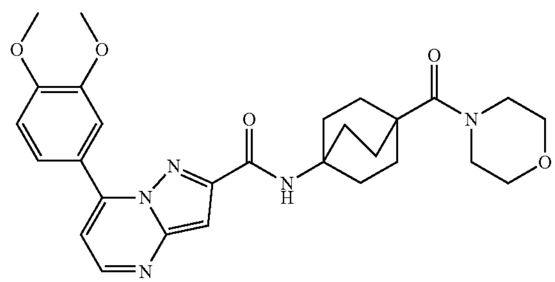 [SMILES: COc1ccc(-c2ccnc3cc(C(=O)NC45CCC(C(=O)N6CCOCC6)(CC4)CC5)nn23)cc1OC] | $^1$H NMR (400 MHz, DMSO-d$_6$) δ 8.64 (d, J = 4.4 Hz, 1H), 8.02 (s, 1H), 7.84 (d, J = 8.5 Hz, 1H), 7.53-7.39 (m, 2H), 7.20 (d, J = 8.6 Hz, 1H), 7.10 (s, 1H), 3.96-3.86 (m, 6H), 3.62-3.51 (m, 8H), 2.05-1.87 (m, 12H). | A |
| 187 | 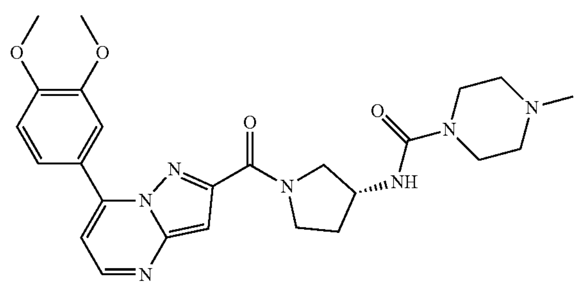 [SMILES: COc1ccc(-c2ccnc3cc(C(=O)N4CC[C@@H](NC(=O)N5CCN(C)CC5)C4)nn23)cc1OC] | $^1$H NMR (400 MHz, DMSO-d$_6$) δ 8.66 (d, J = 3.2 Hz, 1H), 7.90-7.75 (m, 2H), 7.39 (d, J = 4.3 Hz, 1H), 7.20 (t, J = 8.3 Hz, 1H), 7.10 (d, J = 3.1 Hz, 1H), 6.73-6.53 (m, 1H), 4.33-4.11 (m, 2H), 4.09-3.99 (m, 1H), 3.94-3.80 (m, 6H), 3.80-3.64 (m, 2H), 3.61-3.39 (m, 4H), 2.48-2.33 (m, 4H), 2.31-2.20 (m, 3H), 2.13-2.01 (m, 1H), 1.96-1.83 (m, 1H). | D |
| 188 | 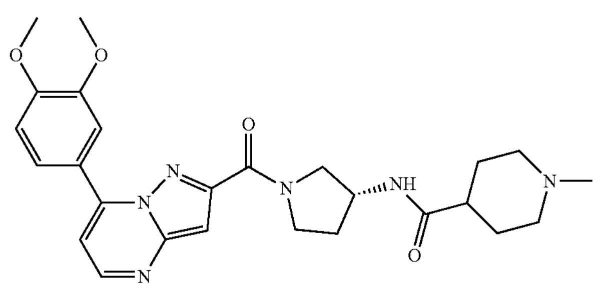 [SMILES: COc1ccc(-c2ccnc3cc(C(=O)N4CC[C@@H](NC(=O)C5CCN(C)CC5)C4)nn23)cc1OC] | $^1$H NMR (400 MHz, DMSO-d$_6$) δ 8.66 (d, J = 3.0 Hz, 1H), 8.20-8.00 (m, 1H), 7.89-7.67 (m, 2H), 7.47-7.36 (m, 1H), 7.28-7.15 (m, 1H), 7.10 (d, J = 5.9 Hz, 1H), 4.36-4.22 (m, 1H), 4.21-3.98 (m, 2H), 3.84 (s, 6H), 3.80-3.54 (m, 2H), 2.80-2.67 (m, 2H), 2.11 (d, J = 3.4 Hz, 3H), 2.08-1.90 (m, 2H), 1.91-1.69 (m, 3H), 1.66-1.43 (m, 4H). | D |
| 189 | 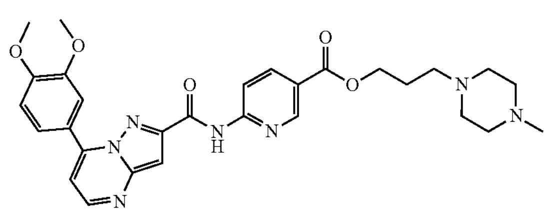 [SMILES: COc1ccc(-c2ccnc3cc(C(=O)Nc4ccc(C(=O)OCCCN5CCN(C)CC5)cn4)nn23)cc1OC] | $^1$H NMR (400 MHz, DMSO-d$_6$) δ 10.48 (s, 1H), 8.92 (s, 1H), 8.72 (d, J = 4.4 Hz, 1H), 8.49-8.27 (m, 2H), 8.03-7.82 (m, 2H), 7.51 (d, J = 4.4 Hz, 1H), 7.44 (s, 1H), 7.24 (d, J = 8.6 Hz, 1H), 4.33 (t, J = 6.5 Hz, 2H), 3.99-3.81 (m, 6H), 2.49-2.18 (m, 10H), 2.13 (s, 3H), 1.95-1.81 (m, 2H). | B |

TABLE 3A-continued

Compound Structures, Characterization Data and Synthetic Method

| Cmpd | Structure | Characterization Data | General Method (Ex. 2) |
|---|---|---|---|
| 190 | 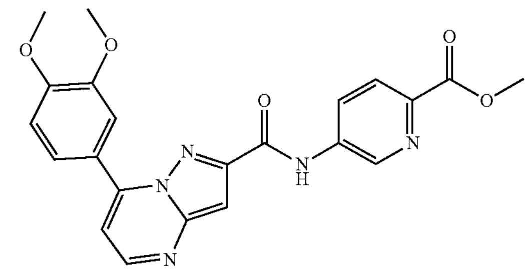 [SMILES: COC(=O)c1ccc(NC(=O)c2cc3nccc(-c4ccc(OC)c(OC)c4)n3n2)cn1] | $^1$H NMR (400 MHz, DMSO-d$_6$) δ 10.85 (s, 1H), 9.12 (s, 1H), 8.71 (d, J = 4.4 Hz, 1H), 8.48 (d, J = 8.4 Hz, 1H), 8.12 (d, J = 8.6 Hz, 1H), 8.00 (d, J = 8.4 Hz, 1H), 7.95 (s, 1H), 7.51 (d, J = 4.4 Hz, 1H), 7.37 (s, 1H), 7.23 (d, J = 8.6 Hz, 1H), 3.98-3.83 (m, 9H). | B |
| 191 | 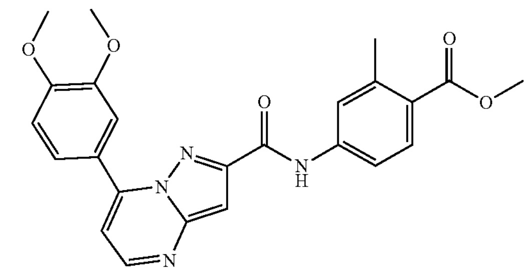 [SMILES: COC(=O)c1ccc(NC(=O)c2cc3nccc(-c4ccc(OC)c(OC)c4)n3n2)cc1C] | $^1$H NMR (400 MHz, DMSO-d$_6$) δ 10.46 (s, 1H), 8.71 (d, J = 4.4 Hz, 1H), 8.03 (d, J = 8.0 Hz, 1H), 7.95 (s, 1H), 7.90 (d, J = 8.5 Hz, 1H), 7.85-7.74 (m, 2H), 7.50 (d, J = 4.4 Hz, 1H), 7.33 (s, 1H), 7.23 (d, J = 8.6 Hz, 1H), 3.97-3.86 (m, 6H), 3.82 (s, 3H), 2.55 (s, 3H). | B |
| 192 | 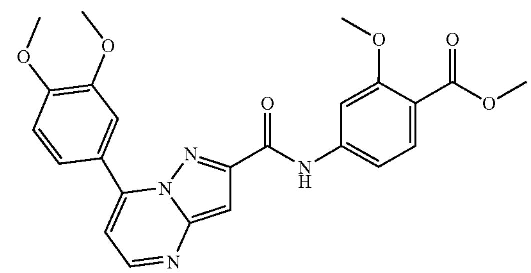 [SMILES: COC(=O)c1ccc(NC(=O)c2cc3nccc(-c4ccc(OC)c(OC)c4)n3n2)cc1OC] | $^1$H NMR (400 MHz, DMSO-d$_6$) δ 10.53 (s, 1H), 8.71 (d, J = 4.4 Hz, 1H), 8.10-7.86 (m, 2H), 7.83-7.64 (m, 2H), 7.64-7.40 (m, 2H), 7.33 (s, 1H), 7.22 (d, J = 8.8 Hz, 1H), 3.97-3.87 (m, 6H), 3.83 (s, 3H), 3.77 (s, 3H). | B |
| 193 | 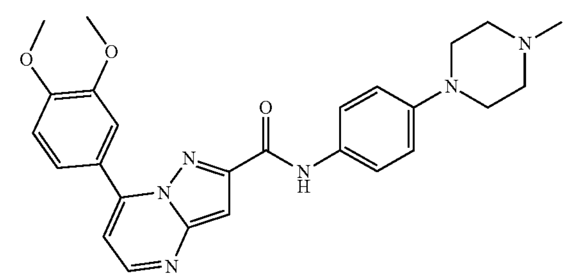 [SMILES: COc1ccc(-c2ccnc3cc(C(=O)Nc4ccc(N5CCN(C)CC5)cc4)nn23)cc1OC] | $^1$H NMR (400 MHz, DMSO-d$_6$) δ 10.05 (s, 1H), 8.68 (d, J = 4.4 Hz, 1H), 8.02 (d, J = 6.8 Hz, 1H), 7.95 (s, 1H), 7.65 (d, J = 8.8 Hz, 2H), 7.47 (d, J = 4.4 Hz, 1H), 7.26 (s, 1H), 7.21 (d, J = 8.6 Hz, 1H), 6.95 (d, J = 8.8 Hz, 2H), 3.98-3.76 (m, 6H), 3.22-3.01 (m, 4H), 2.58-2.52 (m, 4H), 2.28 (s, 3H). | C |
| 194 | 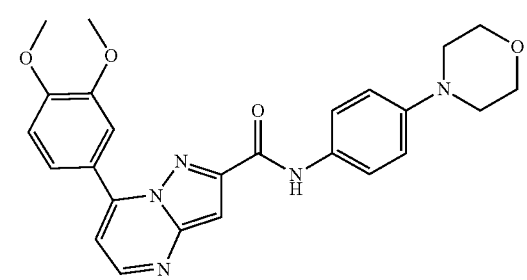 [SMILES: COc1ccc(-c2ccnc3cc(C(=O)Nc4ccc(N5CCOCC5)cc4)nn23)cc1OC] | $^1$H NMR (400 MHz, DMSO-d$_6$) δ 10.06 (s, 1H), 8.68 (d, J = 4.5 Hz, 1H), 8.02 (dd, 8.5, 2.0 Hz, 1H), 7.94 (d, J = 2.0 Hz, 1H), 7.66 (d, J = 9.0 Hz, 2H), 7.47 (d, J = 4.5 Hz, 1H), 7.26 (s, 1H), 7.21 (d, J = 8.6 Hz, 1H), 6.96 (d, J = 9.0 Hz, 2H), 3.97-3.82 (m, 6H), 3.82-3.70 (m, 4H), 3.13-2.97 (m, 4H). | C |

TABLE 3A-continued

Compound Structures, Characterization Data and Synthetic Method

| Cmpd | Structure | Characterization Data | General Method (Ex. 2) |
|---|---|---|---|
| 195 | 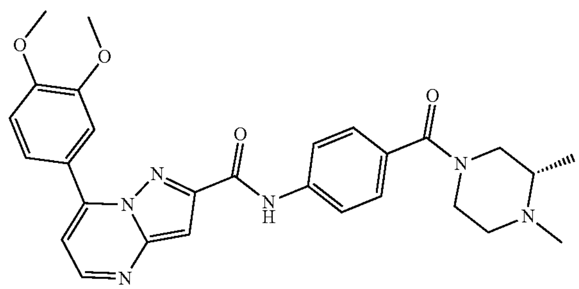 [SMILES: COc1ccc(-c2ccnc3cc(C(=O)Nc4ccc(C(=O)N5CCN(C)[C@@H](C)C5)cc4)nn23)cc1OC] | $^1$H NMR (400 MHz, DMSO-d$_6$) δ 10.46 (s, 1H), 8.71 (d, J = 4.5 Hz, 1H), 8.02 (dd, J = 8.5, 2.1 Hz, 1H), 7.96 (d, J = 2.1 Hz, 1H), 7.90 (d, J = 8.6 Hz, 2H), 7.50 (d, J = 4.5 Hz, 1H), 7.43 (d, J = 8.5 Hz, 2H), 7.33 (s, 1H), 7.22 (d, J = 8.7 Hz, 1H), 4.35-4.07 (m, 1H), 3.96-3.87 (m, 6H), 3.69-3.42 (m, 1H), 3.08-2.58 (m, 3H), 2.34-1.91 (m, 5H), 1.14-0.86 (m, 3H). | C |
| 196 | 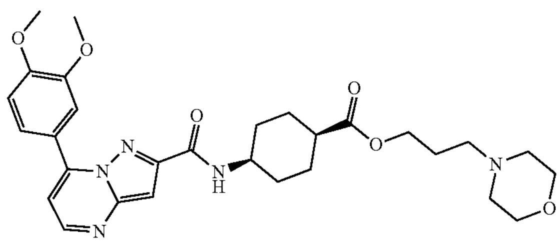 [SMILES: COc1ccc(-c2ccnc3cc(C(=O)N[C@H]4CC[C@@H](C(=O)OCCCN5CCOCC5)CC4)nn23)cc1OC] | $^1$H NMR (400 MHz, DMSO-d$_6$) δ 8.64 (d, J = 4.5 Hz, 1H), 8.08 (d, J = 7.8 Hz, 1H), 8.00 (d, J = 2.1 Hz, 1H), 7.89 (dd, J = 8.5, 2.2 Hz, 1H), 7.43 (d, J = 4.5 Hz, 1H), 7.20 (d, J = 8.6 Hz, 1H), 7.14 (s, 1H), 4.09 (t, J = 4.5 Hz, 2H), 3.96-3.85 (m, 7H), 3.59-3.51 (m, 4H), 2.62-2.55 (m, 1H), 2.40-2.25 (m, 6H), 2.01-1.88 (m, 2H), 1.80-1.57 (m, 8H). | A |
| 197 | 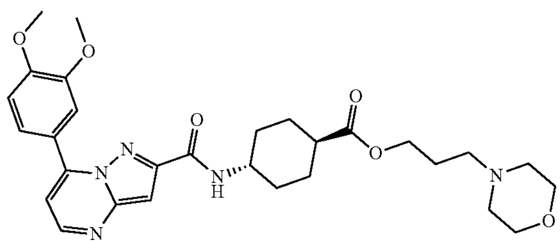 [SMILES: COc1ccc(-c2ccnc3cc(C(=O)N[C@H]4CC[C@H](C(=O)OCCCN5CCOCC5)CC4)nn23)cc1OC] | $^1$H NMR (400 MHz, DMSO-d$_6$) δ 8.64 (d, J = 4.5 Hz, 1H), 8.12 (d, J = 8.2 Hz, 1H), 7.97 (d, J = 2.1 Hz, 1H), 7.90 (dd, J = 8.5, 2.1 Hz, 1H), 7.43 (d, J = 4.5 Hz, 1H), 7.20 (d, J = 8.6 Hz, 1H), 7.13 (s, 1H), 4.06 (t, J = 6.2 Hz, 2H), 3.94-3.83 (m, 6H), 3.85-3.72 (m, 1H), 3.62-3.51 (m, 4H), 2.41-2.22 (m, 7H), 2.01-1.85 (m, 4H), 1.80-1.67 (m, 2H), 1.54-1.38 (m, 4H). | A |
| 198 | 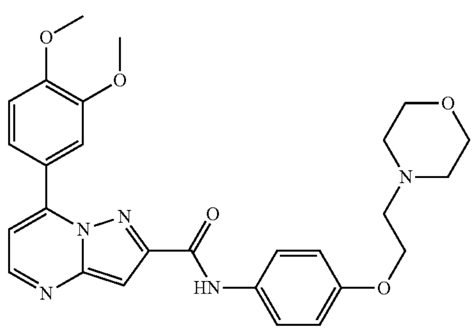 [SMILES: COc1ccc(-c2ccnc3cc(C(=O)Nc4ccc(OCCN5CCOCC5)cc4)nn23)cc1OC] | $^1$H NMR (400 MHz, DMSO-d$_6$) δ 10.13 (s, 1H), 8.68 (d, J = 4.5 Hz, 1H), 8.02 (dd, J = 8.5, 2.1 Hz, 1H), 7.94 (d, J = 2.1 Hz, 1H), 7.70 (d, J = 9.0 Hz, 2H), 7.48 (d, J = 4.5 Hz, 1H), 7.27 (s, 1H), 7.21 (d, J = 8.6 Hz, 1H), 6.96 (d, J = 9.1 Hz, 2H), 4.08 (t, J = 5.8 Hz, 2H), 3.94-3.86 (m, 6H), 3.63-3.54 (m, 4H), 2.69 (t, J = 5.8 Hz, 2H), 2.49-2.44 (m, 4H). | C |
| 199 | 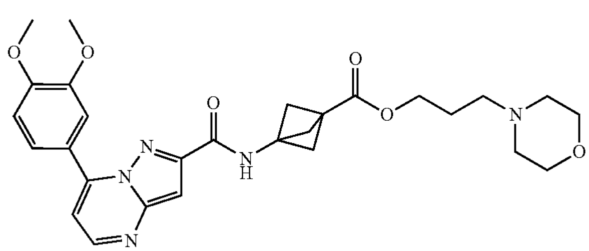 [SMILES: COc1ccc(-c2ccnc3cc(C(=O)NC45CC(C(=O)OCCCN6CCOCC6)(C4)C5)nn23)cc1OC] | $^1$H NMR (400 MHz, DMSO-d$_6$) δ 9.08 (s, 1H), 8.65 (d, J = 4.5 Hz, 1H), 7.97 (dd, J = 8.5, 2.1 Hz, 1H), 7.80 (d, J = 2.1 Hz, 1H), 7.42 (d, J = 4.5 Hz, 1H), 7.19 (d, J = 8.6 Hz, 1H), 7.12 (s, 1H), 4.08 (t, J = 6.6 Hz, 2H), 3.90-3.85 (m, 6H), 3.61-3.51 (m, 4H), 2.49-2.26 (m, J = 8.1 Hz, 12H), 1.80-1.70 (m, 2H). | B |

TABLE 3A-continued

Compound Structures, Characterization Data and Synthetic Method

| Cmpd | Structure | Characterization Data | General Method (Ex. 2) |
|---|---|---|---|
| 200 | 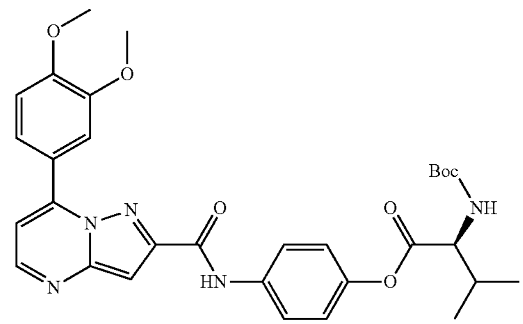 [SMILES: COc1ccc(-c2ccnc3cc(C(=O)Nc4ccc(OC(=O)[C@@H](NC(=O)OC(C)(C)C)C(C)C)cc4)nn23)cc1OC] | $^1$H NMR (400 MHz, DMSO-d$_6$) δ 10.36 (s, 1H), 8.69 (d, J = 4.5 Hz, 1H), 8.02 (dd, J = 8.5, 2.1 Hz, 1H), 7.95 (d, J = 2.1 Hz, 1H), 7.85 (d, J = 8.9 Hz, 2H), 7.49 (d, J = 4.5 Hz, 1H), 7.45 (d, J = 7.6 Hz, 1H), 7.30 (s, 1H), 7.22 (d, J = 8.6 Hz, 1H), 7.09 (d, J = 8.9 Hz, 2H), 4.10-4.01 (m, 1H), 3.94-3.85 (m, 6H), 2.23-2.14 (m, 1H), 1.42 (s, 9H), 1.01 (d, J = 6.8 Hz, 6H). | C |
| 201 | 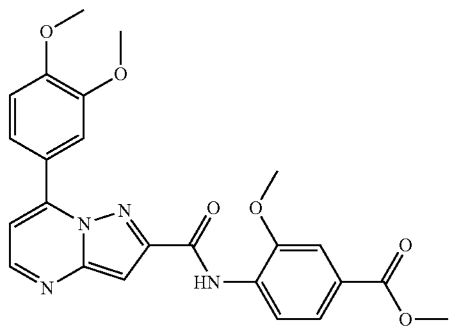 [SMILES: COC(=O)c1ccc(NC(=O)c2cc3nccc(-c4ccc(OC)c(OC)c4)n3n2)c(OC)c1] | $^1$H NMR (400 MHz, DMSO-d$_6$) δ 9.88 (s, 1H), 8.73 (d, J = 4.4 Hz, 1H), 8.54 (d, J = 8.4 Hz, 1H), 7.91 (d, J = 2.1 Hz, 1H), 7.81 (dd, J = 8.4, 2.1 Hz, 1H), 7.69 (dd, J = 8.4, 1.7 Hz, 1H), 7.59 (d, J = 1.7 Hz, 1H), 7.49 (d, J = 4.4 Hz, 1H), 7.31 (s, 1H), 7.26 (d, J = 8.6 Hz, 1H), 3.99-3.84 (m, 12H). | B |
| 202 | 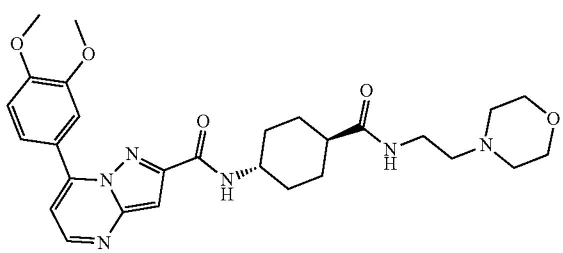 [SMILES: COc1ccc(-c2ccnc3cc(C(=O)N[C@H]4CC[C@H](C(=O)NCCN5CCOCC5)CC4)nn23)cc1OC] | $^1$H NMR (400 MHz, DMSO-d$_6$) δ 8.65 (d, J = 4.5 Hz, 1H), 8.13 (d, J = 8.3 Hz, 1H), 7.99 (d, J = 2.1 Hz, 1H), 7.89 (dd, J = 8.5, 2.2 Hz, 1H), 7.70 (t, J = 5.7 Hz, 1H), 7.43 (d, J = 4.5 Hz, 1H), 7.21 (d, J = 8.6 Hz, 1H), 7.13 (s, 1H), 3.92-3.86 (m, 6H), 3.83-3.72 (m, 1H), 3.59-3.52 (m, 4H), 3.20-3.12 (m, 2H), 2.40-2.28 (m, 6H), 2.12-2.02 (m, 1H), 1.92-1.84 (m, 2H), 1.82-1.73 (m, 2H), 1.53-1.37 (m, 4H). | A |
| 203 | 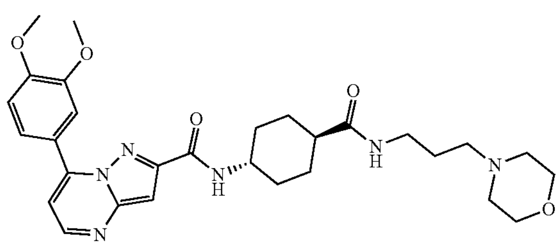 [SMILES: COc1ccc(-c2ccnc3cc(C(=O)N[C@H]4CC[C@H](C(=O)NCCCN5CCOCC5)CC4)nn23)cc1OC] | $^1$H NMR (400 MHz, DMSO-d$_6$) δ 8.65 (d, J = 4.5 Hz, 1H), 8.14 (d, J = 8.3 Hz, 1H), 7.99 (d, J = 2.1 Hz, 1H), 7.89 (dd, J = 8.5, 2.1 Hz, 1H), 7.85-7.77 (m, 1H), 7.43 (d, J = 4.5 Hz, 1H), 7.20 (d, J = 8.6 Hz, 1H), 7.13 (s, 1H), 3.91-3.87 (m, 6H), 3.83-3.71 (m, 1H), 3.69-3.51 (m, 4H), 3.11-3.02 (m, 2H), 2.50-2.29 (m, 6H), 2.11-2.01 (m, 1H), 1.93-1.85 (m, 2H), 1.82-1.72 (m, 2H), 1.65-1.53 (m, 2H), 1.53-1.36 (m, 4H). | A |
| 204 | 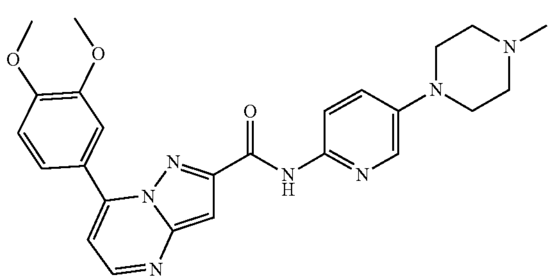 [SMILES: COc1ccc(-c2ccnc3cc(C(=O)Nc4ccc(N5CCN(C)CC5)cn4)nn23)cc1OC] | $^1$H NMR (400 MHz, DMSO-d$_6$) δ 9.87 (s, 1H), 8.70 (d, J = 4.4 Hz, 1H), 8.12-8.00 (m, 2H), 7.95 (d, J = 8.4 Hz, 1H), 7.92-7.85 (m, 1H), 7.56-7.42 (m, 2H), 7.34 (s, 1H), 7.24 (d, J = 8.6 Hz, 1H), 3.95-3.85 (m, 6H), 3.21-3.12 (m, 4H), 2.48-2.44 (m, 4H), 2.23 (s, 3H). | C |

TABLE 3A-continued

Compound Structures, Characterization Data and Synthetic Method

| Cmpd | Structure | Characterization Data | General Method (Ex. 2) |
|---|---|---|---|
| 205 | 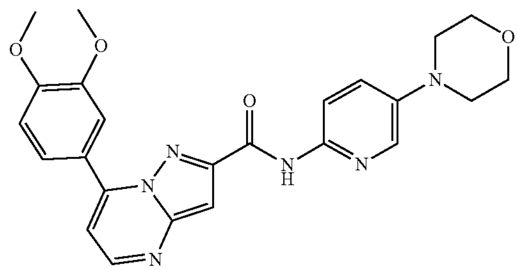 [SMILES: COc1ccc(-c2ccnc3cc(C(=O)Nc4ccc(N5CCOCC5)cn4)nn23)cc1OC] | $^1$H NMR (400 MHz, DMSO-d$_6$) δ 9.90 (s, 1H), 8.70 (d, J = 4.4 Hz, 1H), 8.15-8.03 (m, 2H), 7.95 (d, J = 8.5 Hz, 1H), 7.93-7.82 (m, 1H), 7.63-7.43 (m, 2H), 7.35 (s, 1H), 7.24 (d, J = 8.6 Hz, 1H), 3.99-3.82 (m, 6H), 3.80-3.67 (m, 4H), 3.20-3.07 (m, 4H). | B |
| 206 | 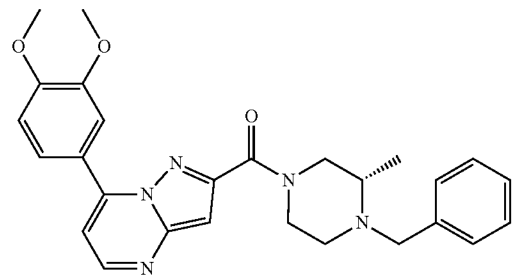 [SMILES: COc1ccc(-c2ccnc3cc(C(=O)N4CCN(Cc5ccccc5)[C@@H](C)C4)nn23)cc1OC] | $^1$H NMR (400 MHz, DMSO-d$_6$) δ 8.70-8.60 (m, 1H), 7.83-7.76 (m, 1H), 7.75 (d, J = 2.1 Hz, 1H), 7.40-7.28 (m, 5H), 7.28-7.22 (m, 1H), 7.17 (t, J = 8.2 Hz, 1H), 7.00 (d, J = 2.8 Hz, 1H), 4.21-3.74 (m, 9H), 3.51-3.42 (m, 1H), 3.32-3.22 (m, 2H), 3.15-3.03 (m, 1H), 2.75-2.57 (m, 1H), 2.20-2.09 (m, 1H), 1.19-0.97 (m, 3H). | D |
| 207 | 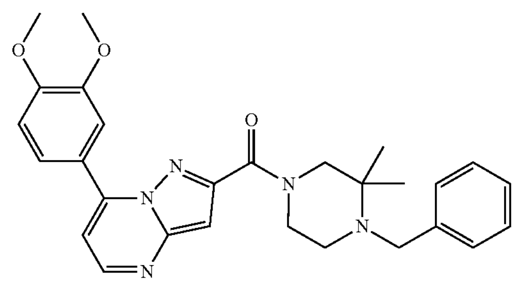 [SMILES: COc1ccc(-c2ccnc3cc(C(=O)N4CCN(Cc5ccccc5)C(C)(C)C4)nn23)cc1OC] | $^1$H NMR (400 MHz, DMSO-d$_6$) δ 8.68-8.59 (m, 1H), 7.84-7.69 (m, 2H), 7.40-7.27 (m, 5H), 7.27-7.11 (m, 2H), 7.01 (d, J = 7.3 Hz, 1H), 3.93-3.76 (m, 6H), 3.76-3.55 (m, 3H), 3.54-3.41 (m, 3H), 2.44-2.35 (m, 2H), 1.15 (s, 3H), 1.01 (s, 3H). | D |
| 208 | 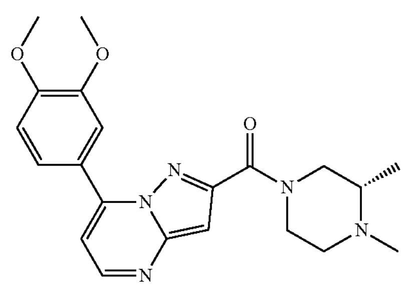 [SMILES: COc1ccc(-c2ccnc3cc(C(=O)N4CCN(C)[C@@H](C)C4)nn23)cc1OC] | $^1$H NMR (400 MHz, DMSO-d$_6$) δ 8.65 (d, J = 4.4 Hz, 1H), 7.82-7.76 (m, 2H), 7.38-7.36 (m, 1H), 7.21-7.16 (m, 1H), 7.01 (s, 1H), 4.33-4.25 (m, 2H), 3.88 (s, 3H), 3.86 (s, 3H), 3.09-2.95 (m, 1H), 2.84-2.66 (m, 2H), 2.20 (s, 3H), 2.15-2.01 (m, 2H), 1.07-0.90 (m, 3H). | D |
| 209 | 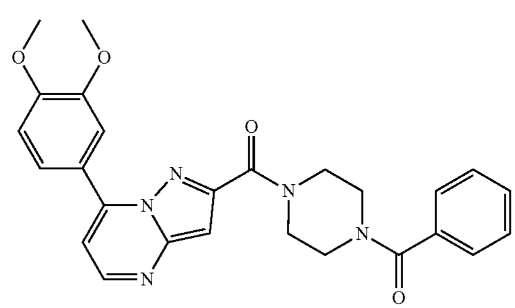 [SMILES: COc1ccc(-c2ccnc3cc(C(=O)N4CCN(C(=O)c5ccccc5)CC4)nn23)cc1OC] | $^1$H NMR (400 MHz, DMSO-d$_6$) δ 8.66 (d, J = 4.1 Hz, 1H), 8.01-7.66 (m, 2H), 7.54-7.31 (m, 6H), 7.28-7.09 (m, 1H), 7.05 (s, 1H), 4.03-3.56 (m, 12H), 3.56-3.40 (m, 2H). | D |

TABLE 3A-continued

Compound Structures, Characterization Data and Synthetic Method

| Cmpd | Structure | Characterization Data | General Method (Ex. 2) |
|---|---|---|---|
| 210 | 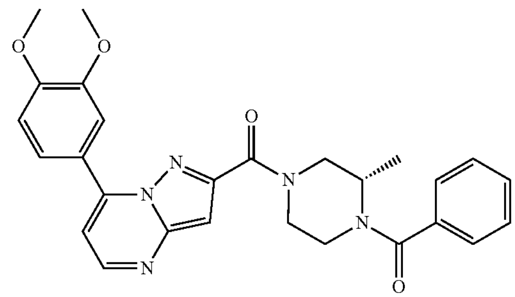 [SMILES: COc1ccc(-c2ccnc3cc(C(=O)N4CCN(C(=O)c5ccccc5)[C@@H](C)C4)nn23)cc1OC] | $^1$H NMR (400 MHz, CDCl$_3$) δ 8.59-8.54 (m, 1H), 7.75-7.55 (m, 2H), 7.49-7.34 (m, 5H), 7.17 (d, J = 7.4 Hz, 1H), 7.07-6.96 (m, 2H), 4.98-4.47 (m, 3H), 4.05-3.79 (m, 7H), 3.54-2.83 (m, 3H), 1.38-1.14 (m, 3H). | D |
| 211 | 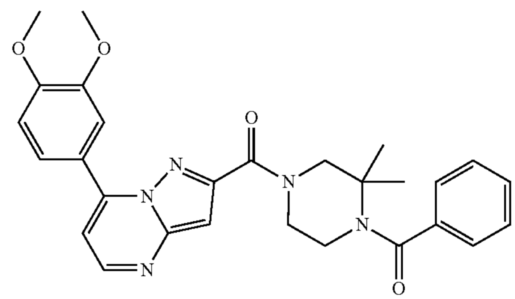 [SMILES: COc1ccc(-c2ccnc3cc(C(=O)N4CCN(C(=O)c5ccccc5)C(C)(C)C4)nn23)cc1OC] | $^1$H NMR (400 MHz, DMSO-d$_6$) δ 8.70-8.60 (m, 1H), 7.88-7.67 (m, 2H), 7.51-7.31 (m, 6H), 7.24-7.00 (m, 2H), 4.14-3.77 (m, 8H), 3.71-3.48 (m, 4H), 1.64-1.35 (m, 6H). | D |
| 212 | 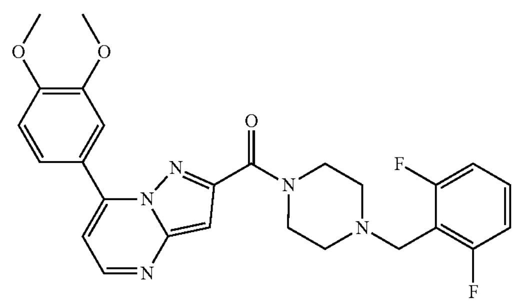 [SMILES: COc1ccc(-c2ccnc3cc(C(=O)N4CCN(Cc5c(F)cccc5F)CC4)nn23)cc1OC] | $^1$H NMR (400 MHz, DMSO-d$_6$) δ 8.65 (d, J = 4.5 Hz, 1H), 7.82 (dd, J = 8.5, 2.1 Hz, 1H), 7.76 (d, J = 2.1 Hz, 1H), 7.49-7.39 (m, 1H), 7.38 (d, J = 4.5 Hz, 1H), 7.18 (d, J = 8.6 Hz, 1H), 7.15-7.05 (m, 2H), 7.00 (s, 1H), 3.89 (s, 3H), 3.84 (s, 3H), 3.82-3.74 (m, 2H), 3.71-3.57 (m, 4H), 2.50-2.45 (m, 2H), 2.46-2.38 (m, 2H). | D |
| 213 | 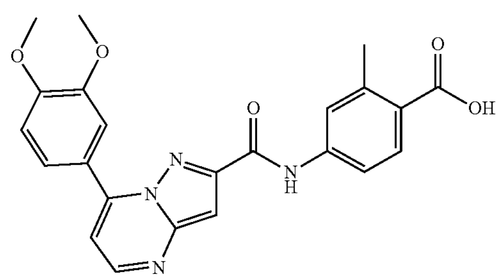 [SMILES: COc1ccc(-c2ccnc3cc(C(=O)Nc4ccc(C(=O)O)c(C)c4)nn23)cc1OC] | $^1$H NMR (400 MHz, DMSO-d$_6$) δ 12.89-12.43 (m, 1H), 10.42 (s, 1H), 8.70 (d, J = 4.5 Hz, 1H), 8.02 (d, J = 8.5 Hz, 1H), 7.94 (s, 1H), 7.89 (d, J = 8.6 Hz, 1H), 7.82-7.73 (m, 2H), 7.53-7.46 (m, 1H), 7.33 (s, 1H), 7.22 (d, J = 8.1 Hz, 1H), 3.96-3.85 (m, 6H), 2.55 (s, 3H). | B |
| 214 | 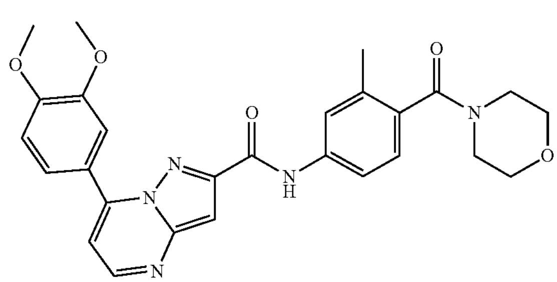 [SMILES: COc1ccc(-c2ccnc3cc(C(=O)Nc4ccc(C(=O)N5CCOCC5)c(C)c4)nn23)cc1OC] | $^1$H NMR (400 MHz, DMSO-d$_6$) δ 10.30 (s, 1H), 8.69 (d, J = 4.4 Hz, 1H), 8.08-7.99 (m, 1H), 7.99-7.87 (m, 1H), 7.81-7.64 (m, 2H), 7.49 (d, J = 4.5 Hz, 1H), 7.30 (s, 1H), 7.21 (t, J = 8.5 Hz, 2H), 3.98-3.81 (m, 6H), 3.65 (s, 4H), 3.56-3.43 (m, 2H), 3.23-3.08 (m, 2H), 2.24 (s, 3H). | B |

TABLE 3A-continued

Compound Structures, Characterization Data and Synthetic Method

| Cmpd | Structure | Characterization Data | General Method (Ex. 2) |
|---|---|---|---|
| 215 | 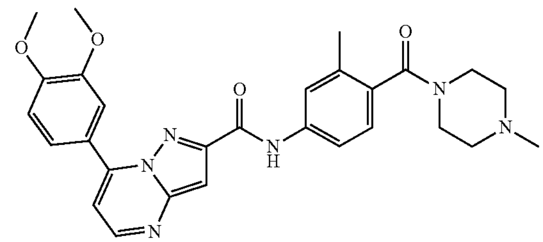 [SMILES: COc1ccc(-c2ccnc3cc(C(=O)Nc4ccc(C(=O)N5CCN(C)CC5)c(C)c4)nn23)cc1OC] | $^1$H NMR (400 MHz, DMSO-d$_6$) δ 10.29 (s, 1H), 8.69 (d, J = 4.4 Hz, 1H), 8.02 (d, J = 8.6 Hz, 1H), 7.94 (s, 1H), 7.77-7.63 (m, 2H), 7.49 (d, J = 4.4 Hz, 1H), 7.30 (s, 1H), 7.22 (d, J = 8.6 Hz, 1H), 7.16 (d, J = 8.3 Hz, 1H), 3.99-3.82 (m, 6H), 3.74-3.53 (m, 2H), 3.20-3.08 (m, 2H), 2.41-2.29 (m, 2H), 2.26-2.13 (m, 8H). | B |
| 216 | 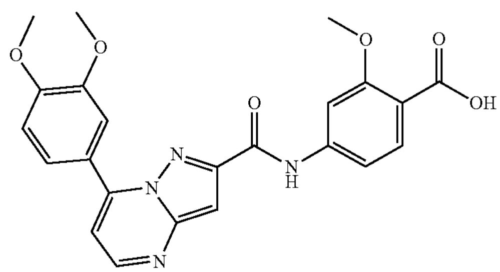 [SMILES: COc1ccc(-c2ccnc3cc(C(=O)Nc4ccc(C(=O)O)c(OC)c4)nn23)cc1OC] | $^1$H NMR (400 MHz, DMSO-d$_6$) δ 10.49 (s, 1H), 8.70 (d, J = 3.7 Hz, 1H), 8.08-7.09 (m, 2H), 7.86-7.62 (m, 2H), 7.60-7.45 (m, 2H), 7.33 (s, 1H), 7.22 (d, J = 8.6 Hz, 1H), 3.96-3.87 (m, 6H), 3.83 (s, 3H). | B |
| 217 | 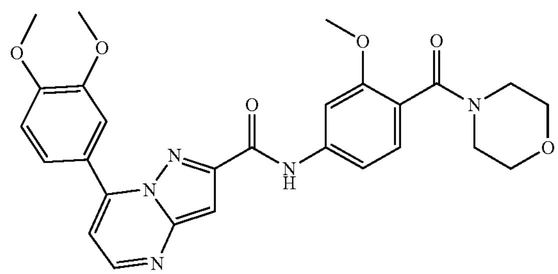 [SMILES: COc1ccc(-c2ccnc3cc(C(=O)Nc4ccc(C(=O)N5CCOCC5)c(OC)c4)nn23)cc1OC] | $^1$H NMR (400 MHz, DMSO-d$_6$) δ 10.39 (s, 1H), 8.70 (d, J = 4.5 Hz, 1H), 8.15-7.88 (m, 2H), 7.67 (s, 1H), 7.59-7.41 (m, 2H), 7.32 (s, 1H), 7.28-7.10 (m, 2H), 4.01-3.58 (m, 6H), 3.82 (s, 3H), 3.69-3.58 (m, 4H), 3.57-3.50 (m, 2H), 3.25-3.05 (m, 2H). | B |
| 218 | 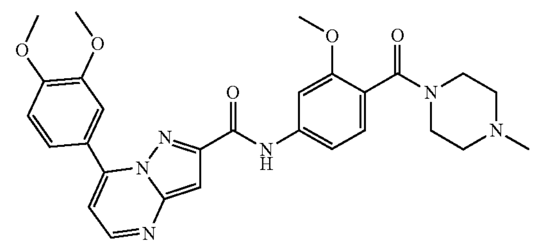 [SMILES: COc1ccc(-c2ccnc3cc(C(=O)Nc4ccc(C(=O)N5CCN(C)CC5)c(OC)c4)nn23)cc1OC] | $^1$H NMR (400 MHz, DMSO-d$_6$) δ 10.38 (s, 1H), 8.70 (d, J = 4.4 Hz, 1H), 8.07-7.87 (m, 2H), 7.66 (s, 1H), 7.50 (d, J = 4.6 Hz, 2H), 7.31 (s, 1H), 7.22 (d, J = 9.2 Hz, 1H), 7.18 (d, J = 8.3 Hz, 1H), 3.93-3.88 (m, 6H), 3.80 (s, 3H), 3.73-3.45 (m, 2H), 3.25-3.03 (m, 2H), 2.37-2.14 (m, 7H). | B |
| 219 | 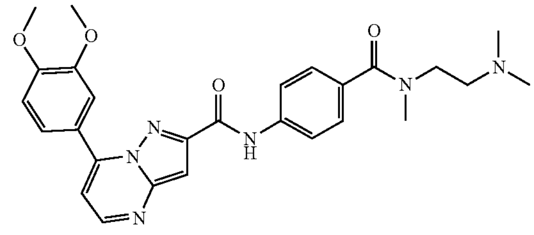 [SMILES: COc1ccc(-c2ccnc3cc(C(=O)Nc4ccc(C(=O)N(C)CCN(C)C)cc4)nn23)cc1OC] | $^1$H NMR (400 MHz, DMSO-d$_6$) δ 10.42 (s, 1H), 8.70 (d, J = 4.5 Hz, 1H), 8.02 (d, J = 8.5 Hz, 1H), 7.95 (s, 1H), 7.88 (d, J = 8.4 Hz, 2H), 7.50 (d, J = 4.5 Hz, 1H), 7.42 (d, J = 8.3 Hz, 2H), 7.32 (s, 1H), 7.22 (d, J = 8.5 Hz, 1H), 3.99-3.79 (m, 6H), 3.64-3.45 (m, 2H), 2.96 (s, 3H), 2.49-2.35 (m, 2H), 2.28 (s, 3H), 2.01 (s, 3H). | C |

TABLE 3A-continued

Compound Structures, Characterization Data and Synthetic Method

| Cmpd | Structure | Characterization Data | General Method (Ex. 2) |
|---|---|---|---|
| 220 | 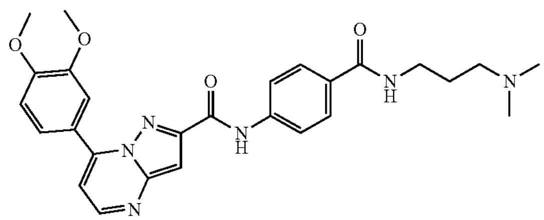 [SMILES: COc1ccc(-c2ccnc3cc(C(=O)Nc4ccc(C(=O)NCCCN(C)C)cc4)nn23)cc1OC] | $^1$H NMR (400 MHz, DMSO-d$_6$) δ 10.48 (s, 1H), 8.71 (d, J = 4.1 Hz, 1H), 8.63-8.44 (m, 1H), 8.02 (d, J = 8.4 Hz, 1H), 7.99-7.79 (m, 5H), 7.51 (d, J = 4.3 Hz, 1H), 7.34 (s, 1H), 7.23 (d, J = 8.7 Hz, 1H), 4.00-3.79 (m, 6H), 2.87-2.66 (m, 2H), 2.59-2.52 (m, 8H), 1.91-1.67 (m, 2H). | C |
| 221 | 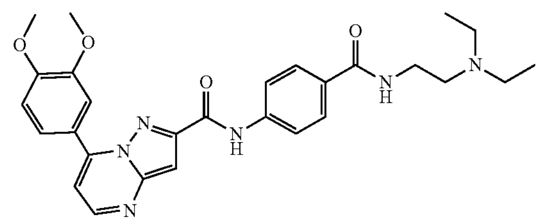 [SMILES: CCN(CC)CCNC(=O)c1ccc(NC(=O)c2cc3nccc(-c4ccc(OC)c(OC)c4)n3n2)cc1] | $^1$H NMR (400 MHz, DMSO-d$_6$) δ 10.51 (s, 1H), 9.77 (s, 1H), 8.78 (s, 1H), 8.71 (d, J = 3.5 Hz, 1H), 8.02 (d, J = 8.4 Hz, 1H), 7.98-7.79 (m, 4H), 7.51 (d, J = 3.5 Hz, 1H), 7.34 (s, 1H), 7.22 (d, J = 8.6 Hz, 1H), 3.97-3.83 (m, 6H), 3.73-3.51 (m, 2H), 3.32-3.00 (m, 6H), 1.38-0.97 (m, 6H). | C |
| 222 | 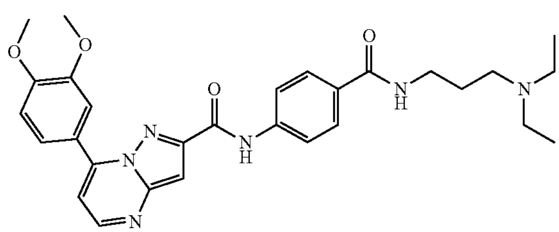 [SMILES: CCN(CC)CCCNC(=O)c1ccc(NC(=O)c2cc3nccc(-c4ccc(OC)c(OC)c4)n3n2)cc1] | $^1$H NMR (400 MHz, DMSO-d$_6$) δ 10.49 (s, 1H), 8.70 (d, J = 4.4 Hz, 1H), 8.66-8.52 (m, 1H), 8.07-7.99 (m, 1H), 7.99-7.82 (m, 5H), 7.51 (d, J = 4.4 Hz, 1H), 7.34 (s, 1H), 7.22 (d, J = 8.6 Hz, 1H), 3.99-3.77 (m, 6H), 3.16-2.79 (m, 6H), 1.95-1.71 (m, 2H), 1.25-1.08 (m, 6H). | C |
| 223 | 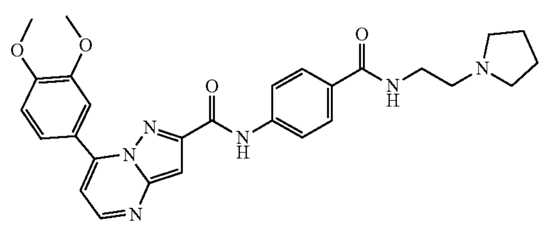 [SMILES: COc1ccc(-c2ccnc3cc(C(=O)Nc4ccc(C(=O)NCCN5CCCC5)cc4)nn23)cc1OC] | $^1$H NMR (400 MHz, DMSO-d$_6$) δ 10.49 (s, 1H), 8.70 (d, J = 4.3 Hz, 1H), 8.67-8.54 (m, 1H), 8.02 (d, J = 8.2 Hz, 1H), 7.98-7.79 (m, 5H), 7.50 (d, J = 4.2 Hz, 1H), 7.33 (s, 1H), 7.22 (d, J = 8.6 Hz, 1H), 3.98-3.80 (m, 6H), 3.63-3.47 (m, 2H), 3.16-2.91 (m, 6H), 1.95-1.74 (m, 4H). | C |
| 224 | 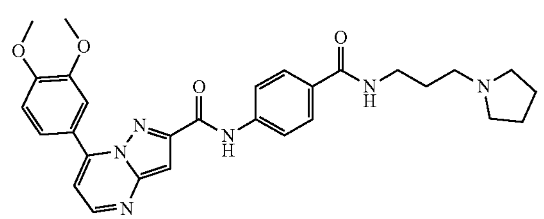 [SMILES: COc1ccc(-c2ccnc3cc(C(=O)Nc4ccc(C(=O)NCCCN5CCCC5)cc4)nn23)cc1OC] | $^1$H NMR (400 MHz, DMSO-d$_6$) δ 10.49 (s, 1H), 8.70 (d, J = 4.4 Hz, 1H), 8.86-8.47 (m, 1H), 8.07-8.00 (m, 1H), 8.00-7.79 (m, 5H), 7.50 (d, J = 4.5 Hz, 1H), 7.34 (s, 1H), 7.22 (d, J = 8.6 Hz, 1H), 4.05-3.74 (m, 6H), 3.45-3.38 (m, 2H), 3.30-2.89 (m, 6H), 2.06-1.74 (m, 6H). | C |
| 225 | 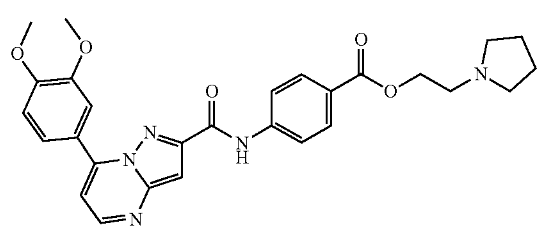 [SMILES: COc1ccc(-c2ccnc3cc(C(=O)Nc4ccc(C(=O)OCCN5CCCC5)cc4)nn23)cc1OC] | $^1$H NMR (400 MHz, DMSO-d$_6$) δ 10.59 (s, 1H), 8.70 (d, J = 4.4 Hz, 1H), 8.17-7.82 (m, 6H), 7.50 (d, J = 4.5 Hz, 1H), 7.34 (s, 1H), 7.22 (d, J = 8.5 Hz, 1H), 4.36 (t, J = 5.6 Hz, 2H), 4.01-3.79 (m, 6H), 2.90-2.70 (m, 2H), 2.62-2.52 (m, 4H), 1.79-1.56 (m, 4H). | C |

TABLE 3A-continued

Compound Structures, Characterization Data and Synthetic Method

| Cmpd | Structure | Characterization Data | General Method (Ex. 2) |
|---|---|---|---|
| 226 | 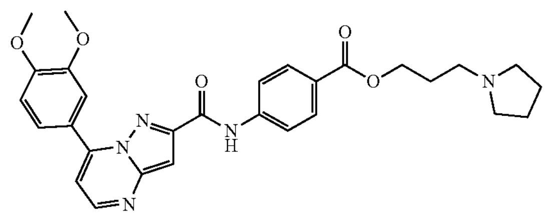 [SMILES: COc1ccc(-c2ccnc3cc(C(=O)Nc4ccc(C(=O)OCCCN5CCCC5)cc4)nn23)cc1OC] | ¹H NMR (400 MHz, DMSO-d₆) δ 10.62 (s, 1H), 8.71 (s, 1H), 8.13-7.87 (m, 6H), 7.62-7.44 (m, 1H), 7.35 (s, 1H), 7.22 (d, J = 8.4 Hz, 1H), 4.38-4.23 (m, 2H), 4.01-3.74 (m, 6H), 3.20-2.70 (m, 6H), 2.13-1.96 (m, 2H), 1.92-1.67 (m, 4H). | C |
| 227 | 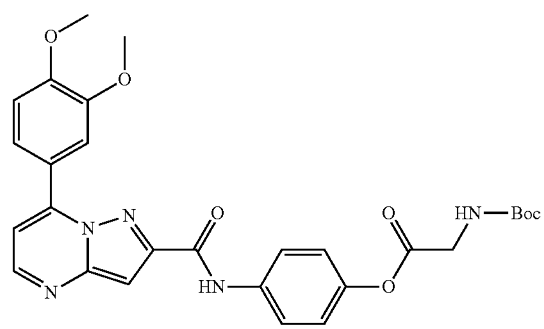 [SMILES: COc1ccc(-c2ccnc3cc(C(=O)Nc4ccc(OC(=O)CNC(=O)OC(C)(C)C)cc4)nn23)cc1OC] | ¹H NMR (400 MHz, DMSO-d₆) δ 10.36 (s, 1H), 8.70 (d, J = 4.5 Hz, 1H), 8.02 (dd, J = 8.5, 2.1 Hz, 1H), 7.95 (d, J = 2.1 Hz, 1H), 7.85 (d, J = 9.0 Hz, 2H), 7.49 (d, J = 4.5 Hz, 1H), 7.42 (t, J = 6.1 Hz, 1H), 7.31 (s, 1H), 7.22 (d, J = 8.6 Hz, 1H), 7.14 (d, J = 8.9 Hz, 2H), 3.97 (d, J = 6.1 Hz, 2H), 3.94-3.87 (m, 6H), 1.42 (s, 9H). | C |
| 228 | 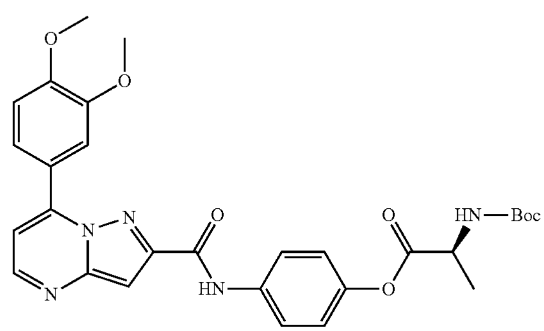 [SMILES: COc1ccc(-c2ccnc3cc(C(=O)Nc4ccc(OC(=O)[C@H](C)NC(=O)OC(C)(C)C)cc4)nn23)cc1OC] | ¹H NMR (400 MHz, DMSO-d₆) δ 10.36 (s, 1H), 8.70 (d, J = 4.3 Hz, 1H), 8.03 (d, J = 8.1 Hz, 1H), 7.95 (s, 1H), 7.85 (d, J = 8.3 Hz, 2H), 7.52 (dd, J = 17.9, 5.6 Hz, 2H), 7.31 (s, 1H), 7.22 (d, J = 8.4 Hz, 1H), 7.11 (d, J = 8.8 Hz, 2H), 4.28-4.19 (m, 1H), 3.95-3.85 (m, 6H), 1.51-1.30 (m, 12H). | C |
| 229 | 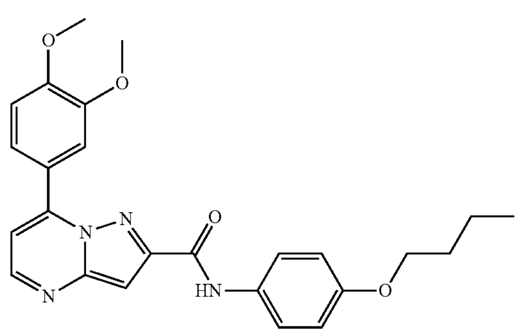 [SMILES: CCCCOc1ccc(NC(=O)c2cc3nccc(-c4ccc(OC)c(OC)c4)n3n2)cc1] | ¹H NMR (400 MHz, DMSO-d₆) δ 10.13 (s, 1H), 8.69 (d, J = 4.5 Hz, 1H), 8.03 (dd, J = 8.5, 2.2 Hz, 1H), 7.94 (d, J = 2.1 Hz, 1H), 7.70 (d, J = 9.1 Hz, 2H), 7.48 (d, J = 4.5 Hz, 1H), 7.27 (s, 1H), 7.22 (d, J = 8.6 Hz, 1H), 6.95 (d, J = 9.1 Hz, 2H), 3.97 (t, J = 6.5 Hz, 2H), 3.92-3.88 (m, 6H), 1.75-1.65 (m, 2H), 1.49-1.40 (m, 2H), 0.95 (t, J = 7.4 Hz, 3H). | C |

TABLE 3A-continued

Compound Structures, Characterization Data and Synthetic Method

| Cmpd | Structure | Characterization Data | General Method (Ex. 2) |
|---|---|---|---|
| 230 | 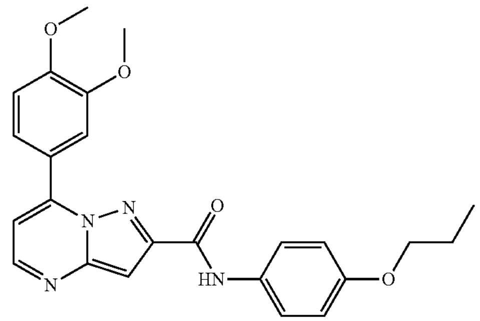 [SMILES: CCCOc1ccc(NC(=O)c2cc3nccc(-c4ccc(OC)c(OC)c4)n3n2)cc1] | $^1$H NMR (400 MHz, DMSO-d$_6$) δ 10.13 (s, 1H), 8.68 (d, J = 4.5 Hz, 1H), 8.03 (d, J = 8.6 Hz, 1H), 7.98-7.92 (m, 1H), 7.70 (d, J = 9.0 Hz, 2H), 7.48 (d, J = 4.5 Hz, 1H), 7.27 (s, 1H), 7.21 (d, J = 8.6 Hz, 1H), 6.94 (d, J = 9.0 Hz, 2H), 3.97-3.86 (m, 8H), 1.77-1.68 (m, 2H), 0.99 (t, J = 7.4 Hz, 3H). | C |
| 231 | 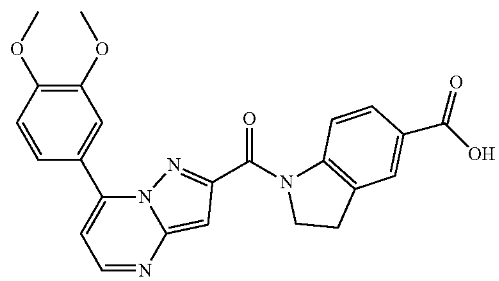 [SMILES: COc1ccc(-c2ccnc3cc(C(=O)N4CCc5cc(C(=O)O)ccc54)nn23)cc1OC] | $^1$H NMR (400 MHz, DMSO-d$_6$) δ 12.79 (s, 1H), 8.76-8.62 (m, 1H), 8.39-8.17 (m, 1H), 7.96-7.71 (m, 4H), 7.45 (d, J = 4.5 Hz, 1H), 7.33-7.12 (m, 2H), 4.81-4.44 (m, 2H), 3.93-3.78 (m, 6H), 3.24 (t, J = 8.4 Hz, 2H). | D |
| 232 | 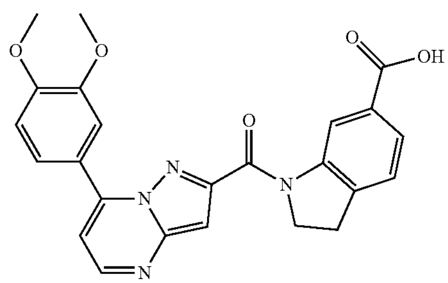 [SMILES: COc1ccc(-c2ccnc3cc(C(=O)N4CCc5ccc(C(=O)O)cc54)nn23)cc1OC] | $^1$H NMR (400 MHz, DMSO-d$_6$) δ 12.95 (s, 1H), 8.83 (s, 1H), 8.73-8.65 (m, 1H), 7.96-7.76 (m, 2H), 7.71 (d, J = 8.2 Hz, 1H), 7.47-7.38 (m, 2H), 7.31-7.14 (m, 2H), 4.66 (t, J = 8.3 Hz, 2H), 3.90-3.84 (m, 6H), 3.26 (t, J = 8.4 Hz, 2H). | D |
| 233 | 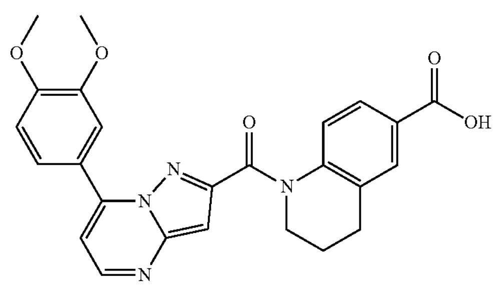 [SMILES: COc1ccc(-c2ccnc3cc(C(=O)N4CCCc5cc(C(=O)O)ccc54)nn23)cc1OC] | $^1$H NMR (400 MHz, DMSO-d$_6$) δ 8.65 (dd, J = 14.3, 4.5 Hz, 1H), 7.86 (m, 2H), 7.61-7.51 (m, 1H), 7.50-7.35 (m, 2H), 7.26-6.90 (m, 3H), 4.00-3.90 (m, 2H), 3.84 (m, 8H), 2.88 (t, J = 6.6 Hz, 1H), 2.04-1.88 (m, 1H). | D |
| 234 | 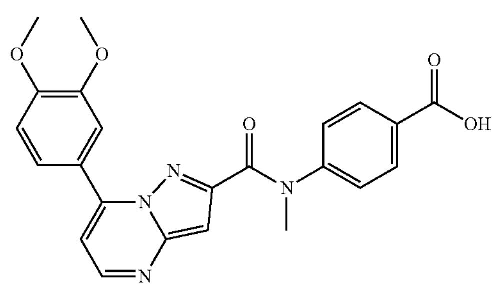 [SMILES: COc1ccc(-c2ccnc3cc(C(=O)N(C)c4ccc(C(=O)O)cc4)nn23)cc1OC] | $^1$H NMR (400 MHz, DMSO-d$_6$) δ 13.06 (s, 1H), 8.58 (d, J = 4.5 Hz, 1H), 7.99-7.85 (m, 2H), 7.44 (d, J = 1.9 Hz, 1H), 7.41-7.31 (m, 3H), 7.03 (d, J = 7.7 Hz, 1H), 6.97 (s, 1H), 6.88 (d, J = 8.6 Hz, 1H), 3.88 (s, 3H), 3.83 (s, 3H), 3.48 (s, 3H). | D |

TABLE 3A-continued

Compound Structures, Characterization Data and Synthetic Method

| Cmpd | Structure | Characterization Data | General Method (Ex. 2) |
|---|---|---|---|
| 235 | 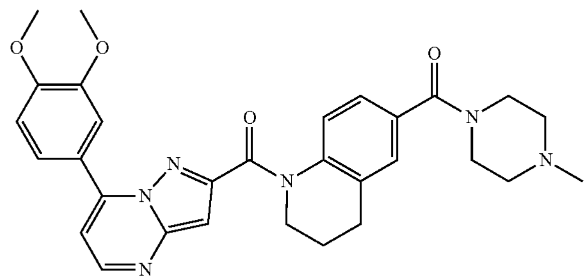 [SMILES: COc1ccc(-c2ccnc3cc(C(=O)N4CCCc5cc(C(=O)N6CCN(C)CC6)ccc54)nn23)cc1OC] | ¹H NMR (400 MHz, DMSO-d₆) δ 8.64 (d, J = 4.5 Hz, 1H), 7.70-7.63 (m, 1H), 7.61-7.51 (m, 1H), 7.41 (d, J = 4.5 Hz, 1H), 7.30 (s, 1H), 7.23-7.08 (m, 2H), 7.08-6.97 (m, 2H), 3.94 (t, J = 5.9 Hz, 2H), 3.87 (s, 3H), 3.80 (s, 3H), 3.69-3.36 (m, 4H), 2.86 (t, J = 6.5 Hz, 2H), 2.40-2.06 (m, 7H), 2.02-1.90 (m, 2H). | D |
| 236 | 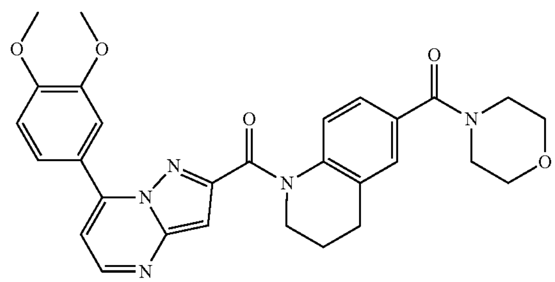 [SMILES: COc1ccc(-c2ccnc3cc(C(=O)N4CCCc5cc(C(=O)N6CCOCC6)ccc54)nn23)cc1OC] | ¹H NMR (400 MHz, DMSO-d₆) δ 8.64 (d, J = 4.5 Hz, 1H), 7.66 (d, J = 1.9 Hz, 1H), 7.57 (d, J = 8.2 Hz, 1H), 7.41 (d, J = 4.5 Hz, 1H), 7.33 (d, J = 1.6 Hz, 1H), 7.26-6.99 (m, 4H), 4.01-3.91 (m, 2H), 3.91-3.83 (m, 3H), 3.80 (s, 3H), 3.71-3.38 (m, 8H), 2.86 (t, J = 6.6 Hz, 2H), 2.04-1.88 (m, 2H). | D |
| 237 | 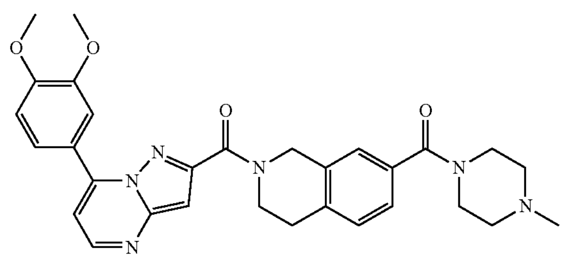 [SMILES: COc1ccc(-c2ccnc3cc(C(=O)N4CCc5ccc(C(=O)N6CCN(C)CC6)cc5C4)nn23)cc1OC] | ¹H NMR (400 MHz, DMSO-d₆) δ 8.68 (dd, J = 4.4, 2.0 Hz, 1H), 7.88 (dd, J = 8.5, 2.1 Hz, 1H), 7.79 (dd, J = 15.8, 2.0 Hz, 1H), 7.41 (d, J = 4.4 Hz, 1H), 7.34-7.12 (m, 4H), 7.07 (d, J = 11.9 Hz, 1H), 5.14 (s, 1H), 4.87 (s, 1H), 4.04 (t, J = 5.7 Hz, 1H), 3.96-3.78 (m, 7H), 3.69-3.51 (m, 2H), 3.49-3.36 (m, 2H), 3.01-2.87 (m, 2H), 2.43-2.10 (m, 7H). | D |
| 238 | 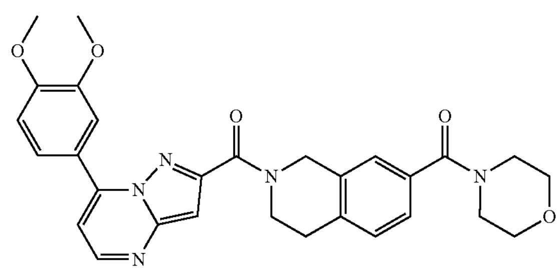 [SMILES: COc1ccc(-c2ccnc3cc(C(=O)N4CCc5ccc(C(=O)N6CCOCC6)cc5C4)nn23)cc1OC] | ¹H NMR (400 MHz, DMSO-d₆) δ 8.68 (d, J = 4.4 Hz, 1H), 7.88 (dd, J = 8.5, 2.1 Hz, 1H), 7.79 (dd, J = 15.4, 2.0 Hz, 1H), 7.41 (d, J = 4.4 Hz, 1H), 7.38-7.13 (m, 4H), 7.07 (d, J = 10.7 Hz, 1H), 5.14 (s, 1H), 4.88 (s, 1H), 4.04 (t, J = 5.8 Hz, 1H), 3.98-3.72 (m, 7H), 3.72-3.35 (m, 8H), 3.02-2.58 (m, 2H). | D |
| 239 | 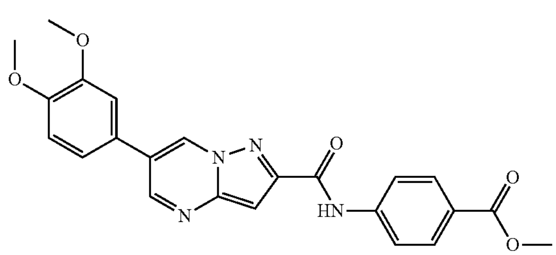 [SMILES: COC(=O)c1ccc(NC(=O)c2cc3ncc(-c4ccc(OC)c(OC)c4)cn3n2)cc1] | ¹H NMR (400 MHz, DMSO-d₆) δ 10.79 (s, 1H), 9.47 (dd, J = 2.2, 0.8 Hz, 1H), 9.11 (d, J = 2.2 Hz, 1H), 8.08-8.02 (m, 2H), 8.02-7.97 (m, 2H), 7.50-7.41 (m, 2H), 7.33 (d, J = 0.7 Hz, 1H), 7.13 (d, J = 8.4 Hz, 1H), 3.90 (s, 3H), 3.88-3.83 (m, 6H). | G |

TABLE 3A-continued

Compound Structures, Characterization Data and Synthetic Method

| Cmpd | Structure | Characterization Data | General Method (Ex. 2) |
|---|---|---|---|
| 240 | 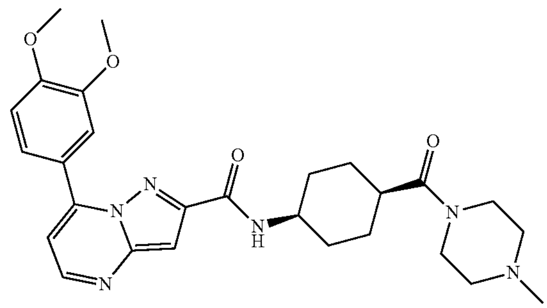 [SMILES: COc1ccc(-c2ccnc3cc(C(=O)N[C@H]4CC[C@@H](C(=O)N5CCN(C)CC5)CC4)nn23)cc1OC] | ¹H NMR (400 MHz, DMSO-d₆) δ 8.65 (d, J = 4.5 Hz, 1H), 7.97 (d, J = 2.1 Hz, 1H), 7.92 (dd, J = 8.5, 2.2 Hz, 1H), 7.87 (d, J = 7.4 Hz, 1H), 7.44 (d, J = 4.5 Hz, 1H), 7.24 (d, J = 8.6 Hz, 1H), 7.16 (s, 1H), 4.10-4.02 (m, 1H), 3.90 (s, 3H), 3.88 (s, 3H), 3.52-3.42 (m, 4H), 2.79-2.71 (m, 1H), 2.35-2.21 (m, 4H), 2.19 (s, 3H), 1.92-1.81 (m, 2H), 1.73-1.63 (m, 4H), 1.61-1.50 (m, 2H). | A |
| 241 | 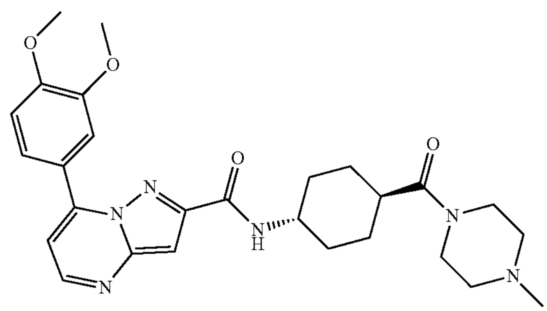 [SMILES: COc1ccc(-c2ccnc3cc(C(=O)N[C@H]4CC[C@H](C(=O)N5CCN(C)CC5)CC4)nn23)cc1OC] | ¹H NMR (400 MHz, DMSO-d₆) δ 8.65 (d, J = 4.5 Hz, 1H), 8.06 (d, J = 8.1 Hz, 1H), 7.97 (d, J = 2.1 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 3.92-3.86 (m, 6H), 3.84-3.72 (m, 1H), 3.52-3.42 (m, 4H), 2.62-2.53 (m, 1H), 2.34-2.21 (m, 4H), 2.19 (s, 3H), 1.95-1.86 (m, 2H), 1.77-1.65 (m, 2H), 1.54-1.42 (m, 4H). | A |
| 242 | 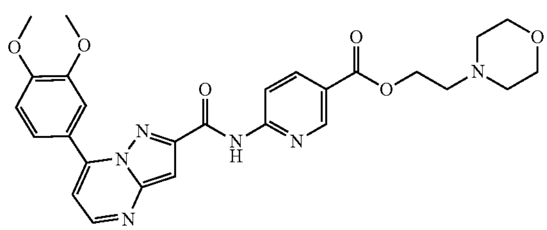 [SMILES: COc1ccc(-c2ccnc3cc(C(=O)Nc4ccc(C(=O)OCCN5CCOCC5)cn4)nn23)cc1OC] | ¹H NMR (400 MHz, DMSO-d₆) δ 10.47 (s, 1H), 8.93-8.90 (m, 1H), 8.73 (d, J = 4.5 Hz, 1H), 8.41-8.38 (m, 2H), 7.97-7.93 (m, 2H), 7.51 (d, J = 4.5 Hz, 1H), 7.45 (s, 1H), 7.24 (d, J = 8.5 Hz, 1H), 4.42 (t, J = 5.7 Hz, 2H), 3.94-3.88 (m, 6H), 3.57 (t, J = 4.6 Hz, 4H), 2.71 (t, J = 5.7 Hz, 2H), 2.49-2.45 (m, 4H). | B |
| 243 | 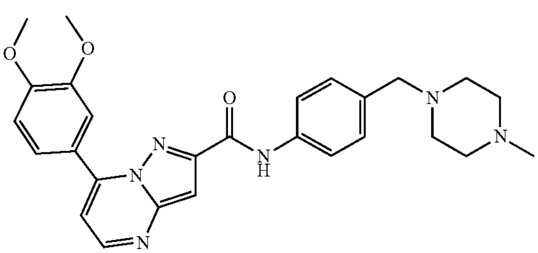 [SMILES: COc1ccc(-c2ccnc3cc(C(=O)Nc4ccc(CN5CCN(C)CC5)cc4)nn23)cc1OC] | ¹H NMR (400 MHz, DMSO-d₆) δ 10.21 (s, 1H), 8.69 (d, J = 4.4 Hz, 1H), 8.01 (d, J = 8.4 Hz, 1H), 7.95 (s, 1H), 7.75 (d, J = 8.2 Hz, 2H), 7.48 (d, J = 4.4 Hz, 1H), 7.37-7.25 (m, 3H), 7.21 (d, J = 8.5 Hz, 1H), 4.00-3.79 (m, 6H), 3.43 (s, 2H), 2.49-2.21 (m, 8H), 2.18 (s, 3H). | B |
| 244 | 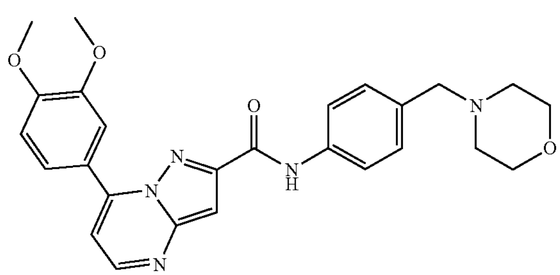 [SMILES: COc1ccc(-c2ccnc3cc(C(=O)Nc4ccc(CN5CCOCC5)cc4)nn23)cc1OC] | ¹H NMR (400 MHz, DMSO-d₆) δ 10.22 (s, 1H), 8.69 (d, J = 4.4 Hz, 1H), 8.01 (d, J = 8.7 Hz, 1H), 7.95 (s, 1H), 7.76 (d, J = 8.2 Hz, 2H), 7.48 (d, J = 4.2 Hz, 1H), 7.39-7.24 (m, 3H), 7.21 (d, J = 8.6 Hz, 1H), 4.02-3.78 (m, 6H), 3.66-3.51 (m, 4H), 3.50-3.42 (m, 2H), 2.43-2.20 (m, 4H). | B |

TABLE 3A-continued

Compound Structures, Characterization Data and Synthetic Method

| Cmpd | Structure | Characterization Data | General Method (Ex. 2) |
|---|---|---|---|
| 245 | 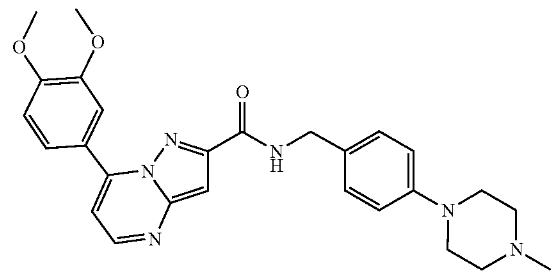 [SMILES: COc1ccc(-c2ccnc3cc(C(=O)NCc4ccc(N5CCN(C)CC5)cc4)nn23)cc1OC] | ¹H NMR (400 MHz, DMSO-d₆) δ 8.89-8.76 (m, 1H), 8.64 (d, J = 4.3 Hz, 1H), 7.92 (d, J = 8.1 Hz, 1H), 7.85 (s, 1H), 7.41 (d, J = 4.2 Hz, 1H), 7.27-7.07 (m, 4H), 6.88 (d, J = 8.2 Hz, 2H), 4.40 (d, J = 5.7 Hz, 2H), 3.91-3.80 (m, 6H), 3.15-2.98 (m, 4H), 2.45-2.37 (m, 4H), 2.20 (s, 3H). | B |
| 246 | 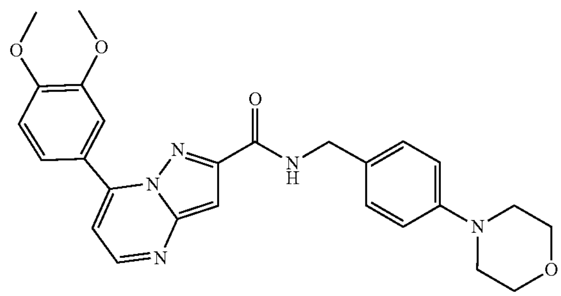 [SMILES: COc1ccc(-c2ccnc3cc(C(=O)NCc4ccc(N5CCOCC5)cc4)nn23)cc1OC] | ¹H NMR (400 MHz, DMSO-d₆) δ 8.92-8.77 (m, 1H), 8.64 (d, J = 4.3 Hz, 1H), 7.92 (d, J = 7.6 Hz, 1H), 7.85 (s, 1H), 7.41 (d, J = 4.4 Hz, 1H), 7.33-7.06 (m, 4H), 6.89 (d, J = 8.4 Hz, 2H), 4.41 (d, J = 5.9 Hz, 2H), 3.89-3.82 (m, 6H), 3.80-3.67 (m, 4H), 3.17-2.98 (m, 4H). | B |
| 247 | 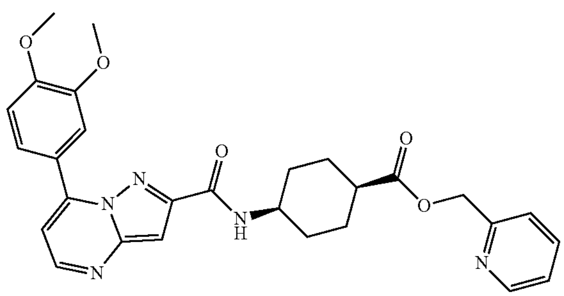 [SMILES: COc1ccc(-c2ccnc3cc(C(=O)N[C@H]4CC[C@@H](C(=O)OCc5ccccn5)CC4)nn23)cc1OC] | ¹H NMR (400 MHz, DMSO-d₆) δ 8.64 (d, J = 4.5 Hz, 1H), 8.57-8.52 (m, 1H), 8.05 (d, J = 7.8 Hz, 1H), 7.98 (d, J = 2.1 Hz, 1H), 7.89 (dd, J = 8.5, 2.2 Hz, 1H), 7.86-7.79 (m, 1H), 7.45-7.39 (m, 2H), 7.35-7.29 (m, 1H), 7.19 (d, J = 8.6 Hz, 1H), 7.14 (s, 1H), 5.20 (s, 2H), 3.99-3.91 (m, 1H), 3.88 (s, 3H), 3.86 (s, 3H), 2.76-2.69 (m, 1H), 2.06-1.96 (m, 2H), 1.77-1.60 (m, 6H). | A |
| 248 | 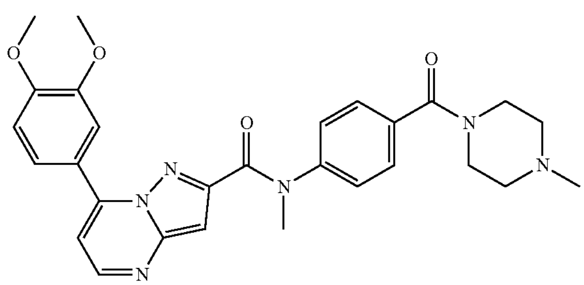 [SMILES: COc1ccc(-c2ccnc3cc(C(=O)N(C)c4ccc(C(=O)N5CCN(C)CC5)cc4)nn23)cc1OC] | ¹H NMR (400 MHz, DMSO-d₆) δ 8.58 (d, J = 4.5 Hz, 1H), 7.50 (s, 1H), 7.43-7.23 (m, 6H), 7.12 (d, J = 8.7 Hz, 1H), 6.91 (s, 1H), 3.89 (s, 3H), 3.84 (s, 3H), 3.68-3.42 (m, 5H), 3.25-3.07 (m, 2H), 2.42-1.97 (m, 7H). | B |
| 249 | 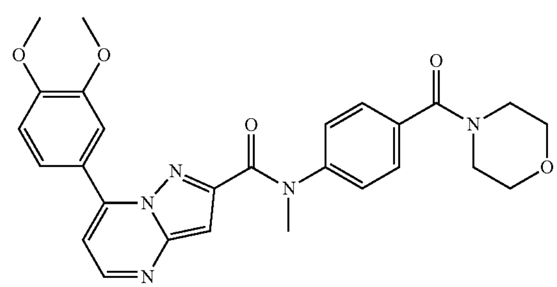 [SMILES: COc1ccc(-c2ccnc3cc(C(=O)N(C)c4ccc(C(=O)N5CCOCC5)cc4)nn23)cc1OC] | ¹H NMR (400 MHz, DMSO-d₆) δ 8.58 (d, J = 4.4 Hz, 1H), 7.50-7.27 (m, 7H), 7.12 (d, J = 8.8 Hz, 1H), 6.91 (s, 1H), 3.90 (s, 3H), 3.84 (s, 3H), 3.75-3.34 (m, 9H), 3.30-3.00 (m, 2H). | B |

TABLE 3A-continued

Compound Structures, Characterization Data and Synthetic Method

| Cmpd | Structure | Characterization Data | General Method (Ex. 2) |
|---|---|---|---|
| 250 | 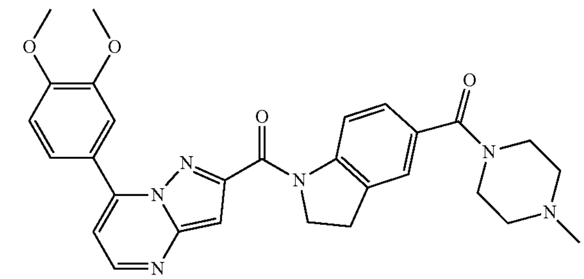 [SMILES: COc1ccc(-c2ccnc3cc(C(=O)N4CCc5cc(C(=O)N6CCN(C)CC6)ccc54)nn23)cc1OC] | $^1$H NMR (400 MHz, DMSO-d$_6$) δ 8.70 (d, J = 4.5 Hz, 1H), 8.33-8.15 (m, 1H), 7.93-7.74 (m, 2H), 7.44 (d, J = 4.5 Hz, 1H), 7.38-7.32 (m, 1H), 7.32-7.14 (m, 3H), 4.73-4.55 (m, 2H), 3.95-3.77 (m, 6H), 3.62-3.36 (m, 4H), 3.23 (t, J = 8.6 Hz, 2H), 2.43-2.24 (m, 4H), 2.21 (s, 3H). | D |
| 251 | 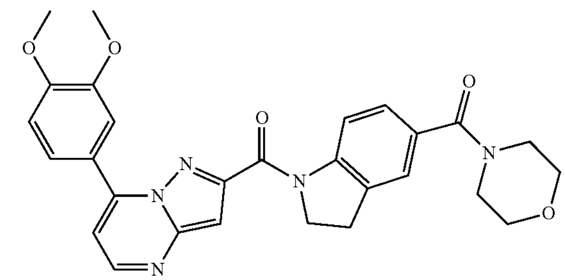 [SMILES: COc1ccc(-c2ccnc3cc(C(=O)N4CCc5cc(C(=O)N6CCOCC6)ccc54)nn23)cc1OC] | $^1$H NMR (400 MHz, DMSO-d$_6$) δ 8.70 (d, J = 4.4 Hz, 1H), 8.33-8.19 (m, 1H), 7.96-7.70 (m, 2H), 7.44 (d, J = 4.4 Hz, 1H), 7.40-7.14 (m, 4H), 4.73-4.55 (m, 2H), 4.02-3.72 (m, 6H), 3.70-3.40 (m, 8H), 3.23 (t, J = 8.6 Hz, 2H). | D |
| 252 | 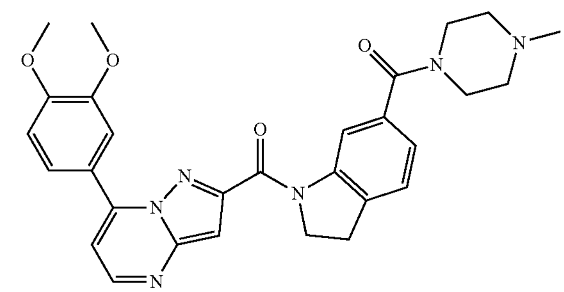 [SMILES: COc1ccc(-c2ccnc3cc(C(=O)N4CCc5ccc(C(=O)N6CCN(C)CC6)cc54)nn23)cc1OC] | $^1$H NMR (400 MHz, DMSO-d$_6$) δ 8.70 (d, J = 4.4 Hz, 1H), 8.26 (s, 1H), 7.92-7.73 (m, 2H), 7.44 (d, J = 4.4 Hz, 1H), 7.38 (d, J = 7.5 Hz, 1H), 7.31-7.18 (m, 2H), 7.11 (d, J = 8.0 Hz, 1H), 4.73-4.53 (m, 2H), 4.01-3.74 (m, 6H), 3.27-3.35 (m, 4H), 3.26-3.18 (m, 2H), 2.44-2.26 (m, 4H), 2.22 (s, 3H). | D |
| 253 | 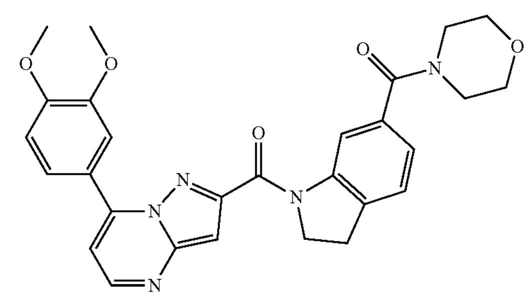 [SMILES: COc1ccc(-c2ccnc3cc(C(=O)N4CCc5ccc(C(=O)N6CCOCC6)cc54)nn23)cc1OC] | $^1$H NMR (400 MHz, DMSO-d$_6$) δ 8.70 (d, J = 4.5 Hz, 1H), 8.28 (s, 1H), 7.94-7.74 (m, 2H), 7.44 (d, J = 4.4 Hz, 1H), 7.38 (d, J = 7.6 Hz, 1H), 7.31-7.17 (m, 2H), 7.14 (d, J = 7.8 Hz, 1H), 4.74-4.50 (m, 2H), 3.96-3.76 (m, 6H), 3.77-3.39 (m, 8H), 3.26-3.18 (m, 2H). | D |
| 254 | 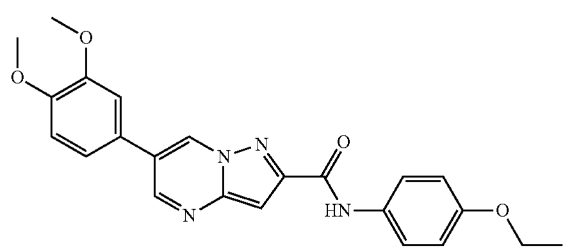 [SMILES: CCOc1ccc(NC(=O)c2cc3ncc(-c4ccc(OC)c(OC)c4)cn3n2)cc1] | $^1$H NMR (400 MHz, DMSO-d$_6$) δ 10.26 (s, 1H), 9.45-9.42 (m, 1H), 9.08 (d, J = 2.3 Hz, 1H), 7.75 (d, J = 9.0 Hz, 2H), 7.46 (d, J = 2.1 Hz, 1H), 7.43 (dd, J = 8.3, 2.2 Hz, 1H), 7.25 (s, 1H), 7.13 (d, J = 8.4 Hz, 1H), 6.94 (d, J = 9.1 Hz, 2H), 4.03 (q, J = 7.0 Hz, 2H), 3.90 (s, 3H), 3.84 (s, 3H), 1.34 (t, J = 7.0 Hz, 3H). | G |

TABLE 3A-continued

Compound Structures, Characterization Data and Synthetic Method

| Cmpd | Structure | Characterization Data | General Method (Ex. 2) |
|---|---|---|---|
| 255 | 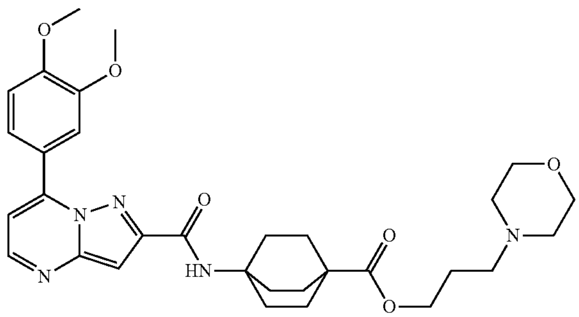 [SMILES: COc1ccc(-c2ccnc3cc(C(=O)NC45CCC(C(=O)OCCCN6CCOCC6)(CC4)CC5)nn23)cc1OC] | ¹H NMR (400 MHz, DMSO-d₆) δ 8.64 (d, J = 4.5 Hz, 1H), 8.01 (d, J = 2.1 Hz, 1H), 7.85 (dd, J = 8.5, 2.2 Hz, 1H), 7.46-7.40 (m, 2H), 7.20 (d, J = 8.6 Hz, 1H), 7.10 (s, 1H), 4.04 (t, J = 6.4 Hz, 2H), 3.91-3.86 (m, 6H), 3.59-3.54 (m, 4H), 2.38-2.30 (m, 6H), 2.04-1.96 (m, 6H), 1.90-1.80 (m, 6H), 1.76-1.69 (m, 2H). | A |
| 256 | 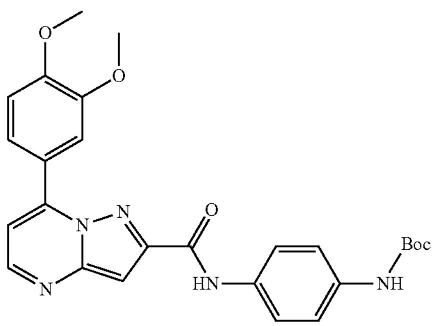 [SMILES: COc1ccc(-c2ccnc3cc(C(=O)Nc4ccc(NC(=O)OC(C)(C)C)cc4)nn23)cc1OC] | ¹H NMR (400 MHz, DMSO-d₆) δ 10.11 (s, 1H), 9.31 (s, 1H), 8.68 (d, J = 4.5 Hz, 1H), 8.02 (dd, J = 8.5, 2.0 Hz, 1H), 7.94 (d, J = 2.0 Hz, 1H), 7.68 (d, J = 9.0 Hz, 2H), 7.49-7.41 (m, 3H), 7.27 (s, 1H), 7.22 (d, J = 8.6 Hz, 1H), 3.94-3.87 (m, 6H), 1.49 (s, 9H). | C |
| 257 | 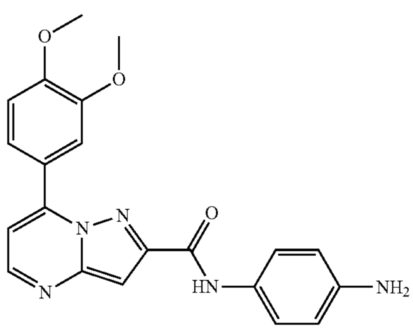 [SMILES: COc1ccc(-c2ccnc3cc(C(=O)Nc4ccc(N)cc4)nn23)cc1OC] | ¹H NMR (400 MHz, DMSO-d₆) δ 9.81 (s, 1H), 8.67 (d, J = 4.5 Hz, 1H), 8.03 (dd, J = 8.5, 2.1 Hz, 1H), 7.92 (d, J = 2.1 Hz, 1H), 7.46 (d, J = 4.5 Hz, 1H), 7.41 (d, J = 8.7 Hz, 2H), 7.24-7.19 (m, 2H), 6.57 (d, J = 8.7 Hz, 2H), 4.97 (s, 2H), 3.93-3.87 (m, 6H). | C |
| 258 | 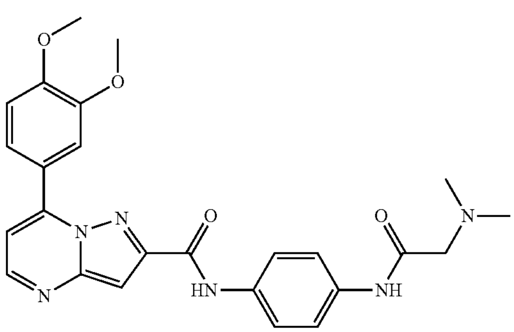 [SMILES: COc1ccc(-c2ccnc3cc(C(=O)Nc4ccc(NC(=O)CN(C)C)cc4)nn23)cc1OC] | ¹H NMR (400 MHz, DMSO-d₆) δ 10.18 (s, 1H), 9.75 (s, 1H), 8.69 (d, J = 4.5 Hz, 1H), 8.02 (dd, J = 8.5, 2.1 Hz, 1H), 7.95 (d, J = 2.1 Hz, 1H), 7.74 (d, J = 9.0 Hz, 2H), 7.65 (d, J = 9.0 Hz, 2H), 7.48 (d, J = 4.5 Hz, 1H), 7.28 (s, 1H), 7.22 (d, J = 8.6 Hz, 1H), 3.93-3.88 (m, 6H), 3.13 (s, 2H), 2.33 (s, 6H). | C |

TABLE 3A-continued

Compound Structures, Characterization Data and Synthetic Method

| Cmpd | Structure | Characterization Data | General Method (Ex. 2) |
|---|---|---|---|
| 259 | 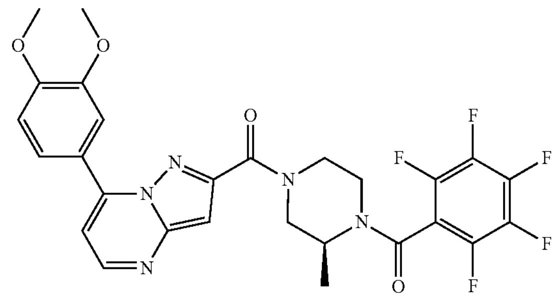 [SMILES: COc1ccc(-c2ccnc3cc(C(=O)N4CCN(C(=O)c5c(F)c(F)c(F)c(F)c5F)[C@@H](C)C4)nn23)cc1OC] | $^1$H NMR (400 MHz, DMSO-d$_6$) δ 8.74-8.58 (m, 1H), 7.93-7.63 (m, 2H), 7.48-7.31 (m, 1H), 7.28-7.00 (m, 2H), 4.94-4.15 (m, 3H), 3.95-3.70 (m, 6H), 3.65-3.36 (m, 2H), 3.29-3.14 (m, 1H), 3.08-2.89 (m, 1H), 1.33-0.97 (m, 3H). | D |
| 260 | 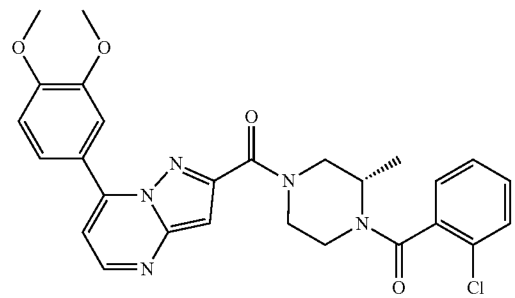 [SMILES: COc1ccc(-c2ccnc3cc(C(=O)N4CCN(C(=O)c5ccccc5Cl)[C@@H](C)C4)nn23)cc1OC] | $^1$H NMR (400 MHz, DMSO-d$_6$) δ 8.73-8.57 (m, 1H), 7.92-7.65 (m, 2H), 7.62-7.29 (m, 5H), 7.27-6.97 (m, 2H), 5.00-4.16 (m, 3H), 3.99-3.67 (m, 6H), 3.61-3.36 (m, 1H), 3.28-2.91 (m, 3H), 1.37-0.89 (m, 3H). | D |
| 261 | 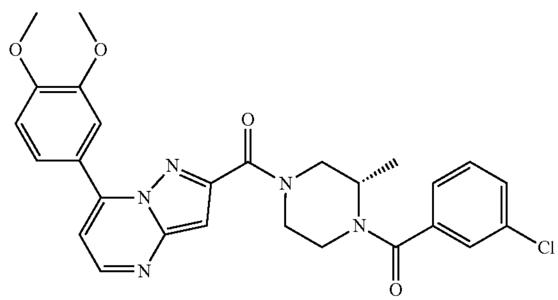 [SMILES: COc1ccc(-c2ccnc3cc(C(=O)N4CCN(C(=O)c5cccc(Cl)c5)[C@@H](C)C4)nn23)cc1OC] | $^1$H NMR (400 MHz, DMSO-d$_6$) δ 8.67 (d, J = 4.3 Hz, 1H), 7.19-7.64 (m, 2H), 7.60-7.43 (m, 3H), 7.43-7.28 (m, 2H), 7.27-7.13 (m, 1H), 7.06 (d, J = 22.4 Hz, 1H), 4.67-4.15 (m, 3H), 3.97-3.69 (m, 6H), 3.59-3.36 (m, 1H), 3.30-2.90 (m, 3H), 1.37-0.99 (m, 3H). | D |
| 262 | 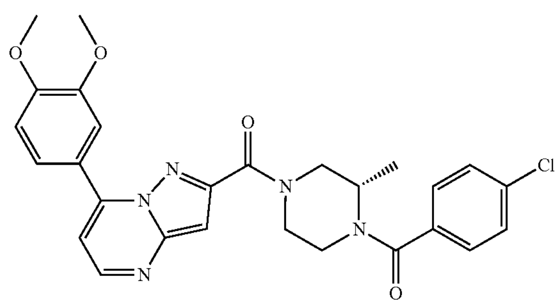 [SMILES: COc1ccc(-c2ccnc3cc(C(=O)N4CCN(C(=O)c5ccc(Cl)cc5)[C@@H](C)C4)nn23)cc1OC] | $^1$H NMR (400 MHz, DMSO-d$_6$) δ 8.66 (s, 1H), 7.88-7.67 (m, 2H), 7.59-7.29 (m, 5H), 7.25-7.13 (m, 1H), 7.06 (d, J = 23.0 Hz, 1H), 4.66-4.15 (m, 3H), 3.95-3.67 (m, 6H), 3.58-3.40 (m, 1H), 3.28-2.89 (m, 3H), 1.28-1.00 (m, 3H). | D |
| 263 | 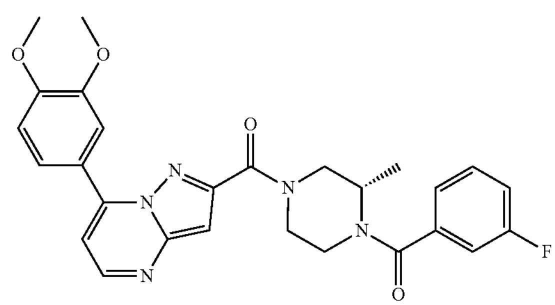 [SMILES: COc1ccc(-c2ccnc3cc(C(=O)N4CCN(C(=O)c5cccc(F)c5)[C@@H](C)C4)nn23)cc1OC] | $^1$H NMR (400 MHz, DMSO-d$_6$) δ 8.66 (d, J = 4.2 Hz, 1H), 7.74 (d, J = 24.2 Hz, 2H), 7.51 (dd, J = 13.6, 7.9 Hz, 1H), 7.45-7.11 (m, 5H), 7.05 (d, J = 22.9 Hz, 1H), 4.43 (m, 3H), 3.84 (m, 6H), 3.60-2.91 (m, 4H), 1.15 (m, 3H). | D |

TABLE 3A-continued

Compound Structures, Characterization Data and Synthetic Method

| Cmpd | Structure | Characterization Data | General Method (Ex. 2) |
|---|---|---|---|
| 264 | 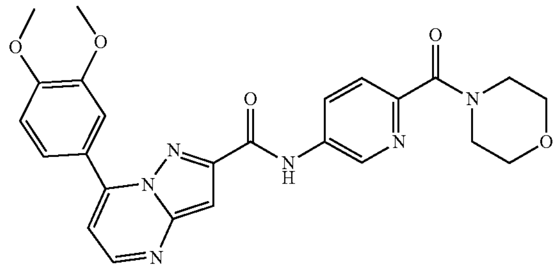 [SMILES: COc1ccc(-c2ccnc3cc(C(=O)Nc4ccc(C(=O)N5CCOCC5)nc4)nn23)cc1OC] | ¹H NMR (400 MHz, DMSO-d₆) δ 10.70 (s, 1H), 9.01 (s, 1H), 8.85-8.61 (m, 1H), 8.37 (d, J = 8.1 Hz, 1H), 8.00 (d, J = 8.7 Hz, 1H), 7.94 (s, 1H), 7.69 (d, J = 8.7 Hz, 1H), 7.58-7.42 (m, 1H), 7.35 (s, 1H), 7.22 (d, J = 8.6 Hz, 1H), 4.00-3.79 (m, 6H), 3.74-3.62 (m, 4H), 3.62-3.51 (m, 4H). | C |
| 265 | 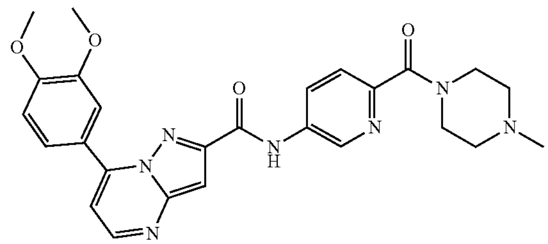 [SMILES: COc1ccc(-c2ccnc3cc(C(=O)Nc4ccc(C(=O)N5CCN(C)CC5)nc4)nn23)cc1OC] | ¹H NMR (400 MHz, DMSO-d₆) δ 10.69 (s, 1H), 9.00 (s, 1H), 8.71 (d, J = 3.7 Hz, 1H), 8.36 (d, J = 8.3 Hz, 1H), 8.00 (d, J = 8.4 Hz, 1H), 7.94 (s, 1H), 7.64 (d, J = 8.9 Hz, 1H), 7.50 (d, J = 4.4 Hz, 1H), 7.34 (s, 1H), 7.22 (d, J = 8.3 Hz, 1H), 4.00-3.72 (m, 6H), 3.73-3.56 (m, 2H), 3.55-3.42 (m, 2H), 2.43-2.34 (m, 2H), 2.34-2.24 (m, 2H), 2.20 (s, 3H). | C |
| 266 | 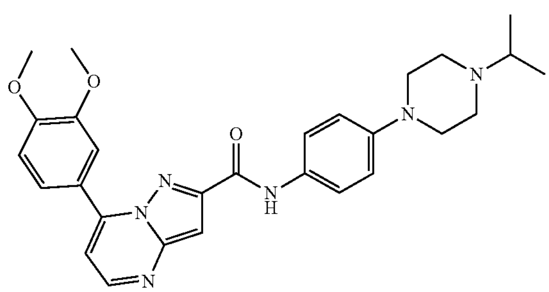 [SMILES: COc1ccc(-c2ccnc3cc(C(=O)Nc4ccc(N5CCN(C(C)C)CC5)cc4)nn23)cc1OC] | ¹H NMR (400 MHz, DMSO-d₆) δ 10.01 (s, 1H), 8.67 (d, J = 4.4 Hz, 1H), 8.01 (d, J = 8.5 Hz, 1H), 7.95 (s, 1H), 7.64 (d, J = 8.8 Hz, 2H), 7.46 (d, J = 4.4 Hz, 1H), 7.25 (s, 1H), 7.21 (d, J = 8.6 Hz, 1H), 6.94 (d, J = 8.8 Hz, 2H), 4.06-3.72 (m, 6H), 3.22-2.99 (m, 4H), 2.84-2.54 (m, 5H), 1.18-0.86 (m, 6H). | B |
| 268 | 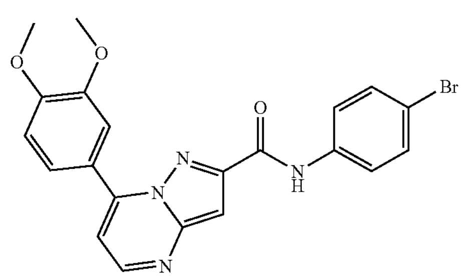 [SMILES: COc1ccc(-c2ccnc3cc(C(=O)Nc4ccc(Br)cc4)nn23)cc1OC] | ¹H NMR (400 MHz, DMSO-d₆) δ 10.40 (s, 1H), 8.70 (d, J = 4.5 Hz, 1H), 8.02 (dd, J = 8.5, 2.1 Hz, 1H), 7.95 (d, J = 2.1 Hz, 1H), 7.82 (d, J = 8.9 Hz, 2H), 7.57 (d, J = 8.9 Hz, 2H), 7.49 (d, J = 4.5 Hz, 1H), 7.30 (s, 1H), 7.21 (d, J = 8.6 Hz, 1H), 3.98-3.70 (m, 6H). | B |
| 269 | 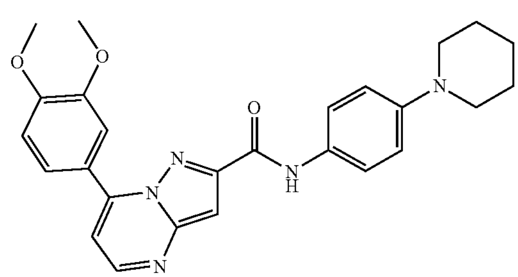 [SMILES: COc1ccc(-c2ccnc3cc(C(=O)Nc4ccc(N5CCCCC5)cc4)nn23)cc1OC] | ¹H NMR (400 MHz, DMSO-d₆) δ 10.02 (s, 1H), 8.68 (d, J = 4.5 Hz, 1H), 8.08-7.99 (m, 1H), 7.94 (s, 1H), 7.62 (d, J = 8.8 Hz, 2H), 7.47 (d, J = 4.4 Hz, 1H), 7.25 (s, 1H), 7.21 (d, J = 8.6 Hz, 1H), 6.94 (d, J = 9.0 Hz, 2H), 4.00-3.79 (m, 6H), 3.19-3.01 (m, 4H), 1.73-1.57 (m, 4H), 1.57-1.44 (m, 2H). | B |

TABLE 3A-continued

Compound Structures, Characterization Data and Synthetic Method

| Cmpd | Structure | Characterization Data | General Method (Ex. 2) |
|---|---|---|---|
| 270 | 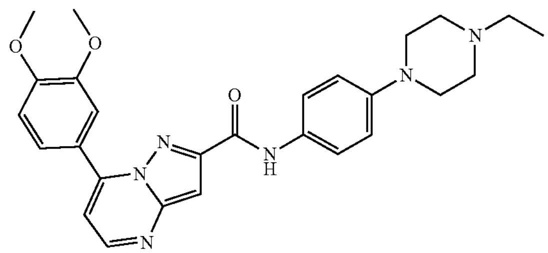 [SMILES: CCN1CCN(c2ccc(NC(=O)c3cc4nccc(-c5ccc(OC)c(OC)c5)n4n3)cc2)CC1] | $^1$H NMR (400 MHz, DMSO-d$_6$) δ 10.05 (s, 1H), 8.68 (d, J = 4.4 Hz, 1H), 8.01 (d, J = 7.2 Hz, 1H), 7.95 (s, 1H), 7.65 (d, J = 8.8 Hz, 2H), 7.47 (d, J = 4.2 Hz, 1H), 7.26 (s, 1H), 7.21 (d, J = 8.3 Hz, 1H), 6.95 (d, J = 8.8 Hz, 2H), 4.01-3.76 (m, 6H), 3.25-3.03 (m, 4H), 2.49-2.32 (m, 4H), 1.18-0.93 (m, 3H). | B |
| 271 | 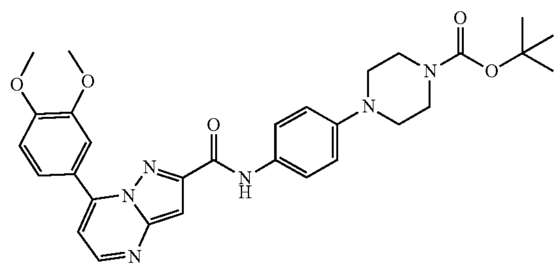 [SMILES: COc1ccc(-c2ccnc3cc(C(=O)Nc4ccc(N5CCN(C(=O)OC(C)(C)C)CC5)cc4)nn23)cc1OC] | $^1$H NMR (400 MHz, DMSO-d$_6$) δ 10.07 (s, 1H), 8.68 (d, J = 4.4 Hz, 1H), 8.09-7.98 (m, 1H), 7.98-7.88 (m, 1H), 7.66 (d, J = 8.9 Hz, 2H), 7.47 (d, J = 4.4 Hz, 1H), 7.26 (s, 1H), 7.21 (d, J = 8.6 Hz, 1H), 6.98 (d, J = 9.0 Hz, 2H), 4.00-3.82 (m, 6H), 3.55-3.43 (m, 4H), 3.15-2.96 (m, 4H), 1.42 (s, 9H). | B |
| 272 | 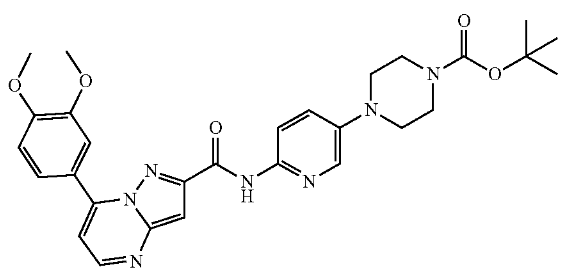 [SMILES: COc1ccc(-c2ccnc3cc(C(=O)Nc4ccc(N5CCN(C(=O)OC(C)(C)C)CC5)cn4)nn23)cc1OC] | $^1$H NMR (400 MHz, DMSO-d$_6$) δ 9.92 (s, 1H), 8.70 (d, J = 4.2 Hz, 1H), 8.23-8.04 (m, 2H), 7.95 (d, J = 8.0 Hz, 1H), 7.91 (s, 1H), 7.61-7.51 (m, 1H), 7.48 (d, J = 4.4 Hz, 1H), 7.35 (s, 1H), 7.23 (d, J = 8.4 Hz, 1H), 3.91 (s, 6H), 3.54-3.43 (m, 4H), 3.19-3.03 (m, 4H), 1.43 (s, 9H). | B |
| 273 | 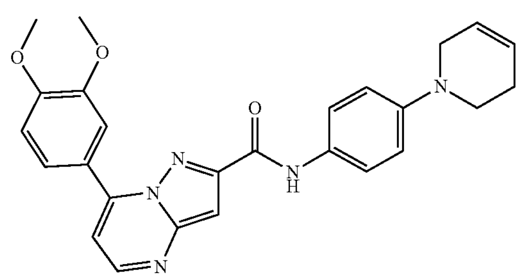 [SMILES: COc1ccc(-c2ccnc3cc(C(=O)Nc4ccc(N5CC=CCC5)cc4)nn23)cc1OC] | $^1$H NMR (400 MHz, DMSO-d$_6$) δ 10.04 (s, 1H), 8.68 (d, J = 4.3 Hz, 1H), 8.03 (d, J = 7.4 Hz, 1H), 7.95 (s, 1H), 7.65 (d, J = 8.6 Hz, 2H), 7.48 (d, J = 3.9 Hz, 1H), 7.26 (s, 1H), 7.22 (d, J = 8.4 Hz, 1H), 6.96 (d, J = 8.8 Hz, 2H), 5.96-5.69 (m, 2H), 4.01-3.79 (m, 6H), 3.74-3.55 (m, 2H), 3.33-3.29 (m, 2H), 2.31-2.14 (m, 2H). | B |
| 274 | 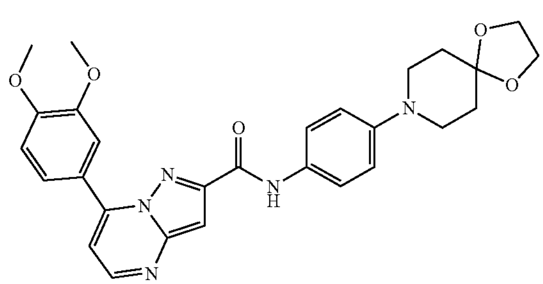 [SMILES: COc1ccc(-c2ccnc3cc(C(=O)Nc4ccc(N5CCC6(CC5)OCCO6)cc4)nn23)cc1OC] | $^1$H NMR (400 MHz, DMSO-d$_6$) δ 10.05 (s, 1H), 8.68 (d, J = 4.4 Hz, 1H), 8.11-8.00 (m, 1H), 7.99-7.91 (m, 1H), 7.64 (d, J = 8.9 Hz, 2H), 7.48 (d, J = 4.4 Hz, 1H), 7.26 (s, 1H), 7.22 (d, J = 8.6 Hz, 1H), 6.98 (d, J = 9.0 Hz, 2H), 4.07-3.73 (m, 10H), 3.31-3.16 (m, 4H), 1.86-1.65 (m, 4H). | B |

TABLE 3A-continued

Compound Structures, Characterization Data and Synthetic Method

| Cmpd | Structure | Characterization Data | General Method (Ex. 2) |
|---|---|---|---|
| 275 | 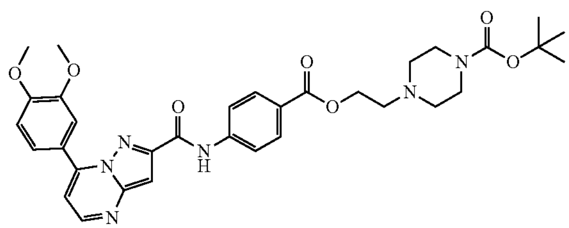 [SMILES: COc1ccc(-c2ccnc3cc(C(=O)Nc4ccc(C(=O)OCCN5CCN(C(=O)OC(C)(C)C)CC5)cc4)nn23)cc1OC] | ¹H NMR (400 MHz, DMSO-d₆) δ 10.61 (s, 1H), 8.71 (d, J = 4.5 Hz, 1H), 8.15-7.81 (m, 6H), 7.51 (d, J = 4.5 Hz, 1H), 7.35 (s, 1H), 7.23 (d, J = 8.6 Hz, 1H), 4.49-4.25 (m, 2H), 4.01-3.76 (m, 6H), 3.33-3.26 (m, 4H), 2.72 (t, J = 5.5 Hz, 2H), 2.49-2.39 (m, 4H), 1.40 (s, 9H). | C |
| 276 | 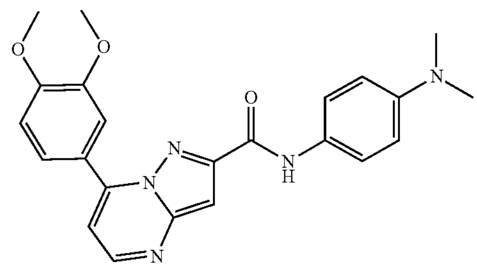 [SMILES: COc1ccc(-c2ccnc3cc(C(=O)Nc4ccc(N(C)C)cc4)nn23)cc1OC] | ¹H NMR (400 MHz, DMSO-d₆) δ 9.98 (s, 1H), 8.68 (d, J = 4.3 Hz, 1H), 8.03 (d, J = 8.5 Hz, 1H), 7.95 (s, 1H), 7.61 (d, J = 8.4 Hz, 2H), 7.47 (d, J = 4.0 Hz, 1H), 7.25 (s, 1H), 7.22 (d, J = 8.7 Hz, 1H), 6.75 (d, J = 8.3 Hz, 2H), 3.99-3.81 (m, 6H), 2.89 (s, 6H). | C |
| 277 | 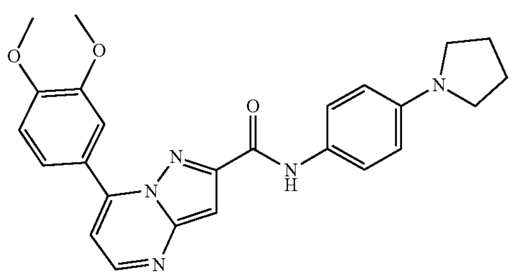 [SMILES: COc1ccc(-c2ccnc3cc(C(=O)Nc4ccc(N5CCCC5)cc4)nn23)cc1OC] | ¹H NMR (400 MHz, DMSO-d₆) δ 9.94 (s, 1H), 8.68 (d, J = 4.4 Hz, 1H), 8.03 (d, J = 6.6 Hz, 1H), 7.94 (s, 1H), 7.58 (d, J = 8.8 Hz, 2H), 7.47 (d, J = 4.5 Hz, 1H), 7.33-7.10 (m, 2H), 6.55 (d, J = 8.9 Hz, 2H), 3.97-3.75 (m, 6H), 3.29-3.13 (m, 4H), 2.06-1.87 (m, 4H). | B |
| 278 | 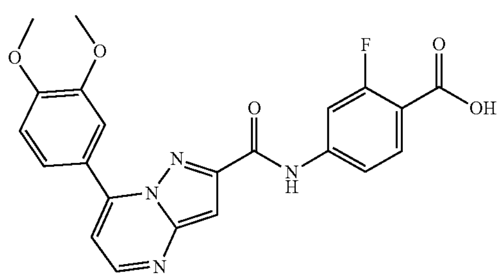 [SMILES: COc1ccc(-c2ccnc3cc(C(=O)Nc4ccc(C(=O)O)c(F)c4)nn23)cc1OC] | ¹H NMR (400 MHz, DMSO-d₆) δ 10.54 (s, 1H), 8.70 (d, J = 4.3 Hz, 1H), 8.07-7.98 (m, 1H), 7.98-7.90 (m, 1H), 7.86-7.69 (m, 2H), 7.60 (d, J = 8.4 Hz, 1H), 7.49 (d, J = 4.4 Hz, 1H), 7.32 (s, 1H), 7.22 (d, J = 8.5 Hz, 1H), 3.99-3.78 (m, 6H). | B |
| 279 | 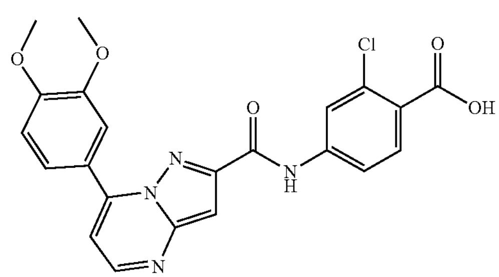 [SMILES: COc1ccc(-c2ccnc3cc(C(=O)Nc4ccc(C(=O)O)c(Cl)c4)nn23)cc1OC] | ¹H NMR (400 MHz, DMSO-d₆) δ 10.58 (s, 1H), 8.71 (d, J = 4.4 Hz, 1H), 8.07 (s, 1H), 8.03 (d, J = 8.7 Hz, 1H), 7.94 (s, 1H), 7.89-7.70 (m, 2H), 7.50 (d, J = 4.4 Hz, 1H), 7.34 (s, 1H), 7.23 (d, J = 8.6 Hz, 1H), 3.98-3.81 (m, 6H). | B |

TABLE 3A-continued

Compound Structures, Characterization Data and Synthetic Method

| Cmpd | Structure | Characterization Data | General Method (Ex. 2) |
|---|---|---|---|
| 280 | 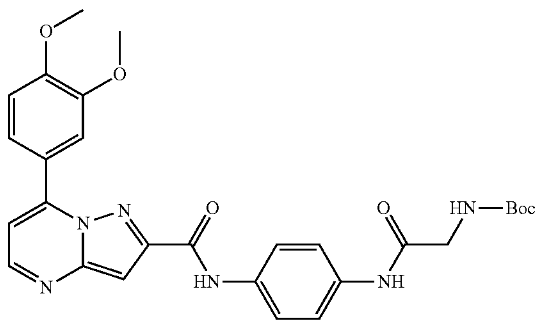 [SMILES: COc1ccc(-c2ccnc3cc(C(=O)Nc4ccc(NC(=O)CNC(=O)OC(C)(C)C)cc4)nn23)cc1OC] | $^1$H NMR (400 MHz, DMSO-d$_6$) δ 10.21 (s, 1H), 9.95 (s, 1H), 8.69 (d, J = 4.5 Hz, 1H), 8.03 (dd, J = 8.5, 2.1 Hz, 1H), 7.94 (d, J = 2.1 Hz, 1H), 7.74 (d, J = 8.9 Hz, 2H), 7.59 (d, J = 9.0 Hz, 2H), 7.49 (d, J = 4.5 Hz, 1H), 7.29 (s, 1H), 7.22 (d, J = 8.6 Hz, 1H), 7.07 (t, J = 6.2 Hz, 1H), 3.93-3.87 (m, 6H), 3.72 (d, J = 6.1 Hz, 2H), 1.41 (s, 9H). | C |
| 281 | 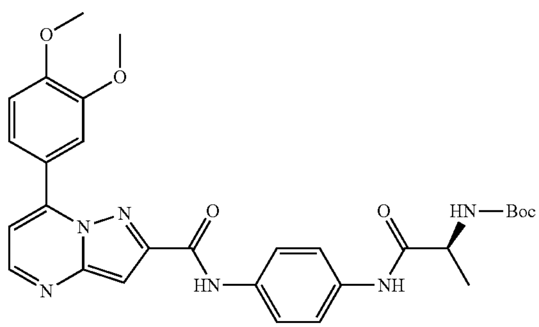 | $^1$H NMR (400 MHz, DMSO-d$_6$) δ 10.20 (s, 1H), 9.94 (s, 1H), 8.69 (d, J = 4.5 Hz, 1H), 8.03 (dd, J = 8.5, 2.0 Hz, 1H), 7.94 (d, J = 2.0 Hz, 1H), 7.74 (d, J = 8.9 Hz, 2H), 7.60 (d, J = 8.9 Hz, 2H), 7.49 (d, J = 4.5 Hz, 1H), 7.29 (s, 1H), 7.22 (d, J = 8.6 Hz, 1H), 7.07 (d, J = 7.5 Hz, 1H), 4.16-4.07 (m, 1H), 3.93-3.88 (m, 6H), 1.40 (s, 9H), 1.27 (d, J = 7.0 Hz, 3H). | C |
| 282 | 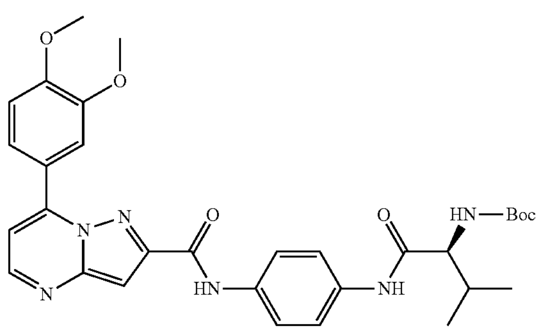 | $^1$H NMR (400 MHz, DMSO-d$_6$) δ 10.18 (s, 1H), 9.97 (s, 1H), 8.69 (d, J = 4.5 Hz, 1H), 8.02 (dd, J = 8.5, 2.1 Hz, 1H), 7.95 (d, J = 2.1 Hz, 1H), 7.74 (d, J = 9.0 Hz, 2H), 7.60 (d, J = 9.0 Hz, 2H), 7.48 (d, J = 4.5 Hz, 1H), 7.29 (s, 1H), 7.22 (d, J = 8.6 Hz, 1H), 6.85 (d, J = 8.7 Hz, 1H), 3.98-3.85 (m, 7H), 2.05-1.94 (m, 1H), 1.40 (s, 9H), 0.91 (d, J = 6.6 Hz, 6H). | C |
| 283 | 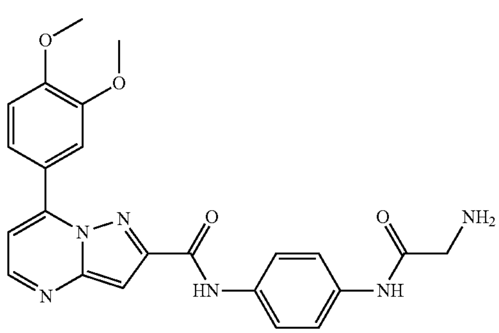 [SMILES: COc1ccc(-c2ccnc3cc(C(=O)Nc4ccc(NC(=O)CN)cc4)nn23)cc1OC] | $^1$H NMR (400 MHz, DMSO-d$_6$) δ 10.17 (s, 1H), 8.69 (d, J = 4.5 Hz, 1H), 8.03 (dd, J = 8.5, 2.1 Hz, 1H), 7.94 (d, J = 2.1 Hz, 1H), 7.74 (d, J = 9.0 Hz, 2H), 7.64 (d, J = 9.0 Hz, 2H), 7.48 (d, J = 4.4 Hz, 1H), 7.28 (s, 1H), 7.22 (d, J = 8.6 Hz, 1H), 3.92-3.89 (m, 6H), 3.29-3.27 (m, 2H). | C |

TABLE 3A-continued

Compound Structures, Characterization Data and Synthetic Method

| Cmpd | Structure | Characterization Data | General Method (Ex. 2) |
|---|---|---|---|
| 284 | 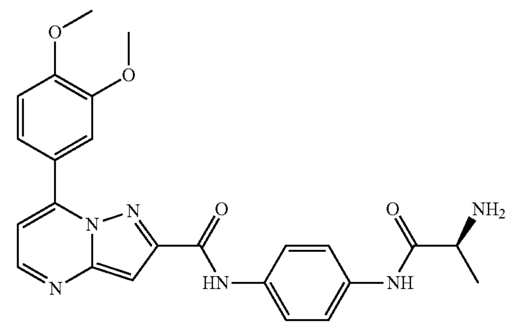 [SMILES: COc1ccc(-c2ccnc3cc(C(=O)Nc4ccc(NC(=O)[C@H](C)N)cc4)nn23)cc1OC] | $^1$H NMR (400 MHz, DMSO-d$_6$) δ 10.16 (s, 1H), 8.68 (d, J = 4.5 Hz, 1H), 8.02 (dd, J = 8.5, 2.1 Hz, 1H), 7.93 (d, J = 2.1 Hz, 1H), 7.73 (d, J = 9.0 Hz, 2H), 7.64 (d, J = 9.0 Hz, 2H), 7.47 (d, J = 4.5 Hz, 1H), 7.27 (s, 1H), 7.21 (d, J = 8.6 Hz, 1H), 3.92-3.88 (m, 6H), 3.42 (q, J = 6.9 Hz, 1H), 1.22 (d, J = 6.9 Hz, 3H). | C |
| 285 | 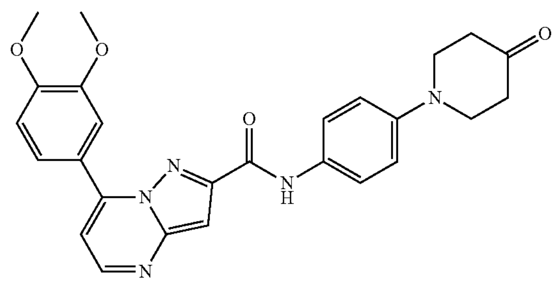 [SMILES: COc1ccc(-c2ccnc3cc(C(=O)Nc4ccc(N5CCC(=O)CC5)cc4)nn23)cc1OC] | $^1$H NMR (400 MHz, DMSO-d$_6$) δ 10.04 (s, 1H), 8.68 (d, J = 4.9 Hz, 1H), 8.02 (dd, J = 8.5, 2.1 Hz, 1H), 7.96-7.95 (m, 1H), 7.68 (d, J = 9.0 Hz, 2H), 7.47 (d, J = 4.9 Hz, 1H), 7.26 (s, 1H), 7.22 (d, J = 8.6 Hz, 1H), 7.06 (d, J = 9.1 Hz, 2H), 3.92-3.88 (m, 6H), 3.59 (t, J = 6.0 Hz, 4H), 2.44 (t, J = 6.0 Hz, 4H). | B |
| 286 | 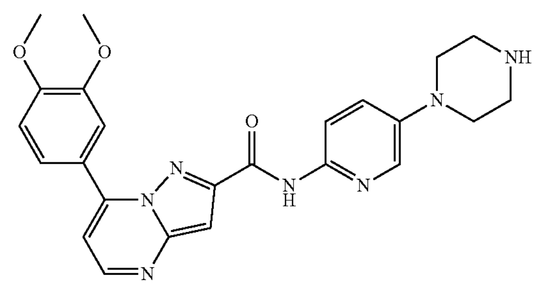 [SMILES: COc1ccc(-c2ccnc3cc(C(=O)Nc4ccc(N5CCNCC5)cn4)nn23)cc1OC] | $^1$H NMR (400 MHz, DMSO-d$_6$) δ 9.90 (s, 1H), 8.71 (d, J = 4.5 Hz, 1H), 8.15-8.12 (m, 2H), 7.96-7.93 (m, 2H), 7.57 (dd, J = 9.0, 3.0 Hz, 1H), 7.48 (d, J = 4.5 Hz, 1H), 7.36 (s, 1H), 7.24 (d, J = 8.2 Hz, 1H), 3.94-3.89 (m, 6H), 3.38-3.36 (m, 4H), 3.24-3.22 (m, 4H). | B |
| 287 | 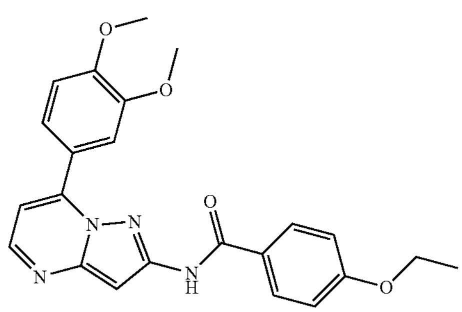 [SMILES: CCOc1ccc(C(=O)Nc2cc3nccc(-c4ccc(OC)c(OC)c4)n3n2)cc1] | $^1$H NMR (400 MHz, DMSO-d$_6$) δ 11.14 (s, 1H), 8.51 (d, J = 4.5 Hz, 1H), 8.05 (d, J = 8.9 Hz, 2H), 7.84-7.78 (m, 2H), 7.20-7.15 (m, 2H), 7.13 (s, 1H), 7.03 (d, J = 9.0 Hz, 2H), 4.12 (q, J = 7.0 Hz, 2H), 3.90-3.84 (m, 6H), 1.35 (t, J = 7.0 Hz, 3H). | F |

TABLE 3A-continued

Compound Structures, Characterization Data and Synthetic Method

| Cmpd | Structure | Characterization Data | General Method (Ex. 2) |
|---|---|---|---|
| 288 | 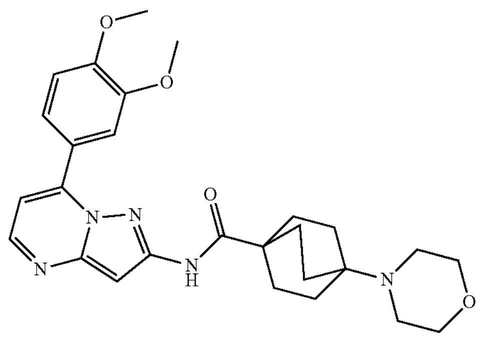 [SMILES: COc1ccc(-c2ccnc3cc(NC(=O)C45CCC(N6CCOCC6)(CC4)CC5)nn23)cc1OC] | $^1$H NMR (400 MHz, DMSO-d$_6$) δ 10.27 (s, 1H), 8.47 (d, J = 4.5 Hz, 1H), 7.80 (dd, J = 8.5, 2.1 Hz, 1H), 7.67 (d, J = 2.0 Hz, 1H), 7.17-7.13 (m, 2H), 6.96 (s, 1H), 3.88-3.84 (m, 6H), 3.55-3.49 (m, 4H), 2.47-2.41 (m, 4H), 1.90-1.82 (m, 6H), 1.56-1.47 (m, 6H). | F |
| 289 | 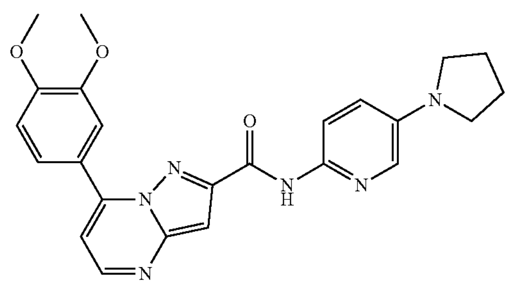 [SMILES: COc1ccc(-c2ccnc3cc(C(=O)Nc4ccc(N5CCCC5)cn4)nn23)cc1OC] | $^1$H NMR (400 MHz, DMSO-d$_6$) δ 9.76 (s, 1H), 8.70 (d, J = 4.5 Hz, 1H), 8.05 (d, J = 8.9 Hz, 1H), 7.96 (dd, J = 8.5 Hz, 2.1 Hz, 1H), 7.90 (d, J = 4.9 Hz, 1H), 7.72 (d, J = 2.9 Hz, 1H), 7.48 (d, J = 4.5 Hz, 1H), 7.33 (s, 1H), 7.24 (d, J = 8.6 Hz, 1H), 7.08 (dd, J = 9.0, 3.0 Hz, 1H), 3.94-3.89 (m, 6H), 3.31-3.25 (m, 4H), 1.99-1.96 (m, 4H). | B |
| 290 | 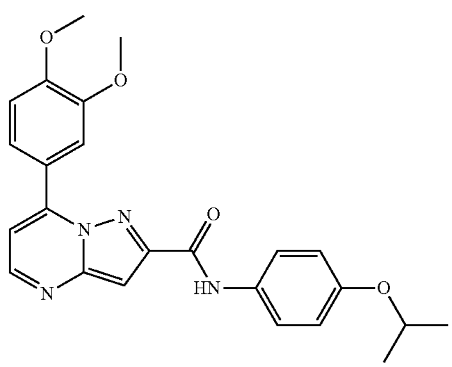 [SMILES: COc1ccc(-c2ccnc3cc(C(=O)Nc4ccc(OC(C)C)cc4)nn23)cc1OC] | $^1$H NMR (400 MHz, DMSO-d$_6$) δ 10.10 (s, 1H), 8.68 (d, J = 4.5 Hz, 1H), 8.02 (dd, J = 8.5, 2.1 Hz, 1H), 7.93 (d, J = 2.1 Hz, 1H), 7.68 (d, J = 9.0 Hz, 2H), 7.47 (d, J = 4.5 Hz, 1H), 7.26 (s, 1H), 7.21 (d, J = 8.6 Hz, 1H), 6.92 (d, J = 9.0 Hz, 2H), 4.63-4.53 (m, 1H), 3.92-3.86 (m, 6H), 1.28-1.24 (m, 6H). | C |
| 291 | 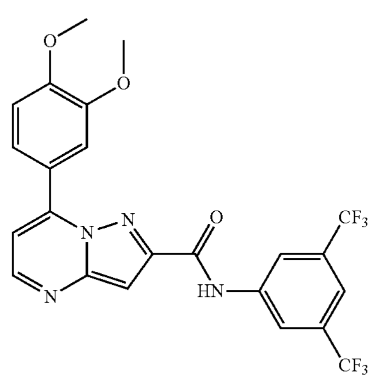 [SMILES: COc1ccc(-c2ccnc3cc(C(=O)Nc4cc(C(F)(F)F)cc(C(F)(F)F)c4)nn23)cc1OC] | $^1$H NMR (400 MHz, DMSO-d$_6$) δ 10.95 (s, 1H), 8.71 (d, J = 4.5 Hz, 1H), 8.60 (s, 2H), 8.01 (dd, J = 8.5, 2.2 Hz, 1H), 7.91 (d, J = 2.1 Hz, 1H), 7.85 (s, 1H), 7.51 (d, J = 4.5 Hz, 1H), 7.35 (s, 1H), 7.22 (d, J = 8.6 Hz, 1H), 3.92-3.88 (m, 6H). | B |

TABLE 3A-continued

Compound Structures, Characterization Data and Synthetic Method

| Cmpd | Structure | Characterization Data | General Method (Ex. 2) |
|---|---|---|---|
| 292 | 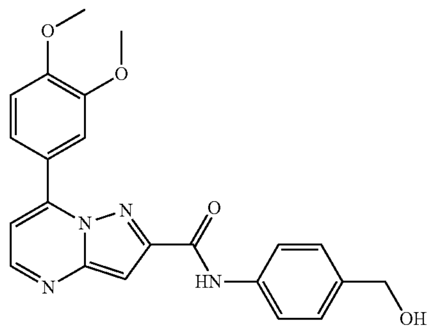 [SMILES: COc1ccc(-c2ccnc3cc(C(=O)Nc4ccc(CO)cc4)nn23)cc1OC] | ¹H NMR (400 MHz, DMSO-d₆) δ 10.23 (s, 1H), 8.69 (d, J = 4.5 Hz, 1H), 8.02 (dd, J = 8.5, 2.1 Hz, 1H), 7.95 (d, J = 2.1 Hz, 1H), 7.76 (d, J = 8.5 Hz, 2H), 7.49 (d, J = 4.5 Hz, 1H), 7.34-7.28 (m, 3H), 7.21 (d, J = 8.6 Hz, 1H), 5.17 (t, J = 5.7 Hz, 1H), 4.47 (d, J = 5.7 Hz, 2H), 3.92-3.86 (m, 6H). | C |
| 293 | 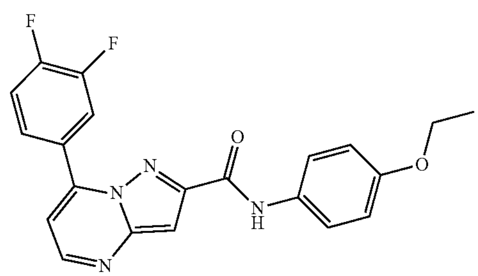 [SMILES: CCOc1ccc(NC(=O)c2cc3nccc(-c4ccc(F)c(F)c4)n3n2)cc1] | ¹H NMR (400 MHz, DMSO-d₆) δ 10.17 (s, 1H), 8.74 (d, J = 4.4 Hz, 1H), 8.52-8.45 (m, 1H), 8.22-8.15 (m, 1H), 7.77-7.65 (m, 3H), 7.49 (d, J = 4.4 Hz, 1H), 7.32 (s, 1H), 6.97-6.91 (m, 2H), 4.01 (q, J = 7.0 Hz, 2H), 1.33 (t, J = 7.0 Hz, 3H). | B |
| 294 | 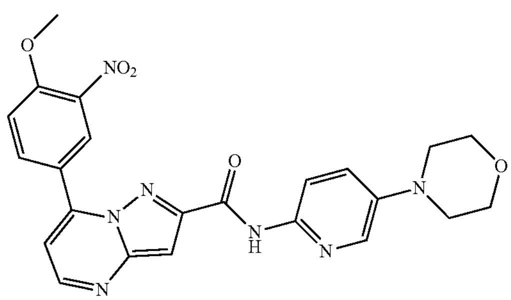 [SMILES: COc1ccc(-c2ccnc3cc(C(=O)Nc4ccc(N5CCOCC5)cn4)nn23)cc1[N+](=O)[O-]] | ¹H NMR (400 MHz, DMSO-d₆) δ 10.10 (s, 1H), 8.86 (d, J = 2.3 Hz, 1H), 8.74 (d, J = 4.4 Hz, 1H), 8.61 (dd, J = 8.9, 2.3 Hz, 1H), 8.12-8.06 (m, 2H), 7.63 (d, J = 9.0 Hz, 1H), 7.54-7.48 (m, 2H), 7.39 (s, 1H), 4.01 (s, 3H), 3.80-3.70 (m, 4H), 3.20-3.10 (m, 4H). | B |
| 295 | 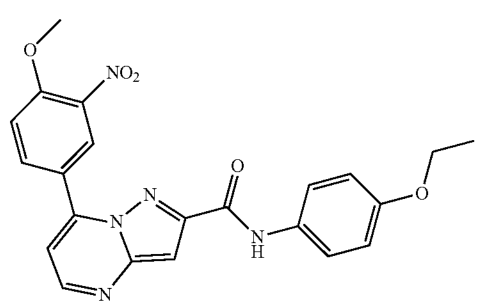 [SMILES: CCOc1ccc(NC(=O)c2cc3nccc(-c4ccc(OC)c([N+](=O)[O-])c4)n3n2)cc1] | ¹H NMR (400 MHz, DMSO-d₆) δ 10.12 (s, 1H), 8.94 (d, J = 2.3 Hz, 1H), 8.73 (d, J = 4.4 Hz, 1H), 8.65 (dd, J = 8.9, 2.3 Hz, 1H), 7.71-7.66 (m, 2H), 7.61 (d, J = 9.0 Hz, 1H), 7.55 (d, J = 4.4 Hz, 1H), 7.31 (s, 1H), 6.98-6.91 (m, 2H), 4.10-3.98 (m, 5H), 1.33 (t, J = 7.0 Hz, 3H). | C |

US 11,827,640 B2

475                                                                         476

TABLE 3A-continued

Compound Structures, Characterization Data and Synthetic Method

| Cmpd | Structure | Characterization Data | General Method (Ex. 2) |
|---|---|---|---|
| 296 | 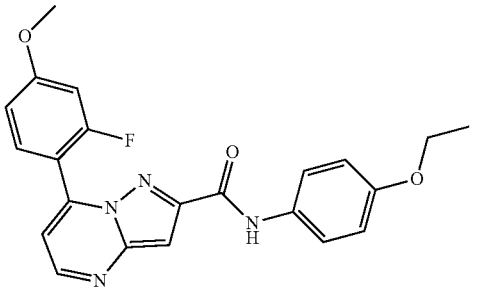 [SMILES: CCOc1ccc(NC(=O)c2cc3nccc(-c4ccc(OC)cc4F)n3n2)cc1] | $^1$H NMR (400 MHz, DMSO-$d_6$) δ 10.04 (s, 1H), 8.70 (d, J = 4.3 Hz, 1H), 7.94 (t, J = 8.6 Hz, 1H), 7.68-7.62 (m, 2H), 7.33-7.29 (m, 2H), 7.13 (dd, J = 12.5, 2.4 Hz, 1H), 7.03 (dd, J = 8.7, 2.5 Hz), 6.93-6.87 (m, 2H), 4.01 (q, J = 7.0 Hz, 2H), 3.90 (s, 3H), 1.32 (t, J = 7.0 Hz, 2H). | C |
| 297 | 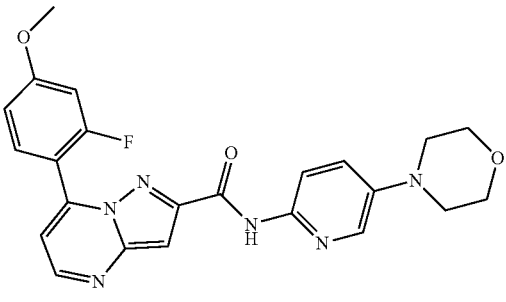 [SMILES: COc1ccc(-c2ccnc3cc(C(=O)Nc4ccc(N5CCOCC5)cn4)nn23)c(F)c1] | $^1$H NMR (400 MHz, DMSO-$d_6$) δ 9.77 (s, 1H), 8.72 (d, J = 4.3 Hz, 1H), 8.10-8.04 (m, 2H), 7.93 (t, J = 8.6 Hz, 1H), 7.50 (dd, J = 9.1, 3.1 Hz, 1H), 7.40 (s, 1H), 7.33 (dd, J = 4.3, 0.8 Hz, 1H), 7.17 (dd, J = 12.5, 2.4 Hz, 1H), 7.06 (dd, J = 8.7, 2.5 Hz, 1H), 3.91 (s, 3H), 3.78-3.71 (m, 4H), 3.17-3.11 (m, 4H). | B |
| 298 | 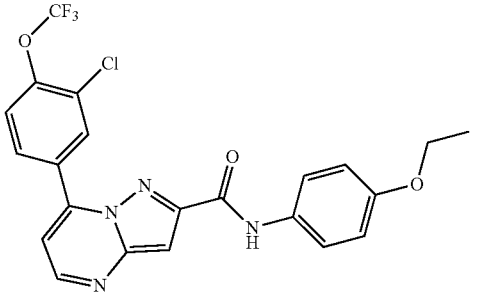 [SMILES: CCOc1ccc(NC(=O)c2cc3nccc(-c4ccc(OC(F)(F)F)c(Cl)c4)n3n2)cc1] | $^1$H NMR (400 MHz, DMSO-$d_6$) δ 10.16 (s, 1H), 8.76 (d, J = 4.4 Hz, 1H), 8.57 (d, J = 2.2 Hz, 1H), 8.41 (dd, J = 8.7, 2.2 Hz, 1H), 7.87-7.81 (m, 1H), 7.71-7.64 (m, 2H), 7.54 (d, J = 4.4 Hz, 1H), 7.34 (s, 1H), 6.96-6.90 (m, 2H), 4.01 (q, J = 7.0 Hz, 2H), 1.32 (t, J = 7..0 Hz, 3H). | C |
| 299 | 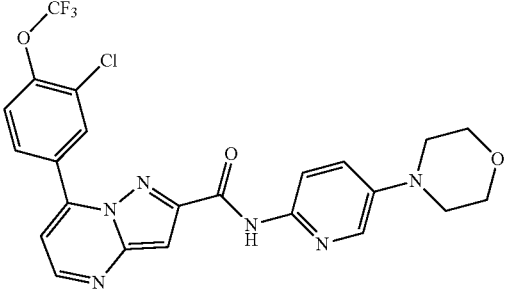 [SMILES: O=C(Nc1ccc(N2CCOCC2)cn1)c1cc2nccc(-c3ccc(OC(F)(F)F)c(Cl)c3)n2n1] | $^1$H NMR (400 MHz, DMSO-$d_6$) δ 10.12 (s, 1H), 8.77 (d, J = 4.4 Hz, 1H), 8.56 (d, J = 2.2 Hz, 1H), 8.37 (dd, J = 8.7, 2.2 Hz, 1H), 8.12-8.05 (m, 2H), 7.90-7.84 (m, 1H), 7.56-7.48 (m, 2H), 7.43 (s, 1H), 3.80-3.70 (m, 4H), 3.18-3.12 (m, 4H). | B |
| 301 | 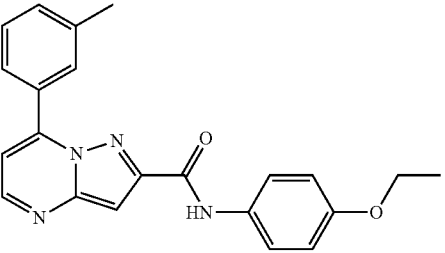 [SMILES: CCOc1ccc(NC(=O)c2cc3nccc(-c4cccc(C)c4)n3n2)cc1] | $^1$H NMR (400 MHz, DMSO-$d_6$) δ 10.11 (s, 1H), 8.71 (d, J = 4.4 Hz, 1H), 8.09-8.04 (m, 2H), 7.69 (d, J = 9.0 Hz, 2H), 7.56-7.47 (m, 2H), 7.40 (d, J = 4.4 Hz, 1H), 7.30 (s, 1H), 6.94 (d, J = 9.0 Hz, 2H), 4.02 (q, J = 7.0 Hz, 2H), 2.46 (s, 1H), 1.33 (t, J = 7.0 Hz, 3H). | B |

TABLE 3A-continued

Compound Structures, Characterization Data and Synthetic Method

| Cmpd | Structure | Characterization Data | General Method (Ex. 2) |
|---|---|---|---|
| 302 | 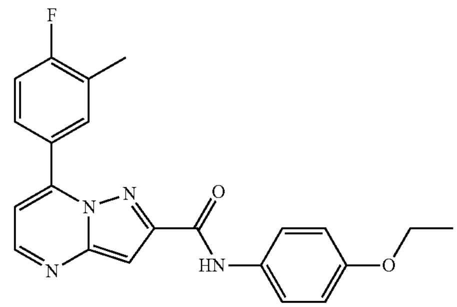 [SMILES: CCOc1ccc(NC(=O)c2cc3nccc(-c4ccc(F)c(C)c4)n3n2)cc1] | $^{1}$H NMR (400 MHz, DMSO-d$_{6}$) δ 10.12 (s, 1H), 8.72 (d, J = 4.4 Hz, 1H), 8.24-8.20 (m, 2H), 7.70-7.68 (m, 2H), 7.44-7.40 (m, 2H), 7.30 (s, 1H), 6.95-6.93 (m, 2H), 4.02 (q, J = 7.0 Hz, 2H), 2.40-2.38 (m, 3H), 1.33 (t, J = 7.0 Hz, 3H). | C |
| 303 | 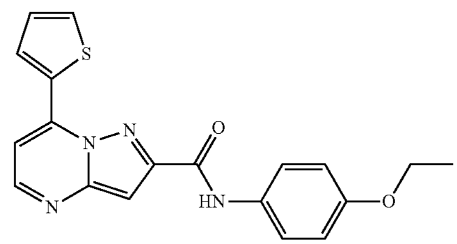 [SMILES: CCOc1ccc(NC(=O)c2cc3nccc(-c4cccs4)n3n2)cc1] | $^{1}$H NMR (400 MHz, DMSO-d$_{6}$) δ 10.14 (s, 1H), 8.75 (dd, J = 3.9, 1.1 Hz, 1H), 8.70 (d, J = 4.7 Hz, 1H), 8.16 (dd, J = 5.0, 1.1 Hz, 1H), 7.84 (d, J = 4.7 Hz, 1H), 7.74-7.72 (m, 2H), 7.45-7.43 (m, 1H), 7.32 (s, 1H), 6.98-6.96 (m, 2H), 4.04 (q, J = 7.0 Hz, 2H), 1.34 (t, J = 7.0 Hz, 3H). | C |
| 304 | 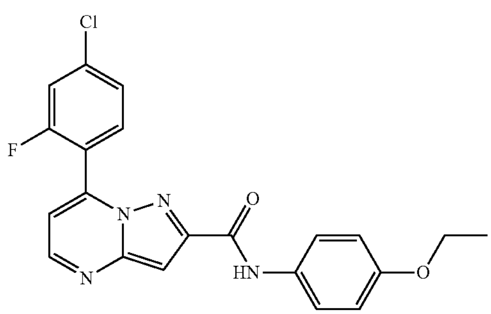 [SMILES: CCOc1ccc(NC(=O)c2cc3nccc(-c4ccc(Cl)cc4F)n3n2)cc1] | $^{1}$H NMR (400 MHz, DMSO-d$_{6}$) δ 10.07 (s, 1H), 8.76 (d, J = 4.2 Hz, 1H), 8.01 (t, J = 8.0 Hz, 1H), 7.79 (dd, J = 10.1, 1.9 Hz, 1H), 7.65 (d, J = 9.0 Hz, 2H), 7.59 (dd, J = 8.4, 1.9 Hz, 1H), 7.39 (d, J = 4.2 Hz, 1H), 7.36 (s, 1H), 6.92 (d, J = 9.0 Hz, 2H), 4.01 (q, J = 7.0 Hz, 2H), 1.32 (t, J = 7.0 Hz, 3H). | C |
| 306 | 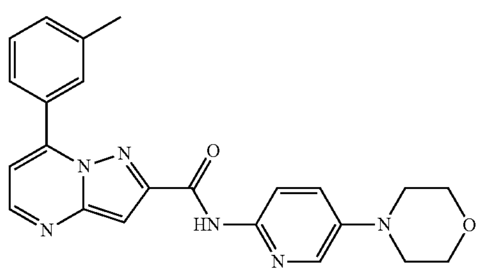 [SMILES: Cc1cccc(-c2ccnc3cc(C(=O)Nc4ccc(N5CCOCC5)cn4)nn23)c1] | $^{1}$H NMR (400 MHz, DMSO-d$_{6}$) δ 9.94 (s, 1H), 8.73 (d, J = 4.4 Hz, 1H), 8.11-8.05 (m, 3H), 7.97 (s, 1H), 7.58-7.48 (m, 3H), 7.40-7.39 (m, 2H), 3.76 (t, J = 4.8 Hz, 4H), 3.15 (t, J = 4.8 Hz, 4H), 2.46 (s, 3H). | B |
| 307 | 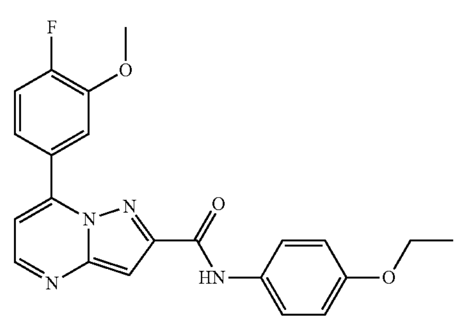 [SMILES: CCOc1ccc(NC(=O)c2cc3nccc(-c4ccc(F)c(OC)c4)n3n2)cc1] | $^{1}$H NMR (400 MHz, DMSO-d$_{6}$) δ 10.13 (s, 1H), 8.73 (d, J = 4.4 Hz, 1H), 8.09 (dd, J = 8.4, 1.2 Hz, 1H), 7.94-7.90 (m, 1H), 7.70-7.68 (m, 2H), 7.52-7.47 (m, 2H), 7.31 (s, 1H), 6.95-6.93 (m, 2H), 4.02 (q, J = 7.0 Hz, 2H), 3.99 (s, 3H), 1.33 (t, J = 7.0 Hz, 3H). | C |

TABLE 3A-continued

Compound Structures, Characterization Data and Synthetic Method

| Cmpd | Structure | Characterization Data | General Method (Ex. 2) |
|---|---|---|---|
| 308 | 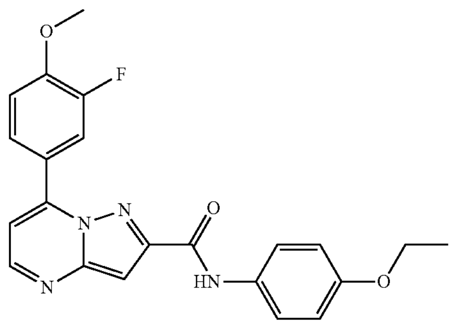 [SMILES: CCOc1ccc(NC(=O)c2cc3nccc(-c4ccc(OC)c(F)c4)n3n2)cc1] | $^1$H NMR (400 MHz, DMSO-d$_6$) δ 10.16 (s, 1H), 8.69 (d, J = 4.5 Hz, 1H), 8.32 (dd, J = 12.9, 2.2 Hz, 1H), 8.25-8.23 (m, 1H), 7.70-7.68 (m, 2H), 7.47 (d, J = 4.5 Hz, 1H), 7.42 (t, J = 8.9 Hz, 1H), 7.28 (s, 1H), 6.95-6.93 (m, 2H), 4.02 (q, J = 7.0 Hz, 2H), 3.98 (s, 3H), 1.33 (t, J = 7.0 Hz, 3H). | C |
| 309 | 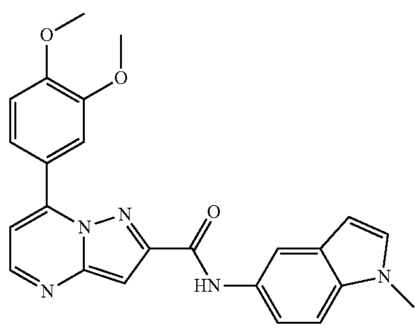 [SMILES: COc1ccc(-c2ccnc3cc(C(=O)Nc4ccc5c(ccn5C)c4)nn23)cc1OC] | $^1$H NMR (400 MHz, DMSO-d$_6$) δ 10.10 (s, 1H), 8.69 (d, J = 4.5 Hz, 1H), 8.07-8.04 (m, 2H), 7.96 (d, J = 2.1 Hz, 1H), 7.49-7.48 (m, 2H), 7.44-7.42 (m, 1H), 7.34 (d, J = 3.2 Hz, 1H), 7.29 (s, 1H), 7.23 (d, J = 8.6 Hz, 1H), 6.43 (dd, J = 3.0, 0.7 Hz, 1H), 3.92 (s, 3H), 3.90 (s, 3H), 3.80 (s, 3H). | C |
| 311 | 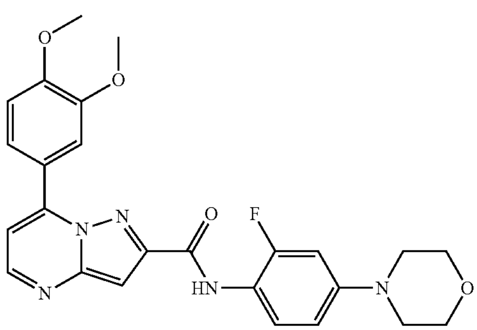 [SMILES: COc1ccc(-c2ccnc3cc(C(=O)Nc4ccc(N5CCOCC5)cc4F)nn23)cc1OC] | $^1$H NMR (400 MHz, DMSO-d$_6$) δ 9.72 (s, 1H), 8.69 (d, J = 4.5 Hz, 1H), 7.97-7.93 (m, 2H), 7.64 (t, J = 9.0 Hz, 1H), 7.48 (d, J = 4.5 Hz, 1H), 7.26 (s, 1H), 7.20 (d, J = 8.5 Hz, 1H), 6.92 (dd, J = 14.1, 2.6 Hz, 1H), 6.81 (dd, J = 8.9, 2.4 Hz, 1H), 3.90 (s, 3H), 3.89 (s, 3H), 3.74 (t, J = 4.8 Hz, 4H), 3.15 (t, J = 4.8 Hz, 4H). | B |
| 312 | 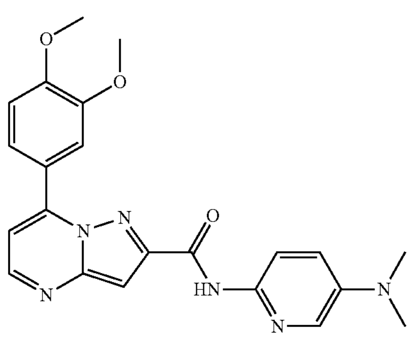 [SMILES: COc1ccc(-c2ccnc3cc(C(=O)Nc4ccc(N(C)C)cn4)nn23)cc1OC] | $^1$H NMR (400 MHz, DMSO-d$_6$) δ 9.78 (s, 1H), 8.69 (d, J = 4.5 Hz, 1H), 8.06 (d, J = 9.0 Hz, 1H), 7.95 (dd, J = 8.5, 2.1 Hz, 1H), 7.91-7.89 (m, 2H), 7.47 (d, J = 4.5 Hz, 1H), 7.33 (s, 1H), 7.29 (dd, J = 9.1, 3.1 Hz, 1H), 7.24 (d, J = 8.6 Hz, 1H), 3.92-3.90 (m, 6H), 2.92 (s, 6H). | B |

TABLE 3A-continued

Compound Structures, Characterization Data and Synthetic Method

| Cmpd | Structure | Characterization Data | General Method (Ex. 2) |
|---|---|---|---|
| 313 | 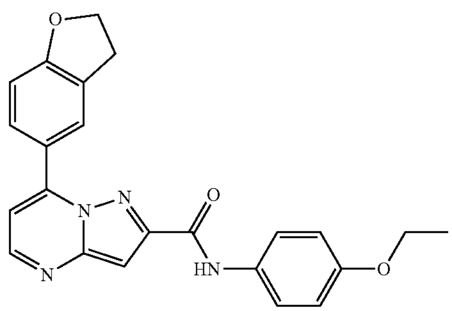 [SMILES: CCOc1ccc(NC(=O)c2cc3nccc(-c4ccc5c(c4)CCO5)n3n2)cc1] | $^1$H NMR (400 MHz, DMSO-d$_6$) δ 10.10 (s, 1H), 8.65 (d, J = 4.8 Hz, 1H), 8.27 (s, 1H), 8.11 (dd, J = 8.5, 2.0 Hz, 1H), 7.71-7.69 (m, 2H), 7.35 (d, J = 4.8 Hz, 1H), 7.25 (s, 1H), 7.01 (d, J = 8.5 Hz, 1H), 6.95-6.92 (m, 2H), 4.68 (t, J = 8.8 Hz, 2H), 4.02 (q, J = 7.0 Hz, 2H), 3.39-3.34 (m, 2H), 1.33 (t, J = 7.0 Hz, 3H). | C |
| 314 | 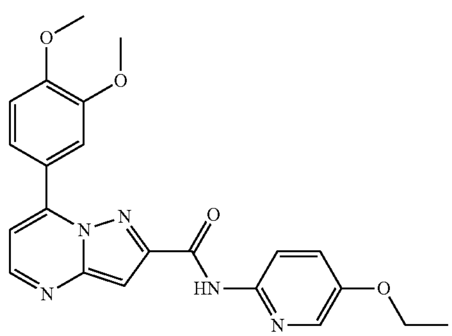 [SMILES: CCOc1ccc(NC(=O)c2cc3nccc(-c4ccc(OC)c(OC)c4)n3n2)nc1] | $^1$H NMR (400 MHz, DMSO-d$_6$) δ 9.98 (s, 1H), 8.70 (d, J = 4.5 Hz, 1H), 8.16 (d, J = 9.1 Hz, 1H), 8.09 (d, J = 2.9 Hz, 1H), 7.96 (dd, J = 8.5, 2.1 Hz, 1H), 7.89 (d, J = 2.1 Hz, 1H), 7.53 (dd, J = 9.0, 3.1 Hz, 1H), 7.48 (d, J = 4.5 Hz, 1H), 7.36 (s, 1H), 7.23 (d, J = 8.6 Hz, 1H), 4.11 (q, J = 7.0 Hz, 2H), 3.93-3.87 (m, 6H), 1.35 (t, J = 7.0 Hz, 3H). | B |
| 315 | 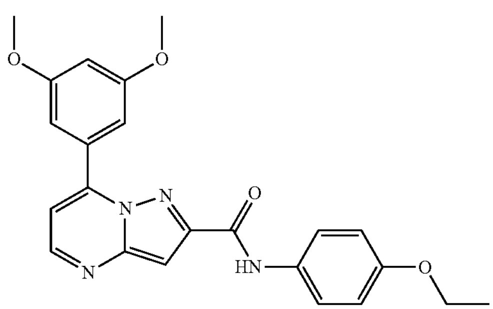 [SMILES: CCOc1ccc(NC(=O)c2cc3nccc(-c4cc(OC)cc(OC)c4)n3n2)cc1] | $^1$H NMR (400 MHz, DMSO-d$_6$) δ 10.13 (s, 1H), 8.71 (d, J = 4.4 Hz, 1H), 7.67 (d, J = 9.1 Hz, 2H), 7.45 (d, J = 4.4 Hz, 1H), 7.38 (d, J = 2.3 Hz, 2H), 7.30 (s, 1H), 6.95-6.90 (m, 2H), 6.78 (t, J = 2.3 Hz, 1H), 4.01 (q, J = 7.0 Hz, 2H), 3.90-3.82 (m, 6H), 1.32 (t, J = 7.0 Hz, 3H). | C |
| 316 | 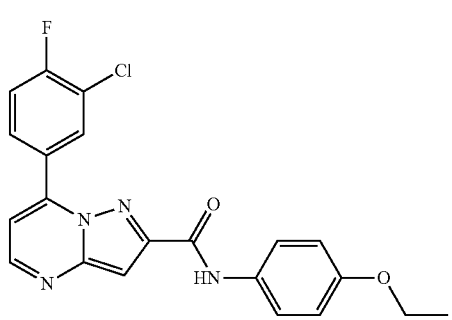 [SMILES: CCOc1ccc(NC(=O)c2cc3nccc(-c4ccc(F)c(Cl)c4)n3n2)cc1] | $^1$H NMR (400 MHz, DMSO-d$_6$) δ 10.15 (s, 1H), 8.74 (d, J = 4.4 Hz, 1H), 8.51 (dd, J = 7.2, 2.3 Hz, 1H), 8.39-8.31 (m, 1H), 7.74-7.64 (m, 3H), 7.49 (d, J = 4.4 Hz, 1H), 7.32 (s, 1H), 6.98-6.89 (m, 2H), 4.01 (q, J = 7.0 Hz, 2H), 1.33 (t, J = 7.0 Hz, 3H). | C |

TABLE 3A-continued

Compound Structures, Characterization Data and Synthetic Method

| Cmpd | Structure | Characterization Data | General Method (Ex. 2) |
|---|---|---|---|
| 317 | 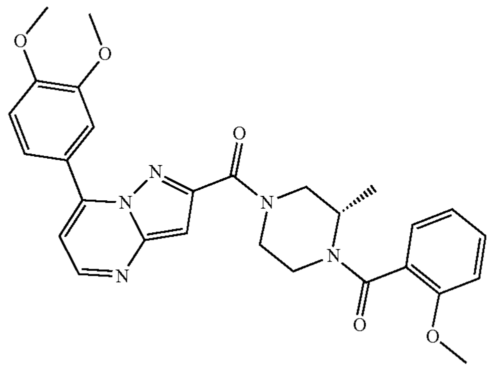 [SMILES: COc1ccc(-c2ccnc3cc(C(=O)N4CCN(C(=O)c5ccccc5OC)[C@@H](C)C4)nn23)cc1OC] | ¹H NMR (400 MHz, CDCl₃) δ 8.61-8.52 (m, 1H), 7.80-7.53 (m, 2H), 7.44-7.28 (m, 1H), 7.25-6.83 (m, 6H), 5.23-4.36 (m, 3H), 4.05-3.74 (m, 10H), 3.70-2.77 (m, 3H), 1.39-1.07 (m, 3H). | D |
| 318 | 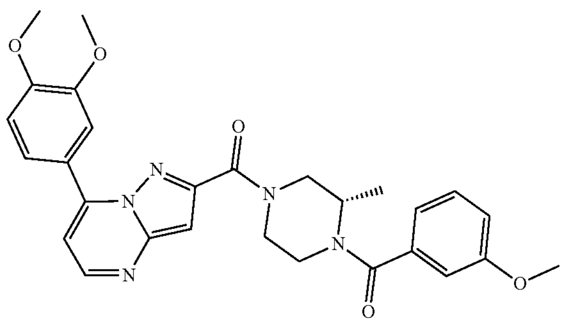 [SMILES: COc1cccc(C(=O)N2CCN(C(=O)c3cc4nccc(-c5ccc(OC)c(OC)c5)n4n3)C[C@@H]2C)c1] | ¹H NMR (400 MHz, CDCl₃) δ 8.61-8.53 (m, 1H), 7.76-7.54 (m, 2H), 7.38-7.30 (m, 1H), 7.17 (d, J = 7.3 Hz, 1H), 7.08-6.89 (m, 5H), 4.95-4.47 (m, 3H), 4.04-3.78 (m, 10H), 3.63-2.69 (m, 3H), 1.41-1.19 (m, 3H). | D |
| 319 | 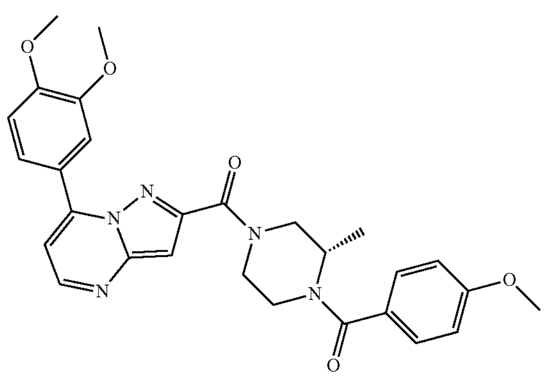 [SMILES: COc1ccc(C(=O)N2CCN(C(=O)c3cc4nccc(-c5ccc(OC)c(OC)c5)n4n3)C[C@@H]2C)cc1] | ¹H NMR (400 MHz, CDCl₃) δ 8.61-8.54 (m, 1H), 7.75-7.54 (m, 2H), 7.41-7.32 (m, 2H), 7.17 (d, J = 7.3 Hz, 1H), 7.07-6.90 (m, 4H), 4.86-4.42 (m, 3H), 4.03-3.79 (m, 10H), 3.46-2.86 (m, 3H), 1.38-1.19 (m, 3H). | D |
| 320 | 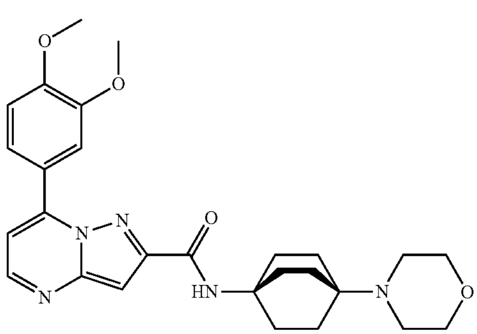 | ¹H NMR (400 MHz, CDCl₃) δ 8.54 (d, J = 4.4 Hz, 1H), 7.75 (d, J = 2.1 Hz, 1H), 7.60 (dd, J = 8.4, 2.1 Hz, 1H), 7.25 (s, 1H), 7.06 (d, J = 8.5 Hz, 1H), 6.99 (d, J = 4.4 Hz, 1H), 6.82 (s, 1H), 4.01 (s, 3H), 3.97 (s, 3H), 3.75-3.68 (m, 4H), 2.60-2.51 (m, 4H), 2.12-2.06 (m, 6H), 1.78-1.69 (m, 6H). | A |

TABLE 3A-continued

Compound Structures, Characterization Data and Synthetic Method

| Cmpd | Structure | Characterization Data | General Method (Ex. 2) |
|---|---|---|---|
| 321 | 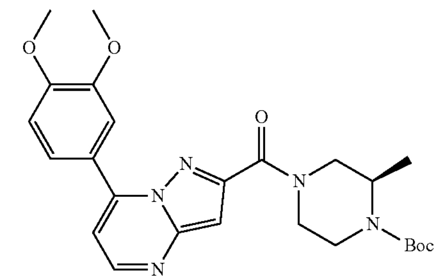 [SMILES: COc1ccc(-c2ccnc3cc(C(=O)N4CCN(C(=O)OC(C)(C)C)[C@H](C)C4)nn23)cc1OC] | ¹H NMR (400 MHz, CDCl₃) δ 8.59-8.53 (m, 1H), 7.74-7.58 (m, 2H), 7.15 (d, J = 7.5 Hz, 1H), 7.07-6.95 (m, 2H), 4.70-4.18 (m, 3H), 4.03-3.80 (m, 7H), 3.43-2.87 (m, 3H), 1.51-1.41 (m, 9H), 1.24-1.08 (m, 3H). | D |
| 322 | 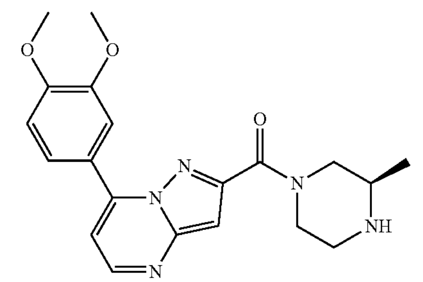 [SMILES: COc1ccc(-c2ccnc3cc(C(=O)N4CCN[C@H](C)C4)nn23)cc1OC] | ¹H NMR (400 MHz, CDCl₃) δ 8.60-8.52 (m, 1H), 7.76-7.65 (m, 2H), 7.12-7.07 (m, 1H), 7.06-6.95 (m, 2H), 4.71-4.43 (m, 2H), 4.01-3.87 (m, 6H), 3.26-3.07 (m, 1H), 3.01-2.45 (m, 4H), 1.18-0.95 (m, 3H). | D |
| 323 | 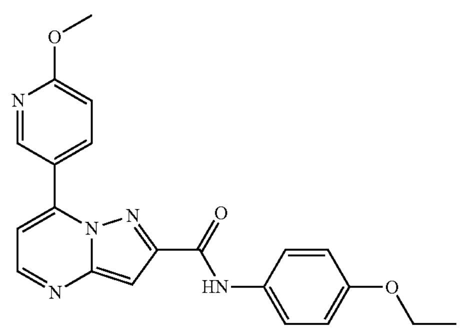 [SMILES: CCOc1ccc(NC(=O)c2cc3nccc(-c4ccc(OC)nc4)n3n2)cc1] | ¹H NMR (400 MHz, DMSO-d₆) δ 10.16 (s, 1H), 9.18 (d, J = 2.3 Hz, 1H), 8.74-8.63 (m, 2H), 7.71-7.64 (m, 2H), 7.50 (d, J = 4.4 Hz, 1H), 7.28 (s, 1H), 7.09 (d, J = 8.8 Hz, 1H), 6.97-6.90 (m, 2H), 4.06-3.98 (m, 5H), 1.33 (t, J = 7.0 Hz, 3H). | C |
| 324 | 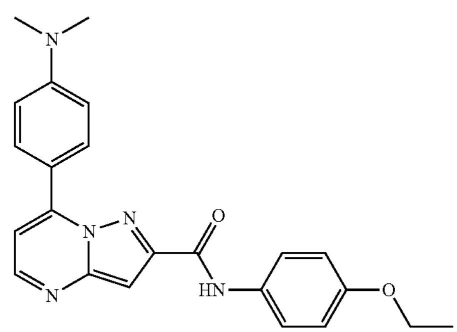 [SMILES: CCOc1ccc(NC(=O)c2cc3nccc(-c4ccc(N(C)C)cc4)n3n2)cc1] | ¹H NMR (400 MHz, DMSO-d₆) δ 10.10 (s, 1H), 8.59 (d, J = 4.6 Hz, 1H), 8.37 (d, J = 9.1 Hz, 2H), 7.74-7.67 (m, 2H), 7.37 (d, J = 4.6 Hz, 1H), 7.19 (s, 1H), 6.98-6.86 (m, 4H), 4.02 (q, J = 7.0 Hz, 2H), 3.07 (s, 6H), 1.33 (t, J = 7.0 Hz, 3H). | C |

TABLE 3A-continued

Compound Structures, Characterization Data and Synthetic Method

| Cmpd | Structure | Characterization Data | General Method (Ex. 2) |
|---|---|---|---|
| 325 | 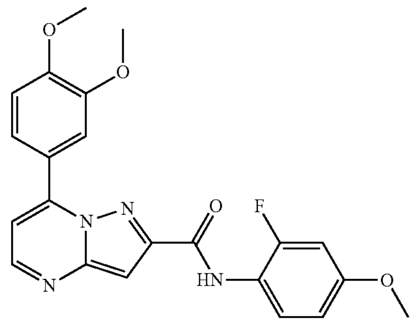 [SMILES: COc1ccc(NC(=O)c2cc3nccc(-c4ccc(OC)c(OC)c4)n3n2)c(F)c1] | $^1$H NMR (400 MHz, DMSO-d$_6$) δ 9.83 (s, 1H), 8.69 (d, J = 4.5 Hz, 1H), 8.10-7.87 (m, 2H), 7.67 (t, J = 9.0 Hz, 1H), 7.48 (d, J = 4.5 Hz, 1H), 7.27 (s, 1H), 7.20 (d, J = 8.6 Hz, 1H), 6.98 (dd, J = 12.4, 2.7 Hz, 1H), 6.90-6.80 (m, 1H), 3.95-3.86 (m, 6H), 3.79 (s, 3H). | C |
| 326 | 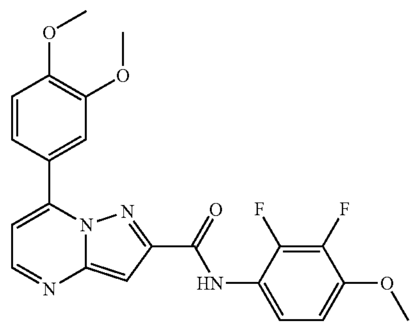 [SMILES: COc1ccc(-c2ccnc3cc(C(=O)Nc4ccc(OC)c(F)c4F)nn23)cc1OC] | $^1$H NMR (400 MHz, DMSO-d$_6$) δ 10.05 (s, 1H), 8.70 (d, J = 4.4 Hz, 1H), 7.98 (d, J = 8.4 Hz, 1H), 7.90 (s, 1H), 7.58-7.38 (m, 2H), 7.28 (s, 1H), 7.20 (d, J = 8.6 Hz, 1H), 7.07 (t, J = 8.4 Hz, 1H), 3.94-3.85 (m, 9H). | C |
| 327 | 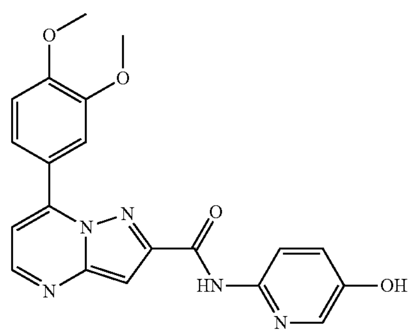 [SMILES: COc1ccc(-c2ccnc3cc(C(=O)Nc4ccc(O)cn4)nn23)cc1OC] | $^1$H NMR (400 MHz, DMSO-d$_6$) δ 9.94-9.67 (m, 2H), 8.70 (d, J = 4.5 Hz, 1H), 8.07 (d, J = 8.9 Hz, 1H), 7.99-7.85 (m, 3H), 7.48 (d, J = 4.5 Hz, 1H), 7.38-7.27 (m, 2H), 7.23 (d, J = 8.6 Hz, 1H), 3.91 (s, 6H). | B |
| 328 | 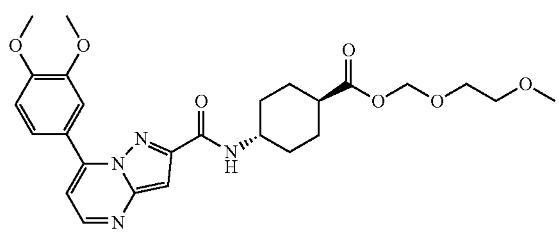 [SMILES: COCCOCOC(=O)[C@H]1CC[C@H](NC(=O)c2cc3nccc(-c4ccc(OC)c(OC)c4)n3n2)CC1] | $^1$H NMR (400 MHz, DMSO-d$_6$) δ 8.64 (d, J = 4.0 Hz, 1H), 8.13 (d, J = 8.0 Hz, 1H), 7.96 (s, 1H), 7.90 (d, J = 8.1 Hz, 1H), 7.43 (d, J = 4.0 Hz, 1H), 7.20 (d, J = 8.4 Hz, 1H), 7.13 (s, 1H), 5.25 (s, 2H), 3.89 (s, 6H), 3.85-3.75 (m, 1H), 3.75-3.65 (m, 2H), 3.53-3.43 (m, 2H), 3.25 (s, 3H), 2.39-2.20 (m, 1H), 2.07-1.82 (m, 4H), 1.58-1.37 (m, 4H). | A |
| 329 | 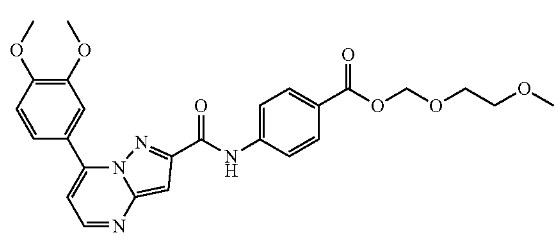 [SMILES: COCCOCOC(=O)c1ccc(NC(=O)c2cc3nccc(-c4ccc(OC)c(OC)c4)n3n2)cc1] | $^1$H NMR (400 MHz, DMSO-d$_6$) δ 10.63 (s, 1H), 8.71 (d, J = 4.5 Hz, 1H), 8.10-7.98 (m, 5H), 7.96 (d, J = 2.1 Hz, 1H), 7.51 (d, J = 4.5 Hz, 1H), 7.35 (s, 1H), 7.22 (d, J = 8.6 Hz, 1H), 5.50 (s, 2H), 3.97-3.86 (m, 6H), 3.86-3.78 (m, 2H), 3.55-3.45 (m, 2H), 3.24 (s, 3H). | C |

TABLE 3A-continued

Compound Structures, Characterization Data and Synthetic Method

| Cmpd | Structure | Characterization Data | General Method (Ex. 2) |
|---|---|---|---|
| 330 | 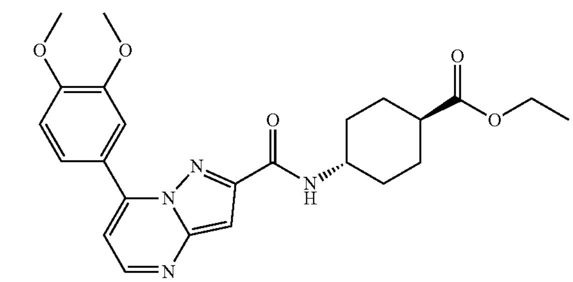 [SMILES: CCOC(=O)[C@H]1CC[C@H](NC(=O)c2cc3nccc(-c4ccc(OC)c(OC)c4)n3n2)CC1] | $^1$H NMR (400 MHz, DMSO-d$_6$) δ 8.64 (d, J = 4.5 Hz, 1H), 8.12 (d, J = 8.2 Hz, 1H), 7.96 (d, J = 2.0 Hz, 1H), 7.90 (dd, J = 8.5, 2.0 Hz, 1H), 7.42 (d, J = 4.5 Hz, 1H), 7.20 (d, J = 8.6 Hz, 1H), 7.13 (s, 1H), 4.06 (q, J = 7.1 Hz, 2H), 3.95-3.85 (m, 6H), 3.84-3.73 (m, 1H), 2.31-2.18 (m, 1H), 2.02-1.81 (m, 4H), 1.53-1.36 (m, 4H), 1.19 (t, J = 7.1 Hz, 3H). | A |
| 331 | 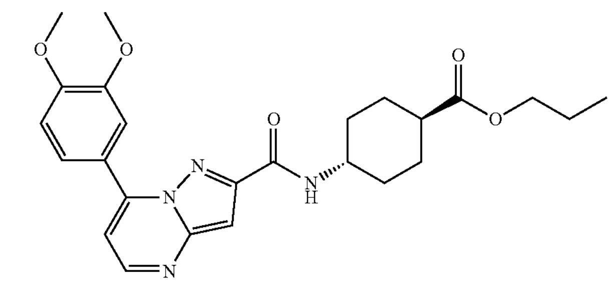 [SMILES: CCCOC(=O)[C@H]1CC[C@H](NC(=O)c2cc3nccc(-c4ccc(OC)c(OC)c4)n3n2)CC1] | $^1$H NMR (400 MHz, DMSO-d$_6$) δ 8.64 (d, J = 4.5 Hz, 1H), 8.13 (d, J = 8.2 Hz, 1H), 7.96 (d, J = 2.0 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 3.98 (t, J = 6.6 Hz, 2H), 3.94-3.86 (m, 6H), 3.85-3.70 (m, 1H), 2.35-2.20 (m, 1H), 2.06-1.81 (m, 4H), 1.68-1.52 (m, 2H), 1.52-1.35 (m, 4H), 0.89 (t, J = 7.4 Hz, 3H). | A |
| 332 | 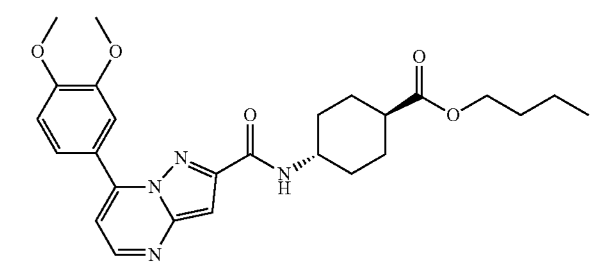 [SMILES: CCCCOC(=O)[C@H]1CC[C@H](NC(=O)c2cc3nccc(-c4ccc(OC)c(OC)c4)n3n2)CC1] | $^1$H NMR (400 MHz, DMSO-d$_6$) δ 8.64 (d, J = 4.5 Hz, 1H), 8.11 (d, J = 8.3 Hz, 1H), 7.96 (d, J = 2.0 Hz, 1H), 7.89 (dd, J = 8.5, 2.0 Hz, 1H), 7.42 (d, J = 4.5 Hz, 1H), 7.20 (d, J = 8.6 Hz, 1H), 7.13 (s, 1H), 4.02 (t, J = 6.5 Hz, 2H), 3.95-3.84 (m, 6H), 3.83-3.72 (m, 1H), 2.33-2.19 (m, 1H), 2.05-1.80 (m, 4H), 1.63-1.51 (m, 2H), 1.51-1.38 (m, 4H), 1.38-1.27 (m, 2H), 0.90 (t, J = 7.4 Hz, 3H). | A |
| 333 | 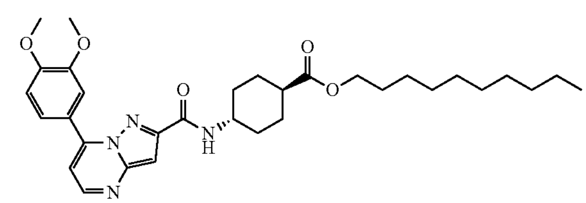 [SMILES: CCCCCCCCCCOC(=O)[C@H]1CC[C@H](NC(=O)c2cc3nccc(-c4ccc(OC)c(OC)c4)n3n2)CC1] | $^1$H NMR (400 MHz, DMSO-d$_6$) δ 8.64 (d, J = 4.5 Hz, 1H), 8.12 (d, J = 8.2 Hz, 1H), 7.96 (d, J = 2.0 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 4.01 (t, J = 6.5 Hz, 2H), 3.94-3.85 (m, 6H), 3.83-3.72 (m, 1H), 2.33-2.20 (m, 1H), 2.03-1.81 (m, 4H), 1.62-1.51 (m, 2H), 1.51-1.36 (m, 4H), 1.33-1.18 (m, 14H), 0.86 (t, J = 6.8 Hz, 3H). | A |
| 335 | 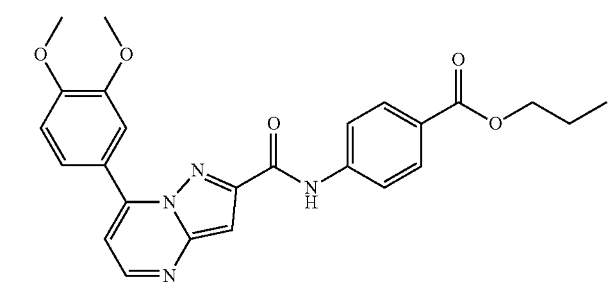 [SMILES: CCCOC(=O)c1ccc(NC(=O)c2cc3nccc(-c4ccc(OC)c(OC)c4)n3n2)cc1] | $^1$H NMR (400 MHz, DMSO-d$_6$) δ 10.59 (s, 1H), 8.70 (d, J = 4.5 Hz, 1H), 8.07-7.91 (m, 6H), 7.50 (d, J = 4.5 Hz, 1H), 7.34 (s, 1H), 7.22 (d, J = 8.6 Hz, 1H), 4.22 (t, J = 6.6 Hz, 2H), 3.94-3.85 (m, 6H), 1.79-1.67 (m, 2H), 0.98 (t, J = 7.4 Hz, 3H). | C |

TABLE 3A-continued

Compound Structures, Characterization Data and Synthetic Method

| Cmpd | Structure | Characterization Data | General Method (Ex. 2) |
|---|---|---|---|
| 336 | 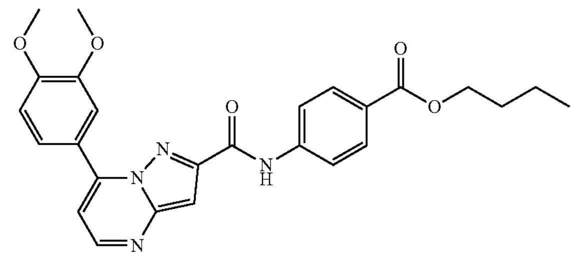 [SMILES: CCCCOC(=O)c1ccc(NC(=O)c2cc3nccc(-c4ccc(OC)c(OC)c4)n3n2)cc1] | $^1$H NMR (400 MHz, DMSO-d$_6$) δ 10.61 (s, 1H), 8.71 (d, J = 4.8 Hz, 1H), 8.08-7.91 (m, 6H), 7.51 (d, J = 4.5 Hz, 1H), 7.34 (s, 1H), 7.22 (d, J = 8.6 Hz, 1H), 4.27 (t, J = 6.5 Hz, 2H), 3.98-3.85 (m, 6H), 1.78-1.63 (m, 2H), 1.51-1.37 (m, 2H), 0.95 (t, J = 7.4 Hz, 3H). | C |
| 337 | 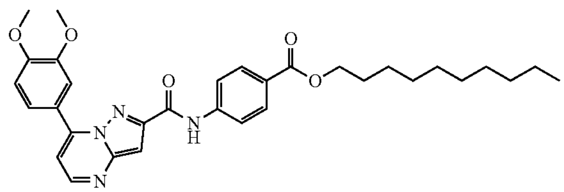 [SMILES: CCCCCCCCCCOC(=O)c1ccc(NC(=O)c2cc3nccc(-c4ccc(OC)c(OC)c4)n3n2)cc1] | $^1$H NMR (400 MHz, DMSO-d$_6$) δ 10.61 (s, 1H), 8.71 (d, J = 4.5 Hz, 1H), 8.09-7.91 (m, 6H), 7.51 (d, J = 4.5 Hz, 1H), 7.35 (s, 1H), 7.22 (d, J = 8.6 Hz, 1H), 4.26 (t, J = 6.5 Hz, 2H), 3.97-3.80 (m, 6H), 1.77-1.65 (m, 2H), 1.49-1.13 (m, 14H), 0.94-0.79 (m, 3H). | C |
| 338 | 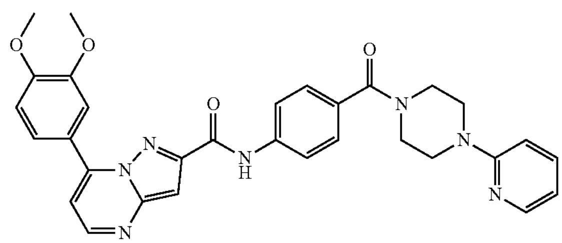 [SMILES: COc1ccc(-c2ccnc3cc(C(=O)Nc4ccc(C(=O)N5CCN(c6ccccn6)CC5)cc4)nn23)cc1OC] | $^1$H NMR (400 MHz, DMSO-d$_6$) δ 10.47 (s, 1H), 8.70 (d, J = 4.5 Hz, 1H), 8.13 (dd, J = 4.8, 1.4 Hz, 1H), 8.02 (dd, J = 8.5, 2.1 Hz, 1H), 7.99-7.88 (m, 3H), 7.61-7.33 (m, 1H), 7.53-7.45 (m, 3H), 7.33 (s, 1H), 7.22 (d, J = 7.6 Hz, 1H), 6.86 (d, J = 8.6 Hz, 1H), 6.71-6.65 (m, 1H), 3.96-3.85 (m, 6H), 3.81-3.43 (m, 8H). | C |
| 339 | 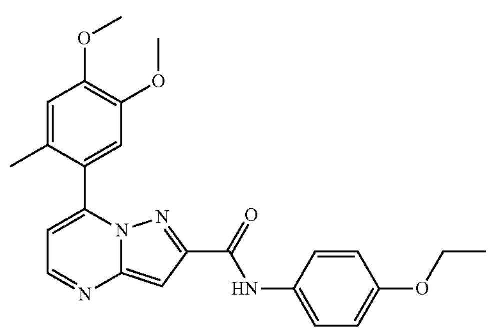 [SMILES: CCOc1ccc(NC(=O)c2cc3nccc(-c4cc(OC)c(OC)cc4C)n3n2)cc1] | $^1$H NMR (400 MHz, DMSO-d$_6$) δ 10.01 (s, 1H), 8.70 (d, J = 4.2 Hz, 1H), 7.68-7.58 (m, 2H), 7.32 (s, 1H), 7.20-7.12 (m, 2H), 7.04 (s, 1H), 6.94-6.86 (m, 2H), 4.00 (q, J = 7.0 Hz, 2H), 3.86 (s, 3H), 3.76 (s, 3H), 2.08 (s, 3H), 1.32 (t, J = 7.0 Hz, 3H). | C |
| 340 | 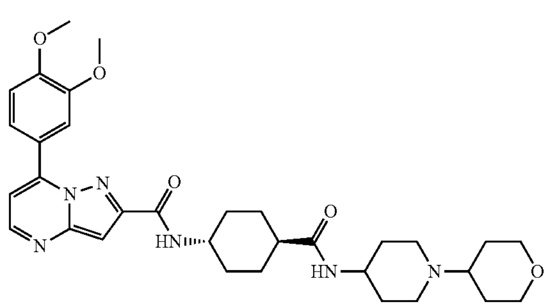 [SMILES: COc1ccc(-c2ccnc3cc(C(=O)N[C@H]4CC[C@H](C(=O)NC5CCN(C6CCOCC6)CC5)CC4)nn23)cc1OC] | $^1$H NMR (400 MHz, DMSO-d$_6$) δ 8.64 (d, J = 4.5 Hz, 1H), 8.15 (d, J = 8.3 Hz, 1H), 7.99 (d, J = 1.7 Hz, 1H), 7.88 (dd, J = 8.5, 1.6 Hz, 1H), 7.75-7.62 (m, 1H), 7.43 (d, J = 4.5 Hz, 1H), 7.20 (d, J = 8.4 Hz, 1H), 7.13 (d, J = 0.5 Hz, 1H), 3.96-3.83 (m, 8H), 3.82-3.71 (m, 1H), 3.59-3.48 (m, 1H), 3.31-3.20 (m, 3H), 3.03-2.81 (m, 2H), 2.43-2.17 (m, 2H), 2.13-1.98 (m, 1H), 1.95-1.83 (m, 2H), 1.81-1.62 (m, 6H), 1.57-1.28 (m, 8H). | A |

TABLE 3A-continued

Compound Structures, Characterization Data and Synthetic Method

| Cmpd | Structure | Characterization Data | General Method (Ex. 2) |
|---|---|---|---|
| 341 | 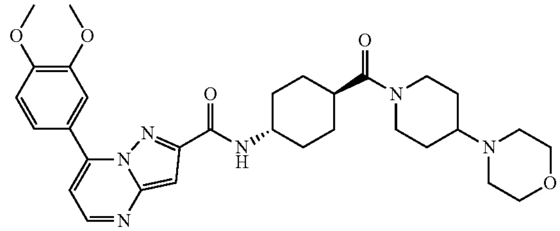 [SMILES: COc1ccc(-c2ccnc3cc(C(=O)N[C@H]4CC[C@H](C(=O)N5CCC(N6CCOCC6)CC5)CC4)nn23)cc1OC] | $^1$H NMR (400 MHz, DMSO-d$_6$) δ 8.64 (d, J = 4.5 Hz, 1H), 8.09 (d, J = 8.1 Hz, 1H), 7.96 (d, J = 2.0 Hz, 1H), 7.89 (dd, J = 8.5, 2.1 Hz, 1H), 7.43 (d, J = 4.5 Hz, 1H), 7.20 (d, J = 8.6 Hz, 1H), 7.13 (s, 1H), 4.44-4.32 (m, 1H), 3.98-3.91 (m, 1H), 3.91-3.84 (m, 6H), 3.83-3.71 (m, 1H), 3.56 (t, J = 4.2 Hz, 4H), 3.06-2.95 (m, 1H), 2.48-2.41 (m, 4H), 2.41-2.30 (m, 1H), 1.95-1.66 (m, 6H), 1.54-1.39 (m, 4H), 1.36-1.07 (m, 4H). | A |
| 342 | 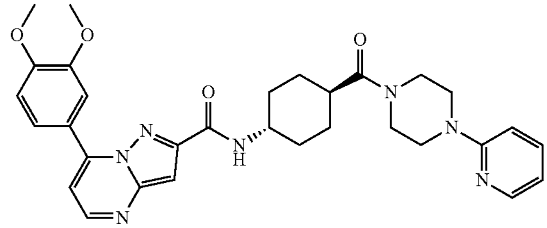 [SMILES: COc1ccc(-c2ccnc3cc(C(=O)N[C@H]4CC[C@H](C(=O)N5CCN(c6ccccn6)CC5)CC4)nn23)cc1OC] | $^1$H NMR (400 MHz, DMSO-d$_6$) δ 8.65 (d, J = 4.5 Hz, 1H), 8.19-8.08 (m, 2H), 7.97 (d, J = 2.1 Hz, 1H), 7.90 (dd, J = 8.5, 2.1 Hz, 1H), 7.61-7.51 (m, 1H), 7.43 (d, J = 4.5 Hz, 1H), 7.20 (d, J = 8.6 Hz, 1H), 7.14 (s, 1H), 6.85 (d, J = 8.6 Hz, 1H), 6.71-6.63 (m, 1H), 3.96-3.84 (m, 6H), 3.85-3.73 (m, 1H), 3.66-3.41 (m, 8H), 2.66-2.55 (m, 1H), 1.98-1.84 (m, 2H), 1.83-1.69 (m, 2H), 1.59-1.38 (m, 4H). | A |
| 343 | 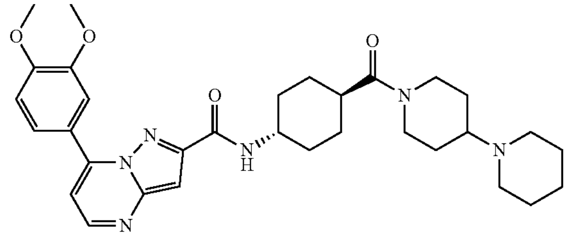 [SMILES: COc1ccc(-c2ccnc3cc(C(=O)N[C@H]4CC[C@H](C(=O)N5CCC(N6CCCCC6)CC5)CC4)nn23)cc1OC] | $^1$H NMR (400 MeOH-d$_4$) δ 8.61 (d, J = 4.5 Hz, 1H), 7.88 (d, J = 2.1 Hz, 1H), 7.80 (dd, J = 8.5, 2.1 Hz, 1H), 7.28 (d, J = 4.5 Hz, 1H), 7.24-7.15 (m, 2H), 4.70-4.60 (m, 1H), 4.22-4.09 (m, 1H), 4.00-3.95 (m, 6H), 3.18-3.06 (m, 1H), 2.82-2.52 (m, 7H), 2.16-1.93 (m, 4H), 1.91-1.79 (m, 2H), 1.75-1.60 (m, 6H), 1.59-1.35 (m, 7H). | A |
| 344 | 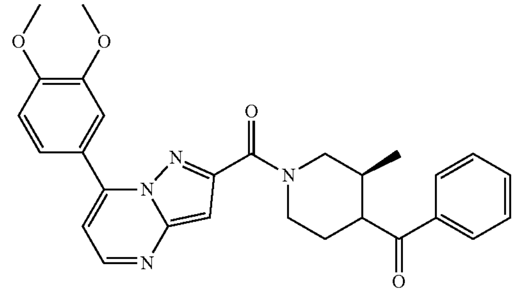 [SMILES: COc1ccc(-c2ccnc3cc(C(=O)N4CCC(C(=O)c5ccccc5)[C@H](C)C4)nn23)cc1OC] | $^1$H NMR (400 MHz, CDCl$_3$) δ 8.57 (s, 1H), 7.75-7.54 (m, 2H), 7.49-7.33 (m, 5H), 7.17 (d, J = 7.4 Hz, 1H), 7.07-6.94 (m, 2H), 5.04-4.44 (m, 3H), 4.07-3.85 (m, 7H), 3.51-2.85 (m, 3H), 1.37-1.22 (m, 3H). | D |
| 345 | 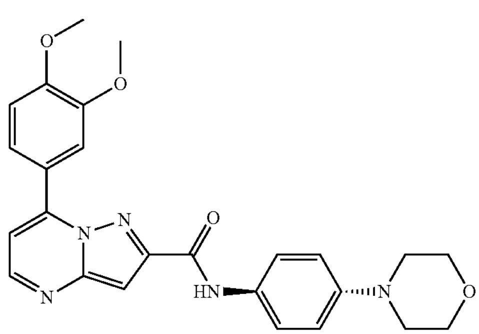 | $^1$H NMR (400 MHz, MEOD-d$_4$) δ 8.59 (d, J = 4.5 Hz, 1H), 7.85 (d, J = 2.1 Hz, 1H), 7.80 (dd, J = 8.5, 2.1 Hz, 1H), 7.27 (d, J = 4.5 Hz, 1H), 7.21-7.14 (m, 2H), 3.98-3.85 (m, 7H), 3.78-3.67 (m, 4H), 2.77-2.63 (m, 4H), 2.51-2.36 (m, 1H), 2.18-2.01 (m, 4H), 1.55-1.38 (m, 4H). | A |

TABLE 3A-continued

Compound Structures, Characterization Data and Synthetic Method

| Cmpd | Structure | Characterization Data | General Method (Ex. 2) |
|---|---|---|---|
| 346 | 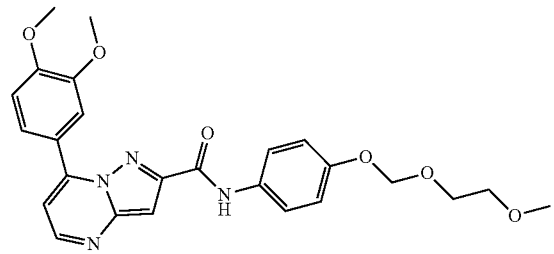 [SMILES: COCCOCOc1ccc(NC(=O)c2cc3nccc(-c4ccc(OC)c(OC)c4)n3n2)cc1] | ¹H NMR (400 MHz, DMSO-d₆) δ 10.13 (s, 1H), 8.64 (d, J = 4.5 Hz, 1H), 7.97 (dd, J = 8.5, 2.1 Hz, 1H), 7.89 (d, J = 2.1 Hz, 1H), 7.70-7.63 (m, 2H), 7.43 (d, J = 4.5 Hz, 1H), 7.23 (s, 1H), 7.16 (d, J = 8.6 Hz, 1H), 7.03-6.96 (m, 2H), 5.19 (s, 2H), 3.90-3.81 (m, 6H), 3.73-3.63 (m, 2H), 3.45-3.39 (m, 2H), 3.18 (s, 3H). | C |
| 347 | 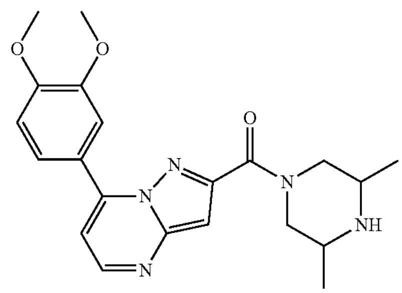 [SMILES: COc1ccc(-c2ccnc3cc(C(=O)N4CC(C)NC(C)C4)nn23)cc1OC] | ¹H NMR (400 MHz, CDCl₃) δ 8.56 (d, J = 4.4 Hz, 1H), 7.72 (dd, J = 8.4, 2.1 Hz, 1H), 7.68 (d, J = 2.1 Hz, 1H), 7.09 (s, 1H), 7.03 (d, J = 8.5 Hz, 1H), 6.99 (d, J = 4.4 Hz, 1H), 4.74-4.65 (m, 1H), 4.54-4.46 (m, 1H), 4.00-3.94 (m, 6H), 3.00-2.85 (m, 2H), 2.77-2.67 (m, 1H), 2.46-2.37 (m, 1H), 1.15 (d, J = 6.3 Hz, 3H), 0.98 (d, J = 6.3 Hz, 3H). | D |
| 348 | 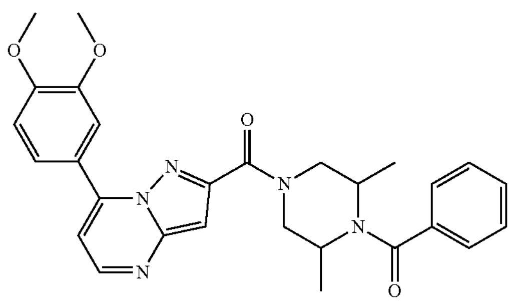 [SMILES: COc1ccc(-c2ccnc3cc(C(=O)N4CC(C)N(C(=O)c5ccccc5)C(C)C4)nn23)cc1OC] | ¹H NMR (400 MHz, CDCl₃) δ 8.57 (d, J = 4.4 Hz, 1H), 7.66 (dd, J = 8.4, 1.6 Hz, 1H), 7.56 (d, J = 2.1 Hz, 1H), 7.45-7.39 (m, 3H), 7.38-7.32 (m, 2H), 7.21 (s, 1H), 7.06-6.94 (m, 2H), 4.86-4.22 (4H), 4.02-3.90 (m, 6H), 3.45-3.30 (m, 1H), 3.09-2.96 (m, 1H), 1.44-1.33 (m, 3H), 1.32-1.24 (m, 3H). | D |
| 349 | 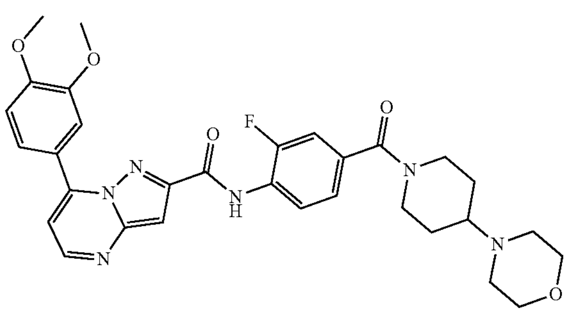 [SMILES: COc1ccc(-c2ccnc3cc(C(=O)Nc4ccc(C(=O)N5CCC(N6CCOCC6)CC5)cc4F)nn23)cc1OC] | ¹H NMR (400 MHz, CDCl₃) δ 9.31 (d, J = 3.1 Hz, 1H), 8.65-8.60 (m, 2H), 7.85 (d, J = 2.1 Hz, 1H), 7.63 (dd, J = 8.4, 2.1 Hz, 1H), 7.43 (s, 1H), 7.28-7.22 (m, 2H), 7.10 (dd, J = 6.4, 2.1 Hz, 2H), 4.80-4.50 (m, 1H), 4.06-3.96 (m, 6H), 3.95-3.79 (m, 1H), 3.78-3.66 (m, 4H), 3.16-2.70 (m, 2H), 2.64-2.52 (m, 4H), 2.51-2.38 (m, 1H), 2.06-1.74 (m, 2H), 1.56-1.35 (m, 2H). | B |
| 350 | 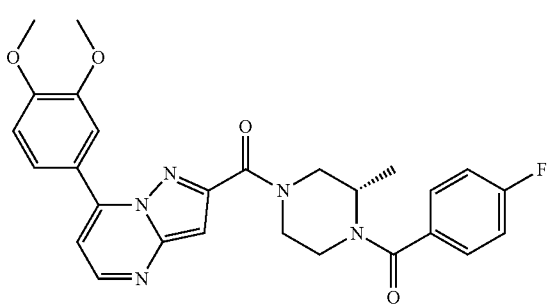 [SMILES: COc1ccc(-c2ccnc3cc(C(=O)N4CCN(C(=O)c5ccc(F)cc5)[C@@H](C)C4)nn23)cc1OC] | ¹H NMR (400 MHz, DMSO-d6) δ 8.67 (dd, J = 4.3, 1.8 Hz, 1H), 7.83-7.70 (m, 2H), 7.53-7.46 (m, 2H), 7.38 (dd, J = 9.1, 4.3 Hz, 1H), 7.34-7.26 (m, 2H), 7.21-7.14 (m, 1H), 7.05 (d, J = 23.7 Hz, 1H), 4.77-4.24 (m, 3H), 3.87 (s, 3H), 3.82 (s, 3H), 3.56-3.47 (m, 1H), 3.27-2.95 (m, 3H), 1.23-1.06 (m, 3H). | D |

TABLE 3A-continued

Compound Structures, Characterization Data and Synthetic Method

| Cmpd | Structure | Characterization Data | General Method (Ex. 2) |
|---|---|---|---|
| 351 | 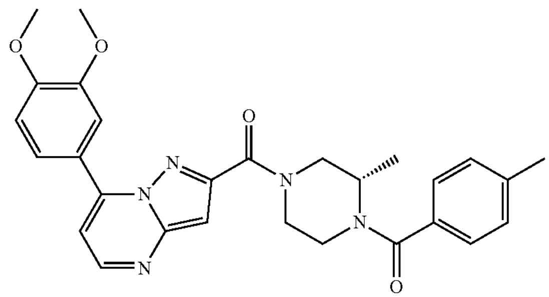 [SMILES: COc1ccc(-c2ccnc3cc(C(=O)N4CCN(C(=O)c5ccc(C)cc5)[C@@H](C)C4)nn23)cc1OC] | ¹H NMR (400 MHz, DMSO-d6) δ 8.66 (dd, J = 4.2, 2.3 Hz, 1H), 7.86-7.69 (m, 2H), 7.38 (dd, J = 9.6, 4.3 Hz, 1H), 7.34-7.24 (m, 4H), 7.22-7.13 (m, 1H), 7.06 (d, J = 24.2 Hz, 1H), 4.62-4.25 (m, 3H), 3.94-3.72 (m, 6H), 3.51-3.47 (m, 1H), 3.29-2.93 (m, 3H), 2.35 (s, 3H), 1.27-1.01 (m, 3H). | D |
| 352 | 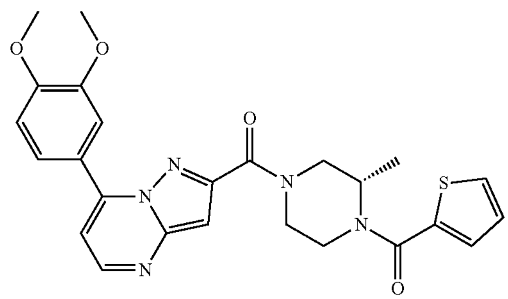 | ¹H NMR (400 MHz, DMSO-d6) δ 8.70-8.63 (m, 1H), 7.85-7.72 (m, 3H), 7.46-7.35 (m, 2H), 7.23-7.12 (m, 2H), 7.07 (d, J = 23.6 Hz, 1H), 4.75-4.03 (m, 5H), 3.94-3.80 (m, 6H), 3.53 (dd, J = 13.5, 3.4 Hz, 1H), 3.20-3.00 (m, 1H), 1.31-1.12 (m, 3H). | D |
| 353 | 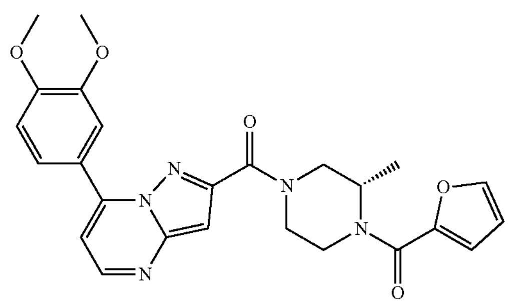 [SMILES: COc1ccc(-c2ccnc3cc(C(=O)N4CCN(C(=O)c5ccco5)[C@@H](C)C4)nn23)cc1OC] | ¹H NMR (400 MHz, DMSO-d6) δ 8.67 (dd, J = 4.3, 1.6 Hz, 1H), 7.89-7.70 (m, 3H), 7.39 (dd, J = 8.8, 4.4 Hz, 1H), 7.20 (dd, J = 8.4, 3.9 Hz, 1H), 7.11-7.01 (m, 2H), 6.67-6.61 (m, 1H), 4.78-4.10 (m, 5H), 3.90-3.81 (m, 6H), 3.57-3.48 (m, 1H), 3.20-2.99 (m, 1H), 1.30-1.12 (m, 3H). | D |
| 354 | 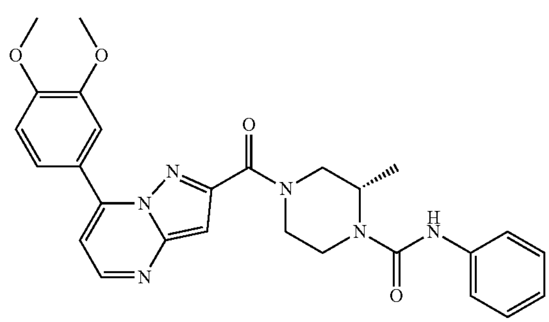 [SMILES: COc1ccc(-c2ccnc3cc(C(=O)N4CCN(C(=O)Nc5ccccc5)[C@@H](C)C4)nn23)cc1OC] | ¹H NMR (400 MHz, DMSO-d6) δ 8.71-8.63 (m, 1H), 8.55 (d, J = 3.8 Hz, 1H), 7.89-7.70 (m, 2H), 7.52-7.35 (m, 3H), 7.30-7.16 (m, 3H), 7.14-7.02 (m, 1H), 6.94 (t, J = 7.3 Hz, 1H), 4.59-4.27 (m, 3H), 4.05-3.97 (m, 1H), 3.95-3.82 (m, 6H), 3.52-3.40 (m, 1H), 3.32-2.93 (m, 2H), 1.20-1.02 (m, 3H). | D |

TABLE 3A-continued

Compound Structures, Characterization Data and Synthetic Method

| Cmpd | Structure | Characterization Data | General Method (Ex. 2) |
|---|---|---|---|
| 355 | 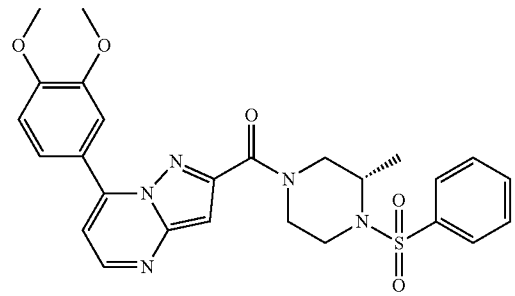 [SMILES: COc1ccc(-c2ccnc3cc(C(=O)N4CCN(S(=O)(=O)c5ccccc5)[C@@H](C)C4)nn23)cc1OC] | ¹H NMR (400 MHz, DMSO-d6) δ 8.65 (t, J = 4.3 Hz, 1H), 7.89-7.73 (m, 4H), 7.73-7.58 (m, 3H), 7.38 (dd, J = 10.9, 4.4 Hz, 1H), 7.19 (dd, J = 12.3, 8.6 Hz, 1H), 7.01 (d, J = 26.4 Hz, 1H), 4.46-3.97 (m, 3H), 3.95-3.77 (m, 6H), 3.77-3.58 (m, 1H), 3.31-3.07 (m, 2H), 2.99-2.77 (m, 1H), 0.99-0.82 (m, 3H). | D |
| 356 | 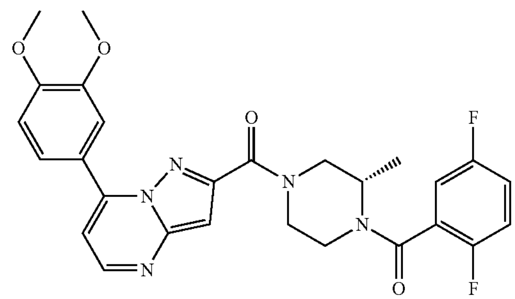 [SMILES: COc1ccc(-c2ccnc3cc(C(=O)N4CCN(C(=O)c5cc(F)ccc5F)[C@@H](C)C4)nn23)cc1OC] | ¹H NMR (400 MHz, DMSO-d6) δ 8.73-8.62 (m, 1H), 7.90-7.66 (m, 2H), 7.49-7.28 (m, 4H), 7.26-7.00 (m, 2H), 4.94-4.19 (m, 3H), 3.97-3.71 (m, 6H), 3.71-3.48 (m, 1H), 3.30-2.90 (m, 3H), 1.32-1.02 (m, 3H). | D |
| 357 | 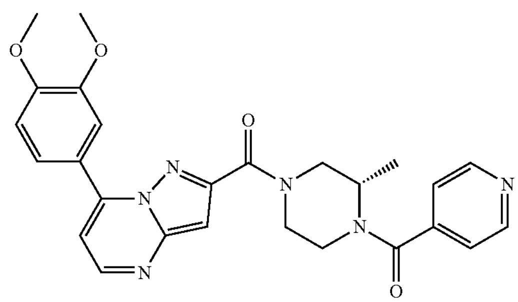 [SMILES: COc1ccc(-c2ccnc3cc(C(=O)N4CCN(C(=O)c5ccncc5)[C@@H](C)C4)nn23)cc1OC] | ¹H NMR (400 MHz, DMSO-d6) δ 8.76-8.59 (m, 3H), 7.90-7.64 (m, 2H), 7.50-7.03 (m, 3H), 7.26-6.98 (m, 2H), 4.93-4.15 (m, 4H), 3.95-3.68 (m, 6H), 3.65-3.46 (m, 1H), 3.19-2.91 (m, 2H), 1.33-1.00 (m, 3H). | D |
| 358 | 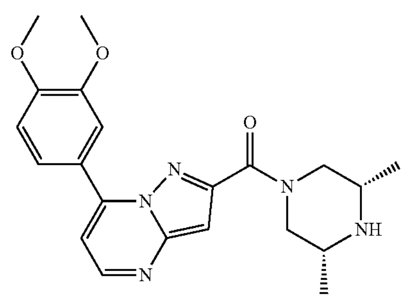 [SMILES: COc1ccc(-c2ccnc3cc(C(=O)N4C[C@@H](C)N[C@@H](C)C4)nn23)cc1OC] | ¹H NMR (400 MHz, DMSO-d6) δ 8.65 (d, J = 4.4 Hz, 1H), 7.84-7.74 (m, 2H), 7.37 (d, J = 4.5 Hz, 1H), 7.17 (d, J = 8.5 Hz, 1H), 7.01 (s, 1H), 4.54-4.31 (m, 2H), 3.91-3.82 (m, 6H), 2.89-2.61 (m, 3H), 2.36 (t, J = 12.2 Hz, 1H), 1.06 (d, J = 6.1 Hz, 3H), 0.91 (d, J = 6.0 Hz, 3H). | D |
| 359 | 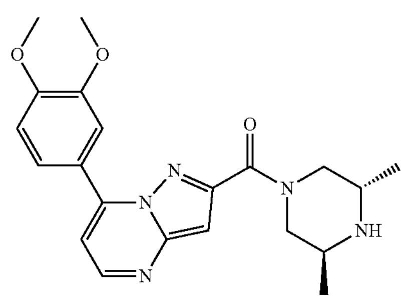 [SMILES: COc1ccc(-c2ccnc3cc(C(=O)N4C[C@H](C)N[C@@H](C)C4)nn23)cc1OC] | ¹H NMR (400 MHz, DMSO-d6) δ 8.65 (d, J = 4.5 Hz, 1H), 7.84-7.73 (m, 2H), 7.37 (d, J = 4.5 Hz, 1H), 7.18 (d, J = 8.5 Hz, 1H), 7.00 (s, 1H), 3.97-3.65 (m, 8H), 3.53-3.42 (m, 2H), 3.22-3.05 (m, 2H), 1.06 (d, J = 6.5 Hz, 3H), 0.94 (d, J = 6.5 Hz, 3H). | D |

TABLE 3A-continued

Compound Structures, Characterization Data and Synthetic Method

| Cmpd | Structure | Characterization Data | General Method (Ex. 2) |
|---|---|---|---|
| 360 | 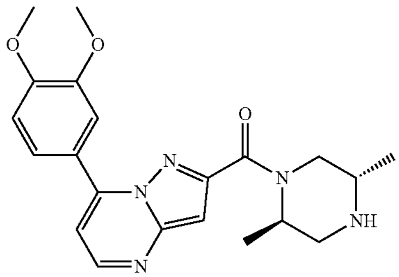 [SMILES: COc1ccc(-c2ccnc3cc(C(=O)N4C[C@H](C)NC[C@H]4C)nn23)cc1OC] | $^1$H NMR (400 MHz, DMSO-d6) δ 8.65 (d, J = 4.4 Hz, 1H), 7.91-7.70 (m, 2H), 7.37 (d, J = 4.5 Hz, 1H), 7.19 (d, J = 8.5 Hz, 1H), 6.99 (s, 1H), 4.73-3.97 (m, 2H), 3.94-3.75 (m, 6H), 3.29-3.01 (m, 4H), 1.30 (d, J = 6.9 Hz, 3H), 1.09 (d, J = 6.4 Hz, 3H). | D |
| 361 | 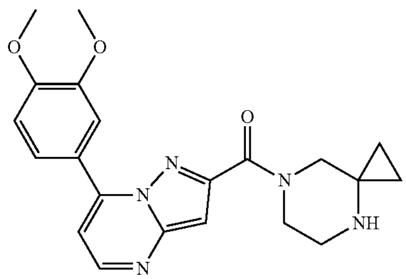 [SMILES: COc1ccc(-c2ccnc3cc(C(=O)N4CCNC5(CC5)C4)nn23)cc1OC] | $^1$H NMR (400 MHz, DMSO-d6) δ 8.65 (d, J = 4.4 Hz, 1H), 7.85-7.64 (m, 2H), 7.36 (dd, J = 18.4, 4.4 Hz, 1H), 7.19 (dd, J = 12.2, 8.6 Hz, 1H), 6.99 (d, J = 18.0 Hz, 1H), 3.92-3.82 (m, 6H), 3.80-3.50 (m, 4H), 2.84-2.73 (m, 2H), 0.56-0.45 (m, 2H), 0.42-0.34 (m, 2H). | D |
| 362 | 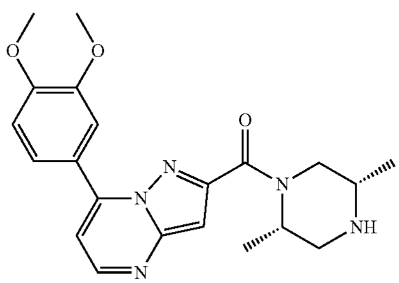 [SMILES: COc1ccc(-c2ccnc3cc(C(=O)N4C[C@H](C)NC[C@@H]4C)nn23)cc1OC] | $^1$H NMR (400 MHz, DMSO-d6) δ 8.64 (dd, J = 6.3, 4.5Hz, 1H), 7.90-7.70 (m, 2H), 7.37 (t, J = 4.6 Hz, 1H), 7.18 (dd, J = 8.4, 5.9 Hz, 1H), 6.99 (s, 1H), 4.72-4.14 (m, 2H), 3.92-3.82 (m, 6H), 2.93-2.53 (m, 4H), 1.37-1.20 (m, 3H), 1.13-0.88 (m, 3H). | D |
| 363 | 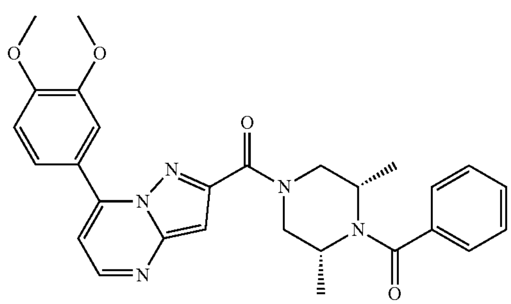 [SMILES: COc1ccc(-c2ccnc3cc(C(=O)N4C[C@@H](C)N(C(=O)c5ccccc5)[C@@H](C)C4)nn23)cc1OC] | $^1$H NMR (400 MHz, DMSO-d6) δ 8.67 (d, J = 4.4 Hz, 1H), 7.83-7.74 (m, 1H), 7.71 (s, 1H), 7.52-7.42 (m, 3H), 7.42-7.32 (m, 3H), 7.17 (d, J = 8.6 Hz, 1H), 7.08 (s, 1H), 4.59-4.21 (m, 3H), 3.87 (s, 3H), 3.80 (s, 3H), 3.52-3.40 (m, 2H), 3.18-3.07 (m, 1H), 1.34-1.04 (m, 6H). | D |
| 364 | 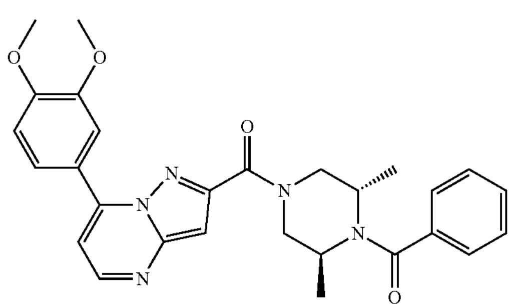 [SMILES: COc1ccc(-c2ccnc3cc(C(=O)N4C[C@H](C)N(C(=O)c5ccccc5)[C@@H](C)C4)nn23)cc1OC] | $^1$H NMR (400 MHz, DMSO-d6) δ 8.74-8.57 (m, 1H), 7.97-7.70 (m, 2H), 7.57-7.27 (m, 6H), 7.20 (d, J = 7.3 Hz, 1H), 7.15-7.02 (m, 1H), 4.48-3.98 (m, 4H), 3.96-3.63 (m, 8H), 1.35-1.00 (m, 6H). | D |

TABLE 3A-continued

Compound Structures, Characterization Data and Synthetic Method

| Cmpd | Structure | Characterization Data | General Method (Ex. 2) |
|---|---|---|---|
| 365 | 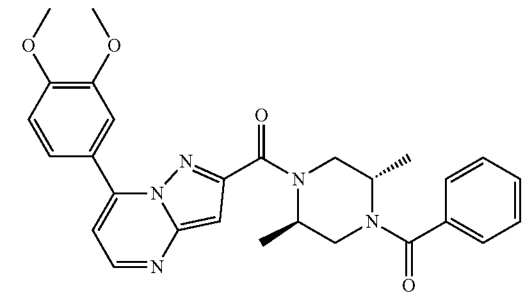 [SMILES: COc1ccc(-c2ccnc3cc(C(=O)N4C[C@H](C)N(C(=O)c5ccccc5)C[C@H]4C)nn23)cc1OC] | ¹H NMR (400 MHz, DMSO-d6) δ 8.71-8.60 (m, 1H), 7.87 (dd, J = 34.8, 7.5 Hz, 1H), 7.78-7.65 (m, 1H), 7.54-7.28 (m, 6H), 7.26-7.10 (m, 1H), 7.04 (dd, J = 24.4, 8.8 Hz, 1H), 5.00-4.49 (m, 1H), 4.38-4.08 (m, 2H), 4.00-3.68 (m, 6H), 3.63-3.43 (m, 1H), 3.32-3.11 (m, 2H), 1.35-1.06 (m, 6H). | D |
| 366 | 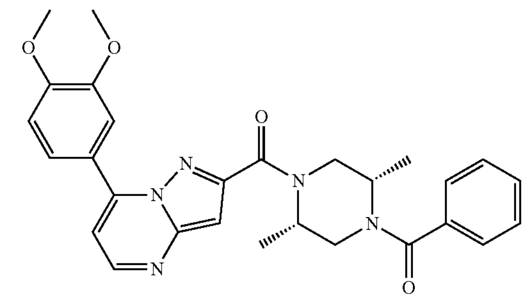 [SMILES: COc1ccc(-c2ccnc3cc(C(=O)N4C[C@H](C)N(C(=O)c5ccccc5)C[C@@H]4C)nn23)cc1OC] | ¹H NMR (400 MHz, DMSO-d6) δ 8.67 (d, J = 4.4 Hz, 1H), 7.88-7.57 (m, 2H), 7.53-7.19 (m, 6H), 7.19-7.00 (m, 2H), 4.83-4.57 (m, 1H), 4.55-4.06 (m, 3H), 3.94-3.74 (m, 6H), 3.31-2.84 (m, 2H), 1.23-0.93 (m, 6H). | D |
| 367 | 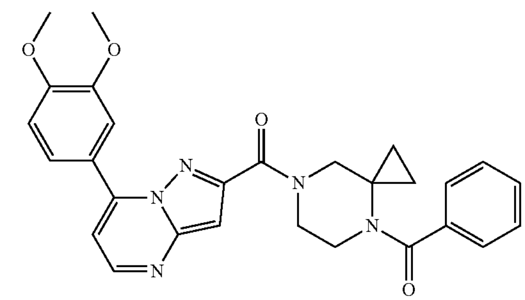 [SMILES: COc1ccc(-c2ccnc3cc(C(=O)N4CCN(C(=O)c5ccccc5)C5(CC5)C4)nn23)cc1OC] | ¹H NMR (400 MHz, DMSO-d6) δ 8.69-8.62 (m, 1H), 7.95-7.64 (m, 2H), 7.53-7.29 (m, 6H), 7.23-7.11 (m, 1H), 7.09-7.00 (m, 1H), 4.07-3.53 (m, 12H), 1.02-0.42 (m, 4H). | D |
| 368 | 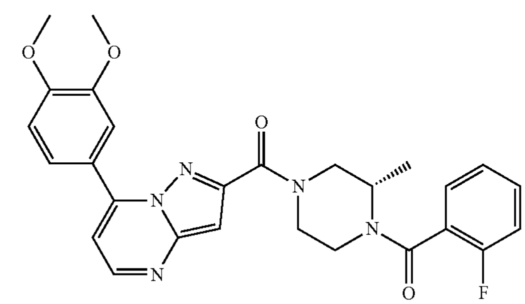 [SMILES: COc1ccc(-c2ccnc3cc(C(=O)N4CCN(C(=O)c5ccccc5F)[C@@H](C)C4)nn23)cc1OC] | ¹H NMR (400 MHz, DMSO-d6) δ 8.72-8.60 (m, 1H), 7.89-7.66 (m, 2H), 7.59-7.16 (m, 6H), 7.15-6.99 (m, 1H), 4.95-4.54 (m, 1H), 4.53-4.23 (m, 2H), 3.96-3.69 (m, 6H), 3.65-3.48 (m, 1H), 3.30-2.87 (m, 3H), 1.31-0.98 (m, 3H). | D |
| 369 | 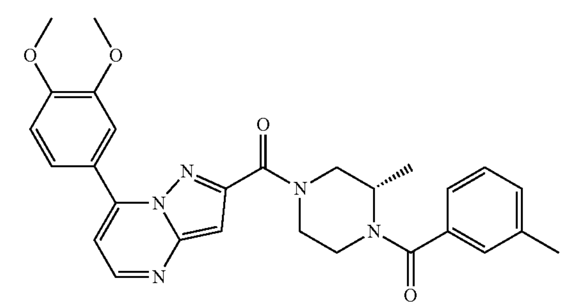 [SMILES: COc1ccc(-c2ccnc3cc(C(=O)N4CCN(C(=O)c5cccc(C)c5)[C@@H](C)C4)nn23)cc1OC] | ¹H NMR (400 MHz, DMSO-d6) δ 8.65 (d, J = 3.3 Hz, 1H), 7.90-7.67 (m, 2H), 7.46-7.00 (m, 7H), 4.72-4.21 (m, 3H), 3.94-3.69 (m, 6H), 3.56-3.42 (m, 1H), 3.32-2.91 (m, 3H), 2.33 (s, 3H), 1.33-0.98 (m, 3H). | D |

TABLE 3A-continued

Compound Structures, Characterization Data and Synthetic Method

| Cmpd | Structure | Characterization Data | General Method (Ex. 2) |
|---|---|---|---|
| 370 | 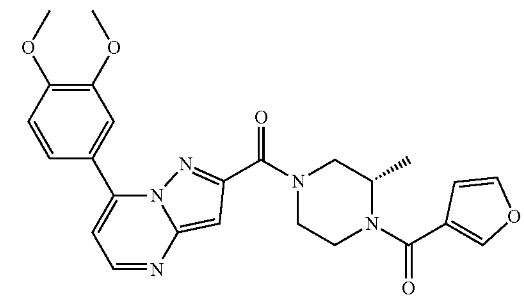 [SMILES: COc1ccc(-c2ccnc3cc(C(=O)N4CCN(C(=O)c5ccoc5)[C@@H](C)C4)nn23)cc1OC] | ¹H NMR (400 MHz, DMSO-d6) δ 8.67 (d, J = 4.3, 1.9 Hz, 1H), 8.05 (d, J = 2.9 Hz, 1H), 7.87-7.69 (m, 3H), 7.39 (dd, J = 9.4, 4.4 Hz, 1H), 7.19 (dd, J = 8.6, 3.7 Hz, 1H), 7.07 (d, J = 22.3 Hz, 1H), 6.69 (s, 1H), 4.62-3.96 (m, 3H), 3.94-3.80 (m, 6H), 3.48 (dd, J = 13.3, 3.1 Hz, 1H), 3.32-2.93 (m, 3H), 1.28-1.08 (m, 3H). | D |
| 371 | 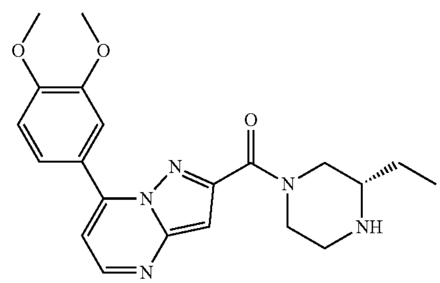 [SMILES: CC[C@H]1CN(C(=O)c2cc3nccc(-c4ccc(OC)c(OC)c4)n3n2)CCN1] | ¹H NMR (400 MHz, DMSO-d6) δ 8.65 (d, J = 4.4 Hz, 1H), 7.86-7.72 (m, 2H), 7.39 (d, J = 4.4 Hz, 1H), 7.19 (dd, J = 11.5, 8.5 Hz, 1H), 7.01 (d, J = 2.1 Hz, 1H), 4.47-4.22 (m, 2H), 3.93-3.81 (m, 6H), 3.21-2.96 (m, 2H), 2.94-2.58 (m, 3H), 1.46-1.18 (m, 2H), 0.97-0.66 (m, 3H). | D |
| 372 | 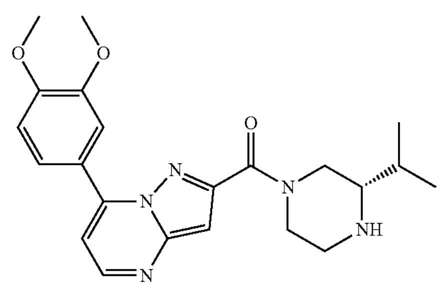 [SMILES: COc1ccc(-c2ccnc3cc(C(=O)N4CCN[C@@H](C(C)C)C4)nn23)cc1OC] | ¹H NMR (400 MHz, DMSO-d6) δ 8.68-8.62 (m, 1H), 7.86-7.71 (m, 2H), 7.38 (d, J = 4.5 Hz, 1H), 7.19 (t, J = 8.9 Hz, 1H), 7.00 (d, J = 4.5 Hz, 1H), 4.49-4.18 (m, 2H), 3.92-3.82 (m, 6H), 3.16-2.97 (m, 1H), 2.91-2.54 (m, 3H), 2.37-2.24 (m, 1H), 1.68-1.35 (m, 1H), 0.95 (d, J = 6.6 Hz, 3H), 0.78-0.56 (m, 3H). | D |
| 373 | 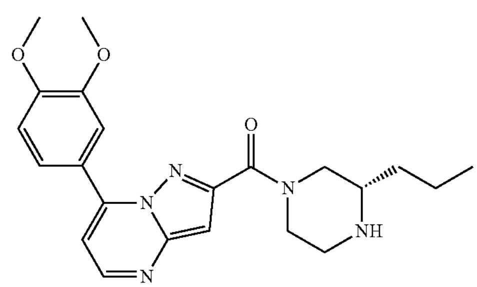 [SMILES: CCC[C@H]1CN(C(=O)c2cc3nccc(-c4ccc(OC)c(OC)c4)n3n2)CCN1] | ¹H NMR (400 MHz, DMSO-d6) δ 8.65 (dd, J = 4.4, 1.6 Hz, 1H), 7.85-7.71 (m, 2H), 7.37 (t, J = 4.6 Hz, 1H), 7.18 (dd, J = 11.9, 8.6 Hz, 1H), 7.00 (d, J = 3.1 Hz, 1H), 4.43-4.19 (m, 2H), 3.91-3.81 (m, 6H), 3.16-2.57 (m, 5H), 1.45-1.29 (m, 2H), 1.24-0.99 (m, 2H), 0.95-0.66 (m, 3H). | D |
| 374 | 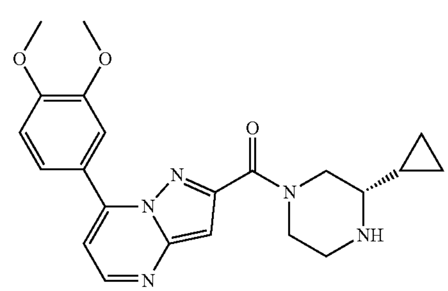 [SMILES: COc1ccc(-c2ccnc3cc(C(=O)N4CCN[C@@H](C5CC5)C4)nn23)cc1OC] | ¹H NMR (400 MHz, DMSO-d6) d 8.65 (t, J = 4.3 Hz, 1H), 7.85-7.71 (m, 2H), 7.38 (dd, J = 4.4, 1.4 Hz, 1H), 7.19 (d, J = 8.6 Hz, 1H), 7.00 (d, J = 9.0 Hz, 1H), 4.49-4.23 (m, 2H), 3.90-3.81 (m, 6H), 3.21-2.53 (m, 5H), 1.96-1.85 (m, 1H), 0.84-0.31 (m, 4H). | D |

TABLE 3A-continued

Compound Structures, Characterization Data and Synthetic Method

| Cmpd | Structure | Characterization Data | General Method (Ex. 2) |
|---|---|---|---|
| 375 | 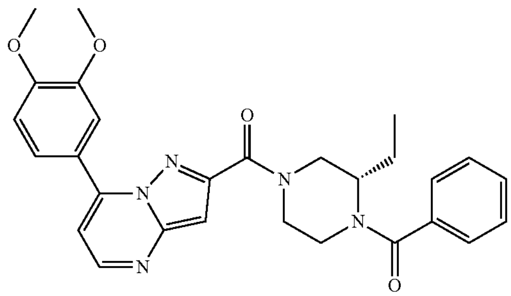 [SMILES: CC[C@H]1CN(C(=O)c2cc3nccc(-c4ccc(OC)c(OC)c4)n3n2)CCN1C(=O)c1ccccc1] | ¹H NMR (400 MHz, DMSO-d6) δ 8.65 (d, J = 3.1 Hz, 7.91-7.64 (m, 2H), 7.45-7.30 (m, 6H), 7.29-6.98 (m, 2H), 4.80-4.21 (m, 3H), 3.99-3.63 (m, 6H), 3.61-3.42 (m, 1H), 3.31-2.85 (m, 3H), 1.80-1.39 (m, 2H), 0.83-0.33 (m, 3H). | D |
| 376 | 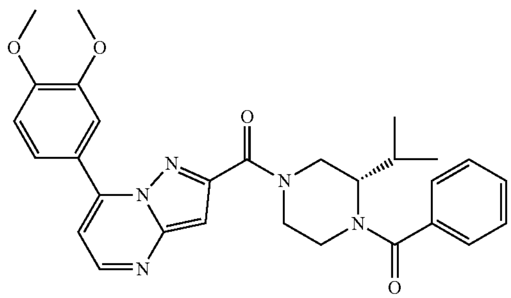 [SMILES: COc1ccc(-c2ccnc3cc(C(=O)N4CCN(C(=O)c5ccccc5)[C@@H](C(C)C)C4)nn23)cc1OC] | ¹H NMR (400 MHz, DMSO-d6) δ 8.65 (dd, J = 12.3, 3.9 Hz, 1H), 7.88-7.66 (m, 2H), 7.53-7.33 (m, 6H), 7.28-7.03 (m, 2H), 4.82-4.15 (m, 3H), 3.95-3.71 (m, 6H), 3.67-3.42 (m, 1H), 3.29-2.84 (m, 3H), 2.11-1.90 (m, 1H), 1.16-0.45 (m, 6H). | D |
| 377 | 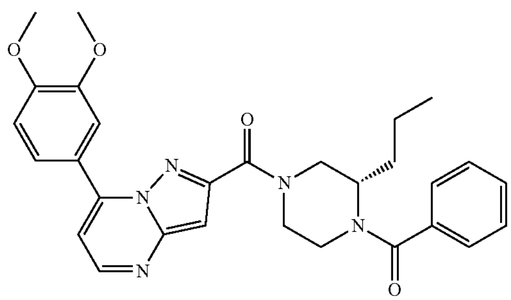 [SMILES: CCC[C@H]1CN(C(=O)c2cc3nccc(-c4ccc(OC)c(OC)c4)n3n2)CCN1C(=O)c1ccccc1] | ¹H NMR (400 MHz, DMSO-d6) δ 8.66 (d, J = 3.4 Hz, 1H), 7.91-7.61 (m, 2H), 7.53-7.29 (m, 6H), 7.26-7.11 (m, 1H), 7.11-7.00 (m, 1H), 4.88-4.16 (m, 3H), 3.97-3.66 (m, 6H), 3.59-3.40 (m, 1H), 3.29-2.83 (m, 3H), 1.80-0.38 (m, 7H). | D |
| 378 | 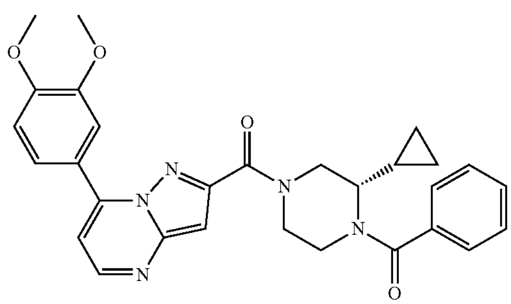 [SMILES: COc1ccc(-c2ccnc3cc(C(=O)N4CCN(C(=O)c5ccccc5)[C@@H](C5CC5)C4)nn23)cc1OC] | ¹H NMR (400 MHz, DMSO-d6) δ 8.66 (d, J = 4.4 Hz, 1H), 7.88-7.68 (m, 2H), 7.51-7.33 (m, 6H), 7.23-7.13 (m, 1H), 7.06 (d, J = 19.0 Hz, 1H), 4.74-4.37 (m, 3H), 3.93-3.71 (m, 6H), 3.62-3.38 (m, 2H), 3.25-3.11 (m, 1H), 3.10-2.97 (m, 1H), 1.39-1.21 (m, 1H), 0.59-0.02 (m, 4H). | D |
| 379 | 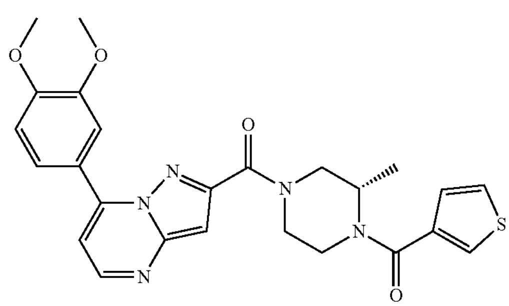 [SMILES: COc1ccc(-c2ccnc3cc(C(=O)N4CCN(C(=O)c5ccsc5)[C@@H](C)C4)nn23)cc1OC] | ¹H NMR (400 MHz, DMSO-d6) δ 8.66 (dd, J = 4.3, 2.3 Hz, 1H), 7.86-7.70 (m, 3H), 7.67-7.61 (m, 1H), 7.38 (dd, J = 9.5, 4.4 Hz, 1H), 7.26-7.14 (m, 2H), 7.07 (d, J = 23.3 Hz, 1H), 4.62-4.27 (m, 3H), 3.92-3.76 (m, 6H), 3.54-3.44 (m, 1H), 3.32-3.08 (m, 2H), 3.06-2.93 (m, 1H), 1.25-1.06 (m, 3H). | D |

TABLE 3A-continued

Compound Structures, Characterization Data and Synthetic Method

| Cmpd | Structure | Characterization Data | General Method (Ex. 2) |
|---|---|---|---|
| 380 | 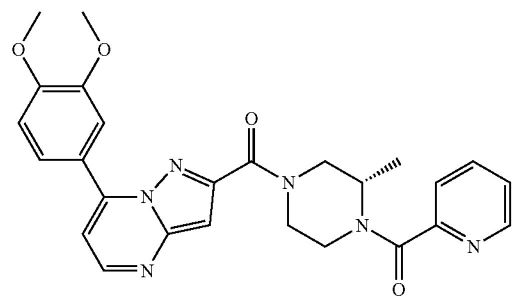 [SMILES: COc1ccc(-c2ccnc3cc(C(=O)N4CCN(C(=O)c5ccccn5)[C@@H](C)C4)nn23)cc1OC] | ¹H NMR (400 MHz, DMSO-d6) δ 8.72-8.54 (m, 2H), 8.01-7.90 (m, 1H), 7.88-7.66 (m, 2H), 7.59 (m, 2H), 7.59 (d, J = 7.6 Hz, 1H), 7.54-7.44 (m, 1H), 7.44-7.32 (m, 1H), 7.27-7.00 (m, 2H), 4.94-4.55 (m, 1H), 4.51-4.26 (m, 2H), 4.15-3.37 (m, 8H), 3.31-2.92 (m, 2H), 1.32-1.06 (m, 3H). | D |
| 381 | 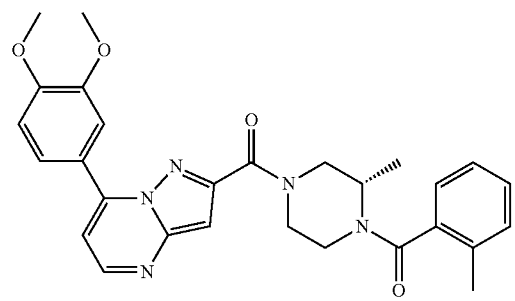 [SMILES: COc1ccc(-c2ccnc3cc(C(=O)N4CCN(C(=O)c5ccccc5C)[C@@H](C)C4)nn23)cc1OC] | ¹H NMR (400 MHz, DMSO-d6) δ 8.66 (dd, J = 11.8, 3.9 Hz, 1H), 7.90-7.76 (m, 1H), 7.76-7.63 (m, 1H), 7.44-7.14 (m, 5H), 7.09 (d, J = 7.4 Hz, 1H), 7.03 (d, J = 8.8 Hz, 1H), 4.98-4.19 (m, 3H), 3.93-3.67 (m, 6H), 3.66-3.44 (m, 1H), 3.28-2.81 (m, 3H), 2.32-2.09 (m, 3H), 1.31-0.95 (m, 3H). | D |
| 382 | 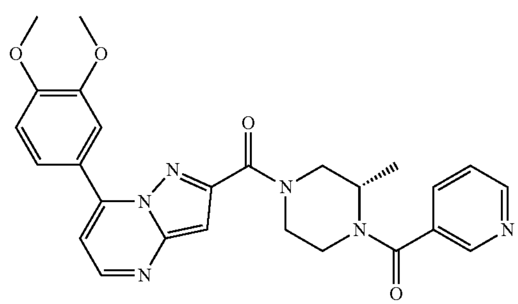 [SMILES: COc1ccc(-c2ccnc3cc(C(=O)N4CCN(C(=O)c5cccnc5)[C@@H](C)C4)nn23)cc1OC] | ¹H NMR (400 MHz, DMSO-d6) δ 8.74-8.59 (m, 3H), 7.93-7.65 (m, 3H), 7.56-7.44 (m, 1H), 7.43-7.32 (m, 1H), 7.27-7.12 (m, 1H), 7.06 (d, J = 23.5 Hz, 1H), 4.95-4.16 (m, 3H), 3.99-3.66 (m, 6H), 3.60-3.40 (m, 1H), 3.31-2.93 (m, 3H), 1.34-1.02 (m, 3H). | D |
| 383 | 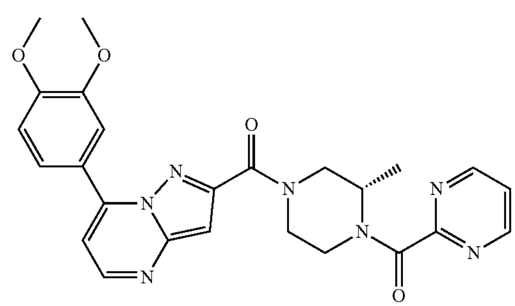 [SMILES: COc1ccc(-c2ccnc3cc(C(=O)N4CCN(C(=O)c5ncccn5)[C@@H](C)C4)nn23)cc1OC] | ¹H NMR (400 MHz, DMSO-d6) δ 8.96-8.86 (m, 2H), 8.71-8.61 (m, 1H), 7.89-7.66 (m, 2H), 7.66-7.56 (m, 1H), 7.44-7.32 (m, 1H), 7.27-7.00 (m, 2H), 4.92-4.56 (m, 1H), 4.50-4.23 (m, 2H), 3.95-3.72 (m, 6H), 3.71-3.55 (m, 1H), 3.28-2.93 (m, 3H), 1.32-1.06 (m, 3H). | D |

TABLE 3A-continued

Compound Structures, Characterization Data and Synthetic Method

| Cmpd | Structure | Characterization Data | General Method (Ex. 2) |
|---|---|---|---|
| 384 | 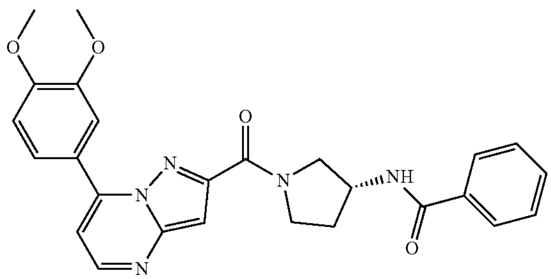 [SMILES: COc1ccc(-c2ccnc3cc(C(=O)N4CC[C@@H](NC(=O)c5ccccc5)C4)nn23)cc1OC] | ¹H NMR (400 MHz, DMSO-d6) δ 8.71-8.61 (m, 2H), 7.90-7.74 (m, 4H), 7.57-7.50 (m, 1H), 7.50-7.36 (m, 3H), 7.23-7.09 (m, 2H), 4.64-4.48 (m, 1H), 4.35-4.26 (m, 1H), 4.19-4.04 (m, 1H), 3.99-3.82 (m, 4H), 3.82-3.73 (m, 3H), 3.71-3.58 (m, 1H), 2.30-1.96 (m, 2H). | D |
| 385 | 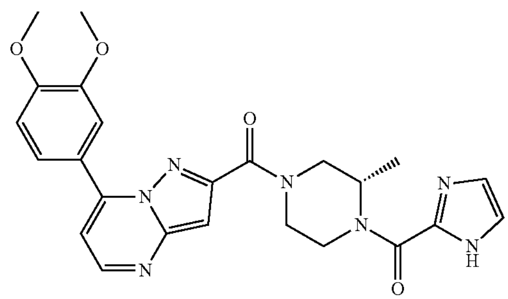 [SMILES: COc1ccc(-c2ccnc3cc(C(=O)N4CCN(C(=O)c5ncc[nH]5)[C@@H](C)C4)nn23)cc1OC] | ¹H NMR (400 MHz, DMSO-d6) δ 12.95 (s, 1H), 8.67 (d, J = 4.1 Hz, 1H), 7.88-7.70 (m, 2H), 7.43-7.34 (m, 1H), 7.27 (s, 1H), 7.24-7.16 (m, 1H), 7.14-7.02 (m, 2H), 6.23-5.63 (m, 1H), 4.94-4.51 (m, 2H), 4.51-4.23 (m, 2H), 3.92-3.80 (m, 6H), 3.66-3.48 (m, 1H), 3.25-3.07 (m, 1H), 1.36-1.07 (m, 3H). | D |
| 386 | 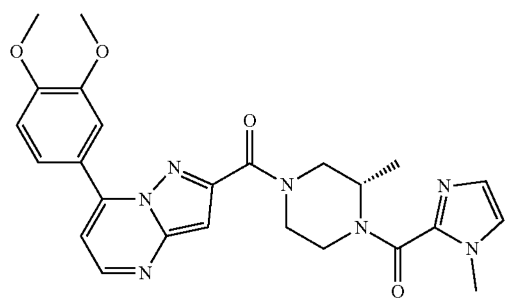 [SMILES: COc1ccc(-c2ccnc3cc(C(=O)N4CCN(C(=O)c5nccn5C)[C@@H](C)C4)nn23)cc1OC] | ¹H NMR (400 MHz, DMSO-d6) δ 8.66 (d, J = 4.0 Hz, 1H), 7.91-7.69 (m, 2H), 7.46-7.27 (m, 2H), 7.26-7.13 (m, 1H), 7.12-6.94 (m, 2H), 5.08-4.27 (m, 4H), 3.94-3.73 (m, 9H), 3.21-3.04 (m, 3H), 1.34-1.10 (m, 3H). | D |
| 387 | 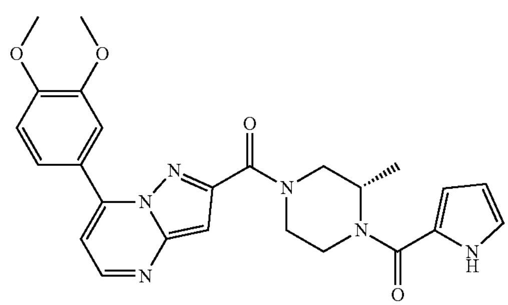 [SMILES: COc1ccc(-c2ccnc3cc(C(=O)N4CCN(C(=O)c5ccc[nH]5)[C@@H](C)C4)nn23)cc1OC] | ¹H NMR (400 MHz, DMSO-d6) δ 11.49 (s, 1H), 8.67 (dd, J = 4.3, 2.0 Hz, 1H), 7.89-7.69 (m, 2H), 7.39 (dd, J = 9.0, 4.4 Hz, 1H), 7.20 (dd, J = 8.6, 3.3 Hz, 1H), 7.07 (d, J = 24.1 Hz, 1H), 6.91 (s, 1H), 6.56-6.45 (m, 1H), 6.14 (s, 1H), 4.91-4.18 (m, 5H), 3.98-3.78 (m, 6H), 3.58-3.47 (m, 1H), 3.19-2.99 (m, 1H), 1.34-1.10 (m, 3H). | D |
| 388 | 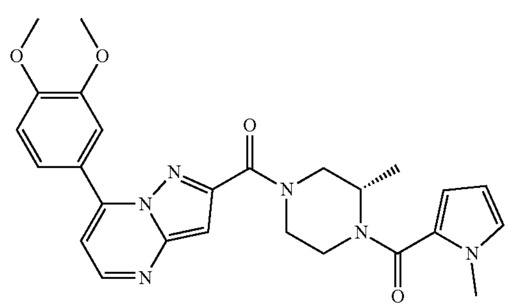 [SMILES: COc1ccc(-c2ccnc3cc(C(=O)N4CCN(C(=O)c5cccn5C)[C@@H](C)C4)nn23)cc1OC] | ¹H NMR (400 MHz, DMSO-d6) δ 8.67 (dd, J = 4.4, 2.3 Hz, 1H), 7.87-7.69 (m, 2H), 7.38 (dd, J = 9.4, 4.5 Hz, 1H), 7.19 (dd, J = 8.5, 3.9 Hz, 1H), 7.06 (d, J = 22.5 Hz, 1H), 6.94-6.88 (m, 1H), 6.36-6.30 (m, 1H), 6.07-6.01 (m, 1H), 4.78-4.04 (m, 5H), 3.91-3.81 (m, 6H), 3.66 (d, J = 1.9 Hz, 3H), 3.52-3.42 (m, 1H), 3.17-2.94 (m, 1H), 1.27-1.09 (m, 3H). | D |

TABLE 3A-continued

Compound Structures, Characterization Data and Synthetic Method

| Cmpd | Structure | Characterization Data | General Method (Ex. 2) |
|---|---|---|---|
| 389 | 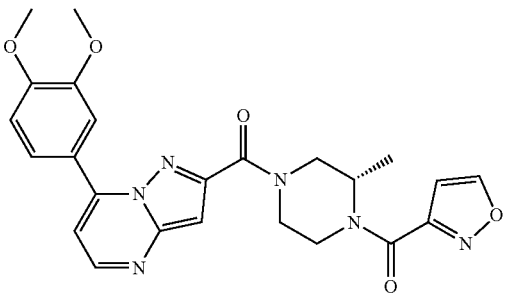 [SMILES: COc1ccc(-c2ccnc3cc(C(=O)N4CCN(C(=O)c5ccon5)[C@@H](C)C4)nn23)cc1OC] | $^1$H NMR (400 MHz, DMSO-d6) δ 9.17-9.07 (m, 1H), 8.73-8.63 (m, 1H), 7.88-7.67 (m, 2H), 7.44-7.33 (m, 1H), 7.26-7.01 (m, 2H), 6.91-6.83 (m, 1H), 4.92-4.07 (m, 5H), 3.92-3.76 (m, 6H), 3.64-3.43 (m, 1H), 3.27-2.93 (m, 1H), 1.28-1.12 (m, 3H). | D |
| 390 | 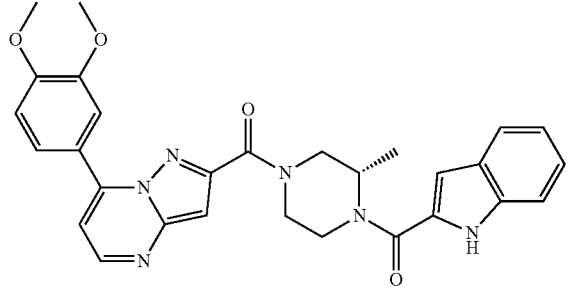 [SMILES: COc1ccc(-c2ccnc3cc(C(=O)N4CCN(C(=O)c5cc6ccccc6[nH]5)[C@@H](C)C4)nn23)cc1OC] | $^1$H NMR (400 MHz, DMSO-d6) δ 11.65-11.59 (m, 1H), 8.67 (dd, J = 4.4, 2.5 Hz, 1H), 7.87-7.71 (m, 2H), 7.61 (d, J = 8.0 Hz, 1H), 7.47-7.37 (m, 2H), 7.24-7.16 (m, 2H), 7.14-7.02 (m, 2H), 6.82 (d, J = 8.0 Hz, 1H), 4.94-4.25 (m, 5H), 3.92-3.81 (m, 6H), 3.57 (dd, J = 13.6, 3.6 Hz, 1H), 3.24-3.05 (m, 1H), 1.35-1.16 (m, 3H). | D |
| 391 | 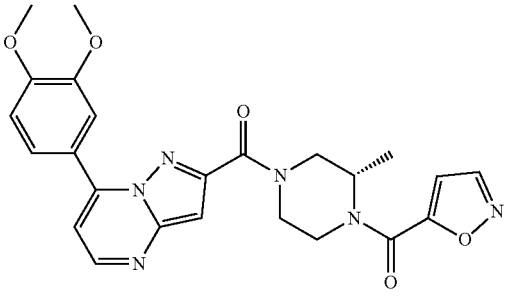 [SMILES: COc1ccc(-c2ccnc3cc(C(=O)N4CCN(C(=O)c5ccno5)[C@@H](C)C4)nn23)cc1OC] | $^1$H NMR (400 MHz, DMSO-d6) δ 8.76 (s, 1H), 8.67 (d, J = 4.3 Hz, 1H), 7.89-7.67 (m, 2H), 7.39 (dd, J = 9.4, 4.4 Hz, 1H), 7.26-7.13 (m, 1H), 7.08 (d, J = 24.6 Hz, 1H), 6.96 (s, 1H), 4.91-3.97 (m, 4H), 3.93-3.74 (m, 6H), 3.64-3.45 (m, 1H), 3.25-2.93 (m, 2H), 1.36-1.09 (m, 3H). | D |
| 392 | 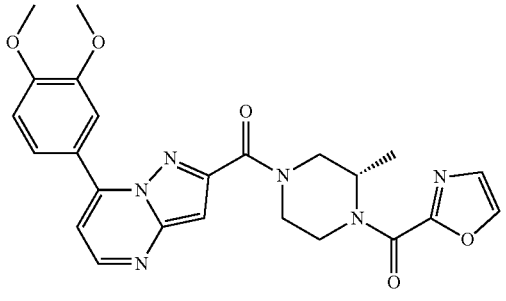 [SMILES: COc1ccc(-c2ccnc3cc(C(=O)N4CCN(C(=O)c5ncco5)[C@@H](C)C4)nn23)cc1OC] | $^1$H NMR (400 MHz, DMSO-d6) δ 8.67 (dd, J = 4.3, 1.8 Hz, 1H), 8.61 (s, 1H), 8.56-8.51 (m, 1H), 7.85-7.71 (m, 2H), 7.38 (dd, J = 9.4, 4.5 Hz, 1H), 7.23-7.16 (m, 1H), 7.07 (d, J = 24.2 Hz, 1H), 4.96-4.23 (m, 5H), 3.91-3.80 (m, 6H), 3.60-3.44 (m, 1H), 3.22-2.91 (m, 1H), 1.28-1.09 (m, 3H). | D |

TABLE 3A-continued

Compound Structures, Characterization Data and Synthetic Method

| Cmpd | Structure | Characterization Data | General Method (Ex. 2) |
|---|---|---|---|
| 393 | 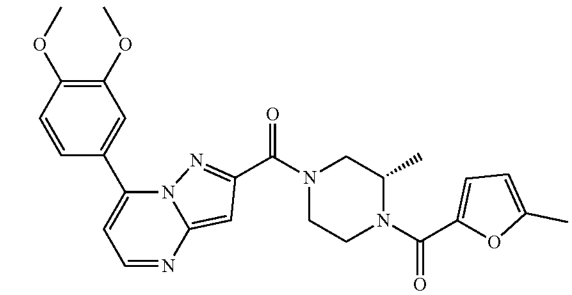 [SMILES: COc1ccc(-c2ccnc3cc(C(=O)N4CCN(C(=O)c5ccc(C)o5)[C@@H](C)C4)nn23)cc1OC] | $^1$H NMR (400 MHz, DMSO-d6) δ 8.67 (dd, J = 4.4, 1.6 Hz, 1H), 7.86-7.71 (m, 2H), 7.39 (dd, J = 8.6, 4.5 Hz, 1H), 7.20 (dd, J = 8.5, 3.6 Hz, 1H), 7.07 (d, J = 22.7 Hz, 1H), 6.90 (t, J = 3.9 Hz, 1H), 6.26 (d, J = 3.3 Hz, 1H), 4.80-4.10 (m, 5H), 3.91-3.81 (m, 6H), 3.52 (dd, J = 14.3, 3.9 Hz, 1H), 3.20-2.98 (m, 1H), 2.32 (s, 3H), 1.30-1.11 (m, 3H). | D |
| 394 | 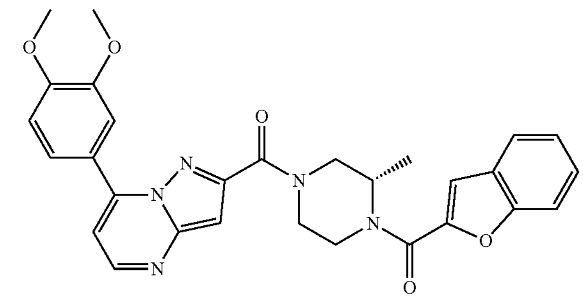 | $^1$H NMR (400 MHz, DMSO-d6) δ 8.67 (dd, J = 4.3, 1.7 Hz, 1H), 7.86-7.71 (m, 3H), 7.70-7.63 (m, 1H), 7.50-7.31 (m, 4H), 7.19 (dd, J = 8.3, 3.4 Hz, 1H), 7.09 (d, J = 23.8 Hz, 1H), 4.84-4.13 (m, 5H), 3.91-3.78 (m, 6H), 3.63-3.52 (m, 1H), 3.24-3.02 (m, 1H), 1.36-1.14 (m, 3H). | D |
| 395 | 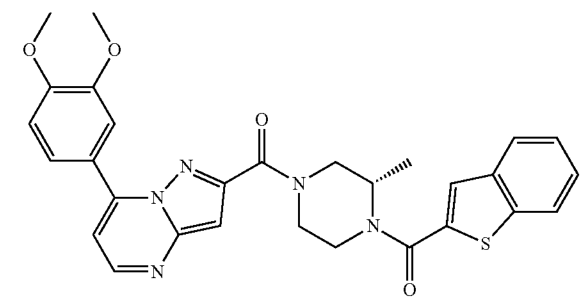 | $^1$H NMR (400 MHz, DMSO-d6) δ 8.67 (dd, J = 4.3, 2.8 Hz, 1H), 8.07-8.00 (m, 1H), 7.97-7.90 (m, 1H), 7.86-7.70 (m, 3H), 7.51-7.42 (m, 2H), 7.39 (dd, J = 10.0, 4.5 Hz, 1H), 7.19 (dd, J = 8.4, 5.1 Hz, 1H), 7.08 (d, J = 23.0 Hz, 1H), 4.79-4.09 (m, 5H), 3.88-3.79 (m, 6H), 3.58 (dd, J = 13.3, 3.0 Hz, 1H), 3.24-3.03 (m, 1H), 1.33-1.14 (m, 3H). | D |

TABLE 3B

Compound Structures, Characterization Data and Synthetic Method

| Cmpd | Structure | Characterization Data | General Method (Example 2) |
|---|---|---|---|
| 3 | 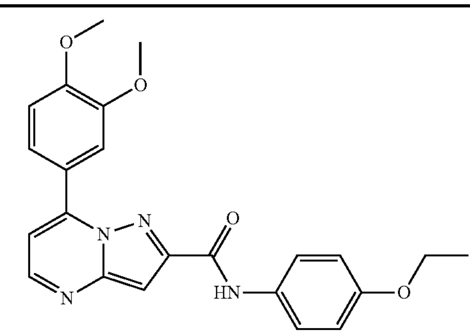 | $^1$H NMR (400 MHz, CDCl$_3$) δ 8.76 (s, 1H), 8.58 (d, J = 4.3 Hz, 1H), 7.70-7.65 (m, 2H), 7.62-7.57 (m, 2H), 7.40 (s, 1H), 7.10 (d, J = 8.2 Hz, 1H), 7.02 (d, J = 4.4 Hz, 1H), 6.93-6.88 (m, 2H), 4.09-3.95 (m, 8H), 1.42 (t, J = 7.0 Hz, 3H). | C |

TABLE 3B-continued

Compound Structures, Characterization Data and Synthetic Method

| Cmpd | Structure | Characterization Data | General Method (Example 2) |
|---|---|---|---|
| 5 | 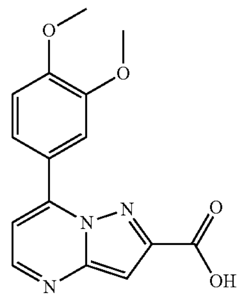 [SMILES: COc1ccc(-c2ccnc3cc(C(=O)O)nn23)cc1OC] | ¹H NMR (400 MHz, DMSO-d₆) δ 13.35 (s, 1H), 8.67 (d, J = 4.4 Hz, 1H), 7.90 (dd, J = 8.5, 2.1 Hz, 1H), 7.79 (d, J = 2.1 Hz, 1H), 7.44 (d, J = 4.4 Hz, 1H), 7.25-7.15 (m, 2H), 3.89 (s, 3H), 3.86 (s, 3H). | A (Example 1) |
| 11 | 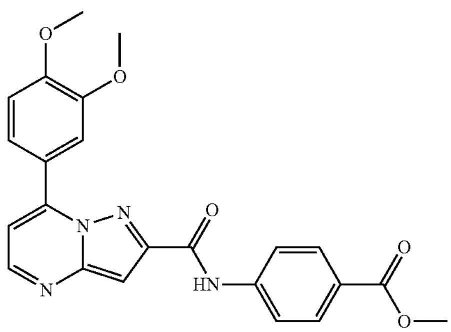 | ¹H NMR (400 MHz, DMSO-d₆) δ 10.59 (s, 1H), 8.71 (d, J = 4.5 Hz, 1H), 8.05-7.94 (m, 6H), 7.51 (d, J = 4.5 Hz, 1H), 7.34 (s, 1H), 7.23 (d, J = 8.6 Hz, 1H), 3.93-3.89 (m, 6H), 3.85 (s, 3H). | C |
| 267 | 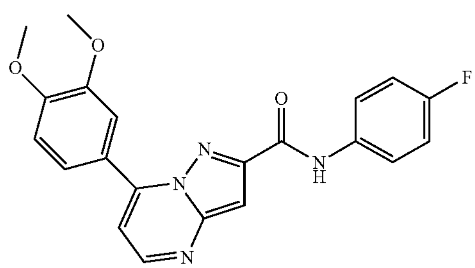 [SMILES: COc1ccc(-c2ccnc3cc(C(=O)Nc4ccc(F)cc4)nn23)cc1OC] | ¹H NMR (400 MHz, DMSO-d₆) δ 10.35 (s, 1H), 8.69 (d, J = 4.5 Hz, 1H), 8.02 (dd, J = 8.5, 1.9 Hz, 1H), 7.94 (d, J = 1.9 Hz, 1H), 7.84 (dd, J = 9.0, 5.0 Hz, 2H), 7.49 (d, J = 4.5 Hz, 1H), 7.29 (s, 1H), 7.26-7.12 (m, 3H), 3.96-3.81 (m, 6H). | B |
| 300 | 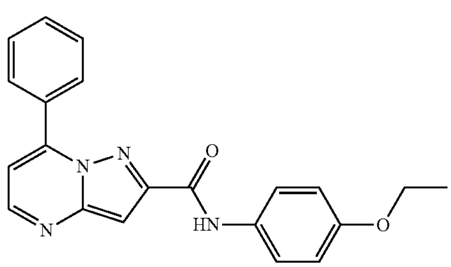 [SMILES: CCOc1ccc(NC(=O)c2cc3nccc(-c4ccccc4)n3n2)cc1] | ¹H NMR (400 MHz, DMSO-d₆) δ 10.11 (s, 1H), 8.73 (d, J = 4.4 Hz, 1H), 8.28-8.26 (m, 2H), 7.69-7.65 (m, 5H), 7.43 (d, J = 4.4 Hz, 1H), 7.31 (s, 1H), 6.95-6.92 (m, 2H), 4.02 (q, J = 7.0 Hz, 2H), 1.33 (t, J = 7.0 Hz, 3H). | C |
| 305 | 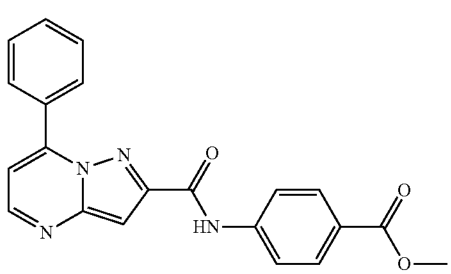 [SMILES: COC(=O)c1ccc(NC(=O)c2cc3nccc(-c4ccccc4)n3n2)cc1] | ¹H NMR (400 MHz, DMSO-d₆) δ 10.57 (s, 1H), 8.75 (d, J = 4.4 Hz, 1H), 8.29-8.26 (m, 2H), 8.00-7.98 (m, 4H), 7.68-7.66 (m, 3H), 7.45 (d, J = 4.4 Hz, 1H), 7.38 (s, 1H), 3.85 (s, 3H). | C |

TABLE 3B-continued

Compound Structures, Characterization Data and Synthetic Method

| Cmpd | Structure | Characterization Data | General Method (Example 2) |
|---|---|---|---|
| 310 | 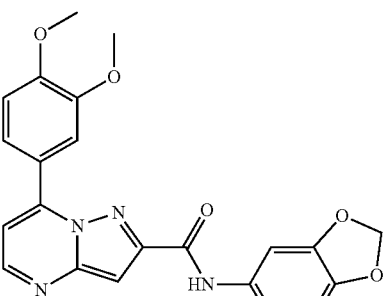 | $^1$H NMR (400 MHz, DMSO-$d_6$) δ 10.19 (s, 1H), 8.69 (d, J = 4.5 Hz, 1H), 8.02 (dd, J = 8.5, 2.1 Hz, 1H), 7.94 (d, J = 2.1 Hz, 1H), 7.49-7.48 (m, 2H), 7.27-7.21 (m, 3H), 6.93 (d, J = 8.4 Hz, 1H), 6.03 (s, 2H), 3.92-3.89 (m, 6H). | C |
| 334 | 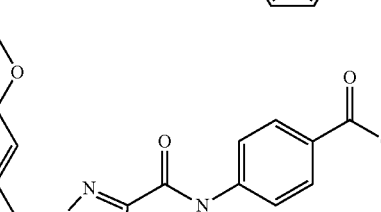 | $^1$H NMR (400 MHz, DMSO-$d_6$) δ 10.59 (s, 1H), 8.70 (d, J = 4.5 Hz, 1H), 8.09-7.90 (m, 6H), 7.50 (d, J = 4.5 Hz, 1H), 7.34 (s, 1H), 7.22 (d, J = 8.6 Hz, 1H), 4.31 (q, J = 7.1 Hz, 1H), 3.98-3.86 (m, 6H), 1.33 (t, J = 7.1 Hz, 3H). | C |

Example 3—Phosphate-Buffered Saline (PBS) Solubility of Compounds

Materials

PBS solutions (pH 7.5) were prepared according to the following compositions and stored at 4° C.

| Reagents | Content |
|---|---|
| 81% 0.0667M Na$_2$HPO$_4$ | 162 mL |
| 19% 0.0667M NaH$_2$PO$_4$ | 38 mL |
| NaCl | 0.8 g |

Test compounds were dissolved in PBS (pH 7.5) at 0.5 mg/mL and vortexed for 90 min. The PBS solution was sequentially filtered through a 0.45, 1.2, 5.0 µM syringe filter.

Analysis

Concentration of test compounds were determined using LC-MS/MS with appropriate dilution of the samples.

Data

The solubility of various compounds in PBS are summarized in Table 4 below. Solubility ranges (ng/mL): (A) refers ≥10,000 ng/mL; (B) refers to 100<B<10,000 ng/mL; and (C) refers to ≤100 ng/mL.

TABLE 4

PBS Solubility of Compounds

| Cmpd No. | Solubility Range | Cmpd No. | Solubility Range | Cmpd No. | Solubility Range |
|---|---|---|---|---|---|
| 1 | C | 2 | C | 3 | C |
| 6 | C | 7 | C | 8 | C |
| 9 | B | 10 | B | 11 | C |
| 12 | C | 14 | B | 15 | C |
| 16 | A | 17 | C | 18 | C |
| 19 | A | 21 | A | 28 | C |
| 31 | C | 32 | C | 33 | C |
| 34 | C | 36 | B | 39 | C |
| 41 | C | 42 | C | 43 | C |
| 46 | C | 47 | C | 48 | C |
| 51 | C | 55 | C | 56 | C |
| 57 | C | 58 | C | 62 | B |
| 63 | B | 65 | C | 69 | A |
| 72 | A | 73 | B | 75 | A |
| 76 | B | 85 | A | 86 | A |
| 92 | C | 96 | B | 97 | B |
| 100 | B | 105 | C | 106 | C |
| 109 | C | 114 | C | 121 | C |
| 125 | C | 126 | B | 127 | C |
| 130 | C | 131 | C | 132 | C |
| 133 | C | 135 | C | 136 | C |
| 139 | C | 140 | C | 141 | C |
| 142 | C | 144 | C | 145 | B |
| 146 | C | 147 | C | 149 | A |
| 151 | A | 156 | B | 157 | C |
| 158 | C | 159 | B | 160 | C |
| 161 | B | 163 | C | 164 | C |
| 165 | C | 166 | C | 167 | C |
| 168 | C | 169 | C | 170 | B |
| 178 | A | 186 | A | 204 | C |
| 210 | B | 212 | B | 256 | C |
| 257 | C | 259 | B | 271 | C |

TABLE 4-continued

PBS Solubility of Compounds

| Cmpd No. | Solubility Range | Cmpd No. | Solubility Range | Cmpd No. | Solubility Range |
|---|---|---|---|---|---|
| 272 | C | 273 | C | 274 | C |
| 276 | C | 277 | C | 280 | C |
| 281 | C | 282 | C | 283 | C |
| 284 | B | | | | |

Example 4—Cell-Based YFP Assay

Materials and Instrumentations

Forskolin (Tocris cat. #1099), Dimethyl sulfoxide (Sigma cat. #D4540), FLUO star Omega microplate reader (BMG Labtech, Ortenberg, Germany), MARS Data Analysis Software (BMG Labtech), GraphPad Prism 5 (GraphPad Software, Inc.)

Cell Culture Conditions

Chinese hamster ovary (CHO-K1) cells expressing human wild type-CFTR and halide sensor YFP-H148Q/I152L were constructed and grown in Dulbecco's modified Eagle's medium (DMEM) supplemented with 10% FBS, 2 mM glutamine, 100 units/ml penicillin and 100 µg/ml streptomycin.

Experimental Procedures

Chinese hamster ovary (CHO-K1) cells expressing human wild type-CFTR and halide sensor YFP-H148Q/I152L were seeded in 96-well microplate with 2×10⁴ cells/well and incubated in 37° C., 48 hours. Then, each well was washed 3 times with PBS and 100 µL PBS was added in each well. Forskolin, test compounds (100×) were added in each well and incubated in 37° C., 10 minutes. YFP fluorescence signal affected by I⁻ ion influx through CFTR channel was measured in 37° C., FLUO star Omega microplate reader according to the following steps:

i) basal 2 seconds;
ii) 140 mM I⁻ solution 100 µL addition to each well;
iii) YFP fluorescence signal measurement start after 6 seconds; and
iv) following 14 seconds signal detection in every 0.4 seconds periods.

The fluorescent signal of forskolin 20 µM per second was used as 100% activity in data normalization of fluorescent signal in each concentration. Experiments were performed in triplicates and the data was averaged. $EC_{50}$ values were calculated with MARS Data Analysis Software (BMG Labtech) and GraphPad Prism 5.

Data

The $EC_{50}$ concentration ranges of compounds are summarized in Table 5 below. $EC_{50}$ (nM) concentration ranges: (A) refers to $EC_{50}$<200 nM; (B) refers to 200≤$EC_{50}$<2000 nM; and (C) refers to $EC_{50}$≥2000 nM.

TABLE 5

Cell-based YFP Assay ($EC_{50}$)

| Cmpd No. | Concentration Range | Cmpd No. | Concentration Range | Cmpd No. | Concentration Range |
|---|---|---|---|---|---|
| 1 | A | 2 | A | 3 | A |
| 4 | B | 5 | C | 6 | A |
| 7 | B | 8 | A | 9 | A |
| 10 | A | 11 | A | 12 | B |
| 13 | B | 14 | B | 15 | A |
| 16 | C | 17 | A | 18 | B |
| 19 | C | 20 | B | 21 | C |
| 22 | C | 23 | C | 24 | C |
| 25 | C | 26 | B | 27 | C |
| 28 | A | 29 | C | 30 | C |
| 31 | A | 32 | A | 33 | B |
| 34 | A | 35 | C | 36 | B |
| 37 | C | 38 | B | 39 | B |
| 40 | C | 41 | A | 42 | A |
| 43 | A | 44 | B | 45 | C |
| 46 | A | 47 | A | 48 | A |
| 49 | B | 50 | C | 51 | A |
| 53 | B | 54 | B | 55 | A |
| 56 | A | 57 | A | 58 | A |
| 59 | A | 60 | A | 61 | C |
| 62 | B | 63 | B | 64 | A |
| 65 | A | 68 | C | 69 | B |
| 70 | C | 71 | C | 72 | B |
| 73 | B | 74 | C | 75 | C |
| 76 | B | 77 | A | 78 | B |
| 80 | C | 81 | C | 82 | C |
| 83 | C | 84 | C | 85 | B |
| 86 | B | 87 | C | 88 | C |
| 89 | C | 90 | C | 91 | C |
| 92 | A | 93 | B | 94 | C |
| 95 | C | 96 | B | 97 | B |
| 98 | C | 99 | C | 100 | B |
| 101 | C | 102 | C | 103 | C |
| 104 | C | 105 | A | 106 | A |
| 107 | C | 108 | C | 109 | B |
| 110 | B | 111 | B | 112 | A |
| 113 | A | 114 | A | 115 | B |
| 116 | B | 117 | C | 118 | C |
| 119 | B | 120 | A | 121 | A |
| 122 | A | 123 | C | 124 | A |
| 125 | A | 126 | B | 127 | B |
| 128 | A | 129 | B | 130 | A |
| 131 | A | 132 | A | 133 | A |
| 134 | A | 135 | A | 136 | A |
| 137 | B | 138 | C | 139 | A |
| 140 | A | 141 | A | 142 | A |
| 144 | A | 145 | B | 146 | A |
| 147 | A | 148 | C | 149 | B |
| 150 | C | 151 | A | 152 | B |
| 153 | B | 154 | B | 155 | C |
| 156 | A | 157 | A | 158 | A |
| 159 | B | 160 | B | 161 | B |
| 162 | C | 163 | B | 164 | A |
| 165 | B | 166 | B | 167 | A |
| 168 | B | 169 | A | 170 | A |
| 171 | A | 172 | A | 173 | A |
| 174 | A | 175 | A | 176 | C |
| 177 | C | 178 | B | 179 | C |
| 180 | C | 181 | C | 182 | C |
| 183 | B | 184 | B | 185 | B |
| 186 | A | 187 | C | 188 | C |
| 189 | A | 190 | B | 191 | A |
| 192 | A | 193 | A | 194 | A |
| 195 | B | 196 | B | 197 | B |
| 198 | A | 199 | B | 200 | A |
| 201 | C | 202 | C | 203 | C |
| 204 | A | 205 | A | 206 | B |
| 207 | B | 208 | C | 209 | A |
| 210 | A | 211 | B | 212 | A |
| 213 | C | 214 | C | 215 | C |
| 216 | C | 217 | C | 218 | C |
| 219 | C | 220 | C | 221 | C |
| 222 | C | 223 | C | 224 | C |
| 225 | C | 226 | C | 227 | A |
| 228 | A | 229 | A | 230 | A |
| 231 | C | 232 | C | 233 | C |
| 234 | C | 235 | C | 236 | C |
| 237 | C | 238 | C | 239 | C |

TABLE 5-continued

Cell-based YFP Assay (EC$_{50}$)

| Cmpd No. | Concentration Range | Cmpd No. | Concentration Range | Cmpd No. | Concentration Range |
|---|---|---|---|---|---|
| 240 | C | 241 | C | 242 | A |
| 243 | B | 244 | A | 245 | C |
| 246 | B | 247 | B | 248 | C |
| 249 | C | 250 | B | 251 | B |
| 252 | C | 253 | B | 254 | C |
| 255 | A | 256 | A | 257 | A |
| 258 | A | 259 | B | 260 | B |
| 261 | B | 262 | B | 263 | B |
| 264 | C | 265 | C | 266 | A |
| 267 | A | 268 | A | 269 | A |
| 270 | A | 271 | A | 272 | A |
| 273 | A | 274 | A | 275 | A |
| 276 | A | 277 | A | 278 | C |
| 279 | C | 280 | A | 281 | A |
| 282 | A | 283 | B | 284 | A |
| 285 | A | 286 | A | 287 | B |
| 288 | C | 289 | A | 290 | B |
| 291 | C | 292 | A | 293 | C |
| 294 | C | 295 | C | 296 | C |
| 297 | C | 298 | C | 299 | C |
| 300 | C | 301 | C | 302 | C |
| 303 | C | 304 | C | 305 | C |
| 306 | C | 307 | B | 308 | B |
| 309 | A | 310 | A | 311 | A |
| 312 | A | 313 | C | 314 | A |
| 315 | C | 316 | C | 317 | B |
| 318 | B | 319 | B | 320 | B |
| 321 | B | 322 | C | 323 | C |
| 324 | C | 325 | A | 326 | B |
| 327 | A | 328 | B | 329 | A |
| 330 | B | 331 | B | 332 | B |
| 333 | C | 334 | A | 335 | A |
| 336 | B | 337 | C | 338 | A |
| 339 | C | 340 | C | 341 | C |
| 342 | B | 343 | C | 344 | B |
| 345 | C | 346 | A | 347 | C |
| 348 | B | 349 | A | 350 | A |
| 351 | A | 352 | A | 353 | A |
| 354 | A | 355 | A | 356 | A |
| 357 | B | 358 | B | 359 | B |
| 360 | B | 361 | B | 362 | B |
| 363 | A | 364 | A | 365 | A |
| 366 | A | 367 | A | 368 | A |
| 369 | A | 370 | A | 371 | B |
| 372 | B | 373 | B | 374 | B |
| 375 | A | 376 | A | 377 | A |
| 378 | A | 379 | A | 380 | A |
| 381 | A | 382 | A | 383 | B |
| 384 | A | | | | |

Example 5—Short-Circuit Current Measurement

Materials and Instrumentations

Forskolin (Tocris cat. #1099), CFTR$_{inh}$-172 (Tocris cat. #3430), amphotericin B (Tocris cat. #6930), dimethyl sulfoxide (Sigma cat. #D4540), EVC4000 Multi-Channel V/I Clamp (World Precision Instruments, Sarasota, FL), PowerLab 4/35 (AD Instruments, Castle Hill, Australia), Labchart Pro 7, GraphPad Prism 5 (GraphPad Software, Inc.).

Cell Culture

Fisher rat thyroid (FRT) cells expressing human wild type-CFTR were provided by Dr. Alan Verkman (University of California, San Francisco) and grown in DMEM/F12 medium (1:1) supplemented with 10% FBS, 2 mM glutamine, 100 units/ml penicillin and 100 µg/ml streptomycin.

Experimental Procedures

Snapwell inserts containing CFTR-expressing FRT cells were mounted in Ussing chambers (Physiologic Instruments, San Diego, CA). The apical bath was filled with a half-Cl-solution and the basolateral bath was filled with HCO$_3$-buffered solution to generate transepithelial Cl-gradient (apical, 64 mM; basolateral, 129 mM), and the basolateral membrane was permeabilized with 250 µg/mL amphotericin B. Cells were bathed for a 20 min stabilization period and aerated with 95% O$_2$/5% CO$_2$ at 37° C. Forskolin, test compounds, and CFTR$_{inh}$-172 were added to the apical and basolateral bath solution. Apical membrane current and short-circuit current were measured with an EVC4000 Multi-Channel V/I Clamp (World Precision Instruments, Sarasota, FL) and recorded using PowerLab 4/35 (AD Instruments, Castle Hill, Australia). Data were collected and analyzed with ADInstruments acquisition software Labchart Pro 7 software. The sampling rate was 4 Hz. The signal of Forskolin 20 µM was used as 100%/activity in data normalization and EC$_{50}$ calculation with GraphPad Prism 5.

Data

The EC$_{50}$ concentration ranges are summarized in Table 6 below. EC$_{50}$ (nM) concentration ranges: (A) refers to EC$_{50}$<200 nM; (B) refers to 200≤EC$_{50}$<2000 nM; and (C) refers to EC$_{50}$≥2000 nM.

TABLE 6

Short-circuit current measurement (EC$_{50}$)

| Cmpd No. | Concentration range | Cmpd No. | Concentration range | Cmpd No. | Concentration range |
|---|---|---|---|---|---|
| 2 | B | 3 | A | 6 | A |
| 7 | C | 8 | B | 9 | C |
| 10 | B | 11 | A | 12 | C |
| 14 | C | 15 | A | 17 | A |
| 28 | A | 31 | A | 33 | C |
| 36 | C | 41 | B | 69 | C |
| 72 | C | 78 | B | 86 | C |
| 96 | C | 97 | B | 100 | B |
| 105 | B | 106 | C | 111 | C |
| 126 | C | 127 | B | 129 | C |
| 130 | B | 131 | A | 132 | B |
| 133 | A | 135 | A | 136 | A |
| 137 | B | 140 | A | 141 | A |
| 142 | A | 144 | A | 146 | A |
| 147 | A | 149 | C | 151 | B |
| 158 | A | 159 | B | 186 | B |
| 197 | B | 198 | A | 200 | A |
| 205 | A | 210 | B | 212 | C |
| 256 | A | 257 | B | 259 | B |
| 271 | A | 274 | A | 277 | A |
| 280 | A | 285 | A | 289 | A |

Example 6—CFTR Modulators in Scopolamine Induced Tear Volume Reduction Model

This example demonstrates the change in tear volume in mice that were dosed with CFTR modulator compounds in the tear volume reduction model as induced by Scopolamine.

Materials

Seven-week old C57BL/6 female mice were used.

Scopolamine hydrobromide was purchased from Sigma Aldrich (Cat No. S0929), dissolved in saline, and sterilized prior to use.

Zone-Quick phenol red thread was obtained from Menicon.

Phosphate buffered saline (PBS, pH 7.5, 17% 0.0667 M NaH$_2$PO$_4$/83% 0.066M Na$_2$HPO$_4$) was prepared.

The test compounds used in this experiment were dissolved in PBS containing 1% of surfactant.

Scopolamine (0.2 ml of 2.5 mg/mL solution) was injected subcutaneously 3 times a day to induce a decrease in the tear volume in the mouse. At the same time, the ophthalmic solution of test compounds or vehicle were topically administered on to both eyes 3 times day. Tear volume was measured by phenol red thread before dosing (basal level) and 1 hour after the last administration of scopolamine and ophthalmic solution. The results were obtained by measuring the length of the phenol red thread turning red by tears. The schedule of study is expressed as FIG. 1.

Results

On day 2, the amount of tear in mice injected with scopolamine decreased to about 50%/of the basal level. This tear reduction showed a tendency to alleviate in mice administered with some test compounds compared to that of vehicle-treated mice.

The results are summarized in Table 7 as the ratio of tear volume of test compound treatment group to that of vehicle treatment group. If the test compound was evaluated twice, the average value was used.

TABLE 7

Tear Volume Reduction Model Results

| Cmpd No. | Ratio of tear volume (test compound to vehicle) | Cmpd No. | Ratio of tear volume (test compound to vehicle) | Cmpd No. | Ratio of tear volume (test compound to vehicle) |
|---|---|---|---|---|---|
| 2 | 1.40 | 3 | 1.20 | 6 | 1.58 |
| 9 | 1.16 | 10 | 1.89 | 15 | 1.29 |
| 36 | 1.23 | 69 | 0.76 | 72 | 1.06 |
| 96 | 1.35 | 97 | 0.95 | 126 | 0.97 |
| 140 | 1.48 | 141 | 1.34 | 144 | 1.18 |
| 147 | 1.03 | 149 | 1.26 | 151 | 1.40 |
| 158 | 1.40 | 159 | 2.11 | 186 | 1.05 |
| 197 | 1.18 | 205 | 1.12 | 210 | 1.43 |
| 212 | 1.43 | 257 | 1.16 | 259 | 0.94 |
| 271 | 1.17 | 272 | 1.14 | 273 | 0.80 |
| 274 | 1.07 | 276 | 1.21 | 280 | 1.32 |

Example 7—Human Phosphodiesterase 4 (PDE4) Inhibition

Experimental Procedures

Chinese Human recombinant PDE4A1A, PDE4B, PDE4C$_1$ and PDE4D2 are respectively expressed in each host cell (insect Sf9 cells, BPS Bioscience). Preincubation of 10 μM test compounds or vehicle was proceeded with 20 ng/ml PDE4A1A or 4 ng/ml PDE4B 1 or 8 ng/ml PDE4C1 or 5 ng/ml PDE4D2 enzyme in Tris-HCl buffer pH 7.2 for 15 minutes at 25° C. 100 nM fluorescein (FAM) labeled cAMP for another 30 minutes incubation period was added in order to initiate the enzymatic reaction and addition of IMAP binding solution was followed for its termination. Specifically, IMAP complexes with phosphate groups on nucleotide monophosphate generated from cyclic nucleotides through PDE activity. The amount of complex formed is determined by reading spectrofluorimetrical signal at 470 nm/525 nm.

Data

The PDE4 inhibitory effects are summarized in Table 8 below. PDE4 inhibition (% at 10 uM) ranges: (A) refers to ≥80% inhibition; (B) refers to 50%≤inhibition <80%; and (C) refers to <50% inhibition.

TABLE 8

Human Phosphodiesterase 4 (hPDE4) inhibition

| Cmpd No. | % inhibition range at 10 uM | | | |
|---|---|---|---|---|
| | PDE4A1A | PDE4B1 | PDE4C1 | PDE4D2 |
| 7 | C | C | C | C |
| 10 | A | A | A | A |
| 11 | A | A | A | A |
| 12 | A | B | B | B |
| 15 | A | A | A | A |
| 33 | B | B | C | B |
| 41 | A | A | A | A |
| 96 | A | A | B | A |
| 97 | A | A | A | A |
| 105 | A | A | A | A |
| 129 | A | A | A | A |
| 135 | A | A | A | A |
| 136 | A | A | A | A |
| 144 | A | A | A | A |
| 147 | A | A | A | A |
| 151 | A | A | A | A |
| 192 | A | A | A | A |
| 194 | A | A | A | A |
| 198 | A | A | A | A |
| 205 | A | A | A | A |
| 210 | A | A | A | A |
| 239 | C | C | C | C |
| 257 | A | A | A | A |
| 287 | B | B | C | B |
| 323 | C | B | C | C |
| 352 | A | A | A | A |
| 355 | A | A | A | A |
| 380 | A | A | B | A |
| 384 | A | A | B | A |

7. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are herein incorporated by reference in their entirety, for all purposes.

What is claimed is:
1. A compound of formula (Ia):

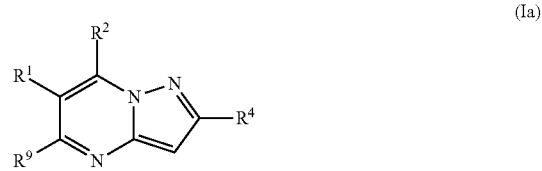

(Ia)

or a pharmaceutically acceptable salt or stereoisomer thereof,
wherein:
R$^1$ is H, halogen, C$_1$-C$_{10}$ alkyl, OC$_1$-C$_{10}$ alkyl, or aryl; wherein the C$_1$-C$_{10}$ alkyl or OC$_1$-C$_{10}$ alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, =S, cycloalkyl, heterocycloalkyl, aryl, and heteroaryl;

wherein the aryl is optionally substituted with one or more substituents independently selected from the group consisting of halogen, CN, NO$_2$, alkyl, alkyl(cycloalkyl), alkyl(heterocycloalkyl), aralkyl, alkyl(heteroaryl), alkenyl, aralkenyl, alkynyl, aralkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, S(O)$_t$OR$^a$, cycloalkyl, heterocycloalkyl, aryl, and heteroaryl;

wherein each alkyl, alkenyl, and alkynyl substituent, unless otherwise specified, is optionally and independently substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;

wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and wherein each aryl portion of aralkyl, heteroaryl portion of alkyl(heteroaryl), aryl portion of aralkenyl, aryl portion of aralkynyl, aryl, and heteroaryl substituent, unless otherwise specified, is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;

R$^2$ is phenyl;

wherein the phenyl is optionally substituted with one or more substituents independently selected from the group consisting of halogen, NO$_2$, C$_1$-C$_5$ alkyl, NH$_2$, OH, and OC$_1$-C$_5$ alkyl;

wherein each NH$_2$ substituent is optionally and independently substituted with one or more substituents independently selected from the group consisting of alkyl, alkyl(cycloalkyl), alkyl(heterocycloalkyl), aralkyl, alkyl(heteroaryl), alkenyl, aralkenyl, alkynyl, aralkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR(C(O)NR$^a$R$^a$, =O, S(O)$_t$R$^a$, S(O)$_t$NR$^a$R$^a$, S(O)$_t$OR$^a$, =S, cycloalkyl, heterocycloalkyl, aryl, and heteroaryl;

wherein each C$_1$-C$_5$ alkyl and OC$_1$-C$_5$ alkyl substituent is optionally and independently substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, =S, cycloalkyl, heterocycloalkyl, aryl, and heteroaryl;

wherein each alkyl, alkenyl, and alkynyl substituent is optionally and independently substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;

wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and wherein each aryl portion of aralkyl, heteroaryl portion of alkyl(heteroaryl), aryl portion of aralkenyl, aryl portion of aralkynyl, aryl, and heteroaryl substituent is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;

R$^4$ is C(O)NR$^5$R$^6$;

R$^5$ and R$^6$, taken together with the nitrogen atom to which they are attached, form piperazin-1-yl;

wherein the piperazin-1-yl is optionally substituted with one or more substituents independently selected from the group consisting of halogen, CN, NO$_2$, alkyl, alkyl(cycloalkyl), alkyl(heterocycloalkyl), aralkyl, alkyl(heteroaryl), alkenyl, aralkenyl, alkynyl, aralkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR(C(O)NR$^a$R$^a$, =O, S(O)$_t$R$^a$, S(O)$_t$NR$^a$R$^a$, S(O)$_t$OR$^a$, S, cycloalkyl, heterocycloalkyl, aryl, and heteroaryl;

wherein each alkyl, alkenyl, and alkynyl substituent is optionally and independently substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_r$R$^a$, S(O)$_t$NR$^a$R$^a$, S(O)$_t$OR$^a$, and =S;
  wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_r$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_r$R$^a$, S(O)$_t$NR$^a$R$^a$, S(O)$_t$OR$^a$, and =S; and
  wherein each aryl portion of aralkyl, heteroaryl portion of alkyl(heteroaryl), aryl portion of aralkenyl, aryl portion of aralkynyl, aryl, and heteroaryl substituent is optionally and independently substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_r$R$^a$, OR$^a$, OC(O)R$^a$, OC(O)NR$^a$R$^a$, OC(O)OR$^a$, OR$^c$C(O)NR$^a$R$^a$, S(O)$_r$R$^a$, S(O)$_t$NR$^a$R$^a$, and S(O)$_t$OR$^a$;

R$^9$ is H or halogen;

each R$^a$ is independently H, alkyl, alkyl(cycloalkyl), alkyl(heterocycloalkyl), aralkyl, alkyl(heteroaryl), cycloalkyl, heterocycloalkyl, aryl, or heteroaryl;
  wherein each alkyl is optionally and independently substituted with one or more substituents independently selected from the group consisting of halogen, CN, NO$_2$, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S;
  wherein each cycloalkyl portion of alkyl(cycloalkyl), heterocycloalkyl portion of alkyl(heterocycloalkyl), cycloalkyl, and heterocycloalkyl is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S; and
  wherein each aryl portion of aralkyl, heteroaryl portion of alkyl(heteroaryl), aryl, and heteroaryl is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, OR$^d$, OC(O)R$^d$, OC(O)NR$^d$R$^d$, OC(O)OR$^d$, OR$^c$C(O)NR$^d$R$^d$, S(O)$_r$R$^d$, S(O)$_t$NR$^d$R$^d$, and R$^e$S(O)$_t$OR$^d$;

each R$^b$ is independently H, alkyl, alkyl(cycloalkyl), alkyl(heterocycloalkyl), aralkyl, alkyl(heteroaryl), cycloalkyl, heterocycloalkyl, aryl, or heteroaryl;
  wherein each alkyl is optionally and independently substituted with one or more substituents independently selected from the group consisting of halogen, CN, NO$_2$, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S;
  wherein each cycloalkyl portion of alkyl(cycloalkyl), heterocycloalkyl portion of alkyl(heterocycloalkyl), cycloalkyl, and heterocycloalkyl is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S; and
  wherein each aryl portion of aralkyl, heteroaryl portion of alkyl(heteroaryl), aryl, and heteroaryl is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, OR$^d$, OC(O)R$^d$, OC(O)NR$^d$R$^d$, OC(O)OR$^d$, OR$^c$C(O)NR$^d$R$^d$, S(O)$_r$R$^d$, S(O)$_t$NR$^d$R$^d$, and R$^e$S(O)$_t$OR$^d$;

each R$^c$ is independently alkylene, alkylene(cycloalkyl), alkylene(heterocycloalkyl), aralkylene, alkylene(heteroaryl), cycloalkylene, heterocycloalkylene, arylene, or heteroarylene;
  wherein each alkylene is optionally and independently substituted with one or more substituents independently selected from the group consisting of halogen, CN, NO$_2$, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S;
  wherein each cycloalkyl portion of alkylene(cycloalkyl), heterocycloalkyl portion of alkylene(heterocycloalkyl), cycloalkylene, and heterocycloalkylene is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, =NH, =NNH$_2$, =NOH, OR$^d$, OC(O)R$^d$, OC(O)NR$^d$R$^d$, OC(O)OR$^d$, OR$^c$C(O)NR$^d$R$^d$, =O, S(O)$_r$R$^d$, S(O)$_t$NR$^d$R$^d$, R$^e$S(O)$_t$OR$^d$, and =S; and
  wherein each aryl portion of aralkylene, heteroaryl portion of alkylene(heteroaryl), arylene, and heteroarylene is optionally and independently substituted with one or more substituents independently selected from the group consisting of halogen, CN, NO$_2$, alkyl, haloalkyl, alkenyl, haloalkenyl, alkynyl, haloalkynyl, C(O)R$^d$, C(O)NR$^d$R$^d$, C(O)OR$^d$, NR$^d$R$^d$, NR$^d$C(O)R$^d$, NR$^d$C(O)OR$^d$, NR$^d$S(O)$_r$R$^d$, OR$^d$, OC(O)R$^d$, OC(O)NR$^d$R$^d$, OC(O)OR$^d$, OR$^c$C(O)NR$^d$R$^d$, S(O)$_r$R$^d$, S(O)$_t$NR$^d$R$^d$, and R$^e$S(O)$_t$OR$^d$;

each R$^d$ is independently H, alkyl, alkyl(cycloalkyl), alkyl(heterocycloalkyl), aralkyl, alkyl(heteroaryl), cycloalkyl, heterocycloalkyl, aryl, or heteroaryl;

each $R^e$ is an independently selected alkylene; and
each t is independently 1 or 2;
wherein any aforementioned $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OR^cC(O)NR^aR^a$, $OC(O)R^a$, $OC(O)NR^aR^a$, $OC(O)OR^a$, $S(O)_tR^a$, $S(O)_tNR^aR^a$, and $S(O)_tOR^a$ substituent is optionally and independently preceded by any $R^b$ other than H.

2. The compound of claim 1, wherein the compound is of formula (Ib):

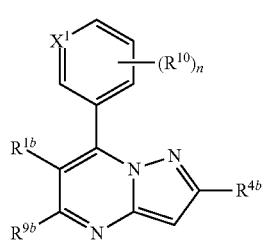

(Ib)

or a pharmaceutically acceptable salt or stereoisomer thereof,
wherein:
$X^1$ is $CR^{10'}$;
$R^{1b}$ is H, halogen, $C_1$-$C_{10}$ alkyl, $OC_1$-$C_{10}$ alkyl, or aryl;
  wherein the $C_1$-$C_{10}$ alkyl or $OC_1$-$C_{10}$ alkyl is optionally substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, =S, cycloalkyl, heterocycloalkyl, aryl, and heteroaryl;
  wherein the aryl is optionally substituted with one or more substituents independently selected from the group consisting of halogen, CN, $NO_2$, alkyl, alkyl(cycloalkyl), alkyl(heterocycloalkyl), aralkyl, alkyl(heteroaryl), alkenyl, aralkenyl, alkynyl, aralkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, $S(O)_tOR^a$, cycloalkyl, heterocycloalkyl, aryl, and heteroaryl;
  wherein each alkyl, alkenyl, and alkynyl substituent, unless otherwise specified, is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S;
  wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein each aryl portion of aralkyl, heteroaryl portion of alkyl(heteroaryl), aryl portion of aralkenyl, aryl portion of aralkynyl, aryl, and heteroaryl substituent, unless otherwise specified, is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, and $S(O)_tOR^a$;
$R^{4b}$ is $C(O)NR^5R^6$;
$R^{9b}$ is H or halogen;
each $R^{10}$ is independently H, halogen, $NO_2$, $C_1$-$C_5$ alkyl, $NH_2$, OH, or $OC_1$-$C_5$ alkyl;
  wherein each $NH_2$ is optionally and independently substituted with one or two independently selected alkyl substituents;
  wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein each $C_1$-$C_5$ alkyl and $OC_1$-$C_5$ alkyl is optionally and independently substituted with one or more independently selected halogen substituents;
$R^{10'}$ is H, halogen, $NO_2$, $C_1$-$C_5$ alkyl, $NH_2$, OH, or $OC_1$-$C_5$ alkyl;
  wherein the $NH_2$ is optionally substituted with one or two independently selected alkyl substituents;
  wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein the $C_1$-$C_5$ alkyl or $OC_1$-$C_5$ alkyl is optionally substituted with one or more independently selected halogen substituents; and
n is 0, 1, 2, 3, or 4;
wherein any aforementioned $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OR^cC(O)NR^aR^a$, $OC(O)R^a$, $OC(O)NR^aR^a$, $OC(O)OR^a$, $S(O)_tR^a$, $S(O)_tNR^aR^a$, and $S(O)_tOR^a$ substituent is optionally and independently preceded by any $R^b$ other than H.

3. The compound of claim 2, or a pharmaceutically acceptable salt or stereoisomer thereof, wherein:
each $R^{10}$ is independently H, F, Cl, $NO_2$, $CH_3$, $CF_3$, $N(CH_3)_2$, OH, $OCH_3$, or $OCF_3$; and
$R^{10'}$ is H, F, Cl, $NO_2$, $CH_3$, $CF_3$, $N(CH_3)_2$, OH, $OCH_3$, or $OCF_3$.

4. The compound of claim 2, wherein the compound is of formula (Ic):

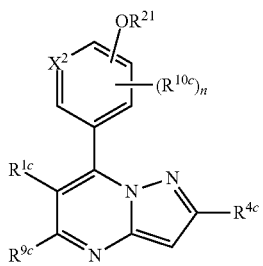
(Ic)

or a pharmaceutically acceptable salt or stereoisomer thereof,
wherein:
$X^2$ is $CR^{10c'}$;
$R^{1c}$ is H, halogen, $C_1$-$C_{10}$ alkyl, $OC_1$-$C_{10}$ alkyl, or aryl;
wherein the $C_1$-$C_{10}$ alkyl or $OC_1$-$C_{10}$ alkyl is optionally substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, =S, cycloalkyl, heterocycloalkyl, aryl, and heteroaryl;
wherein the aryl is optionally substituted with one or more substituents independently selected from the group consisting of halogen, CN, $NO_2$, alkyl, alkyl(cycloalkyl), alkyl(heterocycloalkyl), aralkyl, alkyl(heteroaryl), alkenyl, aralkenyl, alkynyl, aralkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, $S(O)_tOR^a$, cycloalkyl, heterocycloalkyl, aryl, and heteroaryl;
wherein each alkyl, alkenyl, and alkynyl substituent, unless otherwise specified, is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S;
wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and wherein each aryl portion of aralkyl, heteroaryl portion of alkyl(heteroaryl), aryl portion of aralkenyl, aryl portion of aralkynyl, aryl, and heteroaryl substituent, unless otherwise specified, is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, and $S(O)_tOR^a$;
$R^{4c}$ is $C(O)NR^5R^6$;
$R^{9c}$ is H or halogen;
each $R^{10c}$ is independently H, halogen, $NO_2$, $C_1$-$C_5$ alkyl, $NH_2$, OH, or $OC_1$-$C_5$ alkyl;
wherein each $NH_2$ is optionally and independently substituted with one or two independently selected alkyl substituents;
wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
wherein each $C_1$-$C_5$ alkyl and $OC_1$-$C_5$ alkyl is optionally and independently substituted with one or more independently selected halogen substituents;
is H, halogen, $NO_2$, $C_1$-$C_5$ alkyl, $NH_2$, OH, or $OC_1$-$C_5$ alkyl;
wherein the $NH_2$ is optionally substituted with one or two independently selected alkyl substituents;
wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
wherein the $C_1$-$C_5$ alkyl or $OC_1$-$C_5$ alkyl is optionally substituted with one or more independently selected halogen substituents;
$R^{21}$ is H or $C_1$-$C_5$ alkyl, wherein the $C_1$-$C_5$ alkyl is optionally substituted with one or more independently selected halogen substituents; and
n is 0, 1, 2, or 3;
wherein any aforementioned $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, OR', $OR^cC(O)NR^aR^a$, $OC(O)R^a$, $OC(O)NR^aR^a$, $OC(O)OR^a$, $S(O)_tR^a$, $S(O)_tNR^aR^a$, and $S(O)_tOR^a$ substituent is optionally and independently preceded by any $R^b$ other than H.

5. The compound of claim 4, wherein the compound is of formula (Id):

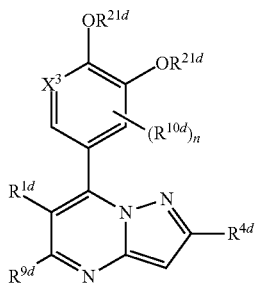

(Id)

or a pharmaceutically acceptable salt or stereoisomer thereof,
wherein:
$X^3$ is $CR^{10d'}$;
$R^{1d}$ is H, halogen, $C_1$-$C_{10}$ alkyl, $OC_1$-$C_{10}$ alkyl, or aryl;
  wherein the $C_1$-$C_{10}$ alkyl or $OC_1$-$C_{10}$ alkyl is optionally substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, =S, cycloalkyl, heterocycloalkyl, aryl, and heteroaryl;
  wherein the aryl is optionally substituted with one or more substituents independently selected from the group consisting of halogen, CN, $NO_2$, alkyl, alkyl(cycloalkyl), alkyl(heterocycloalkyl), aralkyl, alkyl(heteroaryl), alkenyl, aralkenyl, alkynyl, aralkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, $S(O)_tOR^a$, cycloalkyl, heterocycloalkyl, aryl, and heteroaryl;
  wherein each alkyl, alkenyl, and alkynyl substituent, unless otherwise specified, is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S;
  wherein each cycloalkyl portion of alkyl(cycloalkyl), heterocycloalkyl portion of alkyl(heterocycloalkyl), cycloalkyl, and heterocycloalkyl substituent is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein each aryl portion of aralkyl, heteroaryl portion of alkyl(heteroaryl), aryl portion of aralkenyl, aryl portion of aralkynyl, aryl, and heteroaryl substituent, unless otherwise specified, is optionally and independently substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, and $S(O)_tOR^a$;
$R^{4d}$ is $C(O)NR^5R^6$;
$R^{9d}$ is H or halogen;
each $R^{10d}$ is independently H, halogen, $NO_2$, $C_1$-$C_5$ alkyl, $NH_2$, OH, or $OC_1$-$C_5$ alkyl;
  wherein each $NH_2$ is optionally and independently substituted with one or two independently selected alkyl substituents;
  wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein each $C_1$-$C_5$ alkyl and $OC_1$-$C_5$ alkyl is optionally and independently substituted with one or more independently selected halogen substituents;
$R^{10d'}$ is H, halogen, $NO_2$, $C_1$-$C_5$ alkyl, $NH_2$, OH, or $OC_1$-$C_5$ alkyl;
  wherein the $NH_2$ is optionally substituted with one or two independently selected alkyl substituents;
  wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
  wherein the $C_1$-$C_5$ alkyl or $OC_1$-$C_5$ alkyl is optionally substituted with one or more independently selected halogen substituents;
each $R^{21d}$ is independently H or $C_1$-$C_5$ alkyl, wherein each $C_1$-$C_5$ alkyl is optionally and independently substituted with one or more independently selected halogen substituents; and
n is 0, 1, or 2;
wherein any aforementioned $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OR^cC(O)NR^aR^a$, $OC(O)R^a$, $OC(O)NR^aR^a$, $OC(O)OR^a$, $S(O)_tR^a$, $S(O)_tNR^aR^a$, and $S(O)_tOR^a$ substituent is optionally and independently preceded by any $R^b$ other than H.

6. The compound of claim 1, or a pharmaceutically acceptable salt or stereoisomer thereof, wherein:
$R^4$ is C(O)NR$^5$R$^6$; and
$R^5$ and $R^6$, taken together with the nitrogen atom to which they are attached, form:

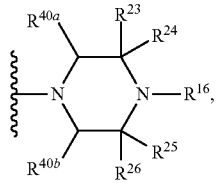

wherein:
$R^{16}$ is H, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;
$R^{23}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;
$R^{24}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;
$R^{25}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S (O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;

R$^{26}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
  wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
  wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
  wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)i0R$^a$;

R$^{40a}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
  wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
  wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
  wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)i0R$^a$; and R$^{40b}$ is H, halogen, NO$_2$, alkyl, C(O)R$^a$, C(O)NR$^a$R$^a$, C(O)OR$^a$, NR$^a$R$^a$, OR$^a$, cycloalkyl, heterocycloalkyl, aryl, or heteroaryl;
  wherein the alkyl is optionally substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
  wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S; and
  wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$.

7. The compound of claim 6, or a pharmaceutically acceptable salt or stereoisomer thereof, wherein:

R$^{23}$ is H, halogen, NO$_2$, C$_1$-C$_6$ alkyl, NH$_2$, OH, OC$_1$-C$_6$ alkyl, cycloalkyl, heterocycloalkyl, aryl, or heteroaryl;
  wherein the NH$_2$ is optionally substituted with one or two independently selected alkyl substituents;
  wherein each alkyl substituent of the NH$_2$ is optionally and independently substituted with one or more substituents independently selected from the group consisting of halogen, CN, NO$_2$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_1$R$^a$, =NH, =NNH$_2$, =NOH, OR$^a$, OC(O)R$^a$, OC(O)NR$^a$R$^a$, OC(O)OR$^a$, OR$^c$C(O)NR$^a$R$^a$, =O, S(O)$_t$R$^a$, S(O)$_t$NR$^a$R$^a$, S(O)$_t$OR$^a$, and =S;
  wherein the C$_1$-C$_6$ alkyl or OC$_1$-C$_6$ alkyl is optionally substituted with one or more independently selected halogen substituents;
  wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, =NH, =NNH$_2$, =NOH, OR$^a$, OC(O)R$^a$, OC(O)NR$^a$R$^a$, OC(O)OR$^a$, ORIC(O)NR$^a$R$^a$, =O, S(O)$_t$R$^a$, S(O)$_t$NR$^a$R$^a$, S(O)$_t$OR$^a$, and =S; and
  wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^a$R$^a$, C(O)OR$^a$, NR$^a$R$^a$, NR$^a$C(O)R$^a$, NR$^a$C(O)OR$^a$, NR$^a$S(O)$_t$R$^a$, OR$^a$, OC(O)R$^a$, OC(O)NR$^a$R$^a$, OC(O)OR$^a$, OR$^c$C(O)NR$^a$R$^a$, S(O)$_t$R$^a$, S(O)$_t$NR$^a$R$^a$, and S(O)$_t$OR$^a$;

R$^{24}$ is H, halogen, NO$_2$, C$_1$-C$_6$ alkyl, NH$_2$, OH, OC$_1$-C$_6$ alkyl, cycloalkyl, heterocycloalkyl, aryl, or heteroaryl;
  wherein the NH$_2$ is optionally substituted with one or two independently selected alkyl substituents;

wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S;

wherein the $C_1$-$C_6$ alkyl or $OC_1$-$C_6$ alkyl is optionally substituted with one or more independently selected halogen substituents;

wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, =NH, =$NNH_2$, =NOH, $OR^a$, $OC(O)R^a$, $OC(O)NR^aR^a$, $OC(O)OR^a$, $ORIC(O)NR^aR^a$, =O, $S(O)_rR^a$, $S(O)_rNR^aR^a$, $S(O)_rOR^a$, and =S; and wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, $OR^a$, $OC(O)R^a$, $OC(O)NR^aR^a$, $OC(O)OR^a$, $OR^cC(O)NR^aR^a$, $S(O)_rR^a$, $S(O)_rNR^aR^a$, and $S(O)_rOR^a$;

$R^{25}$ is H, halogen, $NO_2$, $C_1$-$C_6$ alkyl, $NH_2$, OH, $OC_1$-$C_6$ alkyl, cycloalkyl, heterocycloalkyl, aryl, or heteroaryl;

wherein the $NH_2$ is optionally substituted with one or two independently selected alkyl substituents;

wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S;

wherein the $C_1$-$C_6$ alkyl or $OC_1$-$C_6$ alkyl is optionally substituted with one or more independently selected halogen substituents;

wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S; and wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, $OR^a$, $OC(O)R^a$, $OC(O)NR^aR^a$, $OC(O)OR^a$, $OR^cC(O)NR^aR^a$, $S(O)_rR^a$, $S(O)_rNR^aR^a$, and $S(O)_rOR^a$;

$R^{26}$ is H, halogen, $NO_2$, $C_1$-$C_6$ alkyl, $NH_2$, OH, $OC_1$-$C_6$ alkyl, cycloalkyl, heterocycloalkyl, aryl, or heteroaryl;

wherein the $NH_2$ is optionally substituted with one or two independently selected alkyl substituents;

wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S;

wherein the $C_1$-$C_6$ alkyl or $OC_1$-$C_6$ alkyl is optionally substituted with one or more independently selected halogen substituents;

wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S; and wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_rR^a$, $OR^a$, $OC(O)R^a$, $OC(O)NR^aR^a$, $OC(O)OR^a$, $OR^cC(O)NR^aR^a$, $S(O)_rR^a$, $S(O)_rNR^aR^a$, and $S(O)_rOR^a$;

$R^{40a}$ is H, halogen, $NO_2$, $C_1$-$C_6$ alkyl, $NH_2$, OH, $OC_1$-$C_6$ alkyl, cycloalkyl, heterocycloalkyl, aryl, or heteroaryl;

wherein the $NH_2$ is optionally substituted with one or two independently selected alkyl substituents;

wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_rR^a$, $S(O)_rNR^aR^a$, $S(O)_rOR^a$, and =S;

wherein the $C_1$-$C_6$ alkyl or $OC_1$-$C_6$ alkyl is optionally substituted with one or more independently selected halogen substituents;

wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_1R^a$, $S(O)_rNR^aR^a$, $S(O)_rOR^a$, and =S; and wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, $OR^a$, $OC(O)R^a$, $OC(O)NR^aR^a$, $OC(O)OR^a$, $OR^cC(O)NR^aR^a$, $S(O)_1R^a$, $S(O)_rNR^aR^a$, and $S(O)_rOR^a$; and $R^{40b}$ is H, halogen, $NO_2$, $C_1$-$C_6$ alkyl, $NH_2$, OH, $OC_1$-$C_6$ alkyl, cycloalkyl, heterocycloalkyl, aryl, or heteroaryl;
wherein the $NH_2$ is optionally substituted with one or two independently selected alkyl substituents;
wherein each alkyl substituent of the $NH_2$ is optionally and independently substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S;
wherein the $C_1$-$C_6$ alkyl or $OC_1$-$C_6$ alkyl is optionally substituted with one or more independently selected halogen substituents;
wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, =NH, =$NNH_2$, =NOH, $OR^a$, $OC(O)R^a$, $OC(O)NR^aR^a$, $OC(O)OR^a$, $ORlC(O)NR^aR^a$, =O, $S(O)_1R^a$, $S(O)_tNR^aR^a$, $S(O)_tOR^a$, and =S; and
wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_1R^a$, $OR^a$, $OC(O)R^a$, $OC(O)NR^aR^a$, $OC(O)OR^a$, $OR^cC(O)NR^aR^a$, $S(O)_1R^a$, $S(O)_tNR^aR^a$, and $S(O)_tOR^a$.

8. The compound of claim 6, or a pharmaceutically acceptable salt or stereoisomer thereof, wherein

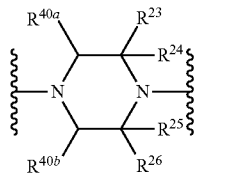

is:

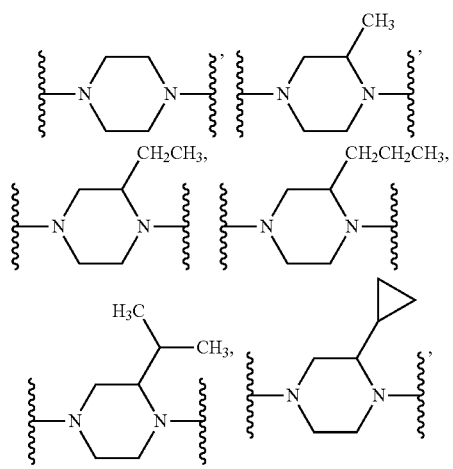

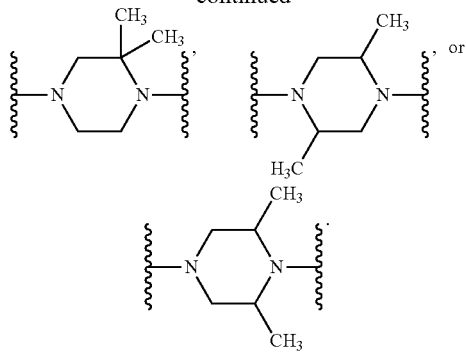

9. The compound of claim 1, or a pharmaceutically acceptable salt or stereoisomer thereof, wherein:
$R^4$ is $C(O)NR^5R^6$; and
$R^5$ and $R^6$, taken together with the nitrogen atom to which they are attached, form:

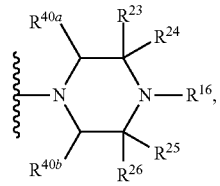

wherein:
(i) $R^{16}$ is —$C_1$-$C_6$ alkylene-$R^{210}$;
wherein the $C_1$-$C_6$ alkylene is optionally substituted with one or more substituents independently selected from the group consisting of halogen, CN, $NO_2$, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
$R^{210}$ is cycloalkyl, heterocycloalkyl, aryl, or heteroaryl;
wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, =NH, =$NNH_2$, =NOH, $OR^a$, $OC(O)R^a$, $OC(O)NR^aR^a$, $OC(O)OR^a$, $OR^cC(O)NR^aR^a$, =O, $S(O)_tR^a$, $S(O)_tNR^aR^a$, $S(O)_tOR^a$, and =S; and
wherein the aryl or heteroaryl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)NR^aR^a$, $C(O)OR^a$, $NR^aR^a$, $NR^aC(O)R^a$, $NR^aC(O)OR^a$, $NR^aS(O)_tR^a$, $OR^a$, $OC(O)R^a$, $OC(O)NR^aR^a$, $OC(O)OR^a$, $OR^cC(O)NR^aR^a$, $S(O)_tR^a$, $S(O)_tNR^aR^a$, and $S(O)_tOR^a$; or
(ii) $R^{16}$ is —$S(O)_t$-$R^{210}$;
$R^{210}$ is cycloalkyl, heterocycloalkyl, aryl, or heteroaryl;
wherein the cycloalkyl or heterocycloalkyl is optionally substituted with one or more substituents independently selected from the group consisting of halogen, CN, $NO_2$, alkyl, haloalkyl, alkenyl, haloalkenyl, alkynyl, haloalkynyl, $C(O)R^a$, $C(O)N$-

$R^aR^a$, $C(O)OR^a$, $NR^aR^a$, $NR^aC(O)R^a$, $NR^aC(O)OR^a$, $NR^aS(O)_tR^a$, =NH, =NNH$_2$, =NOH, OR$^a$, OC(O)R$^a$, OC(O)NR$^aR^a$, OC(O)OR$^a$, OR$^cC(O)NR^aR^a$, =O, S(O)$_t$R$^a$, S(O)$_t$NR$^aR^a$, S(O)$_t$OR$^a$, and =S; and wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, OR$^a$, OC(O)R$^a$, OC(O)NR$^aR^a$, OC(O)OR$^a$, OR$^cC(O)NR^aR^a$, S(O)$_t$R$^a$, S(O)$_t$NR$^aR^a$, and S(O)$_t$OR$^a$; and t is 1 or 2; or (iii) $R^{16}$ is $R^{210}$; and $R^{210}$ is cycloalkyl, heterocycloalkyl, aryl, or heteroaryl;
wherein the cycloalkyl or heterocycloalkyl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, =NH, =NNH$_2$, =NOH, OR$^a$, OC(O)R$^a$, OC(O)NR$^aR^a$, OC(O)OR$^a$, OR$^cC(O)NR^aR^a$, =O, S(O)$_t$R$^a$, S(O)$_t$NR$^aR^a$, S(O)$_t$OR$^a$, and =S; and wherein the aryl or heteroaryl is optionally substituted with one or more substituents independently selected from the group consisting of halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, OR$^a$, OC(O)R$^a$, OC(O)NR$^aR^a$, OC(O)OR$^a$, OR$^cC(O)NR^aR^a$, S(O)$_t$R$^a$, S(O)$_t$NR$^aR^a$, and S(O)$_t$OR$^a$.

10. The compound of claim 9, or a pharmaceutically acceptable salt or stereoisomer thereof, wherein

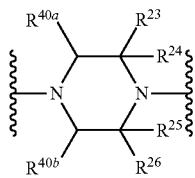

is:

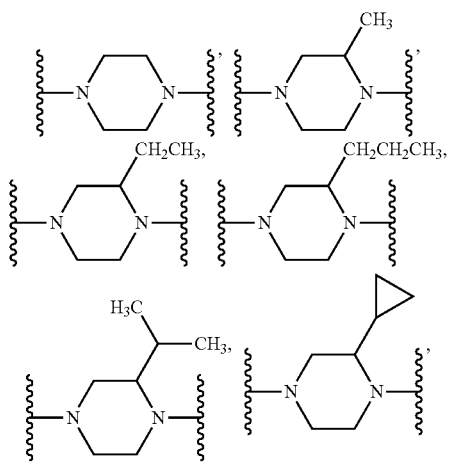

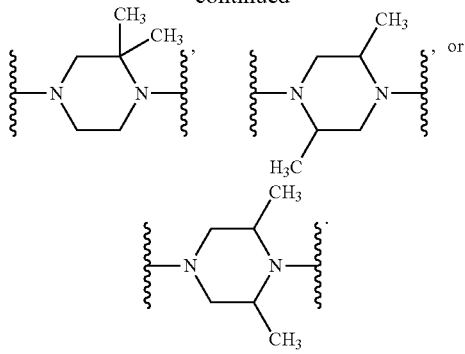

11. The compound of claim 9, or a pharmaceutically acceptable salt or stereoisomer thereof, wherein $R^{210}$ is:

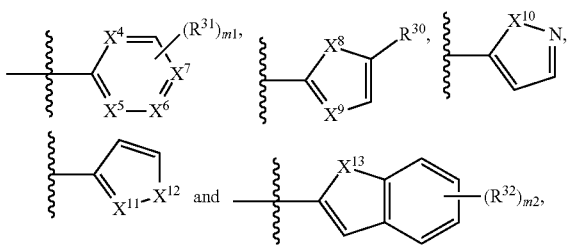

wherein:

$X^4$ is CH, CR$^{31}$, or N;

$X^5$ is CH, CR$^{31}$, or N;

$X^6$ is CH, CR$^{31}$, or N;

$X^7$ is CH, CR$^{31}$, or N;

$X^8$ is —NR$^{29}$—, —O—, or —S—;

$X^9$ is CH, CR$^{31}$, or N;

$X^{10}$ is —NR$^{29}$—, —O—, or —S—;

$X^{11}$ is CH, CR$^{31}$, or N;

$X^{12}$ is —NR$^{29}$—, —O—, or —S—;

$X^{13}$ is —NR$^{29}$—, —O—, or —S—;

$R^{29}$ is H or $C_1$-$C_6$ alkyl;

$R^{30}$ is halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, OR$^a$, OC(O)R$^a$, OC(O)NR$^aR^a$, OC(O)OR$^a$, OR$^cC(O)NR^aR^a$, S(O)$_t$R$^a$, S(O)$_t$NR$^aR^a$, or S(O)$_t$OR$^a$;

$R^{31}$ is halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, OR$^a$, OC(O)R$^a$, OC(O)NR$^aR^a$, OC(O)OR$^a$, OR$^cC(O)NR^aR^a$, S(O)$_t$R$^a$, S(O)$_t$NR$^aR^a$, or S(O)$_t$OR$^a$;

$R^{32}$ is H, halogen, CN, NO$_2$, alkyl, haloalkyl, alkenyl, haloalkenyl, alkynyl, haloalkynyl, C(O)R$^a$, C(O)NR$^aR^a$, C(O)OR$^a$, NR$^aR^a$, NR$^aC(O)R^a$, NR$^aC(O)OR^a$, NR$^aS(O)_tR^a$, OR$^a$, OC(O)R$^a$, OC(O)NR$^aR^a$, OC(O)OR$^a$, OR$^cC(O)NR^aR^a$, S(O)$_t$R$^a$, S(O)$_t$NR$^aR^a$, or S(O)$_t$OR$^a$;

$m^1$ is 0 or 1; and $m^2$ is 0, 1, 2, 3, 4, or 5.

12. The compound of claim 1, or a pharmaceutically acceptable salt or stereoisomer thereof, wherein $R^4$ is:
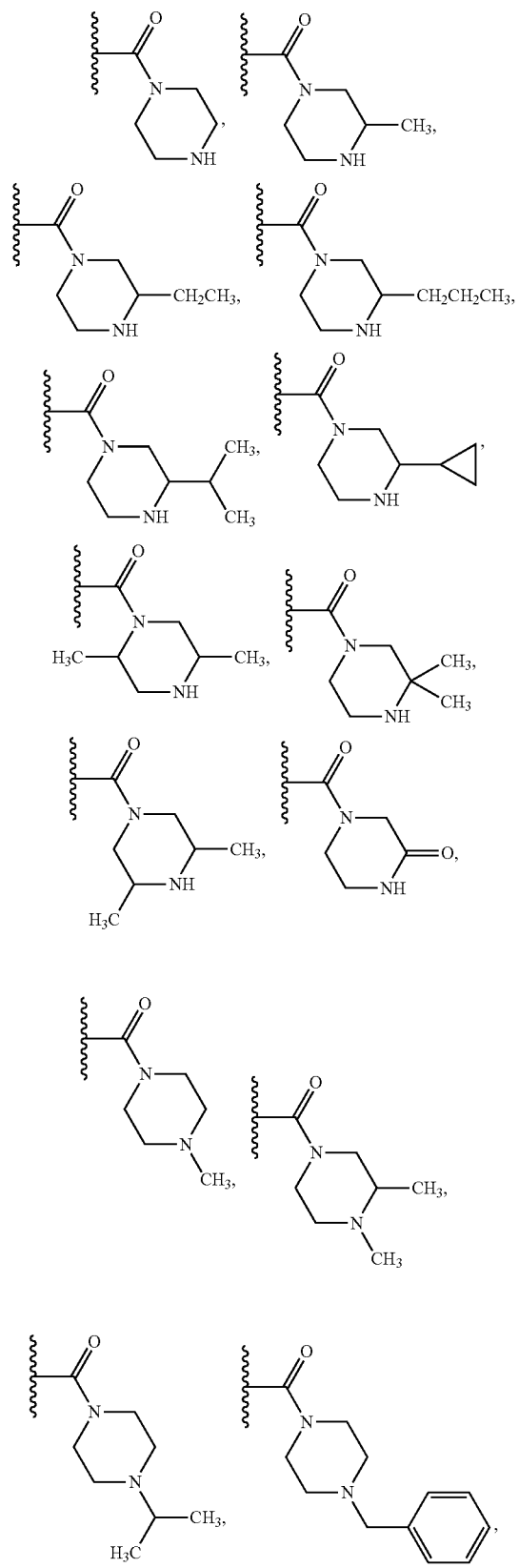
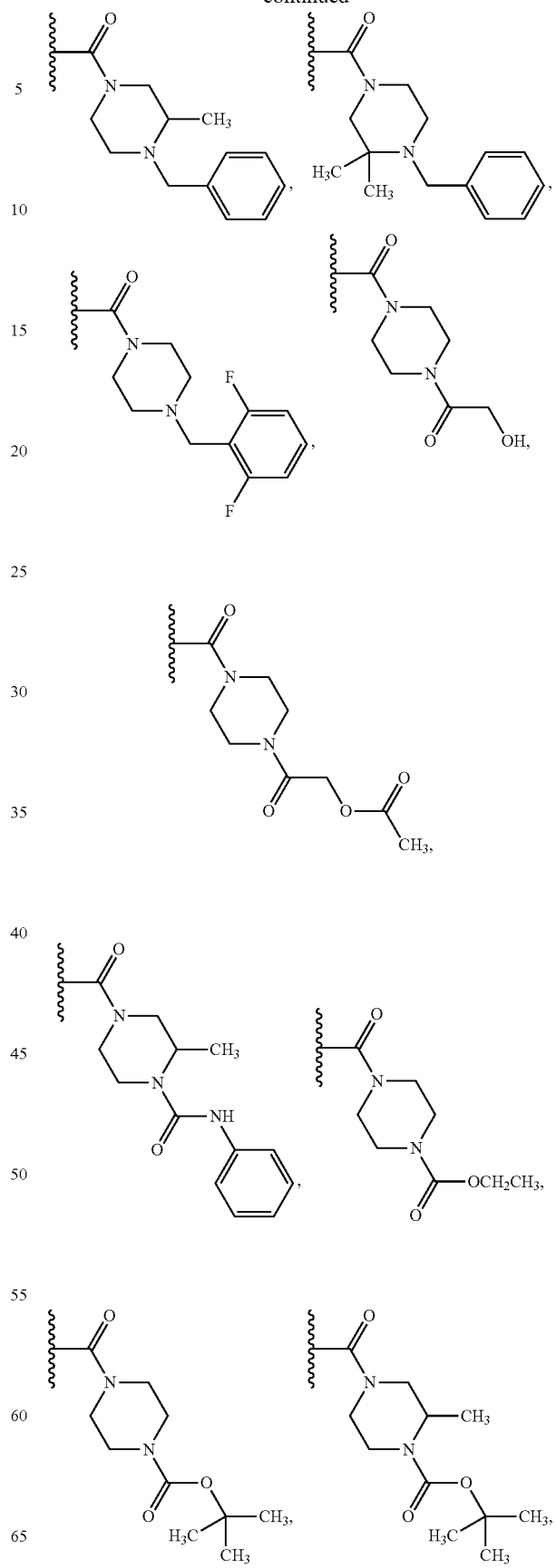

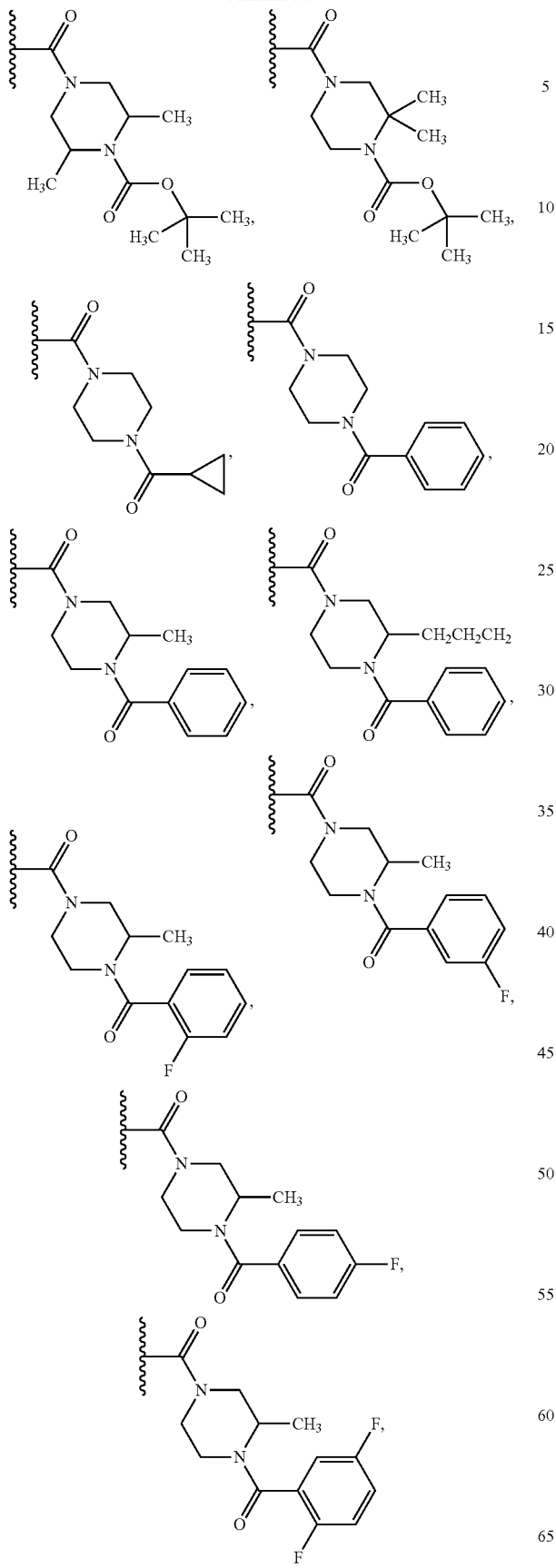
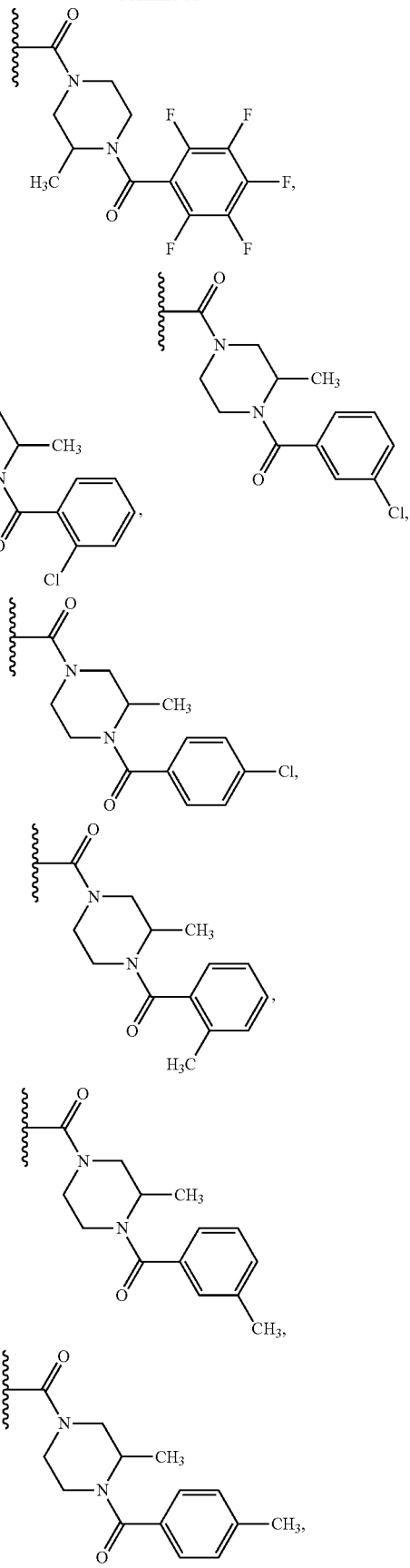

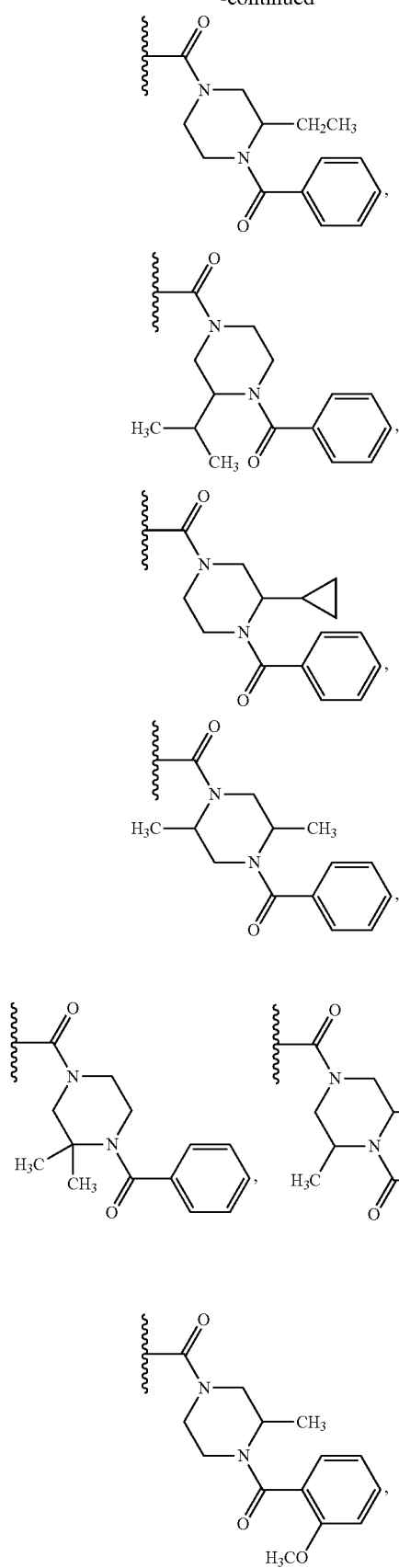
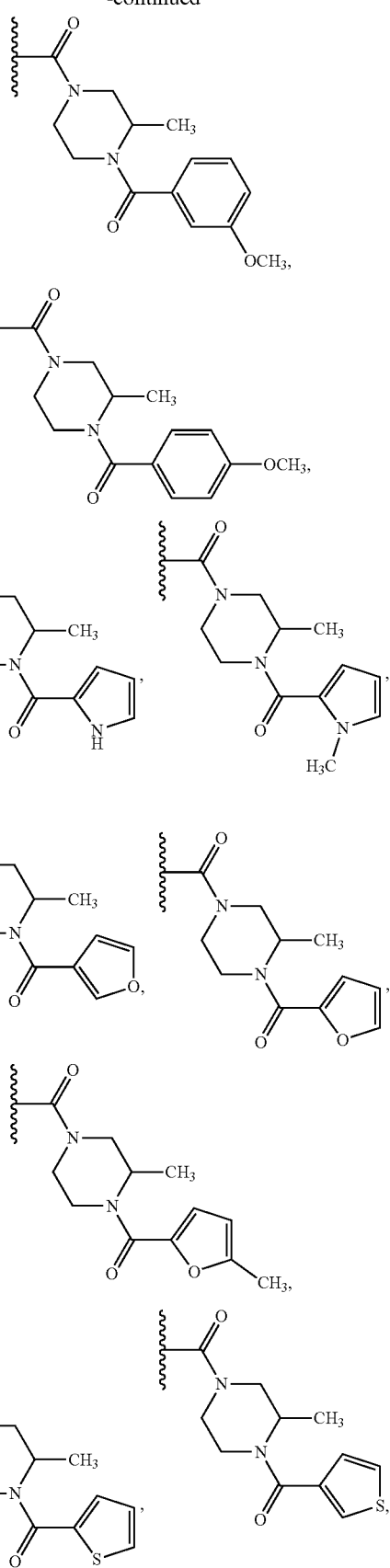

553
-continued
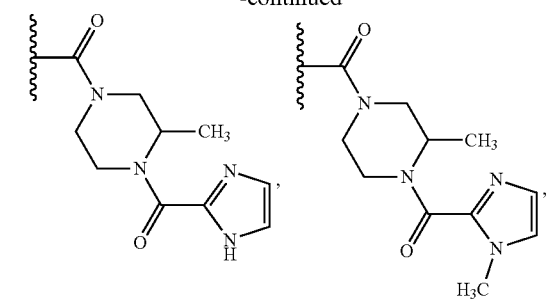
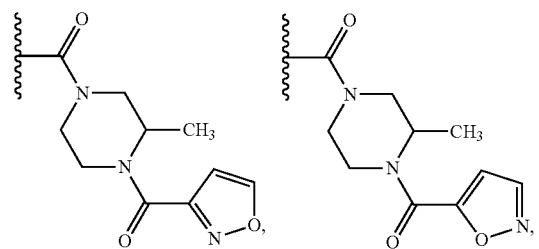
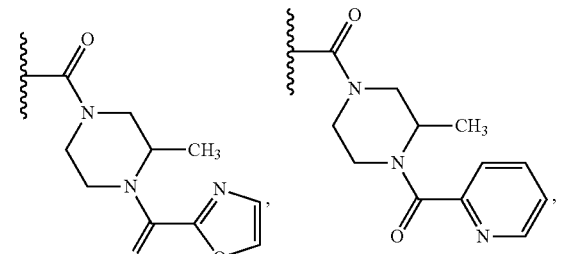
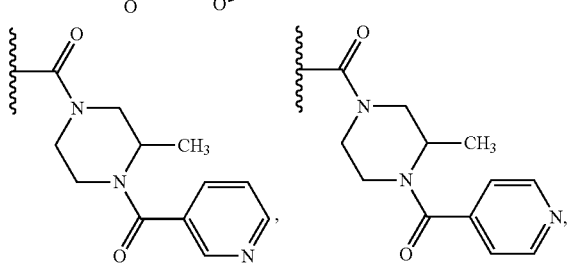
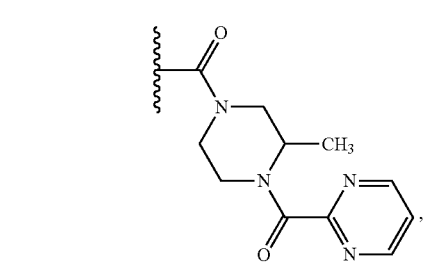
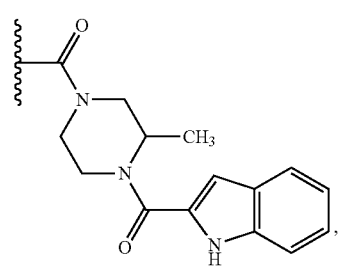
554
-continued
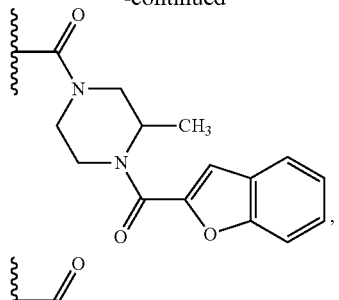
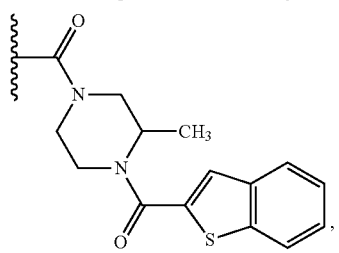
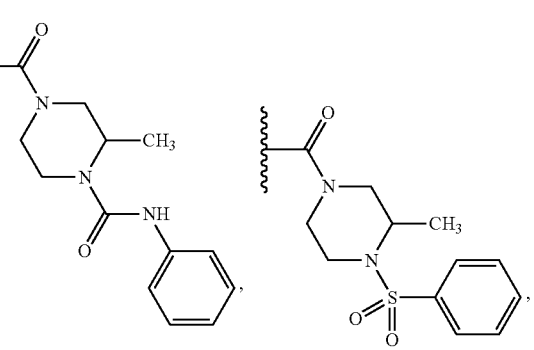
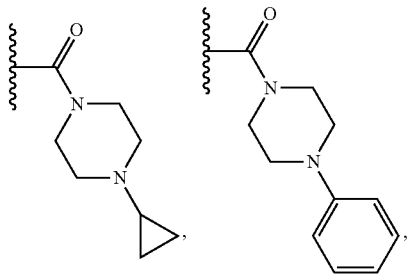
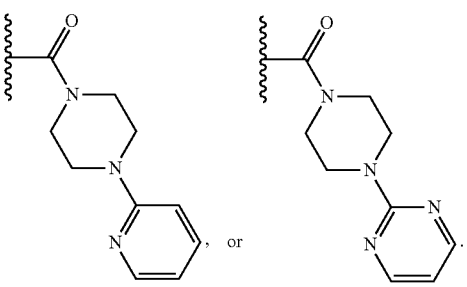

13. The compound of claim 1, wherein the compound is of formula (Ie):
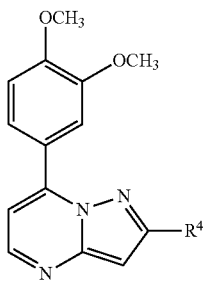
(Ie)
or a pharmaceutically acceptable salt or stereoisomer thereof.
14. The compound of claim 1, wherein the compound is selected from the group consisting of:
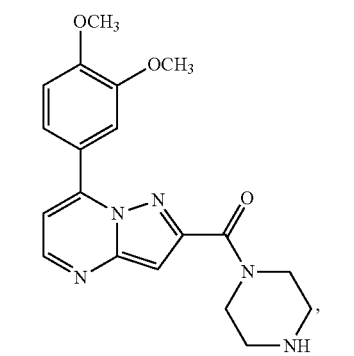
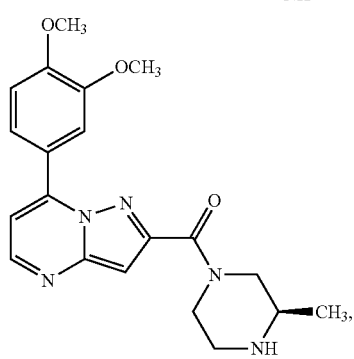
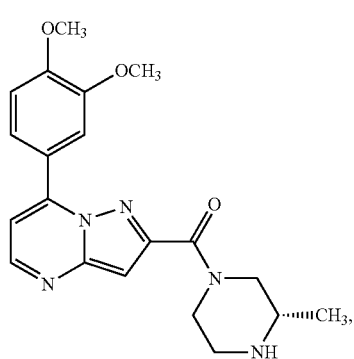
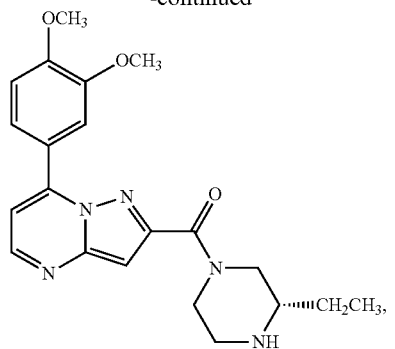
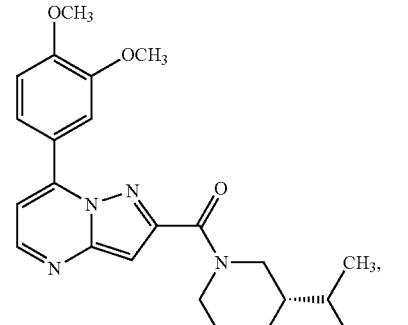
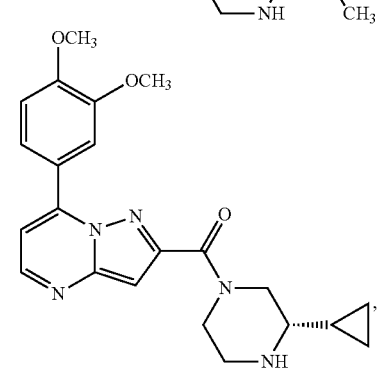
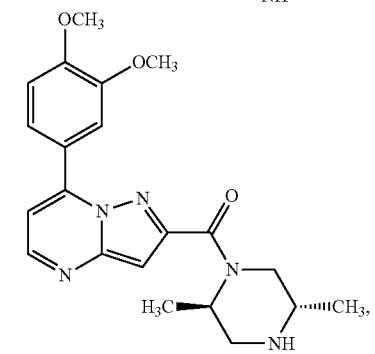
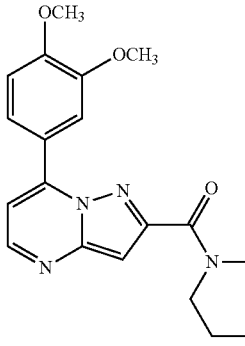

557
-continued
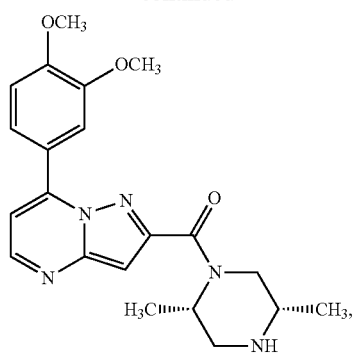
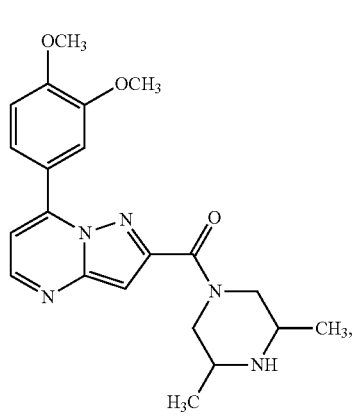
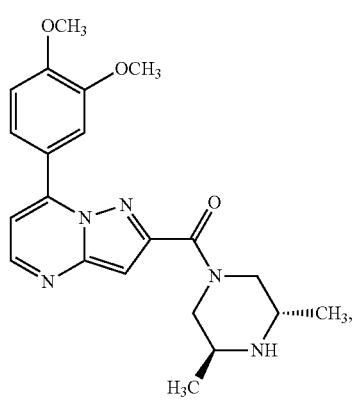
558
-continued
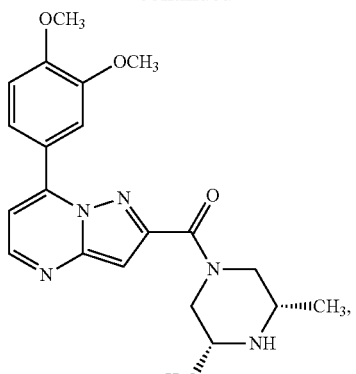
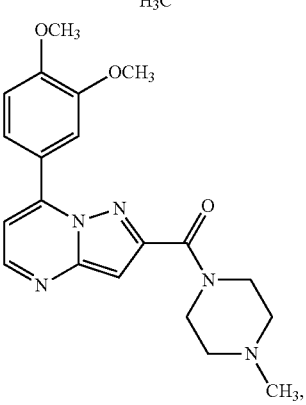
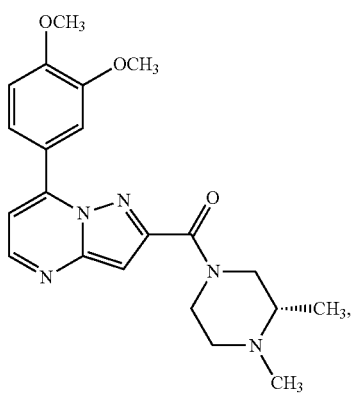

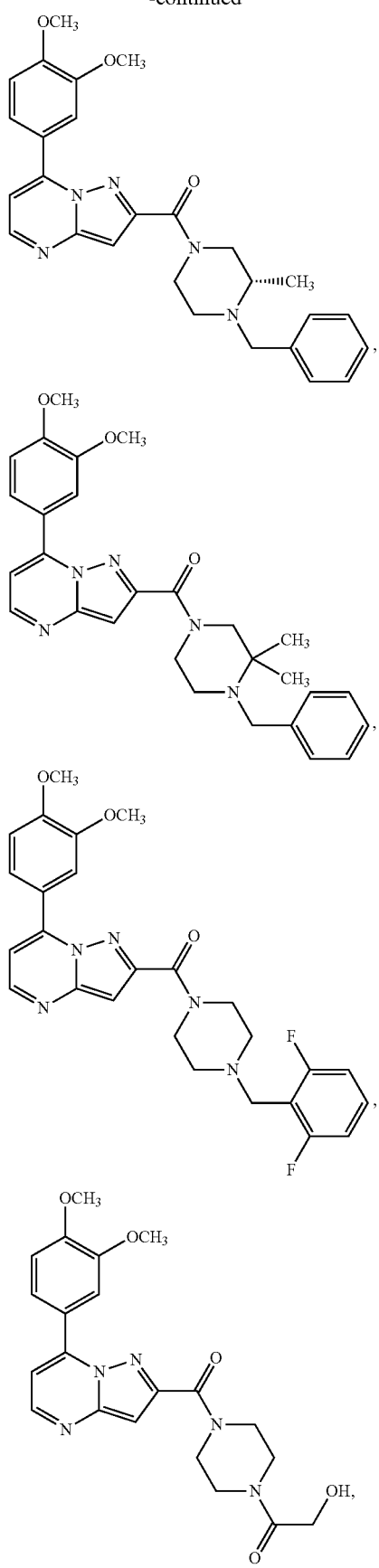
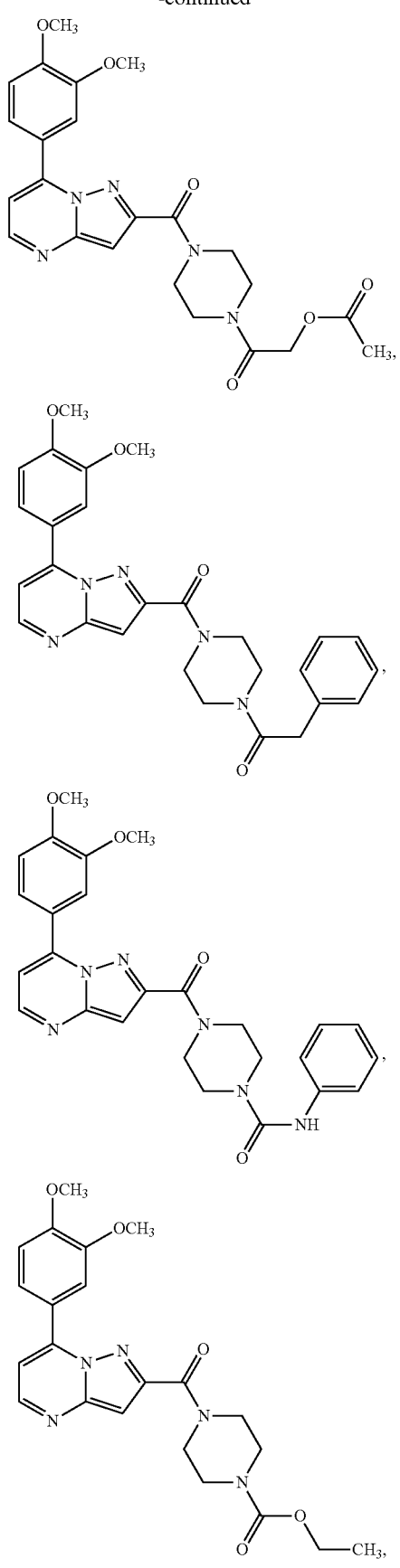

561
-continued
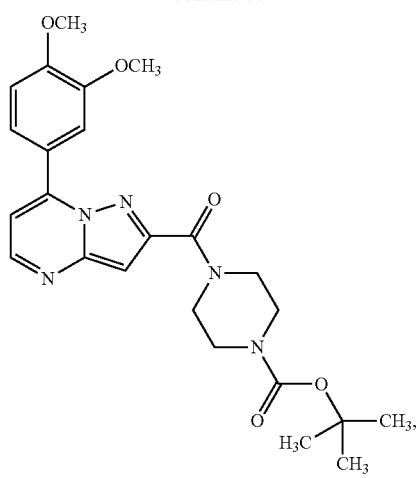
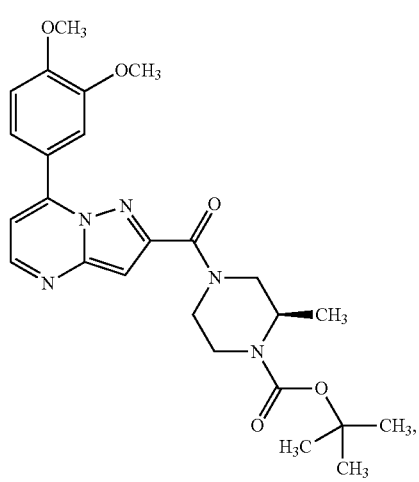
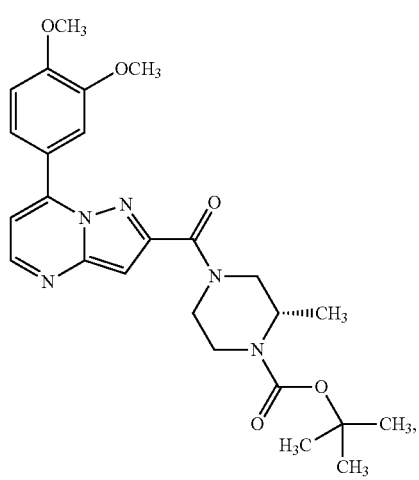
562
-continued
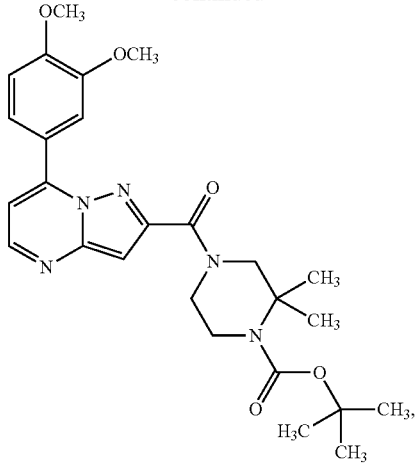
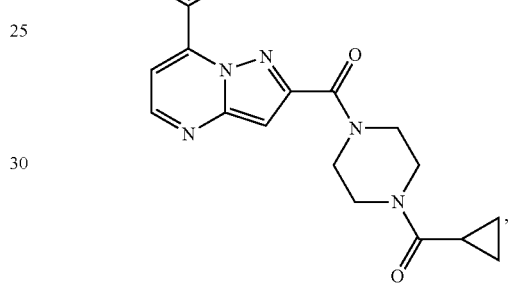
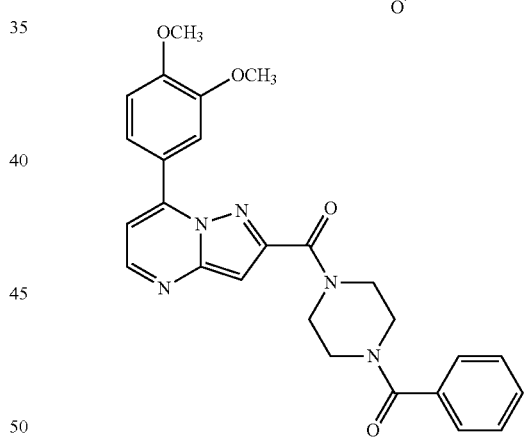
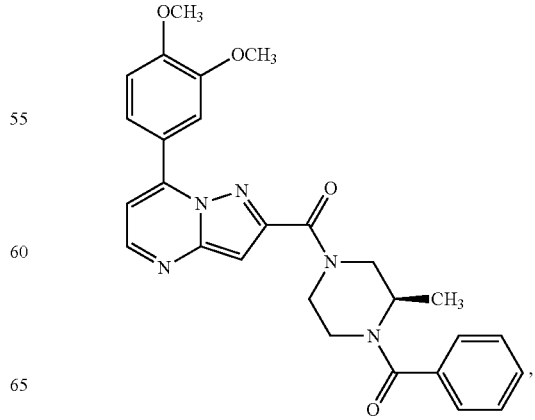

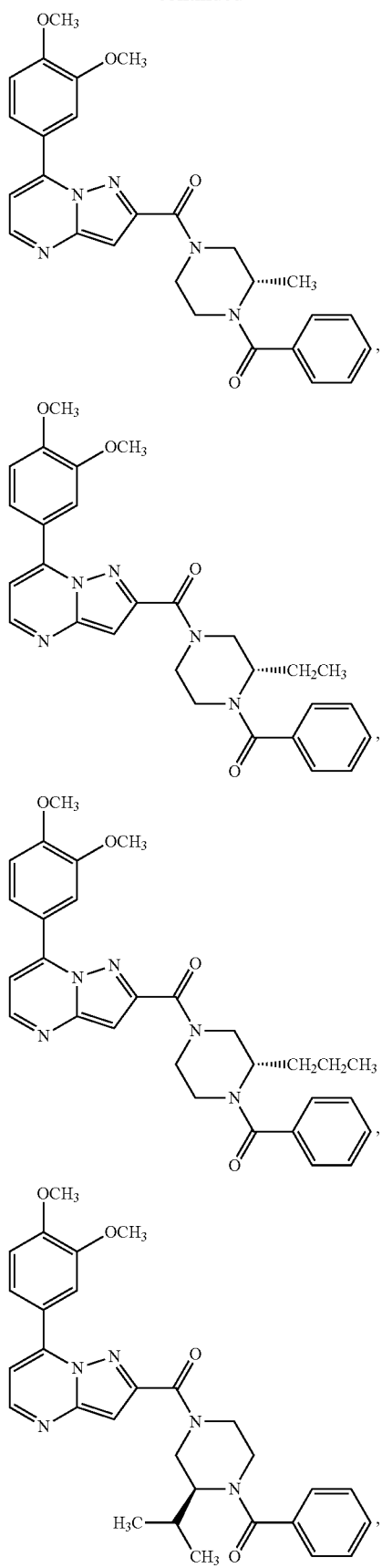
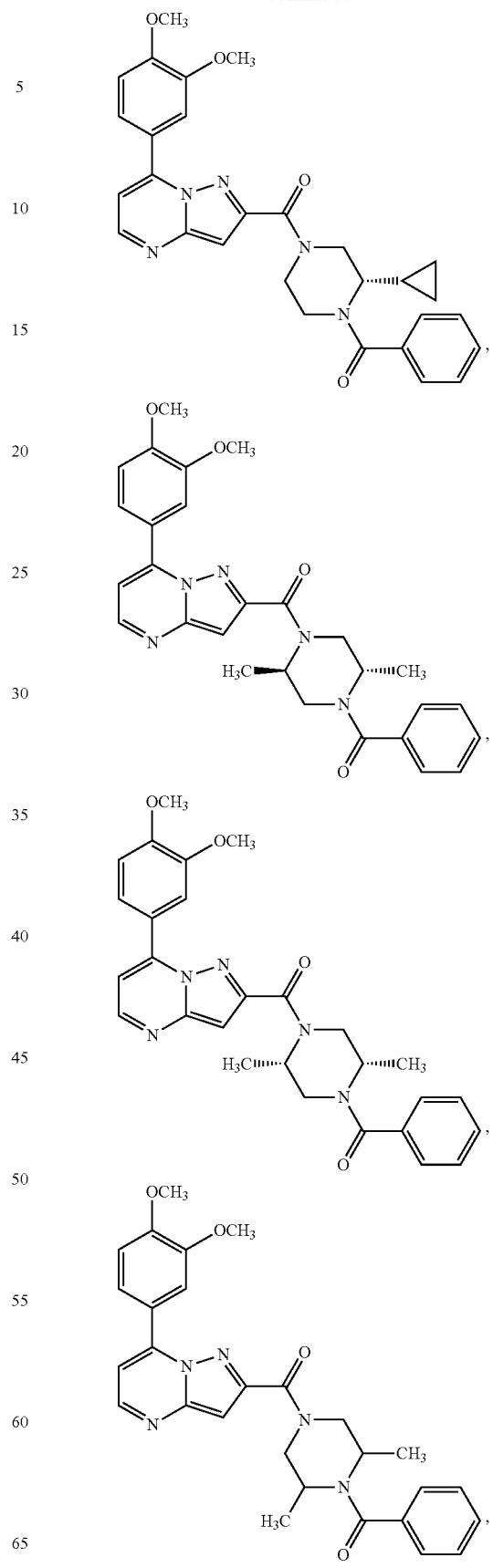

565
-continued
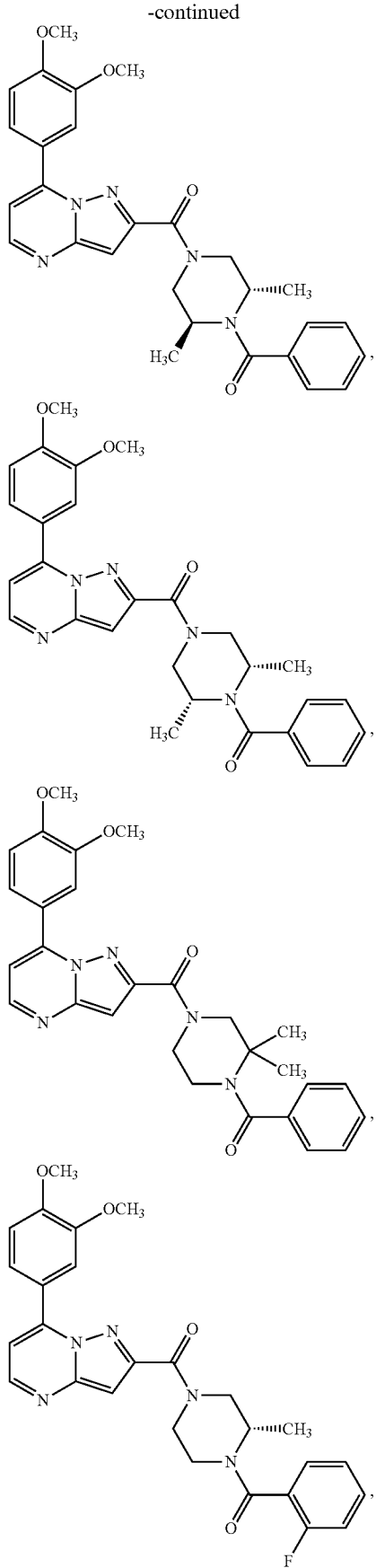
566
-continued
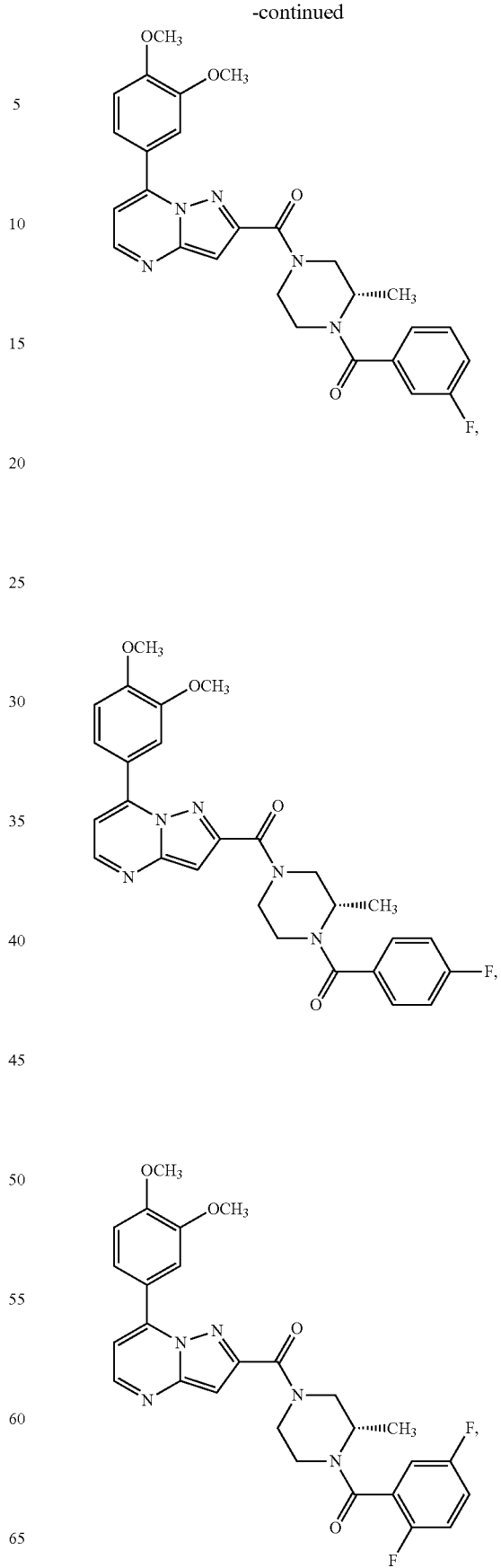

567
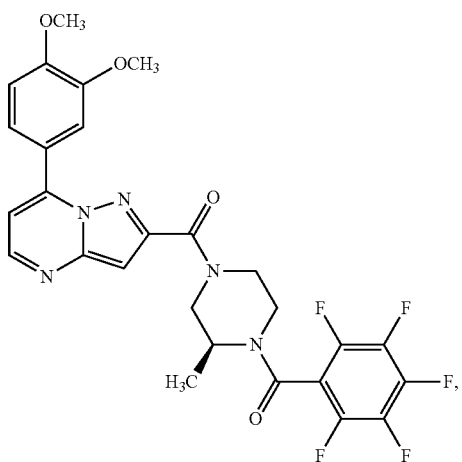
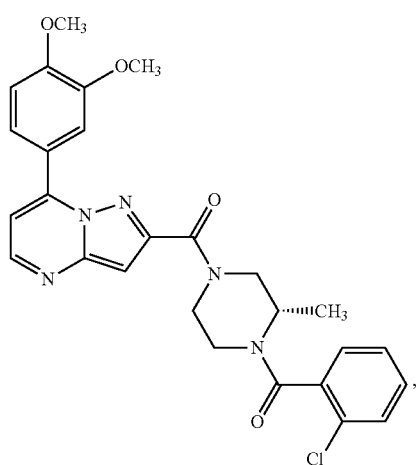
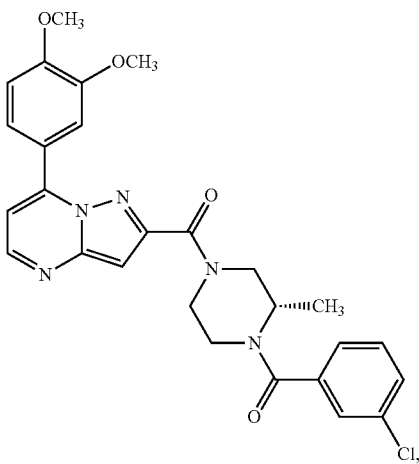
568
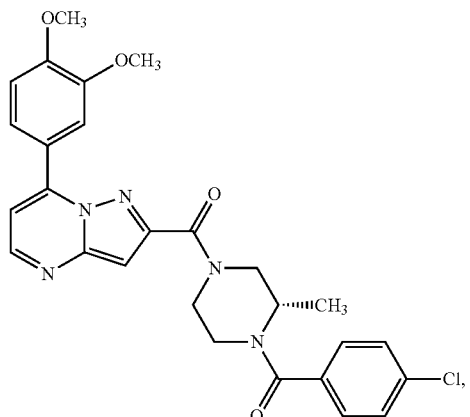
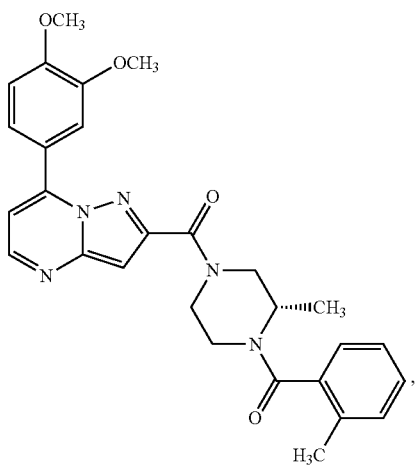
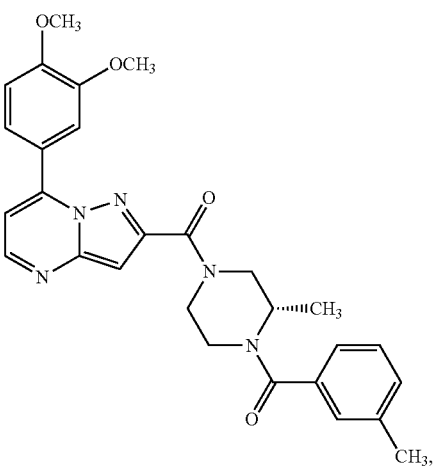

569
-continued
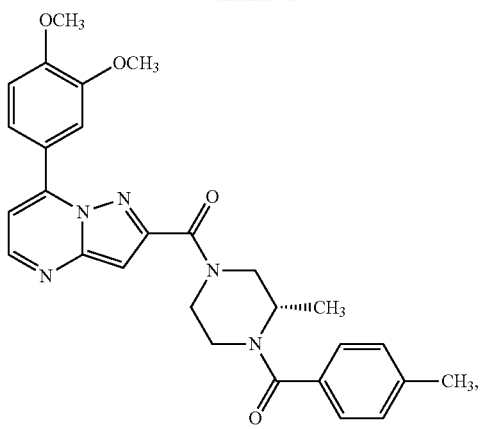
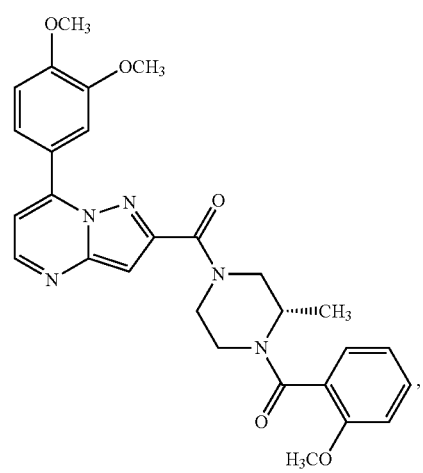
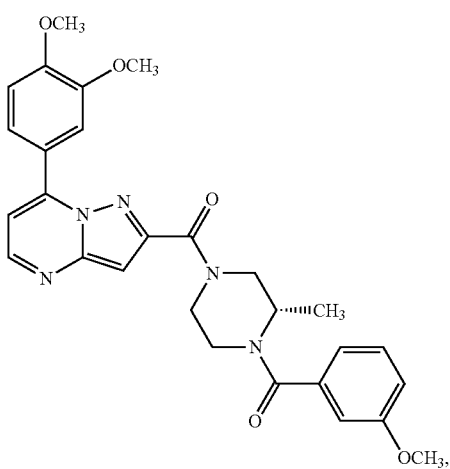
570
-continued
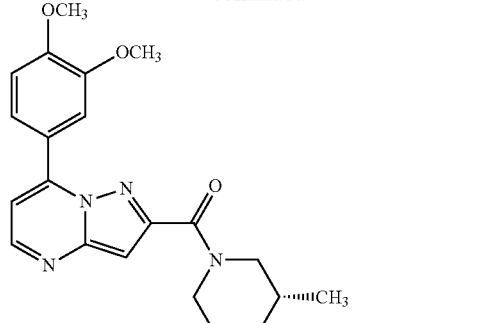
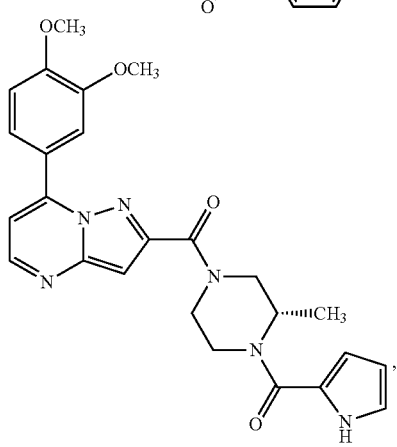
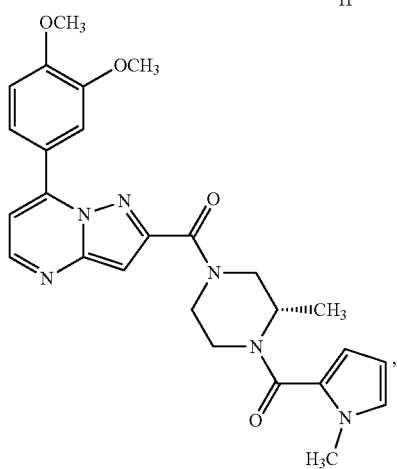
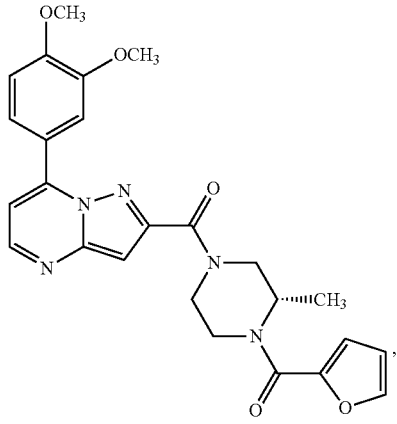

571
-continued
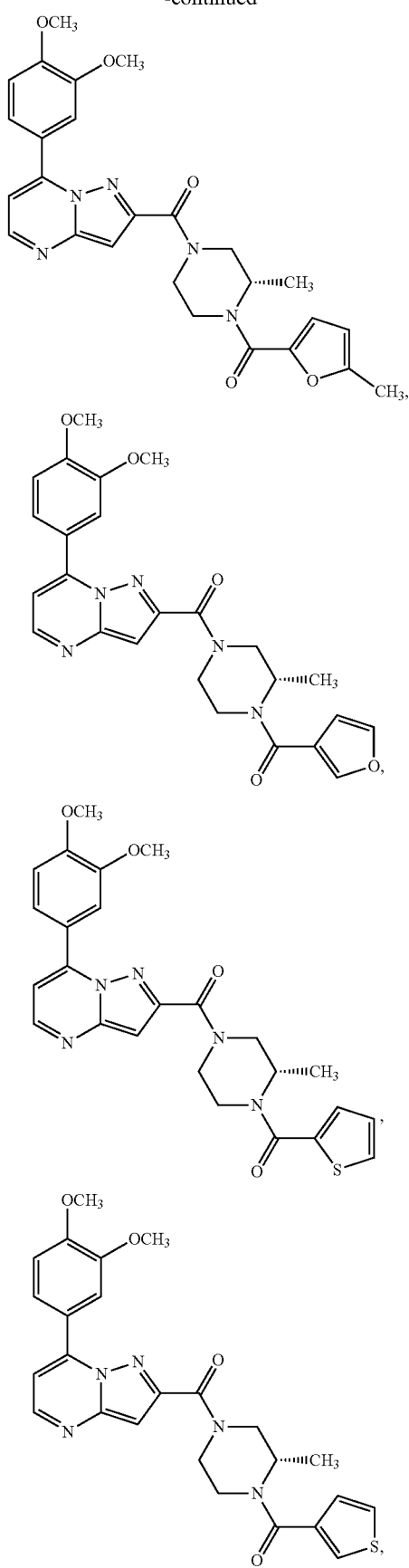
572
-continued
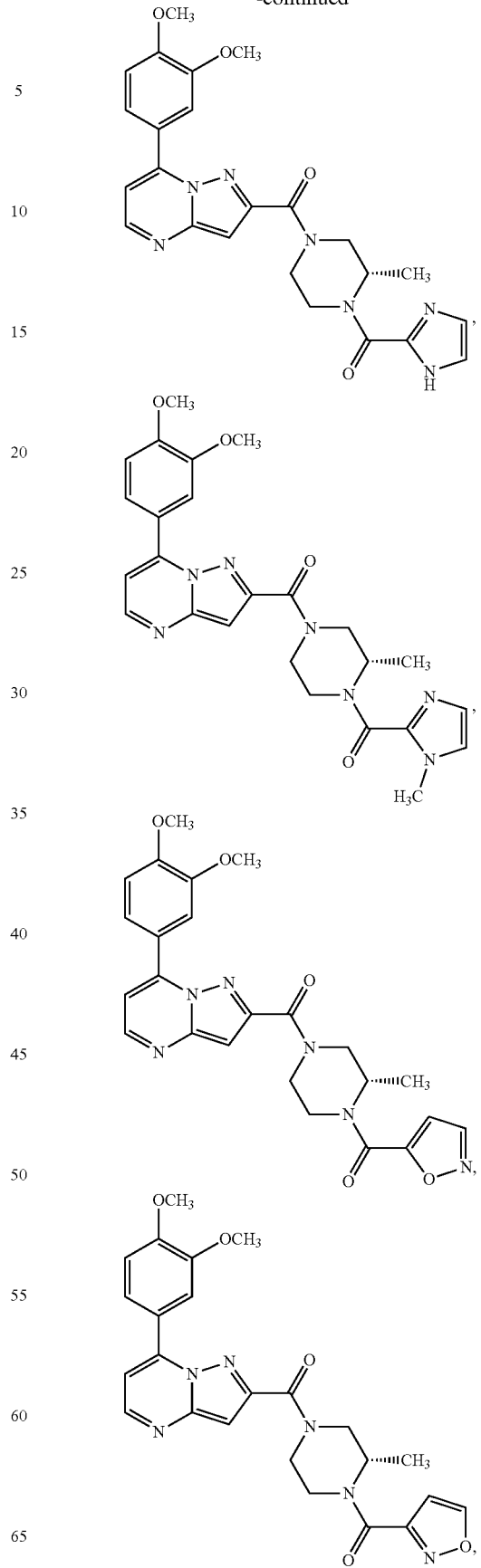

573
-continued
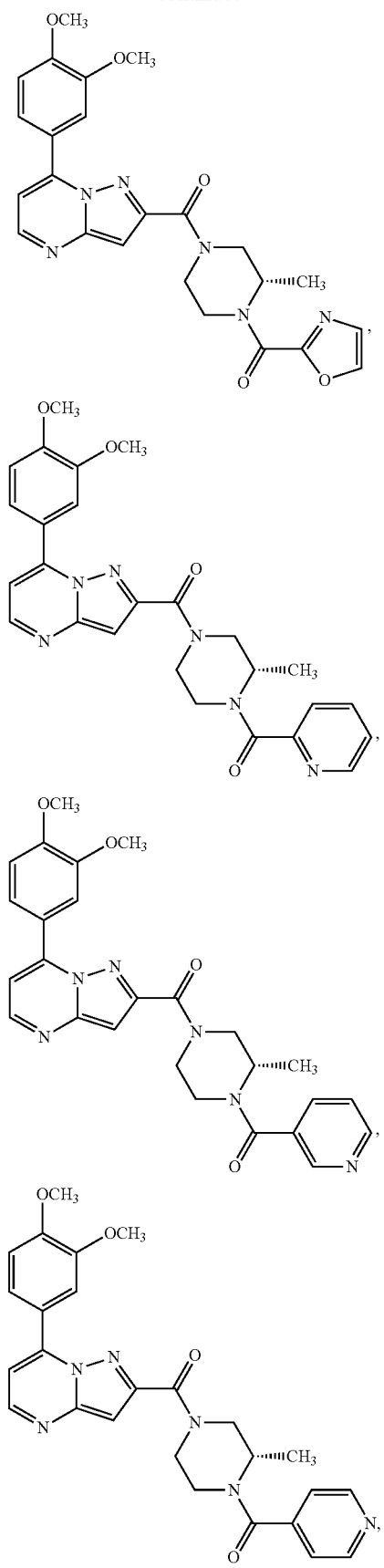
574
-continued
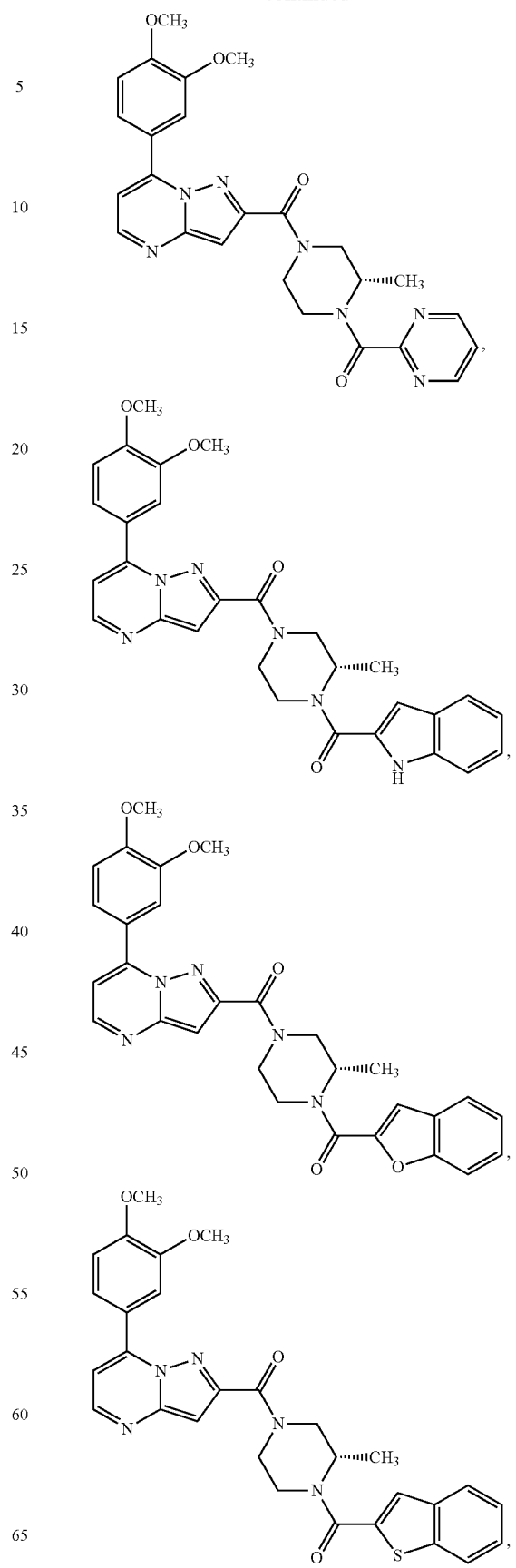

575
-continued
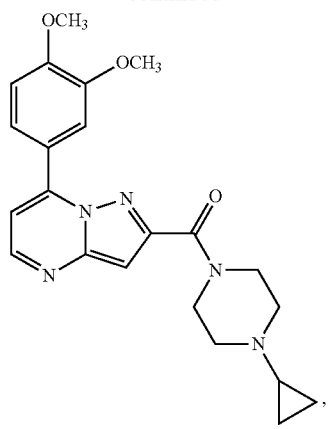
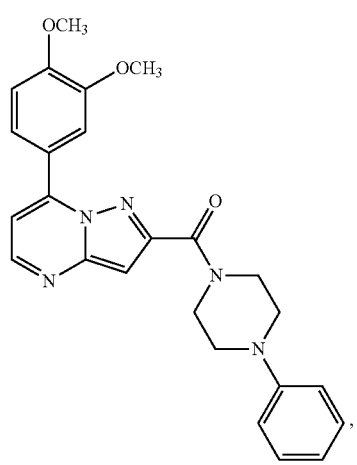
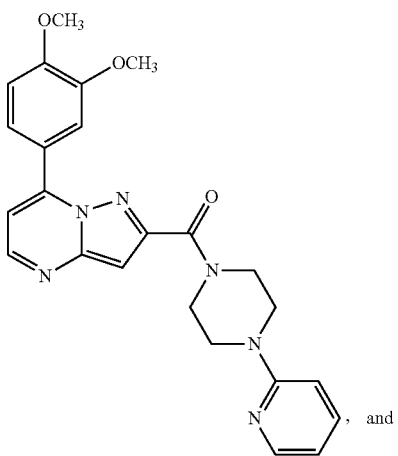
, and
576
-continued
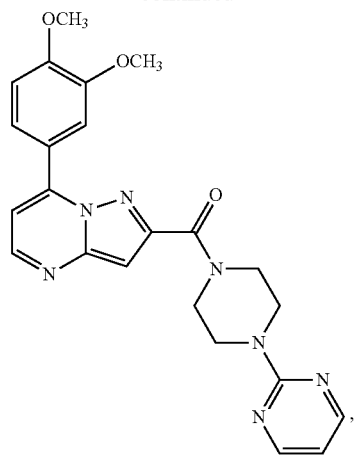
or a pharmaceutically acceptable salt thereof.
15. The compound of claim 1, wherein the compound is:
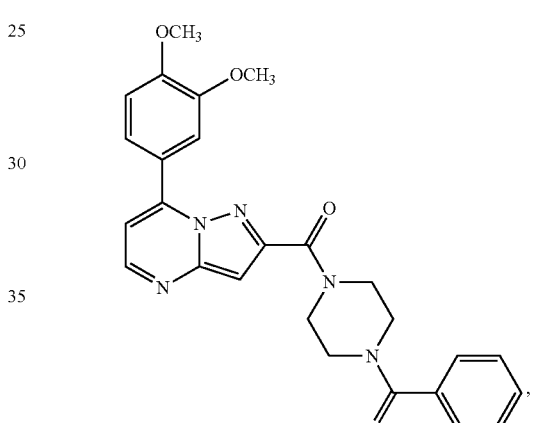
or a pharmaceutically acceptable salt thereof.
16. The compound of claim 1, wherein the compound is:
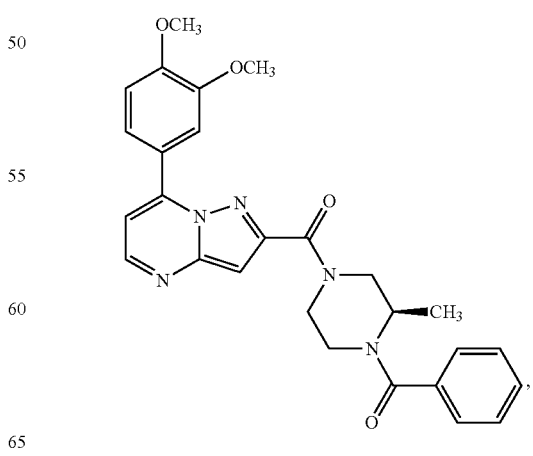
or a pharmaceutically acceptable salt thereof.

17. The compound of claim 1, wherein the compound is:

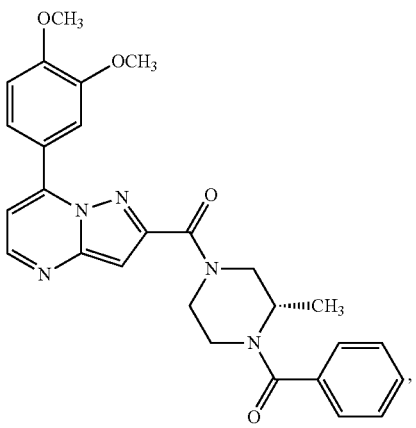 [SMILES: COc1ccc(-c2ccnc3cc(C(=O)N4CCN(C(=O)c5ccccc5)[C@@H](C)C4)nn23)cc1OC]

or a pharmaceutically acceptable salt thereof.

18. The compound of claim 1, wherein the compound is:

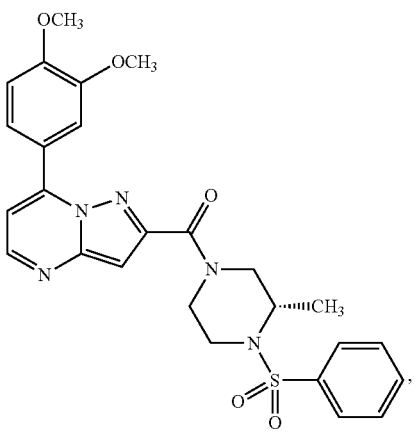 [SMILES: COc1ccc(-c2ccnc3cc(C(=O)N4CCN(S(=O)(=O)c5ccccc5)[C@@H](C)C4)nn23)cc1OC]

or a pharmaceutically acceptable salt thereof.

19. A pharmaceutical composition comprising a pharmaceutically acceptable excipient and a therapeutically effective amount of a compound of claim 1, or a pharmaceutically acceptable salt or stereoisomer thereof.

20. An ophthalmic composition comprising a physiologically compatible ophthalmic vehicle and a therapeutically effective amount of a compound of claim 1, or a pharmaceutically acceptable salt or stereoisomer thereof.

21. A method for inhibiting phosphodiesterase 4 (PDE4) activity in a biological sample or biological system, wherein the method comprises contacting the biological sample or biological system with an effective amount of a compound of claim 1, or a pharmaceutically acceptable salt or stereoisomer thereof.

22. A method for modulating cystic fibrosis transmembrane conductance regulator (CFTR) activity in a biological sample or biological system, wherein the method comprises contacting the biological sample or biological system with an effective amount of a compound of claim 1, or a pharmaceutically acceptable salt or stereoisomer thereof.

23. A method for treating dry eye disease in a subject in need thereof, wherein the method comprises administering to the subject a therapeutically effective amount of a compound of claim 1, or a pharmaceutically acceptable salt or stereoisomer thereof.

24. A method for treating an inflammatory disease in a subject in need thereof, wherein the method comprises administering to the subject a therapeutically effective amount of a compound of claim 1, or a pharmaceutically acceptable salt or stereoisomer thereof.

* * * * *